US012735423B2

(12) United States Patent
Wang et al.

(10) Patent No.: US 12,735,423 B2
(45) Date of Patent: Sep. 15, 2026

(54) (R) AND (S)-3-(TERT-BUTYL)-N-(1-(4-(6-(6-(4-((1-(4-(2,4-DIOXOTETRAHYDROPYRIMIDIN-1(2H)-YL)PHENYL)PIPERIDIN-4-YL)METHYL)PIPERAZIN-1-YL)PYRIDIN-3-YL)-7H-PYRROLO[2,3-D]PYRIMIDIN-4-YL)-2-METHYLPHENYL)ETHYL)-1,2,4-OXADIAZOLE-5-CARBOXAMIDE AS BRUTON'S TYROSINE KINASE (BTK) DEGRADERS

(71) Applicant: BeOne Medicines I GmbH, Basel (CH)

(72) Inventors: Hexiang Wang, Beijing (CN); Bailin Lei, Beijing (CN); Changxin Huo, Beijing (CN); Dongqing Sun, Beijing (CN); Jie Chen, Beijing (CN); Zhiwei Wang, Beijing (CN); Yucheng Wang, Beijing (CN); Huaqing Liu, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 852 days.

(21) Appl. No.: 17/919,847

(22) PCT Filed: Apr. 29, 2021

(86) PCT No.: PCT/CN2021/090898

§ 371 (c)(1),
(2) Date: Oct. 19, 2022

(87) PCT Pub. No.: WO2021/219070

PCT Pub. Date: Nov. 4, 2021

(65) Prior Publication Data

US 2023/0167118 A1 Jun. 1, 2023

(30) Foreign Application Priority Data

Apr. 30, 2020 (WO) ................ PCT/CN2020/088322
Apr. 2, 2021 (WO) ................ PCT/CN2021/085369

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ A61K 31/519; C07D 487/04
USPC ........................................ 514/265.1; 544/280
See application file for complete search history.

(56) References Cited

U.S. PATENT DOCUMENTS

| | | | |
|---|---|---|---|
| 9,630,968 | B1 | 4/2017 | Lapierre et al. |
| 10,584,101 | B2 | 3/2020 | Crew |
| 10,647,698 | B2 | 5/2020 | Crew |
| 12,172,992 | B2 | 12/2024 | Bian |
| 2016/0096834 | A1 | 4/2016 | Gaillard |
| 2018/0194762 | A1 | 7/2018 | Atallah |
| 2019/0276459 | A1 | 9/2019 | Crews |
| 2025/0041429 | A1 | 2/2025 | Lee |

FOREIGN PATENT DOCUMENTS

| | | | | |
|---|---|---|---|---|
| WO | 2013157021 A1 | 10/2013 | | |
| WO | 2014064131 A2 | 1/2014 | | |
| WO | 2015089327 A1 | 6/2015 | | |
| WO | 2015089337 A1 | 6/2015 | | |
| WO | 2016057500 A1 | 4/2016 | | |
| WO | 2017197046 A1 | 11/2017 | | |
| WO | 2018035080 A1 | 2/2018 | | |
| WO | 2018191577 A1 | 10/2018 | | |
| WO | 2018237026 A1 | 12/2018 | | |
| WO | 2019127008 | 7/2019 | | |
| WO | 2019140387 A1 | 7/2019 | | |
| WO | 2019148150 | 8/2019 | | |
| WO | 2019177902 | 9/2019 | | |
| WO | 2019186343 A1 | 10/2019 | | |
| WO | 2019186358 A1 | 10/2019 | | |
| WO | 2019222101 A1 | 11/2019 | | |
| WO | WO-2020/081450 A1 | 4/2020 | | |
| WO | 2021178920 A1 | 9/2021 | | |
| WO | WO-2021219070 A1 * | 11/2021 | ........... | C07D 519/00 |
| WO | 2023080732 A1 | 5/2023 | | |

OTHER PUBLICATIONS

Jordan, V. C. Nature Reviews: Drug Discovery, 2, 2003, 205.*
Hackam, et al. JAMA, 296(14), 2006, 1731-1732.*
Zorba et al., "Delineating the role of cooperativity in the design of potent PROTACs for BTK", PNAS, 115(31): E7285-E7292, 2018.
Sainan et al., "Small-molecule PROTACs: An emerging and promising approach for the development of targeted therapy drugs", EBioMedicine, 36: 552-562, 2018.
Ardley et al., "E3 ubiquitin ligases," Essays Biochem., vol. 41, pp. 15-30, 2005.
Buhimschi et al., "Targeting the C481S Ibrutinib-Resistance Mutation in Bruton's Tyrosine Kinase Using PROTAC-Mediated Degradation," Biochemistry, 57(26): 3564-3575, 2018.
Cermakova et al., "Next-Generation Drugs and Probes for Chromatin Biology: From Targeted Protein Degradation to Phase Separation", Molecules, 23(1958): 26 pages, 2018.
Conley et al., "Primary B Cell Immunodeficiencies: Comparisons and Contrasts," Annu. Rev. Immunol., vol. 27: 199-227, 2009.
Crews et al., "Inducing Protein Degradation as a Therapeutic Strategy":, 61(2), pp. 403-404, 2018.

(Continued)

*Primary Examiner* — Douglas M Willis

(74) *Attorney, Agent, or Firm* — Foley & Lardner LLP

(57) ABSTRACT

(R) and (S)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide useful as Bruton's tyrosine kinase degraders, methods of preparation and uses thereof.

6 Claims, No Drawings

(56) References Cited

OTHER PUBLICATIONS

Dobrovolsky et al., "Bruton tyrosine kinase degradation as a therapeutic strategy for cancer", Blood, 133(9): 952-961, 2019.
Extended European Search Report issued in App. No. EP21797070, dated Jul. 2, 2024, 15 pages.
Grice et al., "The Proteasome Distinguishes between Heterotypic and Homotypic Lysine-11 -Linked Polyubiquitin Chains", Cell Rep., 12(4): 545-553, 2015.
Gurcan et al., "A review of the current use of rituximab in autoimmune diseases", Int. Immunopharmacol., 9: 10-25, 2009.
Humphries et al., "Tee Kinases Mediate Sustained Calcium Influx via Site- specific Tyrosine Phosphorylation of the Phospholipase C Src Homology 2-Src Homology 3 Linker", J. Biol. Chem., 279(36): 37651-37661, 2004.
Khan et al., "Regulation of B lymphocyte development and activation by Bruton's tyrosine kinase", Immunol. Res., vol. 23: 147-156, 2001.
Komander et al., "The Ubiquitin Code," Annu. Rev. Biochem., vol. 81: 203-229, 2012.
Lebraud et al., "Protein degradation: a validated therapeutic strategy with exciting prospects", Essays Biochem., 61 (5): 517-527, 2017.
Liu et al., "Targeted selective degradation of Bruton's tyrosine kinase by PROTACs", Medicinal Chemistry Research, 29: 802-808, 2020.
Lochmuller et al., "Chromatographic Resolution of Enantiomers", Journal of Chromatography, 113: 283-302, 1975.
Lu et al., "Hijacking the E3 ubiquitin ligase cereblon to efficiently target BRD4", Chemistry & Biology, 22.6: 755-763, 2015.
Lu et al., "Discovery of a Keap1-dependent peptide PROTAC to knockdown Tau by ubiquitination-proteasome degradation pathway", European Journal of Medicinal Chemistry, 146: 251-259, 2018.
Neklesa et al., "Targeted protein degradation by PROTACs", Pharmacology & Therapeutics, vol. 174, pp. 138-144, 2017.
Ottis et al., "Proteolysis-Targeting Chimeras: Induced Protein Degradation as a Therapeutic Strategy", ACS Chem. Biol., vol. 12(4): 892-898, 2017.
Sakamoto et al., "Chimeric molecules to target proteins for ubiquitination and degradation", Methods Enzymol., vol. 399: 833-847, 2005.
Smith et al., "Expression of Bruton's Agammaglobulinemia Tyrosine Kinase Gene, BTK, Is Selectively Down-Regulated in T Lymphocytes and Plasma Cells", J. Immunol., 152: 557-565, 1994.
Sun et al., "Degradation of Bruton's tyrosine kinase mutants by PROTACs for potential treatment of ibrutinib-resistant non-Hodgkin lymphomas", Leukemia, vol. 33: 2105-2110, 2019.
Sun et al., "PROTAC-induced BTK degradation as a novel therapy for mutated BTK C481S induced ibrutinib-resistant B-cell malignancies", Cell Research, 28(7): 779-781, 2018.
Swatek et al., "Ubiquitin modifications", Cell Res., 26(4): 399-422, 2016.
Toure et al., "Small-Molecule PROTACS: New Approaches to Protein Degradation", Angew. Chem. Int. Ed., 55(6): 1966-1973, 2016.
Vetrie et al., "The gene involved in X-linked agammaglobulinaemia is a member of the src family of protein-tyrosine kinases", Nature, 361: 226-233, 1993.
Zhou et al., "Harnessing the ubiquitination machinery to target the degradation of specific cellular proteins", Mol. Cell., 6(3): 751-756, 2000.
International Search Report and Written Opinion mailed on Nov. 4, 2023 for PCT/CN2021/090898 (11 pages).
*Abbvie Inc.*, v *BeiGene, Ltd et al.*, Civil Action No. 1:24-cv-08167 filed on Sep. 6, 2024, 59 pages.
Defendants' Memorandum in Support of Motion to Dismiss, citation: Civil Action 1:24-cv-08167 filed on Dec. 19, 2024, 37 pages.
Plaintiff AbbVie Inc.'s Opposition to Defendants' Motion to Dismiss, citation: Civil Action 1:24-cv-08167 filed on Jan. 24, 2025, 44 pages.
Anonymous WeChat Official Account "Drug Exploration" retrieved from WeChat on Dec. 17, 2023. 1 pg.
EP Search Report for EP Appl. Ser. No. 21797070 dated Apr. 8, 2024 (16 pages).
Aqu, Alu et al., "BTK inhibitors in the treatment of hematological malignancies and inflammatory diseases: mechanisms and clinical studies," Journal of Hematology & Oncology, 15:138, 2022.
Bekes, M. et al., "PROTAC targeted protein degraders: the past is prologue," Nature Reviews, 21:181-200, 2022.
Boichenko, I. et al., "Chemical ligand space of cereblon," ACS Omega, 3:1163-1171, 2018.
Bondenson, D. P. et al., "Lessons in PROTAC design from selective degradation with a promiscuos warhead," Cell Chemical Biology, 25:15 pages, 2018.
Burke, M. R. et al., "Overcoming cancer drug resistance utilizing PROTAC technology," Frontiers in Cell and Developmental Biology, 10(872729):1-22, 2022.
Burslem, G. M. et al., "Efficient synthesis of immunomodulatory drug analogues enables exploration of structure-degradation relationships," ChemMedChem, 13:1508-1512, 2018.
Caldwell, R. D. et al., "Discovery of Evobrutinib: an oral, potent, and highly selective, covalent Bruton's tyrosine kinase (BTK) inhibitor for the treatment of immunological diseases," Journal of Medicinal Chemistry, 62:7643-7655, 2019.
Casement, R. et al., "Mechanistic and structural features of PROTAC temary complexes," Chapter 5, Methods in Molecular Biology, 2365:35 pages, 2021.
Crawford, J. J. et al., "Discovery of GDC-0853: a potent, selective, and noncovalent Bruton's tyrosine kinase inhibitor in early clinical development," Journal of Medicinal Chemistry, 61:2227-2245, 2018.
Cromm, P. M. et al., "Targeted protein degradation: from chemical biology to drug discovery," Cell Chemical Biology Review, 24:1181-1190, 2017.
Defendants' reply in support of motion to dismiss, citation: Civil Action No. 1:24-cv-8167, filed Feb. 14, 2025, 27 pages.
Desantis, J. et al., "PROTACs bearing piperazine-containing linkers: what effect on their protonation state?," RSC Adv., 12:21968-21977, 2022.
Di Paolo, J. A. et al., "Specific Btk inhibition suppresses B cell- and myeloid cell-mediated arthritis," Nat. Chem. Biol., 7(1):41-50, 2011.
Dong, Y. et al., "Characteristic roadmap of linker governs the rational design of PROTACs," Acta Pharmaceutica Sinica B, 1-30, 2024.
Feng, Y. et al., "Bruton's tyrosine kinase (BTK) inhibitors in treating cancer: a patent review (2010-2018)," Expert Opinion on Therapeutic Patents, 29(4):217-241, 2019.
Gomez, E. B. et al., "Preclinical characterization of pirtobrutinib, a highly selective, noncovalent (reversible) BTK inhibitor," Blood, 142(1):62-72, 2023.
Han, X. et al., "Discovery of ARD-69 as a highly proteolysis targeting chimera (PROTAC) degrader of androgen receptor (AR) for the treatment of prostate cancer," J. Med. Chem., 62:941-964, 2019.
Han, X. et al., "Strategies for the discovery of oral PROTAC degraders aimed at cancer therapy," Cell Reports Physical Science, 3(101062):1-22, 2022.
Hayama, M. et al., "Taking the next step in double refractory disease: current and future treatment strategies for chronic lymphocytic leukemia," OncoTargets and Therapy, 17:181-198, 2024.
Jarusiewicz, J. A. et al., "Phenyl dihodrouracil: an alternative cereblon binder for PROTAC design," ACS Medicial Chemstry Letters, 14:141-145, 2023.
Kargbo, Robert B., "PROTAC molecules for the treatment of autoimmune disorders," ACS Medicinal Chemistry Letters, 10:276-277, 2019.
Kronke, J. et al., "Lenalidomide induces ubiquitination and degradation of CK1alpha in del (95q) MDS," Nature, 523:20 pages, 2015.
Li, B. et al., "3D based generative PROTAC linker design with reinforcement learning," Briefings in Bioinformatics, 24(5):1-13, 2023.

(56) References Cited

OTHER PUBLICATIONS

Li, W. et al., "Bruton's tyrosine kinase inhibitors with distinct binding modes reveal differential functional impact on B-cell receptor signaling," Molecular Cancer Therapeutics, 23:35-46, 2024.
Li, X. et al., "A patent review of the ubiquitin ligase system: 2015-2018," Expert Opinion on Therapeutic Patents, 28(12):919-937, 2018.
Min, J. et al., "Phenyl-glutarimides: Alternative cereblon binders for the design of PROTACs," Angewandte Chemie, 60:26633-26670, 2021.
Moon, S. et al., "Chemically induced cellular proteolysis: an emerging therapeutic strategy for undruggable targets," Molecules and Cells, 41(11):933-942, 2018.
Nowak, R. P. et al., "Plasticity in binding confers selectivity in ligand-induced protein degradation," Nature chemical biology, 14:706-714, 2018.
Raina, K. et al., "Targeted protein knockdown using small molecule degraders," Current Opinion in Chemical Biology, 39:46-53, 2017.
Rankin, A. L. et al., "Selective inhibition of BTK prevents murine lupus and antibody-mediated glomerulonephritis," The Journal of Immunology, 191(9):4540-4550, 2013.
Shi, Q. et al., "Purine derivatives as potent Bruton's tyrosine kinase (BTK) inhibitors for autoimmune diseases," Bioorganic and Medicinal Chemistry Letters, 24:2206-2211, 2014.
Tasso, B. et al., "The development of BTK inhibitors: a five-year update," Molecules, 26:1-31, 2021.
Tinworth, C. P. et al., "PROTAC-mediated degradation of Bruton's tyrosine kinase is inhibited by covalent binding", ACS Chemical Biology, 14(3):342-347, 2019.
Troup, R. I. et al., "Current strategies for the design of PROTAC linkers: a critical review," Exploration of Targerted Anti-tumor Therapy, 1:273-312, 2020.
Weng, G. et al., "PROTAC-DB: an online database of PROTACs," Nucleic Acids Research, 49:D1381-D1387, 2021.
Winter, G. E. et al., "Phthalimide conjugation as a strategy for in vivo target protein degradation," Science, 348(6241):1376-1381, 2015.
Woodhead, Steve, Presentation: "Structure Guided Design and Optimization of Selective Kinase Inhibitors from Fragment Starting Points," Takeda California, 33 pages, Apr. 14, 2016.
Xiao, M. et al., "Recent advances of degradation technologies based on PROTAC mechanism," Biomolecules, 12(1257):1-15, 2022.
Xie, H. et al., "Development of substituted phenyl dihydrouracil as the novel achiral cereblon ligands for targeted protein degradation," Journal of Medicinal Chemistry, 66:2904-2917, 2023.
Zhou, B. et al., "Discovery of a small-molecule degrader of bromodomain and extra-terminal (BET) proteins with picomolar cellular potencies and capable of achieving tumor regression," Journal of Medicinal Chemistry, 61:462-481, 2018.

* cited by examiner

(R) AND (S)-3-(TERT-BUTYL)-N-(1-(4-(6-(6-(4-((1-(4-(2,4-DIOXOTETRAHYDROPYRIMIDIN-1(2H)-YL)PHENYL)PIPERIDIN-4-YL)METHYL)PIPERAZIN-1-YL)PYRIDIN-3-YL)-7H-PYRROLO[2,3-D]PYRIMIDIN-4-YL)-2-METHYLPHENYL)ETHYL)-1,2,4-OXADIAZOLE-5-CARBOXAMIDE AS BRUTON'S TYROSINE KINASE (BTK) DEGRADERS

CROSS-REFERENCE TO RELATED APPLICATIONS

This application is a U.S. National Stage Application under 35 U.S.C. § 371 of International Application No. PCT/CN2021/090898, filed Apr. 29, 2021, which claims priority to Patent Application Nos. PCT/CN2021/085369 (CN), filed Apr. 2, 2021 and PCT/CN2020/088322 (CN), filed on Apr. 30, 2020.

FIELD OF THE INVENTION

Disclosed herein are novel bifunctional compounds formed by conjugating BTK inhibitor moieties with E3 ligase Ligand moieties, which function to recruit targeted proteins to E3 ubiquitin ligase for degradation, and methods of preparation and uses thereof.

BACKGROUND OF THE INVENTION

Proteolysis-targeting chimera (PROTAC) is a novel strategy for selective knockdown of target proteins by small molecules (Sakamoto K M et al., *Proc Natl Acad Sci* 2001, 98:8554-9; Sakamoto K. M. et al., *Methods Enzymol.* 2005; 399:833-847.). PROTAC utilizes the ubiquitin-protease system to target a specific protein and induce its degradation in the cell (Zhou P. et al., *Mol Cell.* 2000; 6(3):751-756; Neklesa T. K. et al., *Pharmacol Ther.* 2017; 174:138-144; Lu M. et al., *Eur J Med Chem.* 2018; 146:251-259;). The normal physiological function of the ubiquitin-protease system is responsible for clearing denatured, mutated, or harmful proteins in cells. The ubiquitin-proteasome system (UPS), also known as the ubiquitin-proteasome pathway (UPP), is a common posttranslational regulation mechanism that is responsible for protein degradation in normal and pathological states (Ardley H. et al., *Essays Biochem.* 2005, 41, 15-30; Komander D. et al., *Biochem.* 2012, 81, 203-229; Grice G. L. et al., *Cell Rep.* 2015, 12, 545-553; Swatek K. N. et al., *Cell Res.* 2016, 26, 399-422). Ubiquitin, which is highly conserved in eukaryotic cells, is a modifier molecule, composed of 76 amino acids, that covalently binds to and labels target substrates via a cascade of enzymatic reactions involving E1, E2, and E3 enzymes. Subsequently, the modified substrate is recognized by the 26S proteasome complex for ubiquitination-mediated degradation. So far, two E1 enzymes have been discovered, which are termed UBA1 and UBA6. On the other hand, there are about 40 E2 enzymes and more than 600 E3 enzymes that offer the functional diversity to govern the activity of many downstream protein substrates. However, only a limited number of E3 ubiquitin ligases have been successfully hijacked for use by small molecule PROTAC technology: the Von Hippel-Lindau disease tumor suppressor protein (VHL), the Mouse Double Minute 2 homologue (MDM2), the Cellular Inhibitor of Apoptosis (cIAP), and cereblon (Philipp O. et al., *Chem. Biol.* 2017, 12, 2570-2578).

Bifunctional compounds composed of a target protein-binding moiety and an E3 ubiquitin ligase-binding moiety have been shown to induce proteasome-mediated degradation of selected proteins. These drug-like molecules offer the possibility of temporal control over protein expression and could be useful as biochemical reagents for the treatment of diseases. In recent years, this newly developed method has been widely used in antitumor studies (Lu J. et al., *Chem Biol.* 2015; 22(6):755-763; Ottis P. et al., *Chem Biol.* 2017; 12(4):892-898; Crews C. M. et al., *J Med Chem.* 2018; 61(2):403-404; Neklesa T. K. et al., *Pharmacol Ther.* 2017, 174:138-144; Cermakova K. et al., *Molecules,* 2018.23(8); An S. et al., *EBioMedicine,* 2018; Lebraud H. et al., *Essays Biochem.* 2017; 61(5): 517-527; Sun Y. H. et al., *Cell Res.* 2018; 28:779-81; Toure M. et al., *Angew Chem Int Ed Engl.* 2016; 55(6):1966-1973; Yonghui Sun et al., *Leukemia*, volume 33, pages 2105-2110(2019); Shaodong Liu et al., *Medicinal Chemistry Research*, volume 29, pages 802-808 (2020); and has been disclosed or discussed in patent publications, e.g., US20160045607, US20170008904, US20180050021, US20180072711, WO2002020740, WO2014108452, WO2016146985, WO2016149668, WO2016149989, WO2016197032, WO2016197114, WO2017011590, WO2017030814, WO2017079267, WO2017182418, WO2017197036, WO2017197046, WO2017197051, WO2017197056, WO2017201449, WO2017211924, WO2018033556, and WO2018071606.

Bruton's tyrosine kinase (Btk) belongs to the Tec tyrosine kinase family (Vetrie et al., *Nature* 361: 226-233, 1993; *Bradshaw, Cell Signal.* 22: 1175-84, 2010). Btk is primarily expressed in most hematopoietic cells such as B cells, mast cells and macrophages (Smith et al., *J. Immunol.* 152: 557-565, 1994) and is localized in bone marrow, spleen and lymph node tissue. Btk plays an important role in B-cell receptor (BCR) and FcR signaling pathways, which involve in B-cell development, differentiation (Khan, *Immunol*. Res. 23: 147, 2001). Btk is activated by upstream Src-family kinases. Once activated, Btk, in turn, phosphorylates PLC-gamma, leading to effects on B-cell function and survival (Humphries et al., *J. Biol. Chem.* 279: 37651, 2004). These signaling pathways must be precisely regulated. Mutations in the gene encoding Btk cause an inherited B-cell specific immunodeficiency disease in humans, known as X-linked agammaglobulinemia (XLA) (Conley et al., *Annu. Rev. Immunol.* 27: 199-227, 2009). Aberrant BCR-mediated signaling may result in dysregulated B-cell activation leading to a number of autoimmune and inflammatory diseases. Preclinical studies show that Btk deficient mice are resistant to developing collagen-induced arthritis. Moreover, clinical studies of Rituxan, a CD20 antibody to deplete mature B-cells, reveal the key role of B-cells in a number of inflammatory diseases such as rheumatoid arthritis, systemic lupus erythematosus and multiple sclerosis (Gurcan et al., *Int. Immunopharmacol.* 9: 10-25, 2009). Therefore, Btk inhibitors can be used to treat autoimmune and/or inflammatory diseases.

Inhibition of BTK has been shown to affect cancer development (B cell malignancies) and cell viability, and improve autoimmune diseases (e.g., rheumatoid arthritis and lupus). Inhibition of BTK has also been reported via alternative strategies, such as through degradation of BTK (Alexandru D. et al., *Biochemistry* 2018, 57, 26, 3564-3575; Adelajda Z. et al., *PNAS* 2018 115 (31); Dennis D., et al., *Blood,* 2019, 133:952-961; Yonghui S. et al., *Cell Research,* 2018, 28, 779-781; Yonghui S. et al., *Leukemia,* 2019, Degradation of Bruton's tyrosine kinase mutants by PROTACs for the potential treatment of ibrutinib-resistant non-Hodgkin lymphomas) and has been disclosed or discussed in patent publications, e.g. US20190276459, WO2019186343, WO2019186358, WO2019148150, WO2019177902, and WO2019127008.

WO2019/186343A1 discloses that N-(3-(7H-pyrrolo[2,3-D]pyrimidin-4yl)phenyl)-benzamide derivatives as BTK depredator of formula (A), (Formula A)

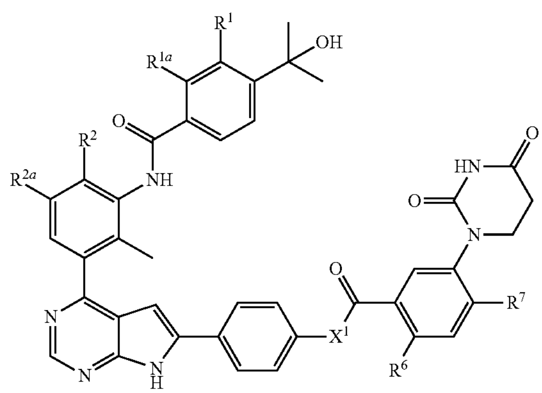

wherein $R^1$, $R^{1a}$, $R^2$ and $R^{2a}$ are independently at each occurrence selected from H and F; $R^6$ is H or F; $R^7$ is selected from H, F, Cl, —$CH_3$, —$OCH_3$, and —$OCH_2CH_3$; and $X^1$ is a group of linkers.

WO2019/186358A1 discloses that 3-hydroxy-N-(3-(7H-pyrrolo[2,3-D]pyrimidin-4yl)phenyl)-benzamide derivatives as BTK depredator of formula (B), (Formula B)

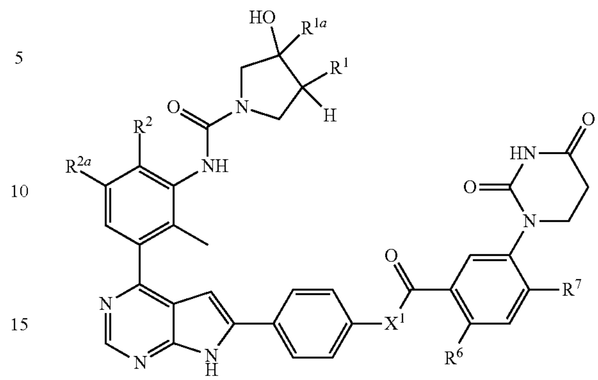

wherein $R^1$ is isobutyl; $R^{1a}$ is H; $R^2$ is H or F; $R^{2a}$ is H or F; $R^6$ is H or F; $R^7$ is selected from H, F, Cl, —$CH_3$, —$OCH_3$, and —$OCH_2CH_3$; and $X^1$ is a group of linkers.

There is a need of new BTK inhibitors or degraders which are more potent than known inhibitors of BTK and inhibit BTK via alternative strategies, such as through degradation of BTK. The present application addresses the need.

SUMMARY OF THE INVENTION

One objective of the present invention is to provide a proteolysis targeting chimera (PROTAC) compound by conjugating a BTK inhibitor with an E3 ligase ligand, which functions to recruit targeted proteins to E3 ubiquitin ligase for degradation, and to provide a method of the preparation and uses thereof. In particular, the present disclosure provides PROTAC compounds with Formula I.

Aspect 1: A compound of Formula (I):

(I)

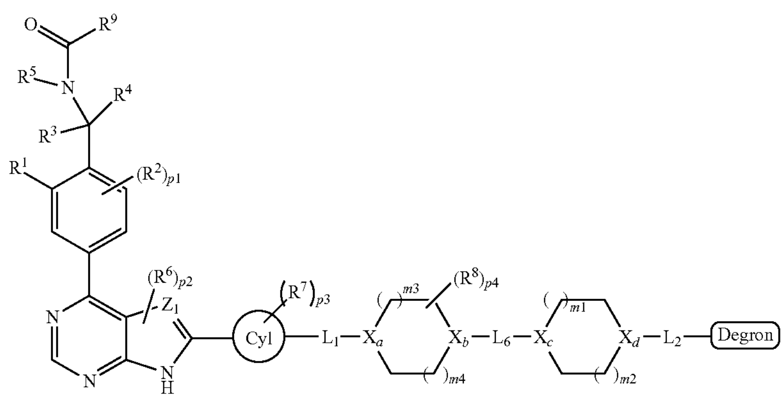

or a pharmaceutically acceptable salt thereof, or a stereoisomer thereof, where:

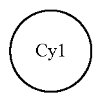

is a 5- or 6-membered aromatic ring comprising 0-3 heteroatoms selected from nitrogen, oxygen and sulfur; the Degron moiety is an E3 Ubiquitin ligase moiety selected from

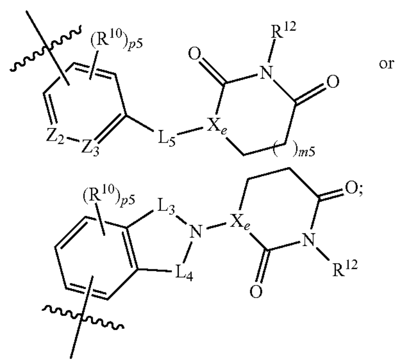

$L_1$, $L_2$, $L_3$, $L_4$ and $L_5$ are each independently a bond, —O—, —CO—, —$(CR_cR_d)_{n2}$— or —$NR_c$—;

$L_6$ is each independently —$(CR_aR_b)_{n1}$—, —CO—$(CR_aR_b)_{n1}$—NH—$(CR_eR_f)_{n3}$—, —CO—$(CR_aR_b)_{n1}$—NH—, or —$(CR_aR_b)_{n1}$—NH—$(CR_eR_f)_{n3}$—;

$Z_1$, $Z_2$ and $Z_3$ are each independently $CR^{12}$ or N;

$X_a$, $X_b$, $X_c$, $X_d$ and $X_e$ are each independently $CR^{12}$ or N;

$R^1$, $R^2$, $R^3$, $R^4$, $R^5$, $R^6$, $R^7$, $R^8$ and $R^{10}$ are each independently, hydrogen, halogen, —$C_{1-8}$alkyl, —$C_{1-8}$alkoxy, —$C_{2-8}$alkenyl, —$C_{2-8}$alkynyl, cycloalkyl, heterocyclyl, aryl, heteroaryl, oxo, —CN, —$NO_2$, —$OR_a$, —$SO_2R_a$, —$COR_a$, —$CO_2R_a$, —$CONR_aR_b$, —C(=$NR_a$)$NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, -halo$C_{1-8}$alkyl, —$C_{1-8}$alkyoxy, cycloalkyl, heterocyclyl, aryl, or heteroaryl;

or $R^4$ and $R^2$ on the ortho position of the phenyl ring form a 5- or 6-membered carbon ring;

or $X_a$ and either of the two adjacent carbon atoms form a double bond, provided that Xa is $CR^{12}$ and $R^{12}$ is absent;

or two non-adjacent $R^8$ on

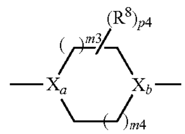

moiety form a bridge comprising one or two or three $CH_2$;

each $R^{12}$ is independently hydrogen or —$C_{1-8}$alkyl;

$R^9$ is 5- or 6-membered aromatic ring comprising 0-3 heteroatoms selected from nitrogen, oxygen and sulfur; each of said aromatic ring is optionally substituted with halogen, —$C_{1-8}$alkyl, —$C_{2-8}$alkenyl, —$C_{2-8}$alkynyl, —$C_{1-8}$alkoxy, cycloalkyl, heterocyclyl, aryl, heteroaryl, —CN, —$NO_2$, —$OR_a$, —$SO_2R_a$, —$COR_a$, —$CO_2R_a$, —$CONR_aR_b$, —C(=$NR_a$)$NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, -halo$C_{1-8}$alkyl, —$C_{1-8}$alkyoxy, cycloalkyl, heterocyclyl, aryl, or heteroaryl;

n1, n2, n3, m1, m2, m3, m4, m5, p1, p2, p3, p4 and p5 are each independently 0, 1, 2, 3 or 4;

$R_a$, $R_b$, $R_c$, $R_d$, $R_e$ and $R_f$ are each independently hydrogen, —$C_{1-8}$alkyl, —$C_{2-8}$alkenyl, —$C_{2-8}$alkynyl, cycloalkyl, heterocyclyl, aryl, or heteroaryl.

Aspect 2: A compound of Formula (II):

(II)

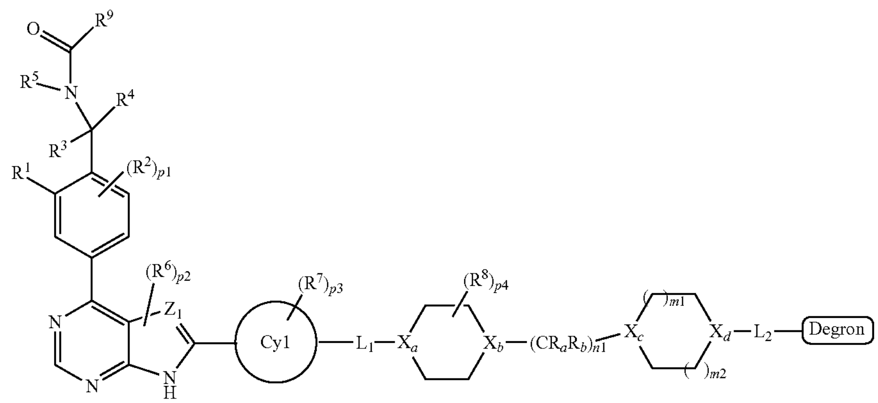

or a pharmaceutically acceptable salt thereof, or a stereoisomer thereof, wherein:

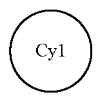

is a 5- or 6-membered aromatic ring comprising 0-3 heteroatoms selected from nitrogen, oxygen and sulfur;

the

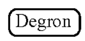

moiety is an E3 Ubiquitin ligase moiety selected from

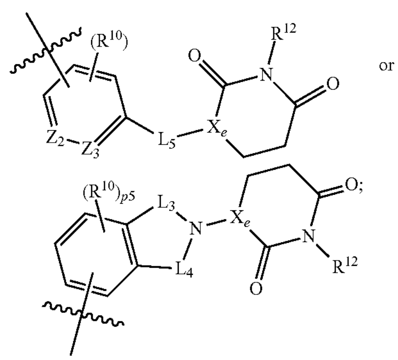

$L_1$, $L_2$, $L_3$, $L_4$ and $L_5$ are each independently a bond, —O—, —CO—, —$(CR_cR_d)_{n2}$— or —$NR_c$—;

$Z_1$, $Z_2$ and $Z_3$ are each independently $CR^{12}$ or N;

$X_a$, $X_b$, $X_c$, $X_d$ and $X_e$ are each independently $CR^{12}$ or N;

$R^1$, $R^2$, $R^3$, $R^4$, $R^5$, $R^6$, $R^7$, $R^8$ and $R^{10}$ are each independently hydrogen, halogen, —$C_{1-8}$alkyl, —$C_{1-8}$alkoxy, —$C_{2-8}$alkenyl, —$C_{2-8}$alkynyl, cycloalkyl, heterocyclyl, aryl, heteroaryl, oxo, —CN, —$NO_2$, —$OR_a$, —$SO_2R_a$, —$COR_a$, —$CO_2R_a$, —$CONR_aR_b$, —$C(=NR_a)NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, -halo$C_{1-8}$alkyl, —$C_{1-8}$ alkyoxy, cycloalkyl, heterocyclyl, aryl, or heteroaryl;

each $R^{12}$ is independently hydrogen or —$C_{1-8}$alkyl;

$R^9$ is 5- or 6-membered aromatic ring comprising 0-3 heteroatoms selected from nitrogen, oxygen and sulfur; each of said aromatic ring is optionally substituted with halogen, —$C_{1-8}$alkyl, —$C_{2-8}$alkenyl, —$C_{2-8}$alkynyl, —$C_{1-8}$alkoxy, cycloalkyl, heterocyclyl, aryl, heteroaryl, —CN, —$NO_2$, —$OR_a$, —$SO_2R_a$, —$COR_a$, —$CO_2R_a$, —$CONR_aR_b$, —$C(=NR_a)NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, -halo$C_{1-8}$alkyl, —$C_{1-8}$alkyoxy, cycloalkyl, heterocyclyl, aryl, or heteroaryl;

n1, n2, m1, m2, p1, p2, p3, p4 and p5 are each independently 0, 1, 2, 3 or 4;

$R_a$, $R_b$, $R_c$, and $R_d$ are each independently hydrogen, —$C_{1-8}$alkyl, —$C_{2-8}$alkenyl, —$C_{2-8}$alkynyl, cycloalkyl, heterocyclyl, aryl, or heteroaryl.

Aspect 3: The compound according to Aspect 1 or 2, wherein

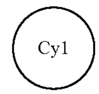

is

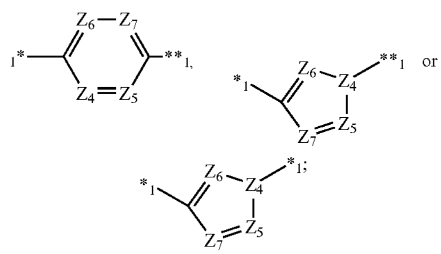

wherein $Z_4$, $Z_5$, $Z_6$ and $Z_7$ are each independently selected from CH or N; wherein *1 refers to the position attached to the

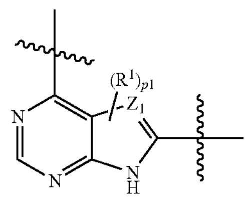

moiety, and **1 refers to the position attached to $L_1$.

Aspect 4: The compound according to Aspect 1, wherein

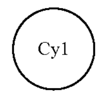

is

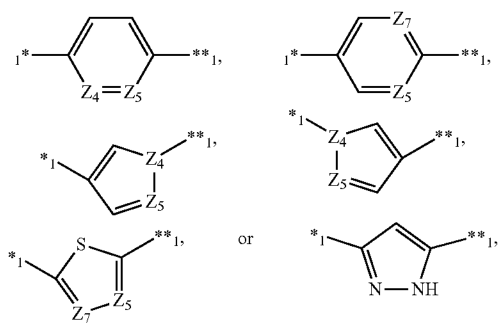

wherein $Z_4$, $Z_5$ and $Z_7$ are each independently selected from CH or N.

Aspect 5: The compound according to Aspect 3 or 4, wherein

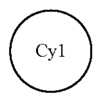

is selected from

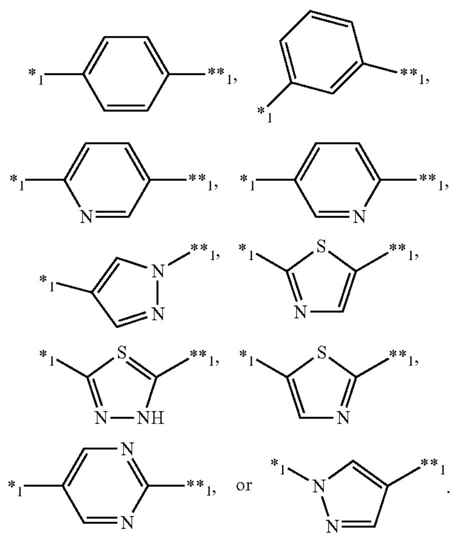

Aspect 6: The compound according to any one of Aspects 3 to 5, wherein p3 is 0, 1, or 2, and each $R^7$ is independently selected from halogen, —$C_{1-8}$alkyl, or —$C_{1-8}$alkoxy, preferably F, C, Br, I, $CH_3$, or —$OCH_3$.

Aspect 7: The compound according to Aspect 1 or 2, wherein the

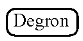

moiety is selected from

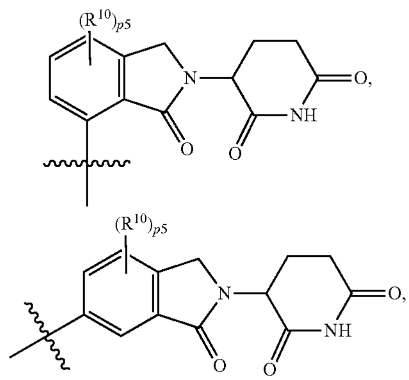

-continued

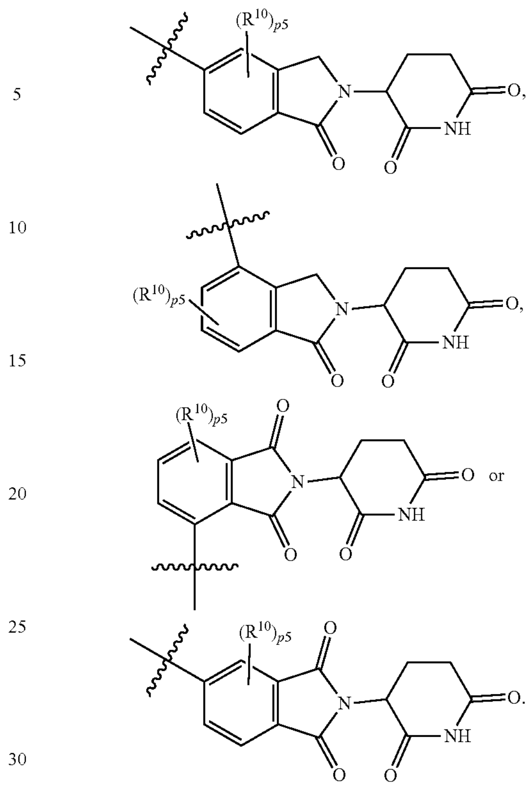

Aspect 8: The compound according to Aspect 7, wherein the

moiety is selected from

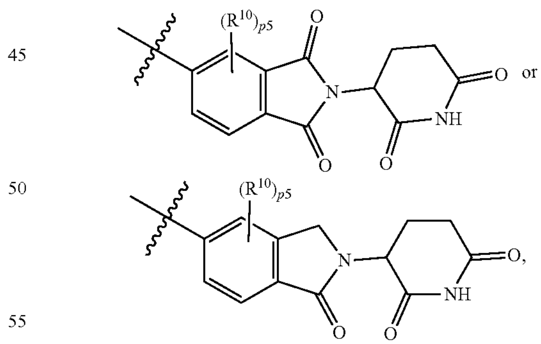

$R^{10}$ is selected from hydrogen or halogen; and p5 is 0 or 1.

Aspect 9: The compound according to Aspect 8, wherein the

moiety is selected from
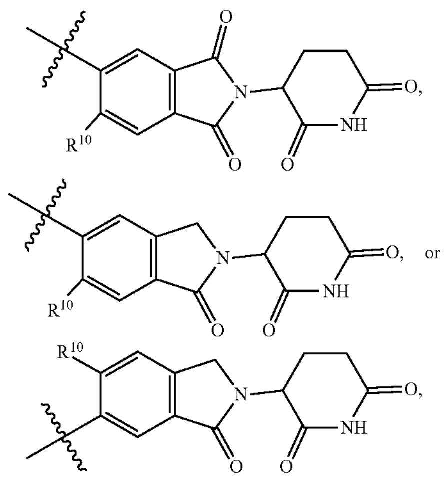
$R^{10}$ is selected from hydrogen, F, Cl, Br and I.
Aspect 10: The compound according to Aspect 1 or 2, wherein the
Degron
moiety is selected from
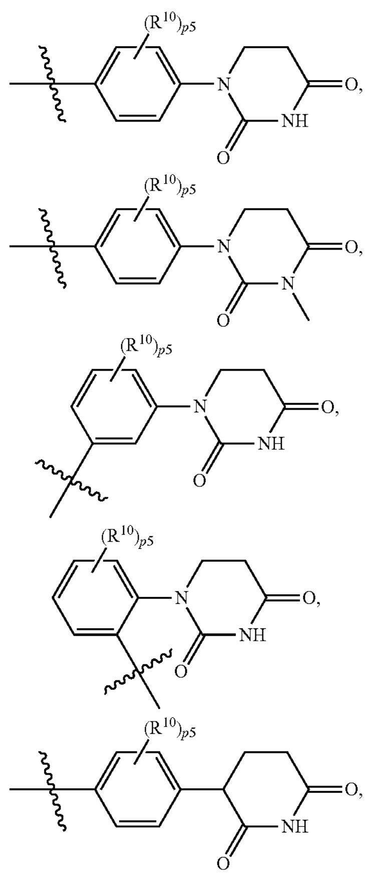
-continued
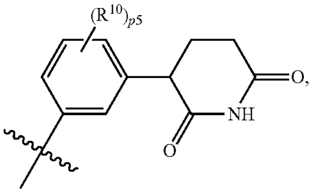
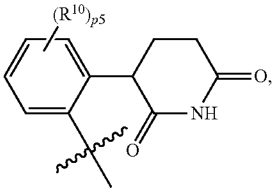
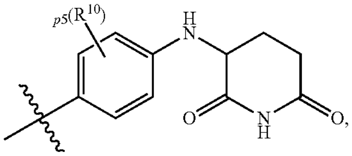
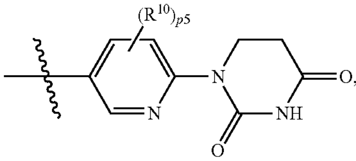
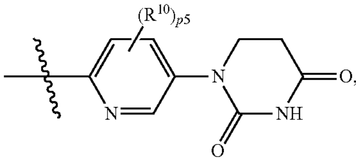
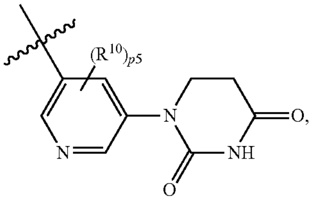
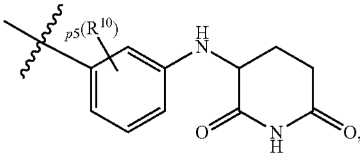
or
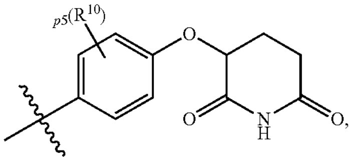
wherein $R^{10}$ hydrogen, halogen, $-C_{1-8}$alkyl, $-OR_a$; $R_a$ is hydrogen or $-C_{1-8}$alkyl; and p5 is 0 or 1.
Aspect 11: The compound according to Aspect 10, wherein the
Degron moiety is selected from
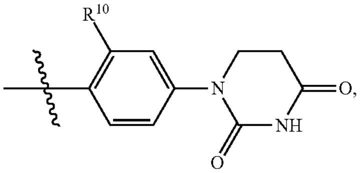
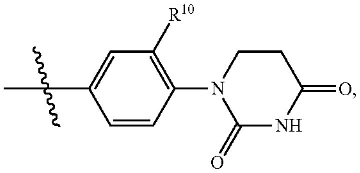
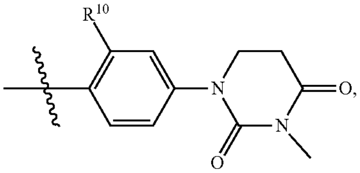
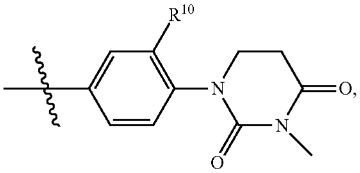
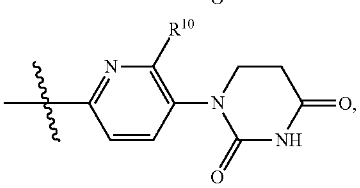
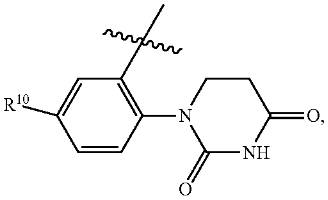
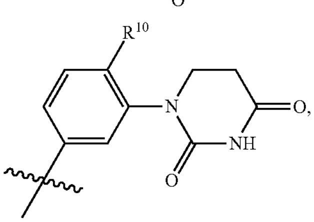
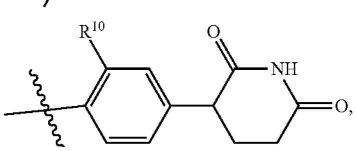
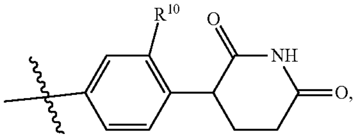
-continued
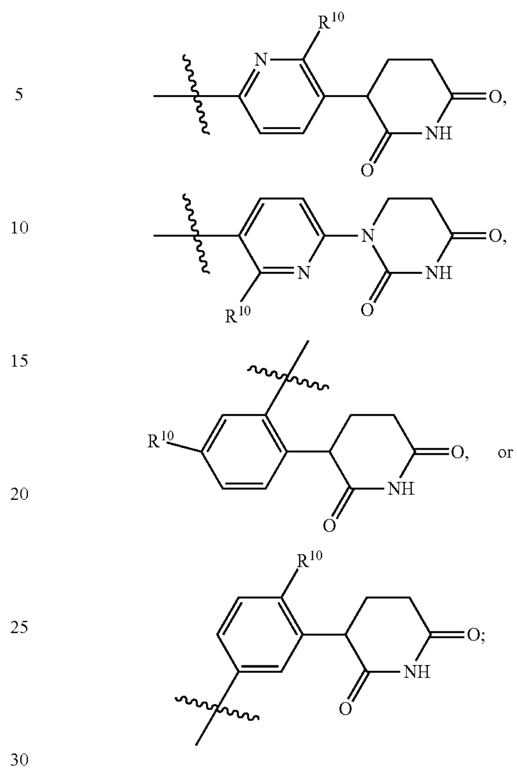
or
wherein $R^{10}$ is hydrogen, halogen, $-C_{1-8}$alkyl, or $-C_{1-8}$alkoxy; preferably fluoro, cholor, methyl or methoxy.
Aspect 12: The compound according to Aspect 11, wherein the
Degron
moiety is selected from
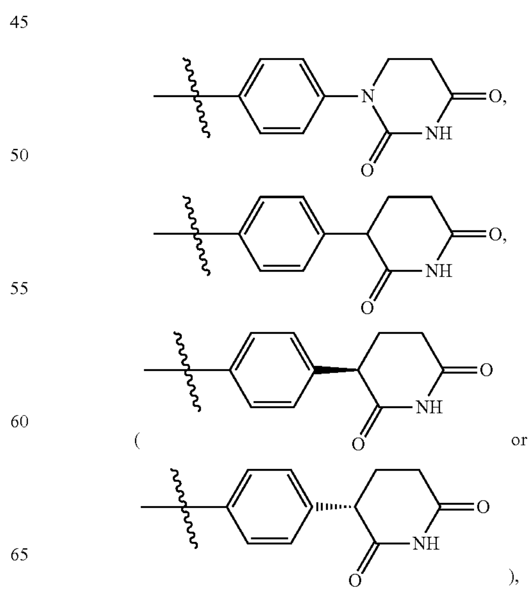
or -continued

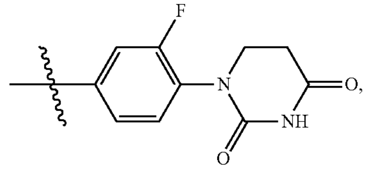

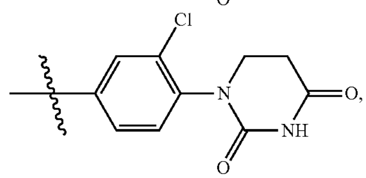

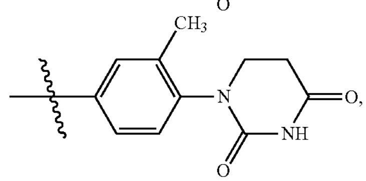

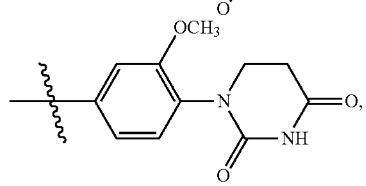

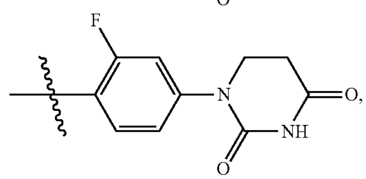

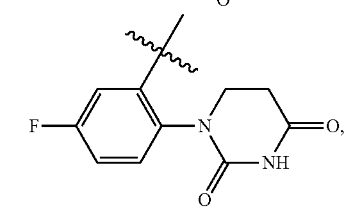

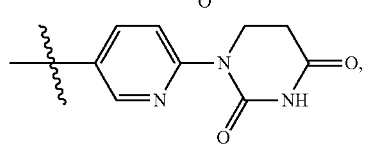

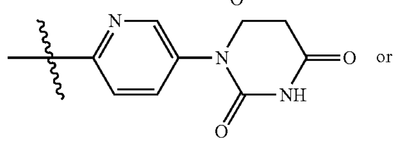

or

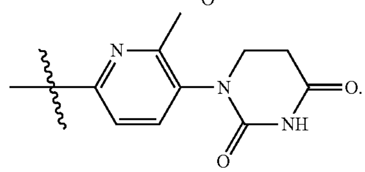

Aspect 13: The compound according to Aspect 1 or 2, wherein $L_1$ is a bond or —O—, and $L_2$ is a bond.

Aspect 14: The compound according to Aspect 1 or 2, wherein $R_a$ and $R_b$ are independently selected from hydrogen or $CH_3$; and n1 is 1 or 2.

Aspect 15: The compound according to Aspect 1 or 2, wherein $X_a$ is selected from CH or N; $X_b$ is N; $X_c$ is CH, and $X_a$ is N.

Aspect 16: The compound according to Aspect 1 or 2, wherein m1, m2, m3, m4 and m5 are each independently selected from 0, 1 or 2, preferably 1.

Aspect 17: The compound according to Aspect 1 or 2, wherein p4 is 0 or 1, $R^8$ is selected from halogen, OH, or —$C_{1-8}$alkyl, preferably $CH_3$.

Aspect 18: The compound according to Aspect 1 or 2, wherein the

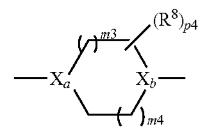

is

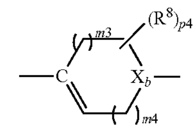

wherein m3 and m4 are each independently 0, 1, 2, 3 or 4, or

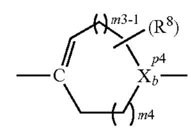

wherein m3 is 1, 2, 3 or 4 and m4 is 0, 1, 2, 3 or 4.

Aspect 19: The compound according to Aspect 1 or 2, wherein p4 is 2, two non-adjacent $R^8$ form a bridge comprising one or two or three $CH_2$.

Aspect 20: The compound according to Aspect 1, wherein

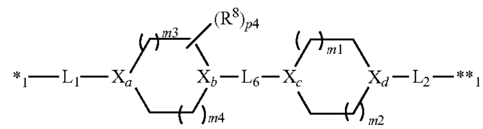

is selected from

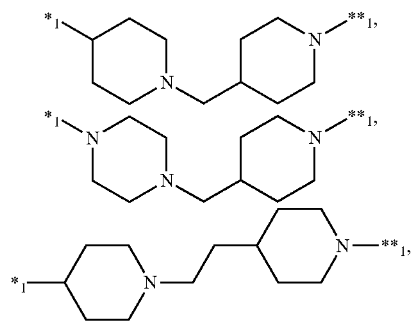

-continued
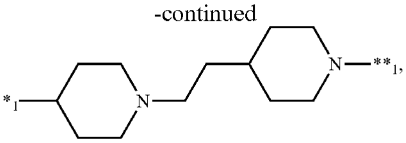
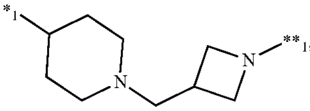
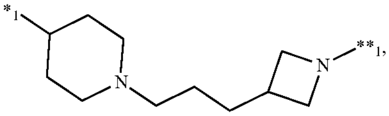
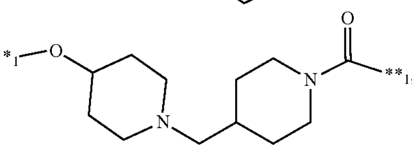
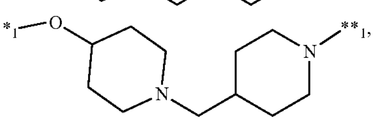
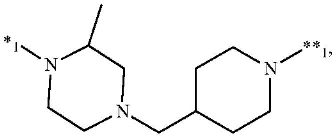
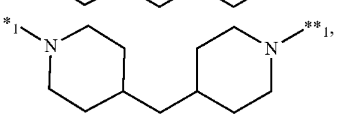
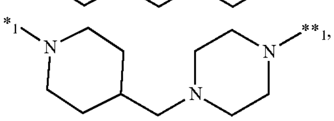
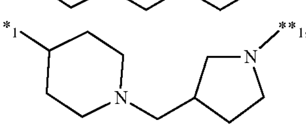
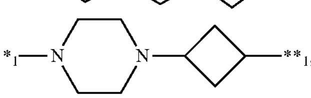
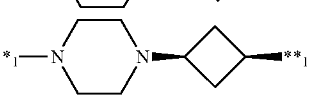
(
or
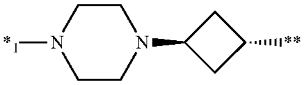
),
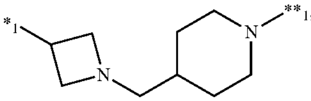
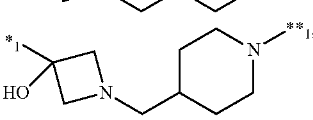
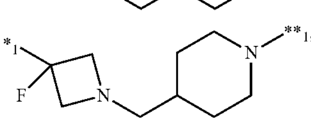
-continued
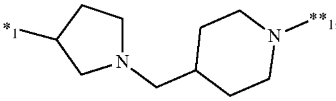
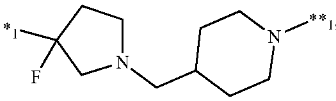
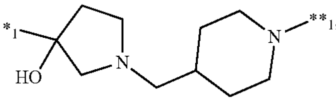
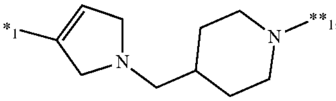
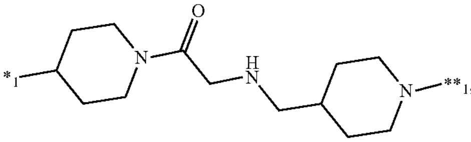
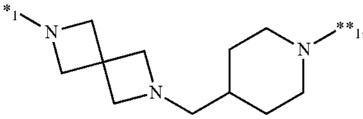
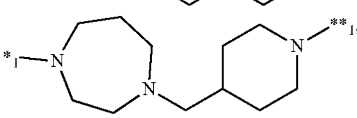
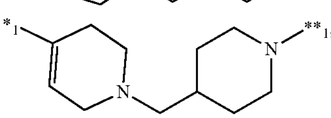
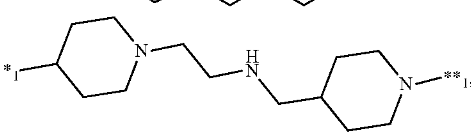
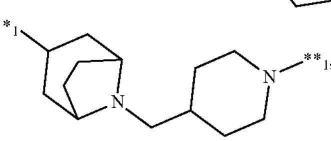
or
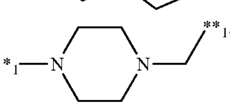
.
Aspect 21: The compound according to Aspect 2, wherein
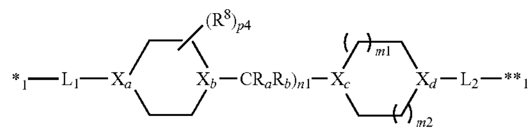
is selected from
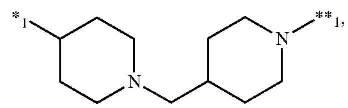

-continued

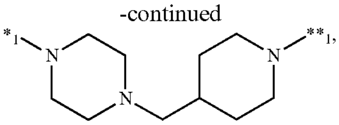

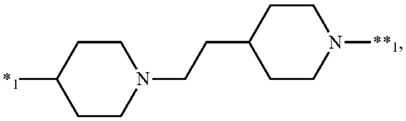

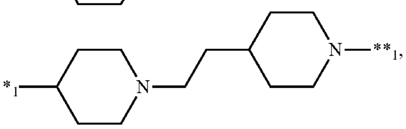

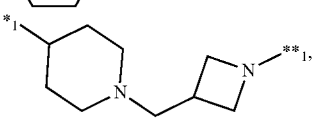

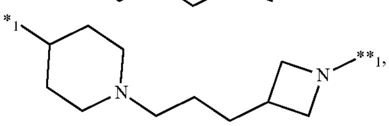

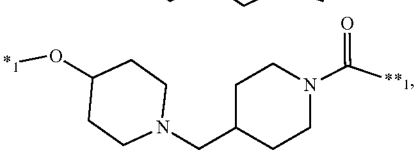

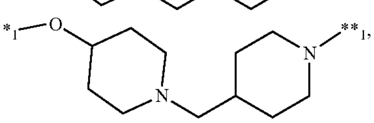

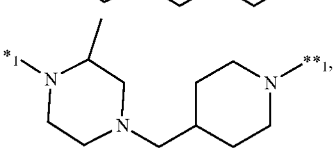

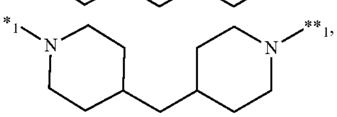

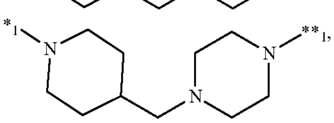

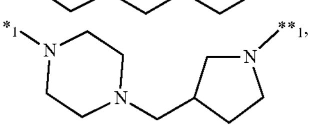

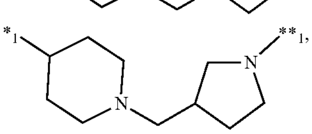

or

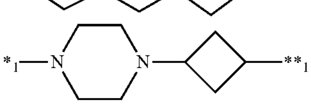

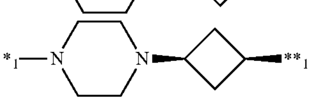

( or

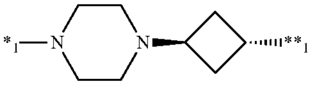

),

Aspect 22: The compound according to any Aspects of 1-21, wherein $Z_1$ is CH or N; and p2=0.

Aspect 23: The compound according to any Aspects of 1-22, wherein $R^1$ is methyl, —$CH_2OH$, —$OCH_3$, —$CH_2OCH_3$ or halogen; p1 is 0 or 1, and $R^2$ is halogen.

Aspect 24: The compound according to any Aspects of 1-23, wherein $R^3$ is hydrogen; $R^4$ and $R^5$ are selected from hydrogen or methyl.

Aspect 25: The compound according to any Aspects of 1-24, wherein $R^9$ is

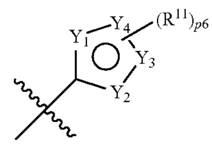

$Y_1$, $Y_2$, $Y_3$ and $Y_4$ are selected from CH, O, S or N; $R^{11}$ is selected from hydrogen, halogen, —$C_{1-8}$alkyl, —$C_{1-8}$alkoxy, —$C_{2-8}$alkenyl, —$C_{2-8}$alkynyl, cycloalkyl, heterocyclyl, aryl, heteroaryl, —CN, —$NO_2$, —$OR_a$, —$SO_2R_a$, —$COR_a$, —$CO_2R_a$, —$CONR_aR_b$, —$C(=NR_a)NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, -halo$C_{1-8}$alkyl, —$C_{1-8}$alkyoxy, cycloalkyl, heterocyclyl, aryl, or heteroaryl; $R_a$, $R_b$, and $R_c$ are each independently hydrogen, —$C_{1-8}$alkyl, —$C_{2-8}$alkenyl, —$C_{2-8}$alkynyl, cycloalkyl, heterocyclyl, aryl, or heteroaryl; and p6 is 0, 1, 2, 3 or 4.

Aspect 26: The compound according to Aspect 25, wherein $Y_1$ is CH, S, N or O; $Y_2$ is CH, O or N; $Y_3$ is O, S or N; and $Y_4$ is S, CH or N.

Aspect 27: The compound according to Aspects 25 or 26, wherein

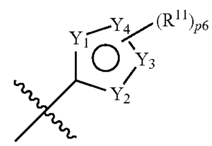

is selected from

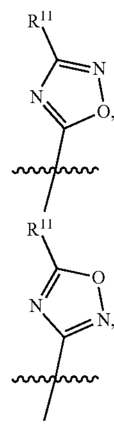

-continued
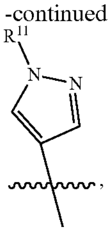
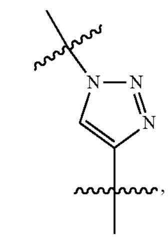
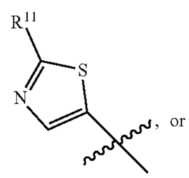
or
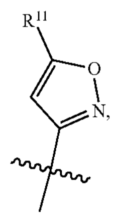
Aspect 28: The compound according to Aspect 27, wherein, $R^{11}$ is selected from
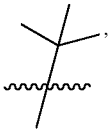
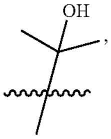
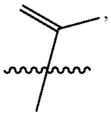
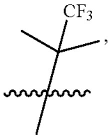
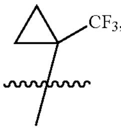
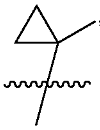
or
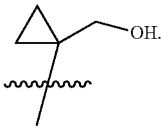
Aspect 29: The compound according to Aspect 1-28, wherein the compound is
(III)
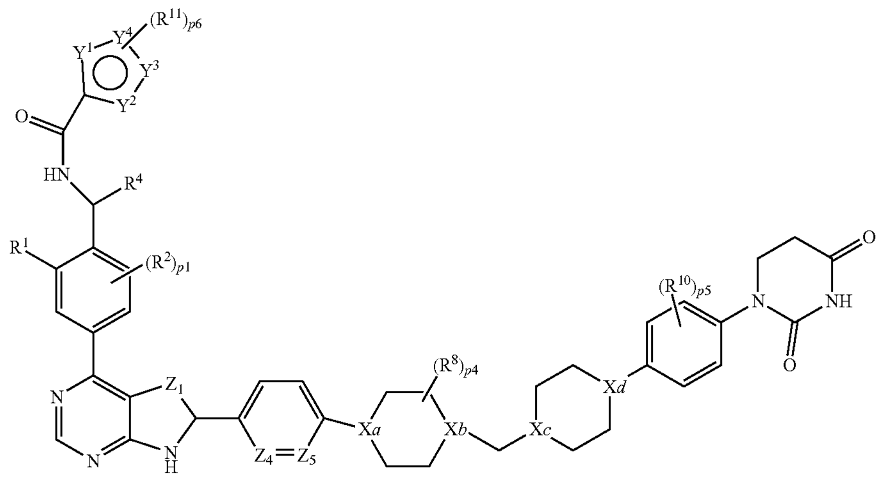
wherein the variables are defined as herein.

In one embodiment, the compound is (IIIA)

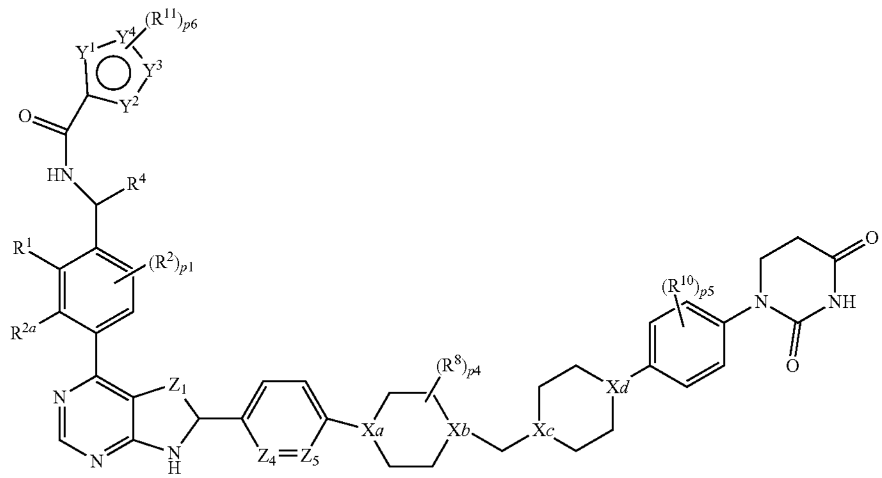

wherein $R^{2a}$ and $R^{2b}$ are each independently hydrogen, halogen, $—C_{1-8}$alkyl, $—C_{1-8}$alkoxy, $—C_{2-8}$alkenyl, $—C_{2-8}$alkynyl, cycloalkyl, heterocyclyl, aryl, heteroaryl, oxo, —CN, $—NO_2$, $—OR_a$, $—SO_2R_a$, $—COR_a$, $—CO_2R_a$, $—CONR_aR_b$, $—C(=NR_a)NR_bR_c$, $—NR_aR_b$, $—NR_aCOR_b$, $—NR_aCONR_bR_c$, $—NR_aCO_2R_b$, $—NR_aSONR_bR_c$, $—NR_aSO_2NR_bR_c$, or $—NR_aSO_2R_b$, each of said $—C_{1-8}$alkyl, $—C_{2-8}$alkenyl, $—C_{2-8}$alkynyl, cycloalkyl, heterocyclyl, aryl, or heteroaryl is optionally substituted with halogen, hydroxy, -halo$C_{1-8}$alkyl, $—C_{1-8}$alkyoxy, cycloalkyl, heterocyclyl, aryl, or heteroaryl.

Aspect 30: The compound according to Aspect 1, wherein the compound is selected from Compounds 1 to 192.

In the second aspect, disclosed herein is a pharmaceutical composition comprising the compound disclosed herein, or a pharmaceutically acceptable salt thereof, and at least one pharmaceutically acceptable carrier or excipient.

In the third aspect, disclosed herein is a method of inhibiting BTK activity, which comprises administering to an individual the compound disclosed herein, or a pharmaceutically acceptable salt thereof, including the compound of formula (I) or the specific compounds exemplified herein.

In the fourth aspect, disclosed herein is a method of treating a disease or disorder in a patient comprising administering to the patient a therapeutically effective amount of the compound disclosed herein, or a pharmaceutically acceptable salt thereof as an BTK kinase inhibitor, wherein the compound disclosed herein includes the compound of formula (I) or the specific compounds exemplified herein. In some embodiments, the disease or disorder is associated with inhibition of BTK. Preferably, the disease or disorder is cancer.

In the fifth aspect, disclosed herein is a method of decreasing BTK activity by inhibition and/or protein degradation, comprising administering to an individual a therapeutically effective amount of the compound disclosed herein, or a pharmaceutically acceptable salt thereof.

DETAILED DESCRIPTION OF THE INVENTION

Definitions

The following terms have the indicated meaning throughout the specification:

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" refers to a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include without limitation to methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "propyl" refers to 1-propyl or n-propyl ("n-Pr"), 2-propyl or isopropyl ("i-Pr").

The term "butyl" refers to 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu").

The term "pentyl" refers to 1-pentyl, 2-pentyl, 3-pentyl, 2-methyl-2-butyl, 3-methyl-2-butyl, 3-methyl-1-butyl, 2-methyl-1-butyl.

The term "hexyl" refers to 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "halogen" refers to fluoro (F), chloro (Cl), bromo (Br) and iodo (I).

The term "haloalkyl" refers to an alkyl group in which one or more hydrogens are replaced by one or more halogen atoms such as fluoro, chloro, bromo, and iodo. Examples of the haloalkyl include without limitation to halo$C_{1-8}$alkyl, halo$C_{1-6}$alkyl or halo $C_{1-4}$alkyl, such as —$CF_3$, —$CH_2C_1$, —$CH_2CF_3$, —$CHCl_2$, —$CF_3$, and the like.

The term "alkenyl" refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include without limitation to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include without limitation to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$cycloalkyl, include without limitation to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to cyclopropyl, cyclobutyl, cyclopentyl, and cyclohexyl. Examples of the bicyclic cycloalkyl groups include those having from 7 to 12 ring atoms arranged as a fused bicyclic ring selected from [4, 4], [4, 5], [5, 5], [5, 6] and [6, 6] ring systems, or as a bridged bicyclic ring selected from bicyclo[2.2.1]heptane, bicyclo[2.2.2]octane, and bicyclo[3.2.2]nonane. Further examples of the bicyclic cycloalkyl groups include those arranged as a bicyclic ring selected from [5, 6] and [6, 6] ring systems.

The term "spiro cycloalkyl" refers to a cyclic structure which contains carbon atoms and is formed by at least two rings sharing one atom. The term "7 to 12 membered spiro cycloalkyl" refers to a cyclic structure which contains 7 to 12 carbon atoms and is formed by at least two rings sharing one atom.

The term "fused cycloalkyl" refers to a bicyclic cycloalkyl group as defined herein which is saturated and is formed by two or more rings sharing two adjacent atoms.

The term "bridged cycloalkyl" refers to a cyclic structure which contains carbon atoms and is formed by two rings sharing two atoms which are not adjacent to each other. The term "7 to 10 membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, cyclohexadienyl, preferably cyclohexenyl.

The term "fused cycloalkenyl" refers to a bicyclic cycloalkyl group as defined herein which contain at least one double bond and is formed by two or more rings sharing two adjacent atoms.

The term "cycloalkynyl" refers to non-aromatic cycloalkyl groups of from 5 to 10 carbon atoms having single or multiple rings and having at least one triple bond.

The term "fused cycloalkynyl" refers to a bicyclic cycloalkyl group as defined herein which contains at least one triple bond and is formed by two or more rings sharing two adjacent atoms.

The term a "benzo fused cycloalkyl" is a bicyclic fused cycloalkyl in which a 4- to 8-membered monocyclic cycloalkyl ring fused to a benzene ring. For example, a benzo fused cycloalkyl is

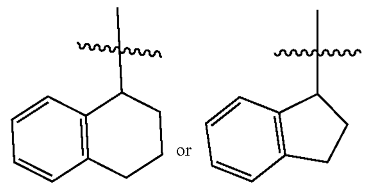

wherein the wavy lines indicate the points of attachment.

The term a "benzo fused cycloalkenyl" is a bicyclic fused cycloalkenyl in which a 4- to 8-membered monocyclic cycloalkenyl ring fused to a benzene ring.

The term a "benzo fused cycloalkynyl" is a bicyclic fused cycloalkynyl in which a 4- to 8-membered monocyclic cycloalkynyl ring fused to a benzene ring.

Examples of fused cycloalkyl, fused cycloalkenyl, or fused cycloalkynyl include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$cycloalkenyl, 2,3-dihydro-1H-indenyl, 1H-indenyl, 1, 2, 3, 4-tetralyl, 1,4-dihydronaphthyl, etc. Preferred embodiments are 8 to 9 membered fused rings, which refer to cyclic structures containing 8 to 9 ring atoms within the above examples.

The term "aryl" used alone or in combination with other terms refers to a group selected from:

a) 5- and 6-membered carbocyclic aromatic rings, e.g., phenyl;
b) bicyclic ring systems such as 7 to 12 membered bicyclic ring systems, wherein at least one ring is carbocyclic and aromatic, e.g., naphthyl and indanyl; and,
c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring include without limitation to phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" refers to a bicyclic aryl ring as defined herein. The typical bicyclic fused aryl is naphthalene.

The term "heteroaryl" refers to a group selected from:

a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;

b) 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" refers to a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

Representative examples of bicyclic fused heteroaryl include without limitation to the following groups: benzisoxazolyl, benzodiazolyl, benzofuranyl, benzofurazanyl, benzofuryl, benzoimidazolyl, benzoisothiazolyl, benzothiadiazolyl, benzothiazolyl, benzothienyl, benzothiophenyl, benzotriazolyl, benzoxadiazolyl, benzoxazolyl, furopyridinyl, furopyrrolyl, imidazopyridinyl, imidazopyridyl, imidazothiazolyl, indazolyl, indolizinyl, indolyl, isobenzofuryl, isoindolyl, isoquinolinyl (or isoquinolyl), naphthyridinyl, phthalazinyl, pteridinyl, purinyl, pyrazinopyridazinyl, pyrazolopyridinyl, pyrazolopyrimidinyl, pyrazolopyridyl, pyrazolotriazinyl, pyridazolopyridyl, pyrrolopyridinyl, quinazolinyl, quinolinyl (or quinolyl), quinoxalinyl, thiazolopyridyl, thienopyrazinyl, thienopyrazolyl, thienopyridyl, thienopyrrolyl, thienothienyl, or triazolopyridyl.

The term a "benzo fused heteroaryl" is a bicyclic fused heteroaryl in which a 5- to 7-membered (preferably, 5- or 6-membered) monocyclic heteroaryl ring as defined herein fused to a benzene ring.

The terms "aromatic heterocyclic ring" and "heteroaryl" are used interchangeably throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1, 2, 3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, oxadiazolyl (such as 1, 2, 3-oxadiazolyl, 1,2,4-oxadiazolyl, or 1,3,4-oxadiazolyl), phthalazinyl, pyrazinyl, pyridazinyl, pyrrolyl, triazolyl (such as 1, 2, 3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), and indazolyl (such as 1H-indazol-5-yl).

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "optionally oxidized sulfur" used herein refer to S, SO or $SO_2$.

The term "monocyclic heterocyclyl" refers to monocyclic groups in which at least one ring member (e.g., 1-3 heteroatoms, 1 or 2 heteroatom(s)) is a heteroatom selected from nitrogen, oxygen or optionally oxidized sulfur. A heterocycle may be saturated or partially saturated.

Exemplary monocyclic 4 to 9-membered heterocyclyl groups include without limitation to pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1- yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term "spiro heterocyclyl" refers to a 5 to 20-membered polycyclic heterocyclyl with rings connected through one common carbon atom (called a spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl could be mono-spiro heterocyclyl, di-spiro heterocyclyl, or poly-spiro heterocyclyl, and preferably refers to mono-spiro heterocyclyl or di-spiro heterocyclyl, and more preferably 4-membered/3-membered, 4-membered/4-membered, 3-membered/5-membered, 4-membered/5-membered, 4-membered/6-membered, 5-membered/5-membered, or 5-membered/6-membered mono-spiro heterocyclyl. Representative examples of spiro heterocyclyls include without limitation to the following groups: 2,3-dihydrospiro[indene-1,2'-pyrrolidine] (e.g., 2,3-dihydrospiro[indene-1,2'-pyrrolidine]-1'-yl), 1,3-dihydrospiro[indene-2,2'-pyrrolidine] (e.g., 1,3-dihydrospiro[indene-2,2'-pyrrolidine]-1'-yl), azaspiro[2.4]heptane (e.g., 5-azaspiro[2.4]heptane-5-yl), 2-oxa-6-azaspiro[3.3]heptane (e.g., 2-oxa-6-azaspiro[3.3]heptan-6-yl), azaspiro[3.4]octane (e.g., 6-azaspiro[3.4]octane-6-yl), 2-oxa-6-azaspiro[3.4]octane (e.g., 2-oxa-6-azaspiro[3.4]octane-6-yl), azaspiro[3.4]octane (e.g., 6-azaspiro[3.4]octan-6-yl), azaspiro[3.4]octane (e.g., 6-azaspiro[3.4]octan-6-yl), 1,7-dioxaspiro[4.5]decane, 2-oxa-7-aza-spiro[4.4]nonane (e.g., 2-oxa-7-aza-spiro[4.4]non-7-yl), 7-oxa-spiro[3.5]nonyl and 5-oxa-spiro[2.4]heptyl.

The term "fused heterocyclyl" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but the fused heterocyclic group does not have a completely conjugated pi-electron system. Preferably, a fused heterocyclyl is 6 to 14-membered, and more preferably 7 to 12-membered, or 7- to 10-membered. According to the number of membered rings, a fused heterocyclyl could be bicyclic, tricyclic, tetracyclic, or polycyclic fused heterocyclyl. The group can be attached to the remainder of the molecule through either ring.

Specifically, the term "bicyclic fused heterocyclyl" refers to a 7 to 12-membered, preferably 7- to 10-membered, more preferably 9- or 10-membered fused heterocyclyl as defined herein comprising two fused rings and comprising 1 to 4 heteroatoms selected from nitrogen, oxygen or optionally oxidized sulfur as ring members. Typically, a bicyclic fused heterocyclyl is 5-membered/5-membered, 5-membered/6-membered, 6-membered/6-membered, or 6-membered/7-membered bicyclic fused heterocyclyl. Representative examples of (bicyclic) fused heterocycles include without limitation to the following groups: octahydrocyclopenta[c]pyrrole, octahydropyrrolo[3,4-c]pyrrolyl, octahydroisoindolyl, isoindolinyl, octahydro-benzo[b][1, 4]dioxin, indolinyl, isoindolinyl, benzopyranyl, dihydrothiazolopyrimidinyl, tetrahydroquinolyl, tetrahydroisoquinolyl (or tetrahydroisoquinolinyl), dihydrobenzofuranyl, dihydrobenzoxazinyl, dihydrobenzoimidazolyl, tetrahydrobenzothienyl, tetrahydrobenzofuranyl, benzodioxolyl, benzodioxonyl, chromanyl, chromenyl, octahydrochromenyl, dihydrobenzodioxynyl, dihydrobenzoxezinyl, dihydrobenzodioxepinyl, dihydrothienodioxynyl, dihydrobenzooxazepinyl, tetrahydrobenzooxazepinyl, dihydrobenzoazepinyl, tetrahydrobenzoazepinyl, isochromanyl, chromanyl, or tetrahydropyrazolopyrimidinyl (e.g., 4,5,6,7-tetrahydropyrazolo[1,5-a]pyrimidin-3-yl).

The term a "benzo fused heterocyclyl" is a bicyclic fused heterocyclyl in which a monocyclic 4 to 9-membered heterocyclyl as defined herein (preferably 5- or 6-membered) fused to a benzene ring.

The term "bridged heterocyclyl" refers to a 5 to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl could be bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include without limitation to the following groups: 2-azabicyclo[2.2.1]heptyl, azabicyclo[3.1.0]hexyl, 2-azabicyclo[2.2.2]octyl and 2-azabicyclo[3.3.2]decyl.

The term "at least one substituent" disclosed herein includes, for example, from 1 to 4, such as from 1 to 3, further as 1 or 2, substituents, provided that the theory of valence is met. For example, "at least one substituent $R^{6d}$" disclosed herein includes from 1 to 4, such as from 1 to 3, further as 1 or 2, substituents selected from the list of $R^{6d}$ as disclosed herein.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refer to stereoisomers of a compound with two or more chiral centers but which are not mirror images of one another. Diastereomeric mixtures can be separated into their individual diastereomers on the basis of their physical or chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers and diastereomers can also be separated by the use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "*Chromatographic resolution of enantiomers: Selective review.*" *J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

"Pharmaceutically acceptable salts" refer to those salts which are, within the scope of sound medical judgment, suitable for use in contact with the tissues of humans and animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" includes salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic agent, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined herein, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical route to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc., a filler such as starch, sucrose, etc., a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, an aromatic, a sweetener, a dye and etc.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Reaction Scheme for Compound Preparation

The subject compounds and pharmaceutically acceptable salts thereof, can be prepared from (a) commercially available starting materials (b) known starting materials which may be prepared as described in literature procedures (c) new intermediates described in the schemes and experimental procedures herein. In making the compounds of the invention, the order of synthetic steps may be varied to increase the yield of the desired product. Some of the compounds in this invention may be generated by the methods as shown in the following reaction schemes and the description thereof.

Scheme A

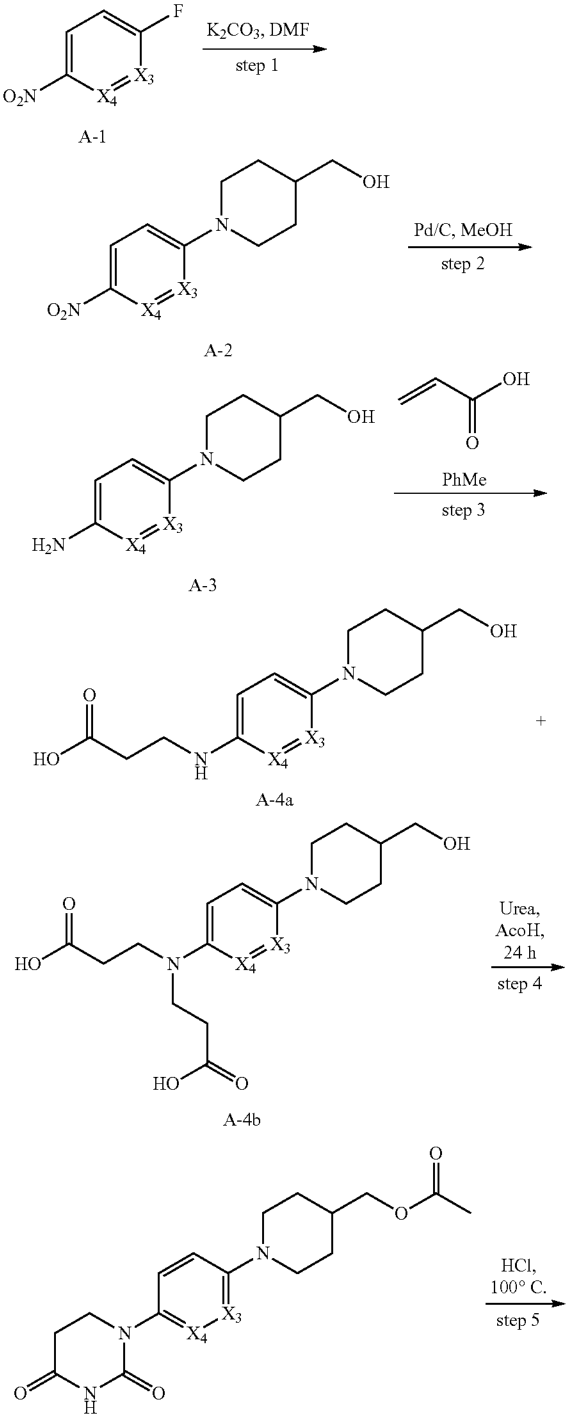

A-1

A-2

A-3

A-4a

+

A-4b

A-5

-continued

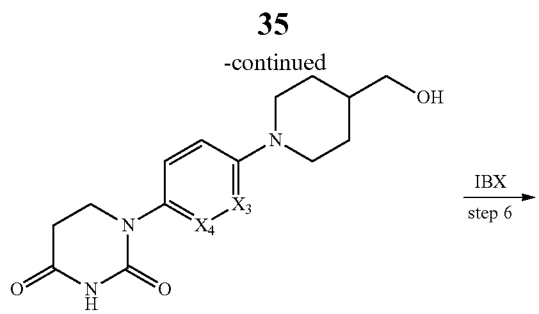

A-6

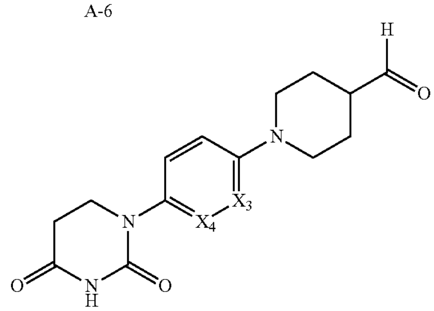

A

Wherein $X_3$ corresponds to $Z_2$ in Formula (I), and $X_4$ corresponds to $Z_3$ in Formula (I). A-2 can be synthesized from A-1 and piperidin-4-ylmethanol in the basic condition, then the nitro group in A-2 was reduced to form A-3, which is mixed with acrylic acid to give a mixture of A-4a and A-4b. Then A-4a and A-4b are heated in the presence of urea to give A-5, which is hydrolyzed in acid condition to give A-6. The final intermediate A is obtained from oxidation of A-6 by using oxidation reagents, such as IBX and so on.

-continued

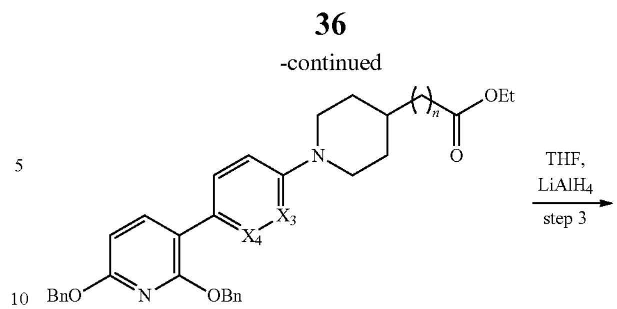

B-5

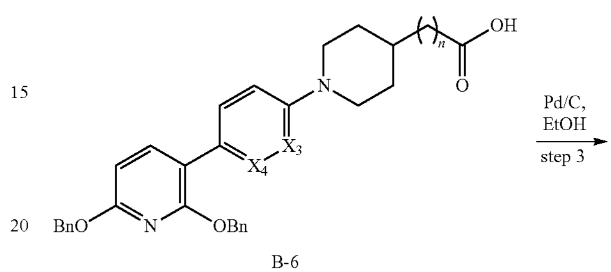

B-6

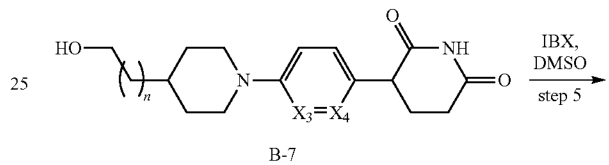

B-7

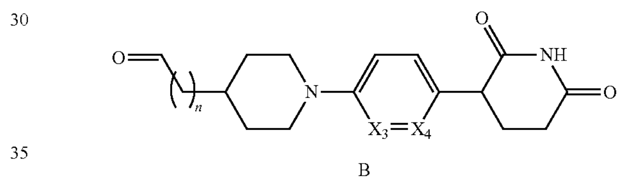

B

Scheme B

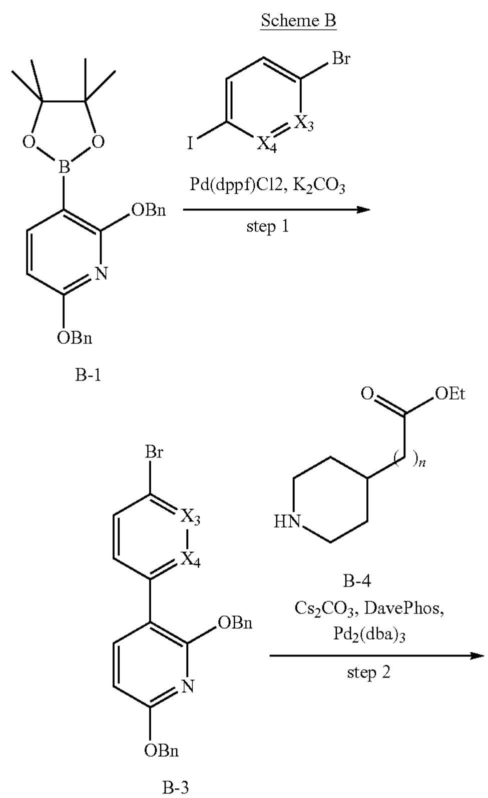

B-1

B-4

B-3

Wherein n corresponds to n1 in Formula (I), $X_3$ corresponds to $Z_2$ in Formula (I), and $X_4$ corresponds to $Z_3$ in Formula (I). B-3 can be synthesized from B-1 and B-2 by using Pd as the catalyst, then B-3 is coupled with B-4 in the presence of a metal catalyst to give B-5. The ester group in the B-5 can be reduced to the alcohol B-6 by using reduction reagent, such as $LiAlH_4$ and so on. B-6 can be further reduced by Pd/C in the presence of hydrogen to give B-7, which is then oxidized to obtain intermediate B by using oxidation reagent, such as IBX and so on.

Scheme C

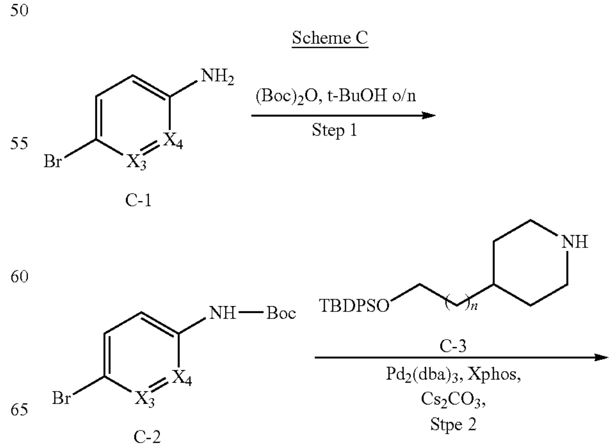

C-1

C-3

C-2

-continued

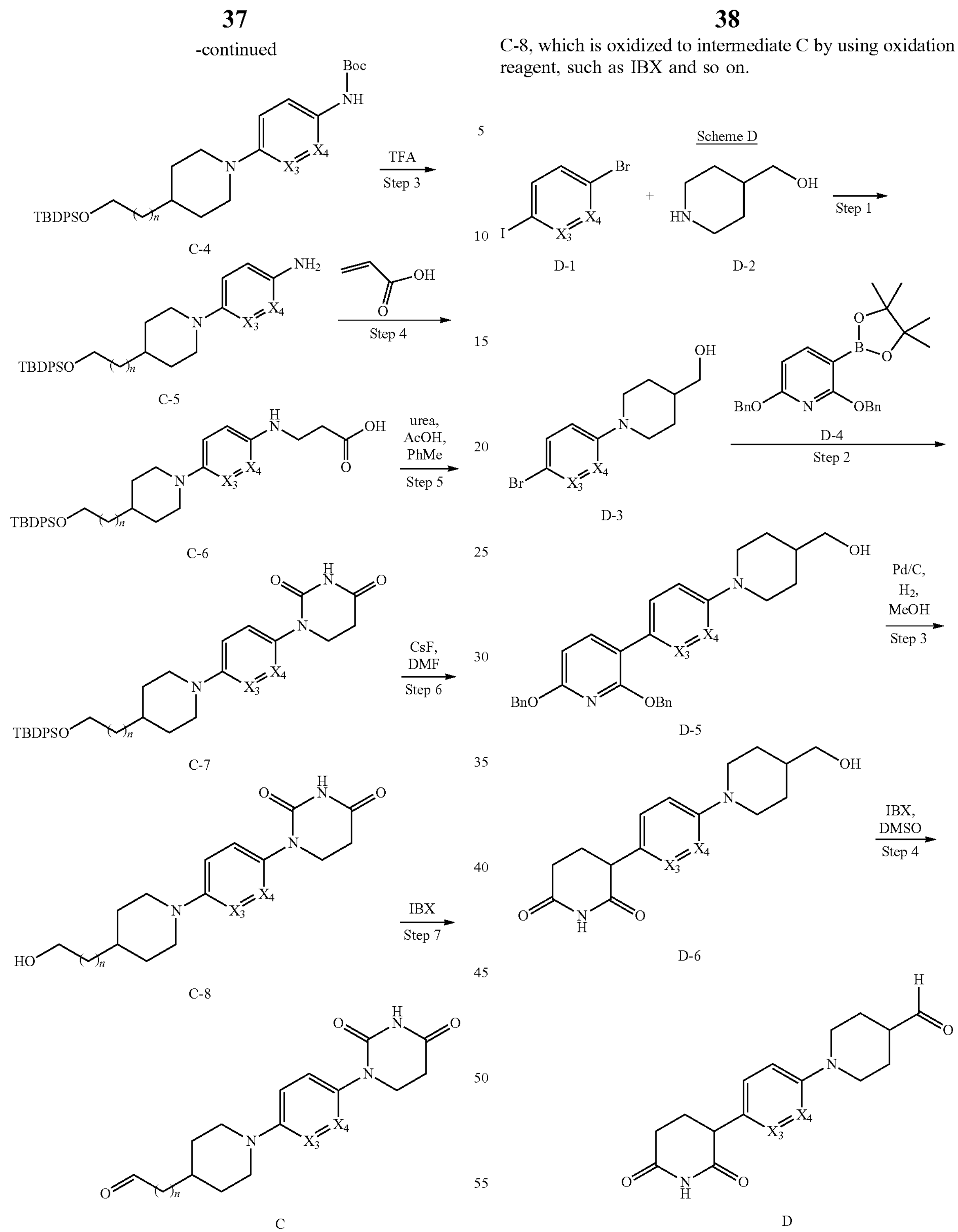

C-4

C-5

C-6

C-7

C-8

C

Scheme D

D-1

D-2

D-3

D-4

D-5

D-6

D

Wherein n corresponds to n1 in Formula (I), $X_3$ corresponds to $Z_2$ in Formula (I), and $X_4$ corresponds to $Z_3$ in Formula (I). C-2 can be synthesized from C-1 and $(BOC)_2O$, then C-2 and C-3 are coupled with Pd as a catalyst to give intermediate C-4. Boc group can be removed in acid condition to form C-5, which is mixed with acrylic acid and heated to give C-6. C-7 can be synthesized from C-6 and urea under the heated condition, and then the TBS group in C-7 can be removed by TBAF or CsF to give intermediate C-8, which is oxidized to intermediate C by using oxidation reagent, such as IBX and so on.

Wherein $X_3$ corresponds to $Z_2$ in Formula (I), and $X_4$ corresponds to $Z_3$ in Formula (I). D-1 and D-2 can be coupled in the metal catalyst (CuI, Pd and so on) to give D-3, which is coupled with D-4 by using Pd as a catalyst to give D-5. The bis(benzyloxy)pyridine group in D-5 can be reduced to piperidine-2,6-dione in D-6 by hydrogen with Pd/C as a catalyst, then the final intermediate D can be oxidized with oxidation reagent, such as IBX and so on.

Scheme E

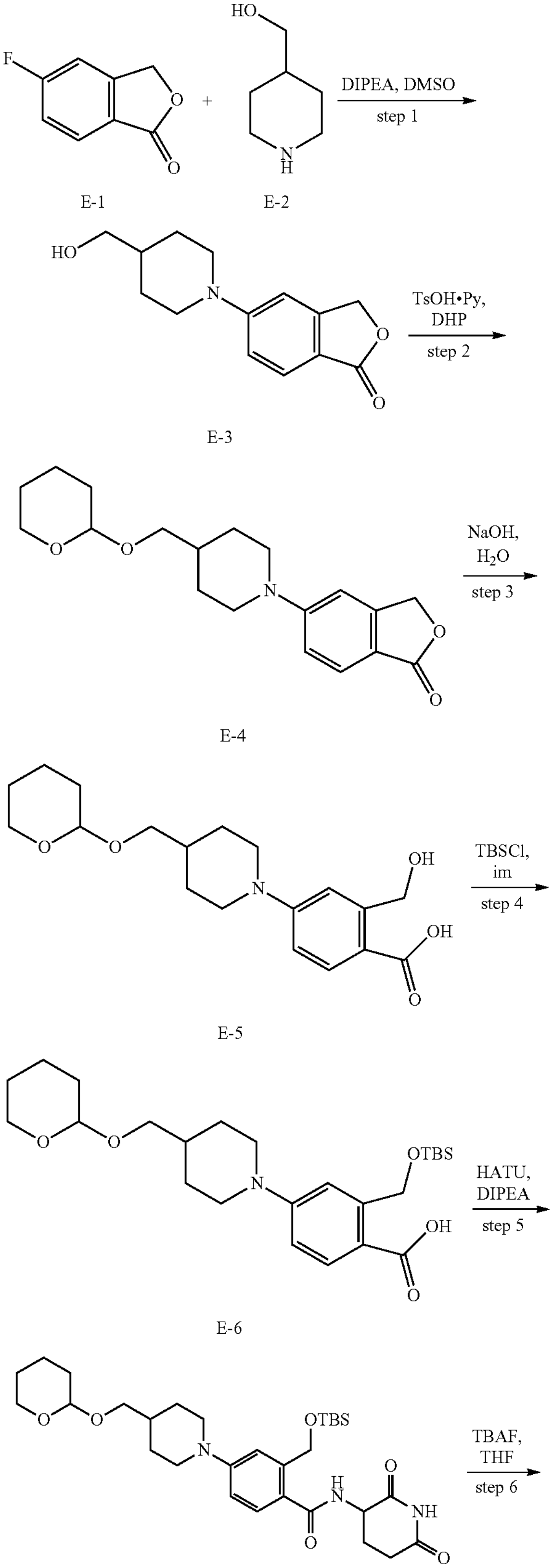

E-1 E-2 E-3 E-4 E-5 E-6 E-7

-continued

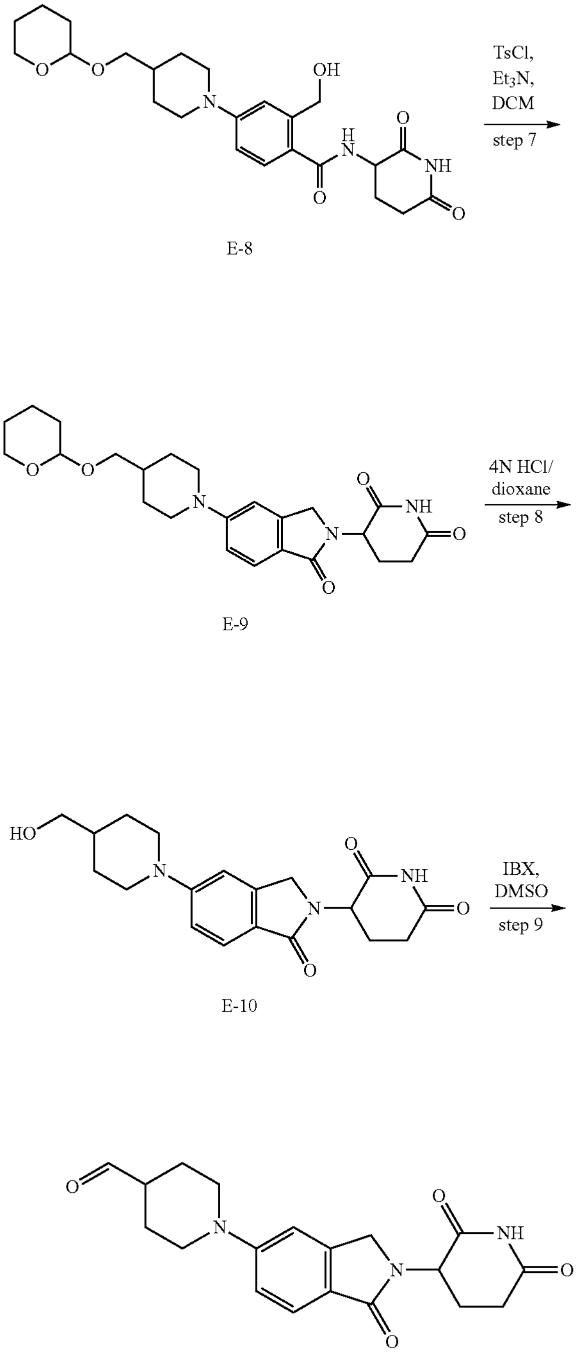

E-8 E-9 E-10 E

E-3 can be synthesized from E-1 and E-2 in basic condition, and the hydroxy group can be protected with THP in acid condition to give E-4. Isobenzofuran-1(3H)-one in E-4 can be hydrolyzed with NaOH/$H_2O$ to give E-5, which is mixed with TBSCl and base to form intermediate E-6. E-6 was coupled with 3-aminopiperidine-2,6-dione with HATU to give E-7, and the TBS group can be removed by TBAF or CsF to form E-8. E-9 can be synthesized from E-8 and TsCl in basic condition, then the THP group can be removed in an acidic condition, which can be oxidized with oxidation reagent to give final intermediate E.

Scheme F
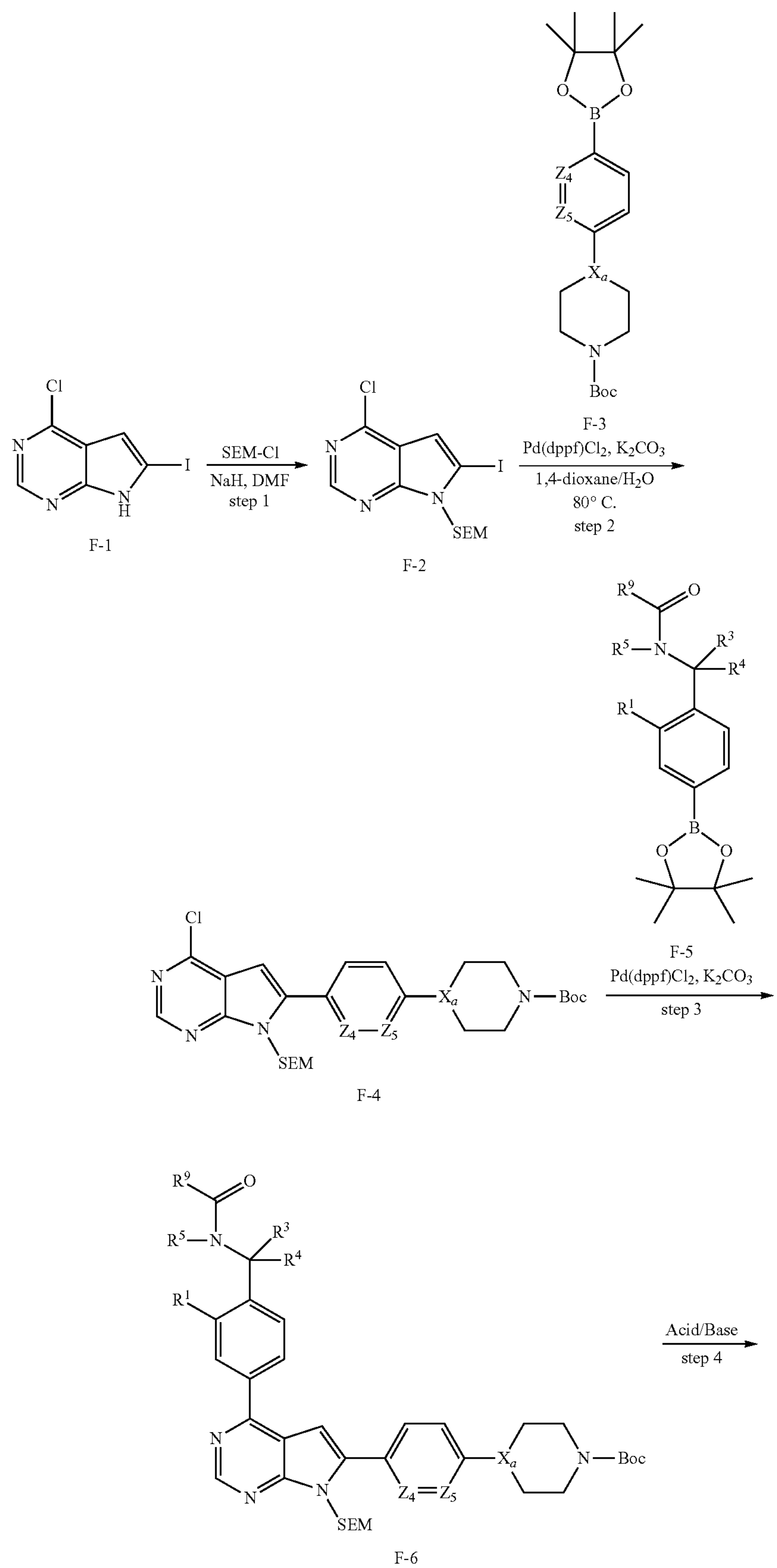

-continued

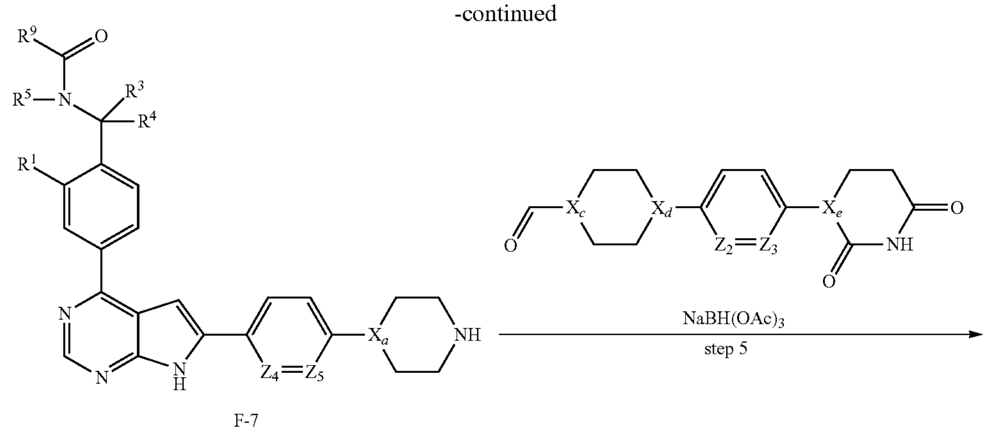

F-7

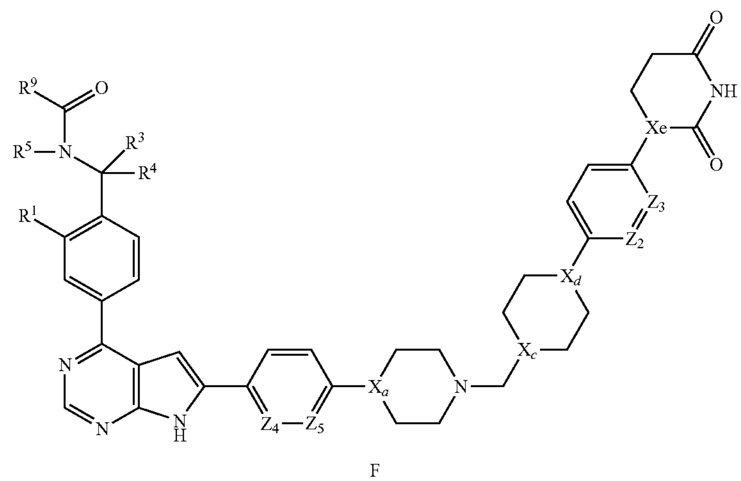

F

Wherein $R^1$, $R^3$, $R^4$, $R^5$, $R^9$, $X_a$, $X_c$, $X_d$, $X_e$, $Z_2$, $Z_3$, $Z_4$ and $Z_5$ are defined as in Formula (I), (II) or (III). F-2 is synthesized from F-1 and SEMCl in basic condition, which is further coupled with F-3 in Pd as a catalyst to form F-4. F-4 is coupled with F-5 in Pd as a catalyst to give F-6, the Boc and SEM group are removed in acid or basic condition to give F-7, which is mixed with an aldehyde in the presence of reduction reagent, such as NaBH(OAc)$_3$ to form F.

Scheme G

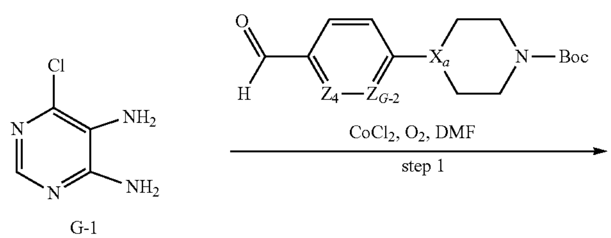

G-1

-continued
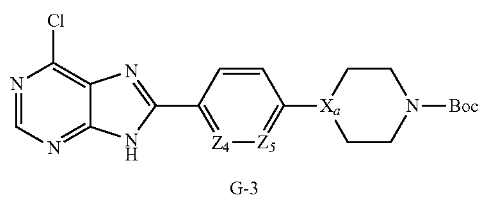
G-3
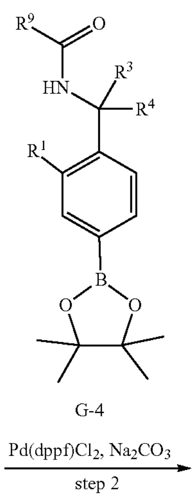
G-4
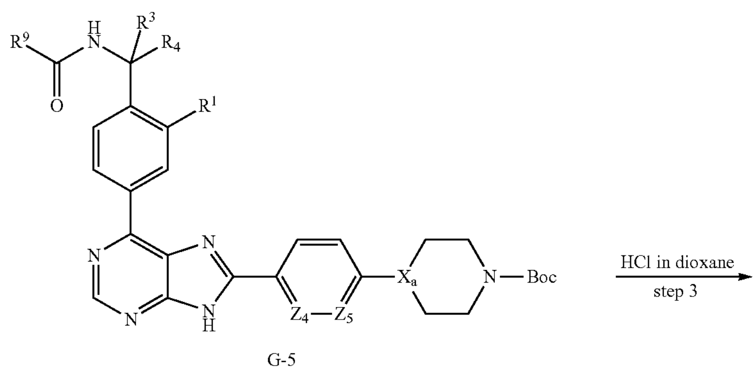
G-5
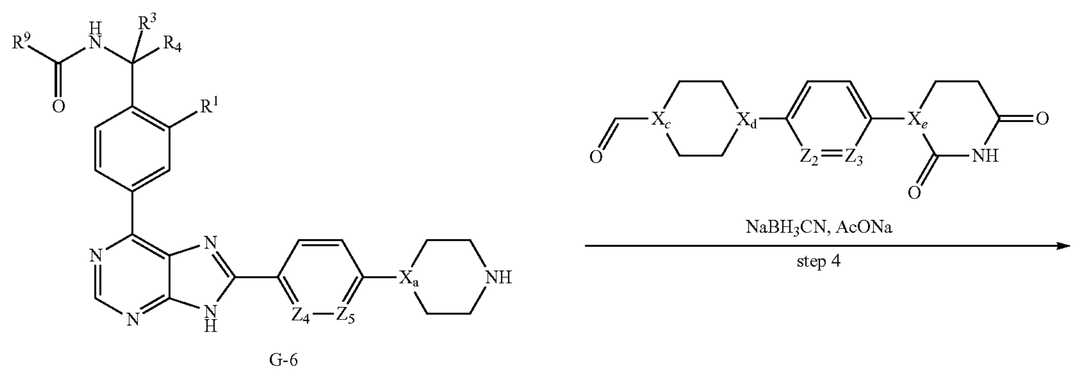
G-6

-continued

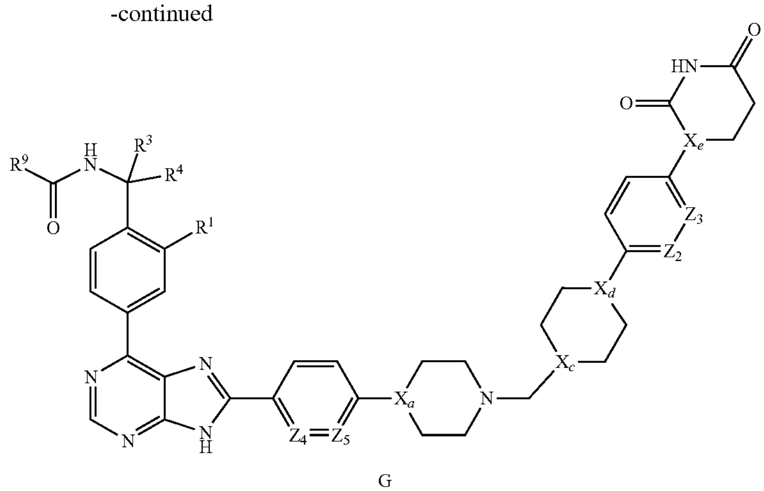

G

Wherein $R^1$, $R^3$, $R^4$, $R^9$, $X_a$, $X_c$, $X_d$, $X_e$, $Z_2$, $Z_3$, $Z_4$ and $Z_5$ are defined as in Formula (I). G-1 and G-2 are mixed with $COCl_2$ as a catalyst to form G-3, which is then coupled with G-4 with Pd as a catalyst to give G-5. Boc group can be removed in acid to form G-6, which is mixed with an aldehyde in the presence of reduction reagent, such as $NaBH(OAc)_3$ to form G.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise. Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on a Agilent instrument operating at 400 MHz. or a Bruker instrument operating at 500 MHz.

$^1$H NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_3CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LCMS-1: LC-MS spectrometer (Agilent 1260 Infinity) Detector: MWD (190-400 nm), Mass detector: 6120 SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A (%) B (%)

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS, LCMS-3: LC-MS spectrometer (Agilent 1260 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A (%) B (%)

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS-2: LC-MS spectrometer (Agilent 1290 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.2 mL/min Time (min) A (%) B (%)

| Time (min) | A(%) | B(%) |
|---|---|---|
| 0.00 | 90 | 10 |
| 1.5 | 5 | 95 |
| 2.0 | 5 | 95 |
| 2.1 | 90 | 10 |
| 3.0 | 90 | 10 |

Preparative HPLC was conducted on a column (150×21.2 mm ID, 5 pm, Gemini NXC 18) at a flow rate of 20 ml/min, injection volume 2 ml, at room temperature and UV Detection at 214 nm and 254 nm.

In the following examples, the abbreviations below are used:

| | |
|---|---|
| AcOH | Acetic acid |
| Aq | Aqueous |
| ACN | Acetonitrile |
| Brine | Saturated aqueous sodium chloride solution |
| Bn | Benzyl |
| BnBr | Benzyl Bromide |
| Boc | Tert-butyloxycarbonyl |
| BrettPhos | Dicyclohexyl[3,6-dimethoxy-2',4',6'-tris(1-methylethyl)[1,1'-biphenyl]-2-yl]phosphine |
| Cbz | benzyloxycarbonyl |
| $CH_2Cl_2$ | Dichloromethane |
| $CoCl_2$ | Cobalt chloride |
| DAST | Diethylaminosulfur trifluoride |
| DavePhos | 2'-(Dicyclohexylphosphino)-N,N-dimethyl-2-biphenylamine |
| DCE | dichloroethane |
| DHP | 3,4-Dihydro-2H-pyran |
| DMF | N,N-Dimethylformamide |
| Dppf | 1,1''-bis(diphenylphosphino)ferrocene |
| DBU | 1,8-diazabicyclo[5.4.0]undec-7-ene |
| DCM | Dichloromethane |
| DIEA or DIPEA | N,N-diisopropylethylamine |
| DIBAL-H | Diisobutylaluminium hydride |
| DMAP | 4-N,N-dimethylaminopyridine |
| DMF | N,N-dimethylformamide |
| DMSO | Dimethyl sulfoxide |
| EA or EtOAc | Ethyl acetate |
| EtOH | Ethanol |
| $Et_2O$ or ether | Diethyl ether |
| FA | Formic acid |
| g | Grams |
| h or hr | Hour |
| HATU | O-(7-Azabenzotriazol-1-yl)-N,N,N',N'-tetramethyluronium hexafluorophosphate |
| HBTU | O-(7-Azabenzotriazol-1-yl)-N,N,N',N'-tetramethyluronium hexafluorophosphate |
| HCl | Hydrochloric acid |
| Hex | Hexane |
| HPLC | High-performance liquid chromatography |
| IBX | 2-Iodoxybenzoic acid |
| IPA | 2-propanol |
| LDA | Lithium diisopropylamide |
| i-PrOH | Isopropyl alcohol |
| mg | Milligrams |
| mL | Milliliters |
| Mmol | Millimole |
| MeCN | Acetonitrile |
| MeOH | Methanol |
| Min | Minutes |
| ms or MS | Mass spectrum |
| MsCl | Methanesulfonyl chloride |
| MTBE | Methyl tert-butyl ether |
| $Na_2SO_4$ | Sodium sulfate |
| o/n | overnight |
| PE | Petroleum ether |
| $Ph_3PO$ | Triphenyl phosphorus oxide |
| PPA | Polyphosphoric acid |
| Rt | Retention time |
| STAB | Sodium triacetoxyborohydride |
| TsOH,Py | Pyridinium toluene-4-sulphonate |
| R.T. or r.t. | Room temperature |
| TBAF | Tetra-butyl ammonium fluoride |
| TBSCl | tert-Butyldimethylsilyl chloride |
| TEA | Triethanolamine |
| TFA | Trifluoroacetic acid |
| $Tf_2O$ | Triflic anhydride |
| THF | Tetrahydrofuran |
| TLC | Thin layer chromatography |
| TMSOK | Potassium trimethylsilanolate |
| Ts | para-T oluenesulfonyl |
| TsCl | 4-Toluenesulfonyl chloride |
| TsOH | 4-Toluenesulfonic acid |
| TBS | tert-Butyldimethylsilyl |
| TBDPS | tert-Butyldiphenylsilyl |
| μL | Microliters |
| Xphos | 2-Dicyclohexylphosphino-2',4',6'-triisopropylbiphenyl |

Example 1: 3-(tert-butyl)-N-(4-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-2-methylbenzyl)-1,2,4-oxadiazole-5-carboxamide
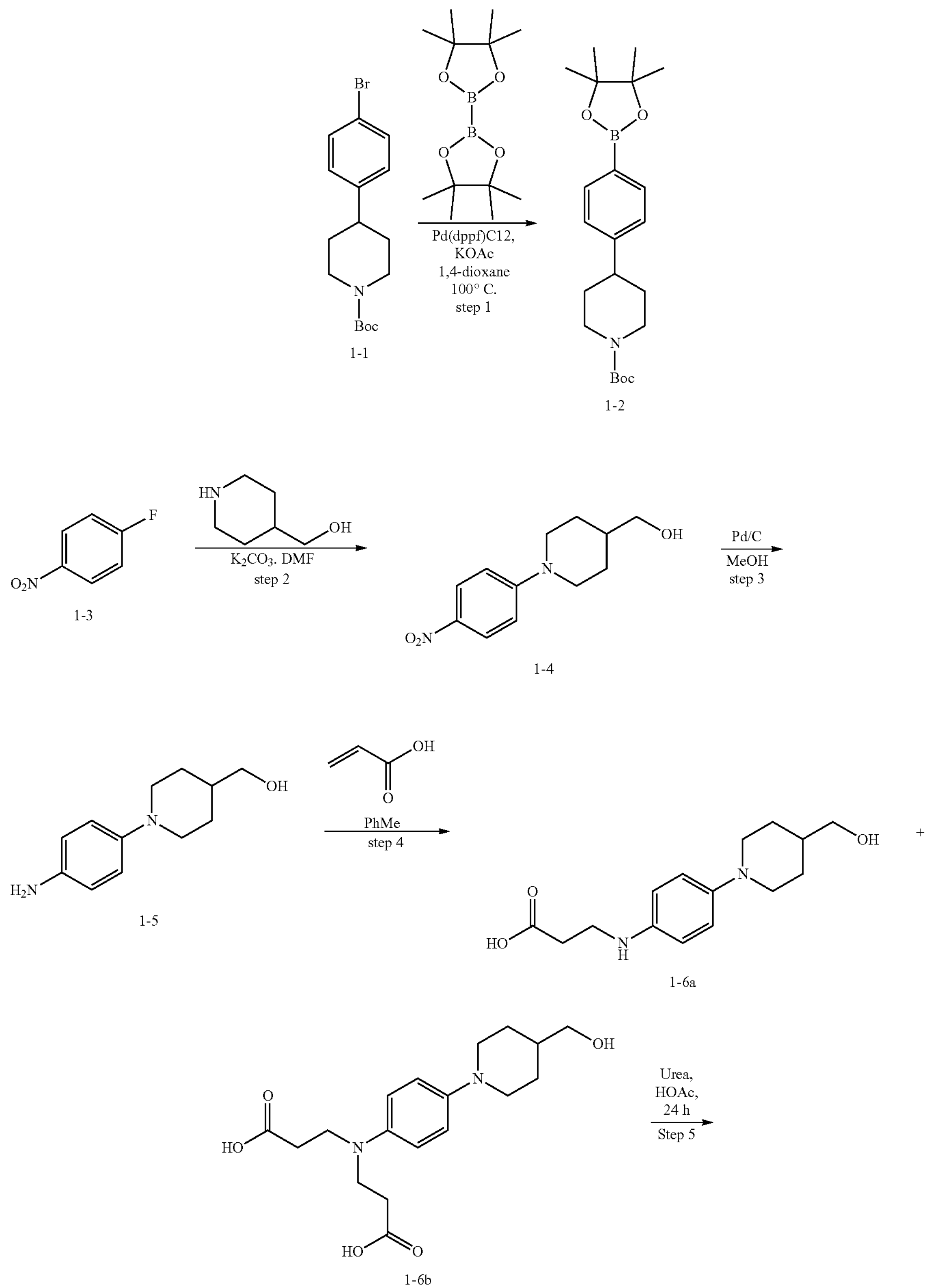
1-1
1-2
1-3
1-4
1-5
1-6a
1-6b -continued
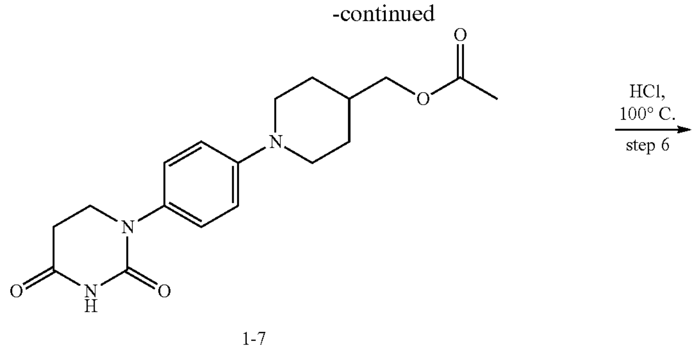
1-7
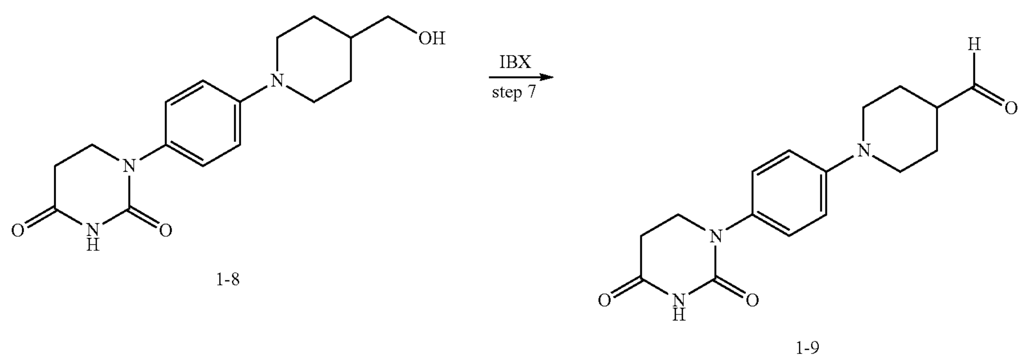
1-8
1-9
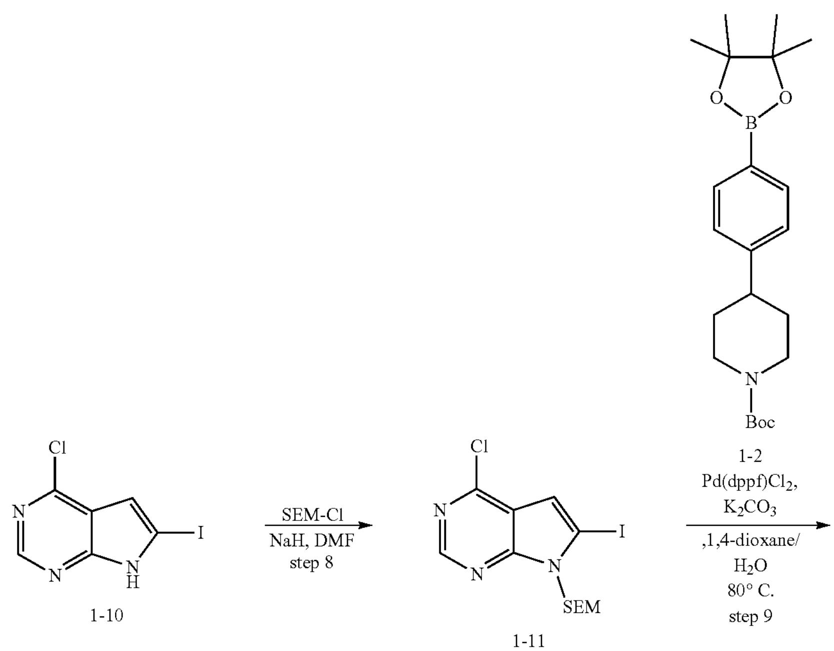
1-10
1-11

-continued
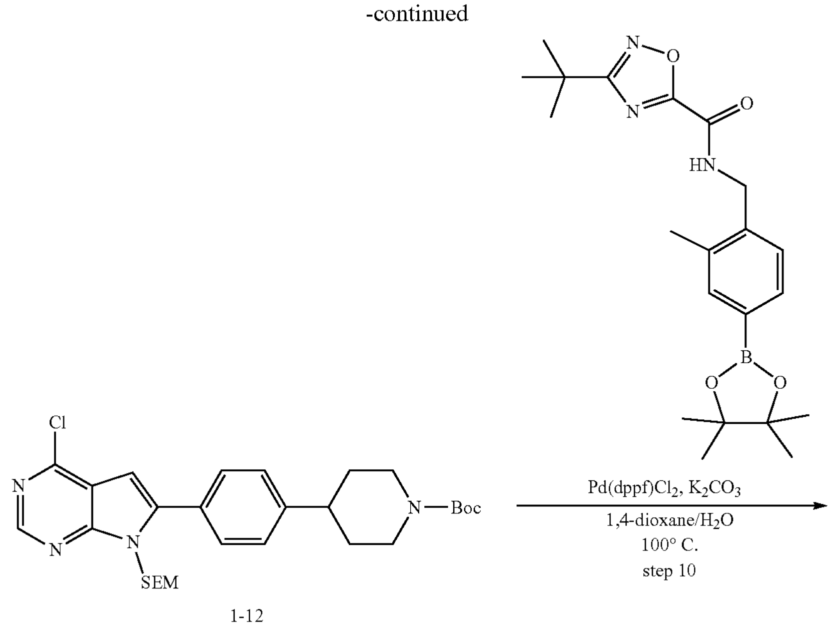
1-12
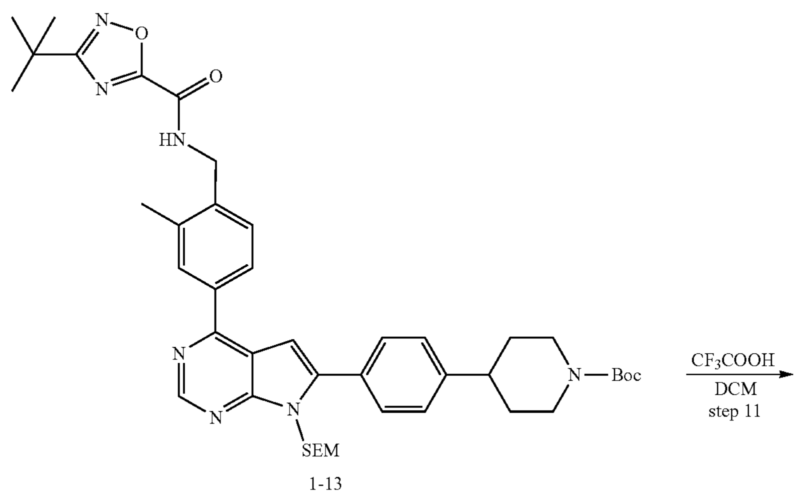
1-13
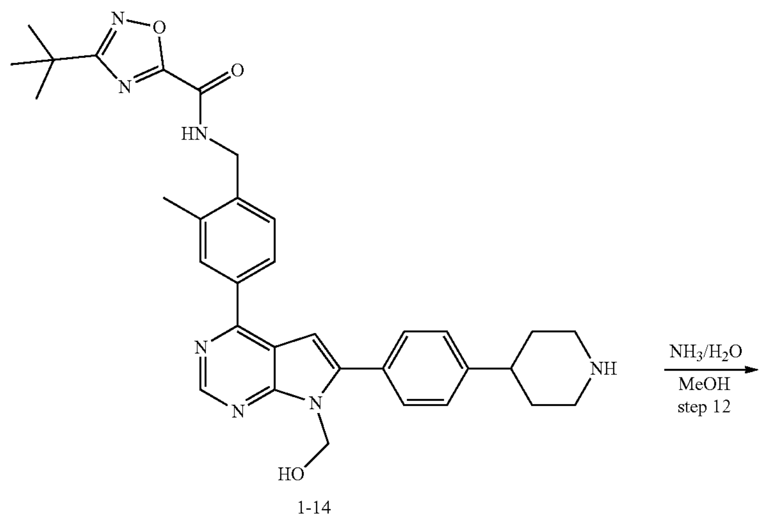
1-14

-continued

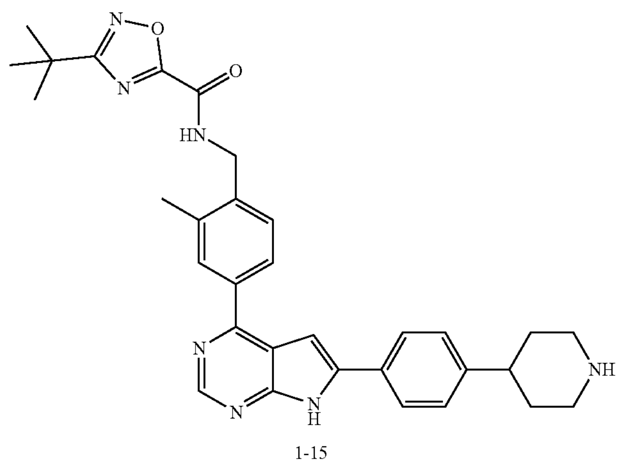

1-15

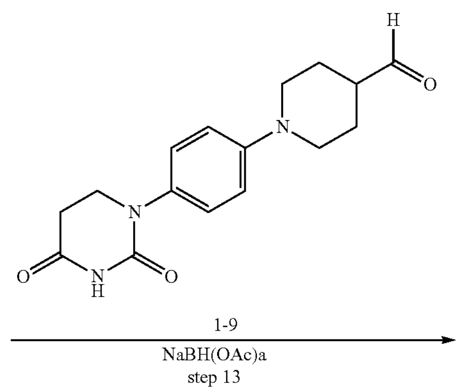

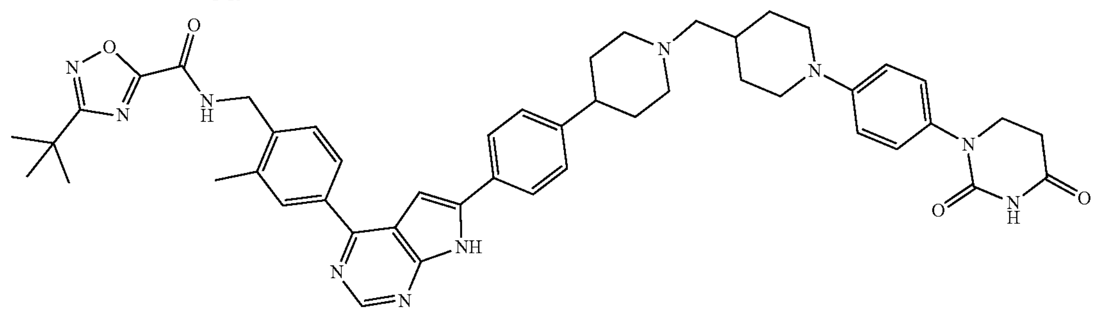

1

Step 1: tert-butyl 4-(4-(4,4,5,5-tetramethyl-1,3,2-dioxaborolan-2-yl)phenyl)piperidine-1-carboxylate

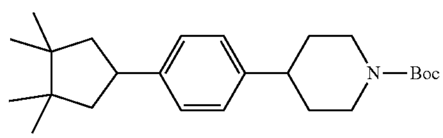 [SMILES: CC(C)(C)OC(=O)N1CCC(c2ccc(C3CC(C)(C)C(C)(C)C3)cc2)CC1]

A mixture of tert-butyl 4-(4-bromophenyl)piperidine-1-carboxylate (10 g, 29.4 mmol), 4,4,4',4',5,5,5',5'-octamethyl-2,2'-bi(1,3,2-dioxaborolane) (9 g, 5.0 mmol), Pd(dppf)$Cl_2$ (2.12 g, 10.6 mmol) and KOAc (4.55 g, 22.75 mmol) in 1,4-dioxane (200 mL) was stirred in a round bottom flask at 100° C. overnight. The mixture was evaporated in vacuum to afford the crude product, which was further purified with silica gel column chromatography (PE:EA=100:0~90:10 gradient elution) to give the title product (11 g, 90%). $[M+H]^+$=388.0.

Step 2: (1-(4-nitrophenyl)piperidin-4-yl)methanol

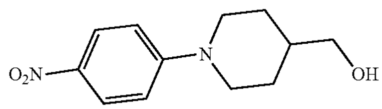

To a solution of 1-fluoro-4-nitrobenzene (100.0 g, 710.0 mmol) and 4-piperidinemethanol (98.0 g, 850 mmol) in DMF (1400.0 mL) was added $K_2CO_3$ (196.0 g) at 25° C. The mixture reaction was stirred at 80° C. for 15 h. Reaction was monitored by HPLC. The reaction was cooled to room temperature, the mixture was poured into ice-water (6000.0 mL) and stirred for 20 mins. The solid was filtered and washed with water (500.0 mL×2), dried to give the product (140.0 g, 83.8%). $^1$H NMR (400 MHz, DMSO) $\delta_H$ 8.03 (d, J=9.4 Hz, 2H), 7.01-6.98 (m, 2H), 4.54 (t, J=5.3 Hz, 1H), 4.07-4.04 (m, 2H), 3.29-3.26 (m, 2H), 3.00-2.93 (m, 2H), 1.76-1.67 (m, 3H), 1.21-1.11 (m, 2H); $[M+H]^+$=237.2.

Step 3: (1-(4-aminophenyl)piperidin-4-yl)methanol

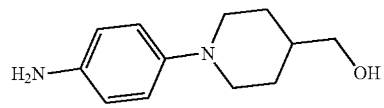 [SMILES: O=[N+]([O-])c1ccc(N2CCC(CO)CC2)cc1]

Under $N_2$, to a solution of (1-(4-nitrophenyl)piperidin-4-yl)methanol (140.0 g, 592.7 mmol) in MeOH (1680.0 mL) was added 10% Pd/C (28.0 g) at 25° C. And then the mixture was exchanged with $H_2$ two times and stirred under $H_2$ atmosphere at 25° C. for 15 h. Reaction was monitored by HPLC. The mixture was filtered through a pad of Celite and washed with MeOH (140.0 mL). The filtrate was concentrated under vacuum to obtain the product (113.0 g, 92.0%). $^1$H NMR (400 MHz, DMSO) $\delta_H$ 6.77-6.61 (m, 2H), 6.54-

6.38 (m, 2H), 4.53 (brs, 2H), 4.45 (t, J=5.3 Hz, 1H), 3.32-3.27 (m, 2H), 2.46-2.41 (m, 2H), 1.76-1.62 (m, 2H), 1.50-1.31 (m, 1H), 1.27-1.08 (m, 2H); $[M+H]^+$=207.2.

Step 4 and 5: (1-(4-(2,4-dioxotetrahydropyrimidin-1(2H)-yl)phenyl)piperidin-4-yl)methyl acetate

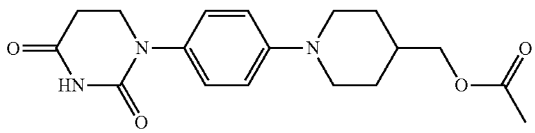 [SMILES: CC(=O)OCC1CCN(c2ccc(N3CCC(=O)NC3=O)cc2)CC1]

To a solution of (1-(4-aminophenyl)piperidin-4-yl)methanol (25.0 g, 121.2 mmol) in PhMe (183.0 mL) was added acrylic acid (13.0 g, 181.8 mmol) at 25° C. The mixture was stirred at 90° C. for 15 h. Reaction was monitored by HPLC. The reaction was cooled to 25° C., then HOAc (183.0 mL) and urea (36.4 g, 606.2 mmol) were added. The mixture was stirred at 110° C. for 24 h. Reaction was monitored by HPLC. The reaction was cooled to 25° C. and concentrated under vacuum. The residue was dissolved with EtOAc (500.0 mL) and then adjusted to pH=7 with sat. $NaHCO_3$. The resulting solution was extracted with 2×200.0 mL of EtOAc and the organic layers were combined. The organic layer was dried over anhydrous sodium sulfate and concentrated under vacuum, and the residual was purified on silica gel (PE:EtOAc=1:1) to give the product (17.5 g, 74%). $^1H$ NMR (400 MHz, DMSO) $\delta_H$ 10.32 (s, 1H), 7.20 (d, J=8.9 Hz, 2H), 6.99 (d, J=9.0 Hz, 2H), 3.98 (d, J=6.2 Hz, 2H), 3.80-3.66 (m, 4H), 2.74-2.72 (m, 4H), 2.09 (s, 3H), 1.80 (d, J=13.8 Hz, 4H), 1.37 (dd, J=12.1, 2.8 Hz, 3H); $[M+H]^+$=346.2.

Step 6: 1-(4-(4-(hydroxymethyl)piperidin-1-yl)phenyl)dihydropyrimidine-2,4(1H,3H)-dione

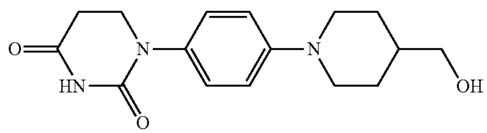

(1-(4-(2,4-Dioxotetrahydropyrimidin-1(2H)-yl)phenyl)piperidin-4-yl)methyl acetate (35.0 g, 121.2 mmol) was added into 2N HCl (260.0 mL) at 25° C. The mixture was stirred at 100° C. for 15 h. Reaction was monitored by HPLC. The reaction was cooled to 10° C. and then adjusted to pH=7 with sat. $NaHCO_3$. The solid was collected by filtrated, washed by water (50.0 mL), and dried to obtain the product (16.9 g, 55%). $^1H$ NMR (400 MHz, DMSO) $\delta_H$ 10.26 (s, 1H), 7.13 (d, J=8.9 Hz, 2H), 6.92 (d, J=9.0 Hz, 2H), 4.49 (s, 1H), 3.78-3.61 (m, 4H), 3.30-3.28 (m, 2H), 2.70-2.66 (m, 4H), 1.75-1.72 (m, 2H), 1.52-1.49 (m, 1H), 1.28-1.18 (m, 2H); $[M+H]^+$=304.2.

Step 7: 1-(4-(2,4-dioxotetrahydropyrimidin-1(2H)-yl)phenyl)piperidine-4-carbaldehyde

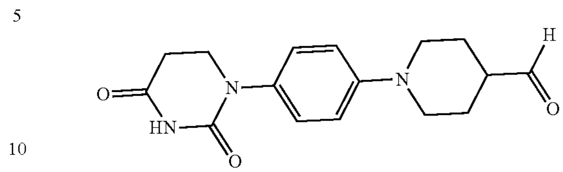

To a solution of 1-(4-(4-(hydroxymethyl)piperidin-1-yl)phenyl)dihydropyrimidine-2,4(1H,3H)-dione (15.0 g, 46.8 mmol) in DMSO (120.0 mL) was added IBX (32.7 g, 117.1 mmol) in portions at 25° C. (caution: exothermal to 40° C.). The mixture was stirred at 25° C. for 15 h. Reaction was monitored by HPLC. Water (300.0 mL) was added to the reaction at 25° C. The solid was filtered and washed with water (100.0 mL) and then EtOAc (100.0 mL). The resulting solution was extracted with 4×200.0 mL of EtOAc. The combined organic layer was dried over $Na_2SO_4$ and concentrated under vacuum to afford a crude residue. The crude product was purified by column chromatography to afford the product (3.1 g, 22.1%). $^1H$ NMR (300 MHz, DMSO) $\delta_H$ 10.26 (s, 1H), 9.63 (s, 1H), 7.15-7.10 (m, 2H), 6.95-6.89 (m, 2H), 3.71-3.51 (m, 4H), 2.86-2.57 (m, 4H), 1.94-1.91 (m, 1H), 1.77-1.73 (m, 1H), 1.64-1.51 (m, 2H), 1.38-1.30 (m, 1H); $[M+H]^+$=302.1.

Step 8: 4-chloro-6-iodo-7-((2-(trimethylsilyl)ethoxy)methyl)-7H-pyrrolo[2,3-d]pyrimidine

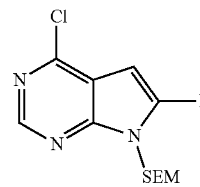

To a mixture of 4-chloro-6-iodo-7H-pyrrolo[2,3-d]pyrimidine (50 g, 179.2 mmol) in DMF (1 L) was added NaH (8.6 g, 215 mmol). The mixture was allowed to stir at 0° C. for 20 min. Then SEM-$C_1$ (62 g, 232 mmol) was added. LCMS showed the reaction was completed. The reaction was concentrated to afford a residue, which was separated by DCM and $H_2O$. The combined organic layer was dried over $Na_2SO_4$ and added MTBE (300 mL) to give the product (55 g, 80%). [M+H]+=410.0.

Step 9: tert-butyl 4-(4-(4-chloro-7-((2-(trimethylsilyl)ethoxy)methyl)-7H-pyrrolo[2,3-d]pyrimidin-6-yl)phenyl)piperidine-1-carboxylate

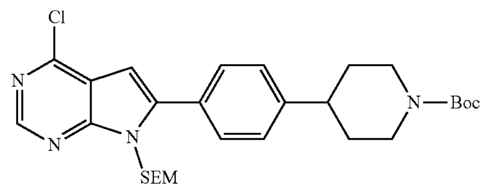 [SMILES: CC(C)(C)OC(=O)N1CCC(c2ccc(-c3cc4c(Cl)ncnc4n3COCC[Si](C)(C)C)cc2)CC1]

A mixture of 4-chloro-6-iodo-7-((2-(trimethylsilyl)ethoxy)methyl)-7H-pyrrolo[2,3-d]pyrimidine (6.42 g, 11.8 mmol), tert-butyl 4-(4-(4,4,5,5-tetramethyl-1,3,2-dioxaborolan-2-yl)phenyl)piperidine-1-carboxylate (5.18 g, 4.5 mmol), Pd(dppf)$Cl_2$ (0.862 g, 0.75 mmol) and $K_2CO_3$ (3.25 g, 23.6 mmol) in 1,4-dioxane (20 mL) and $H_2O$ (4 mL) was stirred in a round bottom flask at 80° C. overnight. The mixture was evaporated in vacuum to afford the crude product, which was further purified with silica gel column chromatography (PE:EA=100:0~3:1 gradient elution) to give the product (5 g, 70%). $[M+H]^+$=543.4.

Step 10: tert-butyl 4-(4-(4-(4-((3-(tert-butyl)-1,2,4-oxadiazole-5-carboxamido)methyl)-3-methylphenyl)-7-((2-(trimethylsilyl)ethoxy)methyl)-7H-pyrrolo[2,3-d]pyrimidin-6-yl)phenyl)piperidin-1-carboxylate

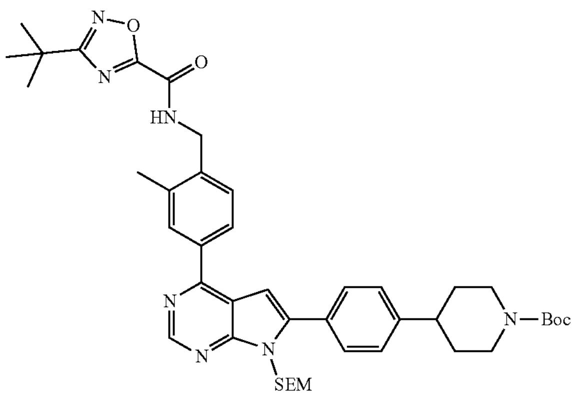 [SMILES: Cc1cc(-c2ncnc3c2cc(-c2ccc(C4CCN(C(=O)OC(C)(C)C)CC4)cc2)n3COCC[Si](C)(C)C)ccc1CNC(=O)c1nc(C(C)(C)C)no1]

A mixture of tert-butyl 4-(4-(4-chloro-7-((2-(trimethylsilyl)ethoxy)methyl)-7H-pyrrolo[2,3-d]pyrimidin-6-yl)phenyl)piperidine-1-carboxylate (6.42 g, 11.8 mmol), 3-(tert-butyl)-N-(2-methyl-4-(4,4,5,5-tetramethyl-1,3,2-dioxaborolan-2-yl)benzyl)-1,2,4-oxadiazole-5-carboxamide (5.18 g, 4.5 mmol), Pd(dppf)$Cl_2$ (0.862 g, 0.75 mmol) and $K_2CO_3$ (3.25 g, 23.6 mmol) in 1,4-dioxane (100 mL) and $H_2O$ (20 mL) was stirred in a round bottom flask at 100° C. overnight. The mixture was evaporated in vacuum to afford the crude product, which was further purified with silica gel column chromatography (PE:EtOAc=100:0~3:1 gradient elution) to give the product (5 g, 70%). $[M+H]^+$=780.4.

Step 11: 3-(tert-butyl)-N-(4-(7-(hydroxymethyl)-6-(4-(piperidin-4-yl)phenyl)-7H-pyrrolo[2,3-d]pyrimidin-4-yl)-2-methylbenzyl)-1,2,4-oxadiazole-5-carboxamide

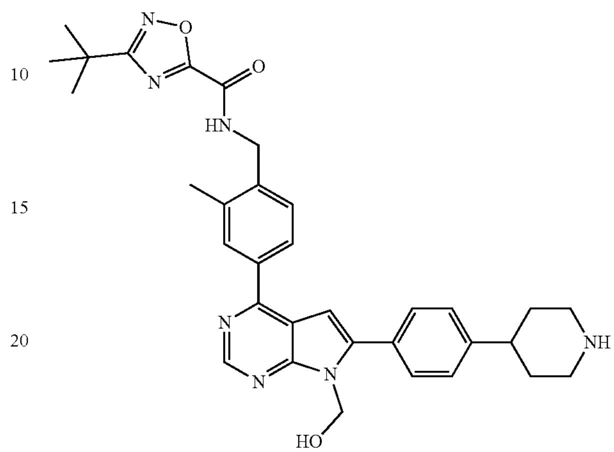

A mixture of tert-butyl 4-(4-(4-(4-((3-(tert-butyl)-1,2,4-oxadiazole-5-carboxamido)methyl)-3-methylphenyl)-7-((2-(trimethylsilyl)ethoxy)methyl)-7H-pyrrolo[2,3-d]pyrimidin-6-yl)phenyl)piperidine-1-carboxylate (7 g, 8.9 mmol) and trifluoroacetic acid (20 mL) in dichloromethane (20 mL) was stirred in a round bottom flask at room temperature overnight. The mixture was evaporated in vacuum to afford the crude product (5 g, 81%), which was used for next step without further purification. $[M+H]^+$=580.4.

Step 12: 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide

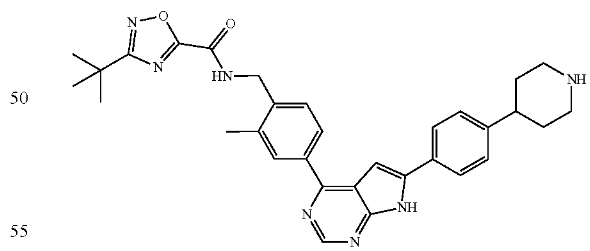

To a stirred solution of 3-(tert-butyl)-N-(4-(7-(hydroxymethyl)-6-(4-(piperidin-4-yl)phenyl)-7H-pyrrolo[2,3-d]pyrimidin-4-yl)-2-methylbenzyl)-1,2,4-oxadiazole-5-carboxamide (5.0 g, 8.6 mmol) in MeOH (20 mL) was added $NH_3/H_2O$ (25%-30%, 10 mL). The mixture was allowed to stir at 0° C. for 30 min. LCMS showed the reaction was completed. The mixture was evaporated in vacuum to afford the crude product, which was further purified with silica gel column chromatography (DCM:MeOH=10:1~2:1 gradient elution) to give the product (3 g, 60%). $[M+H]^+$=550.4.

Step 13: 3-(tert-butyl)-N-(4-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-2-methylbenzyl)-1,2,4-oxadiazole-5-carboxamide

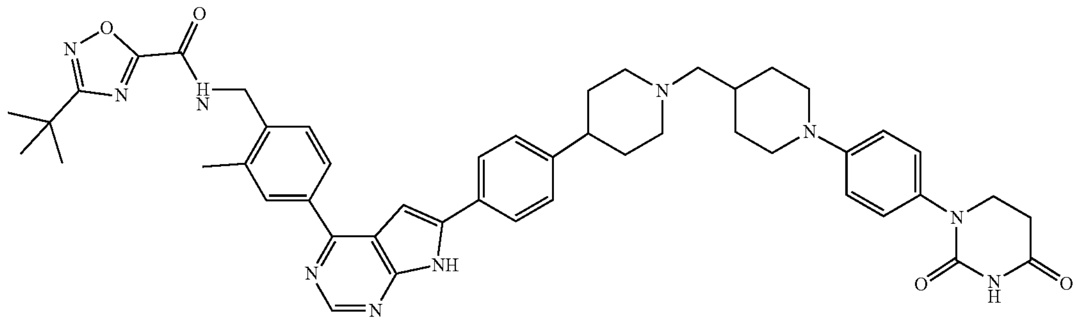 [SMILES: Cc1cc(-c2ncnc3[nH]c(-c4ccc(C5CCN(CC6CCN(c7ccc(N8CCC(=O)NC8=O)cc7)CC6)CC5)cc4)cc23)ccc1CNC(=O)c1nc(C(C)(C)C)no1]

A mixture of 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (3 g, 5.45 mmol) and 1-(4-(2,4-dioxotetrahydropyrimidin-1(2H)-yl)phenyl)piperidine-4-carbaldehyde (1.64 g, 5.45 mmol) in 1,2-dichloromethane (150 mL) and MeOH (30 mL) was stirred in a round bottom flask at room temperature for 1 hour. The mixture was added $NaBH(OAc)_3$ (2.3 g, 10.84 mmol) and stirred in a round bottom flask at room temperature overnight. Then the mixture was evaporated in vacuum to afford the crude product, which was purified with silica gel column chromatography (DCM:MeOH=100:0~80:20 gradient elution) to give the product (3.2 g, 82%). $^1$H NMR (400 MHz, DMSO) $\delta_H$ 12.76 (s, 1H), 10.35 (s, 1H), 9.99 (s, 1H), 8.88 (s, 1H), 8.15 (s, 2H), 8.06 (d, J=6.8 Hz, 2H), 7.55 (s, 1H), 7.45 (s, 3H), 7.21 (d, J=7.2 Hz, 2H), 7.01 (d, J=7.8 Hz, 2H), 4.64 (s, 2H), 3.77 (d, J=5.6 Hz, 4H), 3.41 (s, 2H), 3.04 (s, 2H), 2.76-2.74 (m, 4H), 2.53-2.42 (m, 3H), 2.28 (s, 3H), 2.08 (s, 2H), 1.93-1.70 (m, 8H), 1.45 (s, 9H), 1.35-1.20 (m, 3H); $[M+H]^+$=835.5.

Example 2: 3-(tert-butyl)-N-(4-(6-(4-(1-((1-(2-(2,6-dioxopiperidin-3-yl)-6-fluoro-1,3-dioxoisoindolin-5-yl)piperidin-4-yl)methyl)piperidin-4-yl)phenyl)-7H-pyrrolo[2,3-d]pyrimidin-4-yl)-2-methylbenzyl)-1,2,4-oxadiazole-5-carboxamide

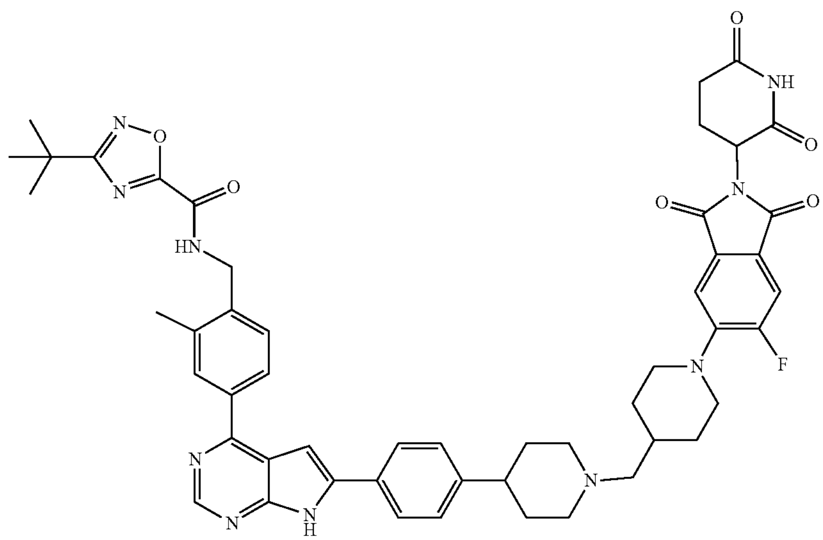 [SMILES: Cc1cc(-c2ncnc3[nH]c(-c4ccc(C5CCN(CC6CCN(c7cc8c(cc7F)C(=O)N(C7CCC(=O)NC7=O)C8=O)CC6)CC5)cc4)cc23)ccc1CNC(=O)c1nc(C(C)(C)C)no1]

The titled compound was synthesized in the procedures similar to Example 1. $^1$H NMR (400 MHz, DMSO) $\delta_H$ 12.68 (s, 1H), 11.13 (s, 1H), 9.93 (s, 1H), 8.80 (s, 1H), 8.07 (s, 2H), 7.98 (d, J=7.7 Hz, 2H), 7.72 (d, J=11.4 Hz, 1H), 7.46 (s, 2H), 7.38 (d, J=8.3 Hz, 3H), 5.11 (d, J=7.3 Hz, 1H), 4.56 (d, J=5.5 Hz, 2H), 3.62 (d, J=12.2 Hz, 2H), 2.98-2.90 (m, 6H), 2.57 (t, J=15.0 Hz, 2H), 2.22 (s, 2H), 2.02 (s, 4H), 1.88-1.65 (m, 8H), 1.38 (s, 9H), 1.34-1.17 (m, 3H); $[M+H]^+$=921.8.

Example 3: 3-(tert-butyl)-N-(4-(6-(4-(1-(2-(1-(4-(2,4-dioxotetrahydropyrimidin-1(2H)-yl)phenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide

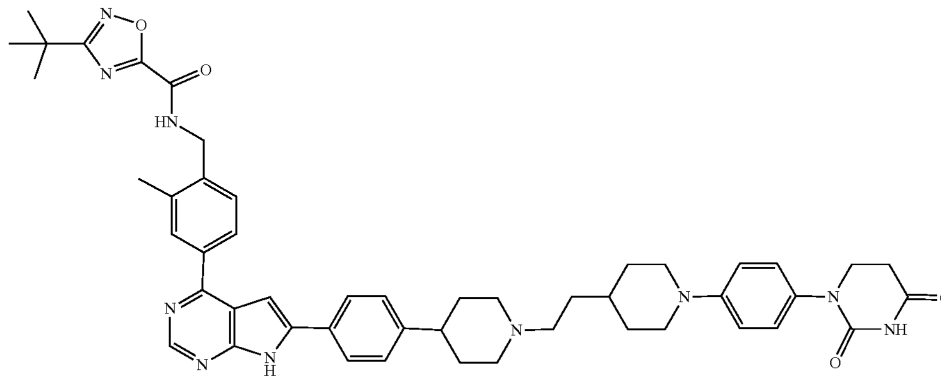 [SMILES: Cc1cc(-c2ncnc3[nH]c(-c4ccc(C5CCN(CCC6CCN(c7ccc(N8CCC(=O)NC8=O)cc7)CC6)CC5)cc4)cc23)ccc1CNC(=O)c1nc(C(C)(C)C)no1]

The titled compound was synthesized in the procedures similar to Example 1. $^1$H NMR (400 MHz, DMSO) $\delta_H$ 12.72 (s, 1H), 10.28 (s, 1H), 9.93 (s, 1H), 8.82 (s, 1H), 8.07 (s, 2H), 8.02 (d, J=7.9 Hz, 2H), 7.48 (d, J=8.2 Hz, 1H), 7.39 (s, 3H), 7.14 (d, J=8.5 Hz, 2H), 6.94 (d, J=8.5 Hz, 2H), 4.56 (d, J=5.4 Hz, 2H), 3.78-3.63 (m, 4H), 3.38 (s, 3H), 2.95 (s, 2H), 2.80 (s, 2H), 2.73-2.65 (m, 4H), 2.49-2.48 (s, 3H), 1.95 (s, 4H), 1.78 (d, J=11.3 Hz, 2H), 1.63 (s, 2H), 1.51 (d, J=17.4 Hz, 1H), 1.38 (s, 9H), 1.30-1.28 (m, 2H); $[M+H]^+$=849.9.

Example 4: 3-(tert-butyl)-N-(4-(6-(4-(1-(2-(1-(4-(2,6-dioxopiperidin-3-yl)phenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide Step 1: 2,6-bis(benzyloxy)-3-(4-bromophenyl)pyridine

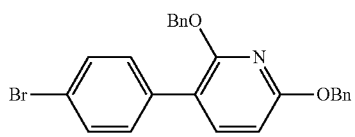 [SMILES: Brc1ccc(-c2ccc(OCc3ccccc3)nc2OCc2ccccc2)cc1]

To a stirred mixture of 2,6-bis(benzyloxy)-3-(4,4,5,5-tetramethyl-1,3,2-dioxaborolan-2-yl)pyridine (25 g, 59.908 mmol) and 4-bromoiodobenzene (20.3 g, 71.897 mmol) in dioxane (250 mL) and $H_2O$ (50 mL) were added $K_2CO_3$ (16.6 g, 119.822 mmol) and Pd(dppf)$Cl_2$ (4.4 g, 5.986 mmol) at room temperature under nitrogen atmosphere. The resulting mixture was stirred for 16 h at 80° C. under nitrogen atmosphere. The reaction mixture was allowed to cool down to room temperature. The resulting mixture was extracted with EtOAc (3×500 mL). The combined organic layers were washed with brine (500 mL), dried over anhydrous $Na_2SO_4$. After filtration, the filtrate was concentrated under reduced pressure. The residue was purified by silica gel column chromatography, eluted with PE/EtOAc (10:1) to afford the product (23 g, 86%). $[M+H]^+$=446.2.

Step 2: ethyl 2-(1-[4-[2,6-bis(benzyloxy)pyridin-3-yl]phenyl]piperidin-4-yl)acetate

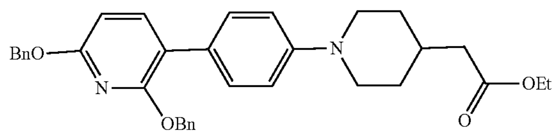 [SMILES: CCOC(=O)CC1CCN(c2ccc(-c3ccc(OCc4ccccc4)nc3OCc3ccccc3)cc2)CC1]

To a stirred solution of 2,6-bis(benzyloxy)-3-(4-bromophenyl)pyridine (15 g, 33.606 mmol) and ethyl 2-(piperidin-4-yl)acetate (8.6 g, 50.410 mmol) in 2-methyl-THF (150 mL) and $H_2O$ (15 mL) were added $Cs_2CO_3$ (32.9 g, 100.819 mmol), DavePhos (2.7 g, 6.721 mmol) and $Pd_2(dba)_3$ (3.1 g, 3.361 mmol) at room temperature under nitrogen atmosphere. The resulting mixture was stirred for 16 h at 100° C. under nitrogen atmosphere. The mixture was allowed to cool down to room temperature. The resulting mixture was concentrated under reduced pressure. The residue was diluted with EtOAc (500 mL), washed with water (3×200 mL) and brine (200 mL). The organic layer was dried over anhydrous $Na_2SO_4$. After filtration, the filtrate was concentrated under reduced pressure. The residue was purified by silica gel column chromatography, eluted with PE/EtOAc (1:1) to afford the product (14 g, 78%). $[M+H]^+$=537.3.

Step 3: 2-(1-[4-[2,6-bis(benzyloxy)pyridin-3-yl]phenyl]piperidin-4-yl)ethanol

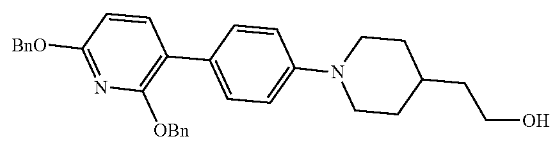 [SMILES: OCCC1CCN(c2ccc(-c3ccc(OCc4ccccc4)nc3OCc3ccccc3)cc2)CC1]

To a stirred solution of ethyl 2-(1-[4-[2,6-bis(benzyloxy)pyridin-3-yl]phenyl]piperidin-4-yl)acetate (13 g, 24.223 mmol) in THF (130 mL) was added $LiAlH_4$ (1 g, 26.646 mmol) in portions at 0° C. The resulting mixture was stirred for 2 h at room temperature. The reaction was quenched by the addition of water/ice (50 mL) at 0° C. The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EtOAc (1:2) to afford the product (11 g, 92%). $[M+H]^+$= 495.3.

Step 4: 3-[4-[4-(2-hydroxyethyl)piperidin-1-yl]phenyl]piperidine-2,6-dione

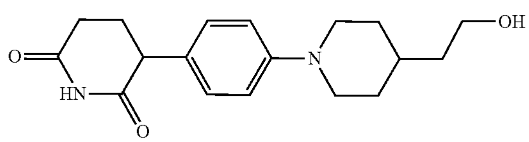 [SMILES: O=C1CCC(c2ccc(N3CCC(CCO)CC3)cc2)C(=O)N1]

To a stirred solution of 2-(1-[4-[2,6-bis(benzyloxy)pyridin-3-yl]phenyl]piperidin-4-yl)ethanol (10.5 g, 21.228 mmol) in EtOH (100 mL), EtOAc (100 mL) and DCM (20.00 mL) was added Pd/C (wet, 10%) (5 g, 46.984 mmol) under nitrogen atmosphere. The resulting mixture was stirred for 16 h at room temperature under hydrogen atmosphere. The resulting mixture was filtered, the filter cake was washed with DCM/$CH_3OH$ (10:1, 200 mL). The filtrate was concentrated under reduced pressure. The residue was purified by silica gel column chromatography, eluted with PE/EtOAc (1:10) to afford the product (5.1 g, 76%). $[M+H]^+$= 317.1.

Step 5: 2-(1-(4-(2,6-dioxopiperidin-3-yl)phenyl)piperidin-4-yl)acetaldehyde

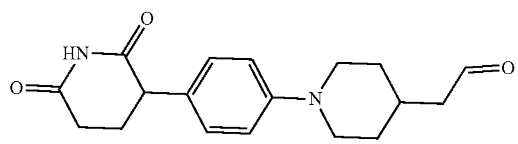 [SMILES: O=CCC1CCN(c2ccc(C3CCC(=O)NC3=O)cc2)CC1]

A mixture of 3-[4-[4-(2-hydroxyethyl)piperidin-1-yl]phenyl]piperidine-2,6-dione (100 mg, 0.32 mmol) and IBX (132 mg, 0.47 mmol) in DMSO (10 mL) was stirred in a round bottom flask at room temperature overnight. The reaction was quenched with water and the mixture was extracted with EtOAc, washed triple with saturated aqueous NaCl and twice with saturated aqueous $NaHCO_3$. The organic layer was dried over anhydrous $Na_2SO_4$ and evaporated in vacuum to afford the product (70 mg, 70%). $[M+H]^+$=315.2.

Step 6: 3-(tert-butyl)-N-(4-(6-(4-(1-(2-(1-(4-(2,6-dioxopiperidin-3-yl)phenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide

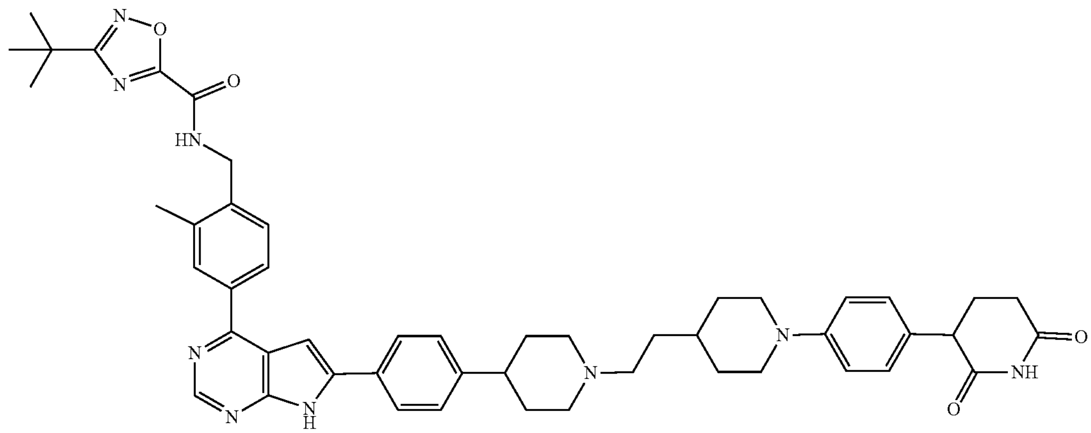 [SMILES: Cc1cc(-c2ncnc3[nH]c(-c4ccc(C5CCN(CCC6CCN(c7ccc(C8CCC(=O)NC8=O)cc7)CC6)CC5)cc4)cc23)ccc1CNC(=O)c1nc(C(C)(C)C)no1]

A mixture of 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (20 mg, 0.036 mmol) and 2-(1-(4-(2,6-dioxopiperidin-3-yl)phenyl)piperidin-4-yl)acetaldehyde (14 mg, 0.044 mmol) in MeOH (5 mL) was stirred in a round bottom flask for 30 min at room temperature. Then $NaBH(AcO)_3$ (15 mg, 0.073 mmol) was added and stirred for 2 h at room temperature. The reaction was quenched with water and the mixture was washed once with saturated aqueous $NaHCO_3$, then extracted with DCM. The organic layer was dried over anhydrous $Na_2SO_4$, and evaporated in vacuum to afford the crude product, which was further purified with pre-HPLC to give the product (13.3 mg, 43%). $^1$H NMR (400 MHz, DMSO) $\delta_H$ 12.80 (s, 1H), 10.81 (s, 1H), 9.96-9.92 (m, 1H), 9.16 (brs, 1H), 8.84 (s, 1H), 8.03-8.01 (m, 4H), 7.52-7.36 (m, 4H), 7.25-7.23 (m, 1H), 7.10-7.06 (m, 2H), 6.99-6.95 (m, 1H), 4.57 (d, J=5.5 Hz, 2H), 3.79-3.61 (m, 5H), 3.38-3.36 (m, 1H), 3.20-3.18 (m, 2H), 3.10-3.04 (m, 3H), 2.91-2.89 (m, 2H), 2.73-2.71 (m, 1H), 2.66-2.64 (m, 1H), 2.54 (s, 3H), 2.23-2.02 (m, 3H), 2.03-1.99 (m, 1H), 1.88 (d, J=11.7 Hz, 2H), 1.81 (d, J=11.0 Hz, 2H), 1.69-1.67 (m, 2H), 1.52-1.50 (m, 1H), 1.38 (s, 9H), 1.24-1.22 (m, 1H); $[M+H]^+$=848.8.

Example 5: 3-(tert-butyl)-N-(4-(6-(4-(1-((1-(4-(2,4-dioxotetrahydropyrimidin-1(2H)-yl)phenyl)azetidin-3-yl)methyl)piperidin-4-yl)phenyl)-7H-pyrrolo[2,3-d]pyrimidin-4-yl)-2-methylbenzyl)-1,2,4-oxadiazole-5-carboxamide Step 1: (1-(4-nitrophenyl)azetidin-3-yl)methanol

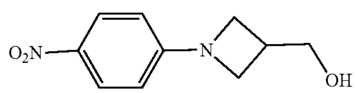 [SMILES: O=[N+]([O-])c1ccc(N2CC(CO)C2)cc1]

The mixture of azetidin-3-ylmethanol HCl salt (8.00 g, 65.041 mmol), 4-fluoronitrobenzene (9.17 g, 65.041 mmol) and $Na_2CO_3$ (17.95 g, 130.082 mmol) in DMSO (40 mL) was stirred for 2 h at 60° C. The reaction was quenched with water. The resulting mixture was extracted with EtOAc. The combined organic layers were washed with brine, dried over anhydrous $Na_2SO_4$. After filtration, the filtrate was concentrated under reduced pressure to give the crude product. The crude product was used in next step without further purification.

Step 2: (1-(4-aminophenyl)azetidin-3-yl)methanol

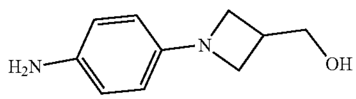

To a stirred mixture of (1-(4-nitrophenyl)azetidin-3-yl) methanol (15.20 g, 73.001 mmol) in MeOH (50.00 mL) was added Pd/C (10% wt, 8.00 g). The resulting mixture was stirred for 1 h at room temperature under hydrogen atmosphere. The resulting mixture was filtered and the filter cake was washed with MeOH. The filtrate was concentrated under reduced pressure to give the product (12.5 g, 96.07%). The crude product was used in the next step directly without further purification.

Step 3: 4-(3-(((tert-butyldiphenylsilyl)oxy)methyl) azetidin-1-yl)aniline

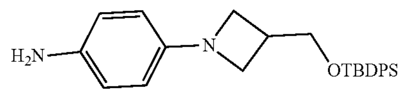

To a stirred mixture of (1-(4-aminophenyl)azetidin-3-yl) methanol (12.50 g, 70.132 mmol), and imidazole (9.55 g, 140.264 mmol) in DMF (50.00 mL) was added TBDPSCl (45.59 mL, 165.875 mmol). The resulting mixture was stirred for 1 h at room temperature. The reaction was quenched with water. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (1:1) to afford the product (21.5 g, 73.58%).

Step 4: methyl 3-((4-(3-(((tert-butyldiphenylsilyl) oxy)methyl)azetidin-1-yl)phenyl)amino)propanoate

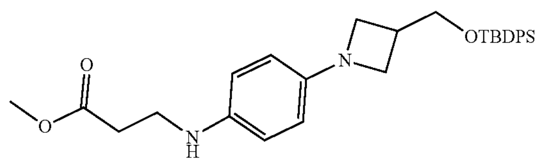

The mixture of 4-(3-(((tert-butyldiphenylsilyl)oxy) methyl)azetidin-1-yl)aniline (10.00 g, 24.002 mmol) and methyl acrylate (2.07 g, 24.002 mmol) in $H_2O$ (50.00 mL) and THF (50.00 mL) was stirred overnight at 50° C. The reaction was quenched with water. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (1:1) to afford the product (2.1 g, 17.40%).

Step 5: methyl 3-(1-(4-(3-(((tert-butyldiphenylsilyl) oxy)methyl)azetidin-1-yl)phenyl)ureido)propanoate

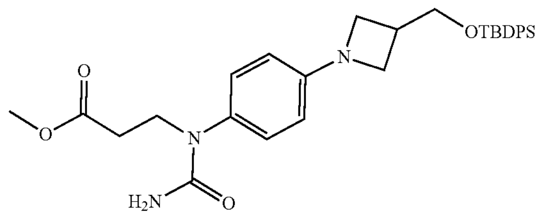

The mixture of methyl 3-((4-(3-(((tert-butyldiphenylsilyl) oxy)methyl)azetidin-1-yl)phenyl)amino)propanoate (2.10 g, 4.177 mmol) and sodium cyanate (543.09 mg, 8.354 mmol) in AcOH (20.00 mL) and $H_2O$ (4.00 mL) was stirred for 1 h at room temperature. The resulting mixture was concentrated under vacuum. The crude product (2.7 g) was used in the next step directly without further purification.

Step 6: 1-(4-(3-(((tert-butyldiphenylsilyl)oxy)methyl)azetidin-1-yl)phenyl)dihydropyrimidine-2,4(1H,3H)-dione

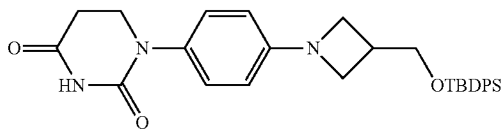

The mixture of methyl 3-(1-(4-(3-(((tert-butyldiphenylsilyl)oxy)methyl)azetidin-1-yl)phenyl)ureido)propanoate (2.70 g, 4.947 mmol) and TMSOK (0.76 g, 5.937 mmol) in THF (30.00 mL) was stirred for 1 h at room temperature. The resulting mixture was concentrated under vacuum to give the product (1.1 g, 43.28%). The crude product was used in the next step directly without further purification.

Step 7: 1-(4-(3-(hydroxymethyl)azetidin-1-yl)phenyl)dihydropyrimidine-2,4(1H,3H)-dione

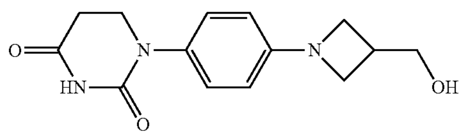 [SMILES: O=C1CCN(c2ccc(N3CC(CO)C3)cc2)C(=O)N1]

The mixture of 1-(4-(3-(((tert-butyldiphenylsilyl)oxy)methyl)azetidin-1-yl)phenyl)dihydropyrimidine-2,4(1H,3H)-dione (3.00 g, 5.840 mmol) and CsF (2.66 g, 17.520 mmol) in DMF (30.00 mL) was stirred for 4 h at room temperature. The resulting mixture was filtered, the filter cake was washed with DMF. The filtration was concentrated under reduced pressure. The residue was purified by slurry in water. The resulting mixture was filtered and the filter cake was washed with water. The filter cake was dried in vacuo to give the product (1.1 g, 68.42%).

Step 8: (1-(4-(2,4-dioxotetrahydropyrimidin-1(2H)-yl)phenyl)azetidin-3-yl)methyl 4-methylbenzenesulfonate

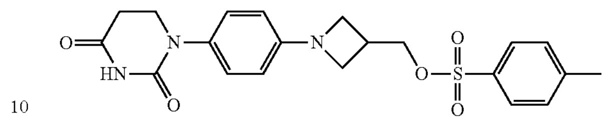

To a stirred mixture of 1-(4-(3-(hydroxymethyl)azetidin-1-yl)phenyl)dihydropyrimidine-2,4(1H,3H)-dione (2.2 g, 7.991 mmol), TEA (2.77 mL) and TsCl (4.57 g, 23.973 mmol) in DCM (20.00 mL) was added DMAP (3.9 g, 31.884 mmol). The resulting mixture was stirred for 4 h at 50° C. The reaction was quenched with water. The resulting mixture was extracted with EtOAc. The combined organic layers were washed with citric acid (aq.) and brine, then dried over anhydrous $Na_2SO_4$. After filtration, the filtrate was concentrated under reduced pressure. The residue was purified by silica gel column chromatography and eluted with $CH_2Cl_2$/MeOH (12:1) to afford the product (995.4 mg, 29.00%). $^1H$ NMR (400 MHz, DMSO) $\delta_H$ 10.23 (s, 1H), 7.94-7.72 (m, 2H), 7.61-7.39 (m, 2H), 7.32-6.94 (m, 2H), 6.50-6.26 (m, 2H), 4.25 (d, J=4 Hz, 2H), 3.83 (t, J=8 Hz, 2H), 3.67 (t, J=4 Hz, 2H), 3.47 (d, J=4 Hz, 2H), 3.06-2.92 (m, 1H), 2.68 (t, J=4 Hz, 2H), 2.44 (s, 3H); $[M+H]^+$=430.0.

Step 9: 3-(tert-butyl)-N-(4-(6-(4-(1-((1-(4-(2,4-dioxotetrahydropyrimidin-1(2H)-yl)phenyl)azetidin-3-yl)methyl)piperidin-4-yl)phenyl)-7H-pyrrolo[2,3-d]pyrimidin-4-yl)-2-methylbenzyl)-1,2,4-oxadiazole-5-carboxamide

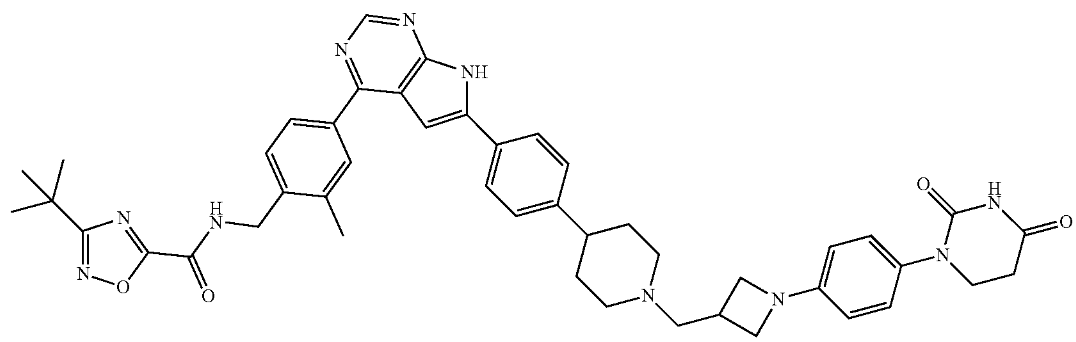 [SMILES: Cc1cc(-c2ncnc3[nH]c(-c4ccc(C5CCN(CC6CN(c7ccc(N8CCC(=O)NC8=O)cc7)C6)CC5)cc4)cc23)ccc1CNC(=O)c1nc(C(C)(C)C)no1]

The mixture of (1-(4-(2,4-dioxotetrahydropyrimidin-1(2H)-yl)phenyl)azetidin-3-yl)methyl 4-methylbenzenesulfonate (50.00 mg, 0.116 mmol), 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (63.99 mg, 0.116 mmol) and DIEA (0.06 mL, 0.471 mmol) in DMSO (1.00 mL) was stirred for 3 h at 80° C. The reaction was quenched with water. The resulting mixture was extracted with EtOAc. The combined organic layers were washed with brine, dried over anhydrous $Na_2SO_4$. After filtration, the filtrate was concentrated under reduced pressure. The crude product was purified by Prep-HPLC with the following conditions: mobile phase, water (10 mmol/L $NH_4HCO_3$) and ACN (46% Phase B up to 52% in 8 min); Detector, UV 254 mm. This resulted in the product (2.6 mg, 2.77%). $^1$H NMR (400 MHz, DMSO) $\delta_H$ 10.22 (s, 1H), 9.89 (d, J=4 Hz, 1H), 8.81 (s, 1H), 8.09 (d, J=4 Hz, 2H), 7.99 (d, J=8.0 Hz, 2H), 7.49 (d, J=8 Hz, 1H), 7.38-7.36 (m, 4H), 7.11 (d, J=8 Hz, 2H), 6.43 (d, J=8 Hz, 2H), 4.57 (d, J=4 Hz, 2H), 3.96 (t, J=8 Hz, 1H), 3.68 (t, J=8 Hz, 2H), 3.63 (s, 2H), 2.97 (d, J=12 Hz, 3H), 2.70 (t, J=8.0 Hz, 2H), 2.61 (d, J=8.0 Hz, 2H), 2.08-2.05 (m, 3H), 1.77 (s, 1H), 1.71 (d, J=16 Hz, 3H), 1.40-1.38 (m, 12H), 1.24 (s, 1H), 0.88 (s, 4H); $[M+H]^+$=807.0.

Example 6: 3-(tert-butyl)-N-(4-(6-(4-(1-(3-(1-(2-(2,6-dioxopiperidin-3-yl)-1,3-dioxoisoindolin-5-yl)azetidin-3-yl)propyl)piperidin-4-yl)phenyl)-7H-pyrrolo[2,3-d]pyrimidin-4-yl)-2-methylbenzyl)-1,2,4-oxadiazole-5-carboxamide Step 1: 3-(azetidin-3-yl)propan-1-ol

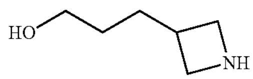

Into a 25-mL round-bottom flask was placed tert-butyl 3-(3-hydroxypropyl) azetidine-1-carboxylate (950.00 mg, 4.413 mmol), DCM (4.0 mL) and TFA (2.0 mL, 2.693 mmol). The resulting solution was stirred for 1 hr at room temperature. The resulting mixture was concentrated under vacuum to give the product (1.4 g, crude).

Step 2: 2-(2,6-dioxopiperidin-3-yl)-5-(3-(3-hydroxypropyl)azetidin-1-yl)isoindoline-1,3-dione

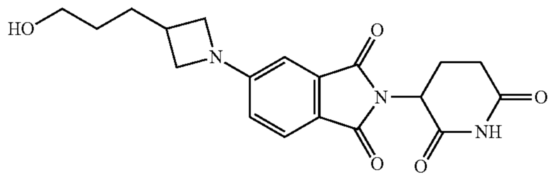 [SMILES: O=C1CCC(N2C(=O)c3ccc(N4CC(CCCO)C4)cc3C2=O)C(=O)N1]

Into a 50-mL round-bottom flask was placed 3-(azetidin-3-yl)propan-1-ol (1.40 g, 3.647 mmol), DMSO (10.00 mL), 2-(2,6-dioxopiperidin-3-yl)-5-fluoroisoindole-1,3-dione (1.21 g, 4.376 mmol) and DIEA (2.83 g, 21.880 mmol). The resulting solution was stirred for 1 hr at 80° C. The reaction mixture was cooled to room temperature. The resulting solution was diluted with EtOAc. The resulting solution was extracted with $H_2O$ and the organic layers were combined, dried over anhydrous sodium sulfate and concentrated under vacuum. The residue was applied onto a silica gel column with dichloromethane/methanol (8:1) to give the product (550 mg, 40.61%).

Step 3: 3-(1-(2-(2,6-dioxopiperidin-3-yl)-1,3-dioxoisoindolin-5-yl)azetidin-3-yl)propyl 4-methylbenzenesulfonate

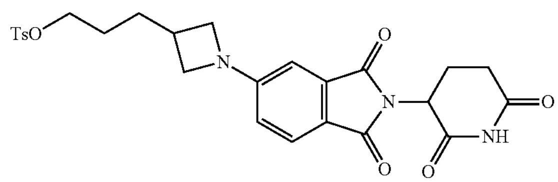 [SMILES: Cc1ccc(S(=O)(=O)OCCCC2CN(c3ccc4c(c3)C(=O)N(C3CCC(=O)NC3=O)C4=O)C2)cc1]

Into a 25-mL round-bottom flask was placed 2-(2,6-dioxopiperidin-3-yl)-5-(3-(3-hydroxypropyl)azetidin-1-yl) isoindoline-1,3-dione (480.00 mg, 1.292 mmol), DCM (10.00 mL), TEA (262.00 mg, 2.589 mmol), TsCl (493.00 mg, 2.586 mmol). The resulting solution was stirred overnight at room temperature. The resulting mixture was concentrated under vacuum. The residue was applied onto a silica gel column with dichloromethane/methanol (7:1) to give the product (400 mg, 58.89%).

Step 4: 3-(tert-butyl)-N-(4-(6-(4-(1-(3-(1-(2-(2,6-dioxopiperidin-3-yl)-1,3-dioxoisoindolin-5-yl)azetidin-3-yl)propyl)piperidin-4-yl)phenyl)-7H-pyrrolo[2,3-d]pyrimidin-4-yl)-2-methylbenzyl)-1,2,4-oxadiazole-5-carboxamide

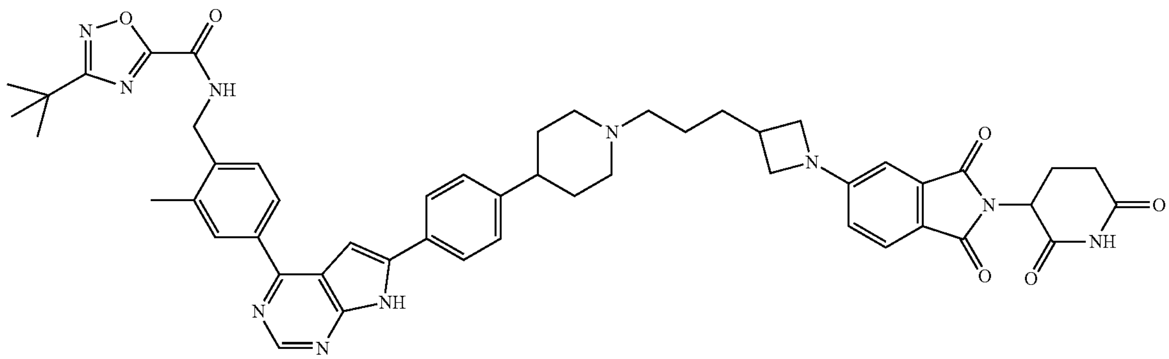 [SMILES: Cc1cc(-c2ncnc3[nH]c(-c4ccc(C5CCN(CCCC6CN(c7ccc8c(c7)C(=O)N(C7CCC(=O)NC7=O)C8=O)C6)CC5)cc4)cc23)ccc1CNC(=O)c1nc(C(C)(C)C)no1]

Into a 25-mL round-bottom flask was placed 3-(1-(2-(2,6-dioxopiperidin-3-yl)-1,3-dioxoisoindolin-5-yl)azetidin-3-yl)propyl 4-methylbenzenesulfonate (50.00 mg, 0.095 mmol), ACN (5.00 mL), 3-(tert-butyl)-N-(2-methyl-4-(6-(4-(piperidin-4-yl)phenyl)-7H-pyrrolo[2,3-d]pyrimidin-4-yl) benzyl)-1,2,4-oxadiazole-5-carboxamide (52.00 mg, 0.095 mmol), KI (3.00 mg, 0.018 mmol), DIEA (0.05 mL, 0.385 mmol). The resulting solution was stirred overnight at 70° C. in an oil bath. The reaction mixture was cooled to room temperature. The resulting mixture was concentrated under vacuum. The residue was applied onto a silica gel column with dichloromethane/methanol (10:1). The crude product (35 mg) was purified by Prep-HPLC with the following conditions: mobile phase, water (10 mmol/L $NH_4HCO_3$) and ACN (40% Phase B up to 52% in 8 min); Detector, UV 254 nm. This resulted in the product (5.3 mg, 6.17%). $^1$H NMR (300 MHz, DMSO) $\delta_H$ 12.66 (s, 1H), 11.05 (s, 1H), 8.80 (s, 1H), 8.06 (s, 3H), 7.98 (d, J=7.8 Hz, 2H), 7.64 (d, J=8.3 Hz, 1H), 7.48 (d, J=8.3 Hz, 1H), 7.37 (d, J=8.6 Hz, 4H), 6.77 (s, 1H), 6.63 (d, J=5.9 Hz, 1H), 5.07-5-05 (m, 1H), 4.56 (s, 2H), 4.15 (t, J=7.8 Hz, 3H), 3.68 (d, J=7.5 Hz, 2H), 2.57 (d, J=16.3 Hz, 10H), 2.04-1.37 (m, 18H), 1.23 (s, 2H); [M+H]$^+$ =903.42.

Example 7: (R)-3-(tert-butyl)-N-(1-(4-(6-(4-(1-((1-(4-(2,4-dioxotetrahydropyrimidin-1(2H)-yl)phenyl) piperidin-4-yl)methyl)piperidin-4-yl)phenyl)-7H-pyrrolo[2,3-d]pyrimidin-4-yl)-2-methylphenyl) ethyl)-1,2,4-oxadiazole-5-carboxamide

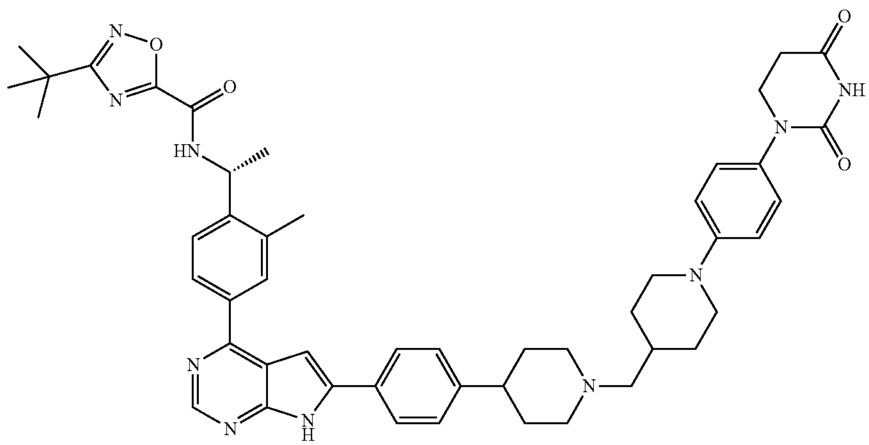 [SMILES: Cc1cc(-c2ncnc3[nH]c(-c4ccc(C5CCN(CC6CCN(c7ccc(N8CCC(=O)NC8=O)cc7)CC6)CC5)cc4)cc23)ccc1[C@@H](C)NC(=O)c1nc(C(C)(C)C)no1]

The titled compound was synthesized in the procedures similar to Example 1. $^1$H NMR (400 MHz, DMSO) $\delta_H$ 12.68 (s, 1H), 10.27 (s, 1H), 9.98 (d, J=8.0 Hz, 1H), 8.80 (s, 1H), 8.17-7.96 (m, 4H), 7.67 (d, J=8.1 Hz, 1H), 7.38 (s, 3H), 7.14 (d, J=8.7 Hz, 2H), 6.94 (d, J=8.5 Hz, 2H), 5.38 (s, 1H), 3.74-3.64 (m, 4H), 3.05 (s, 2H), 2.67 (dd, J=14.9, 8.6 Hz, 5H), 2.54 (s, 3H), 2.32 (s, 2H), 2.13 (s, 2H), 1.66-1.86 (m, 7H), 1.55 (d, J=6.6 Hz, 3H), 1.37 (s, 9H), 1.18-1.28 (m, 2H); [M+H]+=849.5.

Example 8: (S)-3-(tert-butyl)-N-(1-(4-(6-(4-(1-((1-(4-(2,4-dioxotetrahydropyrimidin-1(2H)-yl)phenyl) piperidin-4-yl)methyl)piperidin-4-yl)phenyl)-7H-pyrrolo[2,3-d]pyrimidin-4-yl)-2-methylphenyl) ethyl)-1,2,4-oxadiazole-5-carboxamide

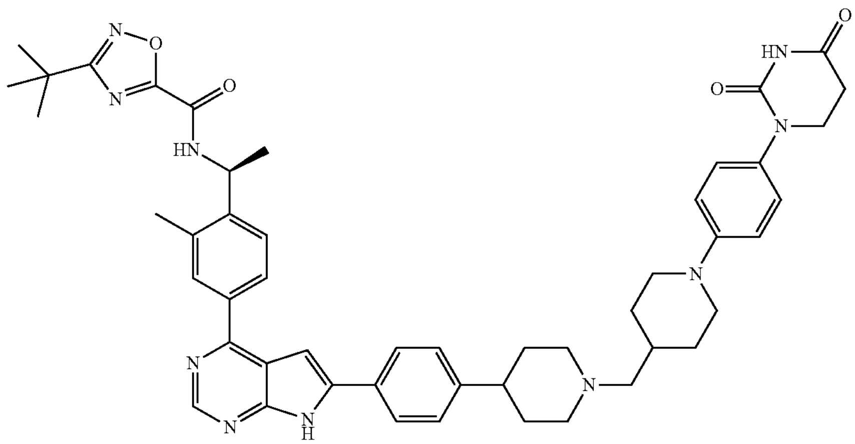 [SMILES: Cc1cc(-c2ncnc3[nH]c(-c4ccc(C5CCN(CC6CCN(c7ccc(N8CCC(=O)NC8=O)cc7)CC6)CC5)cc4)cc23)ccc1[C@H](C)NC(=O)c1nc(C(C)(C)C)no1]

The titled compound was synthesized in the procedures similar to Example 1. $^1$H NMR (400 MHz, DMSO) $\delta_H$ 12.68 (s, 1H), 10.27 (s, 1H), 9.97 (d, J=7.6 Hz, 1H), 8.80 (s, 1H), 8.10 (d, J=8.0 Hz, 1H), 8.04 (s, 1H), 7.99 (d, J=7.6 Hz, 2H), 7.67 (d, J=8.0 Hz, 1H), 7.38 (s, 3H), 7.14 (d, J=8.4 Hz, 2H), 6.93 (d, J=8.0 Hz, 2H), 5.38 (s, 1H), 3.69 (s, 4H), 3.01 (s, 2H), 2.72-2.61 (m, 4H), 2.54 (s, 3H), 2.25 (s, 2H), 2.05 (s, 2H), 1.91 (s, 2H), 1.85-1.65 (m, 7H), 1.55 (d, J=6.0 Hz, 3H), 1.37 (s, 10H), 1.30-1.15 (m, 3H); $[M+H]^+$=849.8.

Example 9: 1-(4-(4-((4-(4-(4-(3-(7,7-dimethyl-1-oxo-1,3,4,6,7,8-hexahydro-2H-cyclopenta[4,5]pyrrolo[1,2-a]pyrazin-2-yl)-2-methylphenyl)-7H-pyrrolo[2,3-d]pyrimidin-6-yl)phenyl)piperidin-1-yl)methyl)piperidin-1-yl)phenyl)dihydropyrimidine-2,4(1H,3H)-dione

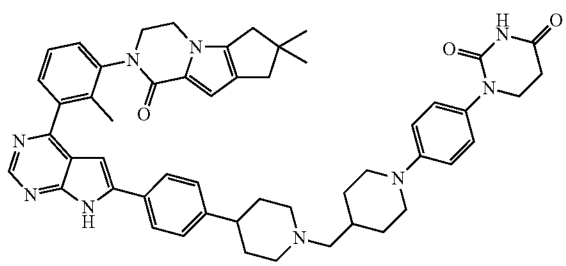 [SMILES: Cc1c(-c2ncnc3[nH]c(-c4ccc(C5CCN(CC6CCN(c7ccc(N8CCC(=O)NC8=O)cc7)CC6)CC5)cc4)cc23)cccc1N1CCn2c(cc3c2CC(C)(C)C3)C1=O]

The titled compound was synthesized in the procedures similar to Example 1. $^1$H NMR (400 MHz, DMSO) $\delta_H$ 12.71 (s, 1H), 10.28 (s, 1H), 8.83 (s, 1H), 8.20 (s, 1H), 7.90 (d, J=6.9 Hz, 2H), 7.47 (d, J=17.7 Hz, 3H), 7.36 (d, J=6.9 Hz, 2H), 7.13 (d, J=7.5 Hz, 2H), 6.93 (d, J=7.6 Hz, 2H), 6.78 (s, 1H), 6.51 (s, 1H), 4.19 (s, 3H), 3.85 (s, 1H), 3.69 (d, J=6.7 Hz, 4H), 2.97 (d, J=8.6 Hz, 3H), 2.72-2.62 (m, 5H), 2.17 (d, J=19.8 Hz, 6H), 1.87-2.10 (m, 3H), 1.85-1.63 (m, 8H), 1.15-1.25 (m, 9H); $[M+H]^+$=856.5.

Example 10: 1-(4-(4-((4-(5-(4-(3-(7,7-dimethyl-1-oxo-1,3,4,6,7,8-hexahydro-2H-cyclopenta[4,5]pyrrolo[1,2-a]pyrazin-2-yl)-2-methylphenyl)-7H-pyrrolo[2,3-d]pyrimidin-6-yl)pyridin-2-yl)piperazin-1-yl)methyl)piperidin-1-yl)phenyl)dihydropyrimidine-2,4(1H,3H)-dione

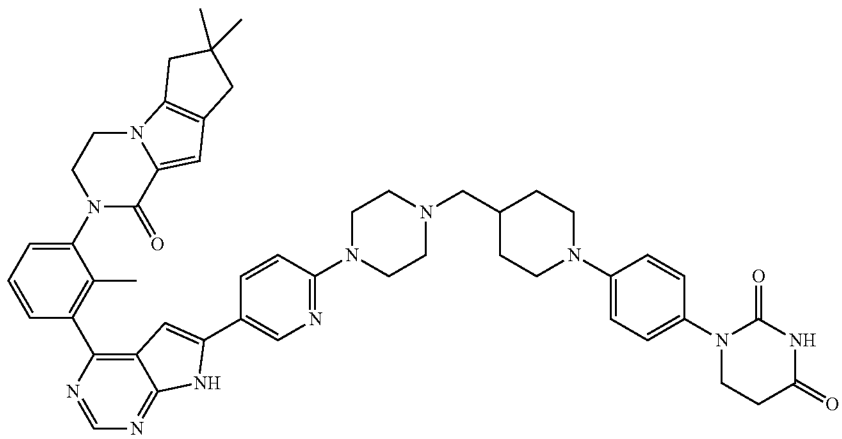 [SMILES: Cc1c(-c2ncnc3[nH]c(-c4ccc(N5CCN(CC6CCN(c7ccc(N8CCC(=O)NC8=O)cc7)CC6)CC5)nc4)cc23)cccc1N1CCn2c(cc3c2CC(C)(C)C3)C1=O]

The titled compound was synthesized in the procedures similar to Example 1. $^1$H NMR (400 MHz, DMSO) $\delta_H$ 12.62 (s, 1H), 10.27 (s, 1H), 8.79 (s, 1H), 8.73 (s, 1H), 8.10 (d, J=9.0 Hz, 1H), 7.46 (d, J=18.9 Hz, 3H), 7.13 (d, J=8.5 Hz, 2H), 6.93 (d, J=7.9 Hz, 3H), 6.69 (s, 1H), 6.50 (s, 1H), 4.17 (d, J=8.7 Hz, 3H), 3.85 (s, 1H), 3.68 (d, J=6.8 Hz, 4H), 3.58 (s, 4H), 2.67 (dd, J=13.8, 9.1 Hz, 4H), 2.56 (s, 2H), 2.46 (s, 4H), 2.41 (s, 2H), 2.22 (d, J=6.3 Hz, 2H), 2.14 (s, 3H), 1.82 (d, J=12.3 Hz, 2H), 1.73 (s, 1H), 1.21 (s, 8H); $[M+H]^+$=858.4.

Example 11: 1-(4-(4-((4-(4-(4-(3-(7,7-dimethyl-1-oxo-1,3,4,6,7,8-hexahydro-2H-cyclopenta[4,5]pyrrolo[1,2-a]pyrazin-2-yl)-2-methylphenyl)-7H-pyrrolo[2,3-d]pyrimidin-6-yl)phenyl)piperazin-1-yl)methyl)piperidin-1-yl)phenyl)dihydropyrimidine-2,4(1H,3H)-dione Step 1: tert-butyl 4-(4-(4-chloro-7-(phenylsulfonyl)-7H-pyrrolo[2,3-d]pyrimidin-6-yl)phenyl)piperazine-1-carboxylate

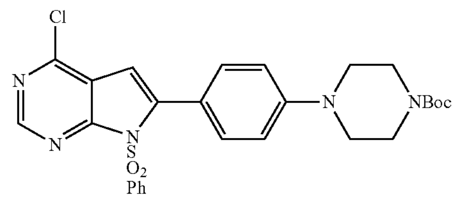

To a solution of 4-chloro-6-iodo-7-(phenylsulfonyl)-7H-pyrrolo[2,3-d]pyrimidine (2.5 g, 14.4 mmol) in dioxane (35 mL) and $H_2O$ (7 mL) was added tert-butyl 4-(4-(4,4,5,5-tetramethyl-1,3,2-dioxaborolan-2-yl)phenyl)piperazine-1-carboxylate (1.6 g, 4.2 mmol), $K_2CO_3$ (1.6 g, 12 mmol) and $Pd(dppf)Cl_2 \cdot CH_2Cl_2$ (0.3 g, 0.4 mmol). The mixture was stirred at 80° C. for 6 hours. The mixture was concentrated, dissolved in $H_2O$ (30 mL) and extracted with EtOAc (30 mL*2). The organic phase was concentrated and purified by flash chromatography with PE/EA (100:1 to 7:3) to give the product (1.9 g, 86.4%).

Step 2: tert-butyl 4-(4-(4-(3-(7,7-dimethyl-1-oxo-1,3,4,6,7,8-hexahydro-2H-cyclopenta[4,5]pyrrolo[1,2-a]pyrazin-2-yl)-2-methylphenyl)-7-(phenylsulfonyl)-7H-pyrrolo[2,3-d]pyrimidin-6-yl)phenyl)piperazine-1-carboxylate

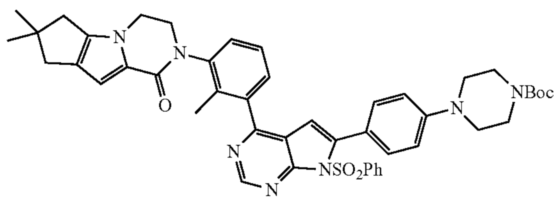

To a solution of tert-butyl 4-(4-(4-chloro-7-(phenylsulfonyl)-7H-pyrrolo[2,3-d]pyrimidin-6-yl)phenyl)piperazine-1-carboxylate (1.9 g, 3.4 mmol) in dioxane (30 mL) and $H_2O$ (6 mL) was added 7,7-dimethyl-2-(2-methyl-3-(4,4,5,5-tetramethyl-1,3,2-dioxaborolan-2-yl)phenyl)-3,4,7,8-tetrahydro-2H-cyclopenta[4,5]pyrrolo[1,2-a]pyrazin-1(6H)-one (1.4 g, 3.4 mmol), $K_2CO_3$ (1.4 g, 10.0 mmol) and Pd(dppf)$Cl_2$·$CH_2Cl_2$ (0.3 g, 0.3 mmol). The mixture was stirred at 100° C. under $N_2$ for 18 hours. The solvent was evaporated, added $H_2O$ (30 mL) and extracted with EtOAc (50 mL*2). The organic phase was combined, concentrated and purified by flash chromatography with PE/EA (100:1 to 1:100) to give the product (1.1 g, crude).

Step 3: 7,7-dimethyl-2-(2-methyl-3-(6-(4-(piperazin-1-yl)phenyl)-7H-pyrrolo[2,3-d]pyrimidin-4-yl)phenyl)-3,4,7,8-tetrahydro-2H-cyclopenta[4,5]pyrrolo[1,2-a]pyrazin-1(6H)-one hydrochloride

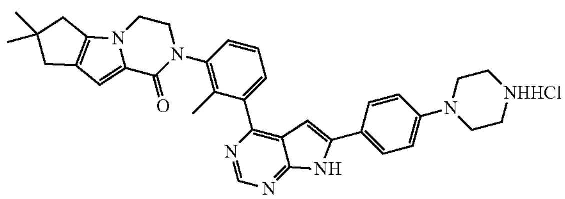

To a solution of tert-butyl 4-(4-(4-(3-(7,7-dimethyl-1-oxo-1,3,4,6,7,8-hexahydro-2H-cyclopenta[4,5]pyrrolo[1,2-a]pyrazin-2-yl)-2-methylphenyl)-7-(phenylsulfonyl)-7H-pyrrolo[2,3-d]pyrimidin-6-yl)phenyl)piperazine-1-carboxylate (1.1 g, 1.4 mmol) in THF (10 mL) was added NaOH in MeOH (4%, 3 mL). The mixture was stirred at 20-30° C. for 1 hour, concentrated and slurried with $H_2O$ (30 mL). The solid was filtered and washed with $H_2O$ (30 mL). The filter cake was dried under reduced pressure. The solid was transferred into a flask and added HCl/MeOH (4 N, 30 mL). The mixture was stirred at 20-30° C. for 3 hours. The solvent was evaporated and slurried with MeOH, filtered and the filter cake was washed with MeOH (30 mL) and MTBE (20 mL). The filter cake was dried and used for next step directly. $^1$H NMR (400 MHz, DMSO) $\delta_H$ 12.54 (s, 1H), 8.77 (s, 1H), 7.82 (d, J=8.4 Hz, 2H), 7.57-7.39 (m, 3H), 6.99 (d, J=8.4 Hz, 2H), 6.62 (s, 1H), 6.50 (s, 1H), 4.18 (br, 3H), 3.84 (br, 1H), 3.15 (s, 4H), 2.84 (s, 4H), 2.56 (s, 2H), 2.50 (br, 2H), 2.41 (s, 2H), 2.11 (s, 3H), 1.21 (s, 6H). $[M+H]^+$= 572.3.

Step 4: 1-(4-(4-((4-(4-(4-(3-(7,7-dimethyl-1-oxo-1,3,4,6,7,8-hexahydro-2H-cyclopenta[4,5]pyrrolo[1,2-a]pyrazin-2-yl)-2-methylphenyl)-7H-pyrrolo[2,3-d]pyrimidin-6-yl)phenyl)piperazin-1-yl)methyl)piperidin-1-yl)phenyl)dihydropyrimidine-2,4(1H,3H)-dione

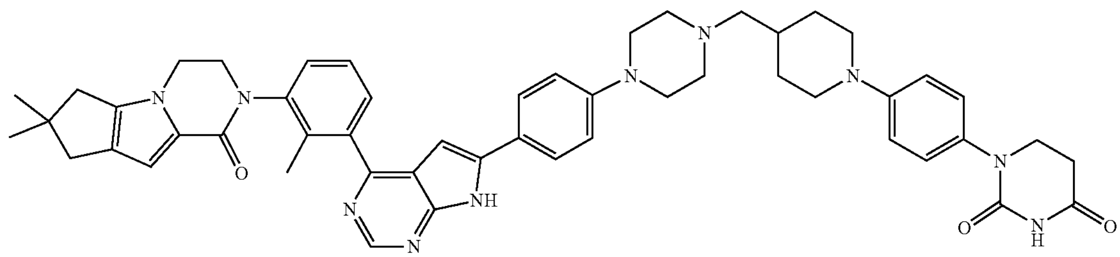 [SMILES: Cc1c(-c2ncnc3[nH]c(-c4ccc(N5CCN(CC6CCN(c7ccc(N8CCC(=O)NC8=O)cc7)CC6)CC5)cc4)cc23)cccc1N1CCn2c(cc3c2CC(C)(C)C3)C1=O]

To a solution of 7,7-dimethyl-2-(2-methyl-3-(6-(4-(piperazin-1-yl)phenyl)-7H-pyrrolo[2,3-d]pyrimidin-4-yl)phenyl)-3,4,7,8-tetrahydro-2H-cyclopenta[4,5]pyrrolo[1,2-a]pyrazin-1(6H)-one (114 mg, 0.2 mmol) in DCM/EtOH (5:1, 30 mL) was added 1-(4-(2,4-dioxotetrahydropyrimidin-1(2H)-yl)phenyl)piperidine-4-carbaldehyde (60 mg, 0.2 mmol) HOAc (1 drop) and NaOAc (32.8 mg, 0.4 mmol). After stirring at 20-30° C. for 60 min, NaBH(OAc)$_3$ (127 mg, 0.6 mmol) was added. The mixture was stirred at 20-30° C. for 3 hours. The solvent was evaporated, added $H_2O$ (30 mL) and extracted with DCM/iPrOH (10:1, 30 mL*3). The organic phase was combined, concentrated and purified by pre-TLC with DCM/MeOH (10:1) to give the product (53 mg, 31%). $^1$H NMR (400 MHz, DMSO) $\delta_H$ 12.55 (s, 1H), 10.27 (s, 1H), 8.77 (s, 1H), 7.82 (d, J=8.4 Hz, 2H), 7.51-7.36 (m, 3H), 7.13 (d, J=8.8 Hz, 2H), 7.01 (d, J=8.4 Hz, 2H), 6.93 (d, J=8.8 Hz, 2H), 6.63 (s, 1H), 6.50 (s, 1H), 4.18 (br, 3H), 3.84 (br, 1H), 3.74-3.67 (m, 4H), 3.24 (br, 4H), 2.69-2.64 (m, 4H), 2.56 (s, 2H), 2.55-2.50 (m, 3H), 2.41 (s, 2H), 2.30-2.06 (m, 5H), 1.87-1.65 (m, 3H), 1.21 (s, 9H); $[M+H]^+$= 857.5.

Example 12: 3-(tert-butyl)-N-(4-(6-(4-(1-(3-(2,4-dioxotetrahydropyrimidin-1(2H)-yl)-4-methoxybenzoyl)piperidin-4-yl)phenyl)-7H-pyrrolo[2,3-d]pyrimidin-4-yl)-2-methylbenzyl)-1,2,4-oxadiazole-5-carboxamide

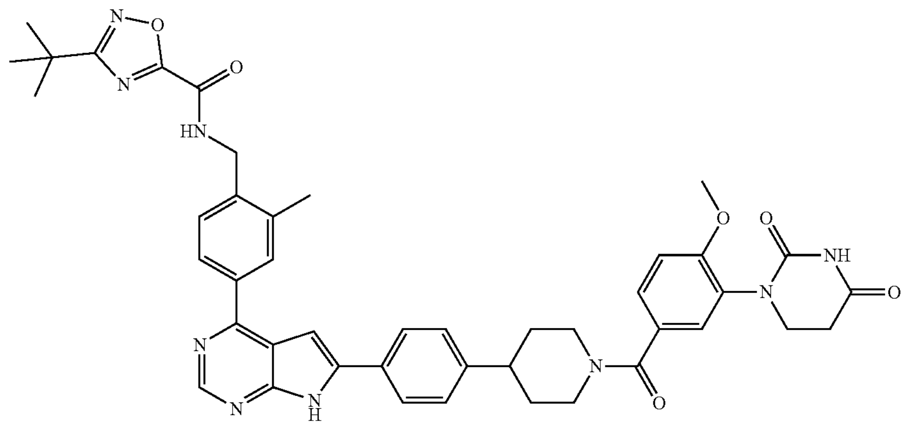 [SMILES: COc1ccc(C(=O)N2CCC(c3ccc(-c4cc5c(-c6ccc(CNC(=O)c7nc(C(C)(C)C)no7)c(C)c6)ncnc5[nH]4)cc3)CC2)cc1N1CCC(=O)NC1=O]

A mixture of 3-(2,4-dioxotetrahydropyrimidin-1(2H)-yl)-4-methoxybenzoic acid (26 mg, 0.1 mmol) and HATU (38 mg, 0.1 mmol) in DMF (1 mL) was stirred in a round bottom flask at room temperature for 1 hour. After the mixture was added 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (62 mg, 0.1 mmol) and DIPEA (39 mg, 0.3 mmol), the mixture was stirred at room temperature overnight. The reaction was purified with C18 column chromatography (0.1% FA in water:acetonitrile=60:40~20:80 gradient elution) to give the product (40 mg, 50%). $^1$H NMR (400 MHz, DMSO) $\delta_H$ 12.69 (s, 1H), 10.36 (s, 1H), 9.92 (s, 1H), 8.81 (s, 1H), 8.10-8.05 (m, 2H), 8.00 (d, J=7.6 Hz, 2H), 7.50-7.35 (m, 6H), 7.18 (d, J=8.4 Hz, 1H), 4.56 (d, J=4.8 Hz, 2H), 3.85 (s, 3H), 3.65-3.58 (m, 2H), 3.33 (s, 2H), 2.96-2.81 (m, 2H), 2.73-2.65 (m, 2H), 1.91-1.76 (m, 2H), 1.75-1.63 (m, 2H), 1.38 (s, 10H); $[M+H]^+$=796.4.

Example 13: 3-(tert-butyl)-N-(4-(6-(4-(1-(2-(1-(5-(2,4-dioxotetrahydropyrimidin-1(2H)-yl)-6-methylpyridin-2-yl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide Step 1: 6-(4-(2-((tert-butyldiphenylsilyl)oxy)ethyl)piperidin-1-yl)-2-methyl-3-nitropyridine

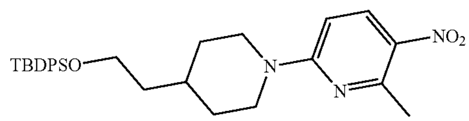

A mixture of 4-(2-((tert-butyldiphenylsilyl)oxy)ethyl)piperidine (5.00 g, 3.601 mmol), 6-fluoro-2-methyl-3-nitropyridine (2123.40 g, 13.601 mmol) and DIEA (5.27 g, 40.804 mmol) in DMSO (60 mL) was stirred for 1 h at 60° C. under air atmosphere. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography and eluted with PE/EA (5:1) to afford the product (5.6 g, 81.74%).

Step 2:6-(4-(2-((tert-butyldiphenylsilyl)oxy)ethyl)piperidin-1-yl)-2-methylpyridin-3-amine

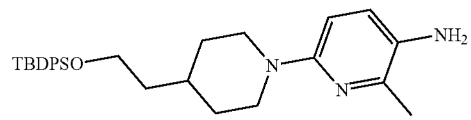

To a stirred mixture of 6-(4-(2-((tert-butyldiphenylsilyl)oxy)ethyl)piperidin-1-yl)-2-methyl-3-nitropyridine (5.40 g, 10.720 mmol) and 10% Pd/C (2.00 g) in DCM (25 mL) and MeOH (25 mL) was added AcOH (0.20 mL, 3.490 mmol) and stirred for 5 h at room temperature under hydrogen atmosphere. The resulting mixture was filtered and the filter cake was washed with MeOH. The filtrate was concentrated under reduced pressure to give the product (5 g, 98.45%).

Step 3: 3-((6-(4-(2-((tert-butyldiphenylsilyl)oxy)ethyl)piperidin-1-yl)-2-methylpyridin-3-yl)amino)propanoic acid

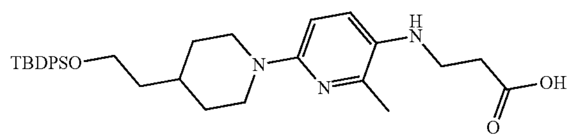

A mixture of 6-(4-(2-((tert-butyldiphenylsilyl)oxy)ethyl)piperidin-1-yl)-2-methylpyridin-3-amine (5.00 g, 10.554 mmol) and acrylic acid (988.76 mg, 13.721 mmol) in toluene (100 mL) was stirred for 12 h at 90° C. under nitrogen atmosphere. LCMS and TLC showed most starting material was converted to product. The mixture (6.1 g, 105.89%) was used directly for next step after concentration.

Step 4: 1-(6-(4-(2-((tert-butyldiphenylsilyl)oxy) ethyl)piperidin-1-yl)-2-methylpyridin-3-yl)dihydro-pyrimidine-2,4(1H,3H-dione

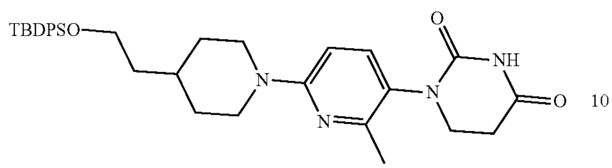

A mixture of 3-((6-(4-(2-((tert-butyldiphenylsilyl)oxy) ethyl)piperidin-1-yl)-2-methylpyridin-3-yl)amino)propanoic acid (6.10 g, 11.176 mmol) and urea (2.01 g, 33.529 mmol) in AcOH (30 mL) and toluene (100 mL) was stirred for 12 h at 105° C. under nitrogen atmosphere. The resulting mixture was concentrated under reduced pressure. The residue was purified by Prep-TLC (PE/EA 1:3) to afford the product (3 g, 47.03%).

Step 5: 1-(6-(4-(2-hydroxyethyl)piperidin-1-yl)-2-methylpyridin-3-yl)dihydropyrimidine-2,4(1H,3H)-dione

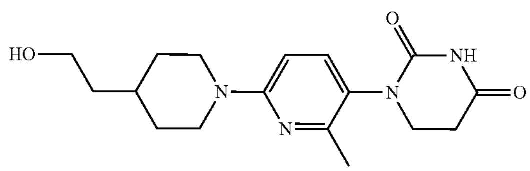 [SMILES: Cc1nc(N2CCC(CCO)CC2)ccc1N1CCC(=O)NC1=O]

A mixture of 1-(6-(4-(2-((tert-butyldiphenylsilyl)oxy) ethyl)piperidin-1-yl)-2-methylpyridin-3-yl)dihydropyrimidine-2,4(1H,3H)-dione (3.00 g, 5.256 mmol) and CsF (3.19 g, 21.023 mmol) in DMF was stirred overnight at 35° C. under air atmosphere. The resulting mixture was extracted with $CH_2Cl_2$. The combined organic layers were washed with water and dried over anhydrous $Na_2SO_4$. After filtration, the filtrate was concentrated under reduced pressure. The residue was purified by Prep-TLC (PE/EtOAc 1:3) to afford the product (1.08 g, 61.82%). $^1$H NMR (300 MHz, DMSO) $\delta_H$ 10.27 (s, 1H), 7.34 (d, J=9 Hz, 1H), 6.64 (d, J=9 Hz, 1H), 4.26 (d, J=15 Hz, 3H), 3.64 (s, 1H), 3.51-3.41 (m, 3H), 2.73 (t, J=15 Hz, 4H), 2.19 (s, 3H), 1.98 (s, 1H), 1.70 (d, J=12 Hz, 2H), 1.61 (s, 1H), 1.37 (q, J=6 Hz, 2H), 1.23 (s, 1H), 1.17-1.03 (m, 2H); [M+H]$^+$=333.0.

Step 6: 3-(tert-butyl)-N-(4-(6-(4-(1-(2-(1-(5-(2,4-dioxotetrahydropyrimidin-1(2H)-yl)-6-methylpyridin-2-yl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide

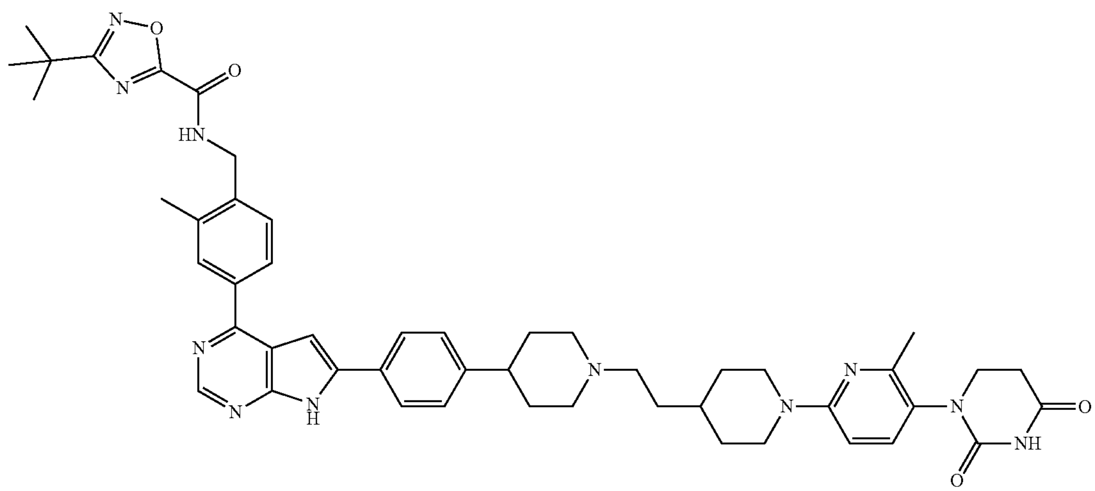 [SMILES: Cc1cc(-c2ncnc3[nH]c(-c4ccc(C5CCN(CCC6CCN(c7ccc(N8CCC(=O)NC8=O)c(C)n7)CC6)CC5)cc4)cc23)ccc1CNC(=O)c1nc(C(C)(C)C)no1]

The titled compound was synthesized in the procedures similar to Example 1. $^1$H NMR (400 MHz, DMSO) $\delta_H$ 12.73 (s, 1H), 10.32 (s, 1H), 9.92 (s, 1H), 9.83 (s, 1H), 8.82 (s, 1H), 8.07 (s, 2H), 8.03 (d, J=7.2 Hz, 2H), 7.48 (d, J=8.4 Hz, 1H), 7.39 (s, 4H), 6.70 (d, J=8.0 Hz, 1H), 4.60-4.52 (m, 2H), 4.40-4.25 (m, 2H), 3.70-3.55 (m, 3H), 3.54-3.45 (m, 1H), 3.20-3.10 (m, 2H), 3.09-2.98 (m, 3H), 2.95-2.63 (m, 6H), 2.21 (s, 3H), 2.08-1.95 (m, 4H), 1.81-1.55 (m, 6H), 1.38 (s, 9H), 1.25-1.10 (m, 3H); [M+H]$^+$=865.5.

Example 14: (R)-3-(tert-butyl)-N-(1-(4-(6-(6-(4-((1-(4-(2,4-dioxotetrahydropyrimidin-1(2H)-yl)phenyl) piperidin-4-yl)methyl)piperazin-1-yl)pyridin-3-yl)-7H-pyrrolo[2,3-d]pyrimidin-4-yl)-2-methylphenyl) ethyl)-1,2,4-oxadiazole-5-carboxamide Step 1: tert-butyl 4-(5-(4-chloro-7H-pyrrolo[2,3-d] pyrimidin-6-yl)pyridin-2-yl)piperazine-1-carboxylate

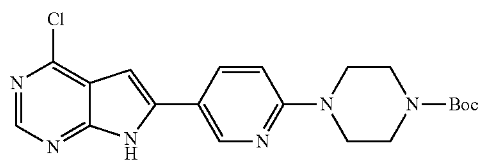 [SMILES: CC(C)(C)OC(=O)N1CCN(c2ccc(-c3cc4c(Cl)ncnc4[nH]3)cn2)CC1]

A mixture of 4-chloro-6-iodo-7H-pyrrolo[2,3-d]pyrimidine (3 g, 10.73 mmol), tert-butyl 4-(5-(4,4,5,5-tetramethyl-1,3,2-dioxaborolan-2-yl)pyridin-2-yl)piperazine-1-carboxylate (4.18 g, 10.73 mmol), $Na_2CO_3$ (1.25 g, 11.80 mmol) and Pd(dppf)$Cl_2$ (0.39 g, 0.537 mmol) in dioxane (120 mL) and $H_2O$ (20 mL) was stirred in a sealed tube at 85° C. overnight. After cooling, the reaction mixture was filtered and the solid was washed with 20 mL of MeOH and dried under vacuum to afford the product (4.05 g, 91%). $[M+H]^+$=415.0.

Step 2: tert-butyl (R)-4 (5 (4 (4 (1 (3 (tert-butyl)-1, 2,4-oxadiazole-5-carboxamido)ethyl)-3-methylphenyl)-7H-pyrrolo[2,3-d]pyrimidin-6-yl)pyridin-2-yl) piperazine-1-carboxylate

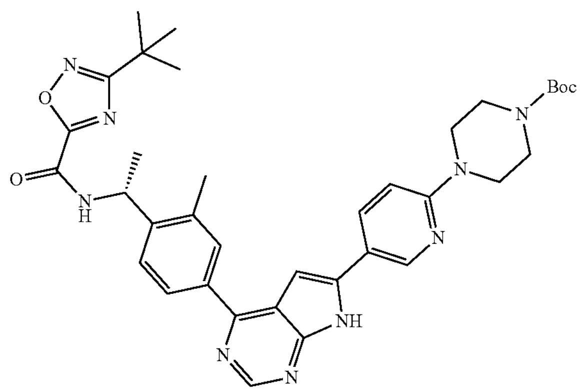 [SMILES: Cc1cc(-c2ncnc3[nH]c(-c4ccc(N5CCN(C(=O)OC(C)(C)C)CC5)nc4)cc23)ccc1[C@@H](C)NC(=O)c1nc(C(C)(C)C)no1]

A mixture of tert-butyl 4-(5-(4-chloro-7H-pyrrolo[2,3-d] pyrimidin-6-yl)pyridin-2-yl)piperazine-1-carboxylate (0.9 g, 2.17 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (0.94 g, 2.28 mmol), $Na_2CO_3$ (0.46 g, 4.34 mmol) and Pd(dppf)$Cl_2$ (79.3 mg, 0.108 mmol) in dioxane (60 mL) and $H_2O$ (10 mL) was stirred in a sealed tube at 100° C. overnight. After cooling, the reaction mixture was filtered and the solid was washed with 5 mL of MeOH and dried under vacuum to afford the product (1.02 g, 70.6%). $[M+H]^+$=666.0.

Step 3: (R)-3-(tert-butyl)-N-(1-(2-methyl-4-(6-(6-(piperazin-1-yl)pyridin-3-yl)-7H-pyrrolo[2,3-d]pyrimidin-4-yl)phenyl)ethyl)-1,2,4-oxadiazole-5-carboxamide, hydrogen chloride salt

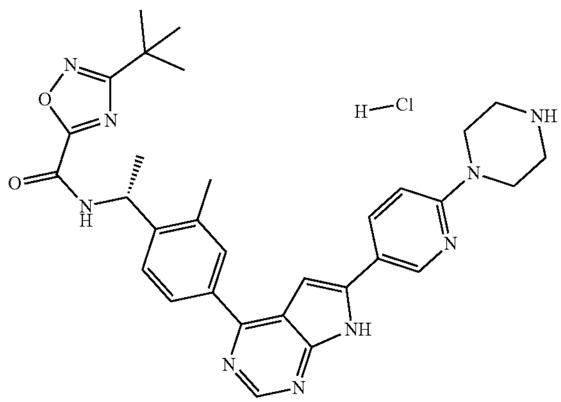 [SMILES: Cc1cc(-c2ncnc3[nH]c(-c4ccc(N5CCNCC5)nc4)cc23)ccc1[C@@H](C)NC(=O)c1nc(C(C)(C)C)no1 ; Cl]

To a solution of tert-butyl (R)-4-(5-(4-(4-(1-(3-(tert-butyl)-1,2,4-oxadiazole-5-carboxamido)ethyl)-3-methylphenyl)-7H-pyrrolo[2,3-d]pyrimidin-6-yl)pyridin-2-yl) piperazine-1-carboxylate (1.02 g, 1.53 mmol) in DCM (50 mL) in a round bottom flask was added HCl in dioxane (4 N, 35 mL) at 0° C. The mixture was stirred for 2 h at 20° C. The precipitate was collected with filtration and dried in vacuum to afford the product (0.92 g, 100%). $^1$H NMR (400 MHz, DMSO) $\delta_H$ 13.53 (s, 1H), 10.06 (d, J=7.5 Hz, 1H), 9.33 (s, 2H), 9.00 (s, 1H), 8.93 (s, 1H), 8.35 (d, J=8.7 Hz, 1H), 8.05 (d, J=8.1 Hz, 1H), 7.99 (s, 1H), 7.75 (d, J=8.0 Hz, 1H), 7.55 (s, 1H), 7.12 (d, J=8.9 Hz, 1H), 5.50-5.28 (m, 1H), 3.89 (s, 4H), 3.20 (s, 4H), 2.57 (s, 3H), 1.56 (d, J=6.9 Hz, 3H), 1.38 (s, 9H). $[M+H]^+$=566.3.

Step 4: (R)-3-(tert-butyl)-N-(1-(4-(6-(6-(4-((1-(4-(2, 4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl) ethyl)-1,2,4-oxadiazole-5-carboxamide

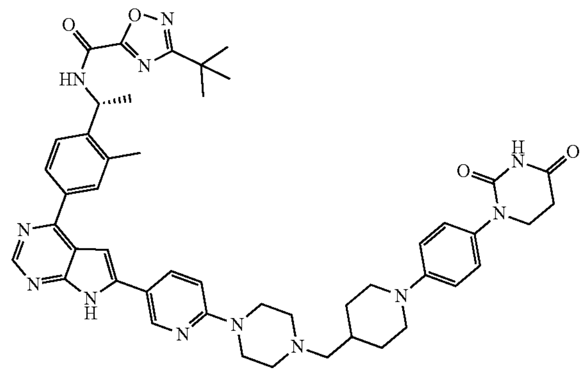 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]

A mixture of (R)-3-(tert-butyl)-N-(1-(2-methyl-4-(6-(6-(piperazin-1-yl)pyridin-3-yl)-7H-pyrrolo[2,3-d]pyrimidin-4-yl)phenyl)ethyl)-1,2,4-oxadiazole-5-carboxamide, hydrogen chloride salt (0.06 g, 0.1 mmol), 1-(4-(2,4-dioxotetrahydropyrimidin-1(2H)-yl)phenyl)piperidine-4-carbaldehyde (0.033 g, 0.11 mmol) and NaOAc (8.2 mg, 0.1 mmol) in DCM/EtOH (30 mL/10 mL) was stirred in a round bottom flask for 1 h at 20° C. Then $NaBH_3CN$ (12.6 mg, 0.2 mmol) was added. The mixture was stirred overnight at 20° C. The mixture was concentrated to dryness and purified with silica gel column chromatography (MeOH in DCM from 0% to 12% gradient elution) to give the product (0.049 g, 57.8%). $^1$H NMR (400 MHz, DMSO) $\delta_H$ 12.60 (s, 1H), 10.27 (s, 1H), 9.97 (d, J=6.1 Hz, 1H), 8.79 (d, J=18.7 Hz, 2H), 8.18 (d, J=7.8 Hz, 1H), 8.09 (d, J=7.0 Hz, 1H), 8.04 (s, 1H), 7.67 (d, J=7.7 Hz, 1H), 7.30 (s, 1H), 7.13 (d, J=6.9 Hz, 2H), 6.97-6.92 (m, 3H), 5.41-5.34 (m, 1H), 3.71-3.68 (m, 4H), 3.64-3.56 (m, 4H), 2.70-2.64 (m, 4H), 2.53 (s, 3H), 2.47-2.43 (m, 4H), 2.25-2.19 (m, 2H), 1.84-1.81 (m, 2H), 1.75-1.70 (m, 1H), 1.56 (t, J=9.1 Hz, 3H), 1.37 (s, 9H), 1.28-1.18 (m, 2H).

Example 15: 3-(tert-butyl)-N-(4-(6-(4-(1-(2-(1-(4-(2,4-dioxotetrahydropyrimidin-1(2H)-yl)-3-fluorophenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide Step 1: tert-butyl (4-bromo-2-fluorophenyl)carbamate

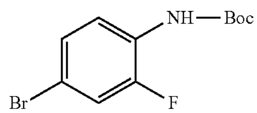

Into a 500 mL round-bottom flask were added 4-bromo-2-fluoroaniline (20.00 g) and $(Boc)_2O$ (49.80 g) in t-BuOH (250.00 mL) at 50° C. overnight. The resulting mixture was stirred overnight at 50° C. under air atmosphere. The aqueous layer was extracted with EtOAc. The residue was purified by silica gel column chromatography, eluted with PE/EtOAc (50:1) to afford the product (20 g, 65.7%).

Step 2: tert-butyl (4-(4-(2-((tert-butyldiphenylsilyl)oxy)ethyl)piperidin-1-yl)-2-fluorophenyl)carbamate

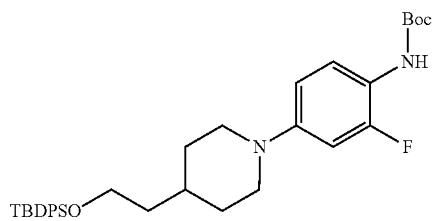

Into a 500 mL round-bottom flask of the mixture of tert-butyl (4-bromo-2-fluorophenyl)carbamate (5.00 g) and 4-(2-((tert-butyldiphenylsilyl)oxy)ethyl)piperidine (10.00 g) was added Xphos (1.65 g), $Cs_2CO_3$ (16.90 g), dioxane (300.00 mL) and $Pd_2(dba)_3$ (1.80 g) at room temperature. The resulting mixture was stirred overnight at 100° C. under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (5:1) to afford the product (8.0 g, 80.6%).

Step 3: 4-(4-(2-((tert-butyldiphenylsilyl)oxy)ethyl)piperidin-1-yl)-2-fluoroaniline

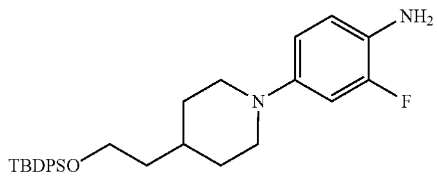

To a stirred mixture of tert-butyl (4-(4-(2-((tert-butyldiphenylsilyl)oxy)ethyl)piperidin-1-yl)-2-fluorophenyl)carbamate (8.00 g) in DCM (40.00 mL) was added TFA (10.00 mL) dropwise at room temperature. The resulting mixture was stirred for 2 h at room temperature under air atmosphere. The resulting mixture was concentrated under vacuum. The crude product was used in the next step directly without further purification.

Step 4: 3-((4-(4-(2-((tert-butyldiphenylsilyl)oxy)ethyl)piperidin-1-yl)-2-fluorophenyl)amino)propanoic acid

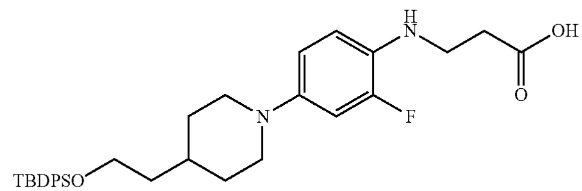

To a stirred mixture of 4-(4-(2-((tert-butyldiphenylsilyl)oxy)ethyl)piperidin-1-yl)-2-fluoroaniline (3.80 g) and acrylic acid (2.00 g) in toluene (100.00 mL) was degassed in vacuo and flushed with nitrogen for 3 times, then the mixture was heated to 100° C. in oil bath for 12 hrs. The mixture was used directly for next step.

Step 5: 1-(4-(4-(2-((tert-butyldiphenylsilyl)oxy)ethyl)piperidin-1-yl)-2-fluorophenyl)dihydropyrimidine-2,4(1H,3H)-dione

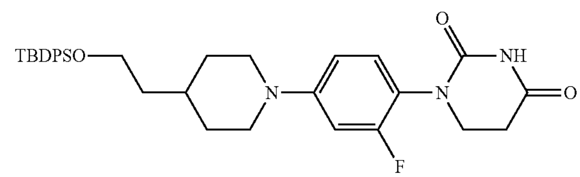

To the mixture of 3-((4-(4-(2-((tert-butyldiphenylsilyl)oxy)ethyl)piperidin-1-yl)-2-fluorophenyl)amino)propanoic acid, was added urea (1.17 g) and AcOH (30.00 mL), then the reaction was heated in 105° C. under nitrogen atmosphere for 12 hrs. The resulting mixture was concentrated under reduced pressure. The residue was purified by silica gel column chromatography, eluted with $CH_2Cl_2$/MeOH (20:1) to afford the product (3 g, 65.6%).

Step 6: 1-(2-fluoro-4-(4-(2-hydroxyethyl)piperidin-1-yl)phenyl)dihydropyrimidine-2,4(1H,3H)-dione

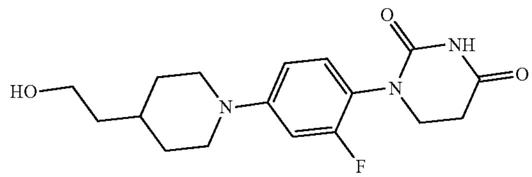 [SMILES: O=C1CCN(c2ccc(N3CCC(CCO)CC3)cc2F)C(=O)N1]

Into a 50 mL round-bottom flask were added 1-(4-(4-(2-((tert-butyldiphenylsilyl)oxy)ethyl)piperidin-1-yl)-2-fluorophenyl)dihydropyrimidine-2,4(1H,3H)-dione (1 g) and CsF (1 g) in DMF (20.00 mL) at 35° C. The final reaction mixture was stirred overnight at 35° C. The resulting mixture was extracted with EtOAc. The combined organic layers were washed with brine, dried over anhydrous $Na_2SO_4$. After filtration, the filtrate was concentrated under reduced pressure. The residue was purified by Prep-TLC ($CH_2Cl_2$/MeOH=8:1) to afford the product (206.7 mg, 35.5%). $^1H$ NMR (300 MHz, DMSO) $\delta_H$ 10.35 (s, 1H), 7.18 (d, J=9 Hz, 1H), 6.76 (m, 2H), 4.36 (t, J=5 Hz, 1H), 3.70 (m, 2H), 3.62 (m, 2H), 3.58 (m, 2H), 2.69 (m, 3H), 1.99 (m, 1H), 1.72 (m, 2H), 1.58 (m, 1H), 1.45 (m, 2H), 1.24 (m, 2H); $[M+H]^+$=336.0.

Step 7: 2-(1-(4-(2,4-dioxotetrahydropyrimidin-1(2H)-yl)-3-fluorophenyl)piperidin-4-yl)acetaldehyde

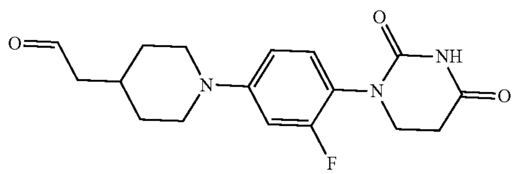 [SMILES: O=CCC1CCN(c2ccc(N3CCC(=O)NC3=O)c(F)c2)CC1]

To a solution of 1-(2-fluoro-4-(4-(2-hydroxyethyl)piperidin-1-yl)phenyl)dihydropyrimidine-2,4(1H,3H)-dione (200 mg, 0.6 mmol) in DMSO (10 mL) was added IBX (338 mg, 1.2 mmol). The mixture was stirred in a round bottom flask at room temperature overnight. After being determined the reaction to be completed by LCMS, the mixture was extracted with EA (30 mL*3), dried over anhydrous $Na_2SO_4$, and evaporated in vacuum to afford the crude product (100 mg, crude), which was used for next step without further purification. $[M+H]^+$=334.1.

Step 8: 3-(tert-butyl)-N-(4-(6-(4-(1-(2-(1-(4-(2,4-dioxotetrahydropyrimidin-1(2H)-yl)-3-fluorophenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide

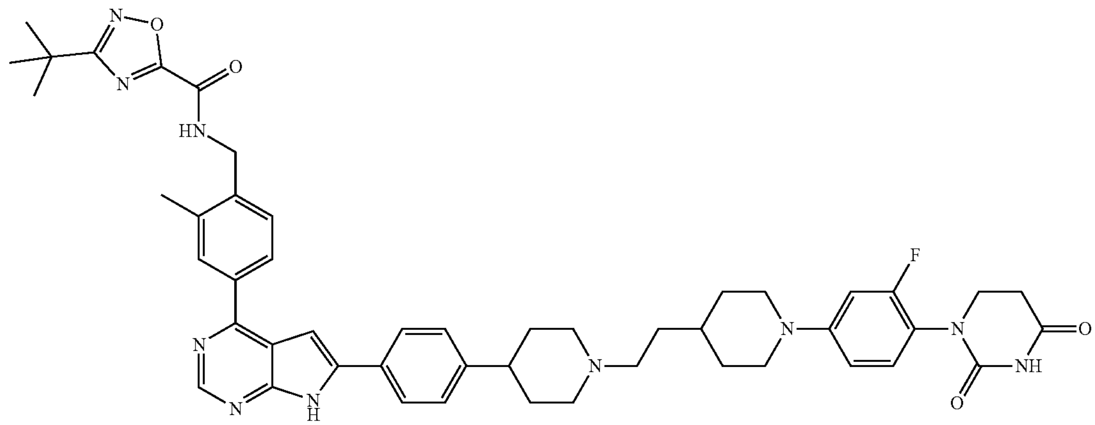 [SMILES: Cc1cc(-c2ncnc3[nH]c(-c4ccc(C5CCN(CCC6CCN(c7ccc(N8CCC(=O)NC8=O)c(F)c7)CC6)CC5)cc4)cc23)ccc1CNC(=O)c1nc(C(C)(C)C)no1]

To a solution of 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (100 mg, 0.182 mmol) in DCM (20 mL) and MeOH (5 mL) was added 2-(1-(4-(2,4-dioxotetrahydropyrimidin-1(2H)-yl)-3-fluorophenyl)piperidin-4-yl)acetaldehyde (61 mg, 0.182 mmol) and AcOH (3 drops). The mixture was stirred overnight at room temperature. To the mixture was added $H_2O$ (30 mL) and extracted with DCM (30 mL×2). The organic layers were dried over with $Na_2SO_4$, filtered and concentrated to give crude product which was further purified by prep-HPLC to give the product (22 mg, 13.9%). $^1H$ NMR (400 MHz, DMSO) $\delta_H$ 12.69 (s, 1H), 10.38 (s, 1H), 9.93-9.91 (m, 1H), 8.80 (s, 1H), 8.37 (s, 2H), 8.07 (s, 2H), 7.98 (d, J=8.0 Hz, 2H), 7.48 (d, J=8.0 Hz, 1H), 7.38-7.36 (m, 3H), 7.20-7.16 (m, 1H), 6.83-6.75 (m, 2H), 4.56 (d, J=8.0 Hz, 2H), 3.75-3.72 (m, 2H), 3.62-3.60 (m, 2H), 3.02-2.99 (m, 5H), 2.70-2.67 (m, 4H), 2.39-2.37 (m, 2H), 2.01-1.96 (m, 2H), 1.77-1.67 (m, 6H), 1.46-1.44 (m, 4H), 1.38 (s, 9H), 1.24-1.21 (m, 2H); $[M+H]^+$=867.5.

Example 16: 3-(tert-butyl)-N-(4-(6-(1-(1-((1-(4-(2,4-dioxotetrahydropyrimidin-1(2H)-yl)phenyl)piperidin-4-yl)methyl)piperidin-4-yl)-1H-pyrazol-4-yl)-7H-pyrrolo[2,3-d]pyrimidin-4-yl)-2-fluorobenzyl)-1,2,4-oxadiazole-5-carboxamide Step 1: tert-butyl 4-(4-(4,4,5,5-tetramethyl-1,3,2-dioxaborolan-2-yl)-1H-pyrazol-1-yl)piperidine-1-carboxylate

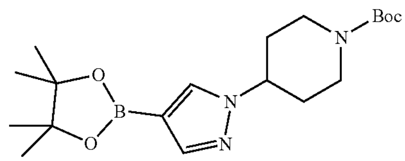 [SMILES: CC(C)(C)OC(=O)N1CCC(n2cc(B3OC(C)(C)C(C)(C)O3)cn2)CC1]

A mixture of tert-butyl 4-(4-bromo-1H-pyrazol-1-yl)piperidine-1-carboxylate (1 g, 3.03 mmol), 4,4,4',4',5,5,5',5'-octamethyl-2,2'-bi(1,3,2-dioxaborolane) (1.54 g, 6.06 mmol), $Pd(dppf)Cl_2$ (0.25 g, 0.303 mmol) and KOAc (0.89 g, 9.09 mmol) in dioxane (20 mL) was stirred in a round bottom flask under $N_2$ at 90° C. overnight. The mixture was evaporated in vacuum to afford the crude product, which was further purified with silica gel column chromatography (PE:EA=100:0~90:10 gradient elution) to give the product (1.01 g, 90%). $[M+H]^+$=378.2.

Step 2: tert-butyl 4-(4-(4-chloro-7-(phenylsulfonyl)-7H-pyrrolo[2,3-d]pyrimidin-6-yl)-1H-pyrazol-1-yl)piperidine-1-carboxylate

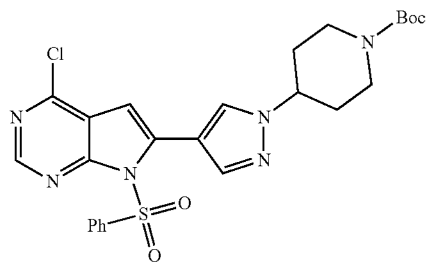 [SMILES: CC(C)(C)OC(=O)N1CCC(n2cc(-c3cc4c(Cl)ncnc4n3S(=O)(=O)c3ccccc3)cn2)CC1]

A mixture of 4-chloro-6-iodo-7-(phenylsulfonyl)-7H-pyrrolo[2,3-d]pyrimidine (0.6 g, 1.43 mmol), tert-butyl 4-(4-(4,4,5,5-tetramethyl-1,3,2-dioxaborolan-2-yl)-1H-pyrazol-1-yl)piperidine-1-carboxylate (1.01 g, 1.72 mmol), Pd(dppf)$Cl_2$ (0.12 g, 0.14 mmol) and $K_2CO_3$ (0.393 g, 2.86 mmol) in a mixture of dioxane (20 mL) and water (4 mL) was stirred in a round bottom flask at 80° C. overnight. The mixture was evaporated in vacuum to afford the crude product, which was further purified with silica gel column chromatography (PE:EA=100:0~1:1 gradient elution) to give the product (0.7 g, 90%). $[M+H]^+$=543.1.

Step 3: tert-butyl 4-(4-(4-(4-((3-(tert-butyl)-1,2,4-oxadiazole-5-carboxamido)methyl)-3-fluorophenyl)-7H-pyrrolo[2,3-d]pyrimidin-6-yl)-1H-pyrazol-1-yl)piperidine-1-carboxylate

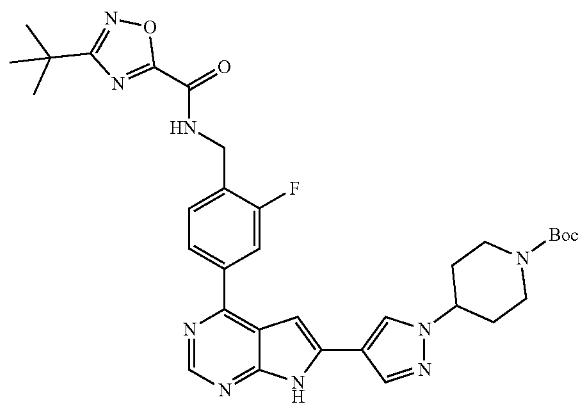 [SMILES: CC(C)(C)OC(=O)N1CCC(n2cc(-c3cc4c(-c5ccc(CNC(=O)c6nc(C(C)(C)C)no6)c(F)c5)ncnc4[nH]3)cn2)CC1]

A mixture of tert-butyl 4-(4-(4-chloro-7-(phenylsulfonyl)-7H-pyrrolo[2,3-d]pyrimidin-6-yl)-1H-pyrazol-1-yl)piperidine-1-carboxylate (0.7 g, 1.29 mmol), 3-(tert-butyl)-N-(2-fluoro-4-(4,4,5,5-tetramethyl-1,3,2-dioxaborolan-2-yl)benzyl)-1,2,4-oxadiazole-5-carboxamide (0.521 g, 1.28 mmol), Pd(dppf)$Cl_2$ (0.105 g, 0.13 mmol) and $K_2CO_3$ (0.357 g, 2.58 mmol) in a mixture of dioxane (20 mL) and water (7 mL) was stirred in a round bottom flask at 90° C. overnight. The mixture was evaporated in vacuum to afford the crude product, which was further purified with silica gel column chromatography (PE:EA=100:0~0:100 gradient elution) to give the product (0.12 g, 15%). $[M+H]^+$=644.0.

Step 4: 3-(tert-butyl)-N-(2-fluoro-4-(6-(1-(piperidin-4-yl)-1H-pyrazol-4-yl)-7H-pyrrolo[2,3-d]pyrimidin-4-yl)benzyl)-1,24-oxadiazole-5-carboxamide

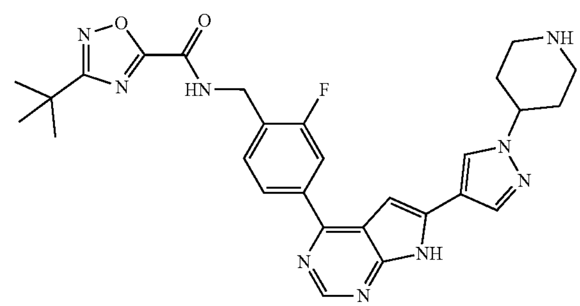 [SMILES: CC(C)(C)c1noc(C(=O)NCc2ccc(-c3ncnc4[nH]c(-c5cnn(C6CCNCC6)c5)cc34)cc2F)n1]

A mixture of tert-butyl 4-(4-(4-(4-((3-(tert-butyl)-1,2,4-oxadiazole-5-carboxamido)methyl)-3-fluorophenyl)-7H-pyrrolo[2,3-d]pyrimidin-6-yl)-1H-pyrazol-1-yl)piperidine-1-carboxylate (0.12 g, 0.18 mmol) and trifluoroacetic acid (1.25 mL) in dichloromethane (5 mL) was stirred in a round bottom flask at room temperature for 1 hour. The mixture was evaporated in vacuum to afford the crude product, which was purified by pre-HPLC to afford the product (0.052 g, 53.1%). [M+H]+=544.0.

Step 5: 3-(tert-butyl)-N-(4-(6-(1-(1-((1-(4-(2,4-dioxotetrahydropyrimidin-1(2H)-yl)phenyl)piperidin-4-yl)methyl)piperidin-4-yl)-1H-pyrazol-4-yl)-7H-pyrrolo[2,3-d]pyrimidin-4-yl)-2-fluorobenzyl)-1,2,4-oxadiazole-5-carboxamide

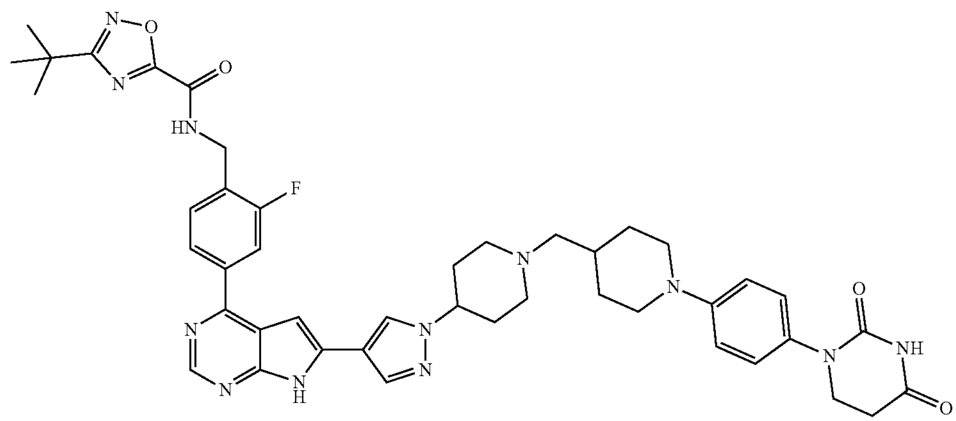 [SMILES: CC(C)(C)c1noc(C(=O)NCc2ccc(-c3ncnc4[nH]c(-c5cnn(C6CCN(CC7CCN(c8ccc(N9CCC(=O)NC9=O)cc8)CC7)CC6)c5)cc34)cc2F)n1]

A mixture of 3-(tert-butyl)-N-(2-fluoro-4-(6-(1-(piperidin-4-yl)-1H-pyrazol-4-yl)-7H-pyrrolo[2,3-d]pyrimidin-4-yl)benzyl)-1,2,4-oxadiazole-5-carboxamide (0.025 g, 0.046 mmol) and 1-(4-(2,4-dioxotetrahydropyrimidin-1(2H)-yl)phenyl)piperidine-4-carbaldehyde (0.018 g, 0.060 mmol) in dichloromethane (2.5 mL) and MeOH (0.5 mL) was stirred in a round bottom flask at room temperature for 1 hour. To the mixture was added $NaBH(OAc)_3$ (0.005 g, 0.069 mmol) and stirred in a round bottom flask at room temperature overnight. Then the mixture was evaporated in vacuum to afford the crude product, which was purified by pre-TLC (DCM:MeOH=15:1 gradient elution) to give the product (0.0283 g, 74.3%). $^1$H NMR (400 MHz, DMSO) $\delta_H$ 12.59 (s, 1H), 10.27 (s, 1H), 9.98 (s, 1H), 8.78 (s, 1H), 8.47 (s, 1H), 8.13 (s, 1H), 8.06 (d, J=7.5 Hz, 1H), 7.96 (d, J=11.4 Hz, 1H), 7.62 (s, 1H), 7.14 (d, J=8.6 Hz, 3H), 6.95 (s, 2H), 4.62 (d, J=5.3 Hz, 2H), 4.21 (s, 1H), 3.75-3.65 (m, 5H), 3.21-2.85 (m, 4H), 2.72-2.65 (m, 5H), 2.20-1.75 (m, 9H), 1.37 (s, 9H); $[M+H]^+$=829.5.

Example 17: 3-(tert-butyl)-N-(4-(6-(4-(1-((1-(2-(2,6-dioxopiperidin-3-yl)-1-oxoisoindolin-5-yl)piperidin-4-yl)methyl)piperidin-4-yl)phenyl)-7H-pyrrolo[2,3-d]pyrimidin-4-yl)-2-methylbenzyl)-1,2,4-oxadiazole-5-carboxamide Step 1: 5-(4-(hydroxymethyl)piperidin-1-yl)isobenzofuran-1(3H)-one

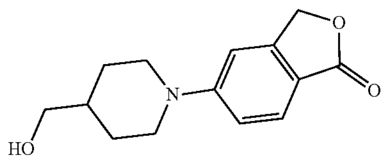 [SMILES: O=C1OCc2cc(N3CCC(CO)CC3)ccc21]

A solution of 5-fluoroisobenzofuran-1(3H)-one (5.0 g, 33 mmol), piperidin-4-ylmethanol (5.0 g, 43 mmol) and DIPEA (10.0 g, 78 mmol) in DMSO (60 mL) was heated at 130° C. for 3 hours. The reaction was quenched with water and extracted with EtOAc. The organic layer was dried over anhydrous $Na_2SO_4$, and evaporated in vacuum to afford the crude product, which was further purified with silica gel column chromatography to give the product (7.0 g, 85%). $[M+H]^+$=248.0.

Step 2: 5-(4-(((tetrahydro-2H-pyran-2-yl)oxy)methyl)piperidin-1-yl)isobenzofuran-1(3H)-one

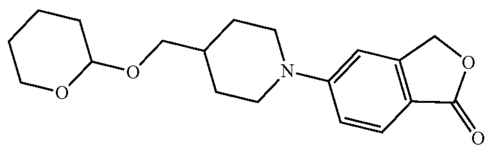 [SMILES: O=C1OCc2cc(N3CCC(COC4CCCCO4)CC3)ccc21]

A solution of 5-(4-(hydroxymethyl)piperidin-1-yl)isobenzofuran-1(3H)-one (6.0 g, 24 mmol), pyridinium toluene-4-sulphonate (700 mg, 2.8 mmol) and 3,4-dihydro-2H-pyran (6.5 g, 77 mmol) in DCM (150 mL) was stirred at room temperature for 16 hours. The reaction was quenched with water and extracted with DCM. The combined organic layers were washed with brine, dried over anhydrous $Na_2SO_4$, and evaporated in vacuum to afford the crude product, which was further purified with silica gel column chromatography to give the product (7.1 g, 87%). $[M+H]^+$=332.3.

Step 3: 2-(hydroxymethyl)-4-(4-(((tetrahydro-2H-pyran-2-yl)oxy)methyl)piperidin-1-yl)benzoic acid

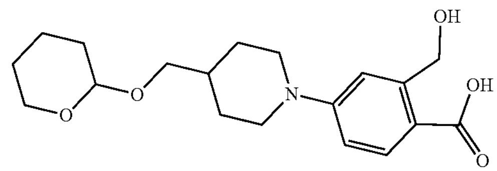 [SMILES: O=C(O)c1ccc(N2CCC(COC3CCCCO3)CC2)cc1CO]

A solution of 5-(4-(((tetrahydro-2H-pyran-2-yl)oxy)methyl)piperidin-1-yl)isobenzofuran-1(3H)-one (7.1 g, 21 mmol) and NaOH (2.5 g, 62.5 mmol) in MeOH (100 mL)/$H_2O$ (100 mL)/THF (100 mL) was stirred at room temperature for 16 hours. The solvent was removed under reduced pressure and the residue's pH value was adjusted to 6 with 1 N HCl. The mixture was extracted with EtOAc. The combined organic layers were washed with brine, dried over anhydrous $Na_2SO_4$, and evaporated in vacuum to afford the crude product (6.6 g). $[M+H]^+$=350.4.

Step 4: 2-(((tert-butyldimethylsilyl)oxy)methyl)-4-(4-(((tetrahydro-2H-pyran-2-yl)oxy)methyl)piperidin-1-yl)benzoic acid

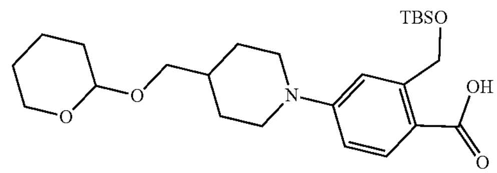 [SMILES: CC(C)(C)[Si](C)(C)OCc1cc(N2CCC(COC3CCCCO3)CC2)ccc1C(=O)O]

A mixture of 2-(hydroxymethyl)-4-(4-(((tetrahydro-2H-pyran-2-yl)oxy)methyl)piperidin-1-yl)benzoic acid (6.6 g, 19 mmol), TBSCl (5.0 g, 33 mmol), and imidazole (5.0 g, 74 mmol) in DCM (200 mL) was stirred at room temperature for 16 hours. The reaction was quenched with water and extracted with DCM. The combined organic layers were washed with brine, dried over anhydrous $Na_2SO_4$, and evaporated in vacuum to afford the crude product, which was further purified with silica gel column chromatography to give the product (8.0 g, 89%). $[M+H]^+$=464.5.

Step 5: 2-(((tert-butyldimethylsilyl)oxy)methyl)-N-(2,6-dioxopiperidin-3-yl)-4-(4-(((tetrahydro-2H-pyran-2-yl)oxy)methyl)piperidin-1-yl)benzamide

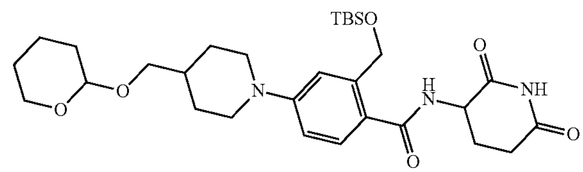 [SMILES: CC(C)(C)[Si](C)(C)OCc1cc(N2CCC(COC3CCCCO3)CC2)ccc1C(=O)NC1CCC(=O)NC1=O]

A solution of 2-(((tert-butyldimethylsilyl)oxy)methyl)-4-(4-(((tetrahydro-2H-pyran-2-yl)oxy)methyl)piperidin-1-yl) benzoic acid (8.0 g, 17 mmol), HATU (7.6 g, 20 mmol), 3-aminopiperidine-2,6-dione hydrochloride (3.7 g, 22 mmol) and DIPEA (14 mL, 80 mmol) in DMF (100 mL) was stirred at room temperature for 16 hours. The reaction was quenched with water and extracted with EtOAc. The organic layer was dried over anhydrous $Na_2SO_4$, and evaporated in vacuum to afford the crude product, which was further purified with silica gel column chromatography to give the product (5.6 g, 57%). $[M+H]^+$=574.4.

Step 6: N-(2,6-dioxopiperidin-3-yl)-2-(hydroxymethyl)-4-(4-(((tetrahydro-2H-pyran-2-yl)oxy)methyl) piperidin-1-yl)benzamide

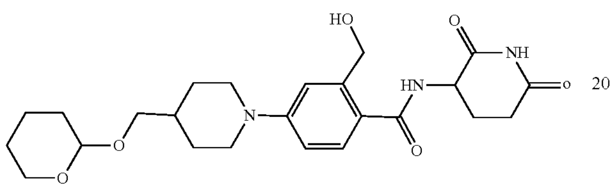

A solution of 2-(((tert-butyldimethylsilyl)oxy)methyl)-N-(2,6-dioxopiperidin-3-yl)-4-(4-(((tetrahydro-2H-pyran-2-yl) oxy)methyl)piperidin-1-yl)benzamide (5.6 g, 9.8 mmol) and TBAF (1 M in THF, 2.5 mmol) in THF (100 mL) was stirred at room temperature for 2 hours. The reaction was quenched with water and extracted with EtOAc. The organic layer was dried over anhydrous $Na_2SO_4$, and evaporated in vacuum to afford the crude product, which was further purified with silica gel column chromatography to give the product (2.5 g, 55%). $[M+H]^+$=460.4.

Step 7: 3-(1-oxo-5-(4-(((tetrahydro-2H-pyran-2-yl) oxy)methyl)piperidin-1-yl)isoindolin-2-yl)piperidine-2,6-dione

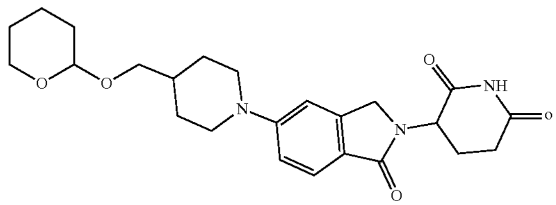

A solution of N-(2,6-dioxopiperidin-3-yl)-2-(hydroxymethyl)-4-(4-(((tetrahydro-2H-pyran-2-yl)oxy)methyl)piperidin-1-yl)benzamide (2.5 g, 5.4 mmol), TsCl (1.5 g, 7.9 mmol) and $Et_3N$ (6 mL, 43 mmol) in DCM (100 mL) was stirred at 40° C. for 16 hours. The reaction was quenched with water and extracted with DCM. The organic layer was dried over anhydrous $Na_2SO_4$, and evaporated in vacuum to afford the crude product, which was further purified with silica gel column chromatography to give the product (1.9 g, 80%). $[M+H]^+$=442.2.

Step 8: 3-(5-(4-(hydroxymethyl)piperidin-1-yl)-1-oxoisoindolin-2-yl)piperidine-2,6-dione

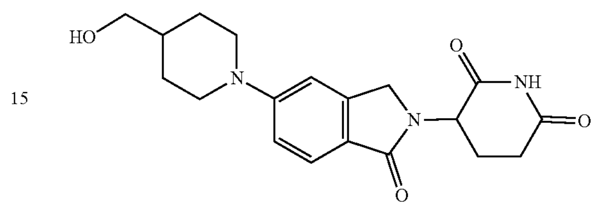

A solution of 3-(1-oxo-5-(4-(((tetrahydro-2H-pyran-2-yl) oxy)methyl)piperidin-1-yl)isoindolin-2-yl)piperidine-2,6-dione (1.8 g, 4.1 mmol) in HCl/dioxane (4 N, 5 mL)/DCM (100 mL)/MeOH (100 mL) was stirred at room temperature for 1 h. The mixture was evaporated in vacuum to afford the crude product (1.7 g). $[M+H]^+$=358.3.

Step 9: 1-(2-(2,6-dioxopiperidin-3-yl)-1-oxoisoindolin-5-yl)piperidine-4-carbaldehyde

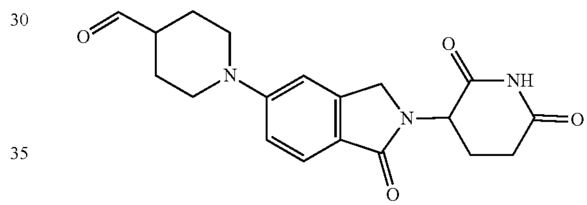

A mixture of 3-(5-(4-(hydroxymethyl)piperidin-1-yl)-1-oxoisoindolin-2-yl)piperidine-2,6-dione (200 mg, 0.51 mmol) and IBX (200 mg, 0.71 mmol) in DMSO (8 mL) was stirred at room temperature for 1 h. The reaction was quenched with water and extracted with EtOAc. The organic layer was dried over anhydrous $Na_2SO_4$ and evaporated in vacuum to give the crude product (180 mg). $[M+H]^+$=356.2.

Step 10: 3-(tert-butyl)-N-(4-(6-(4-(1-((1-(2-(2,6-dioxopiperidin-3-yl)-1-oxoisoindolin-5-yl)piperidin-4-yl)methyl)piperidin-4-yl)phenyl)-7H-pyrrolo[2,3-d]pyrimidin-4-yl)-2-methylbenzyl)-1,2,4-oxadiazole-5-carboxamide

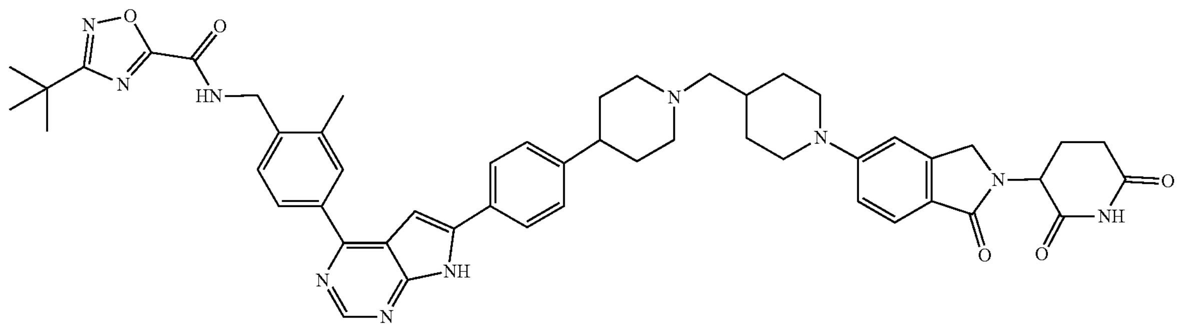 [SMILES: Cc1cc(-c2ncnc3[nH]c(-c4ccc(C5CCN(CC6CCN(c7ccc8c(c7)CN(C7CCC(=O)NC7=O)C8=O)CC6)CC5)cc4)cc23)ccc1CNC(=O)c1nc(C(C)(C)C)no1]

A mixture of 1-(2-(2,6-dioxopiperidin-3-yl)-1-oxoisoindolin-5-yl)piperidine-4-carbaldehyde (180 mg, 0.51 mmol), 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (50 mg, 0.091 mmol) and $NaBH(OAc)_3$ (100 mg, 0.47 mmol) in dichloroethane (10 mL) was stirred at room temperature for 16 hours. Then the mixture was evaporated in vacuum to afford the crude product, which was purified with silica gel column chromatography to give the product (15 mg, 10%). $^1$H NMR (400 MHz, DMSO) $\delta_H$ 12.69 (s, 1H), 10.71 (s, 1H), 9.92 (s, 1H), 8.81 (s, 1H), 8.07 (s, 2H), 8.00 (d, J=7.5 Hz, 2H), 7.55-7.44 (m, 2H), 7.38 (s, 3H), 7.06 (d, J=8.5 Hz, 1H), 7.00 (s, 1H), 5.31 (s, 2H), 4.57 (s, 3H), 3.90 (d, J=11.1 Hz, 2H), 2.85 (t, J=11.7 Hz, 3H), 2.72-2.57 (m, 4H), 2.05-1.94 (m, 3H), 1.89-1.78 (m, 5H), 1.38 (s, 9H); $[M+H]^+$=889.5.

Example 18: 3-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-1,2,4-oxadiazole-5-carboxamide Step 1: tert-butyl 4-(4-(4-chloro-7H-pyrrolo[2,3-d]pyrimidin-6-yl)phenyl)piperazine-1-carboxylate

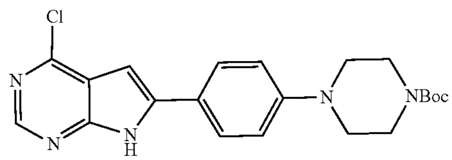 [SMILES: CC(C)(C)OC(=O)N1CCN(c2ccc(-c3cc4c(Cl)ncnc4[nH]3)cc2)CC1]

To a solution of tert-butyl 4-(4-(4-chloro-7-(phenylsulfonyl)-7H-pyrrolo[2,3-d]pyrimidin-6-yl)phenyl)piperazine-1-carboxylate (0.6 g, 1.1 mmol) in THF (20 mL) was added NaOH in MeOH (4%, 3 mL). The mixture was stirred at 20-30° C. for 1 hour. The solvent was evaporated and added $H_2O$ (20 mL). The mixture was filtered and washed with $H_2O$. Filter cake was dried under reduce pressure and used for next step directly.

Step 2: tert-butyl 4-(4-(4-(4-((3-(tert-butyl)-1,2,4-oxadiazole-5-carboxamido)methyl)-3-methylphenyl)-7H-pyrrolo[2,3-d]pyrimidin-6-yl)phenyl)piperazine-1-carboxylate

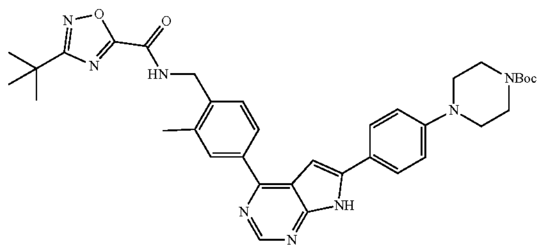 [SMILES: Cc1cc(-c2ncnc3[nH]c(-c4ccc(N5CCN(C(=O)OC(C)(C)C)CC5)cc4)cc23)ccc1CNC(=O)c1nc(C(C)(C)C)no1]

To a solution of tert-butyl 4-(4-(4-chloro-7H-pyrrolo[2,3-d]pyrimidin-6-yl)phenyl)piperazine-1-carboxylate (120 mg, 0.3 mmol) in dioxane (15 mL) and $H_2O$ (3 mL) was added 3-(tert-butyl)-N-(2-methyl-4-(4,4,5,5-tetramethyl-1,3,2-dioxaborolan-2-yl)benzyl)-1,2,4-oxadiazole-5-carboxamide (120 mg, 0.3 mmol), $K_2CO_3$ (124 mg, 0.9 mmol) and $Pd(dppf)Cl_2 \cdot CH_2Cl_2$ (22 mg, 0.03 mmol). The mixture was stirred at 90° C. under $N_2$ for 5 hours. The solvent was evaporated, added $H_2O$ (20 mL) and extracted with DCM/iPrOH (20:1, 30 mL*3). The organic phase was combined, washed with brine, concentrated and purified by pre-TLC with DCM/MeOH (DCM:MeOH=20:1) to give the product (110 mg, crude).

Step 3: 3-(tert-butyl)-N-(2-methyl-4-(6-(4-(piperazin-1-yl)phenyl)-7H-pyrrolo[2,3-d]pyrimidin-4-yl)benzyl)-1,2,4-oxadiazole-5-carboxamide hydrochloride

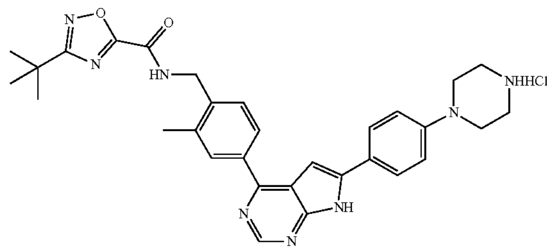

To a solution of tert-butyl 4-(4-(4-(4-((3-(tert-butyl)-1,2,4-oxadiazole-5-carboxamido)methyl)-3-methylphenyl)-7H-pyrrolo[2,3-d]pyrimidin-6-yl)phenyl)piperazine-1-carboxylate (110 mg, 0.17 mmol) in dioxane (3 mL) was added HCl/dioxane (4 N, 20 mL). The mixture was stirred at 20-30° C. for 4 hours, concentrated to 5 mL, filtered. The filter cake was washed to give the crude product which was used for next step directly. $^1$H NMR (400 MHz, DMSO) $\delta_H$ 13.53 (s, 1H), 9.99 (s, 1H), 9.38 (s, 2H), 9.00 (s, 1H), 8.04-8.02 (m, 4H), 7.57 (d, J=8.4 Hz, 1H), 7.48 (s, 1H), 7.14 (d, J=8.4 Hz, 2H), 4.59 (d, J=5.2 Hz, 2H), 3.54 (s, 4H), 3.22 (s, 4H), 2.50 (s, 3H), 1.38 (s, 9H); $[M+H]^+$=551.3.

Step 4: 3-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-1,2,4-oxadiazole-5-carboxamide

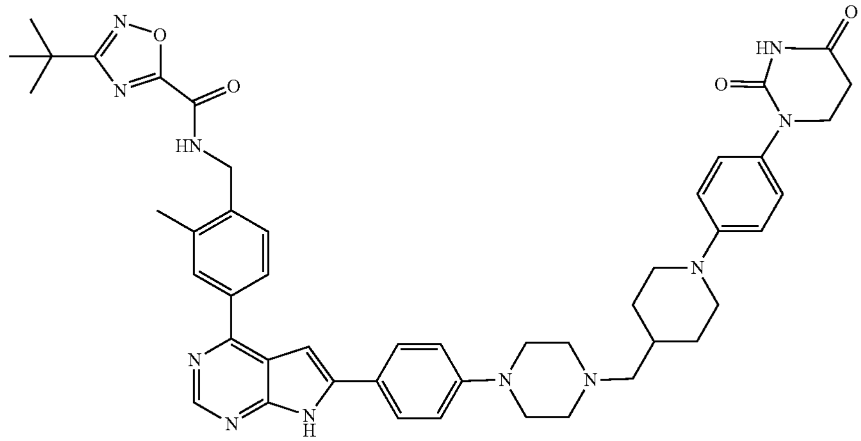 [SMILES: Cc1cc(-c2ncnc3[nH]c(-c4ccc(N5CCN(CC6CCN(c7ccc(N8CCC(=O)NC8=O)cc7)CC6)CC5)cc4)cc23)ccc1CNC(=O)c1nc(C(C)(C)C)no1]

To a solution of 3-(tert-butyl)-N-(2-methyl-4-(6-(4-(piperazin-1-yl)phenyl)-7H-pyrrolo[2,3-d]pyrimidin-4-yl)benzyl)-1,2,4-oxadiazole-5-carboxamide hydrochloride (140 mg, 0.24 mmol) in DCM/EtOH (10:1, 33 mL) was added 1-(4-(4-oxotetrahydropyrimidin-1(2H)-yl)phenyl)piperidine-4-carbaldehyde (71 mg, 0.24 mmol), HOAc (1 drop) and NaOAc (40 mg, 0.48 mmol). After stirring at 20-30° C. for 60 min $NaBH(OAc)_3$ (102 mg, 0.48 mmol) was added. The mixture was stirred at 20-30° C. for 5 hours. The solvent was evaporated, added $H_2O$ (30 mL) and extracted with DCM/iPrOH (20:1, 30 mL*3). The organic phase was combined, concentrated and purified by pre-TLC with DCM/MeOH (10:1) to give the product (100 mg, 49.8%). $^1H$ NMR (400 MHz, DMSO) $\delta_H$ 12.53 (s, 1H), 10.27 (s, 1H), 9.91 (br, 1H), 8.75 (s, 1H), 8.06 (s, 2H), 7.91 (d, J=8.4 Hz, 2H), 7.47 (d, J=8.0 Hz, 1H), 7.22 (s, 1H), 7.13 (d, J=8.4 Hz, 2H), 7.04 (d, J=8.0 Hz, 2H), 6.93 (d, J=8.4 Hz, 2H), 4.56 (d, J=5.6 Hz, 2H), 3.77-3.60 (m, 4H), 3.26 (s, 4H), 2.70-2.64 (m, 4H), 2.23 (d, J=6.0 Hz, 2H), 1.89-1.64 (m, 3H), 1.37 (s, 9H), 1.29-1.17 (m, 3H); $[M+H]^+$=836.5.

Example 19: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide Step 1: tert-butyl 4-(6-(trimethylstannyl)pyridin-3-yl)piperazine-1-carboxylate

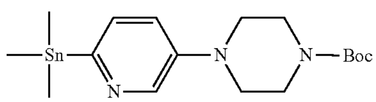 [SMILES: CC(C)(C)OC(=O)N1CCN(c2cc[c]([Sn]([CH3])([CH3])[CH3])nc2)CC1]

A mixture of tert-butyl 4-(6-bromopyridin-3-yl)piperazine-1-carboxylate (1.71 g, 5 mmol), 1,1,1,2,2,2-hexamethyldistannane (1.8 g, 5.5 mmol), $Pd(PPh_3)_4$ (0.289 g, 0.25 mmol) in dioxane (50 mL) was stirred in a sealed tube at 100° C. for 6 hours. LCMS showed that the starting material was converted totally to the target product. The resulting mixture was used directly in the next step. $[M+H]^+$=428.1.

Step 2: tert-butyl 4-(6-(4-chloro-7-((2-(trimethylsilyl)ethoxy)methyl)-7H-pyrrolo[2,3-d]pyrimidin-6-yl)pyridin-3-yl)piperazine-1-carboxylate

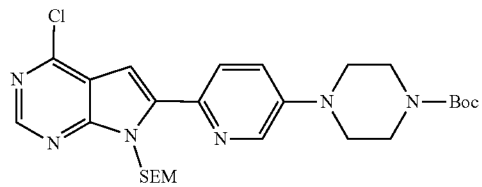 [SMILES: CC(C)(C)OC(=O)N1CCN(c2ccc(-c3cc4c(Cl)ncnc4n3COCC[Si](C)(C)C)nc2)CC1]

To the mixture of tert-butyl 4-(6-(trimethylstannyl)pyridin-3-yl)piperazine-1-carboxylate in dioxane from the previous step was added a solution of 4-chloro-6-iodo-7-((2-(trimethylsilyl)ethoxy)methyl)-7H-pyrrolo[2,3-d]pyrimidine (2.05 g, 5 mmol) and $Pd(PPh_3)_2Cl_2$ (0.178 g, 0.25 mmol) in dioxane 30 mL. The resulting mixture was stirred in a sealed tube at 100° C. for 24 hours. After being cool, the solvent was removed under reduced pressure and the residue was purified with silica gel chromatography (EtOAc in DCM from 0% to 60% gradient elution) to give the product (0.31 g, 11.4%). $[M+H]^+$=545.3.

Step 3: tert-butyl (R)-4-(6-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)pyridin-3-yl)piperazine-1-carboxylate

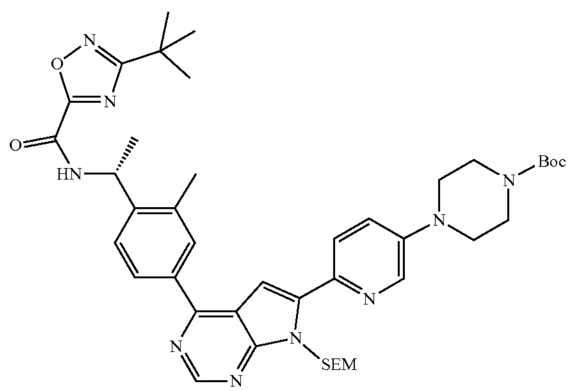 [SMILES: Cc1cc(-c2ncnc3c2cc(-c2ccc(N4CCN(C(=O)OC(C)(C)C)CC4)cn2)n3COCC[Si](C)(C)C)ccc1[C@@H](C)NC(=O)c1nc(C(C)(C)C)no1]

A mixture of tert-butyl 4-(6-(4-chloro-7-((2-(trimethylsilyl)ethoxy)methyl)-7H-pyrrolo[2,3-d]pyrimidin-6-yl)pyridin-3-yl)piperazine-1-carboxylate (0.31 g, 0.569 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (0.235 g, 0.569 mmol), $Na_2CO_3$ (90 mg, 0.853 mmol) and $Pd(dppf)Cl_2$ (20.8 mg, 0.028 mmol) in dioxane (50 mL) and $H_2O$ (10 mL) was stirred in a sealed tube at 100° C. overnight. After being cool, the reaction was quenched with water and the mixture was extracted with EtOAc. The organic layer was dried over anhydrous $Na_2SO_4$, and evaporated in vacuum to afford the crude product, which was further purified with silica gel column chromatography (EtOAc in DCM from 0% to 60% gradient elution) to give the product (0.28 g, 61.9%). $[M+H]^+$=796.0.

Step 4: (R)-3-(tert-butyl)-N-(1-(2-methyl-4-(6-(5-(piperazin-1-yl)pyridin-2-yl)-7H-pyrrolo[2,3-d]pyrimidin-4-yl)phenyl)ethyl)-1,2,4-oxadiazole-5-carboxamide, hydrochloride salt

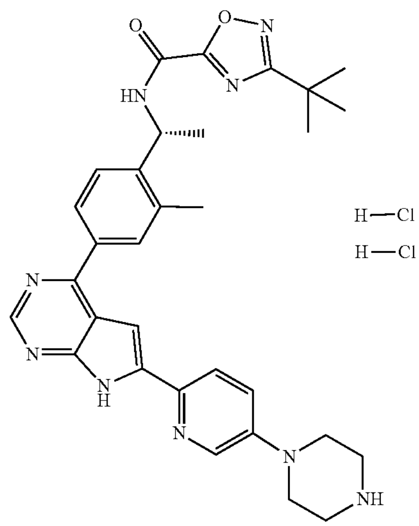

To a solution of tert-butyl (R)-4-(6-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)pyridin-3-yl)piperazine-1-carboxylate (0.28 g, 0.352 mmol) in DCM (50 mL) in a round bottom flask was added HCl in dioxane (4 N, 20 mL) at 0° C. The mixture was stirred for 48 h at 20° C. The solvent was removed under vacuum. The residue was recrystallized from MeOH/acetonitrile to afford the product (0.15 g, 67%). $^1$H NMR (400 MHz, DMSO) $\delta_H$ 12.65 (s, 1H), 9.97 (d, J=7.7 Hz, 1H), 8.80 (s, 1H), 8.44 (s, 1H), 8.09 (dd, J=16.1, 8.6 Hz, 2H), 8.02 (s, 1H), 7.68 (d, J=7.9 Hz, 1H), 7.54 (d, J=9.2 Hz, 1H), 7.45 (d, J=9.2 Hz, 2H), 7.40 (s, 1H), 7.34 (s, 1H), 5.38 (s, 1H), 3.54 (s, 4H), 3.26 (s, 4H), 2.53 (s, 3H), 1.55 (d, J=6.8 Hz, 3H), 1.37 (s, 9H); $[M+H]^+$=566.3.

Step 5: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

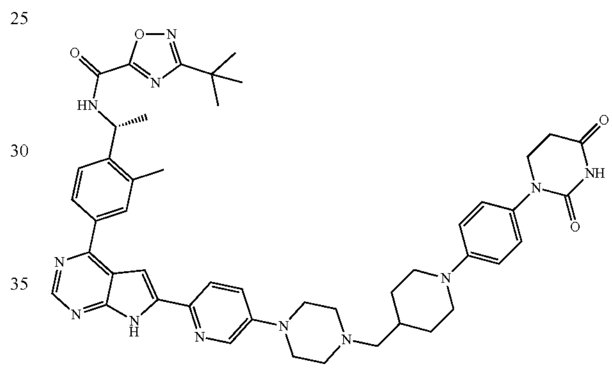

A mixture of (R)-3-(tert-butyl)-N-(1-(2-methyl-4-(6-(5-(piperazin-1-yl)pyridin-2-yl)-7H-pyrrolo[2,3-d]pyrimidin-4-yl)phenyl)ethyl)-1,2,4-oxadiazole-5-carboxamide, hydrochloride salt (0.06 g, 0.094 mmol), 1-(4-(2,4-dioxotetrahydropyrimidin-1(2H)-yl)phenyl)piperidine-4-carbaldehyde (0.033 g, 0.1 mmol) and NaOAc (16.4 mg, 0.2 mmol) in DCM/EtOH (50 mL/10 mL) was stirred in a round bottom flask for 1 h at 20° C. Then $NaBH_3CN$ (12.6 mg, 0.2 mmol) was added. The mixture was stirred for 8 hours at 20° C. The mixture was concentrated to dryness and purified with silica gel column chromatography (MeOH in DCM from 0% to 10% gradient elution) to give the product (0.028 g, 35.0%). $^1$H NMR (400 MHz, DMSO) $\delta_H$ 12.61 (s, 1H), 10.27 (s, 1H), 9.96 (d, J=7.3 Hz, 1H), 8.78 (s, 1H), 8.39 (s, 1H), 8.10-8.12 (m, 3H), 7.68 (d, J=8.0 Hz, 1H), 7.46 (d, J=9.2 Hz, 1H), 7.40 (s, 1H), 7.13 (d, J=8.2 Hz, 2H), 6.93 (d, J=8.1 Hz, 2H), 5.40-5.34 (m, 1H), 3.72-3.66 (m, 4H), 3.32-3.28 (m, 4H), 2.73-2.66 (m, 4H), 2.54-2.52 (m, 7H), 2.24 (d, J=5.9 Hz, 2H), 1.92-1.79 (m, 2H), 1.75-1.71 (m, 1H), 1.55 (d, J=6.4 Hz, 3H), 1.37 (s, 9H), 1.27-1.20 (m, 2H); $[M+H]^+$=851.5.

Example 20: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide Step 1: tert-butyl 4-(4-(4-chloro-7-(phenylsulfonyl)-7H-pyrrolo[2,3-d]pyrimidin-6-yl)phenyl)piperazine-1-carboxylate

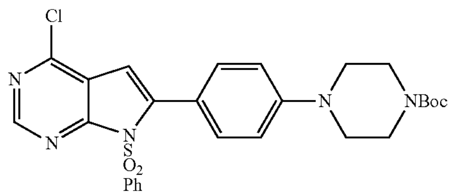

To a solution of 4-chloro-6-iodo-7-(phenylsulfonyl)-7H-pyrrolo[2,3-d]pyrimidine (2.5 g, 14.4 mmol) in dioxane (35 mL) and $H_2O$ (7 mL) was added tert-butyl 4-(4-(4,4,5,5-tetramethyl-1,3,2-dioxaborolan-2-yl)phenyl)piperazine-1-carboxylate (1.6 g, 4.2 mmol), $K_2CO_3$ (1.6 g, 12 mmol) and Pd(dppf)$Cl_2$·$CH_2Cl_2$ (0.3 g, 0.4 mmol). The mixture was stirred at 80° C. for 6 hours and concentrated to dryness. Water (30 mL) was added into the residue and extracted with EtOAc (30 mL*2). The organic phase was concentrated and purified by flash chromatography with PE/EtOAc (100:1 to 7:3) to give the product (1.9 g, 86.4%).

Step 2: tert-butyl 4-(4-(4-chloro-7H-pyrrolo[2,3-d]pyrimidin-6-yl)phenyl)piperazine-1-carboxylate

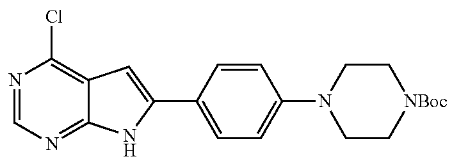 [SMILES: CC(C)(C)OC(=O)N1CCN(c2ccc(-c3cc4c(Cl)ncnc4[nH]3)cc2)CC1]

To a solution of tert-butyl 4-(4-(4-chloro-7-(phenylsulfonyl)-7H-pyrrolo[2,3-d]pyrimidin-6-yl)phenyl)piperazine-1-carboxylate (4.0 g, 7.2 mmol) in THF (30 mL) was added NaOH in MeOH (4%, 5 mL). After being stirred at 20-30° C. for 1 hour, the solvent was evaporated and $H_2O$ (20 mL) was added. The mixture was filtered, and the filter cake was washed with $H_2O$. The product (3 g, crude) was isolated after drying under reduce pressure and used for next step directly.

Step 3: tert-butyl (R)-4-(4-(4-(4-(1-(3-(tert-butyl)-1,2,4-oxadiazole-5-carboxamido)ethyl)-3-methylphenyl)-7H-pyrrolo[2,3-d]pyrimidin-6-yl)phenyl)piperazine-1-carboxylate

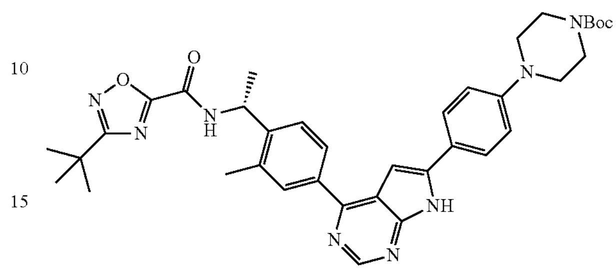

To a solution of tert-butyl 4-(4-(4-chloro-7H-pyrrolo[2,3-d]pyrimidin-6-yl)phenyl)piperazine-1-carboxylate (413 mg, 1 mmol) in dioxane/$H_2O$ (5:1, 45 mL) was added (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (413 mg, 1.0 mmol), $K_2CO_3$ (414 mg, 3.0 mmol) and Pd(dppf)$Cl_2$·$CH_2Cl_2$ (82 mg, 0.1 mmol). The mixture was stirred at 100° C. under $N_2$ for 6 hours. After the solvent was evaporated, water (20 mL) was added. The mixture was extracted with DCM (30 mL*2). The organic phase was combined, concentrated and purified by pre-TLC with DCM/MeOH (100:1 to 20:1) to give the product (600 mg, 90.2%).

Step 4: (R)-3-(tert-butyl)-N-(1-(2-methyl-4-(6-(4-(piperazin-1-yl)phenyl)-7H-pyrrolo[2,3-d]pyrimidin-4-yl)phenyl)ethyl)-1,2,4-oxadiazole-5-carboxamide hydrochloride

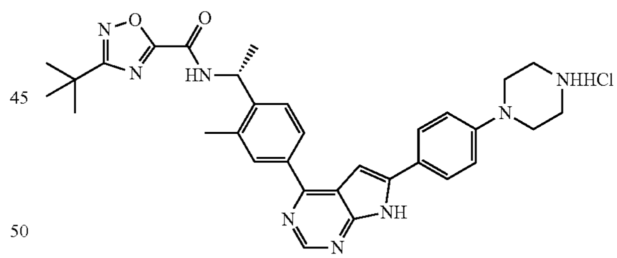

To a solution of tert-butyl (R)-4-(4-(4-(4-(1-(3-(tert-butyl)-1,2,4-oxadiazole-5-carboxamido)ethyl)-3-methylphenyl)-7H-pyrrolo[2,3-d]pyrimidin-6-yl)phenyl)piperazine-1-carboxylate (1.1 g, 1.6 mmol) in dioxane (3 mL) was added HCl/dioxane (4 N, 30 mL). The mixture was concentrated to 10 mL after being stirred at 20-30° C. for 3 hours. The solid was separated by filtration and washed with dioxane (10 mL). The product (1 g, 100%) was isolated after being dried under reduce pressure. $^1H$ NMR (400 MHz, DMSO) $\delta_H$ 13.43 (s, 1H), 10.06 (d, J=7.2 Hz, 1H), 9.34 (s, 2H), 8.98 (s, 1H), 8.19-7.92 (m, 4H), 7.75 (d, J=8.4 Hz, 1H), 7.48 (s, 1H), 7.13 (d, J=8.8 Hz, 2H), 5.38 (t, J=7.2 Hz, 1H), 3.55 (s, 4H), 3.22 (s, 4H), 2.57 (s, 3H), 1.56 (d, J=6.8 Hz, 3H), 1.38 (s, 9H); $[M+H]^+$=565.3.

Step 5: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

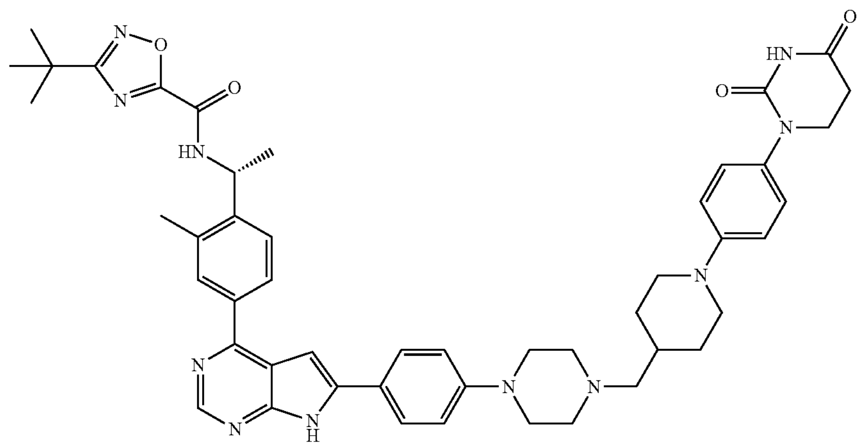 [SMILES: Cc1cc(-c2ncnc3[nH]c(-c4ccc(N5CCN(CC6CCN(c7ccc(N8CCC(=O)NC8=O)cc7)CC6)CC5)cc4)cc23)ccc1[C@@H](C)NC(=O)c1nc(C(C)(C)C)no1]

To a solution of (R)-3-(tert-butyl)-N-(1-(2-methyl-4-(6-(4-(piperazin-1-yl)phenyl)-7H-pyrrolo[2,3-d]pyrimidin-4-yl)phenyl)ethyl)-1,2,4-oxadiazole-5-carboxamide hydrochloride (0.8 g, 1.33 mmol) in DCM/EtOH (5:1, 60 mL) was added 1-(4-(4-oxotetrahydropyrimidin-1(2H)-yl)phenyl)piperidine-4-carbaldehyde (0.4 g, 1.33 mmol) and NaOAc (0.33 g, 4.0 mmol). $NaBH(OAc)_3$ (0.85 g, 4.0 mmol) was added after being stirred at 20-30° C. for 60 min. The mixture was stirred at 20-30° C. for another 2 hours. The solvent was evaporated and purified directly by chromatography on silica gel with DCM/MeOH (100:1 to 20:1) to give the product (400 mg, 35.4%). $^1$H NMR (400 MHz, DMSO) $\delta_H$ 12.52 (s, 1H), 10.27 (s, 1H), 9.97 (d, J=7.6 Hz, 1H), 8.75 (s, 1H), 8.09 (d, J=8.4 Hz, 1H), 8.03 (s, 1H), 7.91 (d, J=8.4 Hz, 2H), 7.66 (d, J=8.0 Hz, 1H), 7.23 (s, 1H), 7.13 (d, J=8.4 Hz, 2H), 7.03 (d, J=8.4 Hz, 2H), 6.93 (d, J=8.8 Hz, 2H), 5.38 (br, 1H), 3.69 (t, J=6.8 Hz, 4H), 3.26 (s, 4H), 2.69-2.67 (m, 5H), 2.60-2.50 (m, 5H), 2.24 (br, 2H), 1.89-1.67 (m, 3H), 1.55 (d, J=7.2 Hz, 3H), 1.37 (s, 9H), 1.24 (br, 3H); $[M+H]^+$ =850.4.

Example 21: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-fluorophenyl)ethyl)-1,2,4-oxadiazole-5-carboxamide

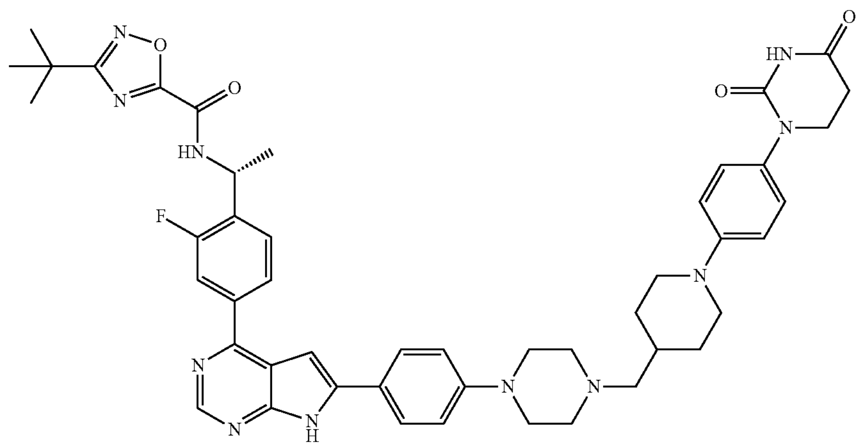 [SMILES: C[C@@H](NC(=O)c1nc(C(C)(C)C)no1)c1ccc(-c2ncnc3[nH]c(-c4ccc(N5CCN(CC6CCN(c7ccc(N8CCC(=O)NC8=O)cc7)CC6)CC5)cc4)cc23)cc1F]

The titled compound was synthesized in the procedures similar to Example 19. $^1$H NMR (400 MHz, DMSO) $\delta_H$ 12.61 (s, 1H), 10.27 (s, 1H), 10.03 (d, J=7.2 Hz, 1H), 8.78 (s, 1H), 8.13 (d, J=8.0 Hz, 1H), 8.00 (d, J=12.0 Hz, 1H), 7.93 (d, J=7.2 Hz, 2H), 7.71 (t, J=8.0 Hz, 1H), 7.30 (s, 1H), 7.13 (d, J=8.8 Hz, 2H), 7.04 (d, J=7.6 Hz, 2H), 6.93 (d, J=8.0 Hz, 2H), 5.58-5.38 (m, 1H), 3.71-3.66 (m, 4H), 3.26 (s, 4H), 2.72-2.65 (m, 5H), 2.60-2.50 (m, 2H), 2.22 (br, 2H), 1.87-1.69 (m, 3H), 1.59 (d, J=6.8 Hz, 3H), 1.38 (s, 9H), 1.24 (br, 3H); $[M+H]^+$=854.4.

Example 22: 3-(tert-butyl)-N-(4-(6-(4-(1-(2-(1-(4-(2,4-dioxotetrahydropyrimidin-1(2H)-yl)-3-methylphenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide Step 1: 4-(2-((tert-butyldiphenylsilyl)oxy)ethyl)piperidine

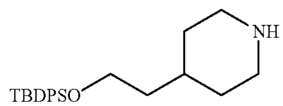

Into a 1000 mL round-bottom flask, was placed 4-piperidineethanol (20.00 g, 154.795 mmol), DMF (300.00 mL), tert-butyl(chloro)diphenylsilane (85.10 g, 309.612 mmol), imidazole (26.35 g, 386.988 mmol). The resulting solution was stirred for 1 hr at room temperature. The resulting solution was diluted with $H_2O$. The resulting solution was extracted with ethyl acetate and the organic layers were combined and dried over anhydrous sodium sulfate and concentrated under vacuum. The residue was applied onto a silica gel column with ethyl acetate/petroleum ether (1:7) to give the product (22 g, 38.66%).

Step 2: 4-(2-((tert-butyldiphenylsilyl)oxy)ethyl)-1-(3-methyl-4-nitrophenyl)piperidine

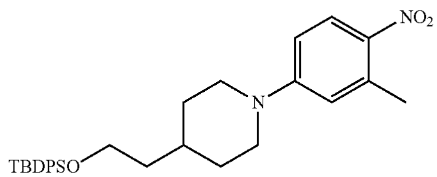

Into a 100 mL round-bottom flask, was placed 4-(2-((tert-butyldiphenylsilyl)oxy)ethyl)piperidine (5.00 g, 13.601 mmol), DMSO (50.00 mL), 4-fluoro-2-methyl-1-nitrobenzene (2.11 g, 13.601 mmol), DIEA (6.80 mL, 39.040 mmol). The resulting solution was stirred for 1 hr at 60° C. The reaction mixture was cooled to room temperature. The resulting solution was diluted with $H_2O$. The resulting solution was extracted with ethyl acetate and the organic layers were combined, dried over anhydrous sodium sulfate and concentrated under vacuum. The residue was applied onto a silica gel column with ethyl acetate/petroleum ether (1:8) to give the product (5.2 g, 76.05%).

Step 3: 4-(4-(2-((tert-butyldiphenylsilyl)oxy)ethyl)piperidin-1-yl)-2-methylaniline

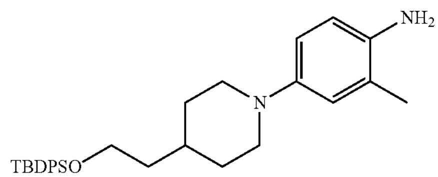

Into a 100 mL round-bottom flask, was placed 4-(2-((tert-butyldiphenylsilyl)oxy)ethyl)-1-(3-methyl-4-nitrophenyl)piperidine (5.20 g, 10.344 mmol), methanol (50.00 mL), acetic acid (0.20 mL), Pd/C (1.00 g, 9.397 mmol). To the above mixture, $H_2$ (g) was introduced in. The resulting solution was stirred for 3 hr at room temperature. The solids were filtered out. The resulting mixture was concentrated under vacuum to give the product (5 g, crude).

Step 4: 3-((4-(4-(2-((tert-butyldiphenylsilyl)oxy)ethyl)piperidin-1-yl)-2-methylphenyl)amino)propanoic acid

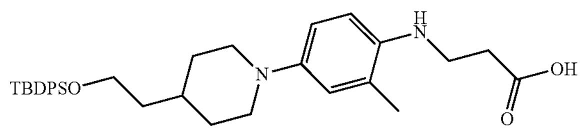

Into a 100 mL round-bottom flask purged and maintained with an inert atmosphere of nitrogen, was placed 4-(4-(2-((tert-butyldiphenylsilyl)oxy)ethyl)piperidin-1-yl)-2-methylaniline (2.50 g, 5.288 mmol), toluene (20.00 mL), acrylic acid (0.65 mL). The resulting solution was stirred overnight at 100° C. The reaction mixture was cooled to room temperature. The resulting mixture was concentrated under vacuum to give the product (2.85 g, 74.19%).

Step 5: 1-(4-(4-(2-((tert-butyldiphenylsilyl)oxy)ethyl)piperidin-1-yl)-2-methylphenyl)dihydropyrimidine-2,4(1H,3H)-dione

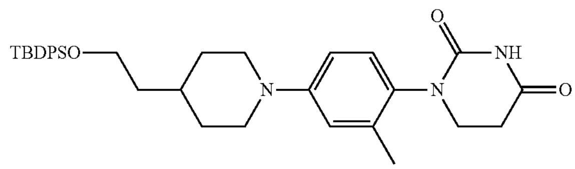

Into a 100 mL round-bottom flask, was placed 3-((4-(4-(2-((tert-butyldiphenylsilyl)oxy)ethyl)piperidin-1-yl)-2-methylphenyl)amino)propanoic acid (2.85 g, 5.231 mmol), toluene (25.00 mL), AcOH (12.00 mL) and urea (1.00 g, 16.651 mmol). The resulting solution was stirred overnight at 105° C. The reaction mixture was cooled to room temperature. The resulting mixture was concentrated under vacuum. The residue was purified by Prep-TLC with ethyl acetate/petroleum ether (3:1) to give the product (1.65 g, 55.35%).

Step 6: 1-(4-(4-(2-hydroxyethyl)piperidin-1-yl)-2-methylphenyl)dihydropyrimidine-2,4(1H,3H)-dione

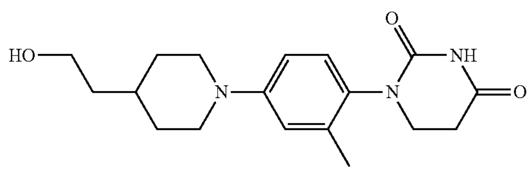 [SMILES: Cc1cc(N2CCC(CCO)CC2)ccc1N1CCC(=O)NC1=O]

Into a 50 mL round-bottom flask, was placed 1-(4-(4-(2-((tert-butyldiphenylsilyl)oxy)ethyl)piperidin-1-yl)-2-methylphenyl)dihydropyrimidine-2,4(1H,3H)-dione (1.37 g, 2.404 mmol), DMF (10.00 mL), CsF (1.82 g, 11.981 mmol). The resulting solution was stirred for 2 hr at 40° C. The resulting solution was diluted with $H_2O$. The resulting solution was extracted with ethyl acetate and the organic layers were combined, dried over anhydrous sodium sulfate and concentrated under vacuum. The residue was purified by Prep-TLC with dichloromethane/methanol (10:1) to give the product (379.2 mg, 47.59%). $^1H$ NMR (300 MHz, DMSO) $\delta_H$ 10.22 (s, 1H), 7.02 (d, J=8.5 Hz, 1H), 6.83-6.70 (m, 2H), 4.35 (t, J=5.0 Hz, 1H), 3.73-3.58 (m, 3H), 3.52-3.38 (m, 3H), 2.80-2.64 (m, 2H), 2.61 (dd, J=12.3, 9.8 Hz, 2H), 2.10 (s, 3H), 1.72 (d, J=12.7 Hz, 2H), 1.38 (q, J=6.6 Hz, 2H), 1.31-1.13 (m, 3H); $[M+H]^+$=332.19.

Step 7: 2-(1-(4-(2,4-dioxotetrahydropyrimidin-1(2H)-yl)-3-methylphenyl)piperidin-4-yl)acetaldehyde

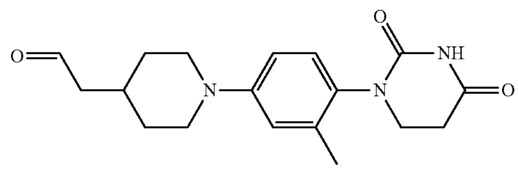 [SMILES: Cc1cc(N2CCC(CC=O)CC2)ccc1N1CCC(=O)NC1=O]

To a solution of 1-(4-(4-(2-hydroxyethyl)piperidin-1-yl)-2-methylphenyl)dihydropyrimidine-2,4(1H,3H)-dione (200 mg, 0.6 mmol) in DMSO (10 mL) was added IBX (338 mg, 1.2 mmol). The mixture was stirred in a round bottom flask at rt overnight. After being determined the reaction to be completed by LCMS, the mixture was extracted with EtOAc (30 mL*3), dried over anhydrous $Na_2SO_4$, and evaporated in vacuum to afford the crude product (100 mg, crude), which was used for next step without further purification. $[M+H]^+$=330.1.

Step 8: 3-(tert-butyl)-N-(4-(6-(4-(1-(2-(1-(4-(2,4-dioxotetrahydropyrimidin-1(2H)-yl)-3-methylphenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide

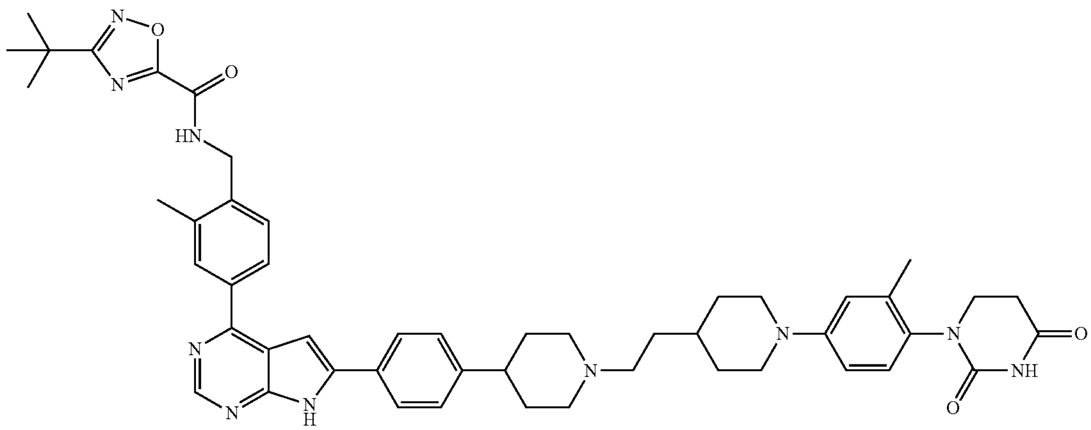 [SMILES: Cc1cc(-c2ncnc3[nH]c(-c4ccc(C5CCN(CCC6CCN(c7ccc(N8CCC(=O)NC8=O)c(C)c7)CC6)CC5)cc4)cc23)ccc1CNC(=O)c1nc(C(C)(C)C)no1]

To a solution of 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (100 mg, 0.182 mmol) in DCM (20 mL) and MeOH (5 mL) was added 2-(1-(4-(2,4-dioxotetrahydropyrimidin-1(2H)-yl)-3-methylphenyl)piperidin-4-yl)acetaldehyde (60 mg, 0.182 mmol) and AcOH (3 drops). The mixture was stirred overnight at room temperature. To the mixture was added $H_2O$ (30 mL) and extracted with DCM (30 mL×2). The organic layers were dried over with $Na_2SO_4$, filtered and concentrated to give crude product which was further purified by prep-HPLC to give the product (32 mg, 20.4%). $^1H$ NMR (400 MHz, DMSO) $\delta_H$ 12.68 (s, 1H), 10.25 (s, 1H), 9.93-9.91 (m, 1H), 8.80 (s, 1H), 8.22 (s, 2H), 8.07 (s, 2H), 7.98 (d, J=8.0 Hz, 2H), 7.48 (d, J=8.0 Hz, 1H), 7.38-7.37 (m, 3H), 7.40 (d, J=8.0 Hz, 1H), 6.81-6.76 (m, 2H), 4.56 (d, J=8.0 Hz, 2H), 3.47-3.44 (m, 2H), 3.04-3.01 (m, 2H), 2.72-2.61 (m, 5H), 2.40-2.39 (m, 2H), 2.12 (s, 3H), 2.05-2.00 (m, 2H), 1.77-1.68 (m, 6H), 1.47-1.45 (m, 3H), 1.37 (s, 9H), 1.26-1.24 (m, 2H); $[M+H]^+$= 863.5.

Example 23: 3-(tert-butyl)-N-(4-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-2-fluorobenzyl)-1,2,4-oxadiazole-5-car)oxamide

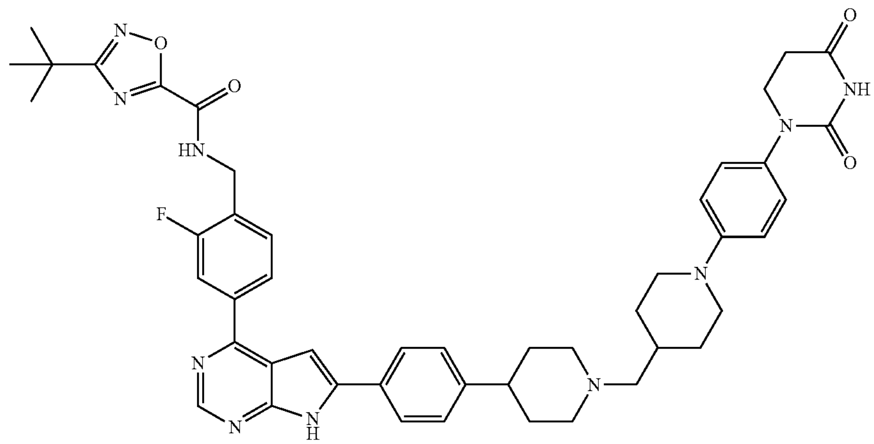 [SMILES: CC(C)(C)c1noc(C(=O)NCc2ccc(-c3ncnc4[nH]c(-c5ccc(C6CCN(CC7CCN(c8ccc(N9CCC(=O)NC9=O)cc8)CC7)CC6)cc5)cc34)cc2F)n1]

The titled compound was synthesized in the procedures similar to Example 22. $^1H$ NMR (400 MHz, DMSO) $\delta_H$ 12.79 (s, 1H), 10.29 (s, 1H), 10.02 (s, 1H), 8.87-8.16 (m, 1H), 8.25-8.03 (m, 5H), 7.64 (s, 1H), 7.46-7.41 (m, 3H), 7.18-7.14 (m, 2H), 6.98-6.93 (m, 2H), 4.65 (s, 2H), 3.73-3.71 (m, 4H), 3.03-3.01 (m, 2H), 2.69-2.60 (m, 6H), 2.25-2.22 (m, 2H), 2.05-2.02 (m, 3H), 1.86-1.82 (m, 4H), 1.40 (s, 9H), 1.28-1.26 (m, 3H); $[M+H]^+$=839.5.

Example 24: 3-(tert-butyl)-N-(4-(6-(4-(1-(2-(1-(3-chloro-4-(2,4-dioxotetrahydropyrimidin-1(2H)-yl)phenyl)piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide Step 1: 2-(1-(3-chloro-4-nitrophenyl)piperidin-4-yl)ethan-1-ol

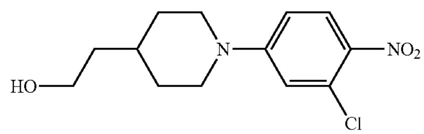

To a solution of 2-chloro-4-fluoro-1-nitrobenzene (141.0 g, 0.8 mol) and $K_2CO_3$ (278 g, 2.01 mol) in DMF (300 mL) was added 2-(piperidin-4-yl)ethan-1-ol (147 g, 0.89 mol). Then the resulting mixture was stirred at 25° C. for 5 hr. TLC (petroleum ether/ethyl acetate=10/1) showed the starting material was consumed completely. The mixture was poured into $H_2O$ (300 mL). The aqueous phase was extract with ethyl acetate (300 mL). The organic layer was dried with anhydrous $Na_2SO_4$, filtered and concentrated in vacuum to afford the product (255 g, crude).

Step 2: 4-(2-((tert-butyldimethylsilyl)oxy)ethyl)-1-(3-chloro-4-nitrophenyl)piperidine

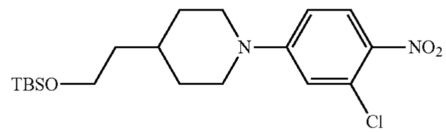

To a solution of 2-(1-(3-chloro-4-nitrophenyl)piperidin-4-yl)ethan-1-ol (255.0 g, 0.90 mol) and imidazole (91.5 g, 1.343 mol) in THF (1280 mL) was added TBSCl (202 g, 1.343 mol). Then the resulting mixture was stirred at 25° C. for 3 hr. TLC (petroleum ether/ethyl acetate=10/1) showed the starting material was consumed completely. The mixture was poured into $H_2O$ (765 mL). The aqueous phase was extracted with dichloromethane (765 mL). The organic layer was dried with anhydrous $Na_2SO_4$, filtered and concentrated in vacuum to afford the product (320 g, 89.5%).

Step 3: 4-(4-(2-((tert-butyldimethylsilyl)oxy)ethyl) piperidin-1-yl)-2-chloroaniline

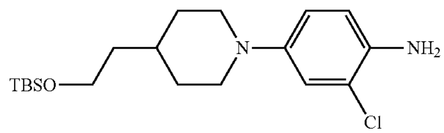 [SMILES: CC(C)(C)[Si](C)(C)OCCC1CCN(c2ccc([N+](=O)[O-])c(Cl)c2)CC1]

To a solution of 4-(2-((tert-butyldimethylsilyl)oxy)ethyl)-1-(3-chloro-4-nitrophenyl)piperidine (320.0 g, 0.8 mol), and Fe (224 g, 4.01 mol) in MeOH (1920 mL) was added HOAc (289 g, 4.81 mol) at 25° C. Then the resulting mixture was stirred at 65° C. for 3 hr. TLC (petroleum ether/ethyl acetate=2/1) showed the starting material was consumed completely. The reaction mixture was filtered and concentrated in vacuo. The residue was purified by column chromatography ($SiO_2$, petroleum ether:ethyl acetate=50:1 to 10:1) to give the product (138.0 g, 46.6%).

Step 4: 3-((4-(4-(2-((tert-butyldimethylsilyl)oxy) ethyl)piperidin-1-yl)-2-chlorophenyl)amino)propanoic acid

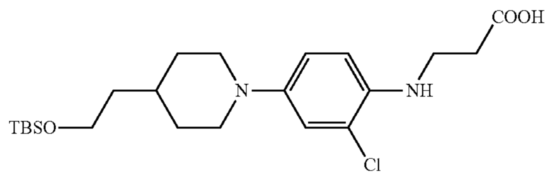 [SMILES: CC(C)(C)[Si](C)(C)OCCC1CCN(c2ccc(NCCC(=O)O)c(Cl)c2)CC1]

To a solution of 4-(4-(2-((tert-butyldimethylsilyl)oxy) ethyl)piperidin-1-yl)-2-chloroaniline (80.0 g, 0.217 mol) in toluene (400 mL) was added acrylic acid (80 mL), the mixture was stirred at 110° C. under $N_2$ for 5 hrs. TLC (dichloromethane:methanol=10:1) showed the starting material was consumed completely. The mixture was concentrated under reduced pressure to afford the product (120.0 g, crude).

Step 5: 2-(1-(3-chloro-4-(2,4-dioxotetrahydropyrimidin-1(2H)-yl)phenyl)piperidin-4-yl)ethyl acetate

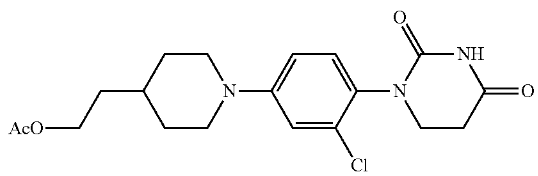 [SMILES: CC(=O)OCCC1CCN(c2ccc(N3CCC(=O)NC3=O)c(Cl)c2)CC1]

To a solution of 3-((4-(4-(2-((tert-butyldimethylsilyl)oxy) ethyl)piperidin-1-yl)-2-chlorophenyl)amino)propanoic acid (120.0 g, 0.272 mol) in HOAc (600 mL) was added urea (32.7 g, 0.544 mol) at 25° C. Then the resulting mixture was stirred at 120° C. for 12 hr. TLC (dichloromethane:methanol=10:1) showed the starting material was consumed completely. The reaction mixture was concentrated in vacuo. The residue was purified by column chromatography ($SiO_2$, petroleum ether:ethyl acetate=10:1 to 1:1) to give the product (30.0 g, 28.0%). $^1$H NMR (400 MHz, DMSO) $\delta_H$ 7.23 (d, J=8.80 Hz, 1H), 7.04 (d, J=2.80 Hz, 1H), 6.94-6.92 (m, 1H), 4.17-4.15 (m, 2H), 3.73-3.71 (m, 4H), 2.83-2.81 (m, 4H), 2.03 (s, 3H), 1.82 (d, J=0.80 Hz, 2H), 1.62-1.60 (m, 3H), 1.35-1.33 (m, 2H); $[M+H]^+$=394.1.

Step 6: 1-(2-chloro-4-(4-(2-hydroxyethyl)piperidin-1-yl)phenyl)dihydropyrimidine-2,4(1H,3H)-dione

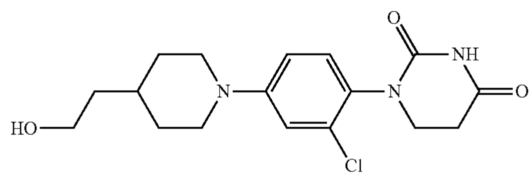 [SMILES: O=C1CCN(c2ccc(N3CCC(CCO)CC3)cc2Cl)C(=O)N1]

To a solution of 2-(1-(3-chloro-4-(2,4-dioxotetrahydropyrimidin-1(2H)-yl)phenyl)piperidin-4-yl)ethyl acetate (40.0 g, 0.102 mol) in MeOH (120 mL)/THF (120 mL) was added $K_2CO_3$ (42.1 g, 0.305 mol) at 25° C. Then the resulting mixture was stirred at 25° C. for 2 hr. TLC (dichloromethane:methanol=10:1) showed the starting material was consumed completely. The reaction mixture was concentrated in vacuo. The residue was purified by column chromatography ($SiO_2$, petroleum ether:ethyl acetate=10:1 to 0:1) to give the product (30.0 g, 83.9%). $^1$H NMR (400 MHz, DMSO) $\delta_H$ 10.4 (s, 1H), 7.22 (d, J=8.80 Hz, 1H), 7.00 (d, J=2.40 Hz, 1H), 6.92 (t, J=4.40 Hz, 1H), 4.37 (s, 1H), 3.73 (d, J=12.8 Hz, 2H), 3.53-3.51 (m, 4H), 2.70-2.68 (m, 4H), 1.72 (d, J=12.0 Hz, 2H), 1.40-1.38 (m, 3H), 1.20-1.18 (m, 2H); $[M+H]^+$=352.1.

Step 7: 2-(1-(3-chloro-4-(2,4-dioxotetrahydropyrimidin-1(2H)-yl)phenyl)piperidin-4-yl)acetaldehyde

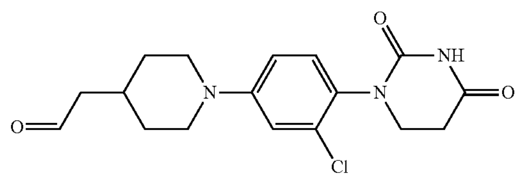 [SMILES: O=CCC1CCN(c2ccc(N3CCC(=O)NC3=O)c(Cl)c2)CC1]

1-(2-chloro-4-(4-(2-hydroxyethyl)piperidin-1-yl)phenyl) dihydropyrimidine-2,4(1H,3H)-dione (1.5 g, 4.26 mmol) was dissolved in DMSO (15 mL) and IBX (1.79 g, 6.39 mmol) was added, the reaction was stirred at 25° C. overnight until LC-MS indicated all the starting material was consumed. EtOAc (30 mL) and water (30 mL) were added to quench the reaction. The mixture was filtered to afford the product (1 g, 70%), which was used directly without further purification. $[M+H]^+$=350.2.

Step 8: 3-(tert-butyl)-N-(4-(6-(4-(1-(2-(1-(3-chloro-4-(2,4-dioxotetrahydropyrimidin-1(2H)-yl)phenyl) piperidin-4-yl)ethyl)piperidin-4-yl)phenyl)-7H-pyrrolo[2,3-d]pyrimidin-4-yl)-2-methylbenzyl)-1,2,4-oxadiazole-5-carboxamide

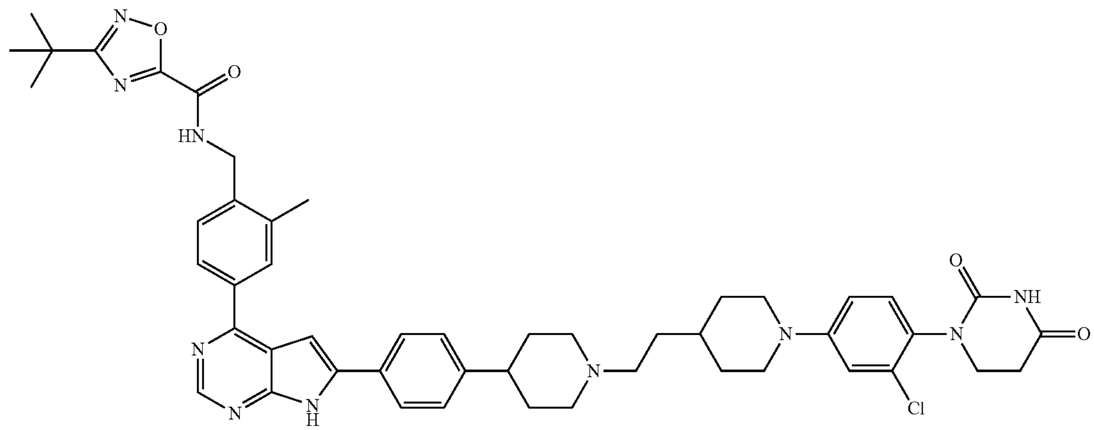 [SMILES: Cc1cc(-c2ncnc3[nH]c(-c4ccc(C5CCN(CCC6CCN(c7ccc(N8CCC(=O)NC8=O)c(Cl)c7)CC6)CC5)cc4)cc23)ccc1CNC(=O)c1nc(C(C)(C)C)no1]

To a solution of compound 3-(tert-butyl)-N-(2-methyl-4-(6-(4-(piperidin-4-yl)phenyl)-7H-pyrrolo[2,3-d]pyrimidin-4-yl)benzyl)-1,2,4-oxadiazole-5-carboxamide (0.15 g, 0.273 mmol) and 2-(1-(3-chloro-4-(2,4-dioxotetrahydropyrimidin-1(2H)-yl)phenyl)piperidin-4-yl)acetaldehyde (0.153 g, 0.436 mmol) in DCE/MeOH (18 mL, 5/1) was added a drop of HOAc. The mixture was stirred for 0.5 h. $NaBH(OAc)_3$ (0.116 g, 0.546 mmol) was added and the reaction was stirred at room temperature overnight. The mixture was concentrated to dryness and purified by PRE-HPLC to afford the product (167.55 mg, 69.47%). $^1H$ NMR (400 MHz, DMSO) $\delta_H$ 12.72 (s, 1H), 10.38 (s, 1H), 9.92 (s, 1H), 8.82 (s, 1H), 8.07-8.04 (m, 5H), 7.48 (d, J=7.2 Hz, 1H), 7.40-7.37 (m, 3H), 7.25 (d, J=9.2 Hz, 1H), 7.05 (s, 1H), 6.96-6.94 (m, 1H), 4.57 (s, 2H), 3.79 (d, J=10.7 Hz, 2H), 3.68-3.48 (m, 4H), 3.21-2.81 (m, 5H), 2.79-2.62 (m, 5H), 2.14-1.43 (m, 10H), 1.38 (s, 9H), 1.33-1.23 (m, 2H); $[M+H]^+$=883.5.

Example 25: (R)-3-(tert-butyl)-N-(1-(4-(8-(4-(4-((1-(4-(2,4-dioxotetrahydropyrimidin-1(2H)-yl)phenyl) piperidin-4-yl)methyl)piperazin-1-yl)phenyl)-9H-purin-6-yl)-2-methylphenyl)ethyl)-1,2,4-oxadiazole-5-carboxamide Step 1: tert-butyl 4-(4-(6-chloro-9H-purin-8-yl)phenyl)piperazine-1-carboxylate

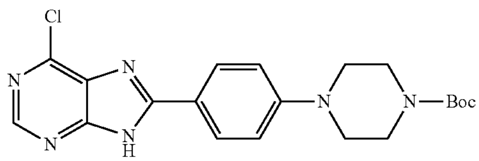 [SMILES: CC(C)(C)OC(=O)N1CCN(c2ccc(-c3nc4c(Cl)ncnc4[nH]3)cc2)CC1]

A mixture of 6-chloropyrimidine-4,5-diamine (1 g, 6.9 mmol), tert-butyl 4-(4-formylphenyl)piperazine-1-carboxylate (2 g, 6.9 mmol) and $CoCl_2$ (0.089 g, 0.69 mmol) in DMF (50 mL) was stirred at 85° C. overnight under 02 atmosphere. After being cooled, the reaction mixture was poured to 100 mL of ice-water. The precipitate was collected by filtration and washed with water. The solid was dried under vacuum to afford the product (2.64 g, 91.9%). $[M+H]^+$= 415.0.

Step 2: tert-butyl (R)-4-(4-(6-(4-(1-(3-(tert-butyl)-1,2,4-oxadiazole-5-carboxamido)ethyl)-3-methylphenyl)-9H-purin-8-yl)phenyl)piperazine-1-carboxylate

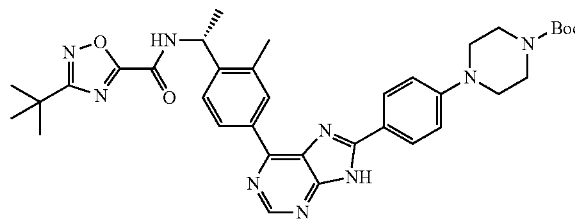 [SMILES: Cc1cc(-c2ncnc3[nH]c(-c4ccc(N5CCN(C(=O)OC(C)(C)C)CC5)cc4)nc23)ccc1[C@@H](C)NC(=O)c1nc(C(C)(C)C)no1]

A mixture of tert-butyl 4-(4-(6-chloro-9H-purin-8-yl)phenyl)piperazine-1-carboxylate (0.415 g, 1 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (0.413 g, 1 mmol), $Na_2CO_3$ (0.212 g, 2 mmol) and $Pd(dppf)Cl_2$ (36.5 mg, 0.05 mmol) in dioxane (50 mL) and $H_2O$ (8 mL) was stirred in a sealed tube at 100° C. for 48 hours. After being cooled, the solvent was removed and the residue was purified with silica gel column (EtOAc in DCM, 0% to 100%) to afford the product (0.48 g, 72.2%). $[M+H]^+$=666.0.

Step 3: (R)-3-(tert-butyl)-N-(1-(2-methyl-4-(8-(4-(piperazin-1-yl)phenyl)-9H-purin-6-yl)phenyl) ethyl)-1,2,4-oxadiazole-5-carboxamide hydrochloride

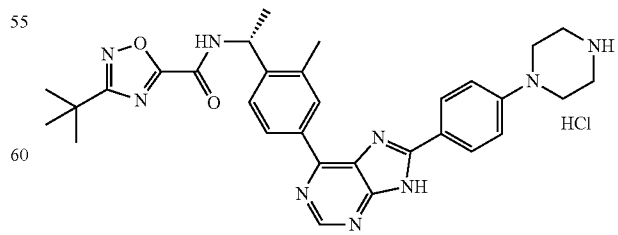

To a solution of tert-butyl (R)-4-(4-(6-(4-(1-(3-(tert-butyl)-1,2,4-oxadiazole-5-carboxamido)ethyl)-3-methylphenyl)-9H-purin-8-yl)phenyl)piperazine-1-carboxylate (0.2 g, 0.3 mmol) in EtOAc (10 mL) was added HCl in dioxane (4 N, 20 mL) at 0° C. The mixture was stirred for 4 h at 20° C. The precipitate was collected with filtration and dried in vacuum to afford the product (0.14 g, 77.8%).

Step 4: (R)-3-(tert-butyl)-N-(1-(4-(8-(4-(4-((1-(4-(2,4-dioxotetrahydropyrimidin-1(2H)-yl)phenyl)piperidin-4-yl)methyl)piperazin-1-yl)phenyl)-9H-purin-6-yl)-2-methylphenyl)ethyl)-1,2,4-oxadiazole-5-carboxamide

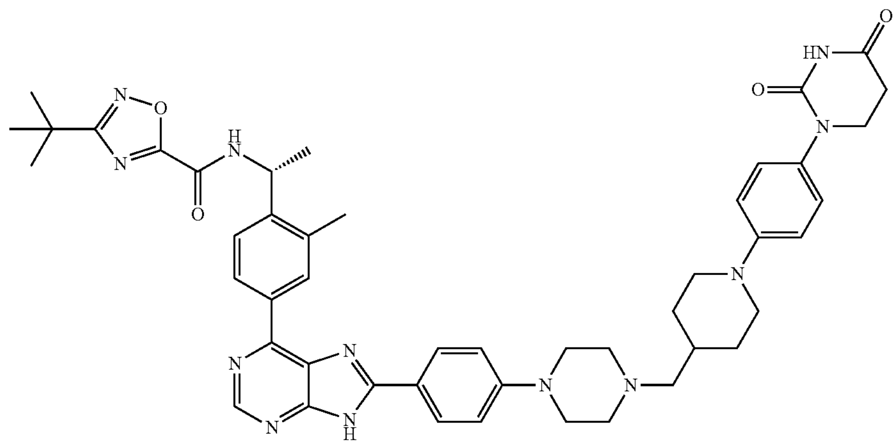 [SMILES: Cc1cc(-c2ncnc3[nH]c(-c4ccc(N5CCN(CC6CCN(c7ccc(N8CCC(=O)NC8=O)cc7)CC6)CC5)cc4)nc23)ccc1[C@@H](C)NC(=O)c1nc(C(C)(C)C)no1]

A mixture of (R)-3-(tert-butyl)-N-(1-(2-methyl-4-(8-(4-(piperazin-1-yl)phenyl)-9H-purin-6-yl)phenyl)ethyl)-1,2,4-oxadiazole-5-carboxamide hydrochloride (0.14 g, 0.232 mmol), 1-(4-(2,4-dioxotetrahydropyrimidin-1(2H)-yl)phenyl)piperidine-4-carbaldehyde (0.07 g, 0.232 mmol) and NaOAc (38 mg, 0.465 mmol) in DCM/EtOH (100 mL/50 mL) was stirred in a round bottom flask for 1 h at 20° C. Then $NaBH_3CN$ (29 mg, 0.465 mmol) was added. The mixture was stirred overnight at 20° C. The mixture was concentrated to dryness and purified with silica gel column chromatography (MeOH in DCM from 0% to 10% gradient elution) to give the product (92.6 mg, 46.7%). $^1H$ NMR (400 MHz, DMSO) $\delta_H$ 13.76 (s, 1H), 10.28 (s, 1H), 9.94 (s, 1H), 8.83 (d, J=18.7 Hz, 2H), 8.68 (s, 1H), 8.20 (s, 2H), 7.71 (s, 1H), 7.15 (s, 4H), 6.95 (s, 2H), 5.40 (s, 1H), 3.71 (s, 4H), 3.36 (s, 4H), 2.70 (s, 4H), 2.55 (s, 3H), 2.51-2.47 (m, 4H), 2.26 (s, 2H), 1.84 (s, 2H), 1.75 (s, 1H), 1.57 (s, 3H), 1.39 (d, J=5.3 Hz, 9H), 1.26 (s, 2H); $[M+H]^+$=851.5.

Example 26: (R)-3-(tert-butyl)-N-(1-(4-(6-(6-(4-(2-(1-(3-chloro-4-(2,4-dioxotetrahydropyrimidin-1(2H)-yl)phenyl)piperidin-4-yl)ethyl)piperazin-1-yl)pyridin-3-yl)-7H-pyrrolo[2,3-d]pyrimidin-4-yl)-2-methylphenyl)ethyl)-1,2,4-oxadiazole-5-carboxamide

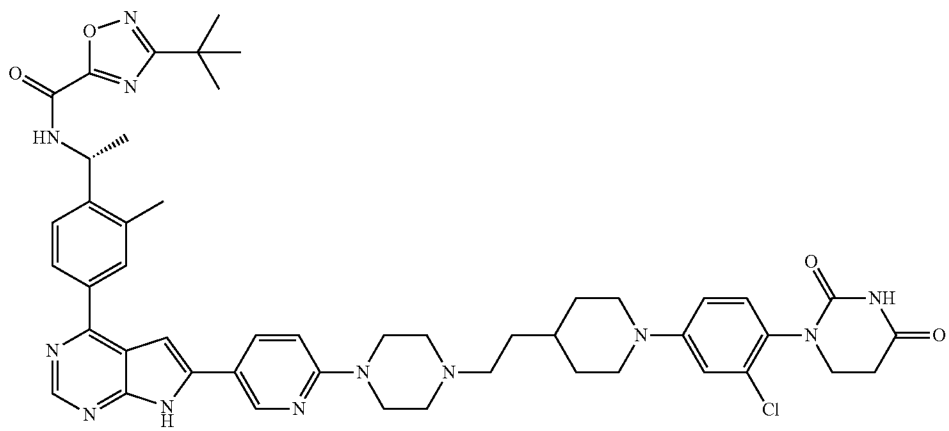 [SMILES: Cc1cc(-c2ncnc3[nH]c(-c4ccc(N5CCN(CCC6CCN(c7ccc(N8CCC(=O)NC8=O)c(Cl)c7)CC6)CC5)nc4)cc23)ccc1[C@@H](C)NC(=O)c1nc(C(C)(C)C)no1]

The titled compound was synthesized in the procedures similar to Example 24. $^1H$ NMR (400 MHz, DMSO) $\delta_H$ 12.61 (s, 1H), 10.38 (s, 1H), 9.97 (s, 1H), 8.82 (s, 1H), 8.78 (s, 1H), 8.20 (s, 1H), 8.09 (s, 1H), 8.05 (s, 1H), 7.69 (s, 1H), 7.31 (s, 1H), 7.23 (s, 1H), 7.03 (s, 1H), 6.95 (s, 2H), 5.39 (s, 1H), 3.75 (d, J=11.5 Hz, 2H), 3.60 (s, 6H), 3.34 (s, 2H), 2.72 (s, 4H), 2.53 (s, 3H), 2.48-2.46 (m, 1H), 2.39 (s, 2H), 1.88 (s, 1H), 1.76 (s, 2H), 1.56 (s, 3H), 1.47 (s, 2H), 1.38 (s, 9H), 1.25 (s, 2H); $[M+H]^+$=899.5.

Example 27: 3-(tert-butyl)-N-(4-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-2-methylbenzyl)-1,2,4-oxadiazole-5-carboxamide Step 1: tert-butyl 4-((4-(4-(4-chloro-7-((2-(trimethylsilyl)ethoxy)methyl)-7H-pyrrolo[2,3-d]pyrimidin-6-yl)phenoxy)piperidin-1-yl)methyl)piperidine-1-carboxylate

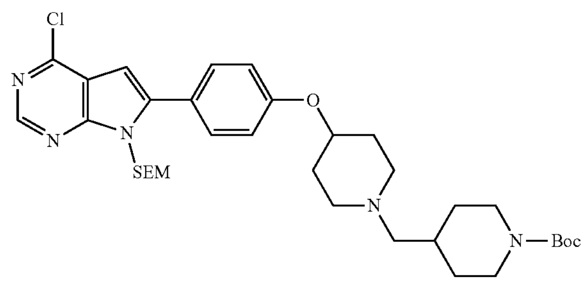 [SMILES: CC(C)(C)OC(=O)N1CCC(CN2CCC(Oc3ccc(-c4cc5c(Cl)ncnc5n4COCC[Si](C)(C)C)cc3)CC2)CC1]

A mixture of 4-chloro-6-iodo-7-((2-(trimethylsilyl)ethoxy)methyl)-7H-pyrrolo[2,3-d]pyrimidine (409 mg, 1.0 mmol), tert-butyl 4-((4-(4-(4,4,5,5-tetramethyl-1,3,2-dioxaborolan-2-yl)phenoxy)piperidin-1-yl)methyl)piperidine-1-carboxylate (550 mg, 1.1 mmol), $Pd(dppf)Cl_2$ (73 mg, 0.1 mmol) and $K_2CO_3$ (276 mg, 2.0 mmol) in dioxane (10 mL) and water (3 mL) was stirred in a round bottom flask at 80° C. overnight. The mixture was used for next step without further purification. $[M+H]^+$=656.6.

Step 2: tert-butyl 4-((4-(4-(4-(4-((3-(tert-butyl)-1,2,4-oxadiazole-5-carboxamido)methyl)-3-methylphenyl)-7-((2-(trimethylsilyl)ethoxy)methyl)-7H-pyrrolo[2,3-d]pyrimidin-6-yl)phenoxy)piperidin-1-yl)methyl)piperidine-1-carboxylate

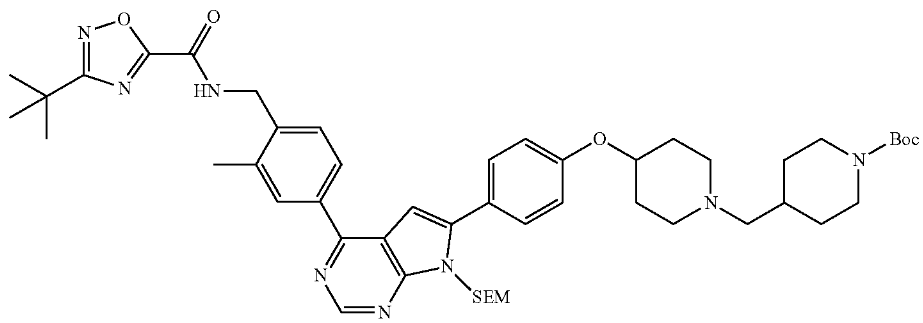 [SMILES: Cc1cc(-c2ncnc3c2cc(-c2ccc(OC4CCN(CC5CCN(C(=O)OC(C)(C)C)CC5)CC4)cc2)n3COCC[Si](C)(C)C)ccc1CNC(=O)c1nc(C(C)(C)C)no1]

A solution of mixture from last step was added 3-(tert-butyl)-N-(2-methyl-4-(4,4,5,5-tetramethyl-1,3,2-dioxaborolan-2-yl)benzyl)-1,2,4-oxadiazole-5-carboxamide (399 mg, 1.0 mmol), Pd(dppf)$Cl_2$ (73 mg, 0.1 mmol) and $Cs_2CO_3$ (650 mg, 2.0 mmol). The mixture reaction was stirred in a round bottom flask at 110° C. overnight. Then the mixture was evaporated in vacuum to afford the crude product, which was purified with silica gel column chromatography (PE:EA=100:0~20:80 gradient elution) to give the product (493 mg, 55%, two step). $[M+H]^+$=893.5.

Step 3: 3-(tert-butyl)-N-(4-(7-(hydroxymethyl)-6-(4-((1-(piperidin-4-ylmethyl)piperidin-4-yl)oxy)phenyl)-7H-pyrrolo[2,3-d]pyrimidin-4-yl)-2-methylbenzyl)-1,2,4-oxadiazole-5-carboxamide

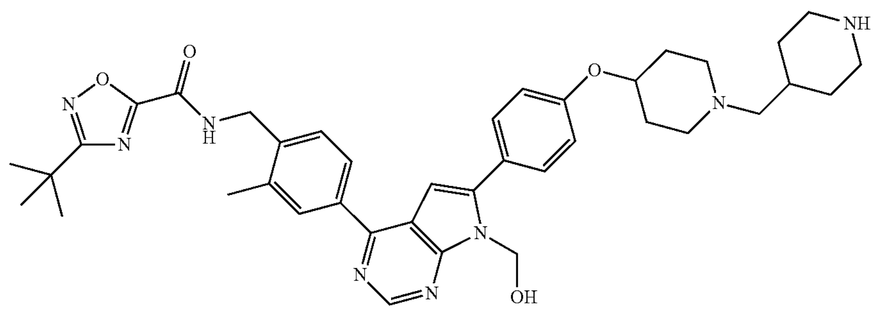 [SMILES: Cc1cc(-c2ncnc3c2cc(-c2ccc(OC4CCN(CC5CCNCC5)CC4)cc2)n3CO)ccc1CNC(=O)c1nc(C(C)(C)C)no1]

A mixture of tert-butyl 4-((4-(4-(4-(4-((3-(tert-butyl)-1,2,4-oxadiazole-5-carboxamido)methyl)-3-methylphenyl)-7-((2-(trimethylsilyl)ethoxy)methyl)-7H-pyrrolo[2,3-d]pyrimidin-6-yl)phenoxy)piperidin-1-yl)methyl)piperidine-1-carboxylate (493 mg, 0.55 mmol) and trifluoroacetic acid (3 mL) in dichloromethane (3 mL) was stirred in a round bottom flask at room temperature overnight. Then the mixture was evaporated in vacuum to afford the crude product (516 mg, crude), which was used for next step without further purification. $[M+H]^+$=693.6.

Step 4: 3-(tert-butyl)-N-(2-methyl-4-(6-(4-((1-(piperidin-4-ylmethyl)piperidin-4-yl)oxy)phenyl)-7H-pyrrolo[2,3-d]pyrimidin-4-yl)benzyl)-1,2,4-oxadiazole-5-carboxamide

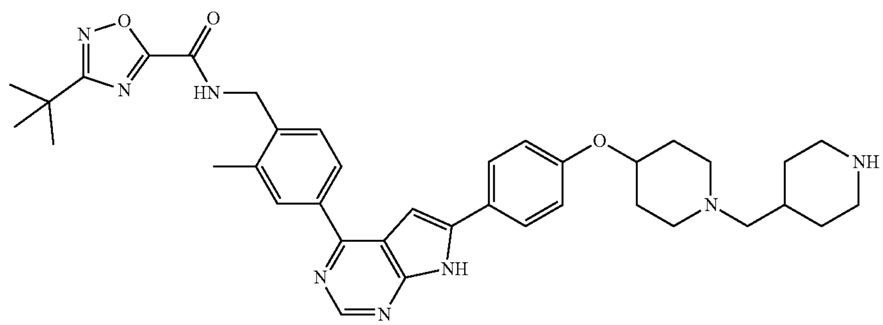 [SMILES: Cc1cc(-c2ncnc3[nH]c(-c4ccc(OC5CCN(CC6CCNCC6)CC5)cc4)cc23)ccc1CNC(=O)c1nc(C(C)(C)C)no1]

A mixture of 3-(tert-butyl)-N-(4-(7-(hydroxymethyl)-6-(4-((1-(piperidin-4-ylmethyl)piperidin-4-yl)oxy)phenyl)-7H-pyrrolo[2,3-d]pyrimidin-4-yl)-2-methylbenzyl)-1,2,4-oxadiazole-5-carboxamide (516 mg, 0.55 mmol) and ammonium hydroxide (2 mL) in methanol (10 mL) was stirred in a round bottom flask at room temperature overnight. Then the mixture was evaporated in vacuum to afford the crude product, which was purified with C18 column chromatography (0.1% FA in water:acetonitrile=90:10~60:40 gradient elution) to give the product (303 mg, 80%). $[M+H]^+$=663.6.

Step 5: 3-(tert-butyl)-N-(4-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-2-methylbenzyl)-1,2,4-oxadiazole-5-carboxamide

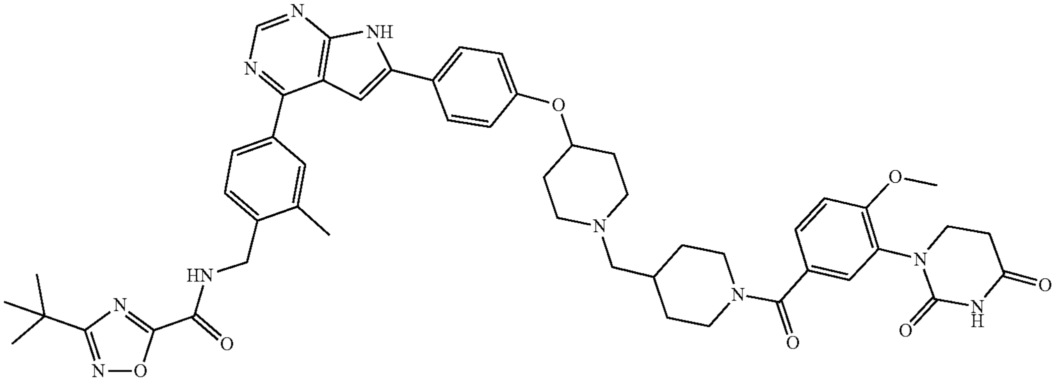 [SMILES: COc1ccc(C(=O)N2CCC(CN3CCC(Oc4ccc(-c5cc6c(-c7ccc(CNC(=O)c8nc(C(C)(C)C)no8)c(C)c7)ncnc6[nH]5)cc4)CC3)CC2)cc1N1CCC(=O)NC1=O]

A mixture of 3-(2,4-dioxotetrahydropyrimidin-1(2H)-yl)-4-methoxybenzoic acid (37 mg, 0.15 mmol) and HATU (57 mg, 0.15 mmol) in DCM (10 mL) and DMF (1 mL) was stirred in a round bottom flask at room temperature for 1 hour. Then to the mixture was added 3-(tert-butyl)-N-(2-methyl-4-(6-(4-((1-(piperidin-4-ylmethyl)piperidin-4-yl)oxy)phenyl)-7H-pyrrolo[2,3-d]pyrimidin-4-yl)benzyl)-1,2,4-oxadiazole-5-carboxamide (100 mg, 0.14 mmol) and DIPEA (56 mg, 0.4 mmol) and stirred at room temperature overnight. The reaction was purified with C18 column chromatography (0.1% FA in water:acetonitrile=60:40~20:80 gradient elution) to give the product (57 mg, 45%). $^1H$ NMR (400 MHz, DMSO) $\delta_H$ 12.62 (s, 1H), 10.36 (s, 1H), 9.92 (s, 1H), 8.79 (s, 1H), 8.14 (s, 1H), 8.07 (s, 2H), 7.99 (d, J=8.0 Hz, 2H), 7.48 (d, J=8.0 Hz, 1H), 7.38 (d, J=7.6 Hz, 1H), 7.31 (d, J=13.8 Hz, 2H), 7.16 (d, J=8.4 Hz, 1H), 7.10 (d, J=8.4 Hz, 2H), 4.65-4.52 (m, 3H), 3.85 (s, 3H), 3.67-3.56 (m, 2H), 3.09-2.84 (m, 4H), 2.78-2.63 (m, 3H), 2.10-2.00 (m, 2H), 1.98-1.87 (m, 1H), 1.83-1.58 (m, 4H), 1.38 (s, 9H), 1.19-1.06 (m, 2H); $[M+H]^+$=909.8.

Example 28: N-(3-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-5-fluoro-2-methylphenyl)-2-fluoro-4-(2-hydroxypropan-2-yl)benzamide Step 1: tert-butyl 4-(4-(4-(5-fluoro-3-(2-fluoro-4-(2-hydroxypropan-2-yl)benzamido)-2-methylphenyl)-7-((2-(trimethylsilyl)ethoxy)methyl)-7H-pyrrolo[2,3-d]pyrimidin-6-yl)phenyl)piperidine-1-carboxylate

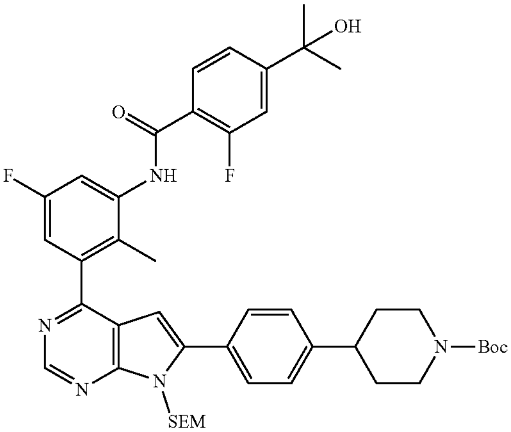 [SMILES: Cc1c(NC(=O)c2ccc(C(C)(C)O)cc2F)cc(F)cc1-c1ncnc2c1cc(-c1ccc(C3CCN(C(=O)OC(C)(C)C)CC3)cc1)n2COCC[Si](C)(C)C]

To a solution of tert-butyl 4-(4-(4-chloro-7-((2-(trimethylsilyl)ethoxy)methyl)-7H-pyrrolo[2,3-d]pyrimidin-6-yl)phenyl)piperidine-1-carboxylate (560 mg, 1.0 mmol) in dioxane (20 mL) and water (5 mL) was added 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (480 mg, 1.1 mmol), Pd(dppf)$Cl_2$ (73 mg, 0.1 mmol) and $Cs_2CO_3$ (850 mg, 2.6 mmol). The mixture reaction was stirred in a round bottom flask at 110° C. overnight. Then the mixture was evaporated in vacuum to afford the crude product, which was purified with silica gel column chromatography (PE:EA=100:0~0:100 gradient elution) to give the product (570 mg, 70%). $[M+H]^+$=812.5.

Step 2: 2-fluoro-N-(5-fluoro-2-methyl-3-(6-(4-(piperidin-4-yl)phenyl)-7H-pyrrolo[2,3-d]pyrimidin-4-yl)phenyl)-4-(2-hydroxypropan-2-yl)benzamide and 2-fluoro-N-(5-fluoro-2-methyl-3-(6-(4-(piperidin-4-yl)phenyl)-7H-pyrrolo[2,3-d]pyrimidin-4-yl)phenyl)-4-(prop-1-en-2-yl)benzamide

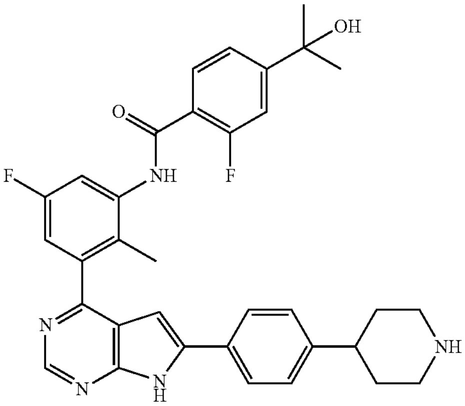

+

-continued

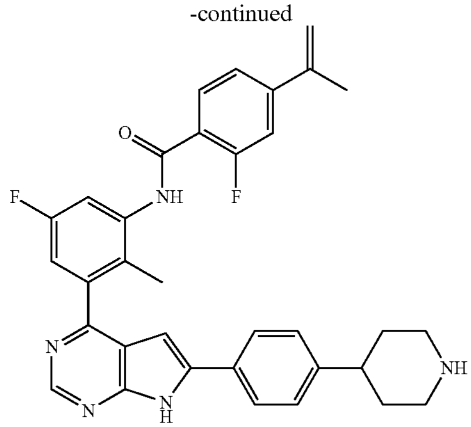

A mixture of tert-butyl 4-(4-(4-(5-fluoro-3-(2-fluoro-4-(2-hydroxypropan-2-yl)benzamido)-2-methylphenyl)-7-((2-(trimethylsilyl)ethoxy)methyl)-7H-pyrrolo[2,3-d]pyrimidin-6-yl)phenyl)piperidine-1-carboxylate (570 mg, 0.70 mmol) and trifluoroacetic acid (3 mL) in dichloromethane (6 mL) was stirred in a round bottom flask at room temperature overnight. Then the mixture was evaporated in vacuum to afford the crude product. A mixture of the crude product and ammonium hydroxide (2 mL) in methanol (10 mL) was stirred in a round bottom flask at room temperature overnight. Then the mixture was evaporated in vacuum to afford the crude product, which was purified with C18 column chromatography (0.1% FA in water:acetonitrile=85:15~40:60 gradient elution) to give 2-fluoro-N-(5-fluoro-2-methyl-3-(6-(4-(piperidin-4-yl)phenyl)-7H-pyrrolo[2,3-d]pyrimidin-4-yl)phenyl)-4-(2-hydroxypropan-2-yl)benzamide (160 mg, 39%). $[M+H]^+$=582.4 and 2-fluoro-N-(5-fluoro-2-methyl-3-(6-(4-(piperidin-4-yl)phenyl)-7H-pyrrolo[2,3-d]pyrimidin-4-yl)phenyl)-4-(prop-1-en-2-yl)benzamide (100 mg, 25%). $[M+H]^+$=564.4.

Step 3: N-(3-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-5-fluoro-2-methylphenyl)-2-fluoro-4-(2-hydroxypropan-2-yl)benzamide

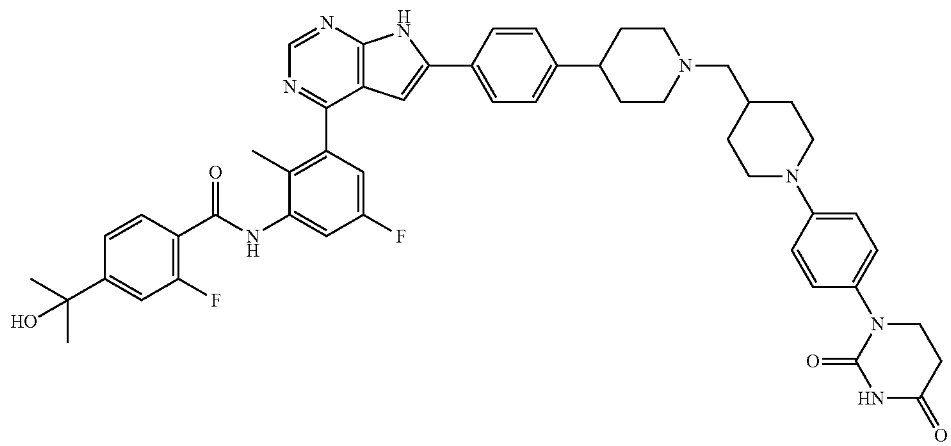 [SMILES: Cc1c(NC(=O)c2ccc(C(C)(C)O)cc2F)cc(F)cc1-c1ncnc2[nH]c(-c3ccc(C4CCN(CC5CCN(c6ccc(N7CCC(=O)NC7=O)cc6)CC5)CC4)cc3)cc12]

A mixture of 2-fluoro-N-(5-fluoro-2-methyl-3-(6-(4-(piperidin-4-yl)phenyl)-7H-pyrrolo[2,3-d]pyrimidin-4-yl)phenyl)-4-(2-hydroxypropan-2-yl)benzamide (86 mg, 0.14 mmol) and 1-(4-(2,4-dioxotetrahydropyrimidin-1(2H)-yl)phenyl)piperidine-4-carbaldehyde (60 mg, 0.20 mmol) in dichloroethane (20 mL) was stirred in a round bottom flask at room temperature for 1 hour. Then to the mixture was added $NaBH(OAc)_3$ (212 mg, 1.0 mmol) and stirred in a round bottom flask at room temperature overnight. The mixture was evaporated in vacuum to afford the crude product, which was purified with C18 column chromatography (0.1% FA in water:acetonitrile=80:20~40:60 gradient elution) to give the product (61 mg, 50%). $^1H$ NMR (400 MHz, DMSO) $\delta_H$ 12.74 (s, 1H), 10.27 (s, 1H), 9.95 (s, 1H), 8.90-8.75 (m, 1H), 8.24-8.04 (m, 1H), 7.98-7.84 (m, 2H), 7.78-7.59 (m, 2H), 7.47-7.30 (m, 4H), 7.27-7.19 (m, 1H), 7.13 (d, J=8.0 Hz, 2H), 6.93 (d, J=8.0 Hz, 2H), 6.85-6.75 (m, 1H), 5.31 (s, 1H), 3.75-3.58 (m, 4H), 3.33 (s, 4H), 3.08-2.91 (m, 3H), 2.77-2.61 (m, 5H), 2.26-2.09 (m, 5H), 2.08-1.95 (m, 2H), 1.86-1.58 (m, 7H), 1.54-1.30 (m, 6H), 1.28-1.13 (m, 2H); $[M+H]^+$=867.8.

Example 29: N-(3-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-5-fluoro-2-methylphenyl)-2-fluoro-4-(prop-1-en-2-yl)benzamide

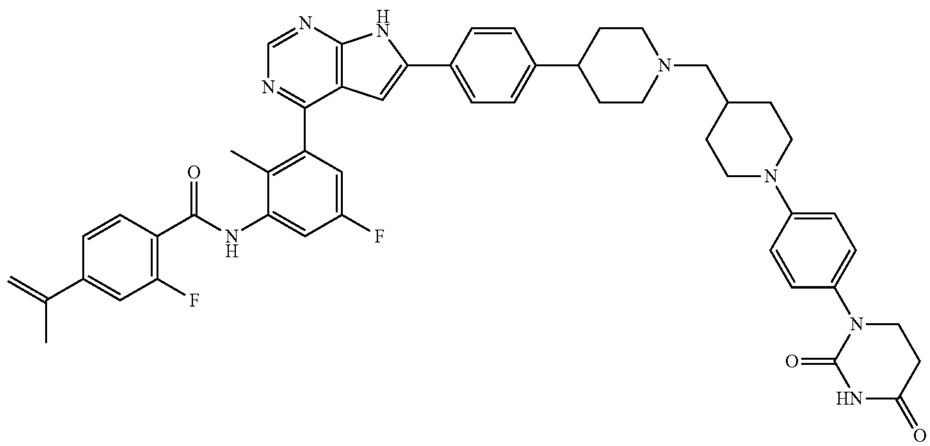 [SMILES: C=C(C)c1ccc(C(=O)Nc2cc(F)cc(-c3ncnc4[nH]c(-c5ccc(C6CCN(CC7CCN(c8ccc(N9CCC(=O)NC9=O)cc8)CC7)CC6)cc5)cc34)c2C)c(F)c1]

A mixture of 2-fluoro-N-(5-fluoro-2-methyl-3-(6-(4-(piperidin-4-yl)phenyl)-7H-pyrrolo[2,3-d]pyrimidin-4-yl)phenyl)-4-(prop-1-en-2-yl)benzamide (10 mg, 0.17 mmol) and 1-(4-(2,4-dioxotetrahydropyrimidin-1(2H)-yl)phenyl)piperidine-4-carbaldehyde (60 mg, 0.20 mmol) in dichloroethane (10 mL) was stirred in a round bottom flask at room temperature for 1 hour. Then to the mixture was added $NaBH(OAc)_3$ (212 mg, 1.0 mmol) and stirred in a round bottom flask at room temperature overnight. The mixture was evaporated in vacuum to afford the crude product, which was purified with C18 column chromatography (0.1% FA in water:acetonitrile=75:25~30:70 gradient elution) to give the product (50 mg, 34%). $^1H$ NMR (400 MHz, DMSO) $\delta_H$ 12.76 (s, 1H), 10.28 (s, 1H), 10.01 (s, 1H), 8.86 (s, 1H), 7.93 (d, J=7.6 Hz, 2H), 7.84-7.75 (m, 1H), 7.71-7.62 (m, 1H), 7.56-7.48 (m, 2H), 7.37 (d, J=7.6 Hz, 2H), 7.26 (d, J=8.4 Hz, 1H), 7.14 (d, J=8.8 Hz, 2H), 6.94 (d, J=8.4 Hz, 2H), 6.82 (s, 1H), 5.64 (s, 1H), 5.29 (s, 1H), 3.76-3.61 (m, 4H), 3.04-2.93 (m, 2H), 2.75-2.63 (m, 4H), 2.26-2.11 (m, 8H), 2.08-1.97 (m, 2H), 1.85-1.63 (m, 7H), 1.30-1.16 (m, 2H); $[M+H]^+$=849.5.

Example 30: 5-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-1,2,4-oxadiazole-3-carboxamide

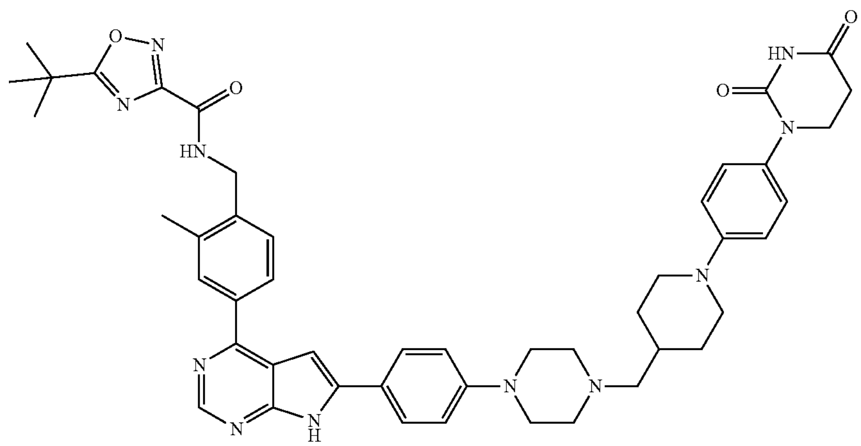

The titled compound was synthesized in the procedures similar to Example 24. $^1$H NMR (400 MHz, DMSO) $\delta_H$ 12.54 (s, 1H), 10.28 (s, 1H), 9.53 (s, 1H), 8.77 (s, 1H), 8.08 (s, 2H), 7.93 (d, J=8.4 Hz, 2H), 7.46 (d, J=8.4 Hz, 1H), 7.24 (s, 1H), 7.15 (d, J=8.8 Hz, 2H), 7.06 (d, J=8.8 Hz, 2H), 6.95 (d, J=8.4 Hz, 2H), 4.57 (d, J=5.2 Hz, 2H), 3.66 (t, J=6.4 Hz, 4H), 3.28 (s, 4H), 2.71-2.65 (m, 5H), 2.55-2.45 (m, 5H), 2.26 (br, 2H), 1.84-1.70 (m, 3H), 1.46 (s, 9H), 1.25 (br, 3H); $[M+H]^+$=836.5.

Example 31: (R)-5-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-fluorophenyl)ethyl)-1,2,4-oxadiazole-3-carboxamide

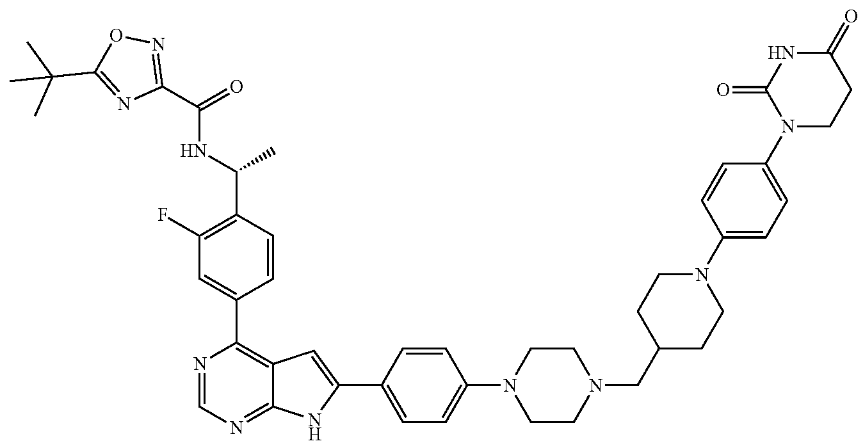 [SMILES: C[C@@H](NC(=O)c1noc(C(C)(C)C)n1)c1ccc(-c2ncnc3[nH]c(-c4ccc(N5CCN(CC6CCN(c7ccc(N8CCC(=O)NC8=O)cc7)CC6)CC5)cc4)cc23)cc1F]

The titled compound was synthesized in the procedures similar to Example 24. $^1$H NMR (400 MHz, DMSO) $\delta_H$ 12.62 (s, 1H), 10.28 (s, 1H), 9.64 (d, J=8.0 Hz, 1H), 8.78 (s, 1H), 8.14 (d, J=8.0 Hz, 1H), 8.00 (d, J=12.0 Hz, 1H), 7.95 (d, J=7.6 Hz, 2H), 7.70 (t, J=7.6 Hz, 1H), 7.32 (s, 1H), 7.14 (d, J=8.8 Hz, 2H), 7.05 (d, J=7.6 Hz, 2H), 6.94 (d, J=8.8 Hz, 2H), 5.47 (t, J=7.6 Hz, 1H), 3.69 (t, J=6.8 Hz, 4H), 3.30 (s, 4H), 2.70-2.55 (m, 7H), 2.29 (br, 2H), 1.85-1.70 (m, 3H), 1.57 (d, J=6.4 Hz, 3H), 1.44 (s, 9H), 1.24 (br, 3H); $[M+H]^+$=854.9.

Example 32: 3-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-fluorobenzyl)-1,2,4-oxadiazole-5-carboxamide

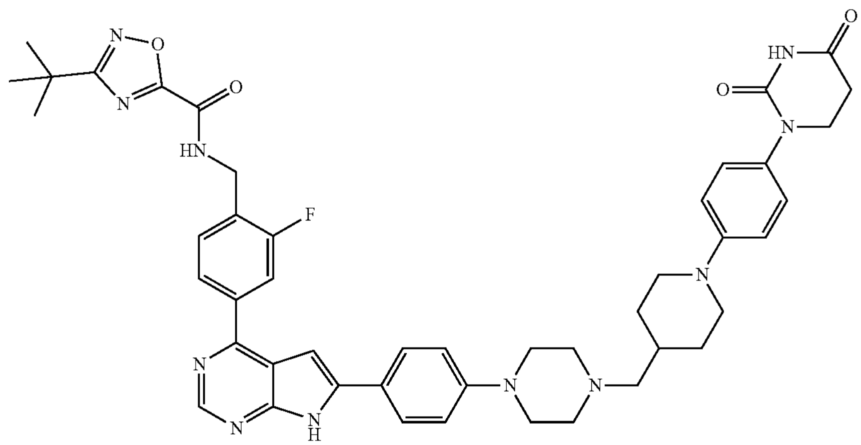 [SMILES: CC(C)(C)c1noc(C(=O)NCc2ccc(-c3ncnc4[nH]c(-c5ccc(N6CCN(CC7CCN(c8ccc(N9CCC(=O)NC9=O)cc8)CC7)CC6)cc5)cc34)cc2F)n1]

The titled compound was synthesized in the procedures similar to Example 24. $^1$H NMR (400 MHz, DMSO) $\delta_H$ 12.62 (s, 1H), 10.28 (s, 1H), 10.01-9.98 (m, 1H), 8.79 (s, 1H), 8.14-8.13 (m, 1H), 8.04-8.01 (m, 1H), 7.94 (d, J=8.0 Hz, 2H), 7.64-7.60 (m, 1H), 7.30 (s, 1H), 7.16-7.13 (m, 2H), 7.07-7.04 (m, 2H), 6.94 (d, J=8.0 Hz, 2H), 4.64-4.63 (m, 2H), 3.72-3.70 (m, 4H), 3.28 (s, 4H), 2.71-2.65 (m, 4H), 2.25-2.22 (m, 2H), 1.86-1.74 (m, 4H), 1.39 (s, 9H), 1.26-1.24 (m, 3H); [M+H]$^+$=840.8.

Example 33: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-fluorophenyl)ethyl)-1,2,4-oxadiazole-5-carboxamide

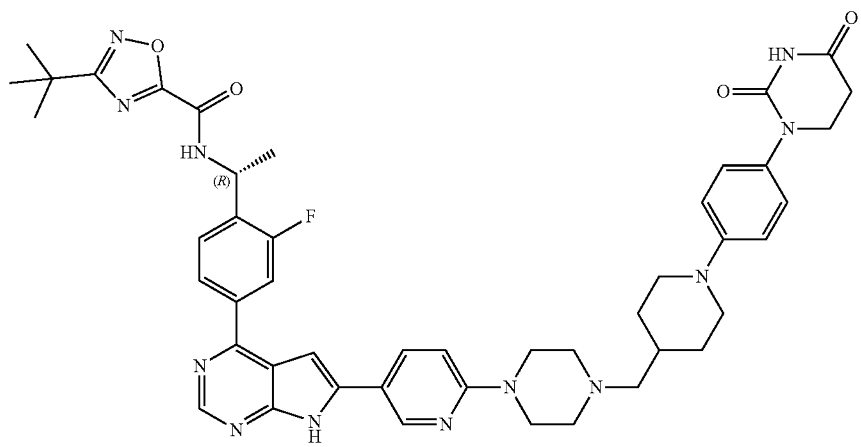

The titled compound was synthesized in the procedures similar to Example 24. $^1$H NMR (400 MHz, DMSO) $\delta_H$ 12.66 (s, 1H), 10.25 (s, 1H), 10.00 (s, 1H), 8.79-8.77 (m, 2H), 8.19-8.11 (m, 2H), 7.99-7.97 (m, 1H), 7.71-7.69 (m, 1H), 7.34 (s, 1H), 7.11-7.10 (m, 2H), 6.95-6.91 (m, 3H), 5.45-5.43 (m, 1H), 3.67-3.58 (m, 8H), 2.68-2.65 (m, 7H), 2.22-2.20 (m, 2H), 1.81-1.71 (m, 3H), 1.59-1.56 (m, 3H), 1.36 (s, 9H), 1.23-1.21 (m, 3H); [M+H]$^+$=855.5.

Example 34: (R)-5-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-fluorophenyl)ethyl)-1,2,4-oxadiazole-3-carboxamide

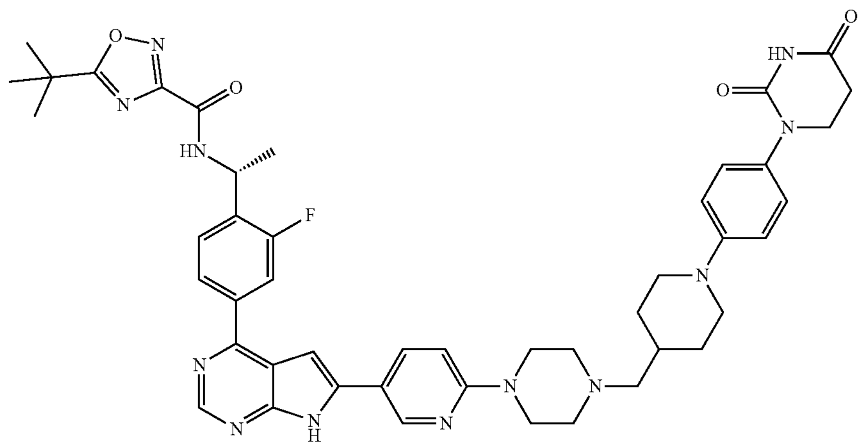 [SMILES: C[C@@H](NC(=O)c1noc(C(C)(C)C)n1)c1ccc(-c2ncnc3[nH]c(-c4ccc(N5CCN(CC6CCN(c7ccc(N8CCC(=O)NC8=O)cc7)CC6)CC5)nc4)cc23)cc1F]

The titled compound was synthesized in the procedures similar to Example 24. $^1$H NMR (400 MHz, DMSO) $\delta_H$ 12.65 (s, 1H), 10.24 (s, 1H), 9.59 (d, J=8.0 Hz, 1H), 8.79-8.76 (m, 2H), 8.18 (d, J=8.0 Hz, 1H), 8.10 (d, J=8.0 Hz, 1H), 7.97 (d, J=8.0 Hz, 1H), 7.68-7.65 (m, 1H), 7.33 (s, 1H), 7.10 (d, J=8.0 Hz, 2H), 6.95-6.89 (m, 3H), 5.46-5.42 (m, 1H), 3.66-3.58 (m, 8H), 2.67-2.65 (m, 4H), 2.47-2.44 (m, 3H), 1.81-1.78 (m, 2H), 1.70 (s, 1H), 1.54 (d, J=8.0 Hz, 3H), 1.41 (s, 9H), 1.22-1.19 (m, 3H); $[M+H]^+$=855.5.

Example 35: 1-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-1H-pyrazole-4-carboxamide

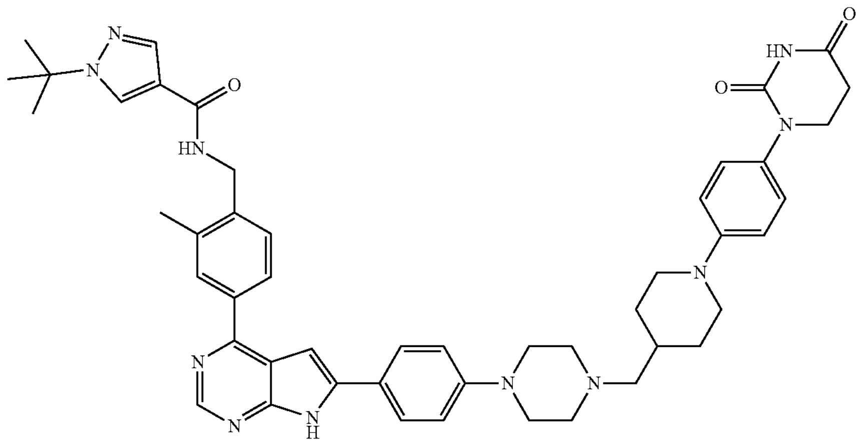

The titled compound was synthesized in the procedures similar to Example 24. $^1$H NMR (400 MHz, DMSO) $\delta_H$ 12.49 (s, 1H), 10.24 (s, 1H), 8.72 (s, 1H), 8.50 (br, 1H), 8.33 (s, 1H), 8.03 (s, 2H), 7.94-7.85 (m, 3H), 7.41 (d, J=7.6 Hz, 1H), 7.19 (s, 1H), 7.11 (d, J=8.8 Hz, 2H), 7.01 (d, J=7.6 Hz, 2H), 6.91 (d, J=8.8 Hz, 2H), 4.48 (br, 2H), 3.66 (t, J=6.8 Hz, 4H), 3.23 (s, 4H), 2.70-2.60 (m, 5H), 2.60-2.40 (m, 5H), 2.22 (br, 2H), 1.85-1.65 (m, 3H), 1.51 (s, 9H), 1.21 (br, 3H); $[M+H]^+$=834.5.

Example 36: N-(4-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-2-fluoro-5-methylbenzyl)-2-fluoro-4-(2-hydroxypropan-2-yl)benzamide Step 1: tert-butyl 4-(4-(4-(5-fluoro-4-((2-fluoro-4-(2-hydroxypropan-2-yl)benzamido)methyl)-2-methylphenyl)-7-((2-(trimethylsilyl)ethoxy)methyl)-7H-pyrrolo[2,3-d]pyrimidin-6-yl)phenyl)piperidine-1-carboxylate

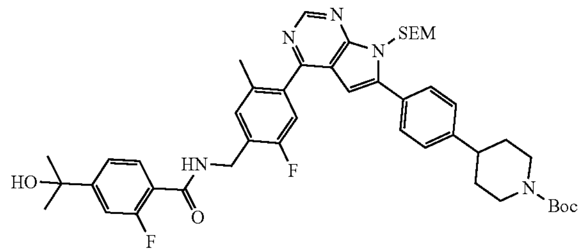 [SMILES: Cc1cc(CNC(=O)c2ccc(C(C)(C)O)cc2F)c(F)cc1-c1ncnc2c1cc(-c1ccc(C3CCN(C(=O)OC(C)(C)C)CC3)cc1)n2COCC[Si](C)(C)C]

A solution of tert-butyl 4-(4-(4-chloro-7-((2-(trimethylsilyl)ethoxy)methyl)-7H-pyrrolo[2,3-d]pyrimidin-6-yl)phenyl)piperidine-1-carboxylate (542 mg, 1.0 mmol) in dioxane (20 mL) and water (2 mL) was added 2-fluoro-N-(2-fluoro-5-methyl-4-(4,4,5,5-tetramethyl-1,3,2-dioxaborolan-2-yl)benzyl)-4-(2-hydroxypropan-2-yl)benzamide (445 mg, 1.0 mmol), Pd(dppf)$Cl_2$ (73 mg, 0.1 mmol) and $Cs_2CO_3$ (650 mg, 2.0 mmol). The mixture reaction was stirred in a round bottom flask at 110° C. overnight. Then the mixture was evaporated in vacuum to afford the crude product, which was purified with silica gel column chromatography (PE: EA=100:0~0:100 gradient elution) to give the product (341 mg, 38%). $[M+H]^+$=826.4.

Step 2: 2-fluoro-N-(2-fluoro-5-methyl-4-(6-(4-(piperidin-4-yl)phenyl)-7H-pyrrolo[2,3-d]pyrimidin-4-yl)benzyl)-4-(2-hydroxypropan-2-yl)benzamide

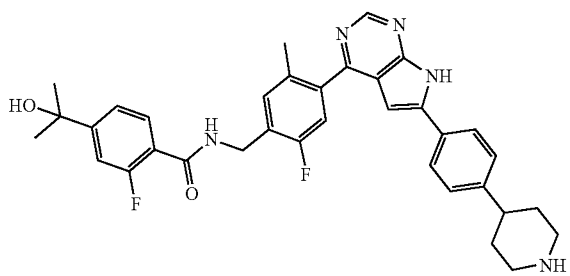 [SMILES: Cc1cc(CNC(=O)c2ccc(C(C)(C)O)cc2F)c(F)cc1-c1ncnc2[nH]c(-c3ccc(C4CCNCC4)cc3)cc12]

A mixture of tert-butyl 4-(4-(4-(5-fluoro-4-((2-fluoro-4-(2-hydroxypropan-2-yl)benzamido)methyl)-2-methylphenyl)-7-((2-(trimethylsilyl)ethoxy)methyl)-7H-pyrrolo[2,3-d]pyrimidin-6-yl)phenyl)piperidine-1-carboxylate (340 mg, 0.38 mmol) and trifluoroacetic acid (3 mL) in dichloromethane (12 mL) was stirred in a round bottom flask at room temperature overnight. Then the mixture was evaporated in vacuum to afford the crude product. A mixture of the crude product and ammonium hydroxide (2 mL) in methanol (10 mL) was stirred in a round bottom flask at room temperature overnight. The mixture was evaporated in vacuum to afford the crude product, which was purified with C18 column chromatography (0.1% HCl in water:acetonitrile=85:15~40:60 gradient elution) to give the product (160 mg, 42%). $[M+H]^+$=596.6.

Step 3: N-(4-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-2-fluoro-5-methylbenzyl)-2-fluoro-4-(2-hydroxypropan-2-yl)benzamide

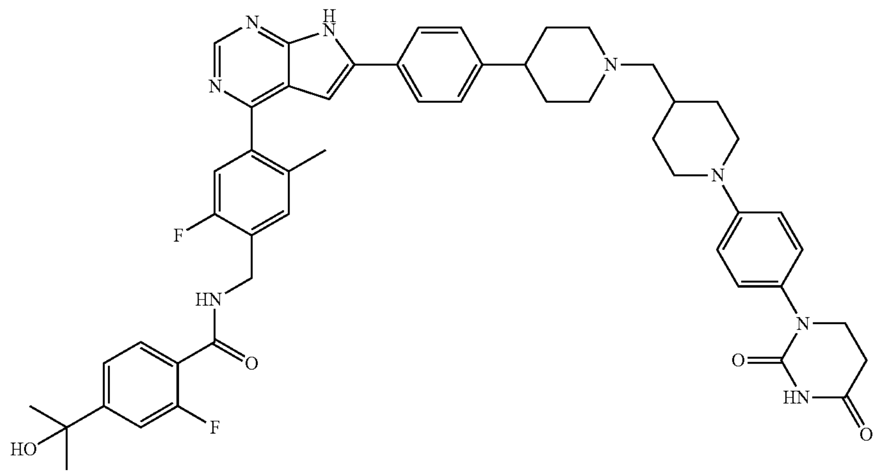 [SMILES: Cc1cc(CNC(=O)c2ccc(C(C)(C)O)cc2F)c(F)cc1-c1ncnc2[nH]c(-c3ccc(C4CCN(CC5CCN(c6ccc(N7CCC(=O)NC7=O)cc6)CC5)CC4)cc3)cc12]

A mixture of 2-fluoro-N-(2-fluoro-5-methyl-4-(6-(4-(piperidin-4-yl)phenyl)-7H-pyrrolo[2,3-d]pyrimidin-4-yl)benzyl)-4-(2-hydroxypropan-2-yl)benzamide (90 mg, 0.15 mmol) and 1-(4-(2,4-dioxotetrahydropyrimidin-1(2H)-yl)phenyl)piperidine-4-carbaldehyde (60 mg, 0.20 mmol) in dichloroethane (20 mL) was stirred in a round bottom flask at room temperature for 1 hour. Then to the mixture was added $NaBH(OAc)_3$ (212 mg, 1.0 mmol) and stirred in a round bottom flask at room temperature overnight. The mixture was evaporated in vacuum to afford the crude product, which was purified with silica gel column chromatography (DCM:MeOH=100:0~80:20 gradient elution) to give the product (49 mg, 37%). $^1H$ NMR (400 MHz, DMSO) $\delta_H$ 12.72 (s, 1H), 10.27 (s, 1H), 8.95-8.79 (m, 2H), 7.94 (d, J=7.2 Hz, 2H), 7.72-7.59 (m, 1H), 7.46-7.28 (m, 6H), 7.14 (d, J=8.0 Hz, 2H), 7.01-6.81 (m, 3H), 5.28 (s, 1H), 4.59 (s, 2H), 3.77-3.63 (m, 4H), 3.15-3.01 (m, 2H), 2.73-2.62 (m, 3H), 2.29 (s, 3H), 2.23-2.09 (m, 2H), 1.96-1.89 (m, 2H), 1.87-1.67 (m, 5H), 1.44 (s, 6H), 1.32-1.15 (m, 4H); $[M+H]^+$=881.8.

Example 37: 1-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-1H-1,2,3-triazole-4-carboxamide

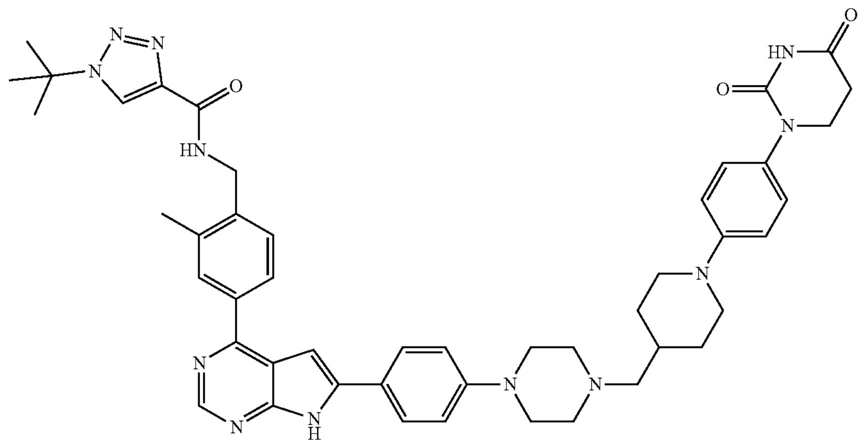

The titled compound was synthesized in the procedures similar to Example 24. $^1$H NMR (400 MHz, DMSO) $\delta_H$ 12.49 (s, 1H), 10.24 (s, 1H), 9.04 (s, 1H), 8.71 (s, 2H), 8.03 (s, 2H), 7.88 (br, 2H), 7.40 (br, 1H), 7.26-6.82 (m, 7H), 4.52 (s, 2H), 3.67 (s, 4H), 3.25 (s, 4H), 2.70-2.50 (m, 10H), 2.30 (br, 2H), 1.82-1.70 (m, 3H), 1.63 (s, 9H), 1.20 (br, 3H). [M+H]$^+$=835.5.

Example 38: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)-3-fluorophenyl)-7H-pyrrolo[2,3-d]pyrimidin-4-yl)-2-methylphenyl)ethyl)-1,2,4-oxadiazole-5-carboxamide, Formate

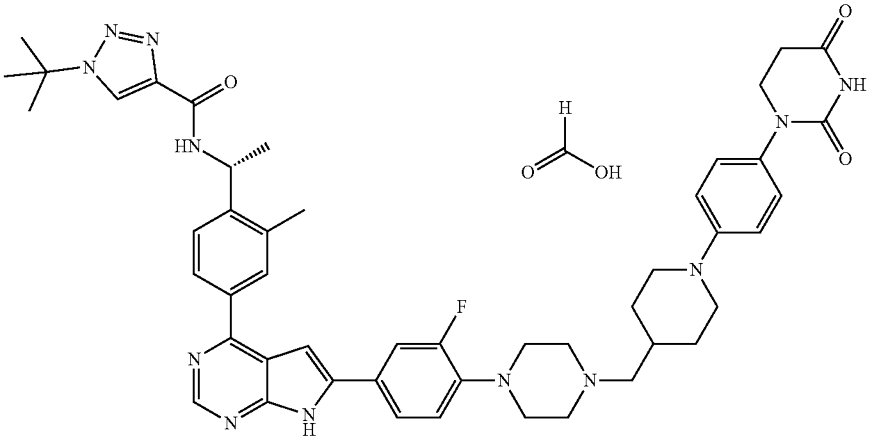 [SMILES: Cc1cc(-c2ncnc3[nH]c(-c4ccc(N5CCN(CC6CCN(c7ccc(N8CCC(=O)NC8=O)cc7)CC6)CC5)c(F)c4)cc23)ccc1[C@@H](C)NC(=O)c1cn(C(C)(C)C)nn1 ; O=CO]

The titled compound was synthesized in the procedures similar to Example 24. $^1$H NMR (400 MHz, DMSO) $\delta_H$ 12.64 (s, 1H), 10.27 (s, 1H), 9.98 (s, 1H), 8.79 (s, 1H), 8.23 (s, 1H), 8.09 (s, 1H), 8.04 (s, 1H), 7.92 (d, J=14.2 Hz, 1H), 7.81 (s, 1H), 7.68 (s, 1H), 7.41 (s, 1H), 7.12 (s, 3H), 6.94 (s, 2H), 5.38 (s, 1H), 3.70 (s, 4H), 3.12 (s, 4H), 2.67 (s, 4H), 2.54 (s, 7H), 2.24 (s, 2H), 1.82 (d, J=12.1 Hz, 2H), 1.72 (s, 1H), 1.55 (s, 3H), 1.37 (s, 9H), 1.23 (d, J=9.8 Hz, 2H); [M+H]$^+$=868.8.

Example 39: 3-(tert-butyl)-N-(4-(6-(4-(1-((1-(4-(2,4-dioxotetrahydropyrimidin-1(2H)-yl)-2-fluorophenyl)piperidin-4-yl)methyl)piperidin-4-yl)phenyl)-7H-pyrrolo[2,3-d]pyrimidin-4-yl)-2-methylbenzyl)-1,2,4-oxadiazole-5-carboxamide Formate

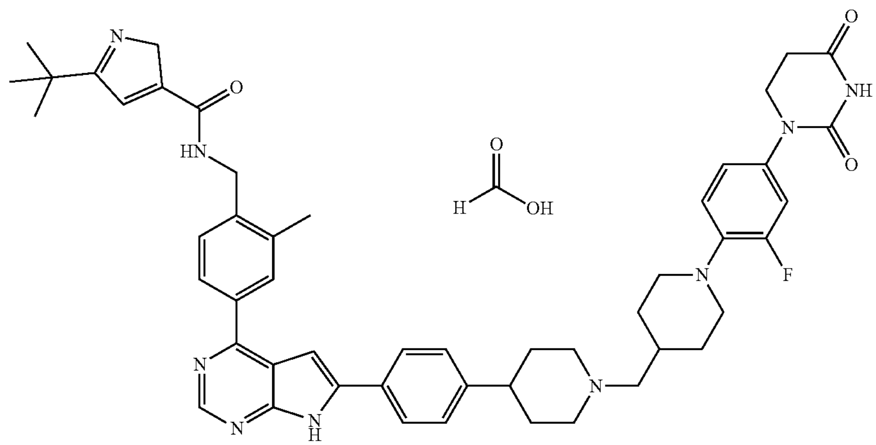 [SMILES: Cc1cc(-c2ncnc3[nH]c(-c4ccc(C5CCN(CC6CCN(c7ccc(N8CCC(=O)NC8=O)cc7F)CC6)CC5)cc4)cc23)ccc1CNC(=O)C1=CC(C(C)(C)C)=NC1 ; O=CO]

The titled compound was synthesized in the procedures similar to Example 24. $^1$H NMR (400 MHz, DMSO) $\delta_H$ 12.68 (s, 1H), 10.37 (s, 1H), 9.91 (s, 1H), 8.80 (s, 1H), 8.22 (s, 1H), 8.07 (s, 2H), 7.97 (s, 2H), 7.48 (s, 1H), 7.37 (s, 3H), 7.17 (d, J=14.2 Hz, 1H), 7.05 (s, 2H), 4.56 (s, 2H), 3.73 (s, 4H), 2.98 (s, 2H), 2.68 (s, 4H), 2.52 (s, 3H), 2.23 (s, 2H), 2.02 (s, 2H), 1.75 (dd, J=34.4, 12.2 Hz, 7H), 1.38 (s, 9H), 1.30 (s, 3H); $[M+H]^+$=853.8.

Example 40: 1-(tert-butyl)-N-(4-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-2-methylbenzyl)-1H-1,2,3-triazole-4-carboxamide Step 1: tert-butyl 4-(4-(4-(4-((1-(tert-butyl)-1H-1,2,3-triazole-4-carboxamido)methyl)-3-methylphenyl)-7-((2-(trimethylsilyl)ethoxy)methyl)-7H-pyrrolo[2,3-d]pyrimidin-6-yl)phenyl)piperidine-1-carboxylate

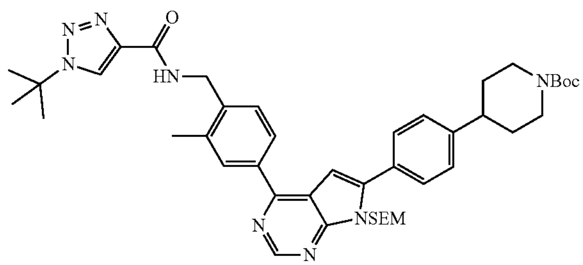 [SMILES: Cc1cc(-c2ncnc3c2cc(-c2ccc(C4CCN(C(=O)OC(C)(C)C)CC4)cc2)n3COCC[Si](C)(C)C)ccc1CNC(=O)c1cn(C(C)(C)C)nn1]

To a solution of tert-butyl 4-(4-(4-chloro-7-((2-(trimethylsilyl)ethoxy)methyl)-7H-pyrrolo[2,3-d]pyrimidin-6-yl)phenyl)piperidine-1-carboxylate (166 mg, 0.4 mmol) in dioxane/$H_2O$ (5:1, 50 mL) was added 1-(tert-butyl)-N-(2-methyl-4-(4,4,5,5-tetramethyl-1,3,2-dioxaborolan-2-yl)benzyl)-1H-1,2,3-triazole-4-carboxamide (150 mg, 0.4 mmol), $K_2CO_3$ (166 mg, 1.2 mmol) and $Pd(dppf)Cl_2 \cdot CH_2Cl_2$ (33 mg, 0.04 mmol). The reaction mixture was stirred at 90° C. under $N_2$ for 5 hours. The solvent was evaporated and $H_2O$ (20 mL) was added. The mixture was extracted with DCM/iPrOH (20:1, 30 mL*3) and the organic phase was combined. The organic phase was washed with brine, concentrated and purified by pre-TLC with DCM/MeOH to give the product (160 mg, crude).

Step 2: 1-(tert-butyl)-N-(2-methyl-4-(6-(4-(piperidin-4-yl)phenyl)-7H-pyrrolo[2,3-d]pyrimidin-4-yl)benzyl)-1H-1,2,3-triazole-4-carboxamide

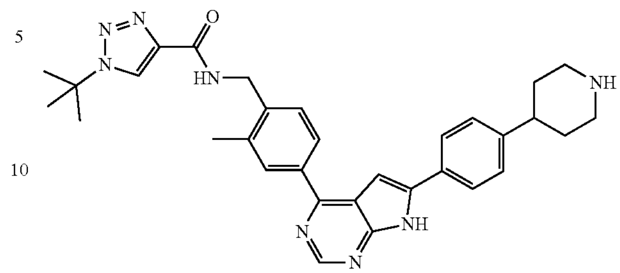

To a solution of tert-butyl 4-(4-(4-(4-((1-(tert-butyl)-1H-1,2,3-triazole-4-carboxamido)methyl)-3-methylphenyl)-7-((2-(trimethylsilyl)ethoxy)methyl)-7H-pyrrolo[2,3-d]pyrimidin-6-yl)phenyl)piperidine-1-carboxylate (230 mg, 0.29 mmol) in DCM (20 mL) was added TFA (20 mL). The mixture was stirred at 20-30° C. for 18 hours. The reaction mixture was concentrated under reduce pressure. The residue was dissolved in MeOH (30 mL) and $K_2CO_3$ was added (230 mg). The reaction mixture was concentrated after being stirred at 20-30° C. for 2 hs. $H_2O$ (30 mL) was added and the mixture was extracted with DCM/iPrOH (10:1, 30 mL). The organic phase was separated, concentrated and used for next step directly.

Step 3: 1-(tert-butyl)-N-(4-(6-(4-(1-((1-(4-(2,4-dioxotetrahydropyrimidin-1(2H)-yl)phenyl)piperidin-4-yl)methyl)piperidin-4-yl)phenyl)-7H-pyrrolo[2,3-d]pyrimidin-4-yl)-2-methylbenzyl)-1H-1,2,3-triazole-4-carboxamide

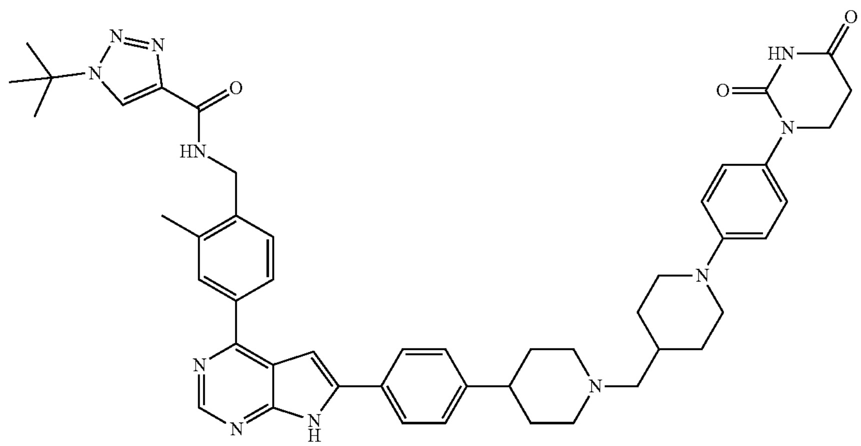 [SMILES: Cc1cc(-c2ncnc3[nH]c(-c4ccc(C5CCN(CC6CCN(c7ccc(N8CCC(=O)NC8=O)cc7)CC6)CC5)cc4)cc23)ccc1CNC(=O)c1cn(C(C)(C)C)nn1]

To a solution of 1-(tert-butyl)-N-(2-methyl-4-(6-(4-(piperidin-4-yl)phenyl)-7H-pyrrolo[2,3-d]pyrimidin-4-yl)benzyl)-1H-1,2,3-triazole-4-carboxamide (200 mg, 0.36 mmol) in DCM/EtOH (5:1, 30 mL) was added 1-(4-(2,4-dioxotetrahydropyrimidin-1(2H)-yl)phenyl)piperidine-4-carbaldehyde (109 mg, 0.36 mmol), HOAc (1 drop) and NaOAc (88 mg, 1.1 mmol). $NaBH(OAc)_3$ (233 mg, 1.1 mmol) was added after being stirred at 20-30° C. for 60 min. The mixture was evaporated after being stirred at 20-30° C. for another 5 hours. To the residue was added $H_2O$ (30 mL) and the mixture was extracted with DCM/iPrOH (20:1, 30 mL*3). The organic phase was combined and purified by pre-TLC with DCM/MeOH (10:1) to give the product (32 mg, 10.7%). $^1$H NMR (400 MHz, DMSO) $\delta_H$ 12.66 (s, 1H), 10.27 (s, 1H), 9.07 (s, 1H), 8.80 (s, 1H), 8.74 (s, 1H), 8.19

(s, 1H), 8.06 (s, 2H), 7.98 (d, J=7.6 Hz, 2H), 7.44 (d, J=8.4 Hz, 1H), 7.37 (d, J=8.0 Hz, 3H), 7.13 (d, J=8.4 Hz, 2H), 6.93 (d, J=8.4 Hz, 2H), 4.56 (s, 2H), 3.76-3.66 (m, 4H), 2.98 (d, J=8.8 Hz, 2H), 2.75-2.52 (m, 7H), 2.22 (br, 2H), 2.07-1.95 (m, 2H), 1.88-1.58 (m, 16H), 1.25-1.15 (m, 2H); $[M+H]^+$=834.6.

Example 41: (R)-5-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-3-carboxamide Step 1: tert-butyl (R)-4-(4-(4-(4-(1-(5-(tert-butyl)-1,2,4-oxadiazole-3-carboxamido)ethyl)-3-methylphenyl)-7H-pyrrolo[2,3-d]pyrimidin-6-yl)phenyl)piperazine-1-carboxylate

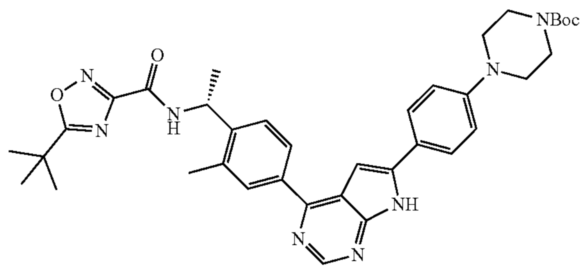 [SMILES: Cc1cc(-c2ncnc3[nH]c(-c4ccc(N5CCN(C(=O)OC(C)(C)C)CC5)cc4)cc23)ccc1[C@@H](C)NC(=O)c1noc(C(C)(C)C)n1]

To a solution of tert-butyl 4-(4-(4-chloro-7H-pyrrolo[2,3-d]pyrimidin-6-yl)phenyl)piperazine-1-carboxylate (271 mg, 0.5 mmol) in dioxane (25 mL) and $H_2O$ (5 mL) was added (R)-5-(tert-butyl)-N-(1-(2-methyl-4-(4,4,5,5-tetramethyl-1,3,2-dioxaborolan-2-yl)phenyl)ethyl)-1,2,4-oxadiazole-3-carboxamide (207 mg, 0.5 mmol), $K_2CO_3$ (207 mg, 1.5 mmol) and $Pd(dppf)Cl_2 \cdot CH_2Cl_2$ (41 mg, 0.05 mmol). The mixture was stirred at 90° C. under $N_2$ for 18 hours. After the solvent was evaporated, water (20 mL) was added. The mixture was extracted with DCM/iPrOH (10:1, 20 mL*2). The organic phase was combined, washed with brine and purified by pre-TLC with DCM/MeOH to give the product (160 mg, crude).

Step 2: (R)-5-(tert-butyl)-N-(1-(2-methyl-4-(6-(4-(piperazin-1-yl)phenyl)-7H-pyrrolo[2,3-d]pyrimidin-4-yl)phenyl)ethyl)-1,2,4-oxadiazole-3-carboxamide hydrochloride

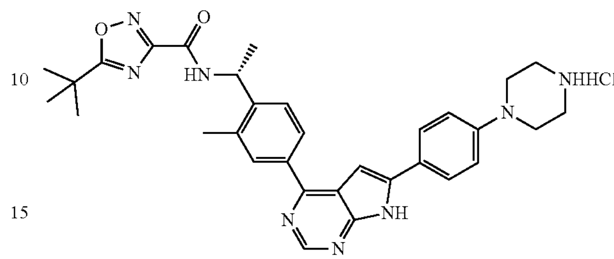

To a solution of tert-butyl (R)-4-(4-(4-(4-(1-(5-(tert-butyl)-1,2,4-oxadiazole-3-carboxamido)ethyl)-3-methylphenyl)-7H-pyrrolo[2,3-d]pyrimidin-6-yl)phenyl)piperazine-1-carboxylate (160 mg, 0.24 mmol) in dioxane (3 mL) was added HCl/dioxane (4 N, 30 mL). The mixture was stirred at 20-30° C. for 3 hours, concentrated to 5 mL and filtered. The filter cake was washed to give the crude product, which was used for next step directly. $^1$H NMR (400 MHz, DMSO) $\delta_H$ 13.41 (s, 1H), 9.64 (d, J=6.8 Hz, 1H), 9.32 (s, 2H), 8.98 (s, 1H), 8.14-7.97 (m, 4H), 7.74 (d, J=7.6 Hz, 1H), 7.48 (s, 1H), 7.13 (d, J=7.6 Hz, 2H), 5.40 (br, 1H), 3.54 (s, 4H), 3.23 (s, 4H), 2.57 (s, 3H), 1.61-1.39 (m, 12H); $[M+H]^+$=565.4.

Step 3: (R)-5-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-3-carboxamide

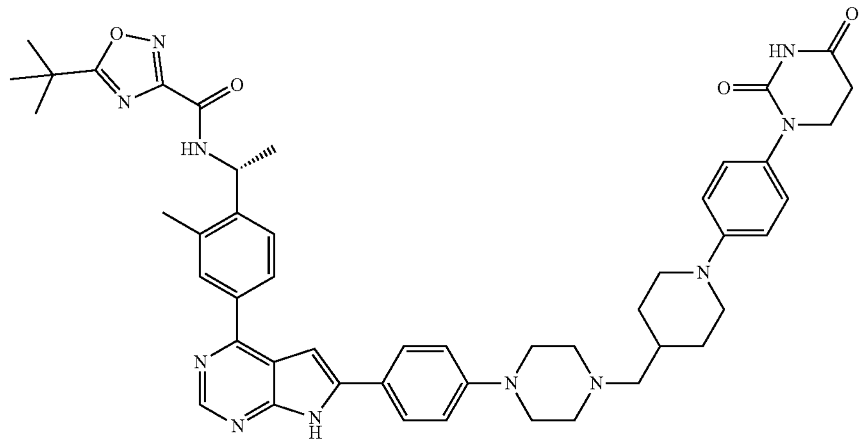

To a solution of (R)-5-(tert-butyl)-N-(1-(2-methyl-4-(6-(4-(piperazin-1-yl)phenyl)-7H-pyrrolo[2,3-d]pyrimidin-4-yl)phenyl)ethyl)-1,2,4-oxadiazole-3-carboxamide hydrochloride (150 mg, 0.25 mmol) in DCM/EtOH (5:1, 30 mL) was added 1-(4-(4-oxotetrahydropyrimidin-1(2H)-yl)phenyl)piperidine-4-carbaldehyde (75 mg, 0.25 mmol) and NaOAc (62 mg, 0.75 mmol). After being stirred at 20-30° C. for 60 min, $NaBH(OAc)_3$ (160 mg, 0.75 mmol) was added. The mixture was stirred at 20-30° C. for 3 hours. The solvent was evaporated and $H_2O$ (30 mL) was added. The mixture was extracted with DCM/iPrOH (20:1, 30 mL*3). The organic phase was combined and concentrated. The residue was purified by pre-TLC with DCM/MeOH (10:1) to give the product (85.7 mg, 40.3%). $^1$H NMR (400 MHz, DMSO) $\delta_H$ 12.53 (s, 1H), 10.27 (s, 1H), 9.54 (d, J=7.2 Hz, 1H), 8.75 (s, 1H), 8.08 (d, J=7.2 Hz, 1H), 8.03 (s, 1H), 7.92 (d, J=6.8 Hz, 2H), 7.65 (d, J=7.2 Hz, 1H), 7.23 (s, 1H), 7.13 (d, J=8.0 Hz, 2H), 7.03 (d, J=8.0 Hz, 2H), 6.93 (d, J=7.2 Hz, 2H), 5.39 (br, 1H), 3.70 (br, 4H), 3.26 (s, 4H), 2.68-2.50 (m, 10H), 2.24 (s, 2H), 1.85-1.69 (m, 3H), 1.54-1.39 (m, 12H), 1.24 (br, 3H); [M+H]$^+$=850.8.

Example 42: 3-(tert-butyl)-N-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-fluorobenzyl)-1,2,4-oxadiazole-5-carboxamide

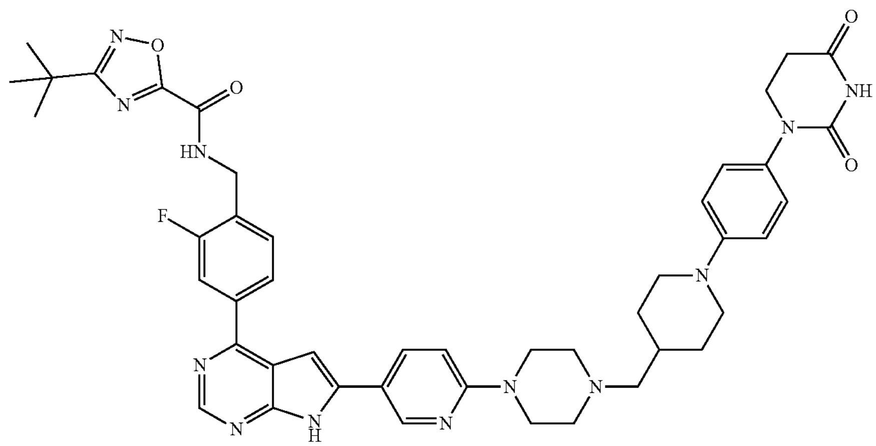 [SMILES: CC(C)(C)c1noc(C(=O)NCc2ccc(-c3ncnc4[nH]c(-c5ccc(N6CCN(CC7CCN(c8ccc(N9CCC(=O)NC9=O)cc8)CC7)CC6)nc5)cc34)cc2F)n1]

The titled compound was synthesized in the procedures similar to Example 24. $^1$H NMR (400 MHz, DMSO) $\delta_H$ 12.70 (s, 1H), 10.27 (s, 1H), 9.99 (s, 1H), 8.82-8.79 (m, 2H), 8.31 (s, 1H), 8.20 (d, J=8.0 Hz, 1H), 8.12 (d, J=8.0 Hz, 1H), 8.03-8.00 (m, 1H), 7.63-7.60 (m, 1H), 7.35 (s, 1H), 7.13 (d, J=8.0 Hz, 2H), 6.98-6.92 (m, 3H), 4.63 (s, 2H), 3.70-3.68 (m, 4H), 3.61-3.59 (m, 4H), 2.69-2.64 (m, 4H), 2.49-2.47 (m, 4H), 2.23-2.21 (m, 2H), 1.84-1.73 (m, 3H), 1.37 (s, 9H), 1.25-1.22 (m, 2H); [M+H]$^+$=841.8.

Example 43: (R)-3-(tert-butyl)-N-(1-(4-(6-(4-(4-((1-(2-(2,4-dioxotetrahydropyrimidin-1(2H)-yl)-5-fluorophenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide Step 1: (1-(5-fluoro-2-nitrophenyl)piperidin-4-yl)methanol

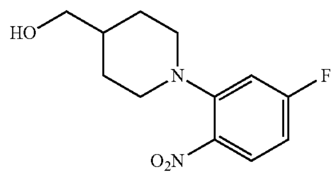

To a solution of 2,4-difluoro-1-nitrobenzene (20.0 g, 142.0 mmol) and 4-piperidinemethanol (19.6 g, 170 mmol) in DMF (200.0 mL) was added $K_2CO_3$ (39.2 g, 284 mmol) at 25° C. The mixture reaction was stirred at 80° C. for 16 h. Reaction was monitored by LC-MS. The reaction was cooled to room temperature, poured into ice-water (600.0 mL) and stirred for 20 mins. The solid was filtered, washed with water (500.0 mL×2) and dried to obtain the product (28.0 g, 84.0%). [M+H]$^+$=255.1.

Step 2: (1-(2-amino-5-fluorophenyl)piperidin-4-yl)methanol

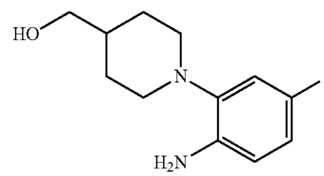

Under $N_2$, to a solution of (1-(5-fluoro-2-nitrophenyl)piperidin-4-yl)methanol (28.0 g, 118.5 mmol) in MeOH (300.0 mL) was added 10% Pd/C (2.80 g) at 25° C. And then the mixture was exchanged with $H_2$ two times and stirred under $H_2$ atmosphere at 25° C. for 15 h. Reaction was monitored by LC-MS. The mixture was filtered through a pad of Celite and washed with MeOH (140.0 mL). The filtrate was concentrated under vacuum to obtain the product (22.6 g, 85.1%). [M+H]$^+$=225.1.

Step 3: (1-(2-(2,4-dioxotetrahydropyrimidin-1(2H)-yl)-5-fluorophenyl)piperidin-4-yl)methyl acetate

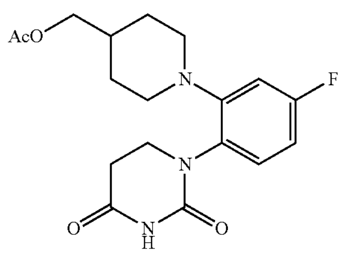 [SMILES: CC(=O)OCC1CCN(c2cc(F)ccc2N2CCC(=O)NC2=O)CC1]

To a solution of (1-(2-amino-5-fluorophenyl)piperidin-4-yl)methanol (22.6 g, 101 mmol) in toluene (200 mL) was added acrylic acid (10.9 g, 151.5 mmol) at 25° C. The mixture reaction was stirred at 90° C. for 15 h. Reaction was monitored by LC-MS. The reaction was cooled to 25° C., and HOAc (200 mL) and urea (30.3 g, 505 mmol) were added. Then the mixture was stirred at 110° C. for 24 h. Reaction was monitored by LC-MS. The reaction was cooled to 25° C. and concentrated under vacuum. The residue was dissolved with EtOAc (500.0 mL) and then adjusted to pH=7 with sat. $NaHCO_3$. The resulting solution was extracted with 2×200.0 mL of EtOAc and the organic layers were combined. The mixture was dried over anhydrous sodium sulfate and concentrated under vacuum. The residue was purified on silica gel to give the product (12.5 g, 34.1%). $[M+H]^+$=364.2.

Step 4: 1-(4-fluoro-2-(4-(hydroxymethyl)piperidin-1-yl)phenyl)dihydropyrimidine-2,4(1H,3H)-dione

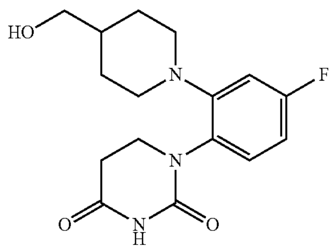 [SMILES: O=C1CCN(c2ccc(F)cc2N2CCC(CO)CC2)C(=O)N1]

(1-(2-(2,4-dioxotetrahydropyrimidin-1(2H)-yl)-5-fluorophenyl)piperidin-4-yl)methyl acetate (12.5 g, 34.4 mmol) was added into 4 N HCl (100.0 mL) at 25° C. The mixture reaction was stirred at 100° C. for 1 h. Reaction was monitored by LC-MS. The reaction was cooled to 10° C. and then adjusted to pH=7 with sat. $NaHCO_3$. The solid was collected by filtration, washed by water (50.0 mL), and dried to obtain the product. $[M+H]^+$=322.1.

Step 5: 1-(2-(2,4-dioxotetrahydropyrimidin-1(2H)-yl)-5-fluorophenyl)piperidine-4-carbaldehyde

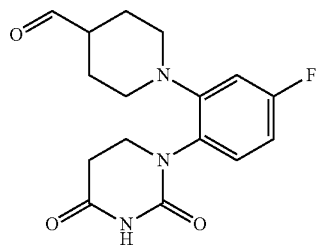 [SMILES: O=CC1CCN(c2cc(F)ccc2N2CCC(=O)NC2=O)CC1]

A mixture of 1-(4-fluoro-2-(4-(hydroxymethyl)piperidin-1-yl)phenyl)dihydropyrimidine-2,4(1H,3H)-dione (650 mg, 2.6 mmol) and IBX (2.3 g, 1.71 mmol) in DMSO (12 mL) was stirred at 55° C. for 1 hour. After EtOAc (50 mL) was added, the solution was washed with brine (50 mL) for 3 times. The organic layer was dried over $Na_2SO_4$, filtered, concentrated and purified by silica gel column chromatography to give the product (350 mg, 54%).

Step 6: (R)-3-(tert-butyl)-N-(1-(4-(6-(4-(4-((1-(2-(2,4-dioxotetrahydropyrimidin-1(2H)-yl)-5-fluorophenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

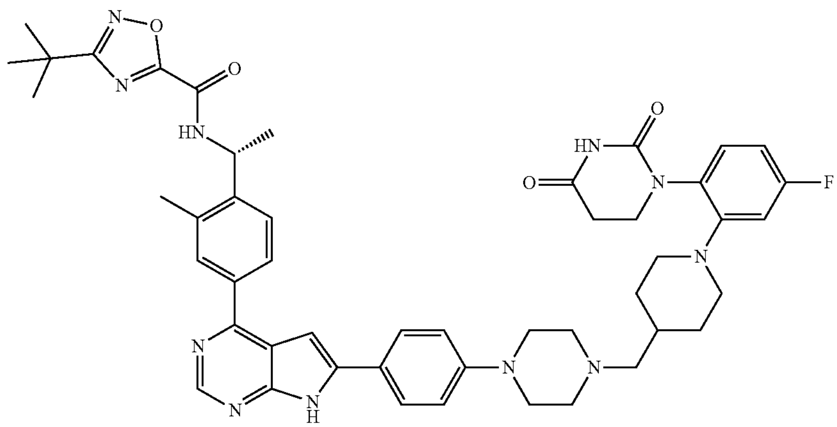 [SMILES: Cc1cc(-c2ncnc3[nH]c(-c4ccc(N5CCN(CC6CCN(c7cc(F)ccc7N7CCC(=O)NC7=O)CC6)CC5)cc4)cc23)ccc1[C@@H](C)NC(=O)c1nc(C(C)(C)C)no1]

To a solution of (R)-3-(tert-butyl)-N-(1-(2-methyl-4-(6-(4-(piperazin-1-yl)phenyl)-7H-pyrrolo[2,3-d]pyrimidin-4-yl)phenyl)ethyl)-1,2,4-oxadiazole-5-carboxamide hydrochloride (100 mg, 0.17 mmol) in DCM/EtOH (5:1, 40 mL) was added 1-(2-(2,4-dioxotetrahydropyrimidin-1(2H)-yl)-5-fluorophenyl)piperidine-4-carbaldehyde (53 mg, 0.17 mmol) and NaOAc (41 mg, 0.5 mmol). After being stirred for 30 min, $NaBH(OAc)_3$ (106 mg, 0.5 mmol) was added. The mixture was stirred at 20-30° C. for 2 hours. The residue was purified by pre-TLC with DCM/MeOH after evaporating the solvent under reduce pressure to give the product (60 mg, 41.6%). $^1H$ NMR (400 MHz, DMSO) $\delta_H$ 12.52 (s, 1H), 10.38 (s, 1H), 9.97 (br, 1H), 8.75 (s, 1H), 8.08 (br, 1H), 8.03 (s, 1H), 7.91 (d, J=6.4 Hz, 2H), 7.67 (s, 1H), 7.23 (br, 2H), 7.03 (d, J=5.2 Hz, 2H), 6.94 (d, J=10.8 Hz, 1H), 6.86 (br, 1H), 5.38 (s, 1H), 3.72 (br, 1H), 3.47 (br, 1H), 3.25-3.0 (m, 6H), 2.80-2.50 (m, 10H), 2.25 (s, 2H), 1.86-1.66 (m, 3H), 1.55 (s, 3H), 1.37-1.24 (m, 12H); $[M+H]^+$=868.8.

Example 44: (R)-3-(tert-butyl)-N-(1-(4-(6-(4-(4-((1-(4-(2,4-dioxotetrahydropyrimidin-1(2H)-yl)-3-methylphenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

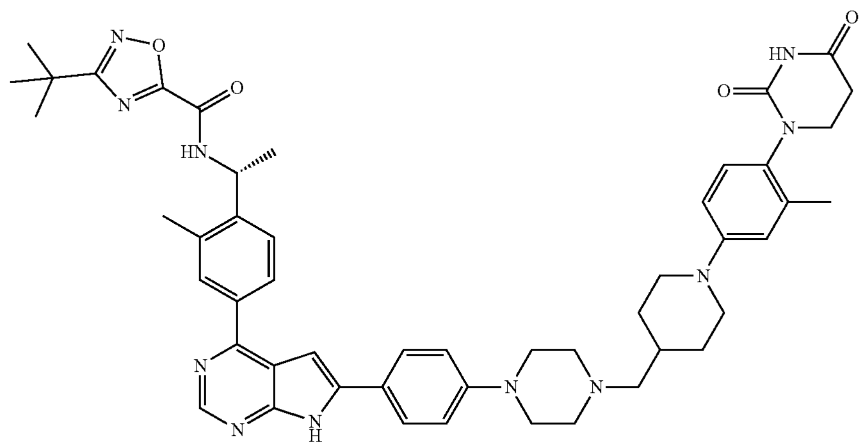 [SMILES: Cc1cc(-c2ncnc3[nH]c(-c4ccc(N5CCN(CC6CCN(c7ccc(N8CCC(=O)NC8=O)c(C)c7)CC6)CC5)cc4)cc23)ccc1[C@@H](C)NC(=O)c1nc(C(C)(C)C)no1]

The titled compound was synthesized in the procedures similar to Example 24. $^1H$ NMR (400 MHz, DMSO) $\delta_H$ 12.52 (s, 1H), 10.25 (s, 1H), 9.97 (s, 1H), 8.75 (s, 1H), 8.08 (s, 1H), 8.03 (s, 1H), 7.92 (br, 2H), 7.67 (br, 1H), 7.23 (s, 1H), 7.03 (br, 3H), 6.86-6.72 (m, 2H), 5.38 (s, 1H), 3.68 (br, 3H), 3.48 (br, 1H), 3.25 (s, 4H), 2.78-2.55 (m, 10H), 2.23 (s, 2H), 2.12 (s, 3H), 1.85-1.65 (m, 3H), 1.55 (s, 3H), 1.37 (s, 9H), 1.28-1.15 (m, 3H); $[M+H]^+$=864.8.

Example 45: (R)-3-(tert-butyl)-N-(1-(4-(6-(4-(4-((1-(4-(2,4-dioxotetrahydropyrimidin-1(2H)-yl)-3-methoxyphenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

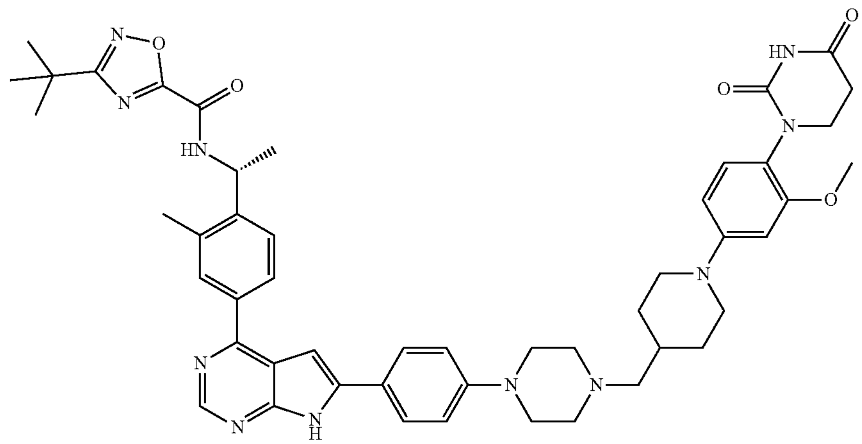 [SMILES: COc1cc(N2CCC(CN3CCN(c4ccc(-c5cc6c(-c7ccc([C@@H](C)NC(=O)c8nc(C(C)(C)C)no8)c(C)c7)ncnc6[nH]5)cc4)CC3)CC2)ccc1N1CCC(=O)NC1=O]

The titled compound was synthesized in the procedures similar to Example 24. $^1$H NMR (400 MHz, DMSO) $\delta_H$ 12.53 (s, 1H), 10.21 (s, 1H), 9.97 (d, J=7.6 Hz, 1H), 8.75 (s, 1H), 8.09 (d, J=7.6 Hz, 1H), 8.04 (s, 1H), 7.91 (d, J=7.6 Hz, 2H), 7.67 (d, J=8.0 Hz, 1H), 7.23 (s, 1H), 7.07-6.98 (m, 3H), 6.59 (s, 1H), 6.49 (d, J=9.2 Hz, 1H), 5.38 (s, 1H), 3.81-3.72 (m, 5H), 3.50 (s, 2H), 3.26 (s, 4H), 2.84-2.53 (m, 10H), 2.24 (s, 2H), 1.87-1.67 (m, 3H), 1.55 (d, J=6.0 Hz, 3H), 1.37 (s, 9H), 1.25 (s, 3H); [M+H]$^+$=880.8.

Example 46: 2-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)thiazole-4-carboxamide

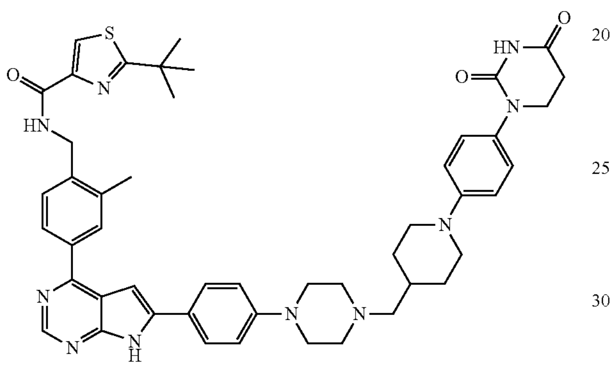

The titled compound was synthesized in the procedures similar to Example 24. $^1$H NMR (400 MHz, DMSO) $\delta_H$ 12.51 (s, 1H), 10.27 (s, 1H), 8.78 (br, 1H), 8.74 (s, 1H), 8.19 (s, 1H), 8.06 (s, 2H), 7.91 (d, J=7.6 Hz, 2H), 7.43 (d, J=7.2 Hz, 1H), 7.23 (s, 1H), 7.13 (d, J=8.4 Hz, 2H), 7.03 (d, J=7.6 Hz, 2H), 6.93 (d, J=8.0 Hz, 2H), 4.57 (s, 2H), 3.80-3.65 (m, 4H), 3.25 (br, 4H), 2.67-2.55 (m, 10H), 2.24 (br, 2H), 1.88-1.65 (m, 3H), 1.44 (s, 9H), 1.24 (br, 3H); [M+H]$^+$=851.8.

Example 47: 2-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)thiazole-5-carboxamide

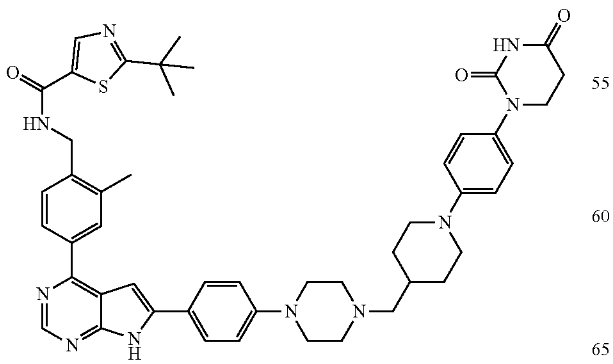

The titled compound was synthesized in the procedures similar to Example 24. $^1$H NMR (400 MHz, DMSO) $\delta_H$ 12.52 (s, 1H), 10.27 (s, 1H), 9.15 (s, 1H), 8.75 (s, 1H), 8.36 (s, 1H), 8.07 (s, 2H), 7.91 (d, J=8.0 Hz, 2H), 7.45 (d, J=7.2 Hz, 1H), 7.22 (s, 1H), 7.13 (d, J=8.0 Hz, 2H), 7.03 (d, J=7.2 Hz, 2H), 6.93 (d, J=8.0 Hz, 2H), 4.54 (s, 2H), 3.75-3.60 (m, 4H), 3.25 (s, 4H), 2.72-2.50 (m, 10H), 2.24 (br, 2H), 1.85-1.61 (m, 3H), 1.40 (s, 9H), 1.24 (br, 3H); [M+H]$^+$=851.8.

Example 48: 3-(tert-butyl)-N-((1R)-1-(4-(6-(6-(4-((1-(4-(2,6-dioxopiperidin-3-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide

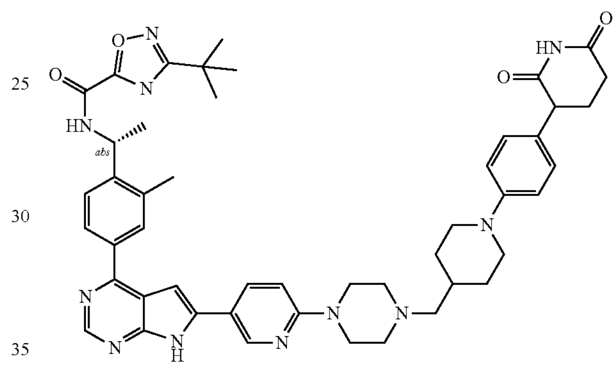

1-(4-(2,6-dioxopiperidin-3-yl)phenyl)piperidine-4-carbaldehyde (100 mg, crude) and (R)-3-(tert-butyl)-N-(1-(2-methyl-4-(6-(6-(piperazin-1-yl)pyridin-3-yl)-7H-pyrrolo[2,3-d]pyrimidin-4-yl)phenyl)ethyl)-1,2,4-oxadiazole-5-carboxamide (93.1 mg, 0.17 mmol) was dissolved in DCM/MeOH (5 mL, 10:1), then AcOH (1 drop) was added to the solution. The resulting mixture was stirred at room temperature for 1 h, and sodium triacetoxyborohydride (180.2 mg, 0.85 mmol) was added to the mixture in one portion. The mixture was stirred for another 1 h until LC-MS indicated all the starting material was consumed. The solid was filtered off. The filtrate was concentrated and purified with Prep-TLC to give the desire product (20 mg, 13.9%). $^1$H NMR (400 MHz, DMSO) $\delta_H$ 12.59 (s, 1H), 10.78 (s, 1H), 10.00-9.96 (m, 1H), 8.81 (s, 1H), 8.76 (s, 1H), 8.10-8.06 (m, 1H), 8.06-8.02 (m, 2H), 7.68-7.64 (m, 1H), 7.29 (s, 1H), 7.06-6.95 (m, 1H), 6.95-6.92 (m, 1H), 6.92-6.88 (m, 1H), 5.42-5.36 (m, 1H), 3.75-3.69 (m, 4H), 3.69-3.55 (m, 4H), 2.62-2.50 (m, 6H), 2.48 (s, 3H), 2.35-2.33 (m, 1H), 2.28-2.25 (m, 2H), 2.15-2.10 (m, 1H), 2.05-1.98 (m, 2H), 1.81-1.70 (m, 2H), 1.70-1.65 (m, 1H), 1.55 (d, J=8.0 Hz, 3H), 1.37 (s, 9H), 1.25-1.20 (m, 2H); [M+H]$^+$=850.6.

Example 49: 3-(tert-butyl)-N-(4-(6-(4-((1-((1-(4-(2,4-dioxotetrahydropyrimidin-1(2H)-yl)phenyl)piperidin-4-yl)methyl)piperidin-4-yl)oxy)phenyl)-7H-pyrrolo[2,3-d]pyrimidin-4-yl)-2-methylbenzyl)-1,2,4-oxadiazole-5-carboxamide Step 1: tert-butyl 4-(4-(4,4,5,5-tetramethyl-1,3,2-dioxaborolan-2-yl)phenoxy)piperidine-1-carboxylate

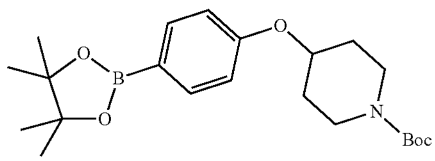 [SMILES: CC(C)(C)OC(=O)N1CCC(Oc2ccc(B3OC(C)(C)C(C)(C)O3)cc2)CC1]

A mixture of tert-butyl 4-(4-bromophenoxy)piperidine-1-carboxylate (710 mg, 2.0 mmol), bis(pinacolato)diboron (508 mg, 2.0 mmol), Pd(dppf)$Cl_2$ (146 mg, 0.2 mmol) and $CH_3COOK$ (300 mg, 3.0 mmol) in dioxane (20 mL) was stirred in a round bottom flask at 110° C. for 4 hours. Then the mixture was used for next step without further purification. $[M-99]^+$=304.2.

Step 2: tert-butyl 4-(4-(4-chloro-7-((2-(trimethylsilyl)ethoxy)methyl)-7H-pyrrolo[2,3-d]pyrimidin-6-yl)phenoxy)piperidine-1-carboxylate

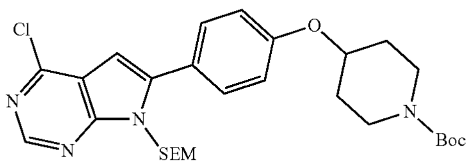 [SMILES: CC(C)(C)OC(=O)N1CCC(Oc2ccc(-c3cc4c(Cl)ncnc4n3COCC[Si](C)(C)C)cc2)CC1]

A solution of last step mixture reaction was added 4-chloro-6-iodo-7-((2-(trimethylsilyl)ethoxy)methyl)-7H-pyrrolo[2,3-d]pyrimidine (818 mg, 2.0 mmol), Pd(dppf)$Cl_2$ (146 mg, 0.1 mmol) and $K_2CO_3$ (400 mg, 3.0 mmol) in dioxane (20 mL) and water (4 mL) was stirred in a round bottom flask at 80° C. overnight. Then the mixture was evaporated in vacuum to afford the crude product, which was purified with silica gel column chromatography (PE:EA=100:0~60:40 gradient elution) to give the product (538 mg, 48%, two steps). $[M+H]^+$=559.3.

Step 3: tert-butyl 4-(4-(4-(4-((3-(tert-butyl)-1,2,4-oxadiazole-5-carboxamido)methyl)-3-methylphenyl)-7-((2-(trimethylsilyl)ethoxy)methyl)-7H-pyrrolo[2,3-d]pyrimidin-6-yl)phenoxy)piperidine-1-carboxylate

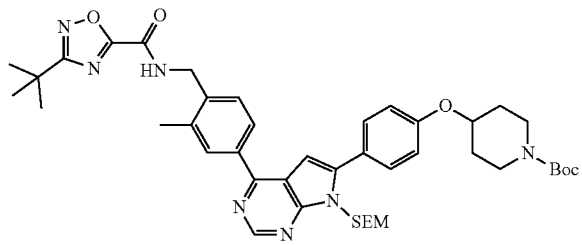 [SMILES: Cc1cc(-c2ncnc3c2cc(-c2ccc(OC4CCN(C(=O)OC(C)(C)C)CC4)cc2)n3COCC[Si](C)(C)C)ccc1CNC(=O)c1nc(C(C)(C)C)no1]

A mixture of tert-butyl 4-(4-(4-chloro-7-((2-(trimethylsilyl)ethoxy)methyl)-7H-pyrrolo[2,3-d]pyrimidin-6-yl)phenoxy)piperidine-1-carboxylate (538 mg, 0.96 mmol), 3-(tert-butyl)-N-(2-methyl-4-(4,4,5,5-tetramethyl-1,3,2-dioxaborolan-2-yl)benzyl)-1,2,4-oxadiazole-5-carboxamide (384 mg, 0.96 mmol), Pd(dppf)$Cl_2$ (70 mg, 0.096 mmol) and $K_2CO_3$ (265 mg, 1.92 mmol) in dioxane (16 mL) and water (4 mL) was stirred in a round bottom flask at 100° C. overnight. Then the mixture was evaporated in vacuum to afford the crude product, which was purified with silica gel column chromatography (PE:EtOAc=100:0~20:80 gradient elution) to give the product (440 mg, 57%). $[M+H]^+$=796.4.

Step 4: 3-(tert-butyl)-N-(2-methyl-4-(6-(4-(piperidin-4-yloxy)phenyl)-7H-pyrrolo[2,3-d]pyrimidin-4-yl)benzyl)-1,2,4-oxadiazole-5-carboxamide

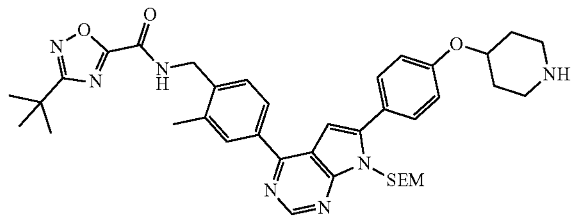 [SMILES: Cc1cc(-c2ncnc3c2cc(-c2ccc(OC4CCNCC4)cc2)n3COCC[Si](C)(C)C)ccc1CNC(=O)c1nc(C(C)(C)C)no1]

A mixture of tert-butyl 4-(4-(4-(4-((3-(tert-butyl)-1,2,4-oxadiazole-5-carboxamido)methyl)-3-methylphenyl)-7-((2-(trimethylsilyl)ethoxy)methyl)-7H-pyrrolo[2,3-d]pyrimidin-6-yl)phenoxy)piperidine-1-carboxylate (440 mg, 0.55 mmol) and trifluoroacetic acid (5 mL) in dichloromethane (5 mL) was stirred in a round bottom flask at room temperature for 2 hours. Then the mixture was evaporated in vacuum to afford the crude product, which was used for next step without further purification. To the crude was added ammonium hydroxide (2 mL) in methanol (10 mL) and stirred in a round bottom flask at room temperature overnight. The mixture was evaporated in vacuum to afford the crude product, which was purified with C18 column chromatography (0.1% HCl in water:acetonitrile=80:20~40:60 gradient elution) to give the product (216 mg, 61%). $[M+H]^+$=566.6.

Step 5: 3-(tert-butyl)-N-(4-(6-(4-((1-((1-(4-(2,4-dioxotetrahydropyrimidin-1(2H)-yl)phenyl)piperidin-4-yl)methyl)piperidin-4-yl)oxy)phenyl)-7H-pyrrolo[2,3-d]pyrimidin-4-yl)-2-methylbenzyl)-1,2,4-oxadiazole-5-carboxamide

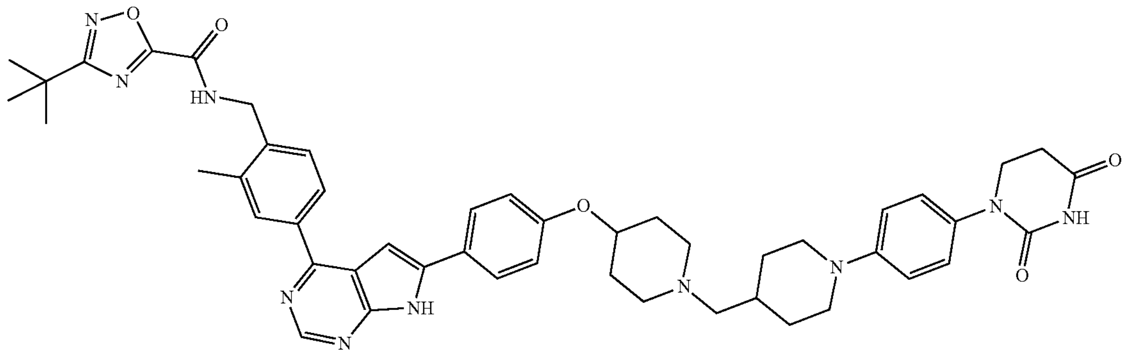 [SMILES: Cc1cc(-c2ncnc3[nH]c(-c4ccc(OC5CCN(CC6CCN(c7ccc(N8CCC(=O)NC8=O)cc7)CC6)CC5)cc4)cc23)ccc1CNC(=O)c1nc(C(C)(C)C)no1]

A mixture of 3-(tert-butyl)-N-(2-methyl-4-(6-(4-(piperidin-4-yloxy)phenyl)-7H-pyrrolo[2,3-d]pyrimidin-4-yl)benzyl)-1,2,4-oxadiazole-5-carboxamide (100 mg, 0.15 mmol) and 1-(4-(2,4-dioxotetrahydropyrimidin-1(2H)-yl)phenyl)piperidine-4-carbaldehyde (60 mg, 0.20 mmol) in dichloroethane (20 mL) was stirred in a round bottom flask at room temperature for 1 hour. Then to the mixture was added $NaBH(OAc)_3$ (212 mg, 1.0 mmol) and stirred in a round bottom flask at room temperature overnight. The mixture was evaporated in vacuum to afford the crude product, which was purified with C18 column chromatography (0.1% FA in water:acetonitrile=80:20~30:70 gradient elution) to give the product (78 mg, 61%). $^1H$ NMR (400 MHz, DMSO) $\delta_H$ 12.62 (s, 1H), 10.27 (s, 1H), 9.91 (s, 1H), 8.78 (s, 1H), 8.07 (s, 2H), 7.98 (d, J=7.6 Hz, 2H), 7.48 (d, J=7.6 Hz, 1H), 7.29 (s, 1H), 7.17-7.01 (m, 4H), 6.92 (d, J=8.4 Hz, 2H), 4.63-4.43 (m, 3H), 3.75-3.64 (m, 4H), 2.86-2.73 (m, 2H), 2.71-2.61 (m, 4H), 2.41-2.22 (m, 4H), 2.07-1.94 (m, 2H), 1.86-1.76 (m, 2H), 1.74-1.59 (m, 3H), 1.38 (s, 9H), 1.24-1.13 (m, 3H); $[M+H]^+$=851.8.

Example 50: N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-5-(1,1,1-trifluoro-2-methylpropan-2-yl)-1,2,4-oxadiazole-3-carboxamide Step 1: ethyl 2-imino-2-(((3,3,3-trifluoro-2,2-dimethylpropanoyl)oxy)amino)acetate

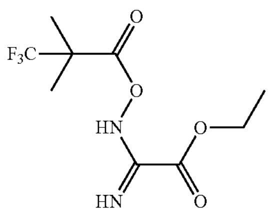 [SMILES: CCOC(=O)C(=N)NOC(=O)C(C)(C)C(F)(F)F]

To a solution of 3,3,3-trifluoro-2,2-dimethylpropanoic acid (24.5 g, 157 mmol) and HATU (60 g, 158 mmol) in DCM (500 mL) was added $Et_3N$ (30 g, 300 mmol). The mixture was stirred at room temperature for 1 hour, then ethyl 2-(hydroxyamino)-2-iminoacetate (21 g, 159 mmol) was added. The reaction mixture was stirred at room temperature for 16 hours. The reaction mixture was washed with water (500 mL) and brine (500 mL). The organic layer was dried over $Na_2SO_4$, filtered, concentrated and purified by silica gel column chromatography to afford the product (35 g, 82%). $[M+H]^+$=271.1.

Step 2: ethyl 5-(1,1,1-trifluoro-2-methylpropan-2-yl)-1,2,4-oxadiazole-3-carboxylate

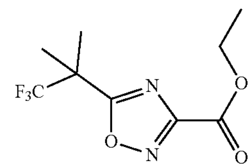 [SMILES: CCOC(=O)c1noc(C(C)(C)C(F)(F)F)n1]

A solution of ethyl 2-imino-2-(((3,3,3-trifluoro-2,2-dimethylpropanoyl)oxy)amino)acetate (13 g, 48 mmol) in DMF (100 mL) was heated to 90° C. for 16 hours. After EtOAc (300 mL) was added, the reaction mixture was washed with water (300 mL) and brine (300 mL). The organic layer was dried over $Na_2SO_4$, filtered, concentrated and purified by silica gel column chromatography to afford the product (7.5 g, 62%). $[M+H]^+$=253.1.

Step 3: 5-(1,1,1-trifluoro-2-methylpropan-2-yl)-1,2,4-oxadiazole-3-carboxylic acid

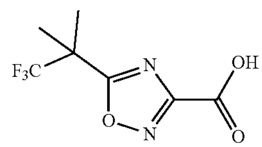

A solution of ethyl 5-(1,1,1-trifluoro-2-methylpropan-2-yl)-1,2,4-oxadiazole-3-carboxylate (7.0 g, 28 mmol) and $LiOH \cdot H_2O$ (1.7 g, 40 mmol) in $MeOH/THF/H_2O$ (30 mL/30 mL/30 mL) was stirred at room temperature for 16 hours, and the mixture was concentrated and adjusted to pH=6 with 1 N HCl aq. to afford the product (8.5 g, crude) by filtration. $[M+H]^+$=225.2.

Step 4: tert-butyl (4-bromo-2-methylbenzyl)carbamate

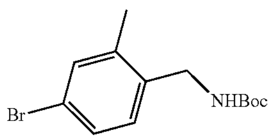 [SMILES: Cc1cc(Br)ccc1CNC(=O)OC(C)(C)C]

To a solution of (4-bromo-2-methylphenyl)methanamine (26 g, 130 mmol) and $Et_3N$ (20 mL, 145 mmol) in DCM (300 mL) was added $Boc_2O$ (30 g, 138 mmol) slowly at room temperature, then stirred for 1 h at room temperature. The reaction mixture was concentrated. EtOAc (200 mL) was added and washed with water (200 mL) and brine (200 mL). The organic phase was dried over $Na_2SO_4$, concentrated and purified by silica gel column chromatography to afford the product (42 g, crude). [M-55]=244.1.

Step 5: tert-butyl (2-methyl-4-(4,4,5,5-tetramethyl-1,3,2-dioxaborolan-2-yl)benzyl)carbamate

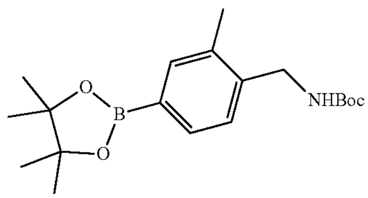 [SMILES: Cc1cc(B2OC(C)(C)C(C)(C)O2)ccc1CNC(=O)OC(C)(C)C]

Under $N_2$, a mixture of tert-butyl (4-bromo-2-methylbenzyl)carbamate (42 g, 140 mmol), bis(pinacolato)diboron (33 g, 130 mmol), $Pd(PPh_3)_2Cl_2$ (2.0 g, 2.8 mmol) and KOAc (30 g, 306 mmol) in dioxane (300 mL) was stirred at 100° C. for 16 hours. After being cooled down, the solvent was evaporated. The crude residue was dissolved with EtOAc (500 mL) and washed with water (500 mL) and brine (500 mL). The organic phase was separated and purified by silica gel column chromatography to give the product (46 g, crude). $[M+Na]^+$=370.4.

Step 6: (2-methyl-4-(4,4,5,5-tetramethyl-1,3,2-dioxaborolan-2-yl)phenyl)methanamine

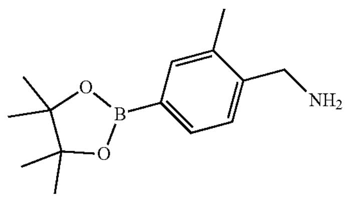 [SMILES: Cc1cc(B2OC(C)(C)C(C)(C)O2)ccc1CN]

To a solution of tert-butyl (2-methyl-4-(4,4,5,5-tetramethyl-1,3,2-dioxaborolan-2-yl)benzyl)carbamate (46 g, 132 mmol) in dioxane (200 mL) was added 4 N HCl/dioxane (200 ml) slowly. The reaction mixture was stirred for 2 hours at room temperature and then concentrated to remove dioxane. The residue was stirred with MTBE (400 mL), and the solid was collected and dried in vacuo to give the product (31 g, crude). $[M-NH_2]^+$=231.3.

Step 7: N-(2-methyl-4-(4,4,5,5-tetramethyl-1,3,2-dioxaborolan-2-yl)benzyl)-5-(1,1,1-trifluoro-2-methylpropan-2-yl)-1,2,4-oxadiazole-3-carboxamide

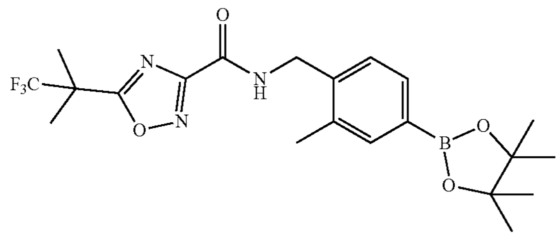 [SMILES: Cc1cc(B2OC(C)(C)C(C)(C)O2)ccc1CNC(=O)c1noc(C(C)(C)C(F)(F)F)n1]

To a mixture of 5-(1,1,1-trifluoro-2-methylpropan-2-yl)-1,2,4-oxadiazole-3-carboxylic acid (1.3 g, 5.8 mmol) and DMF (1 drop) in DCM (50 mL) was added oxalyl dichloride (1.5 mL) dropwise. The reaction mixture was stirred for 1 hour at room temperature and then concentrated to give crude 5-(1,1,1-trifluoro-2-methylpropan-2-yl)-1,2,4-oxadiazole-3-carbonyl chloride. To a solution of (2-methyl-4-(4,4,5,5-tetramethyl-1,3,2-dioxaborolan-2-yl)phenyl)methanamine (1.6 g, 5.6 mmol) and $Et_3N$ (2 mL, 14.5 mmol) in DCM (40 mL) was added a solution of crude 5-(1,1,1-trifluoro-2-methylpropan-2-yl)-1,2,4-oxadiazole-3-carbonyl chloride in DCM (40 mL). The reaction mixture was stirred for 1 hour at room temperature and then quenched with 100 mL water. The DCM layer was dried over $Na_2SO_4$, concentrated and purified by silica gel column chromatography to give the product (1.7 g, 65%). $[M+H]^+$=454.4.

Step 8: tert-butyl 4-(4-(4-(3-methyl-4-((5-(1,1,1-trifluoro-2-methylpropan-2-yl)-1,2,4-oxadiazole-3-carboxamido)methyl)phenyl)-7-((2-(trimethylsilyl)ethoxy)methyl)-7H-pyrrolo[2,3-d]pyrimidin-6-yl)phenyl)piperazin-1-carboxylate

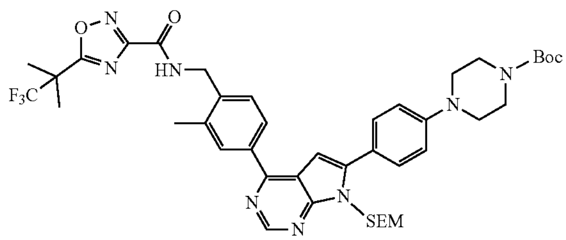 [SMILES: Cc1cc(-c2ncnc3c2cc(-c2ccc(N4CCN(C(=O)OC(C)(C)C)CC4)cc2)n3COCC[Si](C)(C)C)ccc1CNC(=O)c1noc(C(C)(C)C(F)(F)F)n1]

Under $N_2$, a mixture of tert-butyl 4-(4-(4-chloro-7-((2-(trimethylsilyl)ethoxy)methyl)-7H-pyrrolo[2,3-d]pyrimidin-6-yl)phenyl)piperazine-1-carboxylate (250 mg, 0.46 mmol), N-(2-methyl-4-(4,4,5,5-tetramethyl-1,3,2-dioxaborolan-2-yl)benzyl)-5-(1,1,1-trifluoro-2-methylpropan-2-yl)-1,2,4-oxadiazole-3-carboxamide (250 mg, 0.55 mmol), $Pd(dppf)Cl_2$ (30 mg, 0.041 mmol) and $K_2CO_3$ (300 mg, 2.17 mmol) in dioxane (25 mL) and $H_2O$ (5 mL) was stirred at 100° C. for 16 hours. The solvent was evaporated. The crude residue was dissolved with EtOAc (50 mL) and washed with water (50 mL) and brine (50 mL). The organic phase was separated and purified by silica gel column chromatography to give the product (100 mg, 26%).

Step 9: N-(2-methyl-4-(6-(4-(piperazin-1-yl)phenyl)-7H-pyrrolo[2,3-d]pyrimidin-4-yl)benzyl)-5-(1,1,1-trifluoro-2-methylpropan-2-yl)-1,2,4-oxadiazole-3-carboxamide

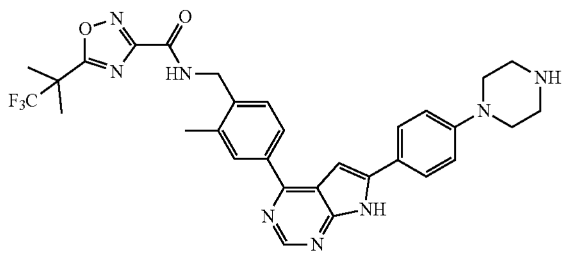 [SMILES: Cc1cc(-c2ncnc3[nH]c(-c4ccc(N5CCNCC5)cc4)cc23)ccc1CNC(=O)c1noc(C(C)(C)C(F)(F)F)n1]

A solution of tert-butyl 4-(4-(4-(3-methyl-4-((5-(1,1,1-trifluoro-2-methylpropan-2-yl)-1,2,4-oxadiazole-3-carboxamido)methyl)phenyl)-7-((2-(trimethylsilyl)ethoxy)methyl)-7H-pyrrolo[2,3-d]pyrimidin-6-yl)phenyl)piperazine-1-carboxylate (100 mg, 0.12 mmol) in TFA/DCM (2 mL/2 mL) was stirred at room temperature for 2 hours. The reaction mixture was concentrated to give a crude which was stirred with $NH_3$/MeOH (1M, 10 mL) for 30 min. Then the mixture was concentrated to give the product (160 mg, crude). $[M+H]^+$=605.6.

Step 10: N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-5-(1,1,1-trifluoro-2-methylpropan-2-yl)-1,2,4-oxadiazole-3-carboxamide

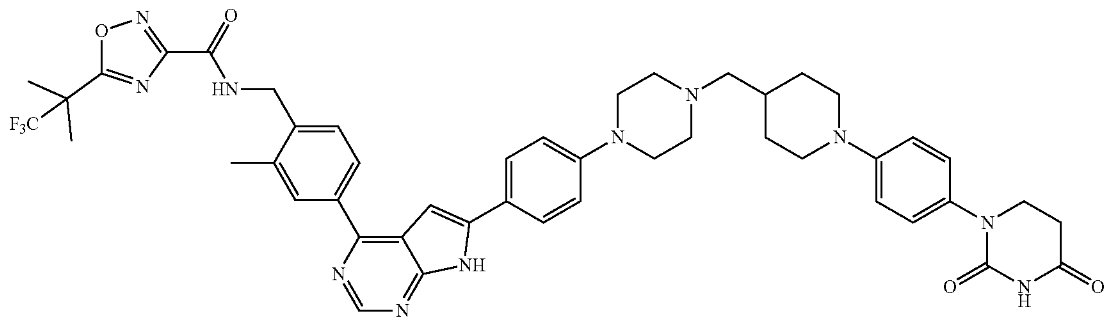 [SMILES: Cc1cc(-c2ncnc3[nH]c(-c4ccc(N5CCN(CC6CCN(c7ccc(N8CCC(=O)NC8=O)cc7)CC6)CC5)cc4)cc23)ccc1CNC(=O)c1noc(C(C)(C)C(F)(F)F)n1]

A mixture of N-(2-methyl-4-(6-(4-(piperazin-1-yl)phenyl)-7H-pyrrolo[2,3-d]pyrimidin-4-yl)benzyl)-5-(1,1,1-trifluoro-2-methylpropan-2-yl)-1,2,4-oxadiazole-3-carboxamide (160 mg, crude), 1-(4-(2,4-dioxotetrahydropyrimidin-1(2H)-yl)phenyl)piperidine-4-carbaldehyde (40 mg, 0.13 mmol) and $NaBH(OAc)_3$ (100 mg, 0.47 mmol) in dichloroethane (20 mL) was stirred at room temperature for 2 hours. After EtOAc (100 mL) was added, the solution was washed with sat. $NaHCO_3$ aq. (50 mL) and brine 50 mL for 3 times. The organic layer was dried over $Na_2SO_4$, filtered, concentrated, and purified by silica gel column chromatography to give the product (30 mg, 28%). $^1$H NMR (400 MHz, DMSO) $\delta_H$ 12.53 (s, 1H), 10.27 (s, 1H), 9.66 (s, 1H), 8.75 (s, 1H), 8.07 (s, 2H), 7.91 (d, J=7.2 Hz, 2H), 7.45 (d, J=8.0 Hz, 1H), 7.27-6.90 (m, 7H), 4.60-4.56 (m, 2H), 3.71-3.66 (m, 4H), 3.26 (s, 3H), 2.70-2.66 (m, 4H), 2.26-2.22 (m, 2H), 1.82 (d, J=11.3 Hz, 2H), 1.72 (s, 6H), 1.32-1.17 (m, 2H); $[M+H]^+$=890.5.

Example 51: N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylbenzyl)-5-(1-(trifluoromethyl)cyclopropyl)-1,2,4-oxadiazole-3-carboxamide

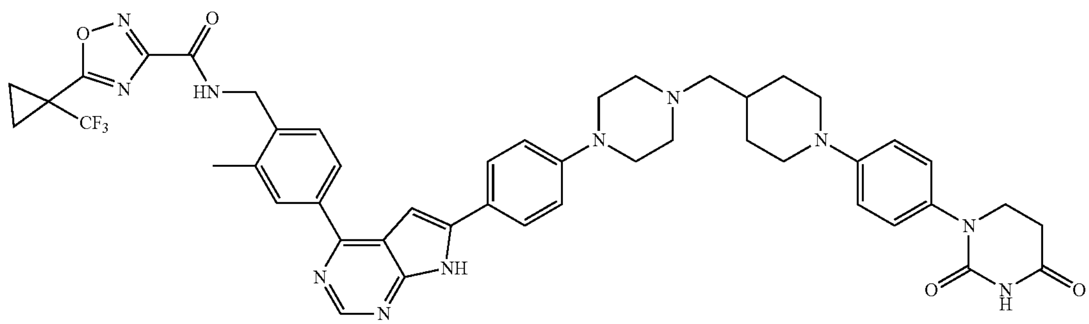 [SMILES: Cc1cc(-c2ncnc3[nH]c(-c4ccc(N5CCN(CC6CCN(c7ccc(N8CCC(=O)NC8=O)cc7)CC6)CC5)cc4)cc23)ccc1CNC(=O)c1noc(C2(C(F)(F)F)CC2)n1]

The titled compound was synthesized in the procedures similar to Example 50. $^{1}H$ NMR (400 MHz, DMSO) $\delta_H$ 12.52 (s, 1H), 10.27 (s, 1H), 9.59 (s, 1H), 8.75 (s, 1H), 8.06 (s, 2H), 7.91 (d, J=7.0 Hz, 2H), 7.44 (d, J=8.1 Hz, 1H), 7.26-6.88 (m, 7H), 4.56 (s, 2H), 3.75-3.63 (m, 4H), 3.26 (s, 3H), 2.68 (s, 5H), 2.24 (s, 2H), 1.84 (s, 6H), 1.72 (s, 1H), 1.32-1.16 (m, 2H); $[M+H]^+$=888.5.

Example 52: (R)-3-(tert-butyl)-N-(1-(4-(6-(6-(4-((1-(4-(2,4-dioxotetrahydropyrimidin-1(2H)-yl)-3-methylphenyl)piperidin-4-yl)methyl)piperazin-1-yl)pyridin-3-yl)-7H-pyrrolo[2,3-d]pyrimidin-4-yl)-2-fluorophenyl)ethyl)-1,2,4-oxadiazole-5-carboxamide

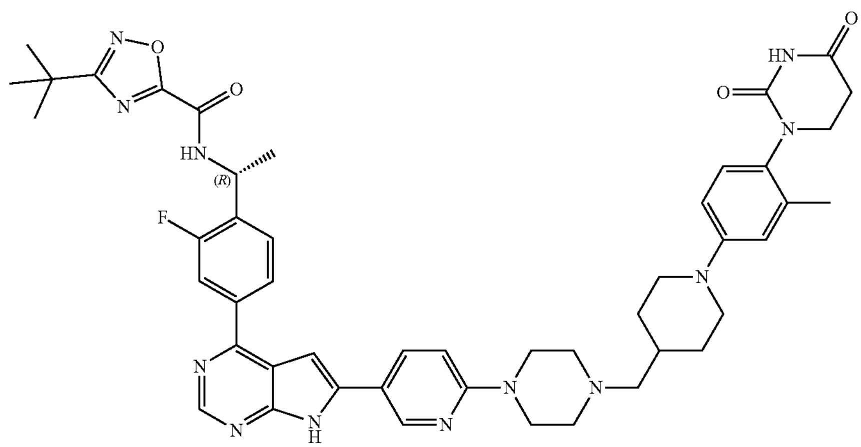

The titled compound was synthesized in the procedures similar to Example 24. $^{1}H$ NMR (400 MHz, DMSO) $\delta_H$ 12.65 (s, 1H), 10.24 (s, 1H), 10.03-10.02 (m, 1H), 8.82-8.79 (m, 2H), 8.22-8.12 (m, 2H), 8.01-7.98 (m, 1H), 7.74-7.69 (m, 1H), 7.37 (s, 1H), 7.05-6.96 (m, 2H), 6.82-6.77 (m, 2H), 5.48-5.45 (m, 1H), 3.71-3.69 (m, 7H), 3.48-3.43 (m, 1H), 2.73-2.63 (m, 4H), 2.49-2.47 (m, 4H), 2.23-2.21 (m, 2H), 2.12 (s, 3H), 1.83-1.71 (m, 3H), 1.60-1.59 (m, 3H), 1.38 (s, 9H), 1.28-1.17 (m, 3H); $[M+H]^+$=869.8.

Example 53: 3-(tert-butyl)-N-((R)-1-(4-(6-(6-(4-(2-(1-(4-((R)-2,6-dioxopiperidin-3-yl)phenyl)piperidin-4-yl)ethyl)piperazin-1-yl)pyridin-3-yl)-7H-pyrrolo[2,3-d]pyrimidin-4-yl)-2-methylphenyl)ethyl)-1,2,4-oxadiazole-5-carboxamide

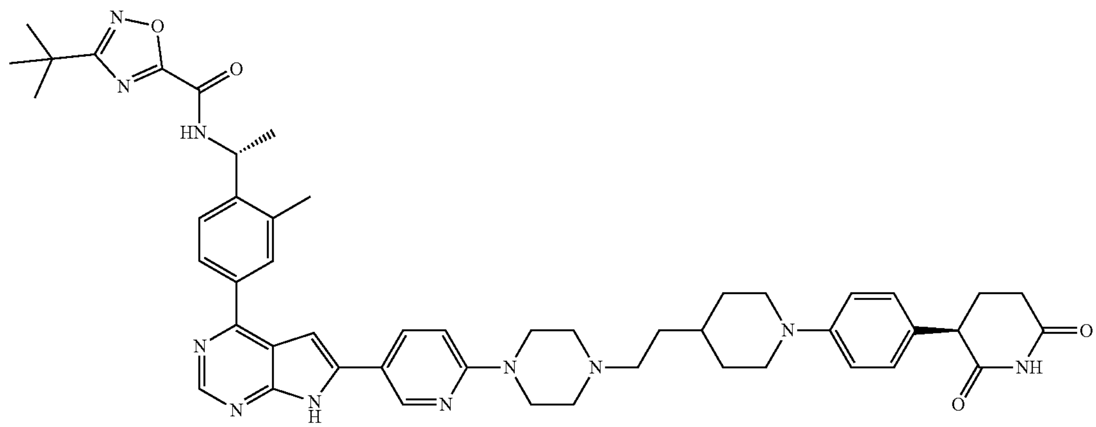 [SMILES: Cc1cc(-c2ncnc3[nH]c(-c4ccc(N5CCN(CCC6CCN(c7ccc([C@H]8CCC(=O)NC8=O)cc7)CC6)CC5)nc4)cc23)ccc1[C@@H](C)NC(=O)c1nc(C(C)(C)C)no1]

The titled compound was synthesized in the procedures similar to Example 24. $^1$H NMR (400 MHz, DMSO) $\delta_H$ 12.59 (s, 1H), 10.78 (s, 1H), 9.97 (d, J=7.4 Hz, 1H), 8.81 (s, 1H), 8.76 (s, 1H), 8.17 (s, 2H), 8.09 (d, J=7.2 Hz, 1H), 8.04 (s, 1H), 7.66 (d, J=8.1 Hz, 1H), 7.30 (s, 1H), 7.03 (d, J=8.2 Hz, 2H), 6.96 (d, J=8.5 Hz, 1H), 6.88 (d, J=8.2 Hz, 2H), 5.38 (s, 1H), 3.75-3.55 (m, 8H), 3.45-3.21 (m, 3H), 2.69-2.38 (m, 9H), 2.18-1.96 (m, 2H), 1.77 (d, J=11.7 Hz, 2H), 1.55 (d, J=6.3 Hz, 3H), 1.46 (s, 3H), 1.37 (s, 9H), 1.32-1.20 (m, 2H); [M+H]$^+$=864.8.

Example 54: 3-(tert-butyl)-N-((R)-1-(4-(6-(6-(4-(2-(1-(4-((S)-2,6-dioxopiperidin-3-yl)phenyl)piperidin-4-yl)ethyl)piperazin-1-yl)pyridin-3-yl)-7H-pyrrolo[2,3-d]pyrimidin-4-yl)-2-methylphenyl)ethyl)-1,2,4-oxadiazole-5-carboxamide

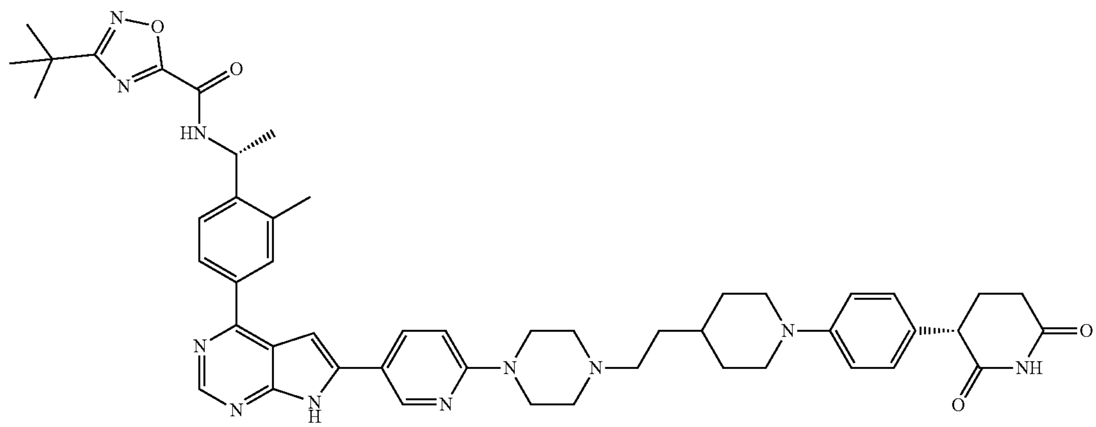 [SMILES: Cc1cc(-c2ncnc3[nH]c(-c4ccc(N5CCN(CCC6CCN(c7ccc([C@@H]8CCC(=O)NC8=O)cc7)CC6)CC5)nc4)cc23)ccc1[C@@H](C)NC(=O)c1nc(C(C)(C)C)no1]

The titled compound was synthesized in the procedures similar to Example 24. $^1$H NMR (400 MHz, DMSO) $\delta_H$ 12.60 (s, 1H), 10.78 (s, 1H), 9.97 (d, J=7.8 Hz, 1H), 8.79 (d, J=18.9 Hz, 2H), 8.10 (dd, J=35.4, 27.5 Hz, 4H), 7.66 (d, J=8.0 Hz, 1H), 7.30 (s, 1H), 7.03 (d, J=8.3 Hz, 2H), 6.96 (d, J=9.1 Hz, 1H), 6.88 (d, J=8.2 Hz, 2H), 5.38 (s, 1H), 3.75-3.54 (m, 8H), 2.68-2.33 (m, 12H), 2.19-1.96 (m, 2H), 1.77 (d, J=12.0 Hz, 2H), 1.55 (d, J=6.6 Hz, 3H), 1.46 (s, 3H), 1.37 (s, 9H), 1.33-1.21 (m, 2H); [M+H]$^+$=864.8.

Example 55: (R)-3-(tert-butyl)-N-(1-(4-(6-(4-(4-((1-(4-(2,6-dioxopiperidin-3-yl)phenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide Step 1: (1-(4-bromophenyl)piperidin-4-yl)methanol

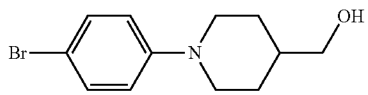 [SMILES: OCC1CCN(c2ccc(Br)cc2)CC1]

1-bromo-4-iodobenzene (2.0 g, 7.1 mmol), piperidin-4-ylmethanol (894.0 mg, 7.8 mmol), CuI (270.0 mg, 1.4 mmol), L-proline (163.0 mg, 1.4 mmol), $K_3PO_4$ (3.0 g, 14.2 mmol) were placed in DMSO (20 mL). The resulting mixture was then heated to 80° C. overnight until LC-MS indicated all the starting material was consumed. The mixture was cooled to room temperature, filtered off the solid, diluted with EtOAc (200 mL), and washed with brine for 3 times. The organic layer was dried over $Na_2SO_4$, and concentrated to afford crude product (2.8 g, crude), which was used directly without further purification. [M+H]$^+$=270.0.

Step 2: (1-(4-(2,6-bis(benzyloxy)pyridin-3-yl)phenyl)piperidin-4-yl)methanol

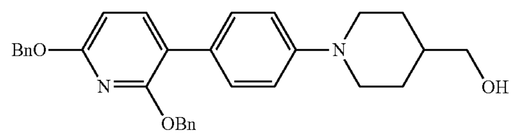 [SMILES: OCC1CCN(c2ccc(-c3ccc(OCc4ccccc4)nc3OCc3ccccc3)cc2)CC1]

(1-(4-bromophenyl)piperidin-4-yl)methanol (2.8 g, crude), Pd(dppf)$Cl_2$ (580.0 mg, 0.71 mmol), 2,6-bis(benzyloxy)-3-(4,4,5,5-tetramethyl-1,3,2-dioxaborolan-2-yl)pyridine (3.0 g, 7.1 mmol) and $Cs_2CO_3$ (4.6 g, 14.2 mmol) were placed in dioxane/water (300 mL, 10:1). The mixture was stirred at 100° C. overnight until LC-MS indicated all the starting material was consumed. The reaction was cooled to room temperature and filtered off the solid. The filtrate was concentrated and purified with $SiO_2$-gel column (eluted with EtOAc/Hexane=1:1) to give the titled product (3.0 g, 88%, 2 steps). [M+H]$^+$=481.2.

Step 3: 3-(4-(4-(hydroxymethyl)piperidin-1-yl)phenyl)piperidine-2,6-dione

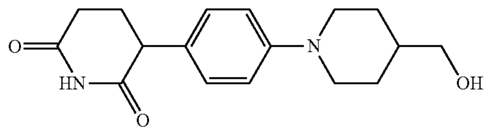 [SMILES: O=C1CCC(c2ccc(N3CCC(CO)CC3)cc2)C(=O)N1]

(1-(4-(2,6-bis(benzyloxy)pyridin-3-yl)phenyl)piperidin-4-yl)methanol (3.0 g, 6.3 mmol) was dissolved in MeOH (30 mL). Pd/C (10%, w/w, 0.3 g) was added to the solution in one portion. The resulting mixture was stirred under $H_2$ atmosphere (1 atm) overnight until LC-MS indicated all the starting material was consumed. The solid was filtered off and the filtrate was concentrated to give the crude product. The crude was slurred with MTBE to give the desired product (1.2 g, 63.5%). $[M+H]^+$=303.0.

Step 4: 1-(4-(2,6-dioxopiperidin-3-yl)phenyl)piperidine-4-carbaldehyde

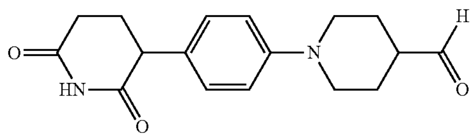 [SMILES: O=CC1CCN(c2ccc(C3CCC(=O)NC3=O)cc2)CC1]

3-(4-(4-(hydroxymethyl)piperidin-1-yl)phenyl)piperidine-2,6-dione (100.0 mg, 0.33 mmol) was dissolved in DMSO (2 mL). IBX (184.8 mg, 0.66 mmol) was added to the solution in portions at 0° C. and the mixture was stirred at 0° C. for 30 min. Then the mixture was warmed to room temperature for another 1 h until TLC indicated all the starting material was consumed. The mixture was diluted with water, extracted with EtOAc, washed with brine, dried over $Na_2SO_4$, and concentrated to give crude desire product (100.0 mg, crude) which was used directly without further purification.

Step 5: (R)-3-(tert-butyl)-N-(1-(4-(6-(4-(4-((1-(4-(2,6-dioxopiperidin-3-yl)phenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

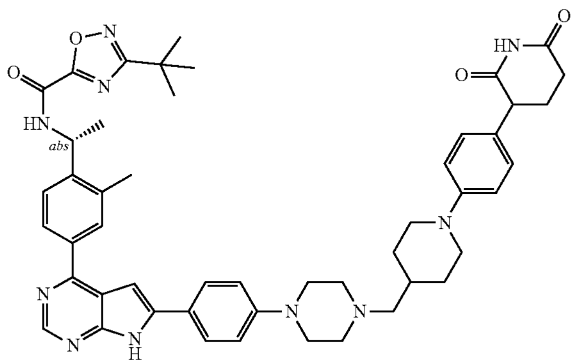

1-(4-(2,6-dioxopiperidin-3-yl)phenyl)piperidine-4-carbaldehyde (100.0 mg, crude) and (R)-3-(tert-butyl)-N-(1-(2-methyl-4-(6-(4-(piperazin-1-yl)phenyl)-7H-pyrrolo[2,3-d]pyrimidin-4-yl)phenyl)ethyl)-1,2,4-oxadiazole-5-carboxamide (93.1 mg, 0.17 mmol) were dissolved in DCM/MeOH (5 mL, 10:1), then AcOH (1 drop) was added to the solution. The resulting mixture was stirred at room temperature for 1 h, and sodium triacetoxyborohydride (180.2 mg, 0.85 mmol) was added to the mixture in one portion. The mixture was stirred for another 1 h until LC-MS indicated all the starting material was consumed. The solid was filtered off, concentrated and purified with Prep-TLC to give the desire product (20.7 mg, 14.3%). $^1$H NMR (400 MHz, DMSO) $\delta_H$ 12.52 (s, 1H), 10.78 (s, 1H), 9.97 (d, J=8.0 Hz, 1H), 8.75 (s, 1H), 8.09 (d, J=8.0 Hz, 1H), 8.03 (s, 1H), 7.91 (d, J=8.0 Hz, 2H), 7.66 (d, J=8.0 Hz, 1H), 7.23 (s, 1H), 7.07-7.01 (m, 4H), 6.89 (d, J=8.0 Hz, 2H), 5.42-5.33 (m, 1H), 3.76-3.64 (m, 3H), 3.30-3.22 (m, 3H), 3.10-2.90 (m, 2H), 2.68-2.57 (m, 5H), 2.48 (s, 3H), 2.30-2.20 (m, 2H), 2.15-2.08 (m, 1H), 2.05-1.96 (m, 1H), 1.85-1.77 (m, 2H), 1.77-1.70 (m, 1H), 1.55 (d, J=8.0 Hz, 3H), 1.37 (s, 9H), 1.28-1.18 (m, 3H); $[M+H]^+$=849.9.

Example 56: 5-(tert-butyl)-N-((1R)-1-(4-(6-(6-(4-((1-(4-(2,6-dioxopiperidin-3-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-3-carboxamide

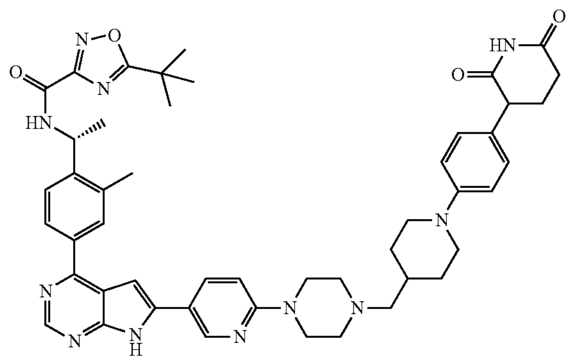 [SMILES: Cc1cc(-c2ncnc3[nH]c(-c4ccc(N5CCN(CC6CCN(c7ccc(C8CCC(=O)NC8=O)cc7)CC6)CC5)nc4)cc23)ccc1[C@@H](C)NC(=O)c1noc(C(C)(C)C)n1]

Example 57: 5-(tert-butyl)-N-((1R)-1-(4-(6-(5-(4-((1-(4-(2,6-dioxopiperidin-3-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-3-carboxamide

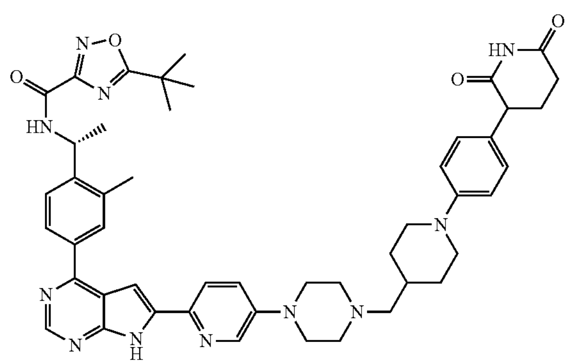 [SMILES: Cc1cc(-c2ncnc3[nH]c(-c4ccc(N5CCN(CC6CCN(c7ccc(C8CCC(=O)NC8=O)cc7)CC6)CC5)cn4)cc23)ccc1[C@@H](C)NC(=O)c1noc(C(C)(C)C)n1]

Example 58: (R)-3-(tert-butyl)-N-(1-(4-(6-(6-(4-((1-(4-(2,4-dioxotetrahydropyrimidin-1(2H)-yl)-3-methylphenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide

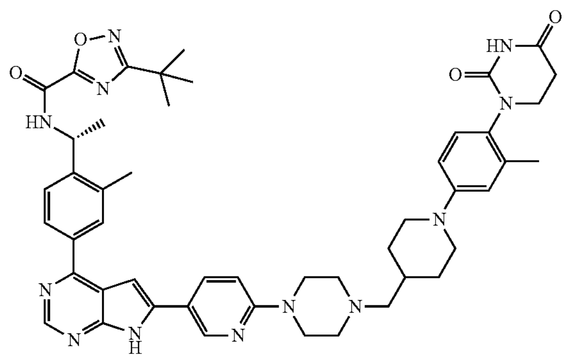 [SMILES: Cc1cc(-c2ncnc3[nH]c(-c4ccc(N5CCN(CC6CCN(c7ccc(N8CCC(=O)NC8=O)c(C)c7)CC6)CC5)nc4)cc23)ccc1[C@@H](C)NC(=O)c1nc(C(C)(C)C)no1]

A mixture of (R)-3-(tert-butyl)-N-(1-(2-methyl-4-(6-(6-(piperazin-1-yl)pyridin-3-yl)-7H-pyrrolo[2,3-d]pyrimidin-4-yl)phenyl)ethyl)-1,2,4-oxadiazole-5-carboxamide (50 mg, 0.083 mmol), 1-(4-(2,4-dioxotetrahydropyrimidin-1(2H)-yl)-3-methylphenyl)piperidine-4-carbaldehyde (30 mg, 0.095 mmol) and $NaBH(OAc)_3$ (50 mg, 0.24 mmol) in dichloroethane (20 mL) was stirred at room temperature for 2 hours. After EtOAc (100 mL) was added, the solution was washed with sat. $NaHCO_3$ aq. (50 mL) and brine (50 mL) for 3 times. The organic layer was dried over $Na_2SO_4$, filtered, concentrated, and purified by silica gel column chromatography to give the product (15 mg, 21%). $^1H$ NMR (400 MHz, DMSO) $\delta_H$ 12.60 (s, 1H), 10.25 (s, 1H), 9.99-9.95 (m, 1H), 8.82-8.77 (m, 2H), 8.23-8.15 (m, 1H), 8.13-7.99 (m, 2H), 7.67 (d, J=6.6 Hz, 1H), 7.30 (s, 1H), 7.09-6.91 (m, 2H), 6.87-6.71 (m, 2H), 5.41-5.36 (m, 1H), 3.76-3.55 (m, 7H), 3.52-3.41 (m, 1H), 3.19-2.88 (m, 2H), 2.78-2.62 (m, 4H), 2.24-2.20 (m, 2H), 2.12 (s, 3H), 1.86-1.68 (m, 3H), 1.58-1.49 (m, 3H), 1.37 (s, 9H), 1.29-1.16 (m, 2H); $[M+H]^+$ =865.8.

Example 59: (R)-3-(tert-butyl)-N-(1-(4-(6-(5-(4-((1-(4-(2,4-dioxotetrahydropyrimidin-1(2H)-yl)-3-methylphenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

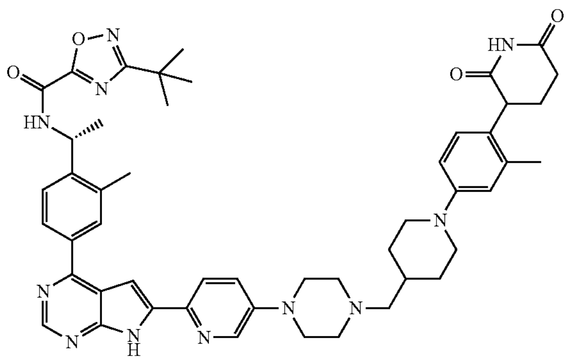 [SMILES: Cc1cc(N2CCC(CN3CCN(c4ccc(-c5cc6c(-c7ccc([C@@H](C)NC(=O)c8nc(C(C)(C)C)no8)c(C)c7)ncnc6[nH]5)nc4)CC3)CC2)ccc1C1CCC(=O)NC1=O]

Example 60: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-2-methylphenyl)ethyl)-1,2,4-oxadiazole-5-carboxamide Step 1: tert-butyl 4-((methylsulfonyl)oxy)piperidine-1-carboxylate

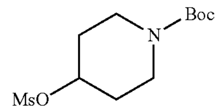

To a mixture of tert-butyl 4-hydroxypiperidine-1-carboxylate (2 g, 9.93 mmol) and TEA (1.5 g, 14.89 mmol) in DCM (20 mL), methanesulfonyl chloride (1.37 g, 11.92 mmol) was added at 0° C. and the resulting mixture was allowed to stir at 25° C. for 2 hours. The mixture was washed by brine, dried over $Na_2SO_4$, filtered and evaporated in vacuum to afford the product (3 g, 92%), which was used directly for next step. $[M+H]^+$=280.2.

Step 2: tert-butyl 4-(3,5-dimethyl-4-(4,4,5,5-tetramethyl-1,3,2-dioxaborolan-2-yl)-1H-pyrazol-1-yl)piperidine-1-carboxylate

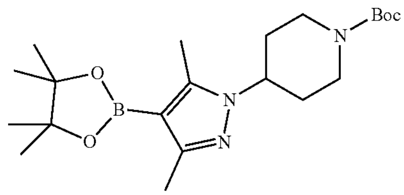 [SMILES: Cc1nn(C2CCN(C(=O)OC(C)(C)C)CC2)c(C)c1B1OC(C)(C)C(C)(C)O1]

To a mixture of 3,5-dimethyl-4-(4,4,5,5-tetramethyl-1,3,2-dioxaborolan-2-yl)-1H-pyrazole (0.6 g, 2.70 mmol) in dry DMF (10 mL), NaH (0.119 g, 3.0 mmol) was added at 0° C. and the resulting mixture was stirred at 0° C. for 1 hour. After tert-butyl 4-((methylsulfonyl)oxy)piperidine-1-carboxylate (0.91 g, 3.0 mmol) was added to the mixture, the reaction was heated to 95° C. for 1 hour. The mixture was cooled down, quenched by brine (20 mL) at 0-10° C., then extracted by EtOAc (30 mL*3). The combined organic layer was washed by brine and evaporated in vacuum to afford the crude product, which was further purified with silica gel column chromatography (PE:EA=100: 0-70:30 gradient elution) to give the product (0.41 g, 37.4%). $[M+H]^+$=406.1.

Step 3: tert-butyl 4-(4-(4-chloro-7-((2-(trimethylsilyl)ethoxy)methyl)-7H-pyrrolo[2,3-d]pyrimidin-6-yl)-3,5-dimethyl-1H-pyrazol-1-yl)piperidine-1-carboxylate

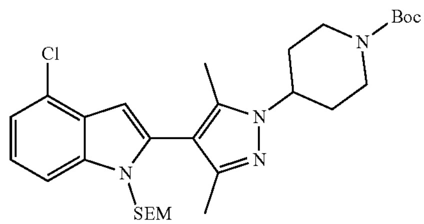 [SMILES: Cc1nn(C2CCN(C(=O)OC(C)(C)C)CC2)c(C)c1-c1cc2c(Cl)cccc2n1COCC[Si](C)(C)C]

A mixture of 4-chloro-6-iodo-7-((2-(trimethylsilyl)ethoxy)methyl)-7H-pyrrolo[2,3-d]pyrimidine (0.394 g, 0.96 mmol), tert-butyl 4-(3,5-dimethyl-4-(4,4,5,5-tetramethyl-1,3,2-dioxaborolan-2-yl)-1H-pyrazol-1-yl)piperidine-1-carboxylate (0.41 g, 1.01 mmol), Pd(dppf)$Cl_2$ (0.077 g, 0.096 mmol) and $K_2CO_3$ (0.265 g, 1.92 mmol) in a mixture of dioxane (10 mL) and water (2.5 mL) was stirred in a round bottom flask at 90° C. overnight. The mixture was evaporated in vacuum to afford the crude product, which was further purified with silica gel column chromatography (PE:EA=100:0~1:1 gradient elution) to give the product (0.365 g, 67.7%). $[M+H]^+$=561.1.

Step 4: tert-butyl (R)-4-(4-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)-3,5-dimethyl-1H-pyrazol-1-yl)piperidine-1-carboxylate

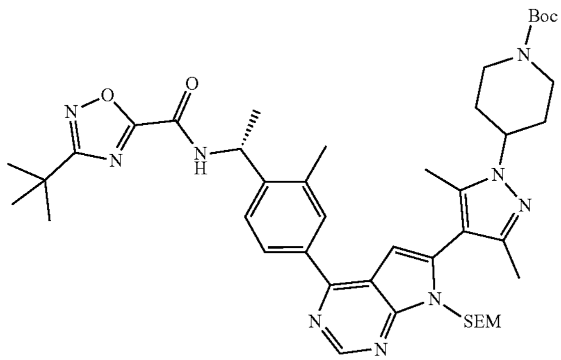 [SMILES: Cc1cc(-c2ncnc3c2cc(-c2c(C)nn(C4CCN(C(=O)OC(C)(C)C)CC4)c2C)n3COCC[Si](C)(C)C)ccc1[C@@H](C)NC(=O)c1nc(C(C)(C)C)no1]

A mixture of tert-butyl 4-(4-(4-chloro-7-((2-(trimethylsilyl)ethoxy)methyl)-7H-pyrrolo[2,3-d]pyrimidin-6-yl)-3,5-dimethyl-1H-pyrazol-1-yl)piperidine-1-carboxylate (0.365 g, 0.65 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (0.284 g, 0.684 mmol), Pd($Ph_3P)_4$ (0.074 g, 0.065 mmol) and $K_2CO_3$ (0.18 g, 1.3 mmol) in a mixture of dioxane (16 mL) and water (4 mL) was stirred in a round bottom flask at 100° C. overnight. The mixture was evaporated in vacuum to afford the crude product, which was further purified with silica gel column chromatography (PE:EA=100:0~0:100 gradient elution) to give the product (0.28 g, 53%). $[M+H]^+$=812.0.

Step 5: (R)-3-(tert-butyl)-N-(1-(4-(6-(3,5-dimethyl-1-(piperidin-4-yl)-1H-pyrazol-4-yl)-7-(hydroxymethyl)-7H-pyrrolo[2,3-d]pyrimidin-4-yl)-2-methylphenyl)ethyl)-1,2,4-oxadiazole-5-carboxamide

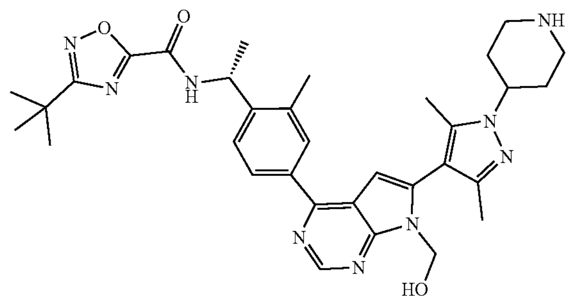 [SMILES: Cc1cc(-c2ncnc3c2cc(-c2c(C)nn(C4CCNCC4)c2C)n3CO)ccc1[C@@H](C)NC(=O)c1nc(C(C)(C)C)no1]

A mixture of tert-butyl (R)-4-(4-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)-3,5-dimethyl-1H-pyrazol-1-yl)piperidine-1-carboxylate (0.28 g, 0.345 mmol) and trifluoroacetic acid (5 mL) in dichloromethane (5 mL) was stirred in a round bottom flask at room temperature for 1 hour. The mixture was evaporated in vacuum to afford the crude product, which was used directly for next step $[M+H]^+$=612.0.

Step 6: (R)-3-(tert-butyl)-N-(1-(4-(6-(3,5-dimethyl-1-(piperidin-4-yl)-1H-pyrazol-4-yl)-7H-pyrrolo[2,3-d]pyrimidin-4-yl)-2-methylphenyl)ethyl)-1,2,4-oxadiazole-5-carboxamide

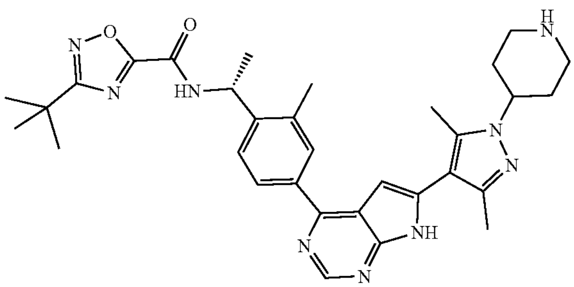 [SMILES: Cc1cc(-c2ncnc3[nH]c(-c4c(C)nn(C5CCNCC5)c4C)cc23)ccc1[C@@H](C)NC(=O)c1nc(C(C)(C)C)no1]

A mixture of (R)-3-(tert-butyl)-N-(1-(4-(6-(3,5-dimethyl-1-(piperidin-4-yl)-1H-pyrazol-4-yl)-7-(hydroxymethyl)-7H-pyrrolo[2,3-d]pyrimidin-4-yl)-2-methylphenyl)ethyl)-1,2,4-oxadiazole-5-carboxamide (crude from step 5) and ammonia water (1 mL, 25%) in methanol (5 mL) was stirred in a round bottom flask at room temperature for 12 hours. The mixture was evaporated in vacuum to afford the crude product, which was purified by pre-HPLC to afford the product (0.124 g, 59.7%, 2 steps). $[M+H]^+$=582.1.

Step 7: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-2-methylphenyl)ethyl)-1,2,4-oxadiazole-5-carboxamide

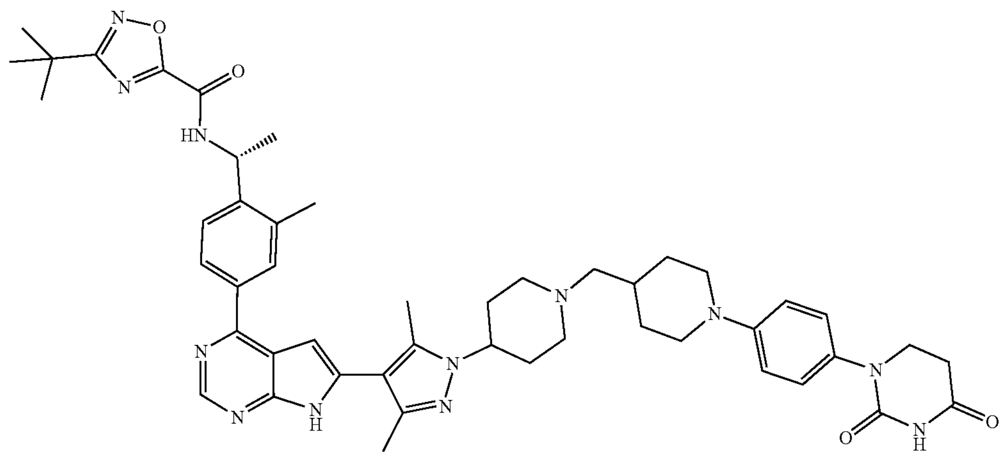 [SMILES: Cc1cc(-c2ncnc3[nH]c(-c4c(C)nn(C5CCN(CC6CCN(c7ccc(N8CCC(=O)NC8=O)cc7)CC6)CC5)c4C)cc23)ccc1[C@@H](C)NC(=O)c1nc(C(C)(C)C)no1]

A mixture of (R)-3-(tert-butyl)-N-(1-(4-(6-(3,5-dimethyl-1-(piperidin-4-yl)-1H-pyrazol-4-yl)-7H-pyrrolo[2,3-d]pyrimidin-4-yl)-2-methylphenyl)ethyl)-1,2,4-oxadiazole-5-carboxamide (0.112 g, 0.192 mmol) and 1-(4-(2,4-dioxotetrahydropyrimidin-1(2H)-yl)phenyl)piperidine-4-carbaldehyde (0.087 g, 0.288 mmol) in dichloromethane (10 mL) and MeOH (2 mL) was stirred in a round bottom flask at room temperature for 0.5 hour. To the mixture was added $NaBH(OAc)_3$ (0.061 g, 0.288 mmol) and stirred in a round bottom flask at room temperature for 1 hour. Then the mixture was evaporated in vacuum to afford the crude product, which was purified by pre-HPLC to give the product (0.093 g, 55.7%). $^1H$ NMR (400 MHz, DMSO) $\delta_H$ 12.14 (s, 1H), 10.27 (s, 1H), 9.94 (d, J=6.4 Hz, 1H), 8.78 (s, 1H), 8.14 (s, 1H), 8.06-7.97 (m, 2H), 7.66 (d, J=8.2 Hz, 1H), 7.14 (d, J=7.6 Hz, 2H), 6.94 (d, J=6.9 Hz, 2H), 6.75 (s, 1H), 5.42-5.33 (m, 1H), 4.20 (s, 1H), 3.72-3.68 (m, 4H), 3.07 (s, 2H), 2.69-2.67 (m, 4H), 2.52 (s, 3H), 2.39-2.08 (m, 12H), 1.89-1.67 (m, 5H), 1.54 (d, J=5.6 Hz, 3H), 1.36 (s, 9H), 1.32-1.17 (m, 2H); $[M+H]^+$=867.8.

Example 61: (R)-3-(tert-butyl)-N-(1-(4-(6-(1-(1-((1-(4-(2,4-dioxotetrahydropyrimidin-1(2H)-yl)-3-methylphenyl)piperidin-4-yl)methyl)piperidin-4-yl)-3,5-dimethyl-1H-pyrazol-4-yl)-7H-pyrrolo[2,3-d]pyrimidin-4-yl)-2-methylphenyl)ethyl)-1,2,4-oxadiazole-5-carboxamide

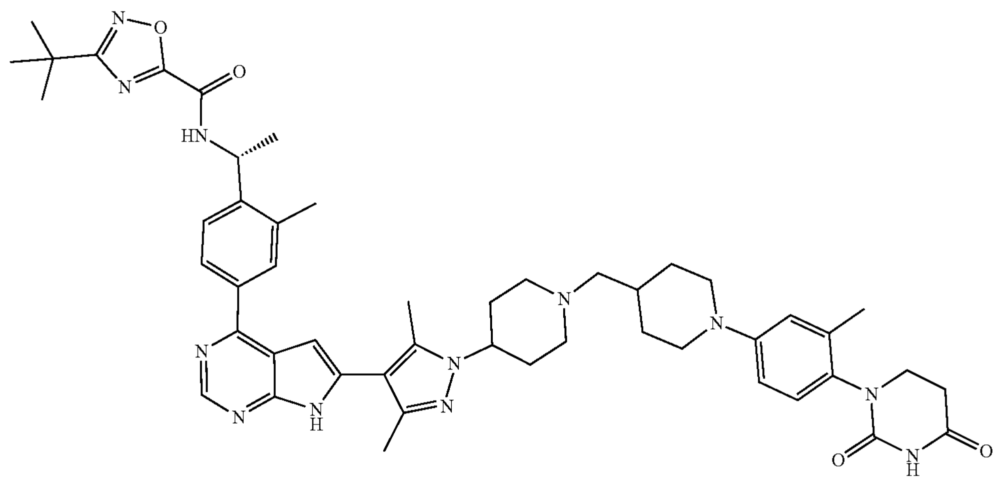 [SMILES: Cc1cc(-c2ncnc3[nH]c(-c4c(C)nn(C5CCN(CC6CCN(c7ccc(N8CCC(=O)NC8=O)c(C)c7)CC6)CC5)c4C)cc23)ccc1[C@@H](C)NC(=O)c1nc(C(C)(C)C)no1]

A mixture of (R)-3-(tert-butyl)-N-(1-(4-(6-(3,5-dimethyl-1-(piperidin-4-yl)-1H-pyrazol-4-yl)-7H-pyrrolo[2,3-d]pyrimidin-4-yl)-2-methylphenyl)ethyl)-1,2,4-oxadiazole-5-carboxamide (0.12 g, 0.206 mmol) and 1-(4-(2,4-dioxotetrahydropyrimidin-1(2H)-yl)-3-methylphenyl) piperidine-4-carbaldehyde (0.097 g, 0.309 mmol) in dichloromethane (10 mL) and MeOH (2 mL) was stirred in a round bottom flask at room temperature for 0.5 hour. To the mixture was added $NaBH(OAc)_3$ (0.066 g, 0.309 mmol) and stirred in a round bottom flask at room temperature for 1 hour. Then the mixture was evaporated in vacuum to afford the crude product, which was purified by pre-HPLC to give the product (0.037 g, 20.4%). $^1$H NMR (400 MHz, DMSO) $\delta_H$ 12.13 (s, 1H), 10.25 (s, 1H), 9.94 (d, J=7.5 Hz, 1H), 8.78 (s, 1H), 8.18 (s, 1H), 8.06-7.96 (m, 2H), 7.65 (d, J=7.8 Hz, 1H), 7.04 (d, J=8.6 Hz, 1H), 6.82-6.74 (m, 3H), 5.42-5.33 (m, 1H), 4.14 (s, 1H), 3.69-3.67 (m, 3H), 3.49-3.47 (m, 1H), 2.99-2.95 (m, 2H), 2.68-2.66 (m, 4H), 2.38-2.18 (m, 10H), 2.14-2.03 (m, 8H), 1.85-1.63 (m, 6H), 1.54 (d, J=6.3 Hz, 3H), 1.36 (s, 9H), 1.27-1.13 (m, 2H); $[M+H]^+$=881.9.

Example 62: (R)-5-(tert-butyl)-N-(1-(4-(6-(1-(1-((1-(4-(2,4-dioxotetrahydropyrimidin-1(2H)-yl)phenyl) piperidin-4-yl)methyl)piperidin-4-yl)-3,5-dimethyl-1H-pyrazol-4-yl)-7H-pyrrolo[2,3-d]pyrimidin-4-yl)-2-methylphenyl)ethyl)-1,2,4-oxadiazole-3-carboxamide

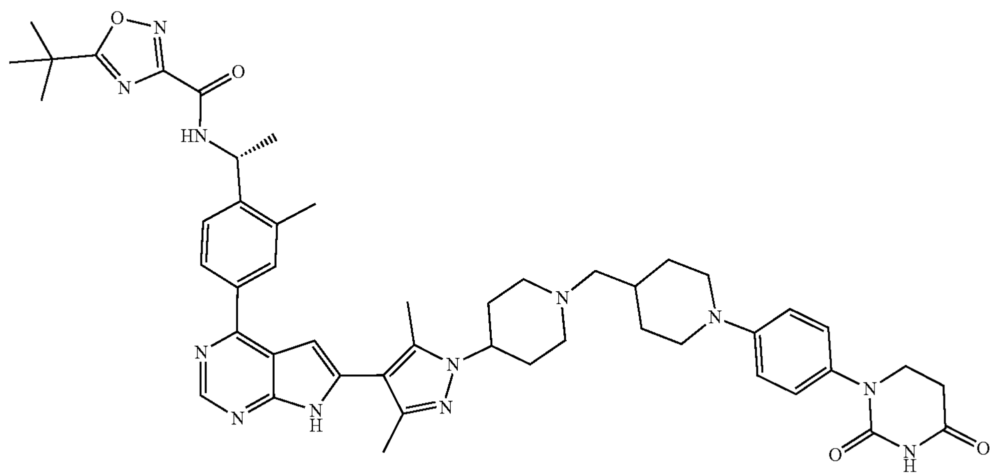 [SMILES: Cc1cc(-c2ncnc3[nH]c(-c4c(C)nn(C5CCN(CC6CCN(c7ccc(N8CCC(=O)NC8=O)cc7)CC6)CC5)c4C)cc23)ccc1[C@@H](C)NC(=O)c1noc(C(C)(C)C)n1]

The titled compound was synthesized in the procedures similar to Example 25. $^1$H NMR (400 MHz, DMSO) $\delta_H$ 12.14 (s, 1H), 10.27 (s, 1H), 9.52 (s, 1H), 8.78 (s, 1H), 8.14 (s, 1H), 7.99 (s, 2H), 7.64 (d, J=7.8 Hz, 1H), 7.14 (d, J=7.3 Hz, 2H), 6.94 (d, J=7.4 Hz, 2H), 6.74 (s, 1H), 5.38 (s, 1H), 4.18 (s, 1H), 3.70 (s, 4H), 3.02 (s, 2H), 2.72-2.63 (m, 4H), 2.56-2.48 (m, 4H), 2.37 (s, 3H), 2.35-2.04 (m, 10H), 1.82 (d, J=11.2 Hz, 4H), 1.71 (s, 1H), 1.52 (d, J=5.0 Hz, 3H), 1.42 (d, J=1.2 Hz, 9H), 1.29-1.16 (m, 2H); $[M+H]^+$=867.6.

Example 63: (R)-3-(tert-butyl)-N-(1-(4-(8-(6-(4-((1-(4-(2,4-dioxotetrahydropyrimidin-1(2H)-yl)phenyl) piperidin-4-yl)methyl)piperazin-1-yl)pyridin-3-yl)-9H-purin-6-yl)-2-methylphenyl)ethyl)-1,2,4-oxadiazole-5-carboxamide

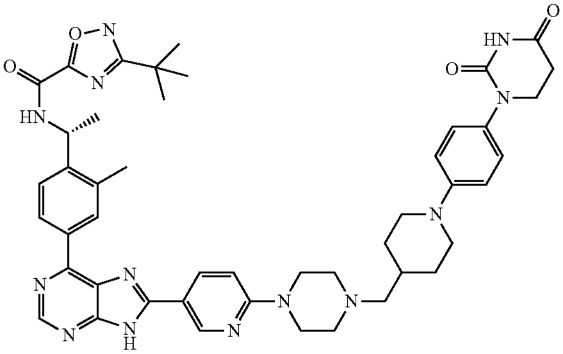

Example 64: (R)-3-(tert-butyl)-N-(1-(4-(8-(5-(4-((1-(4-(2,4-dioxotetrahydropyrimidin-1(2H)-yl)phenyl)piperidin-4-yl)methyl)piperazin-1-yl)pyridin-2-yl)-9H-purin-6-yl)-2-methylphenyl)ethyl)-1,2,4-oxadiazole-5-carboxamide

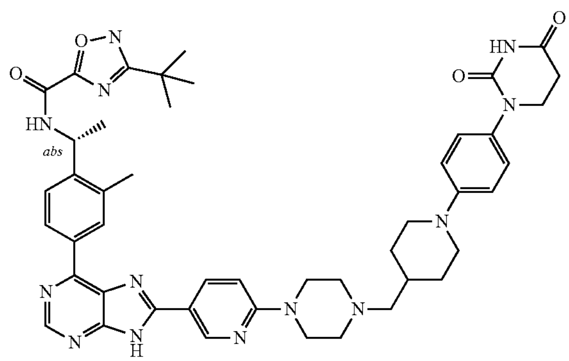

Example 65: (R)-3-(tert-butyl)-N-(1-(4-(8-(6-(4-((1-(4-(2,4-dioxotetrahydropyrimidin-1(2H)-yl)-3-methylphenyl)piperidin-4-yl)methyl)piperazin-1-yl)pyridin-3-yl)-9H-purin-6-yl)-2-methylphenyl)ethyl)-1,2,4-oxadiazole-5-carboxamide

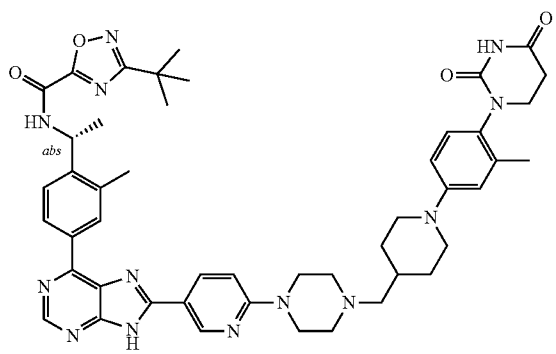 [SMILES: Cc1cc(-c2ncnc3[nH]c(-c4ccc(N5CCN(CC6CCN(c7ccc(N8CCC(=O)NC8=O)c(C)c7)CC6)CC5)nc4)nc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 13.83 (s, 1H), 10.24 (s, 1H), 9.91 (s, 1H), 9.02 (s, 1H), 8.85 (s, 1H), 8.75 (s, 1H), 8.67 (s, 1H), 8.41-8.28 (m, 1H), 7.75-7.59 (m, 1H), 7.07-6.99 (m, 2H), 6.85-6.70 (m, 3H), 5.37 (s, 1H), 3.77-3.59 (m, 8H), 3.50-3.43 (m, 1H), 2.74-2.60 (m, 6H), 2.26-2.19 (m, 2H), 2.14-2.05 (m, 4H), 2.00-1.86 (m, 2H), 1.86-1.65 (m, 3H), 1.54 (s, 3H), 1.41-1.33 (m, 9H), 1.30-1.15 (m, 2H); $[M+H]^+$=866.5.

Example 66: (R)-3-(tert-butyl)-N-(1-(4-(8-(5-(4-((1-(4-(2,4-dioxotetrahydropyrimidin-1(2H)-yl)-3-methylphenyl)piperidin-4-yl)methyl)piperazin-1-yl)pyridin-2-yl)-9H-purin-6-yl)-2-methylphenyl)ethyl)-1,2,4-oxadiazole-5-carboxamide

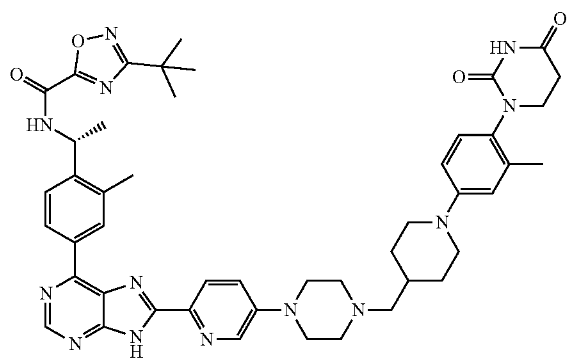 [SMILES: Cc1cc(-c2ncnc3[nH]c(-c4ccc(N5CCN(CC6CCN(c7ccc(N8CCC(=O)NC8=O)c(C)c7)CC6)CC5)cn4)nc23)ccc1[C@@H](C)NC(=O)c1nc(C(C)(C)C)no1]

Example 67: (R)-3-(tert-butyl)-N-(1-(4-(8-(4-(4-((1-(4-(2,4-dioxotetrahydropyrimidin-1(2H)-yl)-3-methylphenyl)piperidin-4-yl)methyl)piperazin-1-yl)phenyl)-9H-purin-6-yl)-2-methylphenyl)ethyl)-1,2,4-oxadiazole-5-carboxamide

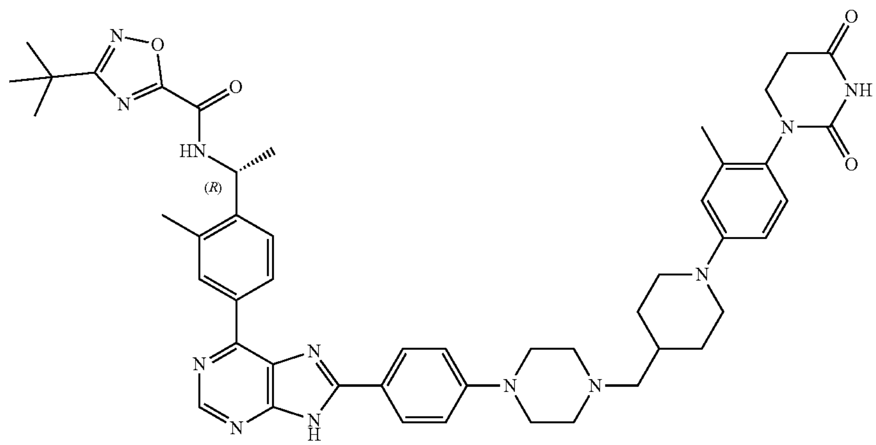

The titled compound was synthesized in the procedures similar to Example 25. $^1$H NMR (400 MHz, DMSO) $\delta_H$ 13.76 (s, 1H), 10.25 (s, 1H), 9.93 (d, J=6.8 Hz, 1H), 8.84 (s, 1H), 8.79 (d, J=7.6 Hz, 1H), 8.67 (s, 1H), 8.19 (s, 2H), 7.69 (d, J=8.4 Hz, 1H), 7.14 (s, 2H), 7.05 (d, J=7.2 Hz, 1H), 6.82-6.79 (m, 2H), 5.39-5.37 (m, 1H), 3.75-3.60 (m, 3H), 3.50-3.40 (m, 1H), 2.76-2.60 (m, 4H), 2.24 (s, 2H), 2.12 (s, 3H), 1.85-1.78 (m, 2H), 1.55 (d, J=6.4 Hz, 3H), 1.37 (s, 9H), 1.35-1.16 (m, 2H); [M+H]$^+$=865.8.

Example 68: (R)-5-(tert-butyl)-N-(1-(4-(8-(4-(4-((1-(4-(2,4-dioxotetrahydropyrimidin-1(2H)-yl)phenyl)piperidin-4-yl)methyl)piperazin-1-yl)phenyl)-9H-purin-6-yl)-2-methylphenyl)ethyl)-1,2,4-oxadiazole-3-carboxamide

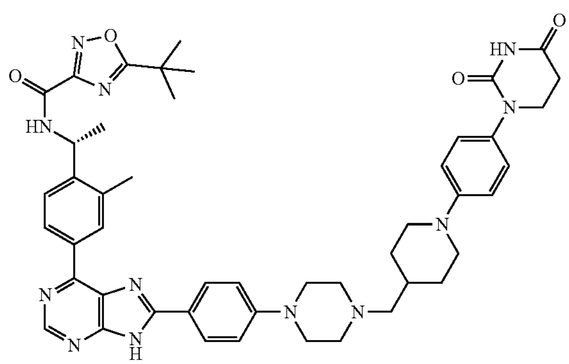 [SMILES: Cc1cc(-c2ncnc3[nH]c(-c4ccc(N5CCN(CC6CCN(c7ccc(N8CCC(=O)NC8=O)cc7)CC6)CC5)cc4)nc23)ccc1[C@@H](C)NC(=O)c1noc(C(C)(C)C)n1]

Example 69: (R)-5-(tert-butyl)-N-(1-(4-(8-(6-(4-((1-(4-(2,4-dioxotetrahydropyrimidin-1(2H)-yl)phenyl)piperidin-4-yl)methyl)piperazin-1-yl)pyridin-3-yl)-9H-purin-6-yl)-2-methylphenyl)ethyl)-1,2,4-oxadiazole-3-carboxamide

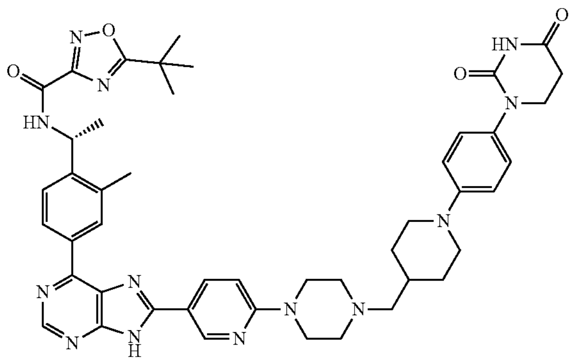 [SMILES: Cc1cc(-c2ncnc3[nH]c(-c4ccc(N5CCN(CC6CCN(c7ccc(N8CCC(=O)NC8=O)cc7)CC6)CC5)nc4)nc23)ccc1[C@@H](C)NC(=O)c1noc(C(C)(C)C)n1]

Example 70: (R)-5-(tert-butyl)-N-(1-(4-(8-(5-(4-((1-(4-(2,4-dioxotetrahydropyrimidin-1(2H)-yl)phenyl)piperidin-4-yl)methyl)piperazin-1-yl)pyridin-2-yl)-9H-purin-6-yl)-2-methylphenyl)ethyl)-1,2,4-oxadiazole-3-carboxamide

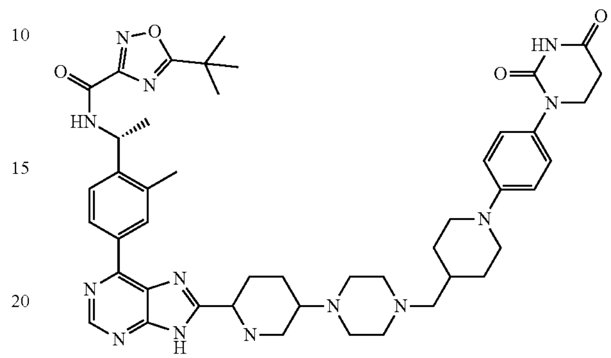

Example 71: (R)-5-(tert-butyl)-N-(1-(4-(8-(6-(4-((1-(4-(2,4-dioxotetrahydropyrimidin-1(2H)-yl)-3-methylphenyl)piperidin-4-yl)methyl)piperazin-1-yl)pyridin-3-yl)-9H-purin-6-yl)-2-methylphenyl)ethyl)-1,2,4-oxadiazole-3-carboxamide

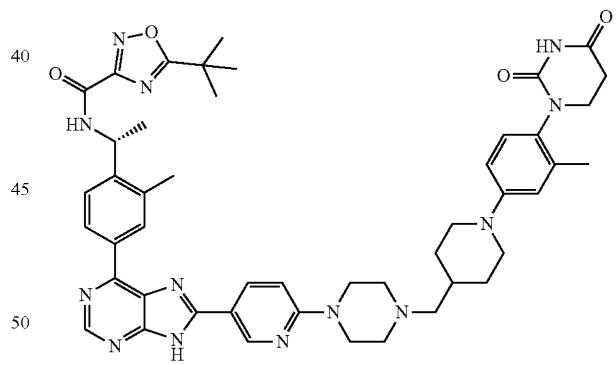

The titled compound was synthesized in the procedures similar to Example 25. $^1$H NMR (400 MHz, DMSO) $\delta_H$ 13.87 (s, 1H), 10.25 (s, 1H), 9.52 (d, J=6.4 Hz, 1H), 9.04 (s, 1H), 8.85 (s, 1H), 8.76 (d, J=7.6 Hz, 1H), 8.67 (s, 1H), 8.38 (d, J=8.4 Hz, 1H), 7.67 (d, J=7.6 Hz, 1H), 7.04 (d, J=8.4 Hz, 2H), 6.85-6.72 (m, 2H), 5.45-5.32 (m, 1H), 3.75-3.61 (m, 7H), 3.53-3.41 (m, 1H), 2.77-2.60 (m, 4H), 2.57-2.52 (m, 2H), 2.29-2.17 (m, 2H), 2.12 (s, 3H), 1.93-1.87 (m, 1H), 1.87-1.63 (m, 3H), 1.53 (d, J=5.2 Hz, 3H), 1.42 (s, 9H), 1.30-1.16 (m, 3H); [M+H]$^+$=866.5.

Example 72: (R)-5-(tert-butyl)-N-(1-(4-(8-(5-(4-((1-(4-(2,4-dioxotetrahydropyrimidin-1(2H)-yl)-3-methylphenyl)piperidin-4-yl)methyl)piperazin-1-yl)pyridin-2-yl)-9H-purin-6-yl)-2-methylphenyl)ethyl)-1,2,4-oxadiazole-3-carboxamide

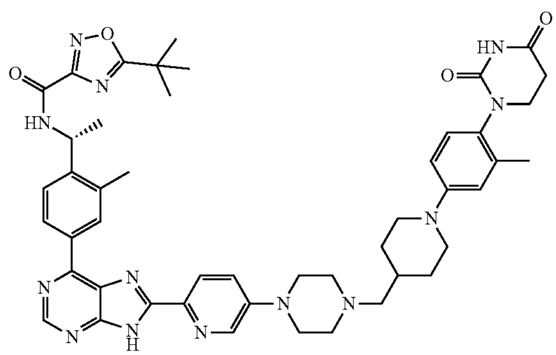 [SMILES: Cc1cc(-c2ncnc3[nH]c(-c4ccc(N5CCN(CC6CCN(c7ccc(N8CCC(=O)NC8=O)c(C)c7)CC6)CC5)cn4)nc23)ccc1[C@@H](C)NC(=O)c1noc(C(C)(C)C)n1]

Example 73: (R)-5-(tert-butyl)-N-(1-(4-(8-(4-(4-((1-(4-(2,4-dioxotetrahydropyrimidin-1(2H)-yl)-3-methylphenyl)piperidin-4-yl)methyl)piperazin-1-yl)phenyl)-9H-purin-6-yl)-2-methylphenyl)ethyl)-1,2,4-oxadiazole-3-carboxamide

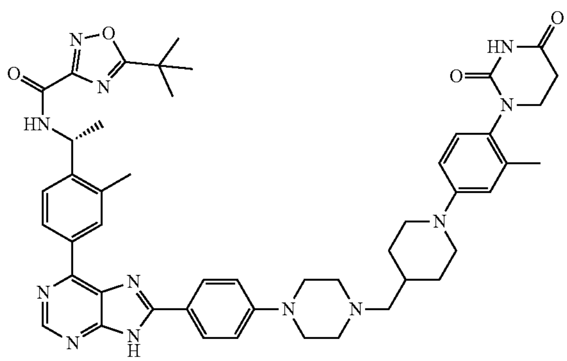 [SMILES: Cc1cc(-c2ncnc3[nH]c(-c4ccc(N5CCN(CC6CCN(c7ccc(N8CCC(=O)NC8=O)c(C)c7)CC6)CC5)cc4)nc23)ccc1[C@@H](C)NC(=O)c1noc(C(C)(C)C)n1]

The titled compound was synthesized in the procedures similar to Example 25. $^1$H NMR (400 MHz, DMSO) $\delta_H$ 13.85 (s, 1H), 10.26 (s, 1H), 9.57-9.46 (m, 1H), 8.89-8.83 (m, 1H), 8.82-8.74 (m, 1H), 8.70-8.63 (m, 1H), 8.27-8.15 (m, 2H), 7.73-7.61 (m, 1H), 7.27-7.19 (m, 1H), 7.18-7.11 (m, 1H), 7.09-7.01 (m, 2H), 6.82 (s, 3H), 5.45-5.35 (m, 1H), 4.11-3.98 (m, 1H), 3.82-3.59 (m, 5H), 3.55-3.41 (m, 2H), 3.24-3.07 (m, 5H), 2.82-2.61 (m, 5H), 2.56-2.53 (m, 3H), 2.37-2.20 (m, 2H), 2.13 (s, 3H), 1.91 (s, 2H), 1.90-1.75 (m, 1H), 1.53 (s, 3H), 1.43 (s, 9H); $[M+H]^+$=865.5.

Example 74: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-(hydroxymethyl)phenyl)ethyl-1,2,4-oxadiazole-5-carboxamide

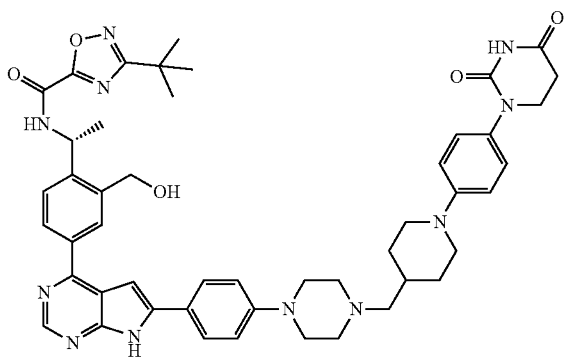 [SMILES: C[C@@H](NC(=O)c1nc(C(C)(C)C)no1)c1ccc(-c2ncnc3[nH]c(-c4ccc(N5CCN(CC6CCN(c7ccc(N8CCC(=O)NC8=O)cc7)CC6)CC5)cc4)cc23)cc1CO]

The titled compound was synthesized in the procedures similar to Example 25. $^1$H NMR (400 MHz, DMSO) $\delta_H$ 12.54 (s, 1H), 10.27 (s, 1H), 9.99 (d, J=8.0 Hz, 1H), 8.76 (s, 1H), 8.27 (s, 1H), 8.15 (d, J=8.0 Hz, 1H), 7.90 (d, J=8.0 Hz, 2H), 7.73 (d, J=8.0 Hz, 1H), 7.23 (s, 1H), 7.13 (d, J=8.0 Hz, 2H), 7.04 (d, J=8.0 Hz, 2H), 6.93 (d, J=8.0 Hz, 2H), 5.46-5.36 (m, 2H), 4.95-4.72 (m, 2H), 3.74-3.64 (m, 4H), 3.26 (s, 4H), 2.72-2.62 (m, 5H), 2.23 (s, 2H), 1.82 (d, J=12.0 Hz, 2H), 1.73 (s, 1H), 1.57 (d, J=8.0 Hz, 3H), 1.37 (s, 9H), 1.27-1.21 (m, 3H); $[M+H]^+$=866.7.

Example 75: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-(methoxymethyl)phenyl)ethyl)-2,4-oxadiazole-5-carboxamide

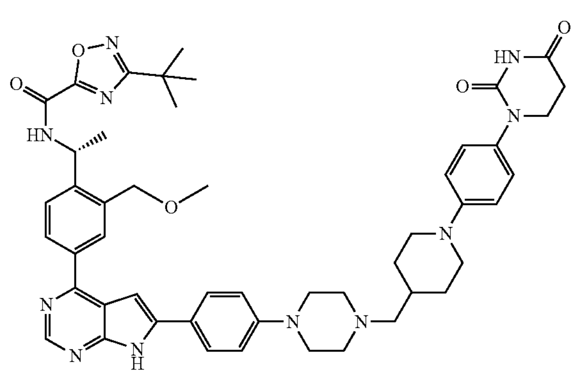 [SMILES: COCc1cc(-c2ncnc3[nH]c(-c4ccc(N5CCN(CC6CCN(c7ccc(N8CCC(=O)NC8=O)cc7)CC6)CC5)cc4)cc23)ccc1[C@@H](C)NC(=O)c1nc(C(C)(C)C)no1]

Example 76: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-(methoxymethyl)phenyl)ethyl)-1,2,4-oxadiazole-5-carboxamide

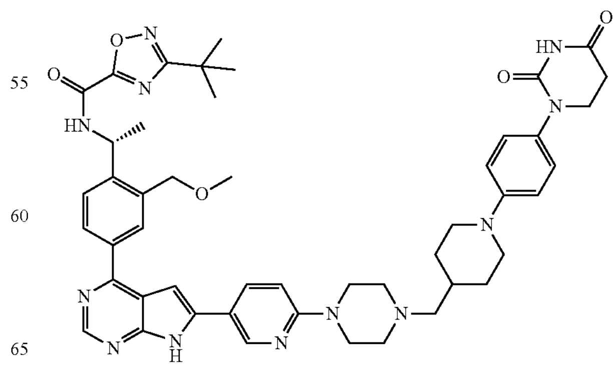

Example 77: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-(methoxymethyl)phenyl)ethyl)-1,2,4-oxadiazole-5-carboxamide

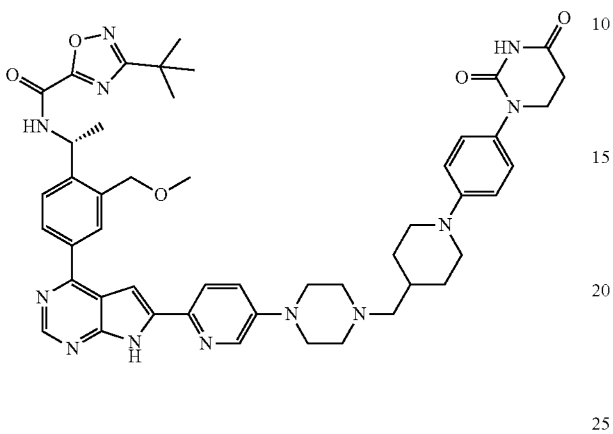

Example 78: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-3-fluoro-2-methylphenyl)ethyl)-1,2,4-oxadiazole-5-carboxamide

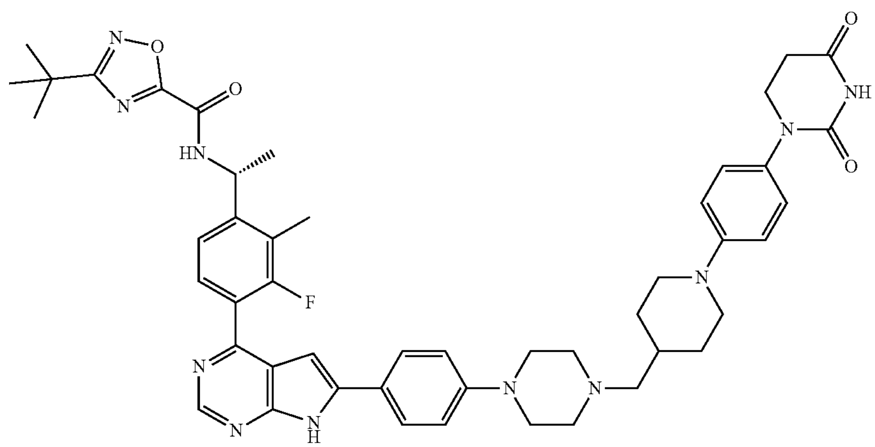 [SMILES: Cc1c([C@@H](C)NC(=O)c2nc(C(C)(C)C)no2)ccc(-c2ncnc3[nH]c(-c4ccc(N5CCN(CC6CCN(c7ccc(N8CCC(=O)NC8=O)cc7)CC6)CC5)cc4)cc23)c1F]

The titled compound was synthesized in the procedures similar to Example 24. $^1$H NMR (400 MHz, DMSO) $\delta_H$ 12.53 (s, 1H), 10.27 (s, 1H), 10.00 (d, J=7.1 Hz, 1H), 8.77 (s, 1H), 8.21 (s, 1H), 7.85 (d, J=7.7 Hz, 2H), 7.65 (s, 1H), 7.49 (d, J=8.2 Hz, 1H), 7.13 (d, J=8.4 Hz, 2H), 7.01 (d, J=7.9 Hz, 2H), 6.93 (d, J=8.5 Hz, 2H), 6.78 (s, 1H), 5.42-5.38 (m, 1H), 3.75-3.64 (m, 4H), 3.25 (s, 5H), 2.73-2.62 (m, 4H), 2.52 (s, 3H), 2.41 (s, 3H), 2.22 (d, J=4.1 Hz, 2H), 1.81 (d, J=11.9 Hz, 2H), 1.72 (s, 1H), 1.56 (d, J=6.1 Hz, 3H), 1.37 (s, 9H), 1.29-1.17 (m, 2H); $[M+H]^+$=868.8.

Example 79: (R)-3-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-5-fluoro-2-methylphenyl)ethyl)-1,2,4-oxadiazole-5-carboxamide

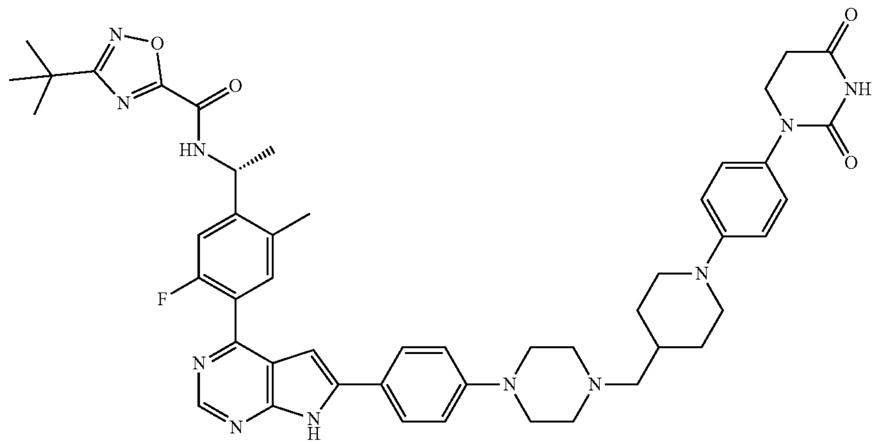 [SMILES: Cc1cc(-c2ncnc3[nH]c(-c4ccc(N5CCN(CC6CCN(c7ccc(N8CCC(=O)NC8=O)cc7)CC6)CC5)cc4)cc23)c(F)cc1[C@@H](C)NC(=O)c1nc(C(C)(C)C)no1]

The titled compound was synthesized in the procedures similar to Example 24. $^1$H NMR (400 MHz, DMSO) $\delta_H$ 12.54 (s, 1H), 10.27 (s, 1H), 9.95 (d, J=7.8 Hz, 1H), 8.78 (s, 1H), 8.22 (s, 1H), 7.84 (d, J=8.5 Hz, 2H), 7.63 (d, J=7.3 Hz, 1H), 7.50 (d, J=12.1 Hz, 1H), 7.13 (d, J=8.5 Hz, 2H), 7.01 (d, J=7.8 Hz, 2H), 6.93 (d, J=8.6 Hz, 2H), 6.77 (s, 1H), 5.35 (s, 1H), 3.68 (d, J=6.8 Hz, 4H), 3.24 (s, 4H), 2.72-2.61 (m, 5H), 2.52 (s, 3H), 2.46 (s, 3H), 2.22 (d, J=6.0 Hz, 2H), 1.81 (d, J=12.0 Hz, 2H), 1.72 (s, 1H), 1.55 (d, J=6.8 Hz, 3H), 1.38 (s, 9H), 1.28-1.15 (m, 3H); [M+H]$^+$=868.8.

Example 80: 3-(tert-butyl)-N-((R)-1-(4-(6-(6-((S)-4-((1-(4-(2,4-dioxotetrahydropyrimidin-1(2H)-yl)phenyl)piperidin-4-yl)methyl)-2-methylpiperazin-1-yl)pyridin-3-yl)-7H-pyrrolo[2,3-d]pyrimidin-4-yl)-2-fluorophenyl)ethyl)-1,2,4-oxadiazole-5-carboxamide Step 1: tert-butyl (S)-4-(5-bromopyridin-2-yl)-3-methylpiperazine-1-carboxylate

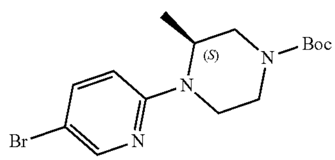

A mixture of 5-bromo-2-fluoropyridine (12.5 g, 0.0714 mol), tert-butyl (S)-3-methylpiperazine-1-carboxylate (15.7 g, 0.0786 mol) and DIEA (18.5 g, 0.143 mol) in DMF (80 mL) was stirred in a round bottom flask at 110° C. for 2 days. Then the mixture was allowed to cool, extracted with EtOAc (200 mL*3), and washed with brine (200 mL). The organic phase was dried over $Na_2SO_4$ and concentrated in vacuo. The residue was purified by silica gel column chromatography (PE:EA=100%:0%~0%:100%) to give the product (2.81 g, 11%). [M+H]$^+$=356.3.

Step 2: (S)-(6-(4-(tert-butoxycarbonyl)-2-methylpiperazin-1-yl)pyridin-3-yl)boronic acid

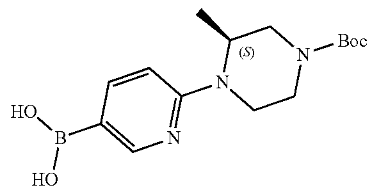

A mixture of tert-butyl (S)-4-(5-bromopyridin-2-yl)-3-methylpiperazine-1-carboxylate (2.71 g, 0.00766 mol), 4,4,4',4',5,5,5',5'-octamethyl-2,2'-bi(1,3,2-dioxaborolane) (3.89 g, 0.0153 mol), Pd(dppf)$Cl_2$ (560 mg, 0.0008 mmol) and KOAc (2.4 g, 0.0245 mol) in dioxane (50 mL) was stirred in a round bottom flask overnight at 100° C. under the atmosphere of $N_2$. After the reaction was complete determined by LCMS, the reaction was allowed to cool. The mixture was extracted with EtOAc (60 mL*3). The organic layer was combined and washed with brine (100 mL), dried over anhydrous $Na_2SO_4$, and concentrated in vacuo. The residue was purified by silica gel column chromatography (PE:EA=100%:0%~0%:100%) to afford the product (2.2 g, crude). [M+H]$^+$=322.2.

Step 3: tert-butyl (S)-4-(5-(4-chloro-7-((2-(trimethylsilyl)ethoxy)methyl)-7H-pyrrolo[2,3-d]pyrimidin-6-yl)pyridin-2-yl)-3-methylpiperazine-1-carboxylate

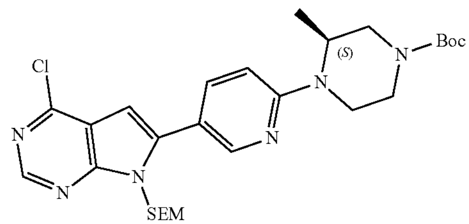

A mixture of 4-chloro-6-iodo-7-((2-(trimethylsilyl)ethoxy)methyl)-7H-pyrrolo[2,3-d]pyrimidine (200 mg, 0.489 mmol), (S)-(6-(4-(tert-butoxycarbonyl)-2-methylpiperazin-1-yl)pyridin-3-yl)boronic acid (157 mg, 0.489 mmol), Pd(dppf)$Cl_2$ (20 mg, 0.0244 mmol) and $K_2CO_3$ (108 mg, 0.782 mmol) in dioxane/water (10 mL/3 mL) was stirred in a round bottom flask overnight at 100° C. under the atmosphere of $N_2$. Then the mixture was allowed to cool down. The mixture was concentrated in vacuo and the residue was purified by silica gel column chromatography (PE:EA=100%:0%~50%:50%) to afford the product (124 mg, 45%). $[M+H]^+$=559.3.

Step 4: tert-butyl (S)-4-(5-(4-(4-((R)-1-(3-(tert-butyl)-1,2,4-oxadiazole-5-carboxamido)ethyl)-3-fluorophenyl)-7-((2-(trimethylsilyl)ethoxy)methyl)-7H-pyrrolo[2,3-d]pyrimidin-6-yl)pyridin-2-yl)-3-methylpiperazine-1-carboxylate

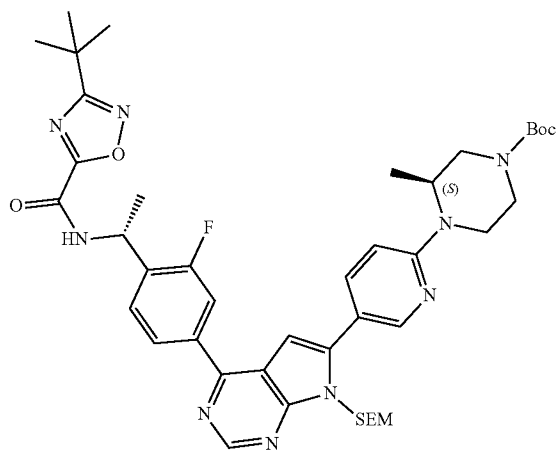

A mixture of tert-butyl (S)-4-(5-(4-chloro-7-((2-(trimethylsilyl)ethoxy)methyl)-7H-pyrrolo[2,3-d]pyrimidin-6-yl) pyridin-2-yl)-3-methylpiperazine-1-carboxylate (124 mg, 0.222 mmol), (R)-3-(tert-butyl)-N-(1-(2-fluoro-4-(4,4,5,5-tetramethyl-1,3,2-dioxaborolan-2-yl)phenyl)ethyl)-1,2,4-oxadiazole-5-carboxamide (107.1 mg, 0.255 mmol), Pd(dppf)$Cl_2$ (11.4 mg, 0.0155 mmol) and $K_2CO_3$ (49 mg, 0.355 mmol) in dioxane/water (10 mL/3 mL) was stirred in a round bottom flask overnight at 100° C. under the atmosphere of $N_2$. After the reaction was complete determined by LCMS, the mixture was allowed to cool down, and then concentrated in vacuo. The residue was purified by silica gel column chromatography (PE:EA=100%:0%~70%:30%) to afford the product (155 mg, 86%). $[M+H]^+$=814.5.

Step 5: 3-(tert-butyl)-N-((R)-1-(2-fluoro-4-(6-(6-((S)-2-methylpiperazin-1-yl)pyridin-3-yl)-7H-pyrrolo[2,3-d]pyrimidin-4-yl)phenyl)ethyl)-1,2,4-oxadiazole-5-carboxamide

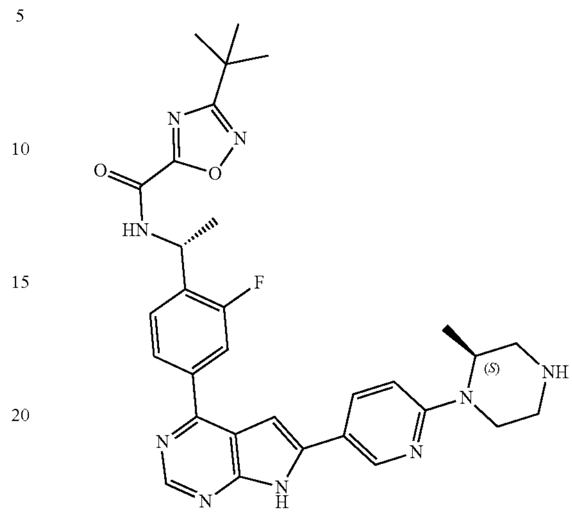

To a solution of tert-butyl (S)-4-(5-(4-(4-((R)-1-(3-(tert-butyl)-1,2,4-oxadiazole-5-carboxamido)ethyl)-3-fluorophenyl)-7-((2-(trimethylsilyl)ethoxy)methyl)-7H-pyrrolo[2,3-d]pyrimidin-6-yl)pyridin-2-yl)-3-methylpiperazine-1-carboxylate (155 mg, 0.190 mmol) in DCM (6 mL), TFA (3 mL) was added. The mixture was stirred at room temperature overnight. Then the mixture was concentrated in vacuo. The residue was dissolved in MeOH (10 mL) and the pH value was adjusted to 8 with $NH_3$ (7M in MeOH). The mixture was stirred for 30 mins at room temperature and concentrated in vacuo. The residue was diluted with DCM: MeOH (50 mL:5 mL) and filtered. The filtrate was concentrated in vacuo to afford the product (147 mg, crude), which was used for next step without further purification. $[M+H]^+$=584.5.

Step 6: 3-(tert-butyl)-N-((R)-1-(4-(6-(6-((S)-4-((1-(4-(2,4-dioxotetrahydropyrimidin-1(2H)-yl)phenyl)piperidin-4-yl)methyl)-2-methylpiperazin-1-yl)pyridin-3-yl)-7H-pyrrolo[2,3-d]pyrimidin-4-yl)-2-fluorophenyl)ethyl)-1,2,4-oxadiazole-5-carboxamide

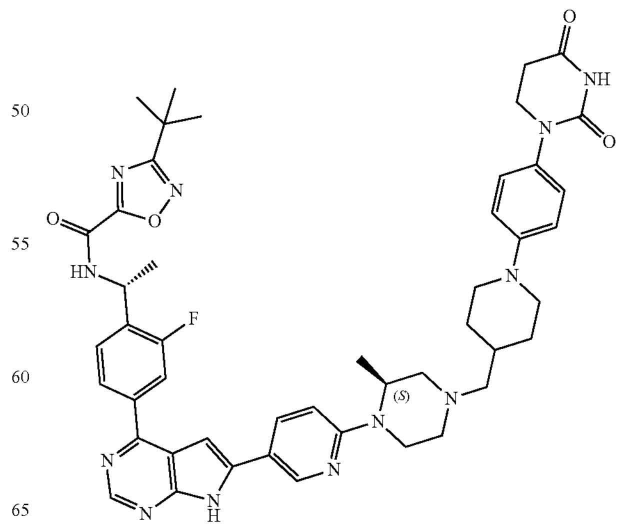

A mixture of 3-(tert-butyl)-N-((R)-1-(2-fluoro-4-(6-(6-((S)-2-methylpiperazin-1-yl)pyridin-3-yl)-7H-pyrrolo[2,3-d]pyrimidin-4-yl)phenyl)ethyl)-1,2,4-oxadiazole-5-carboxamide (147 mg, 0.247 mmol), 1-(4-(2,4-dioxotetrahydropyrimidin-1(2H)-yl)phenyl)piperidine-4-carbaldehyde (97 mg, 0.322 mmol) in DCM (4 mL)/MeOH (4 mL) was stirred in a round bottom flask for 5 mins and HOAc was added dropwise (3 drops). The mixture was stirred at room temperature for 2 h, then $NaBH(OAc)_3$ was added. The mixture was stirred at room temperature overnight. After the reaction was complete determined by LCMS, the reaction mixture was concentrated in vacuo. The residue was purified by silica gel column chromatography (DCM:MeOH=95%:5%) to afford the product (50.88 mg, 23.6%). $^1$H NMR (400 MHz, DMSO) $\delta_H$ 12.66 (s, 1H), 10.27 (s, 1H), 10.02 (d, J=8.0 Hz, 1H), 8.80 (d, J=12.0 Hz, 2H), 8.19 (d, J=8.0 Hz, 1H), 8.13 (d, J=8.0 Hz, 1H), 7.99 (d, J=12.0 Hz, 1H), 7.71 (t, J=8.0 Hz, 1H), 7.34 (s, 1H), 7.13 (d, J=8.0 Hz, 2H), 6.98-6.86 (m, 3H), 5.46 (t, J=8.0 Hz, 1H), 4.58 (s, 1H), 4.13 (d, J=12.0 Hz, 1H), 3.75-3.65 (m, 4H), 3.08 (t, J=12.0 Hz, 1H), 2.93 (d, J=8.0 Hz, 1H), 2.82 (d, J=8.0 Hz, 1H), 2.70-2.66 (m, 4H), 2.28-2.20 (m, 1H), 2.21-2.10 (m, 2H), 2.01 (t, J=8.0 Hz, 1H), 1.84 (t, J=12.0 Hz, 2H), 1.73 (s, 1H), 1.59 (d, J=8.0 Hz, 3H), 1.38 (s, 9H), 1.27-1.17 (m, 5H); $[M+H]^+$=869.8.

Example 81: 5-(tert-butyl)-N-((R)-1-(4-(6-(6-((R)-4-((1-(4-(2,4-dioxotetrahydropyrimidin-1(2H)-yl)phenyl)piperidin-4-yl)methyl)-2-methylpiperazin-1-yl)pyridin-3-yl)-7H-pyrrolo[2,3-d]pyrimidin-4-yl)-2-fluorophenyl)ethyl)-1,2,4-oxadiazole-3-carboxamide

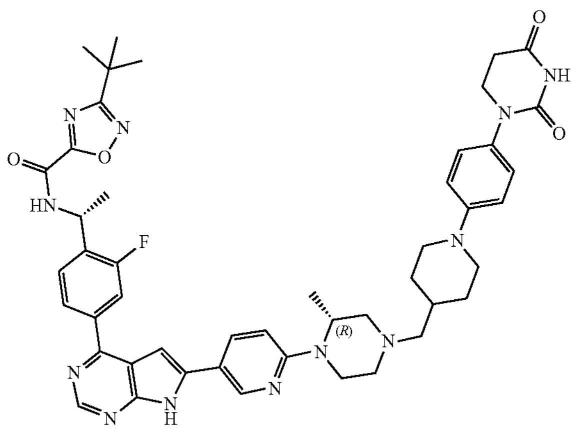

The titled compound was synthesized in the procedures similar to Example 80. $^1$H NMR (400 MHz, DMSO) $\delta_H$ 12.67 (s, 1H), 10.27 (s, 1H), 10.02 (d, J=8.0 Hz, 1H), 8.80 (d, J=12.0 Hz, 2H), 8.19 (d, J=8.0 Hz, 1H), 8.13 (d, J=8.0 Hz, 1H), 8.00 (d, J=12.0 Hz, 1H), 7.71 (t, J=8.0 Hz, 1H), 7.35 (s, 1H), 7.14 (d, J=8.0 Hz, 2H), 6.92 (dd, J=14.9, 8.2 Hz, 3H), 5.46 (t, J=8.0 Hz, 1H), 4.58 (s, 1H), 4.13 (d, J=12.0 Hz, 1H), 3.70 (s, 4H), 3.15-3.02 (m, 1H), 2.93 (d, J=8.0 Hz, 1H), 2.82 (d, J=8.0 Hz, 1H), 2.68 (s, 4H), 2.28-2.21 (m, 1H), 2.20-2.11 (m, 2H), 2.06-1.97 (m, 1H), 1.84 (t, J=12.0 Hz, 3H), 1.74 (s, 1H), 1.59 (d, J=8.0 Hz, 3H), 1.38 (s, 9H), 1.26-1.18 (m, 5H); $[M+H]^+$=869.8.

Example 82: (R)-3-(tert-butyl)-N-(1-(4-(6-(5-(4-((1-(4-(2,4-dioxotetrahydropyrimidin-1(2H)-yl)-3-fluorophenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

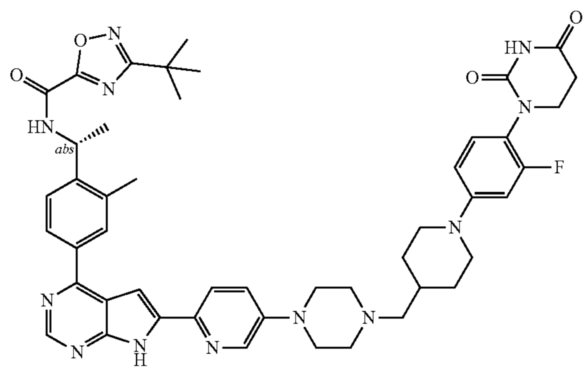 [SMILES: Cc1cc(-c2ncnc3[nH]c(-c4ccc(N5CCN(CC6CCN(c7ccc(N8CCC(=O)NC8=O)c(F)c7)CC6)CC5)cn4)cc23)ccc1[C@@H](C)NC(=O)c1nc(C(C)(C)C)no1]

Example 83: (R)-3-(tert-butyl)-N-(1-(4-(6-(6-(4-((1-(4-(2,4-dioxotetrahydropyrimidin-1(2H)-yl)-3-fluorophenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide

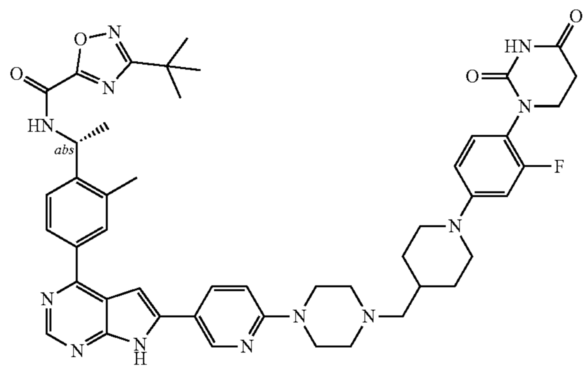 [SMILES: Cc1cc(-c2ncnc3[nH]c(-c4ccc(N5CCN(CC6CCN(c7ccc(N8CCC(=O)NC8=O)c(F)c7)CC6)CC5)nc4)cc23)ccc1[C@@H](C)NC(=O)c1nc(C(C)(C)C)no1]

Example 84: (R)-N-(1-(4-(6-(4-(4-((1-(4-(2,4-dioxo-tetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-5-(1-(trifluoromethyl)cyclopropyl)-1,2,4-oxadiazole-3-carboxamide

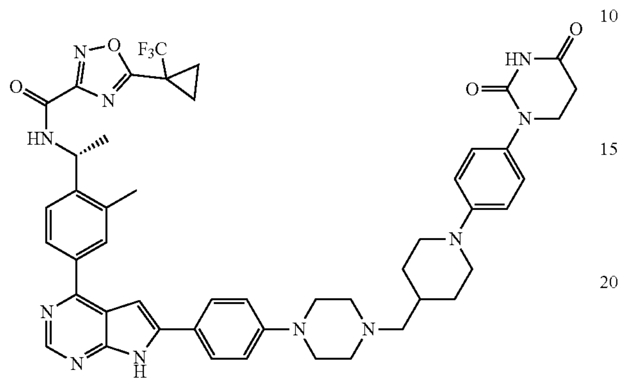

Example 85: (R)-N-(1-(4-(6-(4-(4-((1-(4-(2,4-dioxo-tetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-5-(1,1,1-trifluoro-2-methylpropan-2-yl)-1,2,4-oxadiazole-3-carboxamide

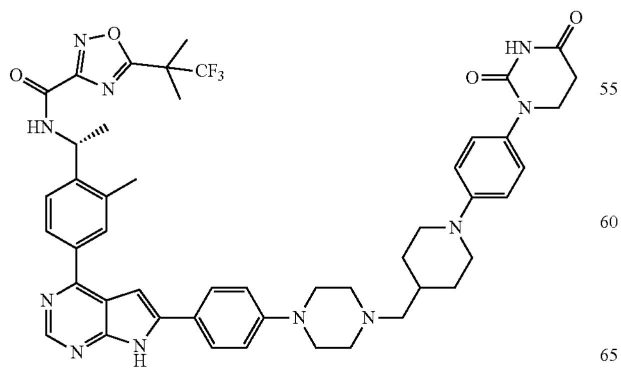

Example 86: (R)-N-(1-(4-(6-(6-(4-((1-(4-(2,4-dioxo-tetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-5-(1-(trifluoromethyl)cyclopropyl)-1,2,4-oxadiazole-3-carboxamide

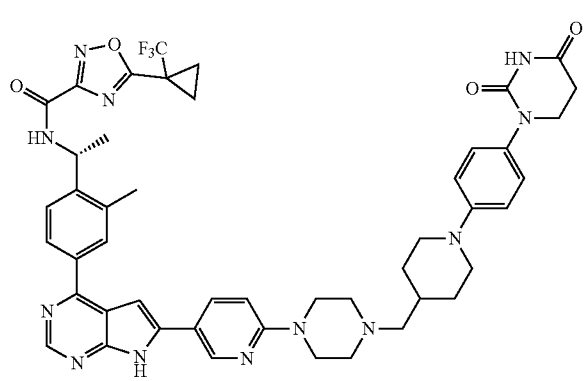 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1noc(C2(C(F)(F)F)CC2)n1]

Example 87: (R)-N-(1-(4-(6-(5-(4-((1-(4-(2,4-dioxo-tetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-5-(1-(trifluoromethyl)cyclopropyl)-1,2,4-oxadiazole-3-carboxamide

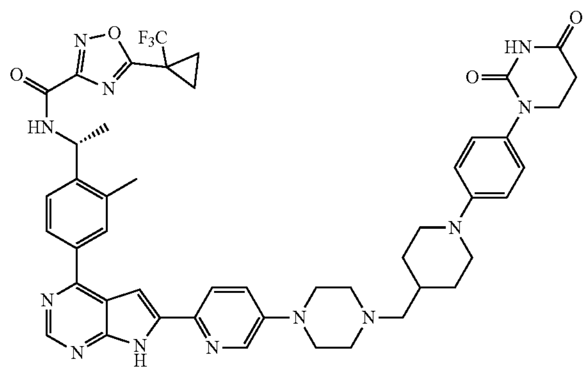 [SMILES: Cc1cc(-c2ncnc3[nH]c(-c4ccc(N5CCN(CC6CCN(c7ccc(N8CCC(=O)NC8=O)cc7)CC6)CC5)cn4)cc23)ccc1[C@@H](C)NC(=O)c1noc(C2(C(F)(F)F)CC2)n1]

Example 88: (R)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-5-(1,1,1-trifluoro-2-methylpropan-2-yl)-1,2,4-oxadiazole-3-carboxamide

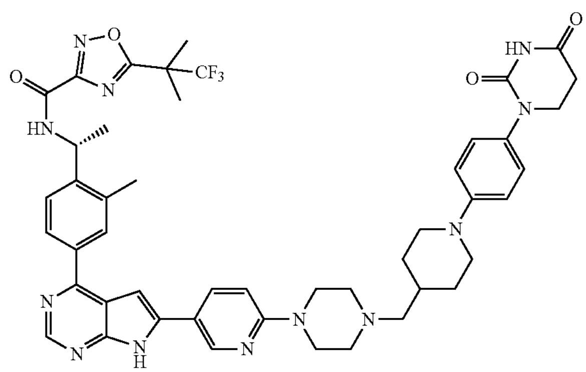

Example 89: (R)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-5-(1,1,1-trifluoro-2-methylpropan-2-yl)-1,2,4-oxadiazole-3-carboxamide

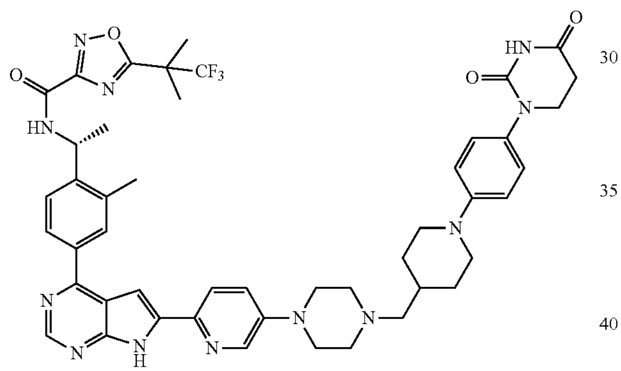

Example 90: (R)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-5-(1-methylcyclopropyl)-1,2,4-oxadiazole-3-carboxamide

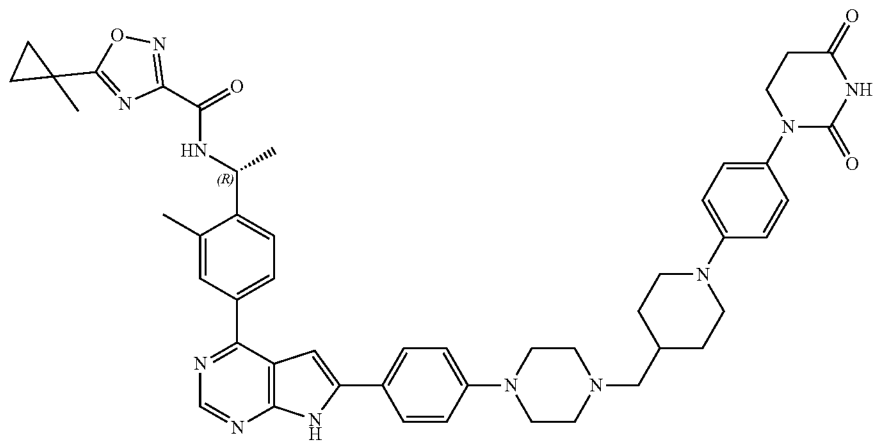

The titled compound was synthesized in the procedures similar to Example 25. $^1$H NMR (400 MHz, DMSO) $\delta_H$ 12.53 (s, 1H), 10.27 (s, 1H), 9.49 (d, J=7.2 Hz, 1H), 8.75 (s, 1H), 8.11-7.99 (m, 2H), 7.91 (d, J=7.6 Hz, 2H), 7.64 (d, J=7.6 Hz, 1H), 7.23 (s, 1H), 7.13 (d, J=7.6 Hz, 2H), 7.03 (d, J=7.6 Hz, 2H), 6.93 (d, J=7.6 Hz, 2H), 5.45-5.30 (m, 1H), 3.75-3.62 (m, 4H), 3.29-3.20 (m, 5H), 2.73-2.60 (m, 4H), 2.58-2.52 (m, 6H), 2.28-2.17 (m, 2H), 1.87-1.78 (m, 2H), 1.76-1.65 (m, 1H), 1.57-1.49 (m, 6H), 1.42-1.35 (m, 2H), 1.31-1.20 (m, 2H), 1.19-1.14 (m, 2H); $[M+H]^+$=848.5.

Example 91: (R)-3-(tert-butyl)-N-(1-(4-(6-(4-(4-((1-(5-(2,4-dioxotetrahydropyrimidin-1(2H)-yl)pyridin-2-yl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

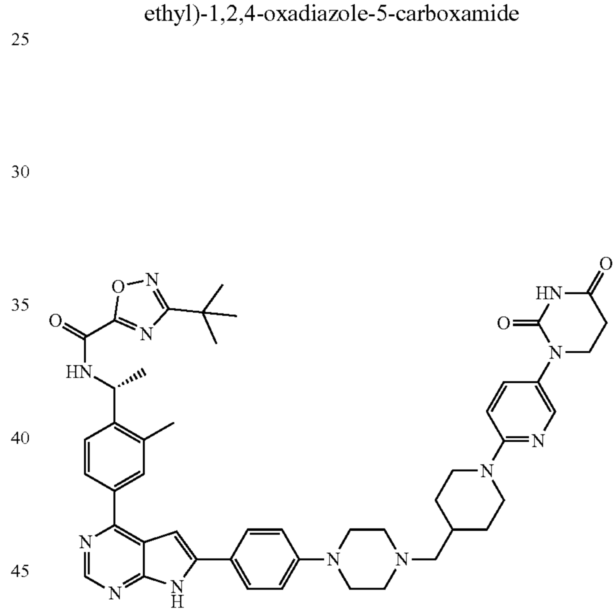

Example 92: (R)-3-(tert-butyl)-N-(1-(4-(6-(4-(4-((1-(6-(2,4-dioxotetrahydropyrimidin-1(2H)-yl)pyridin-3-yl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

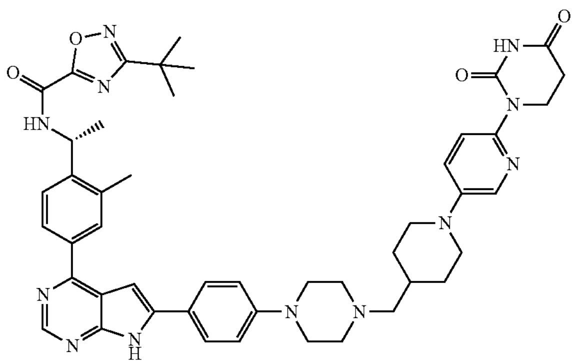

Example 93: (R)-3-(tert-butyl)-N-(1-(4-(6-(5-(4-((1-(5-(2,4-dioxotetrahydropyrimidin-1(2H)-yl)pyridin-2-yl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

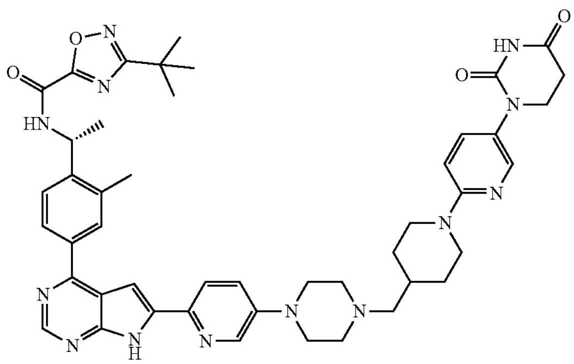

Example 94: (R)-3-(tert-butyl)-N-(1-(4-(6-(5-(4-((1-(6-(2,4-dioxotetrahydropyrimidin-1(2H)-yl)pyridin-3-yl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

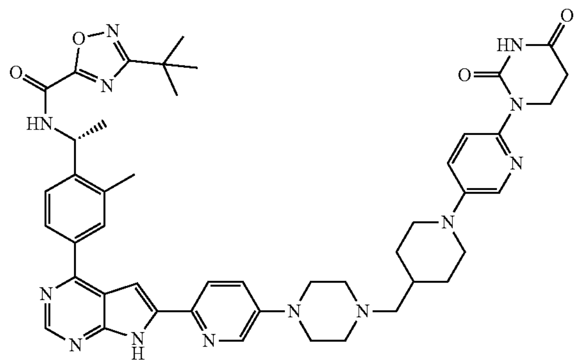 [SMILES: Cc1cc(-c2ncnc3[nH]c(-c4ccc(N5CCN(CC6CCN(c7ccc(N8CCC(=O)NC8=O)nc7)CC6)CC5)cc4)cc23)ccc1[C@@H](C)NC(=O)c1nc(C(C)(C)C)no1]

Example 95: (R)-3-(tert-butyl)-N-(1-(4-(6-(6-(4-((1-(5-(2,4-dioxotetrahydropyrimidin-1(2H)-yl)pyridin-2-yl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide

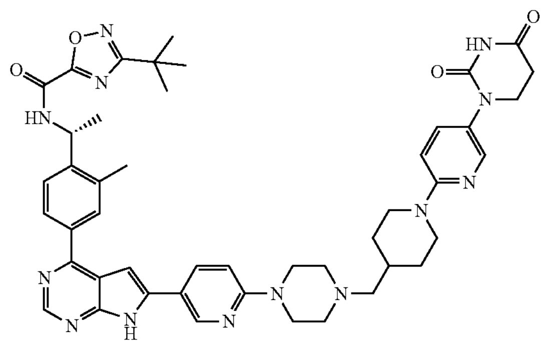 [SMILES: Cc1cc(-c2ncnc3[nH]c(-c4ccc(N5CCN(CC6CCN(c7ccc(N8CCC(=O)NC8=O)cn7)CC6)CC5)nc4)cc23)ccc1[C@@H](C)NC(=O)c1nc(C(C)(C)C)no1]

Example 96: (R)-3-(tert-butyl)-N-(1-(4-(6-(6-(4-((1-(6-(2,4-dioxotetrahydropyrimidin-1(2H)-yl)pyridin-3-yl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide

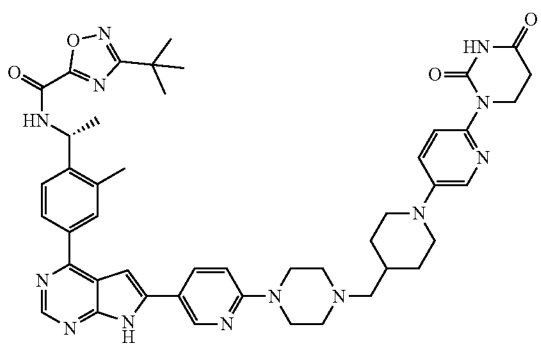 [SMILES: Cc1cc(-c2ncnc3[nH]c(-c4ccc(N5CCN(CC6CCN(c7ccc(N8CCC(=O)NC8=O)nc7)CC6)CC5)nc4)cc23)ccc1[C@@H](C)NC(=O)c1nc(C(C)(C)C)no1]

Example 97: (R)-3-(tert-butyl)-N-(1-(4-(6-(4-(4-((4-(4-(2,4-dioxotetrahydropyrimidin-1(2H)-yl)phenyl)piperazin-1-yl)methyl)piperidin-1-yl)phenyl)-7H-pyrrolo[2,3-d]pyrimidin-4-yl)-2-methylphenyl)ethyl)-1,2,4-oxadiazole-5-carboxamide

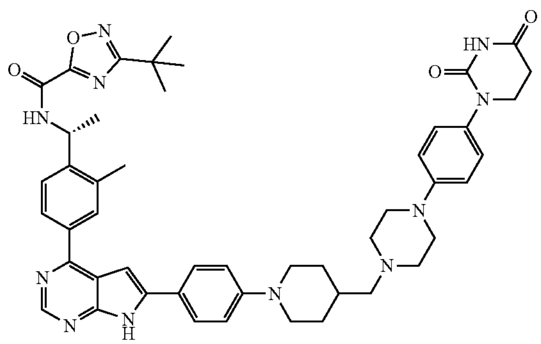 [SMILES: Cc1cc(-c2ncnc3[nH]c(-c4ccc(N5CCC(CN6CCN(c7ccc(N8CCC(=O)NC8=O)cc7)CC6)CC5)cc4)cc23)ccc1[C@@H](C)NC(=O)c1nc(C(C)(C)C)no1]

Example 98: (R)-3-(tert-butyl)-N-(1-(4-(6-(4-(4-((4-(5-(2,4-dioxotetrahydropyrimidin-1(2H)-yl)pyridin-2-yl)piperazin-1-yl)methyl)piperidin-1-yl)phenyl)-7H-pyrrolo[2,3-d]pyrimidin-4-yl)-2-methylphenyl)ethyl)-1,2,4-oxadiazole-5-carboxamide

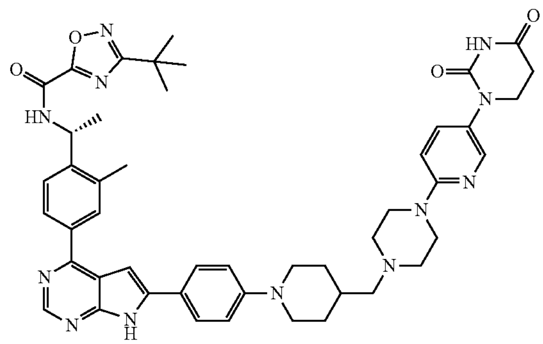 [SMILES: Cc1cc(-c2ncnc3[nH]c(-c4ccc(N5CCC(CN6CCN(c7ccc(N8CCC(=O)NC8=O)cn7)CC6)CC5)cc4)cc23)ccc1[C@@H](C)NC(=O)c1nc(C(C)(C)C)no1]

Example 99: (R)-3-(tert-butyl)-N-(1-(4-(6-(4-(4-((4-(6-(2,4-dioxotetrahydropyrimidin-1(2H)-yl)pyridin-3-yl)piperazin-1-yl)methyl)piperidin-1-yl)phenyl)-7H-pyrrolo[2,3-d]pyrimidin-4-yl)-2-methylphenyl)ethyl)-1,2,4-oxadiazole-5-carboxamide

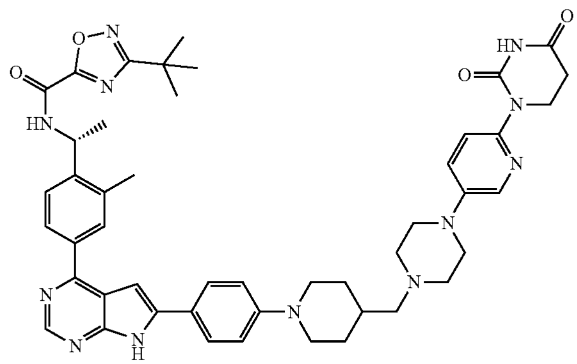

Example 100: (R)-3-(tert-butyl)-N-(1-(4-(6-(6-(4-((4-(4-(2,4-dioxotetrahydropyrimidin-1(2H)-yl)phenyl)piperazin-1-yl)methyl)piperidin-1-yl)pyridin-3-yl)-7H-pyrrolo[2,3-d]pyrimidin-4-yl)-2-methylphenyl)ethyl)-1,2,4-oxadiazole-5-carboxamide

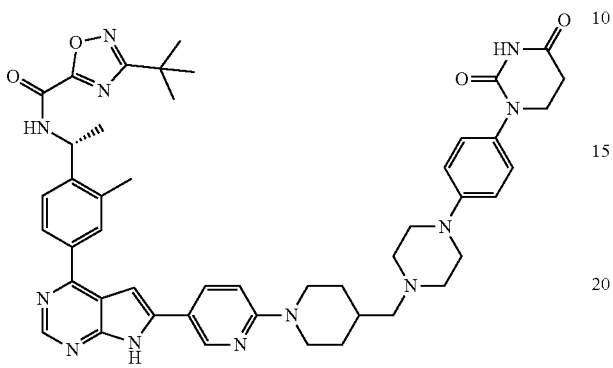

Example 101: (R)-3-(tert-butyl)-N-(1-(4-(6-(5-(4-((4-(4-(2,4-dioxotetrahydropyrimidin-1(2H)-yl)phenyl)piperazin-1-yl)methyl)piperidin-1-yl)pyridin-2-yl)-7H-pyrrolo[2,3-d]pyrimidin-4-yl)-2-methylphenyl)ethyl)-1,2,4-oxadiazole-5-carboxamide

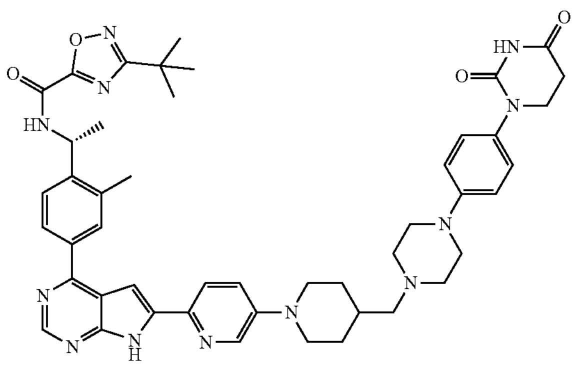

Example 102: (R)-3-(tert-butyl)-N-(1-(4-(6-(6-(4-((4-(5-(2,4-dioxotetrahydropyrimidin-1(2H)-yl)pyridin-2-yl)piperazin-1-yl)methyl)piperidin-1-yl)pyridin-3-yl)-7H-pyrrolo[2,3-d]pyrimidin-4-yl)-2-methylphenyl)ethyl)-1,2,4-oxadiazole-5-carboxamide

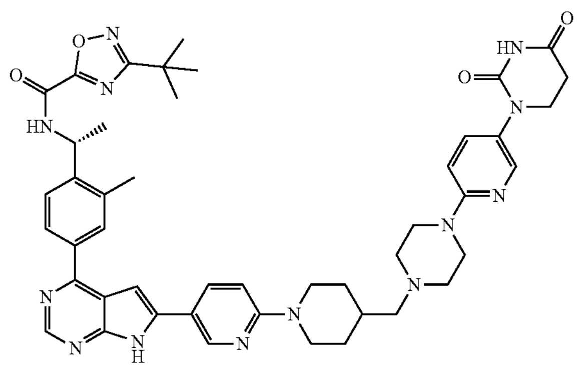 [SMILES: Cc1cc(-c2ncnc3[nH]c(-c4ccc(N5CCC(CN6CCN(c7ccc(N8CCC(=O)NC8=O)cn7)CC6)CC5)nc4)cc23)ccc1[C@@H](C)NC(=O)c1nc(C(C)(C)C)no1]

Example 103: (R)-3-(tert-butyl)-N-(1-(4-(6-(5-(4-((4-(5-(2,4-dioxotetrahydropyrimidin-1(2H)-yl)pyridin-2-yl)piperazin-1-yl)methyl)piperidin-1-yl)pyridin-2-yl)-7H-pyrrolo[2,3-d]pyrimidin-4-yl)-2-methylphenyl)ethyl)-1,2,4-oxadiazole-5-carboxamide

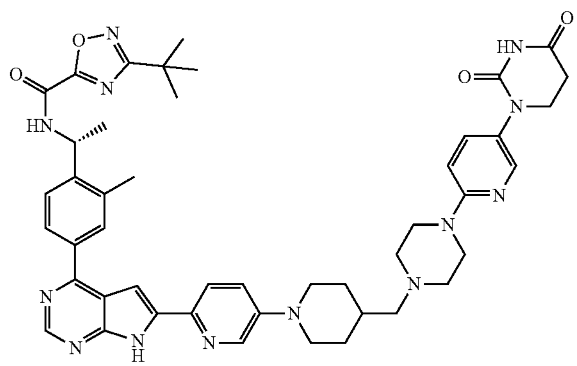 [SMILES: Cc1cc(-c2ncnc3[nH]c(-c4ccc(N5CCC(CN6CCN(c7ccc(N8CCC(=O)NC8=O)cn7)CC6)CC5)cn4)cc23)ccc1[C@@H](C)NC(=O)c1nc(C(C)(C)C)no1]

Example 104: (R)-5-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-3-carboxamide

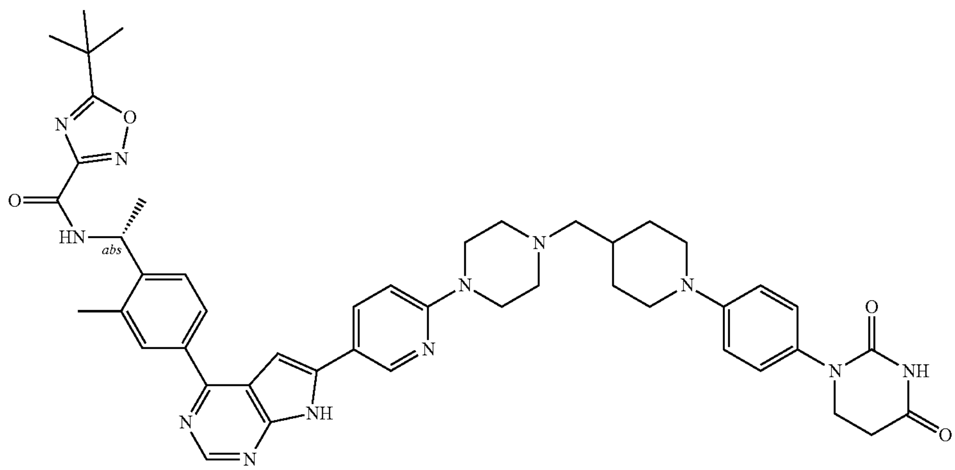 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1noc(C(C)(C)C)n1]

The titled compound was synthesized in the procedures similar to Example 14. $^1$H NMR (400 MHz, DMSO) $\delta_H$ 12.60 (s, 1H), 10.27 (s, 1H), 9.55 (d, J=7.2 Hz, 1H), 8.82 (s, 1H), 8.76 (s, 1H), 8.19 (d, J=8.0 Hz, 1H), 8.08 (d, J=7.2 Hz, 1H), 8.04 (s, 1H), 7.65 (d, J=7.6 Hz, 1H), 7.30 (s, 1H), 7.13 (d, J=8.0 Hz, 2H), 7.00-6.93 (m, 3H), 5.39 (s, 1H), 3.70 (brs, 4H), 3.60 (brs, 4H), 2.68 (brs, 4H), 2.53-2.41 (m, 7H), 2.22 (s, 2H), 1.83-1.65 (m, 3H), 1.52 (d, J=5.2 Hz, 3H), 1.43 (s, 9H), 1.23 (brs, 2H); [M+H]$^+$=851.6.

Example 105: 3-(tert-butyl)-N-((R)-1-(4-(6-(6-((R)-4-((1-(4-(2,4-dioxotetrahydropyrimidin-1(2H)-yl)phenyl)piperidin-4-yl)methyl)-2-methylpiperazin-1-yl)pyridin-3-yl)-7H-pyrrolo[2,3-d]pyrimidin-4-yl)-2-methylphenyl)ethyl)-1,2,4-oxadiazole-5-carboxamide

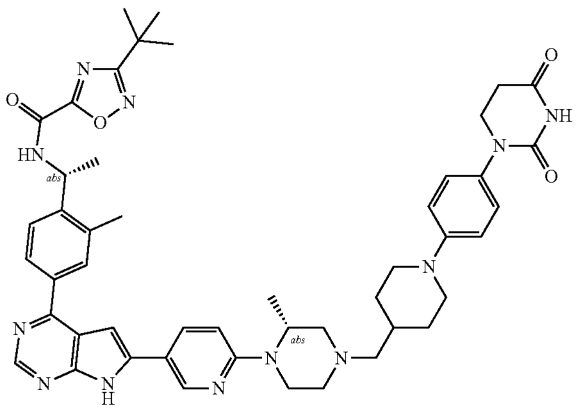 [SMILES: Cc1cc(-c2ncnc3[nH]c(-c4ccc(N5CCN(CC6CCN(c7ccc(N8CCC(=O)NC8=O)cc7)CC6)C[C@H]5C)nc4)cc23)ccc1[C@@H](C)NC(=O)c1nc(C(C)(C)C)no1]

The titled compound was synthesized in the procedures similar to Example 14. $^1$H NMR (400 MHz, DMSO) $\delta_H$ 12.58 (s, 1H), 10.26 (s, 1H), 9.96 (d, J=8.0 Hz, 1H), 8.81 (s, 1H), 8.76 (s, 1H), 8.17 (d, J=8.0 Hz, 1H), 8.09 (d, J=8.0 Hz, 1H), 8.04 (s, 1H), 7.66 (d, J=8.0 Hz, 1H), 7.28 (s, 1H), 7.13 (d, J=4.0 Hz, 2H), 6.97-6.85 (m, 3H), 5.37 (t, J=8.0 Hz, 1H), 4.58 (s, 1H), 4.12 (d, J=12.0 Hz, 1H), 3.69 (s, 4H), 3.07 (t, J=16.0 Hz, 2H), 2.93 (d, J=8.0 Hz, 2H), 2.82 (d, J=12.0 Hz, 2H), 2.68 (s, 5H), 2.52 (s, 3H), 2.25-2.08 (m, 4H), 2.01 (t, J=12.0 Hz, 1H), 1.84 (t, J=12.0 Hz, 2H), 1.73 (s, 1H), 1.55 (d, J=4.0 Hz, 4H), 1.37 (s, 9H); [M+H]$^+$=865.5.

Example 106: 3-(tert-butyl)-N-((R)-1-(4-(6-(6-((S)-4-((1-(4-(2,4-dioxotetrahydropyrimidin-1(2H)-yl)phenyl)piperidin-4-yl)methyl)-2-methylpiperazin-1-yl)pyridin-3-yl)-7H-pyrrolo[2,3-d]pyrimidin-4-yl)-2-methylphenyl)ethyl)-1,2,4-oxadiazole-5-carboxamide

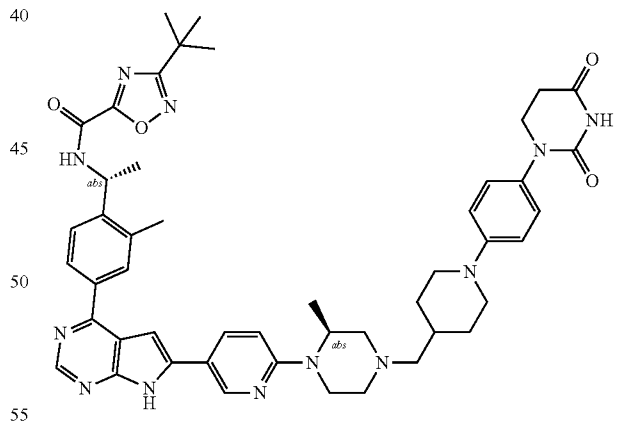

The titled compound was synthesized in the procedures similar to Example 14. $^1$H NMR (400 MHz, DMSO) $\delta_H$ 12.58 (s, 1H), 10.29 (s, 1H), 9.96 (d, J=8.0 Hz, 1H), 8.81 (s, 1H), 8.76 (s, 1H), 8.17 (d, J=8.0 Hz, 1H), 8.09 (d, J=8.0 Hz, 1H), 8.04 (s, 1H), 7.66 (d, J=8.0 Hz, 1H), 7.28 (s, 1H), 7.14 (d, J=8.0 Hz, 2H), 6.97-6.83 (m, 3H), 5.42-5.31 (m, 1H), 4.58 (s, 1H), 4.12 (d, J=8.0 Hz, 1H), 3.70 (s, 4H), 3.12-3.03 (m, 2H), 2.93 (d, J=8.0 Hz, 2H), 2.82 (d, J=8.0 Hz, 2H), 2.68 (s, 6H), 2.19-2.12 (m, 3H), 2.05-1.97 (m, 2H), 1.88-1.80 (m, 3H), 1.73 (s, 1H), 1.55 (d, J=8.0 Hz, 3H), 1.37 (s, 9H); [M+H]$^+$=865.6.

Example 107: (R)-5-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-5-fluoro-2-methylphenyl)ethyl)-1,2,4-oxadiazole-3-carboxamide

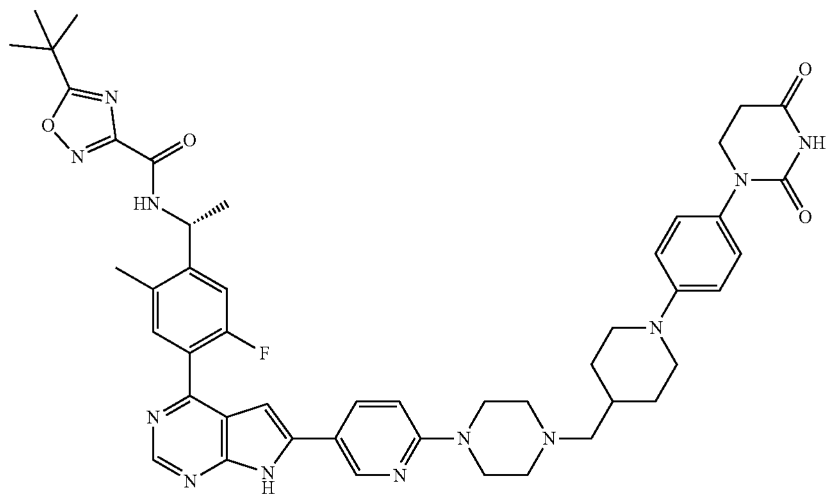 [SMILES: Cc1cc(-c2ncnc3[nH]c(-c4ccc(N5CCN(CC6CCN(c7ccc(N8CCC(=O)NC8=O)cc7)CC6)CC5)nc4)cc23)c(F)cc1[C@@H](C)NC(=O)c1noc(C(C)(C)C)n1]

The titled compound was synthesized in the procedures similar to Example 24. $^1$H NMR (400 MHz, DMSO) $\delta_H$ 12.52 (s, 1H), 10.26 (s, 1H), 9.55 (s, 1H), 8.78 (s, 1H), 8.15 (s, 1H), 7.84 (d, J=7.8 Hz, 2H), 7.63 (d, J=6.7 Hz, 1H), 7.48 (d, J=12.2 Hz, 1H), 7.13 (d, J=8.1 Hz, 2H), 7.01 (d, J=7.6 Hz, 2H), 6.93 (d, J=7.7 Hz, 2H), 6.77 (s, 1H), 5.36 (s, 1H), 3.69 (d, J=6.3 Hz, 4H), 3.28 (d, J=30.9 Hz, 9H), 2.73-2.62 (m, 4H), 2.46 (s, 3H), 2.23 (d, J=5.6 Hz, 2H), 1.87-1.66 (m, 3H), 1.53 (d, J=5.9 Hz, 3H), 1.44 (s, 9H), 1.23 (q, J=14.1 Hz, 2H); [M+H]$^+$=868.8.

Example 108: (R)-5-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-fluorophenyl)ethyl)-1,2,4-oxadiazole-3-carboxamide

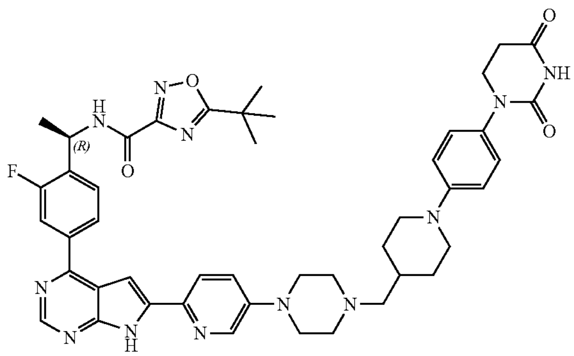

The titled compound was synthesized in the procedures similar to Example 19. $^1$H NMR (400 MHz, DMSO) $\delta_H$ 12.70 (s, 1H), 10.27 (s, 1H), 9.26 (d, J=8.0 Hz, 1H), 8.81 (s, 1H), 8.39 (m, 1H), 8.12-8.07 (m, 2H), 7.99-7.96 (m, 1H), 7.72-7.70 (m, 1H), 7.47-7.46 (m, 2H), 7.13 (d, J=8.0 Hz, 2H), 6.93 (d, J=8.0 Hz, 2H), 5.48-5.46 (m, 1H), 3.69-3.68 (m, 4H), 2.69-2.66 (m, 4H), 2.52-2.51 (m, 7H), 2.25-2.24 (m, 2H), 1.82-1.75 (m, 4H), 1.57 (d, J=8.0 Hz, 3H), 1.44 (s, 9H), 1.25-1.22 (m, 2H); [M+H]$^+$=855.5.

Example 109: 3-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-(hydroxymethyl)benzyl)-1,2,4-oxadiazole-5-carboxamide Step 1: (2-(aminomethyl)-5-(4,4,5,5-tetramethyl-1,3,2-dioxaborolan-2-yl)phenyl)methanol hydrochloride

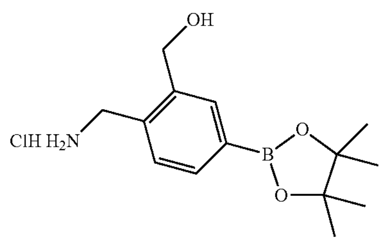

To a solution of tert-butyl (2-(hydroxymethyl)-4-(4,4,5,5-tetramethyl-1,3,2-dioxaborolan-2-yl)benzyl)carbamate (2 g, 0.0055 mol) in dioxane (20 mL), 4 M HCl in dioxane (20 mL) was added. The mixture was stirred at room temperature for 2.5 h. After the reaction was completed determined by LCMS, the mixture was concentrated in vacuo. Then the residue was diluted with MTBE (30 mL) and stirred at room temperature for 30 mins. The mixture was filtered to collect the filter cake to give the product (1.6 g, crude), which was used directly without further purification. [M+H]$^+$=264.3.

Step 2: 3-(tert-butyl)-N-(2-(hydroxymethyl)-4-(4,4,5,5-tetramethyl-1,3,2-dioxaborolan-2-yl)benzyl)-1,2,4-oxadiazole-5-carboxamide

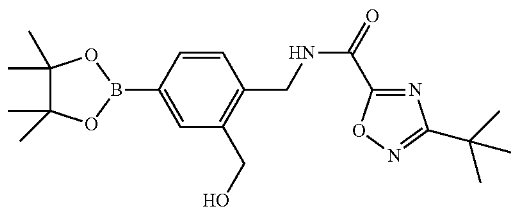 [SMILES: CC(C)(C)c1noc(C(=O)NCc2ccc(B3OC(C)(C)C(C)(C)O3)cc2CO)n1]

A mixture of sodium 3-(tert-butyl)-1,2,4-oxadiazole-5-carboxylate (340 mg, 2.0 mmol), HOBT (450.9 mg, 3.34 mmol) and EDCI (634.6 mg, 3.34 mmol) in DMF (10 mL) was stirred in a round bottom flask at rt for 5 mins. Then (2-(aminomethyl)-5-(4,4,5,5-tetramethyl-1,3,2-dioxaborolan-2-yl)phenyl)methanol hydrochloride (500 mg, 1.67 mmol) was added. The mixture was stirred at room temperature for 2.5 h. After the reaction was completed determined by LCMS, the mixture was extracted with EtOAc (50 mL*3), washed with brine (40 mL), dried over $Na_2SO_4$, and concentrated in vacuo. The residue was purified by silica gel column chromatography PE:EA=100%: 0%-50%: 50% to afford the desired product (242 mg, 30%). $[M+H-H_2O]^+$=398.3.

Step 3: tert-butyl 4-(4-(4-(4-((3-(tert-butyl)-1,2,4-oxadiazole-5-carboxamido)methyl)-3-(hydroxymethyl)phenyl)-7-((2-(trimethylsilyl)ethoxy)methyl)-7H-pyrrolo[2,3-d]pyrimidin-6-yl)phenyl)piperazine-1-carboxylate

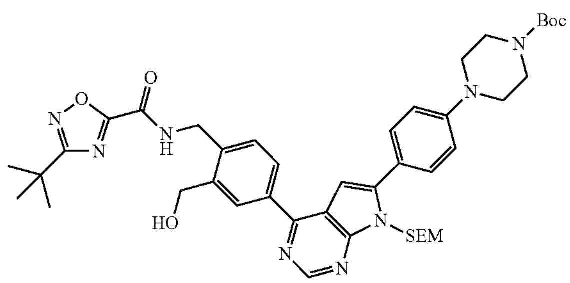 [SMILES: CC(C)(C)OC(=O)N1CCN(c2ccc(-c3cc4c(-c5ccc(CNC(=O)c6nc(C(C)(C)C)no6)c(CO)c5)ncnc4n3COCC[Si](C)(C)C)cc2)CC1]

A mixture of tert-butyl 4-(4-(4-chloro-7-((2-(trimethylsilyl)ethoxy)methyl)-7H-pyrrolo[2,3-d]pyrimidin-6-yl)phenyl)piperazine-1-carboxylate (100 mg, 0.184 mmol), 3-(tert-butyl)-N-(2-(hydroxymethyl)-4-(4,4,5,5-tetramethyl-1,3,2-dioxaborolan-2-yl)benzyl)-1,2,4-oxadiazole-5-carboxamide (160 mg, 0.386 mmol), $K_2CO_3$ (81.2 mg, 0.588 mmol) and Pd(dppf)$Cl_2$ (13.4 mg, 0.0184 mmol) in dioxane:water (10 mL: 3 mL) was stirred in a round bottom flask at 90° C. overnight. Then the mixture was allowed to cool and concentrated in vacuo. The residue was purified by silica gel column chromatography (PE:EA=100%:0%~0%:100%) to give the target product (57 mg, 39%). $[M+H]^+$=797.5.

Step 4: 3-(tert-butyl)-N-(2-(hydroxymethyl)-4-(6-(4-(piperazin-1-yl)phenyl)-7H-pyrrolo[2,3-d]pyrimidin-4-yl)benzyl)-1,2,4-oxadiazole-5-carboxamide

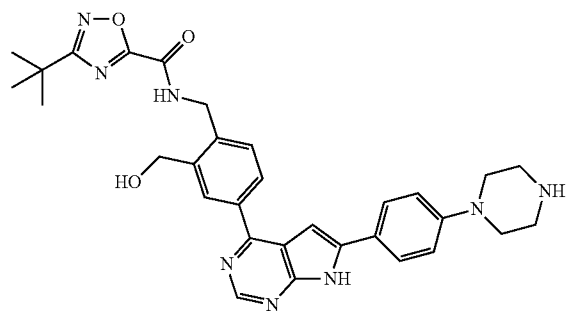 [SMILES: CC(C)(C)c1noc(C(=O)NCc2ccc(-c3ncnc4[nH]c(-c5ccc(N6CCNCC6)cc5)cc34)cc2CO)n1]

To a solution of tert-butyl 4-(4-(4-(4-((3-(tert-butyl)-1,2,4-oxadiazole-5-carboxamido)methyl)-3-(hydroxymethyl)phenyl)-7-((2-(trimethylsilyl)ethoxy)methyl)-7H-pyrrolo[2,3-d]pyrimidin-6-yl)phenyl)piperazine-1-carboxylate (56 mg, 0.170 mmol) in DCM (10 mL), TFA (10 mL) was added. The mixture was stirred at room temperature overnight. Then the mixture was concentrated in vacuo. The residue was dissolved in MeOH (10 mL) and the pH value was adjusted to 8 with $NH_3$ (7 M in MeOH). The mixture was stirred 30 mins at rt and concentrated in vacuo to afford the desired product (50 mg, crude), which was used for next step without further purification. $[M+H]^+$=567.5.

Step 5: 3-(tert-butyl)-N-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-(hydroxymethyl)benzyl)-1,2,4-oxadiazole-5-carboxamide

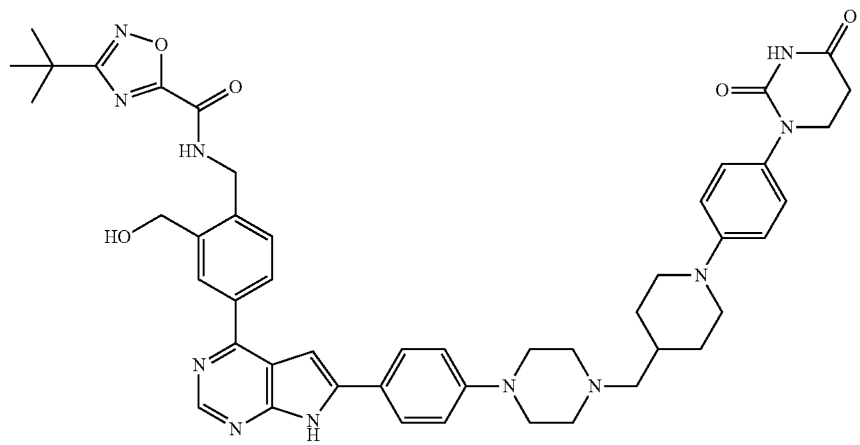 [SMILES: CC(C)(C)c1noc(C(=O)NCc2ccc(-c3ncnc4[nH]c(-c5ccc(N6CCN(CC7CCN(c8ccc(N9CCC(=O)NC9=O)cc8)CC7)CC6)cc5)cc34)cc2CO)n1]

A mixture of 3-(tert-butyl)-N-(2-(hydroxymethyl)-4-(6-(4-(piperazin-1-yl)phenyl)-7H-pyrrolo[2,3-d]pyrimidin-4-yl)benzyl)-1,2,4-oxadiazole-5-carboxamide (50 mg, 0.088 mmol), 1-(4-(2,4-dioxotetrahydropyrimidin-1(2H)-yl)phenyl)piperidine-4-carbaldehyde (32 mg, 0.106 mmol) in DCM (5 mL):MeOH (5 mL), was stirred in a round bottom flask. The mixture was stirred at room temperature for 5 mins and HOAc was added dropwise (3 drops). The mixture was stirred at room temperature for 2 h. Then $NaBH(OAc)_3$ (93.3 mg 0.44 mmol) was added. The mixture was stirred at room temperature overnight. After the reaction was complete determined by LCMS, the reaction mixture was concentrated in vacuo. The residue was purified by silica gel column chromatography (DCM:MeOH=95%:5%) to afford target product (18.11 mg, 24.1%). $^1H$ NMR (400 MHz, DMSO) $\delta_H$ 12.54 (s, 1H), 10.27 (s, 1H), 9.87 (s, 1H), 8.77 (s, 1H), 8.31 (s, 1H), 8.14 (d, J=8.0 Hz, 1H), 7.90 (d, J=4.0 Hz, 2H), 7.51 (d, J=8.0 Hz, 1H), 7.22 (s, 1H), 7.14 (d, J=8.0 Hz, 2H), 7.05 (d, J=4.0 Hz, 2H), 6.94 (d, J=8.0 Hz, 2H), 5.40 (s, 1H), 4.76 (s, 2H), 4.62 (s, 2H), 3.73-3.67 (m, 4H), 3.29-3.23 (m, 4H), 3.05-2.84 (m, 2H), 2.70-2.65 (m, 5H), 2.23 (s, 2H), 1.83 (d, J=12.0 Hz, 2H), 1.77-1.67 (m, 1H), 1.37 (s, 9H), 1.25 (s, 3H); $[M+H]^+$=852.8.

Example 110: (R)-3-(tert-butyl)-N-(1-(2-methyl-4-(6-(5-(4-((1-(4-(3-methyl-2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)phenyl)ethyl)-1,2,4-oxadiazole-5-carboxamide Step 1: 1-(4-(3-methyl-2,4-dioxotetrahydropyrimidin-1(2H)-yl)phenyl)piperidine-4-carbaldehyde

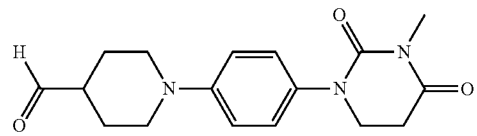 [SMILES: CN1C(=O)CCN(c2ccc(N3CCC(C=O)CC3)cc2)C1=O]

1-(4-(2,4-dioxotetrahydropyrimidin-1(2H)-yl)phenyl)piperidine-4-carbaldehyde (100 mg, 0.3 mmol), $K_2CO_3$ (229 mg, 1.7 mmol) and MeI (236 mg, 1.7 mmol) was placed in DMF (5 mL). The mixture was stirred at room temperature overnight until LC-MS indicated all the starting material was consumed. The mixture was diluted with water (50 mL) and extracted with EtOAc (50 mL*3). The combined organic layer was washed with brine (100 mL*3), dried over $Na_2SO_4$, and concentrated to give desired product (100 mg, 96%). $[M+H]^+$=315.2.

Step 2: (R)-3-(tert-butyl)-N-(1-(2-methyl-4-(6-(5-(4-((1-(4-(3-methyl-2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)phenyl)ethyl-1,2,4-oxadiazole-5-carboxamide

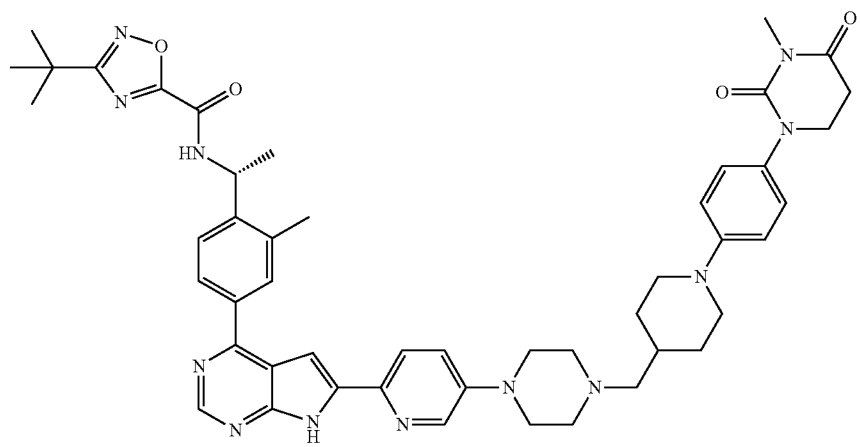 [SMILES: Cc1cc(-c2ncnc3[nH]c(-c4ccc(N5CCN(CC6CCN(c7ccc(N8CCC(=O)N(C)C8=O)cc7)CC6)CC5)cn4)cc23)ccc1[C@@H](C)NC(=O)c1nc(C(C)(C)C)no1]

(R)-3-(tert-butyl)-N-(1-(2-methyl-4-(6-(5-(piperazin-1-yl)pyridin-2-yl)-7H-pyrrolo[2,3-d]pyrimidin-4-yl)phenyl)ethyl)-1,2,4-oxadiazole-5-carboxamide (100 mg, 0.2 mmol), 1-(4-(3-methyl-2,4-dioxotetrahydropyrimidin-1(2H)-yl)phenyl)piperidine-4-carbaldehyde (100 mg, 0.3 mmol) and AcOH (1 drop) were placed in DCM/MeOH (5 mL, 10:1). The mixture was stirred at room temperature for 30 min. $NaBH(OAc)_3$ (84.8 mg, 0.4 mmol) was added to the mixture in one portion and the mixture was stirred at room temperature for another 1 h until LC-MS indicated all the starting material was consumed. The mixture was concentrated and purified with Prep-TLC (eluted with MeOH/DCM=1:10) to give the desired product (33 mg, 38.2%). $^1H$ NMR (400 MHz, DMSO) $\delta_H$ 12.61 (s, 1H), 9.96 (d, J=7.1 Hz, 1H), 8.78 (s, 1H), 8.39 (s, 1H), 8.06-8.02 (m, 3H), 7.68 (d, J=8.0 Hz, 1H), 7.51-7.47 (m, 1H), 7.40 (s, 1H), 7.14 (d, J=8.1 Hz, 2H), 6.94 (d, J=8.3 Hz, 2H), 5.42-5.38 (m, 1H), 3.75-3.64 (m, 5H), 3.41-3.38 (m, 4H), 3.03 (s, 3H), 2.84-2.78 (m, 2H), 2.74-2.66 (m, 3H), 2.54 (s, 3H), 2.50-2.45 (m, 3H), 2.24 (s, 1H), 1.82 (d, J=12.2 Hz, 2H), 1.55 (d, J=6.2 Hz, 3H), 1.37 (s, 9H), 1.26-1.22 (m, 3H); $[M+H]^+$=865.5.

Example 111: (R)-3-(tert-butyl)-N-(1-(4-(6-(4-(4-((1-(4-(2,4-dioxotetrahydropyrimidin-1(2H)-yl)-3-fluorophenyl)piperidin-4-yl)methyl)piperazin-1-yl) phenyl)-7H-pyrrolo[2,3-d]pyrimidin-4-yl)-2-methylpheyl)ethyl)-1,2,4-oxadiazole-5-carboxamide

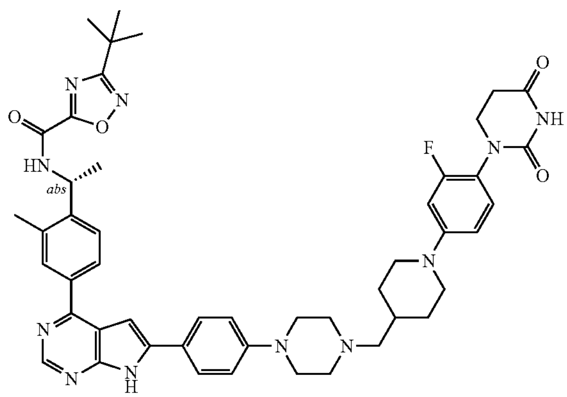 [SMILES: Cc1cc(-c2ncnc3[nH]c(-c4ccc(N5CCN(CC6CCN(c7ccc(N8CCC(=O)NC8=O)c(F)c7)CC6)CC5)cc4)cc23)ccc1[C@@H](C)NC(=O)c1nc(C(C)(C)C)no1]

The titled compound was synthesized in the procedures similar to Example 20. $^1$H NMR (400 MHz, DMSO) $\delta_H$ 12.52 (s, 1H), 10.38 (s, 1H), 9.95 (s, J=8.0 Hz, 1H), 8.75 (s, 1H), 8.08 (s, J=8.4 Hz, 1H), 8.04 (s, 1H), 7.91 (d, J=8.0 Hz, 2H), 7.66 (d, J=8.4 Hz, 1H), 7.23-7.06 (m, 2H), 7.04 (d, J=7.2 Hz, 2H), 6.83-6.75 (m, 2H), 5.38 (brs, 1H), 3.76 (d, J=11.2 Hz, 2H), 3.62 (s, 2H), 3.26 (s, 4H), 2.80-2.64 (m, 4H), 2.55-2.45 (m, 7H), 2.22 (s, 2H), 1.83-1.65 (m, 3H), 1.55 (d, J=6.4 Hz, 3H), 1.37 (s, 9H), 1.21 (brs, 2H); [M+H]$^+$=868.5.

Example 112: (R)-3-(tert-butyl)-N-(1-(4-(8-(4-(4-((1-(4-(2,4-dioxotetrahydropyrimidin-1(2H)-yl)-3-methylphenyl)piperidin-4-yl)methyl)piperazin-1-yl)-3-methylphenyl)-9H-purin-6-yl)-2-methylphenyl) ethyl)-1,2,4-oxadiazole-5-carboxamide

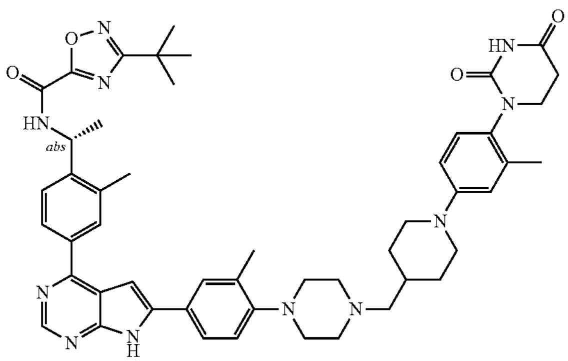 [SMILES: Cc1cc(-c2ncnc3[nH]c(-c4ccc(N5CCN(CC6CCN(c7ccc(N8CCC(=O)NC8=O)c(C)c7)CC6)CC5)c(C)c4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 13.85 (s, 1H), 10.26 (s, 1H), 9.94 (d, J=6.4 Hz, 1H), 8.88 (s, 1H), 8.83-8.73 (m, 1H), 8.64 (s, 1H), 8.22-8.05 (m, 2H), 7.70 (d, J=8.4 Hz, 1H), 7.20 (d, J=8.0 Hz, 1H), 7.04 (d, J=8.4 Hz, 1H), 6.87-6.72 (m, 2H), 5.51-5.23 (m, 1H), 3.76-3.61 (m, 3H), 3.51-3.40 (m, 1H), 2.97 (s, 4H), 2.75-2.62 (m, 4H), 2.58-2.53 (m, 7H), 2.37 (s, 3H), 2.30-2.21 (m, 2H), 2.12 (s, 3H), 1.87-1.78 (m, 2H), 1.76-1.66 (m, 1H), 1.59-1.50 (m, 3H), 1.37 (s, 9H), 1.28-1.15 (m, 2H); [M+H]$^+$=879.8.

Example 113: (R)-3-(tert-butyl)-N-(1-(4-(8-(4-(4-((1-(4-(2,4-dioxotetrahydropyrimidin-1(2H)-yl)-3-methylphenyl)piperidin-4-yl)methyl)piperazin-1-yl)-3-methoxyphenyl)-9H-purin-6-yl)-2-methylphenyl) ethyl)-1,2,4-oxadiazole-5-carboxamide

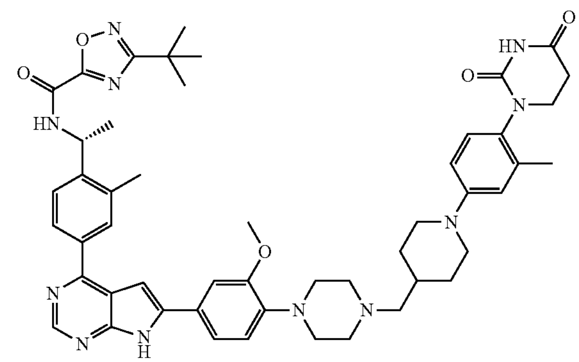 [SMILES: COc1cc(-c2cc3c(-c4ccc([C@@H](C)NC(=O)c5nc(C(C)(C)C)no5)c(C)c4)ncnc3[nH]2)ccc1N1CCN(CC2CCN(c3ccc(N4CCC(=O)NC4=O)c(C)c3)CC2)CC1]

The titled compound was synthesized in the procedures similar to Example 25. $^1$H NMR (400 MHz, DMSO) $\delta_H$ 10.26 (s, 1H), 9.93 (d, J=6.4 Hz, 1H), 8.88 (s, 1H), 8.85-8.75 (m, 1H), 8.70 (s, 1H), 8.01-7.85 (m, 2H), 7.70 (d, J=8.0 Hz, 1H), 7.20-7.70 (m, 2H), 6.87-6.73 (m, 2H), 5.38 (s, 1H), 3.95 (s, 3H), 3.80-3.55 (m, 5H), 3.50-3.40 (m, 2H), 3.25-3.15 (m, 5H), 2.80-2.60 (m, 5H), 2.35-2.15 (m, 2H), 2.12 (s, 3H), 1.91-1.81 (m, 3H), 1.55 (d, J=6.0 Hz, 3H), 1.37 (s, 9H), 1.30-1.17 (m, 2H); [M+H]$^+$=895.8.

Example 114: (R)-3-(tert-butyl)-N-(1-(4-(8-(4-(4-((1-(4-(2,4-dioxotetrahydropyrimidin-1(2H)-yl)-3-methylphenyl)piperidin-4-yl)methyl)piperazin-1-yl)-2-methylphenyl)-9H-purin-6-yl)-2-methylphenyl) ethyl)-1,2,4-oxadiazole-5-carboxamide

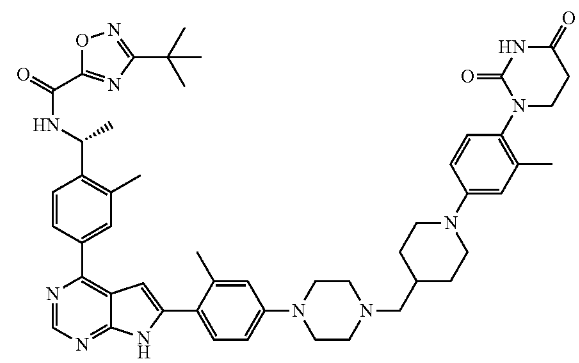 [SMILES: Cc1cc(N2CCN(CC3CCN(c4ccc(N5CCC(=O)NC5=O)c(C)c4)CC3)CC2)ccc1-c1cc2c(-c3ccc([C@@H](C)NC(=O)c4nc(C(C)(C)C)no4)c(C)c3)ncnc2[nH]1]

The titled compound was synthesized in the procedures similar to Example 25. $^1$H NMR (400 MHz, DMSO) $\delta_H$ 13.56 (s, 1H), 10.26 (s, 1H), 9.91 (d, J=7.2 Hz, 1H), 8.87 (s, 1H), 8.76 (s, 2H), 7.86 (s, 1H), 7.69 (d, J=8.0 Hz, 1H), 7.09-6.90 (m, 3H), 6.85-6.75 (m, 2H), 5.38 (s, 1H), 3.76-3.60 (m, 3H), 3.50-3.40 (m, 1H), 3.34 (s, 4H), 2.79 (s, 3H), 2.75-2.60 (m, 4H), 2.27-2.18 (m, 2H), 2.12 (s, 3H), 1.91-1.65 (m, 3H), 1.55 (d, J=4.8 Hz, 3H), 1.36 (s, 9H), 130-1.15 (m, 2H); [M+H]$^+$=879.6.

Example 115: (R)-5-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-3-fluoro-2-methylphenyl)ethyl)-1,2,4-oxadiazole-3-carboxamide

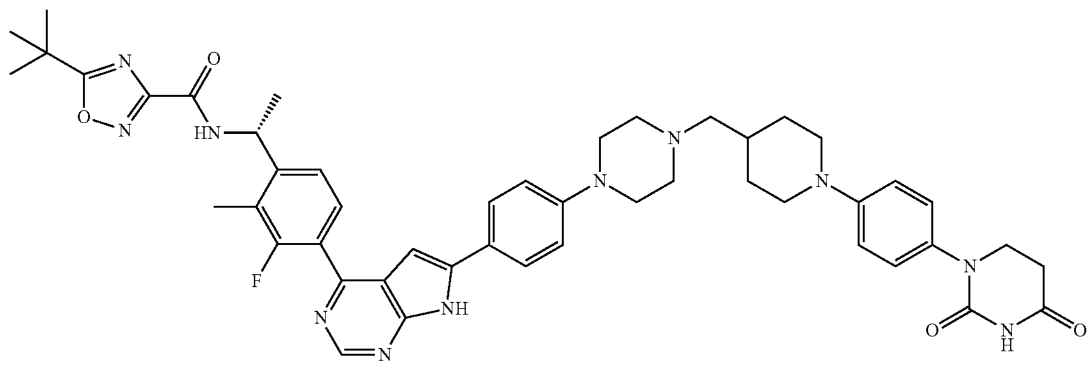 [SMILES: Cc1c([C@@H](C)NC(=O)c2noc(C(C)(C)C)n2)ccc(-c2ncnc3[nH]c(-c4ccc(N5CCN(CC6CCN(c7ccc(N8CCC(=O)NC8=O)cc7)CC6)CC5)cc4)cc23)c1F]

The titled compound was synthesized in the procedures similar to Example 25. $^1H$ NMR (400 MHz, DMSO) $\delta_H$ 12.53 (s, 1H), 10.27 (s, 1H), 9.60 (d, J=6.7 Hz, 1H), 8.77 (s, 1H), 7.85 (d, J=8.1 Hz, 2H), 7.64 (s, 1H), 7.47 (d, J=6.9 Hz, 1H), 7.13 (d, J=8.2 Hz, 2H), 7.01 (d, J=7.8 Hz, 2H), 6.93 (d, J=6.8 Hz, 2H), 6.78 (s, 1H), 5.41 (s, 1H), 3.70 (s, 4H), 3.25 (s, 4H), 3.10-2.86 (m, 1H), 2.68 (s, 4H), 2.51-2.57 (m, 2H), 2.37 (d, J=31.5 Hz, 4H), 2.22 (s, 2H), 1.79 (t, J=21.4 Hz, 3H), 1.53 (d, J=4.6 Hz, 3H), 1.43 (s, 9H), 1.23 (d, J=11.7 Hz, 2H); $[M+H]^+$=868.8.

Example 116: (R)-3-(tert-butyl)-N-(1-(4-(6-(3-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-methylphenyl)ethyl)-1,2,4-oxadiazole-5-carboxamide

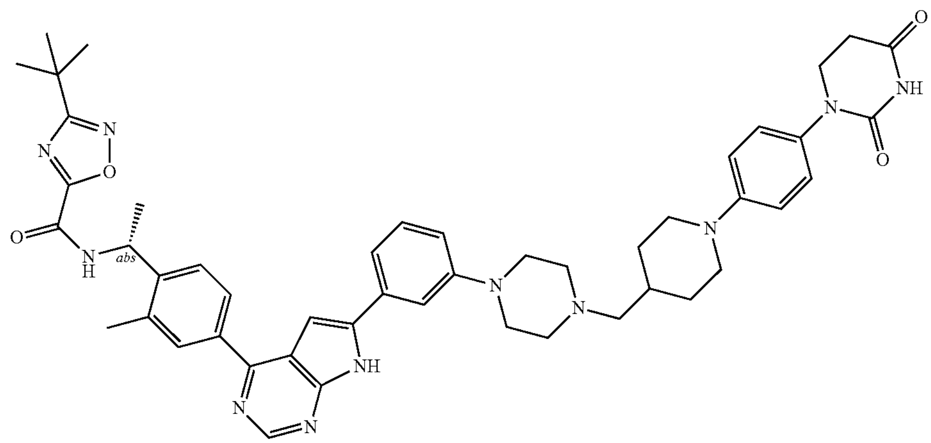 [SMILES: Cc1cc(-c2ncnc3[nH]c(-c4cccc(N5CCN(CC6CCN(c7ccc(N8CCC(=O)NC8=O)cc7)CC6)CC5)c4)cc23)ccc1[C@@H](C)NC(=O)c1nc(C(C)(C)C)no1]

The titled compound was synthesized in the procedures similar to Example 25. $^1H$ NMR (400 MHz, DMSO) $\delta_H$ 12.67 (s, 1H), 10.27 (s, 1H), 9.98 (d, J=6.8 Hz, 1H), 8.81 (s, 1H), 8.10 (d, J=8.4 Hz, 1H), 8.04 (s, 1H), 7.68 (d, J=7.2 Hz, 1H), 7.60 (s, 1H), 7.49 (d, J=7.4 Hz, 1H), 7.41 (s, 1H), 7.33 (t, J=8.0 Hz, 1H), 7.14 (d, J=8.0 Hz, 2H), 7.00-6.85 (m, 3H), 5.38 (s, 1H), 3.69 (brs, 4H), 3.27 (brs, 4H), 2.68 (brs, 4H), 2.54 (s, 6H), 2.24 (d, J=5.6 Hz, 2H), 1.91 (d, J=1.2 Hz, 1H), 1.83 (d, J=12.0 Hz, 2H), 1.74 (brs, 1H), 1.55 (d, J=6.0 Hz, 3H), 1.37 (s, 9H), 1.32-1.15 (m, 2H); $[M+H]^+$=850.8.

Example 117: (R)-5-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)isoxazole-3-carboxamide

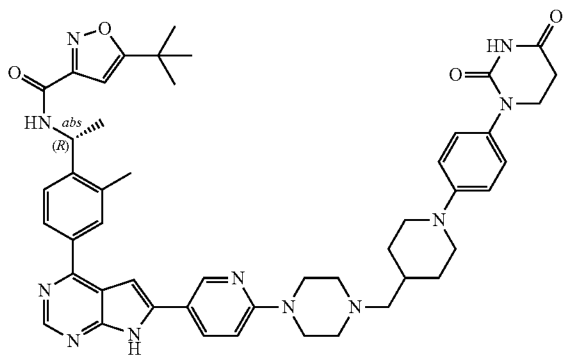

The titled compound was synthesized in the procedures similar to Example 25. $^1$H NMR (400 MHz, DMSO) $\delta_H$ 12.59 (s, 1H), 10.27 (s, 1H), 9.35-9.24 (m, 1H), 8.81 (s, 1H), 8.76 (s, 1H), 8.19 (d, J=8.8 Hz, 1H), 8.06 (d, J=8.0 Hz, 1H), 8.02 (s, 1H), 7.64 (d, J=8.0 Hz, 1H), 7.29 (s, 1H), 7.14 (d, J=8.4 Hz, 2H), 6.99-6.91 (m, 3H), 6.56 (s, 1H), 5.41-5.32 (m, 1H), 3.73-3.66 (m, 4H), 3.65-3.56 (m, 4H), 2.73-2.65 (m, 5H), 2.55-2.52 (m, 5H), 2.26-2.19 (m, 2H), 1.94-1.89 (m, 2H), 1.87-1.78 (m, 2H), 1.54-1.46 (m, 3H), 1.32 (s, 9H), 1.27-1.21 (m, 2H); [M+H]$^+$=850.5.

Example 118: (R)-5-(tert-butyl)-N-(1-(4-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2-(hydroxymethyl)phenyl)ethyl)-1,2,4-oxadiazole-3-carboxamide

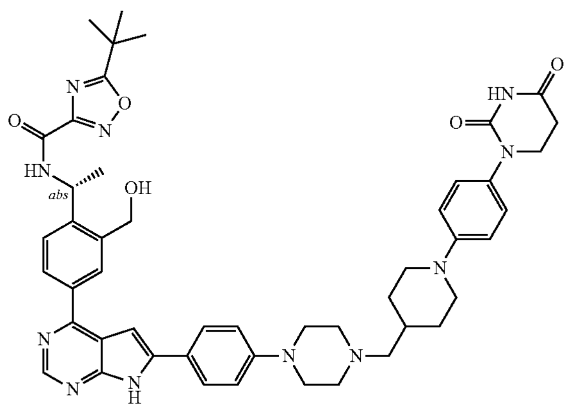 [SMILES: C[C@@H](NC(=O)c1noc(C(C)(C)C)n1)c1ccc(-c2ncnc3[nH]c(-c4ccc(N5CCN(CC6CCN(c7ccc(N8CCC(=O)NC8=O)cc7)CC6)CC5)cc4)cc23)cc1CO]

The titled compound was synthesized in the procedures similar to Example 1. $^1$H NMR (400 MHz, dmso) δ 12.53 (s, 1H), 10.26 (s, 1H), 9.57 (d, J=8.0 Hz, 1H), 8.76 (s, 1H), 8.27 (s, 1H), 8.14 (d, J=8.0 Hz, 1H), 7.90 (d, J=8.0 Hz, 2H), 7.71 (d, J=8.0 Hz, 1H), 7.23 (s, 1H), 7.14 (d, J=8.0 Hz, 2H), 7.04 (d, J=8.0 Hz, 2H), 6.93 (d, J=8.0 Hz, 2H), 5.46-5.30 (m, 2H), 4.93-4.70 (m, 2H), 3.75-3.63 (m, 4H), 3.26 (s, 4H), 3.02-2.89 (m, 2H), 2.72-2.65 (m, 4H), 2.57-2.53 (m, 2H), 2.23 (d, J=4.0 Hz, 2H), 1.81 (d, J=8.0 Hz, 2H), 1.78-1.66 (m, 1H), 1.55 (d, J=8.0 Hz, 3H), 1.42 (s, 9H), 1.29-1.24 (m, 2H). [M+H]$^+$=866.8.

Example 119: (R)-3-(tert-butyl)-N-(1-(4-(6-(5-(4-((1-(3-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

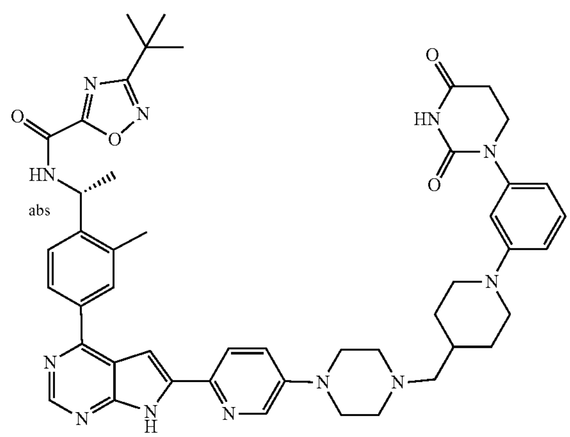 [SMILES: Cc1cc(-c2ncnc3[nH]c(-c4ccc(N5CCN(CC6CCN(c7cccc(N8CCC(=O)NC8=O)c7)CC6)CC5)cn4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.60 (s, 1H), 10.30 (s, 1H), 9.95 (d, J=8.0 Hz, 1H), 8.78 (s, 1H), 8.39 (s, 1H), 8.10-8.00 (m, 3H), 7.68 (d, J=8.0 Hz, 1H), 7.46 (d, J=8.0 Hz, 1H), 7.40 (s, 1H), 7.19 (t, J=8.0 Hz, 1H), 6.88 (s, 1H), 6.82 (d, J=8.0 Hz, 1H), 6.68 (d, J=8.0 Hz, 1H), 5.38 (s, 1H), 3.80-3.61 (m, 4H), 3.09-2.89 (m, 1H), 2.75-2.63 (m, 5H), 2.24 (d, J=6.0 Hz, 2H), 1.82 (d, J=12.0 Hz, 2H), 1.74 (s, 1H), 1.55 (d, J=8.0 Hz, 3H), 1.37 (s, 9H), 1.27-1.17 (m, 2H); [M+H]$^+$=851.8.

Example 120: (R)-5-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-2-(hydroxymethyl)phenyl)ethyl)-1,2,4-oxadiazole-3-carboxamide

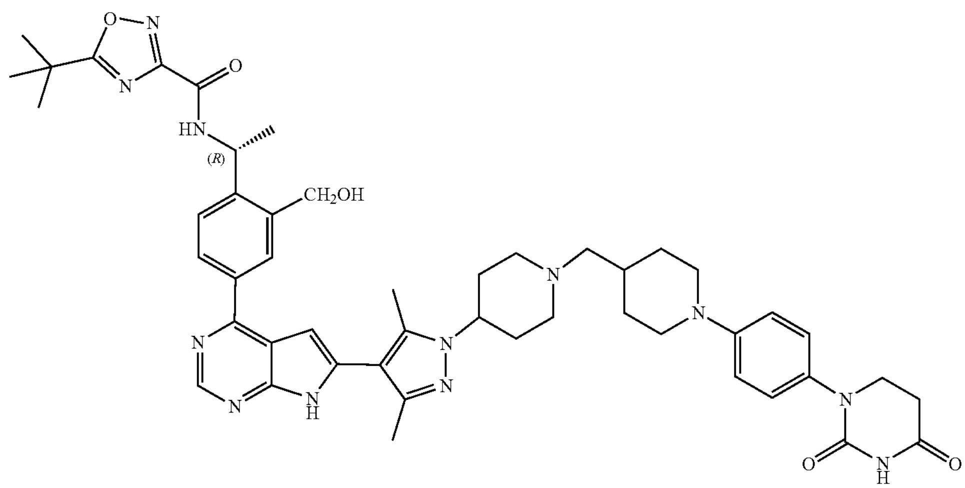

The titled compound was synthesized in the procedures similar to Example 25. $^1$H NMR (400 MHz, DMSO) $\delta_H$ 12.13 (s, 1H), 10.26 (s, 1H), 9.55 (d, J=8.0 Hz, 1H), 8.77 (s, 1H), 8.23 (s, 1H), 8.08 (d, J=8.0 Hz, 1H), 7.68 (d, J=8.0 Hz, 1H), 7.12 (d, J=8.0 Hz, 2H), 6.92 (d, J=8.0 Hz, 2H), 6.73 (s, 1H), 5.37-5.35 (m, 2H), 4.83-4.71 (m, 2H), 4.12 (s, 1H), 3.67-3.66 (m, 4H), 2.94 (s, 2H), 2.68-2.61 (m, 4H), 2.35 (s, 3H), 2.25-2.20 (m, 5H), 2.09-2.03 (m, 4H), 1.81-1.77 (m, 4H), 1.51 (d, J=8.0 Hz, 3H), 1.39 (s, 9H), 1.23-1.19 (m, 3H); $[M+H]^+$=883.9.

Example 121: (R)-1-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-2-methylphenyl)ethyl)-1H-1,2,3-triazole-4-carboxamide

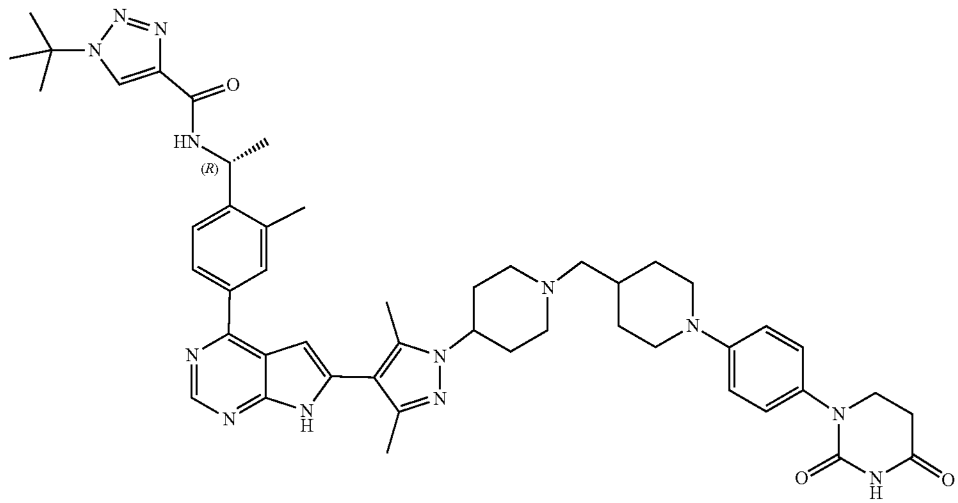

The titled compound was synthesized in the procedures similar to Example 25. $^1$H NMR (400 MHz, DMSO) $\delta_H$ 12.11 (s, 1H), 10.26 (s, 1H), 8.95 (d, J=8.0 Hz, 1H), 8.75 (s, 1H), 8.64 (s, 1H), 7.98-7.95 (m, 2H), 7.65 (d, J=8.0 Hz, 1H), 7.12 (d, J=8.0 Hz, 2H), 6.92 (d, J=8.0 Hz, 2H), 5.39-5.36 (m, 1H), 4.14 (s, 1H), 3.69-3.66 (m, 4H), 2.96 (s, 2H), 2.68-2.61 (m, 5H), 2.34-2.32 (m, 4H), 2.25-2.06 (m, 9H), 1.81-1.65 (m, 5H), 1.60 (s, 9H), 1.49 (d, J=8.0 Hz, 3H), 1.24-1.19 (m, 3H); [M+H]$^+$=866.7.

Example 122: (R)-1-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-2-(hydroxymethyl)phenyl)ethyl)-1H-1,2,3-triazole-4-carboxamide

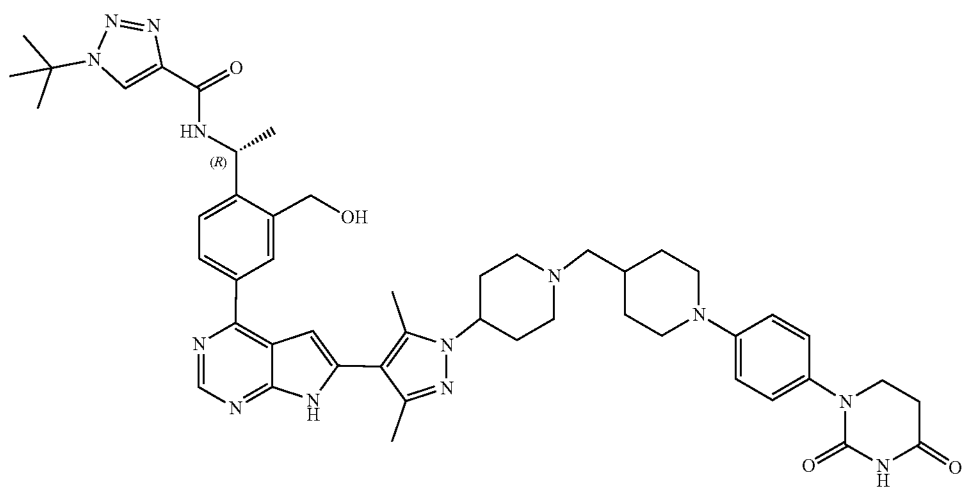

The titled compound was synthesized in the procedures similar to Example 25. $^1$H NMR (400 MHz, DMSO) $\delta_H$ 12.12 (s, 1H), 10.26 (s, 1H), 9.03 (d, J=8.0 Hz, 1H), 8.76 (s, 1H), 8.62 (s, 1H), 8.21 (s, 1H), 8.05 (d, J=8.0 Hz, 1H), 7.72 (d, J=8.0 Hz, 1H), 7.12 (d, J=8.0 Hz, 2H), 6.92 (d, J=8.0 Hz, 2H), 6.72 (s, 1H), 5.40-5.33 (m, 2H), 4.85-4.74 (m, 2H), 4.12 (s, 1H), 3.69-3.66 (m, 4H), 2.94 (s, 2H), 2.68-2.61 (m, 4H), 2.34 (s, 3H), 2.25-2.08 (m, 9H), 1.81-1.78 (m, 4H), 1.59 (s, 9H), 1.50 (d, J=8.0 Hz, 3H), 1.24-1.19 (m, 3H); [M+H]$^+$=882.9.

Example 123: (R)-N-(1-(4-(6-(5-(4-((1-(4-(2,4-dioxotetrahydropyrimidin-1(2H)-yl)-3-methylphenyl)piperidin-4-yl)methyl)piperazin-1-yl)pyridin-2-yl)-7H-pyrrolo[2,3-d]pyrimidin-4-yl)-2-methylphenyl)ethyl)-5-(1-(hydroxymethyl)cyclopropyl)-1,2,4-oxadiazole-3-carboxamide

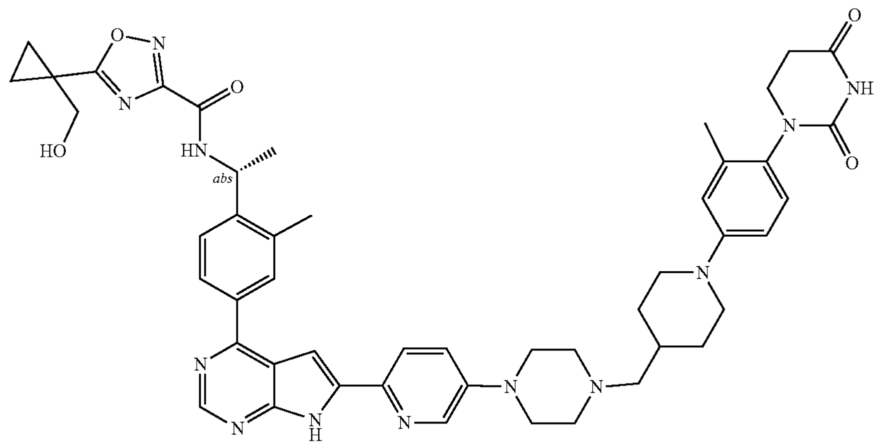 [SMILES: Cc1cc(-c2ncnc3[nH]c(-c4ccc(N5CCN(CC6CCN(c7ccc(N8CCC(=O)NC8=O)c(C)c7)CC6)CC5)cn4)cc23)ccc1[C@@H](C)NC(=O)c1noc(C2(CO)CC2)n1]

The titled compound was synthesized in the procedures similar to Example 25. $^{1}H$ NMR (400 MHz, DMSO) $\delta_H$ 13.63 (s, 1H), 10.91 (s, 1H), 10.38 (s, 1H), 9.60 (d, J=8.0 Hz, 1H), 9.00 (s, 1H), 8.48 (s, 1H), 8.22 (d, J=8.8 Hz, 1H), 8.00 (d, J=8.0 Hz, 1H), 7.95 (s, 1H), 7.72 (d, J=8.0 Hz, 1H), 7.67 (s, 1H), 7.62 (d, J=6.4 Hz, 1H), 7.42-7.23 (m, 2H), 5.42-5.33 (m, 1H), 4.14-4.00 (m, 3H), 3.79-3.76 (m, 5H), 3.68-3.65 (m, 5H), 3.24-3.09 (m, 7H), 2.77-2.72 (m, 1H), 2.68-2.63 (m, 1H), 2.55 (s, 3H), 2.19 (s, 3H), 2.15-2.07 (m, 2H), 1.85-1.67 (m, 2H), 1.51 (d, J=7.2 Hz, 3H), 1.34-1.28 (m, 2H), 1.26-1.20 (m, 2H); $[M+H]^+$=879.6.

Example 124: (R)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-5-(1-methylcyclopropyl)-1,2,4-oxadiazole-3-carboxamide

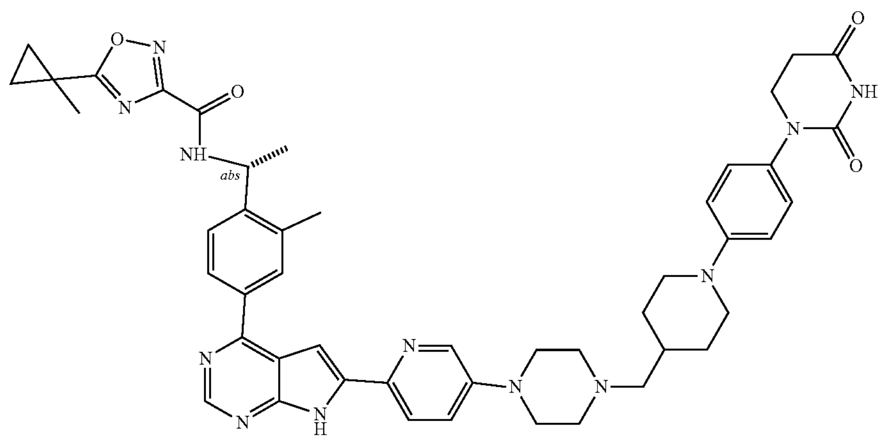 [SMILES: Cc1cc(-c2ncnc3[nH]c(-c4ccc(N5CCN(CC6CCN(c7ccc(N8CCC(=O)NC8=O)cc7)CC6)CC5)cn4)cc23)ccc1[C@@H](C)NC(=O)c1noc(C2(C)CC2)n1]

The titled compound was synthesized in the procedures similar to Example 25. $^{1}H$ NMR (400 MHz, DMSO) $\delta_H$ 12.62 (s, 1H), 10.27 (s, 1H), 9.50 (s, 1H), 8.98-8.55 (m, 2H), 8.19 (s, 1H), 8.11-7.90 (m, 2H), 7.63 (s, 1H), 7.29 (s, 1H), 7.20-7.07 (m, 2H), 7.04-6.84 (m, 3H), 5.44-5.26 (m, 1H), 3.77-3.51 (m, 9H), 3.47-3.42 (m, 3H), 2.74-2.61 (m, 4H), 2.45-2.39 (m, 2H), 2.30-2.09 (m, 2H), 1.93-1.62 (m, 3H), 1.61-1.43 (m, 6H), 1.41-1.30 (m, 2H), 1.29-1.08 (m, 5H); $[M+H]^+$=849.6.

Example 125: (R)-N-(1-(4-(6-(5-(4-((1-(4-(2,4-dioxotetrahydropyrimidin-1(2H)-yl)-3-methylphenyl)piperidin-4-yl)methyl)piperazin-1-yl)pyridin-2-yl)-7H-pyrrolo[2,3-d]pyrimidin-4-yl)-2-methylphenyl)ethyl)-5-(1-methylcyclopropyl)-1,2,4-oxadiazole-3-carboxamide

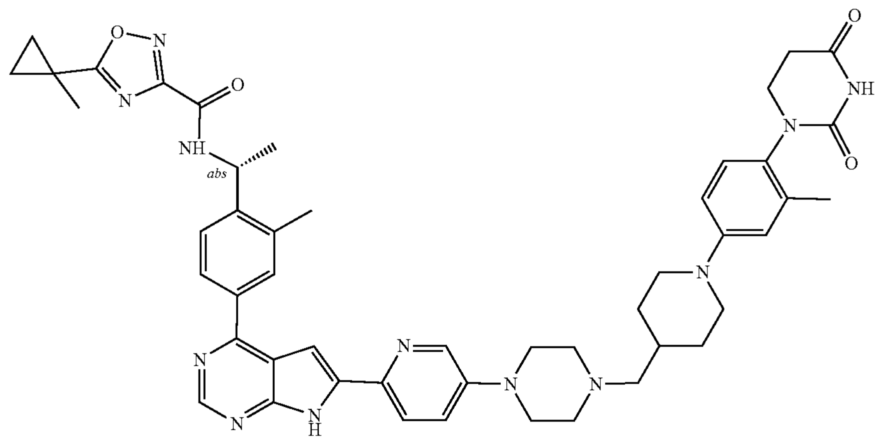 [SMILES: Cc1cc(-c2ncnc3[nH]c(-c4ccc(N5CCN(CC6CCN(c7ccc(N8CCC(=O)NC8=O)c(C)c7)CC6)CC5)cn4)cc23)ccc1[C@@H](C)NC(=O)c1noc(C2(C)CC2)n1]

The titled compound was synthesized in the procedures similar to Example 25. $^1$H NMR (400 MHz, DMSO) $\delta_H$ 12.60 (s, 1H), 10.25 (s, 1H), 9.49 (s, 1H), 9.01-8.62 (m, 2H), 8.18 (s, 1H), 8.11-7.94 (m, 2H), 7.64 (s, 1H), 7.29 (s, 1H), 7.08-6.89 (m, 2H), 6.86-6.67 (m, 2H), 5.46-5.28 (m, 1H), 3.79-3.54 (m, 7H), 3.53-3.39 (m, 3H), 3.38-3.36 (m, 3H), 2.83-2.61 (m, 5H), 2.26-2.17 (m, 2H), 2.12 (s, 3H), 1.89-1.70 (m, 3H), 1.60-1.47 (m, 6H), 1.41-1.32 (m, 2H), 1.30-1.11 (m, 5H); $[M+H]^+$=863.6.

Example 126: (R)-N-(1-(4-(6-(6-(4-((1-(4-(2,4-dioxotetrahydropyrimidin-1(2H)-yl)-3-methylphenyl)piperidin-4-yl)methyl)piperazin-1-yl)pyridin-3-yl)-7H-pyrrolo[2,3-d]pyrimidin-4-yl)-2-methylphenyl)ethyl)-5-(1-methylcyclopropyl)-1,2,4-oxadiazole-3-carboxamide

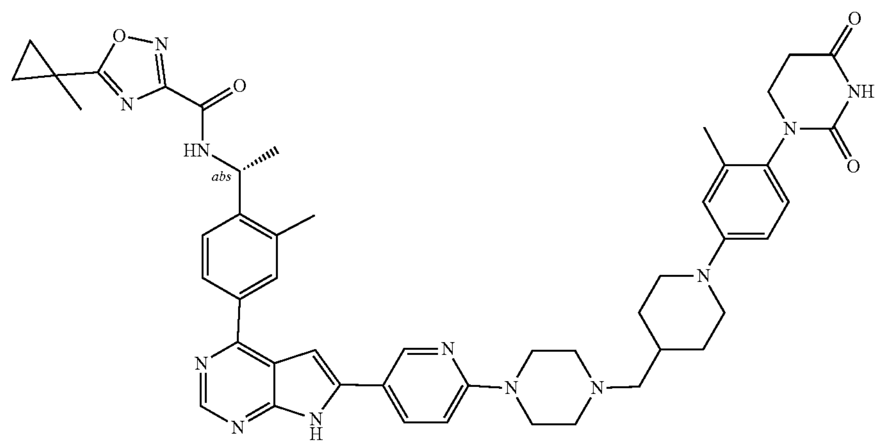 [SMILES: Cc1cc(-c2ncnc3[nH]c(-c4ccc(N5CCN(CC6CCN(c7ccc(N8CCC(=O)NC8=O)c(C)c7)CC6)CC5)nc4)cc23)ccc1[C@@H](C)NC(=O)c1noc(C2(C)CC2)n1]

The titled compound was synthesized in the procedures similar to Example 25. $^1$H NMR (400 MHz, DMSO) $\delta_H$ 12.61 (s, 1H), 10.25 (s, 1H), 9.49 (d, J=7.2 Hz, 1H), 8.39 (s, 1H), 8.16-7.90 (m, 3H), 7.65 (d, J=8.0 Hz, 1H), 7.53-7.31 (m, 2H), 7.04 (d, J=8.4 Hz, 1H), 6.87-6.71 (m, 2H), 5.45-5.24 (m, 1H), 3.75-3.63 (m, 3H), 3.53-3.36 (m, 4H), 2.74-2.62 (m, 4H), 2.56-2.53 (m, 4H), 2.29-2.20 (m, 2H), 2.12 (s, 3H), 1.90-1.61 (m, 7H), 1.57-1.47 (m, 6H), 1.42-1.35 (m, 2H), 1.31-1.11 (m, 5H); $[M+H]^+$=863.6.

Example 127: (R)-5-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-3-fluoro-2-methylphenyl)ethyl)-1,2,4-oxadiazole-3-carboxamide

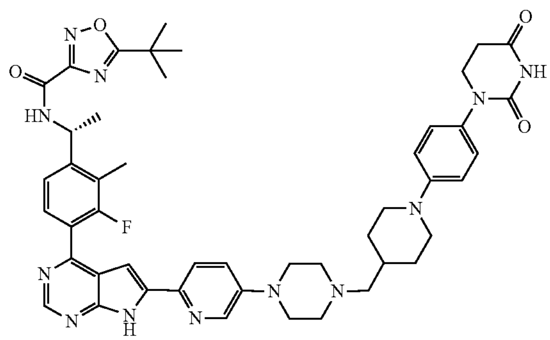 [SMILES: Cc1c([C@@H](C)NC(=O)c2noc(C(C)(C)C)n2)ccc(-c2ncnc3[nH]c(-c4ccc(N5CCN(CC6CCN(c7ccc(N8CCC(=O)NC8=O)cc7)CC6)CC5)cn4)cc23)c1F]

The titled compound was synthesized in the procedures similar to Example 25. $^1$H NMR (400 MHz, DMSO) $\delta_H$ 12.62 (s, 1H), 10.26 (s, 1H), 9.59 (s, 1H), 8.80 (s, 1H), 8.37 (s, 1H), 7.97 (s, 1H), 7.65 (s, 1H), 7.48 (s, 2H), 7.12 (s, 2H), 6.92 (s, 3H), 5.40 (s, 1H), 3.69 (s, 4H), 2.67 (s, 5H), 2.36-2.51 (m, 7H), 2.23 (s, 2H), 1.65-1.84 (m, 3H), 1.53 (s, 3H), 1.43 (s, 9H), 1.23 (s, 2H); [M+H]$^+$=869.7.

Example 128: (R)-5-(tert-butyl)-N-(1-(4-(6-(5-(4-((1-(4-(2,4-dioxotetrahydropyrimidin-1(2H)-yl)-3-methylphenyl)piperidin-4-yl)methyl)piperazin-1-yl)pyridin-2-yl)-7H-pyrrolo[2,3-d]pyrimidin-4-yl)-3-fluoro-2-methylphenyl)ethyl)-1,2,4-oxadiazole-3-carboxamide

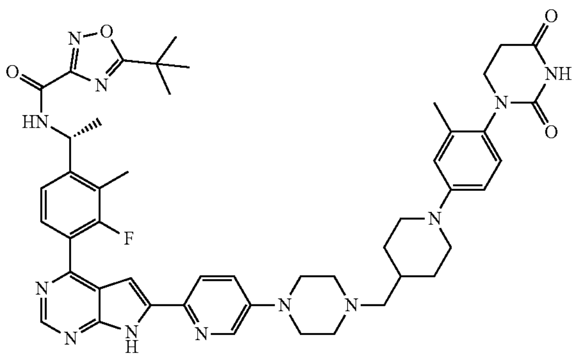 [SMILES: Cc1cc(N2CCC(CN3CCN(c4ccc(-c5cc6c(-c7ccc([C@@H](C)NC(=O)c8noc(C(C)(C)C)n8)c(C)c7F)ncnc6[nH]5)nc4)CC3)CC2)ccc1N1CCC(=O)NC1=O]

The titled compound was synthesized in the procedures similar to Example 25. $^1$H NMR (400 MHz, DMSO) $\delta_H$ 12.62 (s, 1H), 10.25 (s, 1H), 9.60 (d, J=7.7 Hz, 1H), 8.38 (s, 1H), 7.99 (d, J=9.0 Hz, 1H), 7.65 (s, 1H), 7.50-7.39 (m, 2H), 7.09-6.96 (m, 2H), 6.87-6.75 (m, 2H), 5.41 (s, 1H), 3.60-3.75 (m, 3H), 3.48 (s, 1H), 2.60-2.77 (m, 5H), 2.45-2.51 (m, 3H), 2.42 (s, 3H), 2.23 (s, 2H), 2.12 (s, 3H), 1.65-1.84 (m, 3H), 1.53 (d, J=6.5 Hz, 3H), 1.43 (s, 9H), 1.15-1.29 (m, 3H); [M+H]$^+$=883.8.

Example 129: (R)-5-(tert-butyl)-N-(1-(4-(6-(5-(4-((1-(4-(2,4-dioxotetrahydropyrimidin-1(2H)-yl)-3-methylphenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-3-carboxamide

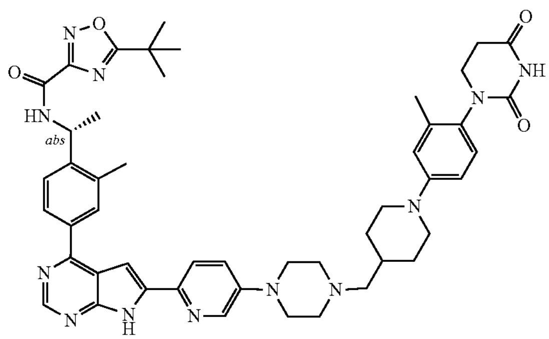 [SMILES: Cc1cc(-c2ncnc3[nH]c(-c4ccc(N5CCN(CC6CCN(c7ccc(N8CCC(=O)NC8=O)c(C)c7)CC6)CC5)cn4)cc23)ccc1[C@@H](C)NC(=O)c1noc(C(C)(C)C)n1]

The titled compound was synthesized in the procedures similar to Example 25. $^1$H NMR (400 MHz, DMSO) $\delta_H$ 12.61 (s, 1H), 10.25 (s, 1H), 9.54 (d, J=7.6 Hz, 1H), 8.39 (s, 1H), 8.11-7.98 (m, 3H), 7.66 (d, J=8.0 Hz, 1H), 7.46 (d, J=7.6 Hz, 1H), 7.40 (s, 1H), 7.04 (d, J=8.8 Hz, 1H), 6.85-6.74 (m, 2H), 5.46-5.33 (m, 1H), 3.81-3.42 (m, 6H), 3.08-2.53 (m, 14H), 2.24 (s, 2H), 2.12 (s, 3H), 1.89-1.68 (m, 3H), 1.53 (d, J=6.0 Hz, 3H), 1.43 (s, 9H), 1.31-1.16 (m, 2H); [M+H]$^+$=865.8.

Example 130: (R)-5-(tert-butyl)-N-(1-(4-(6-(5-(4-((1-(4-(2,4-dioxotetrahydropyrimidin-1(2H)-yl)-3-methylphenyl)piperidin-4-yl)methyl)piperazin-1-yl)pyridin-2-yl)-7H-pyrrolo[2,3-d]pyrimidin-4-yl)-5-fluoro-2-methylphenyl)ethyl)-1,2,4-oxadiazole-3-carboxamide

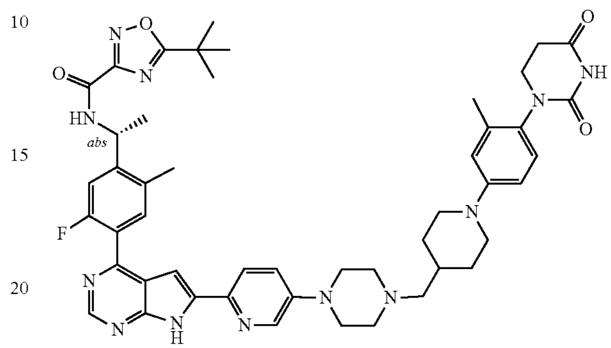

The titled compound was synthesized in the procedures similar to Example 25. $^1$H NMR (400 MHz, DMSO) $\delta_H$ 12.63 (s, 1H), 10.25 (s, 1H), 9.57 (d, J=7.6 Hz, 1H), 8.37 (s, 1H), 7.98 (d, J=8.4 Hz, 1H), 7.64 (d, J=7.2 Hz, 1H), 7.49 (d, J=11.8 Hz, 1H), 7.42 (d, J=8.4 Hz, 1H), 7.04 (d, J=8.4 Hz, 1H), 6.98 (s, 1H), 6.82 (s, 1H), 6.77 (d, J=8.6 Hz, 1H), 5.42-5.31 (m, 1H), 3.76-3.41 (m, 6H), 3.08-2.53 (m, 11H), 2.46 (s, 3H), 2.23 (s, 2H), 2.12 (s, 3H), 1.88-1.65 (m, 3H), 1.53 (d, J=6.2 Hz, 3H), 1.44 (s, 9H), 1.25-1.19 (m, 2H); [M+H]$^+$=883.7.

Example 131: (R)-5-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-5-fluoro-2-methylphenyl)ethyl)-1,2,4-oxadiazole-3-carboxamide

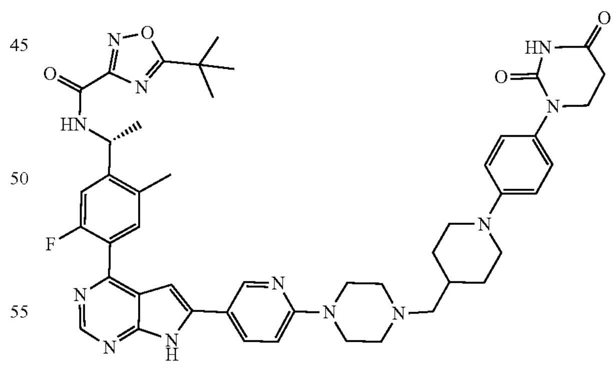

The titled compound was synthesized in the procedures similar to Example 25. $^1$H NMR (400 MHz, DMSO) $\delta_H$ 12.62 (s, 1H), 10.27 (s, 1H), 9.59 (d, J=7.6 Hz, 1H), 8.77 (s, 1H), 8.12 (d, J=8.4 Hz, 1H), 7.63 (d, J=7.6 Hz, 1H), 7.49 (d, J=11.2 Hz, 1H), 7.13 (d, J=8.4 Hz, 2H), 6.99-6.88 (m, 3H), 6.84 (s, 1H), 5.43-5.26 (m, 1H), 3.72-3.64 (m, 4H), 3.63-3.47 (m, 4H), 2.73-2.62 (m, 4H), 2.47-2.41 (m, 6H), 2.26-2.14 (m, 2H), 1.86-1.67 (m, 5H), 1.57-1.48 (m, 3H), 1.44 (s, 9H), 1.28-1.15 (m, 2H); [M+H]$^+$=869.7.

Example 132: (R)-5-(tert-butyl)-N-(1-(4-(6-(6-(4-((1-(4-(2,4-dioxotetrahydropyrimidin-1(2H)-yl)-3-methylphenyl)piperidin-4-yl)methyl)piperazin-1-yl)pyridin-3-yl)-7H-pyrrolo[2,3-d]pyrimidin-4-yl)-5-fluoro-2-methylphenyl)ethyl)-1,2,4-oxadiazole-3-carboxamide

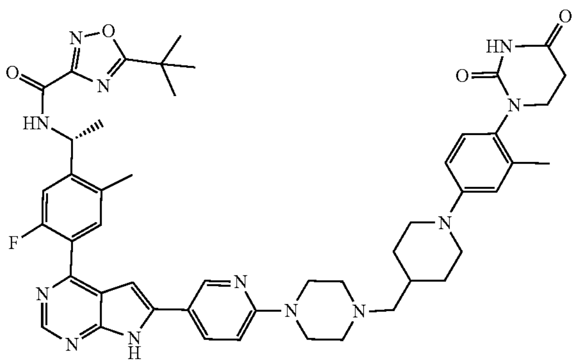 [SMILES: Cc1cc(-c2ncnc3[nH]c(-c4ccc(N5CCN(CC6CCN(c7ccc(N8CCC(=O)NC8=O)c(C)c7)CC6)CC5)nc4)cc23)c(F)cc1[C@@H](C)NC(=O)c1noc(C(C)(C)C)n1]

The titled compound was synthesized in the procedures similar to Example 25, $^1$H NMR (400 MHz, DMSO) $\delta_H$ 12.62 (s, 1H), 10.25 (s, 1H), 9.58 (d, J=8.0 Hz, 1H), 8.77 (s, 1H), 8.12 (d, J=8.4 Hz, 1H), 7.63 (d, J=7.6 Hz, 1H), 7.48 (d, J=12.0 Hz, 1H), 7.04 (d, J=8.4 Hz, 1H), 6.92 (d, J=8.8 Hz, 1H), 6.86-6.80 (m, 2H), 6.78 (d, J=8.4 Hz, 1H), 5.50-5.31 (m, 1H), 3.80-3.62 (m, 4H), 3.61-3.55 (m, 4H), 2.74-2.62 (m, 4H), 2.47-2.43 (m, 6H), 2.25-2.16 (m, 2H), 2.12 (s, 3H), 1.84-1.71 (m, 5H), 1.55-1.50 (m, 3H), 1.44 (s, 9H), 1.27-1.17 (m, 2H); [M+H]$^+$=883.8.

Example 133: (R)-5-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-3-carboxamide

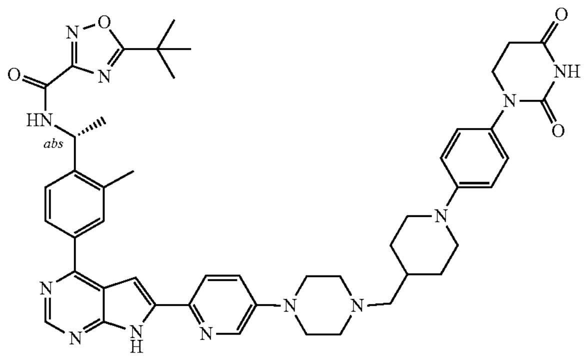 [SMILES: Cc1cc(-c2ncnc3[nH]c(-c4ccc(N5CCN(CC6CCN(c7ccc(N8CCC(=O)NC8=O)cc7)CC6)CC5)cn4)cc23)ccc1[C@@H](C)NC(=O)c1noc(C(C)(C)C)n1]

The titled compound was synthesized in the procedures similar to Example 25. $^1$H NMR (400 MHz, DMSO) $\delta_H$ 12.61 (s, 1H), 10.25 (s, 1H), 9.54 (d, J=7.6 Hz, 1H), 8.39 (s, 1H), 8.11-7.98 (m, 3H), 7.66 (d, J=8.0 Hz, 1H), 7.46 (d, J=8.0 Hz, 1H), 7.40 (s, 1H), 7.18-7.10 (m, 1H), 6.89-6.96 (m, 1H), 5.46-5.33 (m, 1H), 3.69 (s, 6H), 2.76-2.53 (m, 14H), 2.24 (s, 2H), 1.89-1.68 (m, 5H), 1.53 (d, J=6.0 Hz, 3H), 1.43 (s, 9H), 1.31-1.16 (m, 2H); [M+H]$^+$=851.6.

Example 134: (R)-5-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-5-fluoro-2-methylphenyl)ethyl)-1,2,4-oxadiazole-3-carboxamide

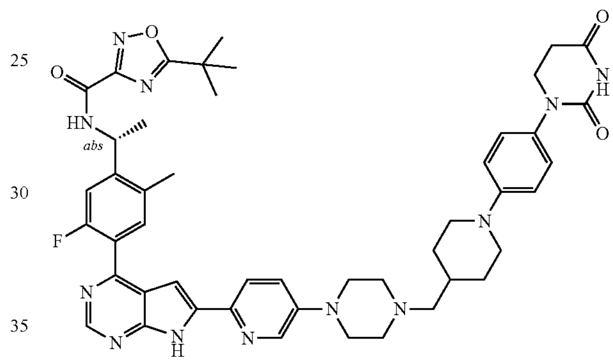

The titled compound was synthesized in the procedures similar to Example 25. $^1$H NMR (400 MHz, DMSO) $\delta_H$ 12.62 (s, 1H), 10.26 (s, 1H), 9.56 (d, J=7.6 Hz, 1H), 8.37 (s, 1H), 7.98 (d, J=8.4 Hz, 1H), 7.64 (d, J=7.2 Hz, 1H), 7.49 (d, J=11.8 Hz, 1H), 7.42 (d, J=7.0 Hz, 1H), 7.13 (d, J=8.2 Hz, 2H), 7.01-6.89 (m, 3H), 5.41-5.31 (m, 1H), 3.77-3.63 (m, 5H), 2.74-2.53 (m, 12H), 2.46 (s, 3H), 2.23 (d, J=4.6 Hz, 2H), 1.88-1.66 (m, 3H), 1.53 (d, J=6.4 Hz, 3H), 1.44 (s, 9H), 1.26-1.21 (m, 2H); [M+H]$^+$=869.6.

Example 135: (R)-3-(tert-butyl)-N-(1-(1-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)piperidin-4-yl)ethyl)-1,2,4-oxadiazole-5-carboxamide

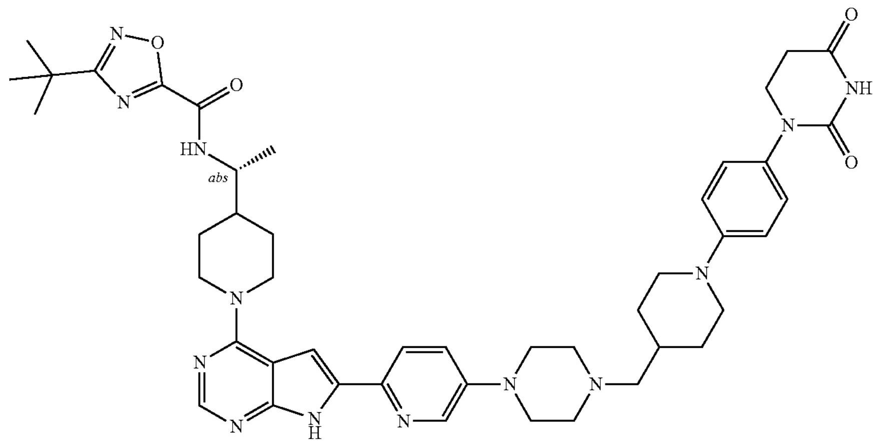 [SMILES: C[C@@H](NC(=O)c1nc(C(C)(C)C)no1)C1CCN(c2ncnc3[nH]c(-c4ccc(N5CCN(CC6CCN(c7ccc(N8CCC(=O)NC8=O)cc7)CC6)CC5)cn4)cc23)CC1]

The titled compound was synthesized in the procedures similar to Example 25. $^1$H NMR (500 MHz, DMSO) $\delta_H$ 12.06 (s, 1H), 10.25 (s, 1H), 9.22 (d, J=8.0 Hz, 1H), 8.66 (s, 1H), 8.12 (s, 1H), 8.03 (d, J=8.0 Hz, 1H), 7.20-6.78 (m, 6H), 4.86-4.65 (m, 2H), 3.90-3.77 (m, 1H), 3.75-3.64 (m, 4H), 3.54 (s, 3H), 3.29-3.23 (m, 1H), 3.11 (s, 1H), 3.00 (dd, J=24.0, 12.0 Hz, 2H), 2.75-2.61 (m, 4H), 2.46 (s, 4H), 2.21 (s, 1H), 1.90-1.62 (m, 6H), 1.36 (s, 9H), 1.27-1.22 (m, 2H), 1.22-1.16 (m, 4H); $[M+H]^+$=844.6.

Example 136: (R)-5-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-(hydroxymethyl)phenyl)ethyl)-1,2,4-oxadiazole-3-carboxamide

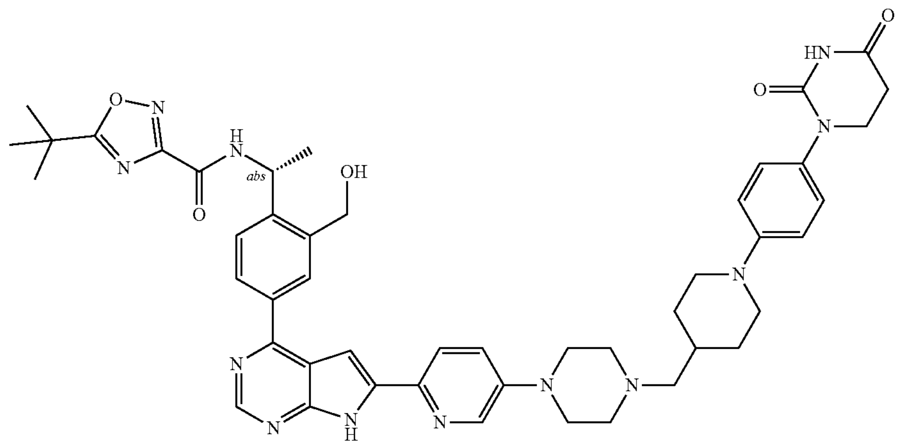 [SMILES: C[C@@H](NC(=O)c1noc(C(C)(C)C)n1)c1ccc(-c2ncnc3[nH]c(-c4ccc(N5CCN(CC6CCN(c7ccc(N8CCC(=O)NC8=O)cc7)CC6)CC5)cn4)cc23)cc1CO]

The titled compound was synthesized in the procedures similar to Example 25. $^1$H NMR (400 MHz, DMSO) $\delta_H$ 12.62 (s, 1H), 10.26 (s, 1H), 9.57 (d, J=8.0 Hz, 1H), 8.79 (s, 1H), 8.40 (s, 1H), 8.27 (s, 1H), 8.13 (d, J=8.0 Hz, 1H), 8.02 (d, J=8.0 Hz, 1H), 7.72 (d, J=8.0 Hz, 1H), 7.47 (d, J=8.0 Hz, 1H), 7.41 (s, 1H), 7.13 (d, J=8.0 Hz, 2H), 6.93 (d, J=8.0 Hz, 2H), 5.45-5.33 (m, 2H), 4.95-4.65 (m, 2H), 3.76-3.64 (m, 6H), 2.75-2.61 (m, 6H), 2.54 (s, 4H), 2.24 (s, 3H), 1.82 (d, J=12.0 Hz, 2H), 1.73 (s, 1H), 1.55 (d, J=8.0 Hz, 3H), 1.42 (s, 9H); $[M+H]^+$=867.7.

Example 137: (R)-5-(tert-butyl)-N-(1-(4-(6-(5-(4-((1-(4-(2,4-dioxotetrahydropyrimidin-1(2H)-yl)-3-methylphenyl)piperidin-4-yl)methyl)piperazin-1-yl)pyridin-2-yl)-7H-pyrrolo[2,3-d]pyrimidin-4-yl)-2-(hydroxymethyl)phenyl)ethyl)-1,2,4-oxadiazole-3-carboxamide

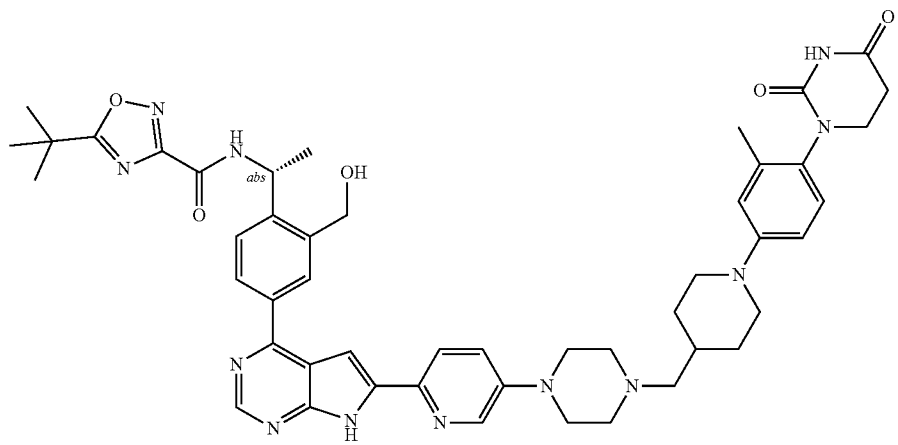 [SMILES: Cc1cc(N2CCC(CN3CCN(c4ccc(-c5cc6c(-c7ccc([C@@H](C)NC(=O)c8noc(C(C)(C)C)n8)c(CO)c7)ncnc6[nH]5)nc4)CC3)CC2)ccc1N1CCC(=O)NC1=O]

The titled compound was synthesized in the procedures similar to Example 25. $^1$H NMR (400 MHz, DMSO) $\delta_H$ 12.62 (s, 1H), 10.24 (s, 1H), 9.56 (d, J=8.0 Hz, 1H), 8.79 (s, 1H), 8.40 (s, 1H), 8.27 (s, 1H), 8.13 (d, J=8.0 Hz, 1H), 8.02 (d, J=8.0 Hz, 1H), 7.72 (d, J=8.0 Hz, 1H), 7.46 (d, J=8.0 Hz, 1H), 7.41 (s, 1H), 7.04 (d, J=8.0 Hz, 1H), 6.82 (s, 1H), 6.78 (d, J=8.0 Hz, 1H), 5.46-5.36 (m, 2H), 4.95-4.75 (m, 2H), 3.75-3.62 (m, 3H), 3.52-3.42 (m, 2H), 2.80-2.61 (m, 5H), 2.54 (s, 4H), 2.24 (s, 2H), 2.12 (s, 3H), 1.81 (d, J=12.0 Hz, 2H), 1.73 (s, 1H), 1.55 (d, J=8.0 Hz, 3H), 1.42 (s, 9H), 1.30-1.18 (m, 5H); $[M+H]^+$=881.9.

Example 138: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-2-(hydroxymethyl)phenyl)ethyl)-1,2,4-oxadiazole-5-carboxamide

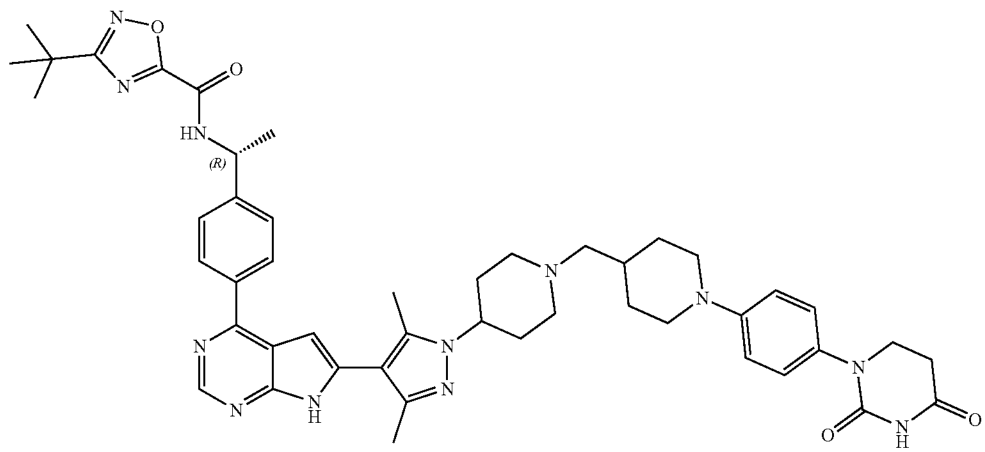

The titled compound was synthesized in the procedures similar to Example 25. $^1$H NMR (400 MHz, DMSO) $\delta_H$ 12.15 (s, 1H), 10.27 (s, 1H), 9.97 (d, J=8.0 Hz, 1H), 8.79 (s, 1H), 8.25 (s, 1H), 8.11 (d, J=8.0 Hz, 1H), 7.72 (d, J=8.0 Hz, 1H), 7.14 (d, J=8.0 Hz, 2H), 6.94 (d, J=8.0 Hz, 2H), 6.76 (s, 1H), 5.41-5.36 (m, 2H), 4.87-4.73 (m, 2H), 4.15 (s, 1H), 3.71-3.68 (m, 4H), 2.96 (s, 2H), 2.70-2.64 (m, 4H), 2.37 (s, 3H), 2.27-2.09 (m, 8H), 1.81-1.77 (m, 4H), 1.69 (s, 1H), 1.56 (d, J=8.0 Hz, 3H), 1.36 (s, 9H), 1.24-1.19 (m, 3H); $[M+H]^+$=883.7.

Example 139: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-5-fluoro-2-(hydroxymethyl)phenyl)ethyl)-1,2,4-oxadiazole-5-carboxamide To a mixture of tert-butyl 4-(5-(4-chloro-7H-pyrrolo[2,3-d]pyrimidin-6-yl)pyridin-2-yl)piperazine-1-carboxylate (2.05 g, 5.0 mmol) in DMF (25 mL) was added NaH (0.24 g of a 60% dispersion in mineral oil, 6.0 mmol). The mixture was stirred at 0° C. for 60 min. Then SEM-$C_1$ (1.02 g, 6.0 mmol) was added. LCMS showed the reaction was completed. The reaction was quenched with 10% aqueous NaCl (10 mL). The resulting suspension was sonicated for 5 minutes, filtered and concentrated in vacuo to afford the product (2.97 g, crude), which was used for next step without further purification. $[M+H]^+$=545.8.

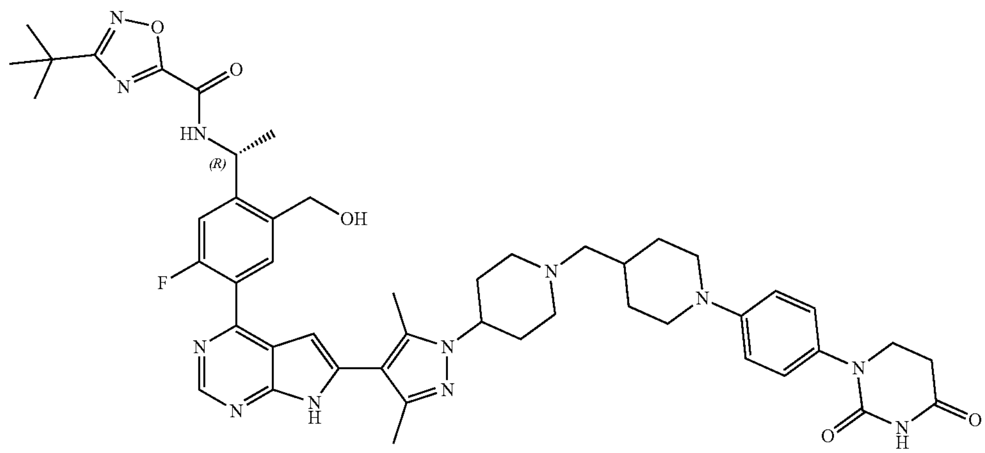

The titled compound was synthesized in the procedures similar to Example 25. $^1$H NMR (400 MHz, DMSO) $\delta_H$ 12.15 (s, 1H), 10.26 (s, 1H), 9.93 (d, J=8.0 Hz, 1H), 8.82 (s, 1H), 7.88 (d, J=8.0 Hz, 1H), 7.56 (d, J=8.0 Hz, 1H), 7.13 (d, J=8.0 Hz, 2H), 6.93 (d, J=8.0 Hz, 2H), 6.35 (s, 1H), 5.41-5.37 (m, 2H), 4.79-4.67 (m, 2H), 4.14 (s, 1H), 3.70-3.68 (m, 4H), 2.97 (s, 2H), 2.68-2.64 (m, 4H), 2.34 (s, 3H), 2.25-2.20 (m, 4H), 2.09-2.03 (m, 4H), 1.81-1.77 (m, 4H), 1.69 (s, 1H), 1.57 (d, J=8.0 Hz, 3H), 1.37 (s, 9H), 1.24-1.19 (m, 3H); $[M+H]^+$=901.7.

Example 140: (R)-5-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-3-fluoro-2-methylphenyl)ethyl)-1,2,4-oxadiazole-3-carboxamide Step 1: tert-butyl 4-(5-(4-chloro-7-((2-(trimethylsilyl)ethoxy)methyl)-7H-pyrrolo[2,3-d]pyrimidin-6-yl)pyridin-2-yl)piperazine-1-carboxylate

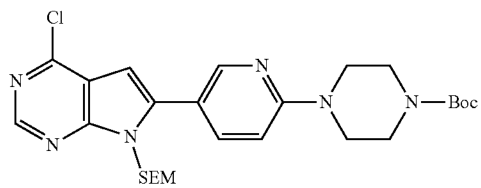 [SMILES: CC(C)(C)OC(=O)N1CCN(c2ccc(-c3cc4c(Cl)ncnc4n3COCC[Si](C)(C)C)cn2)CC1]

Step 2: tert-butyl (R)-4-(5-(4-(4-(1-(5-(tert-butyl)-1,2,4-oxadiazole-3-carboxamido)ethyl)-2-fluoro-3-methylphenyl)-7-((2-(trimethylsilyl)ethoxy)methyl)-7H-pyrrolo[2,3-d]pyrimidin-6-yl)pyridin-2-yl)piperazine-1-carboxylate

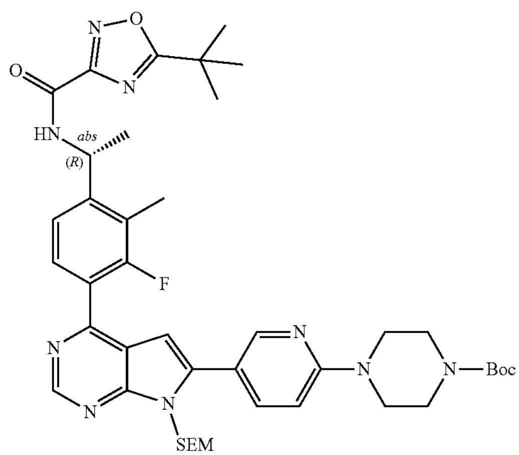

A mixture of tert-butyl 4-(5-(4-chloro-7-((2-(trimethylsilyl)ethoxy)methyl)-7H-pyrrolo[2,3-d]pyrimidin-6-yl)pyridin-2-yl)piperazine-1-carboxylate (147 mg, 0.27 mmol), (R)-5-(tert-butyl)-N-(1-(3-fluoro-2-methyl-4-(4,4,5,5-tetramethyl-1,3,2-dioxaborolan-2-yl)phenyl)ethyl)-1,2,4-oxadiazole-3-carboxamide (120 mg, 0.27 mmol), $Pd(dppf)Cl_2$ (20 mg, 0.027 mmol) and $Cs_2CO_3$ (270 mg, 0.81 mmol) in 1,4-dioxane (10 mL) and $H_2O$ (2 mL) was stirred in a round bottom flask at 100° C. overnight. The mixture was evaporated in vacuum to afford the crude product, which was further purified with silica gel column chromatography (PE:EtOAc=100:1~1:2 gradient elution) to give the product (138 mg, 62%). $[M+H]^+$=814.7.

Step 3: (R)-5-(tert-butyl)-N-(1-(3-fluoro-2-methyl-4-(6-(6-(piperazin-1-yl)pyridin-3-yl)-7H-pyrrolo[2,3-d]pyrimidin-4-yl)phenyl)ethyl)-1,2,4-oxadiazole-3-carboxamide

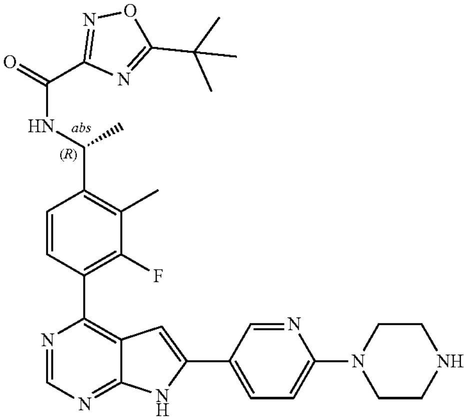

A mixture of tert-butyl (R)-4-(5-(4-(4-(1-(5-(tert-butyl)-1,2,4-oxadiazole-3-carboxamido)ethyl)-2-fluoro-3-methylphenyl)-7-((2-(trimethylsilyl)ethoxy)methyl)-7H-pyrrolo[2,3-d]pyrimidin-6-yl)pyridin-2-yl)piperazine-1-carboxylate (138 mg, 0.17 mmol) and trifluoroacetic acid (16 mL) in dichloromethane (5 mL) was stirred in a round bottom flask at room temperature for 3 hours. The mixture was evaporated in vacuum. The residue was dissolved in MeOH (10 mL) and $NH_3/H_2O$ (2 mL) was added. The mixture was stirred at room temperature for 30 min. LCMS showed the reaction was completed. The mixture was evaporated in vacuum to afford the product (415 mg, crude), which was used for next step without further purification. $[M+H]^+$=584.4.

Step 4: (R)-5-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-3-fluoro-2-methylphenyl)ethyl)-1,2,4-oxadiazole-3-carboxamide

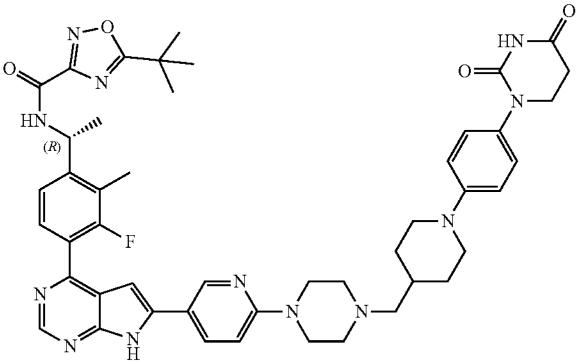

A mixture of (R)-5-(tert-butyl)-N-(1-(3-fluoro-2-methyl-4-(6-(6-(piperazin-1-yl)pyridin-3-yl)-7H-pyrrolo[2,3-d]pyrimidin-4-yl)phenyl)ethyl)-1,2,4-oxadiazole-3-carboxamide (207 mg, crude) and 1-(4-(2,4-dioxotetrahydropyrimidin-1(2H)-yl)phenyl)piperidine-4-carbaldehyde (40 mg, 0.14 mmol) in DCM (10 mL) and MeOH (2 mL) was stirred in a round bottom flask at room temperature for 2 hours. To the mixture was added $NaBH(OAc)_3$ (212 mg, 1.0 mmol) and stirred in a round bottom flask at room temperature overnight. Then the mixture was purified with Pre-TLC (DCM:MeOH=7:1) to give the product (40 mg, 57%). $^1H$ NMR (400 MHz, DMSO) $\delta_H$ 12.64 (s, 1H), 10.27 (s, 1H), 9.62 (d, J=7.6 Hz, 1H), 8.76 (s, 1H), 8.14 (d, J=8.4 Hz, 1H), 7.74-7.57 (m, 1H), 7.48 (d, J=8.0 Hz, 1H), 7.13 (d, J=8.8 Hz, 2H), 7.03-6.88 (m, 3H), 6.84 (s, 1H), 5.48-5.32 (m, 1H), 3.73-3.65 (m, 4H), 3.62-3.54 (m, 4H), 2.71-2.61 (m, 4H), 2.48-2.43 (m, 4H), 2.41 (s, 3H), 2.26-2.16 (m, 2H), 1.89-1.67 (m, 4H), 1.56-1.50 (m, 3H), 1.43 (s, 9H), 1.28-1.18 (m, 2H); $[M+H]^+$=869.8.

Example 141: (R)-5-(tert-butyl)-N-(1-(4-(6-(6-(4-((1-(4-(2,4-dioxotetrahydropyrimidin-1(2H)-yl)-3-methylphenyl)piperidin-4-yl)methyl)piperazin-1-yl)pyridin-3-yl)-7H-pyrrolo[2,3-d]pyrimidin-4-yl)-3-fluoro-2-methylphenyl)ethyl)-1,2,4-oxadiazole-3-carboxamide

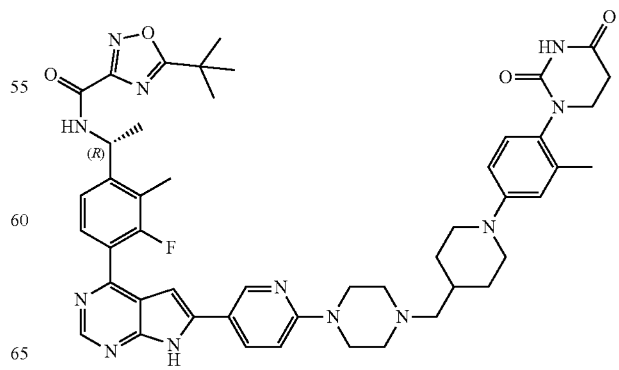

The titled compound was synthesized in the procedures similar to Example 25. $^1$H NMR (400 MHz, DMSO) $\delta_H$ 12.61 (s, 1H), 10.24 (s, 1H), 9.60 (d, J=7.6 Hz, 1H), 8.75 (s, 1H), 8.13 (d, J=7.2 Hz, 1H), 7.64 (t, J=7.2 Hz, 1H), 7.47 (d, J=8.0 Hz, 1H), 7.04 (d, J=8.4 Hz, 1H), 6.92 (d, J=9.2 Hz, 1H), 6.87-6.80 (m, 2H), 6.77 (d, J=8.0 Hz, 1H), 5.53-5.29 (m, 1H), 3.74-3.64 (m, 3H), 3.62-3.53 (m, 4H), 2.75-2.63 (m, 4H), 2.47-2.39 (m, 6H), 2.25-2.17 (m, 2H), 2.12 (s, 3H), 1.90-1.64 (m, 7H), 1.53 (d, J=6.4 Hz, 3H), 1.43 (s, 9H), 1.27-1.17 (m, 2H); [M+H]$^+$=883.8.

Example 142: (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-5-fluoro-7H-pyrrolo[2,3-d]pyrimidin-4-yl)-2-meth ylphenyl)ethyl)-1,2,4-oxadiazole-5-carboxamide

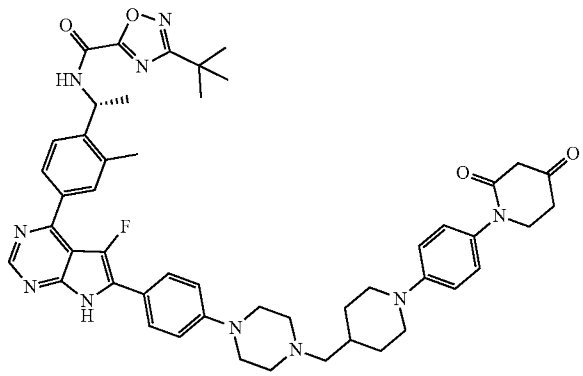 [SMILES: Cc1cc(-c2ncnc3[nH]c(-c4ccc(N5CCN(CC6CCN(c7ccc(N8CCC(=O)CC8=O)cc7)CC6)CC5)cc4)c(F)c23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.60 (s, 1H), 10.26 (s, 1H), 9.92 (d, J=7.9 Hz, 1H), 8.82 (s, 1H), 8.67 (s, 1H), 8.03 (d, J=8.7 Hz, 1H), 7.83 (s, 2H), 7.66 (d, J=8.0 Hz, 1H), 7.13 (d, J=8.8 Hz, 2H), 7.00 (d, J=9.0 Hz, 1H), 6.93 (d, J=8.9 Hz, 2H), 5.43-5.31 (m, 1H), 3.70 (t, J=7.7 Hz, 4H), 3.60 (s, 4H), 2.67 (t, J=11.0 Hz, 4H), 2.50 (s, 3H), 2.46 (s, 4H), 2.22 (d, J=5.7 Hz, 2H), 1.82 (d, J=12.2 Hz, 2H), 1.72 (s, 1H), 1.55 (d, J=6.8 Hz, 3H), 1.37 (s, 9H), 1.23 (d, J=11.3 Hz, 2H); $^{19}$F NMR (376.42 MHz, DMSO) $\delta_F$ −160.30; [M+H]$^+$=869.7.

Example 143: 3-(tert-butyl)-N-((1R)-1-(4-(6-(4-(4-((1-(4-(2,6-dioxopiperidin-3-yl)phenyl)pyrrolidin-3-yl)methyl)piperazin-1-yl)phenyl)-7H-pyrrolo[2,3-d]pyrimidin-4-yl)-2-methylphenyl)ethyl)-1,2,4-oxadiazole-5-carboxamide

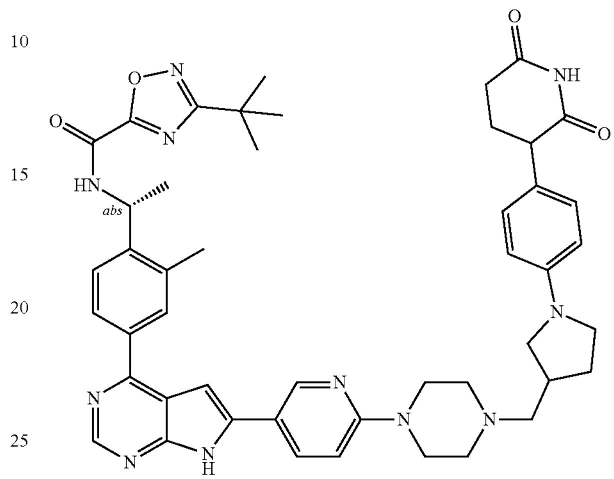

The titled compound was synthesized in the procedures similar to Example 25. $^1$H NMR (400 MHz, DMSO) $\delta_H$ 12.52 (s, 1H), 10.74 (s, 1H), 9.95 (d, J=7.7 Hz, 1H), 8.09 (d, J=8.1 Hz, 1H), 8.04 (s, 1H), 7.92 (d, J=8.3 Hz, 2H), 7.66 (d, J=8.3 Hz, 1H), 7.23 (s, 1H), 7.04-7.01 (m, 4H), 6.49 (d, J=8.5 Hz, 2H), 5.41-5.37 (m, 1H), 3.69-3.65 (m, 1H), 3.3-3.23 (m, 5H), 3.05-2.98 (m, 2H), 2.65-2.58 (m, 4H), 2.53-2.49 (m, 3H), 2.50-2.47 (m, 5H), 2.45-2.40 (m, 2H), 2.15-2.10 (m, 2H), 2.05-1.98 (m, 1H), 1.78-1.72 (m, 1H), 1.55 (d, J=6.6 Hz, 3H), 1.37 (s, 9H); [M+H]$^+$=835.7.

Example 144: (R)-5-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-(hydroxymethyl)phenyl)ethyl)-1,2,4-oxadiazole-3-carboxamide

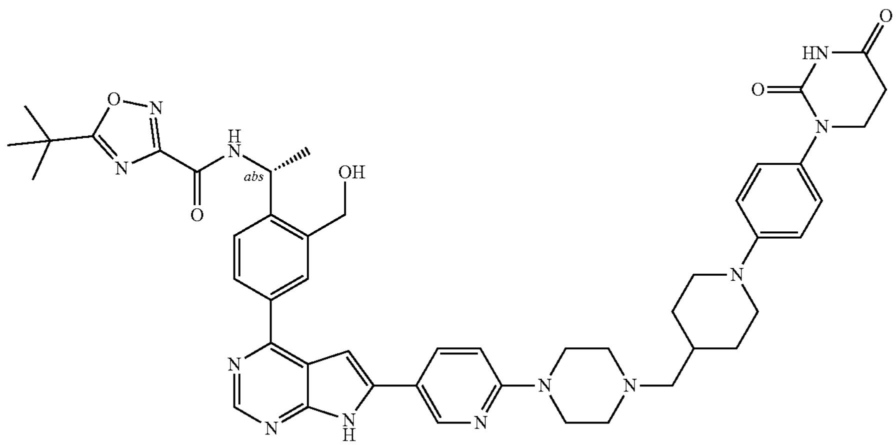 [SMILES: C[C@@H](NC(=O)c1noc(C(C)(C)C)n1)c1ccc(-c2ncnc3[nH]c(-c4ccc(N5CCN(CC6CCN(c7ccc(N8CCC(=O)NC8=O)cc7)CC6)CC5)nc4)cc23)cc1CO]

The titled compound was synthesized in the procedures similar to Example 25. $^1$H NMR (400 MHz, DMSO) $\delta_H$ 12.61 (s, 1H), 10.26 (s, 1H), 9.58 (d, J=8.0 Hz, 1H), 8.79 (d, J=8.0 Hz, 1H), 8.27 (s, 1H), 8.15 (t, J=8.0 Hz, 2H), 7.71 (d, J=8.0 Hz, 1H), 7.28 (s, 1H), 7.13 (d, J=8.0 Hz, 2H), 6.99-6.88 (m, 3H), 5.50-5.27 (m, 2H), 4.91-4.74 (m, 2H), 3.74-3.55 (m, 9H), 3.42 (s, 1H), 2.74-2.61 (m, 5H), 2.47 (s, 4H), 2.22 (d, J=4.0 Hz, 2H), 1.82 (d, J=12.0 Hz, 2H), 1.73 (s, 1H), 1.55 (d, J=8.0 Hz, 3H), 1.42 (s, 9H); [M+H]$^+$=867.8.

Example 145: (R)-5-(tert-butyl)-N-(1-(4-(6-(6-(4-((1-(4-(2,4-dioxotetrahydropyrimidin-1(2H)-yl)-3-methylphenyl)piperidin-4-yl)methyl)piperazin-1-yl)pyridin-3-yl)-7H-pyrrolo[2,3-d]pyrimidin-4-yl)-2-(hydroxymethyl)phenyl)ethyl)-1,2,4-oxadiazole-3-carboxamide

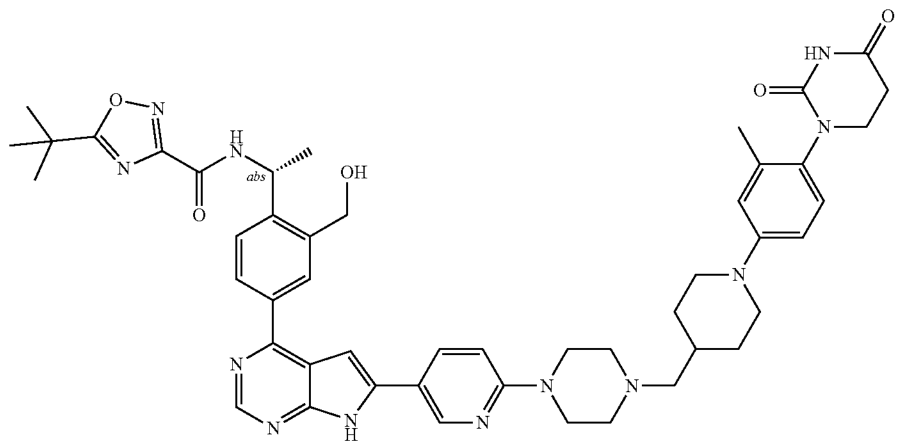

The titled compound was synthesized in the procedures similar to Example 25. $^1$H NMR (400 MHz, DMSO) $\delta_H$ 12.60 (s, 1H), 10.24 (s, 1H), 9.58 (d, J=8.0 Hz, 1H), 8.79 (d, J=8.0 Hz, 1H), 8.27 (s, 1H), 8.15 (t, J=8.0 Hz, 2H), 7.71 (d, J=8.0 Hz, 1H), 7.28 (s, 1H), 7.04 (d, J=8.0 Hz, 1H), 6.96 (d, J=8.0 Hz, 1H), 6.86-6.72 (m, 2H), 5.46-5.23 (m, 2H), 4.95-4.69 (m, 3H), 3.74-3.64 (m, 4H), 3.60 (s, 4H), 3.46 (dd, J=12.0, 6.0 Hz, 3H), 2.74-2.60 (m, 5H), 2.48 (s, 3H), 2.22 (d, J=4.0 Hz, 2H), 2.12 (s, 3H), 1.81 (d, J=8.0 Hz, 2H), 1.75-1.71 (m, 1H), 1.54 (d, J=8.0 Hz, 3H), 1.42 (s, 9H); [M+H]$^+$=881.8.

Example 146: (R)-3-(tert-butyl)-N-(1-(2-methyl-4-(6-(6-(4-((1-(4-(3-methyl-2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)phenyl)ethyl)-1,2,4-oxadiazole-5-carboxamide

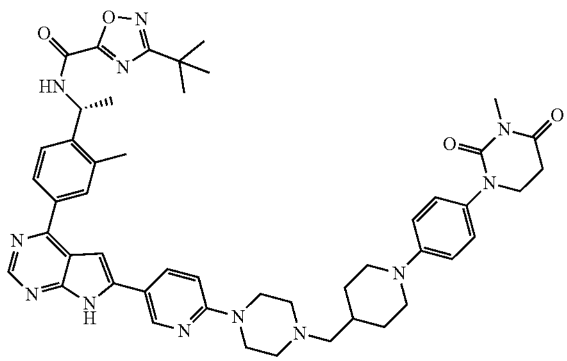 [SMILES: Cc1cc(-c2ncnc3[nH]c(-c4ccc(N5CCN(CC6CCN(c7ccc(N8CCC(=O)N(C)C8=O)cc7)CC6)CC5)nc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.60 (s, 1H), 9.96 (d, J=8.0 Hz, 1H), 8.81 (s, 1H), 8.77 (s, 1H), 8.11-8.09 (m, 1H), 8.05-8.02 (m, 1H), 7.66-7.64 (m, 1H), 7.25 (s, 1H), 7.14 (d, J=8.0 Hz, 2H), 6.96-6.92 (m, 3H), 5.40-5.36 (m, 1H), 3.69-3.66 (m, 4H), 3.62-3.58 (m, 4H), 3.02 (s, 3H), 3.10-3.00 (m, 2H), 2.75-2.70 (m, 4H), 2.52-2.50 (m, 4H), 2.25-2.20 (m, 4H), 2.03-1.97 (m, 1H), 1.86-1.84 (m, 2H), 1.84-1.82 (m, 2H), 1.55 (d, J=6.6 Hz, 3H), 1.37 (s, 9H); [M+H]$^+$=865.8.

Example 147: (S)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

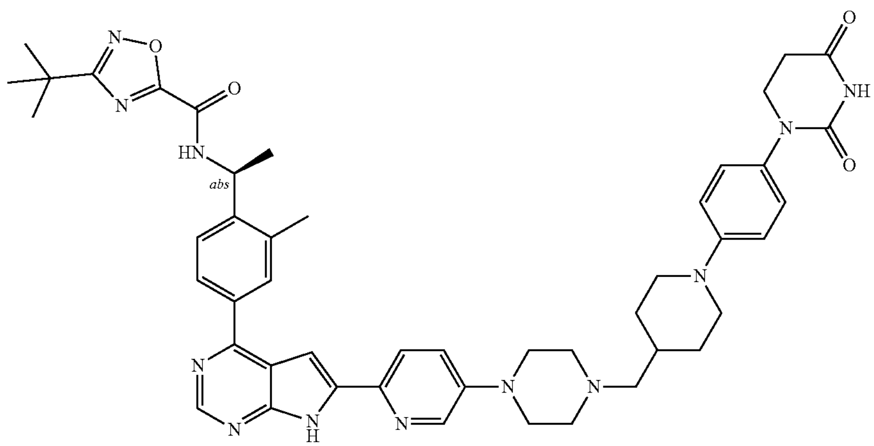

The titled compound was synthesized in the procedures similar to Example 25. $^1$H NMR (400 MHz, DMSO) $\delta_H$ 12.60 (s, 1H), 10.25 (s, 1H), 9.94 (d, J=8.0 Hz, 1H), 8.79 (s, 1H), 8.39 (s, 1H), 8.13-7.96 (m, 3H), 7.68 (d, J=8.0 Hz, 1H), 7.54-7.34 (m, 2H), 7.13 (d, J=8.0 Hz, 2H), 6.93 (d, J=8.0 Hz, 2H), 5.45-5.33 (m, 1H), 3.75-3.63 (m, 4H), 2.73-2.60 (m, 5H), 2.53 (s, 6H), 2.51 (d, J=4.0 Hz, 3H), 2.24 (d, J=4.0 Hz, 2H), 1.81 (d, J=12.0 Hz, 2H), 1.72 (s, 1H), 1.56 (d, J=4.0 Hz, 3H), 1.37 (s, 9H), 1.29-1.17 (m, 3H); [M+H]$^+$=851.7.

Example 148: (S)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide

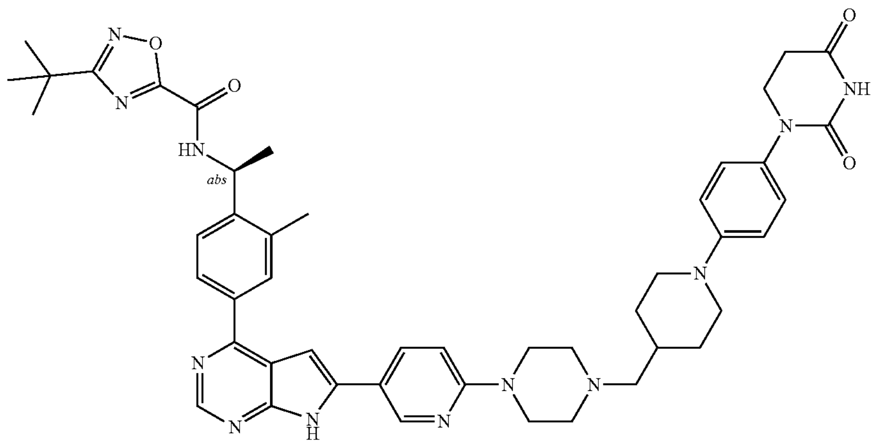 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@H](C)NC(=O)c1nc(C(C)(C)C)no1]

The titled compound was synthesized in the procedures similar to Example 25. $^1$H NMR (400 MHz, DMSO) $\delta_H$ 12.58 (s, 1H), 10.25 (s, 1H), 9.98-9.90 (m, 1H), 8.93-8.65 (m, 2H), 8.22-8.13 (m, 1H), 8.12-8.00 (m, 2H), 7.71-7.61 (m, 1H), 7.29 (s, 1H), 7.17-7.09 (m, 2H), 7.00-6.88 (m, 3H), 5.38 (s, 1H), 3.75-3.50 (m, 9H), 2.67 (s, 5H), 2.55-2.52 (m, 3H), 2.47-2.42 (m, 2H), 2.22 (s, 2H), 1.82 (d, J=12.0 Hz, 2H), 1.73 (s, 1H), 1.58-1.51 (m, 3H), 1.37 (s, 9H), 1.29-1.17 (m, 3H); [M+H]$^+$=851.8.

Example 149: (R)-5-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-5-fluoro-2-(hydroxymethyl)phenyl)ethyl)-1,2,4-oxadiazole-3-carboxamide

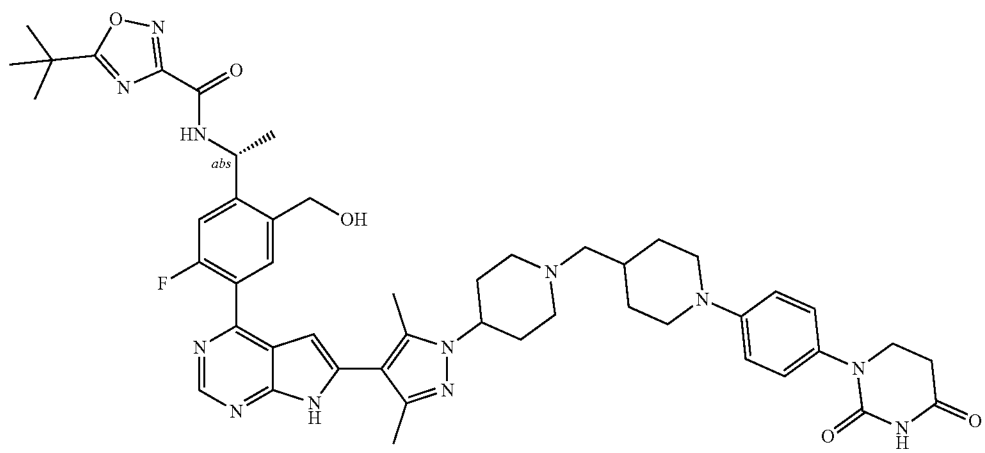 [SMILES: Cc1nn(C2CCN(CC3CCN(c4ccc(N5CCC(=O)NC5=O)cc4)CC3)CC2)c(C)c1-c1cc2c(-c3cc(CO)c([C@@H](C)NC(=O)c4noc(C(C)(C)C)n4)cc3F)ncnc2[nH]1]

The titled compound was synthesized in the procedures similar to Example 25. $^1$H NMR (400 MHz, DMSO) $\delta_H$ 12.14 (s, 1H), 10.25 (s, 1H), 9.55 (d, J=8.0 Hz, 1H), 8.82 (s, 1H), 7.89 (d, J=8.0 Hz, 1H), 7.53 (d, J=8.0 Hz, 1H), 7.13 (d, J=8.0 Hz, 2H), 6.93 (d, J=8.0 Hz, 2H), 6.34 (s, 1H), 5.42-5.34 (m, 2H), 4.81-4.67 (m, 2H), 4.14 (s, 1H), 3.70-3.68 (m, 4H), 2.99 (s, 2H), 2.68-2.64 (m, 4H), 2.34 (s, 3H), 2.25-2.20 (m, 4H), 2.09-2.03 (m, 4H), 1.83-1.80 (m, 4H), 1.69 (s, 1H), 1.54 (d, J=8.0 Hz, 3H), 1.43 (s, 9H), 1.27-1.21 (m, 3H); [M+H]$^+$=901.7.

Example 150: (R)-3-(tert-butyl)-N-(5-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2,3-dihydro-1H-inden-1-yl)-1,2,4-oxadiazole-5-carboxamide

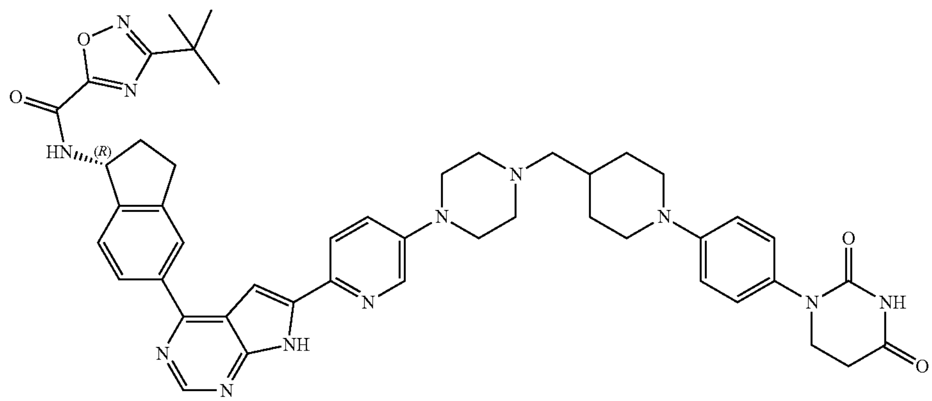

The titled compound was synthesized in the procedures similar to Example 25. $^1$H NMR (400 MHz, DMSO) $\delta_H$ 12.61 (s, 1H), 10.25 (s, 1H), 9.82 (d, J=8.0 Hz, 1H), 8.79 (s, 1H), 8.39 (s, 1H), 8.13-8.02 (m, 3H), 7.48-7.39 (m, 3H), 7.13 (d, J=8.0 Hz, 2H), 6.93 (d, J=8.0 Hz, 2H), 5.63-5.61 (m, 1H), 3.69-3.68 (m, 4H), 3.23-3.17 (m, 1H), 3.05-2.95 (m, 1H), 2.70-2.64 (m, 4H), 2.55-2.53 (m, 8H), 2.24-2.20 (m, 3H), 1.84-1.69 (m, 3H), 1.37 (s, 9H), 1.28-1.19 (m, 3H); $[M+H]^+$=849.7.

Example 151: (R)-3-(tert-butyl)-N-(5-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2,3-dihydro-1H-inden-1-yl)-1,2,4-oxadiazole-5-carboxamide

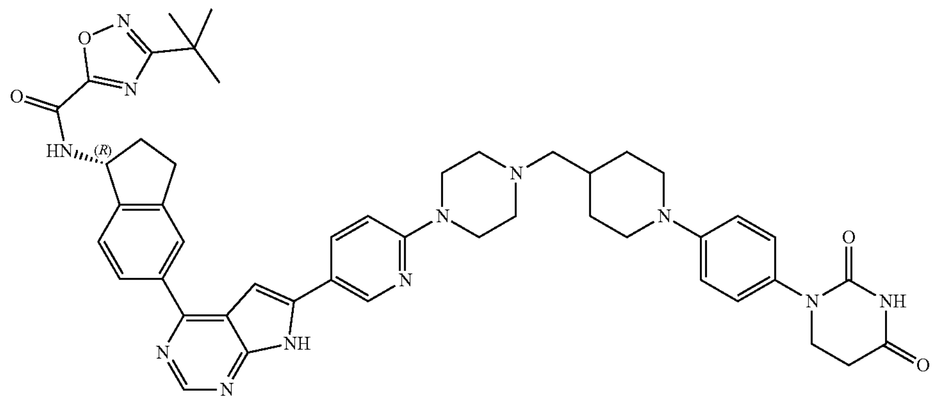

The titled compound was synthesized in the procedures similar to Example 25. $^1$H NMR (400 MHz, DMSO) $\delta_H$ 12.60 (s, 1H), 10.25 (s, 1H), 9.82 (d, J=8.0 Hz, 1H), 8.81 (s, 1H), 8.77 (s, 1H), 8.14-8.10 (m, 3H), 7.47 (d, J=8.0 Hz, 1H), 7.28 (s, 1H), 7.13 (d, J=8.0 Hz, 2H), 6.97-6.91 (m, 3H), 5.62-5.60 (m, 1H), 3.69-3.60 (m, 8H), 3.20-3.17 (m, 1H), 3.00-2.95 (m, 1H), 2.67-2.63 (m, 4H), 2.47-2.44 (m, 4H), 2.23-2.21 (m, 3H), 1.84-1.69 (m, 3H), 1.36 (s, 9H), 1.28-1.19 (m, 3H); $[M+H]^+$=849.7.

Example 152: (R)-3-(tert-butyl)-N-(1-(4-(6-(4-(1-((1-(4-(2,4-dioxotetrahydropyrimidin-1(2H)-yl)phenyl)piperidin-4-yl)methyl)piperidin-4-yl)-3,5-dimethyl-1H-pyrazol-1-yl)-7H-pyrrolo[2,3-d]pyrimidin-4-yl)-2-methylphenyl)ethyl)-1,2,4-oxadiazole-5-carboxamide

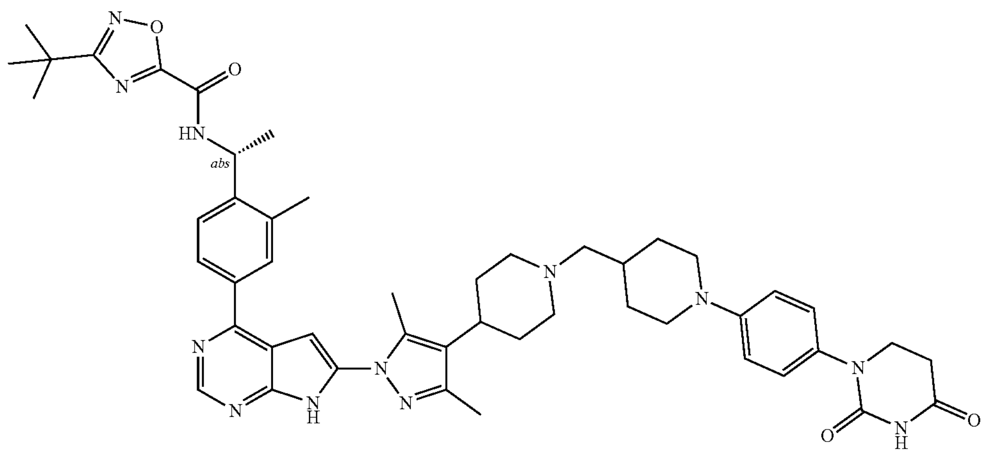 [SMILES: Cc1cc(-c2ncnc3[nH]c(-n4nc(C)c(C5CCN(CC6CCN(c7ccc(N8CCC(=O)NC8=O)cc7)CC6)CC5)c4C)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.68 (s, 1H), 10.26 (s, 1H), 9.86 (d, J=7.6 Hz, 1H), 8.61 (s, 1H), 7.86-7.72 (m, 2H), 7.57 (d, J=8.0 Hz, 1H), 7.36 (d, J=2.0 Hz, 1H), 7.15 (d, J=8.8 Hz, 2H), 6.96 (d, J=8.4 Hz, 2H), 5.42-5.21 (m, 1H), 3.86-3.54 (m, 6H), 3.18-2.87 (m, 5H), 2.80-2.64 (m, 7H), 2.48-2.25 (m, 8H), 2.11-1.80 (m, 5H), 1.51 (d, J=6.8 Hz, 3H), 1.36 (s, 9H); [M+H]$^+$=867.9.

Example 153: 3-(tert-butyl)-N-((1R)-1-(4-(6-(4-(4-(3-(4-(2,6-dioxopiperidin-3-yl)phenyl)cyclobutyl)piperazin-1-yl)phenyl)-7H-pyrrolo[2,3-d]pyrimidin-4-yl)-2-methylphenyl)ethyl)-1,2,4-oxadiazole-5-carboxamide

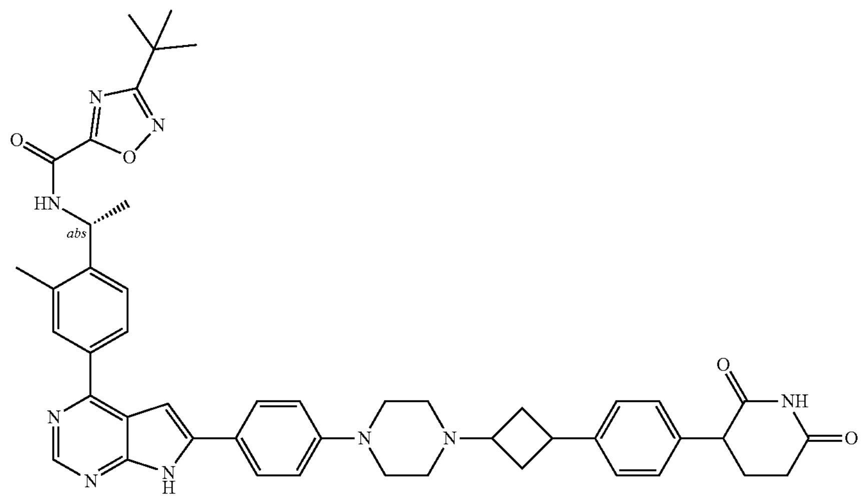 [SMILES: Cc1cc(-c2ncnc3[nH]c(-c4ccc(N5CCN(C6CC(c7ccc(C8CCC(=O)NC8=O)cc7)C6)CC5)cc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.53 (s, 1H), 10.81 (s, 1H), 9.95 (d, J=7.2 Hz, 1H), 8.75 (s, 1H), 8.09 (d, J=7.6 Hz, 1H), 8.03 (s, 1H), 7.92 (d, J=8.4 Hz, 2H), 7.67 (d, J=7.8 Hz, 1H), 7.22-7.14 (m, 5H), 7.03 (d, J=8.4 Hz, 2H), 5.38 (t, J=7.6 Hz, 1H), 3.86-3.78 (m, 1H), 3.26 (s, 4H), 3.20-3.10 (m, 1H), 3.00 (brs, 1H), 2.81-2.59 (m, 3H), 2.53 (s, 3H), 2.46 (s, 4H), 2.25-2.10 (m, 1H), 2.03 (s, 1H), 1.95-1.82 (m, 3H), 1.55 (d, J=6.4 Hz, 3H), 1.37 (s, 9H); [M+H]$^+$=806.8.

Example 154: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-fluorophenyl)ethyl)-1,2,4-oxadiazole-5-carboxamide

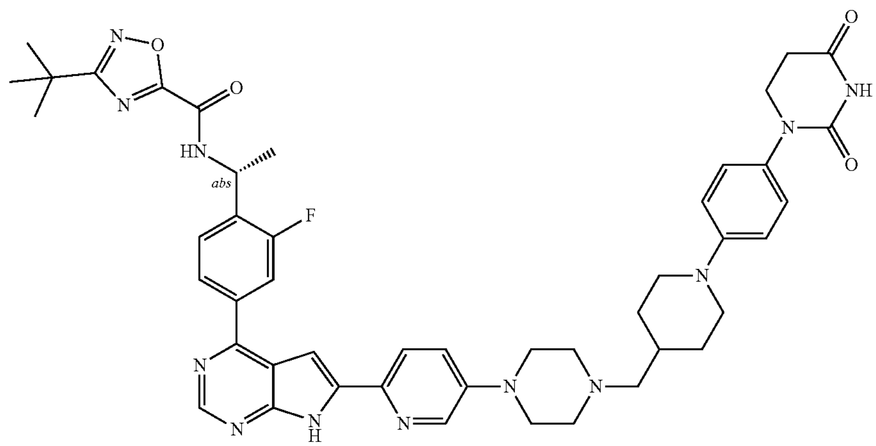 [SMILES: C[C@@H](NC(=O)c1nc(C(C)(C)C)no1)c1ccc(-c2ncnc3[nH]c(-c4ccc(N5CCN(CC6CCN(c7ccc(N8CCC(=O)NC8=O)cc7)CC6)CC5)cn4)cc23)cc1F]

The titled compound was synthesized in the procedures similar to Example 25. $^1$H NMR (400 MHz, DMSO) $\delta_H$ 12.68 (s, 1H), 10.25 (s, 1H), 10.00 (d, J=8.0 Hz, 1H), 8.81 (s, 1H), 8.39 (s, 1H), 8.15-8.04 (m, 2H), 7.98 (d, J=12.0 Hz, 1H), 7.73 (t, J=8.0 Hz, 1H), 7.51-7.42 (m, 2H), 7.13 (d, J=8.0 Hz, 2H), 6.93 (d, J=8.0 Hz, 2H), 5.62-5.42 (m, 1H), 3.81-3.58 (m, 4H), 3.10-2.82 (m, 1H), 2.75-2.62 (m, 4H), 2.54 (s, 6H), 2.24 (s, 2H), 1.82 (d, J=12.0 Hz, 2H), 1.74 (s, 1H), 1.60 (d, J=8.0 Hz, 3H), 1.38 (s, 9H), 1.23 (s, 3H); $[M+H]^+$=855.8.

Example 155: (R)-3-(tert-butyl)-N-(1-(4-(6-(1-(1-((1-(4-(2,4-dioxotetrahydropyrimidin-1(2H)-yl)phenyl)piperidin-4-yl)methyl)piperidin-4-yl)-3,5-dimethyl-1H-pyrazol-4-yl)-7H-pyrrolo[2,3-d]pyrimidin-4-yl)-2-methylphenyl)ethyl)-N-methyl-1,2,4-oxadiazole-5-carboxamide

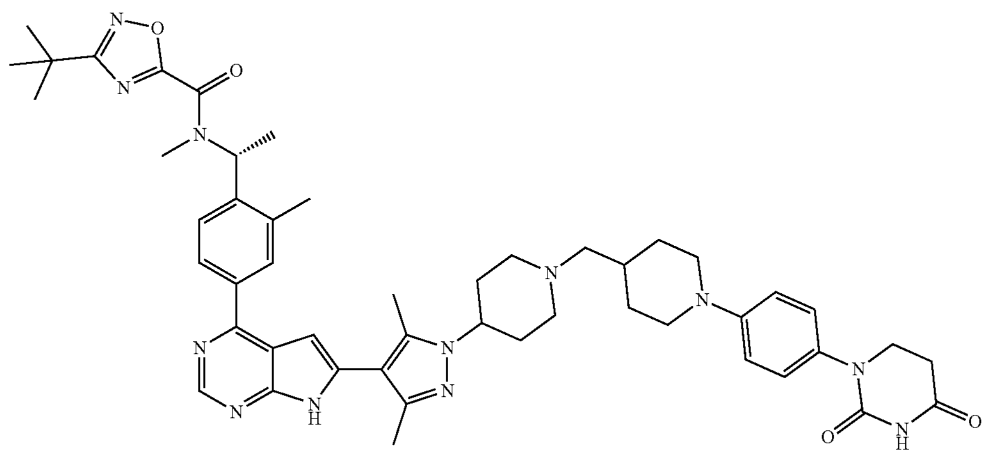 [SMILES: Cc1cc(-c2ncnc3[nH]c(-c4c(C)nn(C5CCN(CC6CCN(c7ccc(N8CCC(=O)NC8=O)cc7)CC6)CC5)c4C)cc23)ccc1[C@@H](C)N(C)C(=O)c1nc(C(C)(C)C)no1]

The titled compound was synthesized in the procedures similar to Example 25. $^1$H NMR (400 MHz, DMSO) $\delta_H$ 12.19 (s, 1H), 10.23 (s, 1H), 8.80 (s, 1H), 8.15-8.01 (m, 2H), 7.73-7.55 (m, 1H), 7.15 (d, J=8.4 Hz, 2H), 6.95 (d, J=8.4 Hz, 2H), 6.83-6.71 (m, 1H), 6.02-5.87 (m, 1H), 3.71 (d, J=6.8 Hz, 4H), 3.21-3.11 (m, 1H), 3.10-2.91 (m, 2H), 2.82-2.78 (m, 1H), 2.76-2.73 (m, 2H), 2.72-2.65 (m, 4H), 2.44-2.32 (m, 6H), 2.32-2.20 (m, 5H), 2.05 (s, 2H), 1.93-1.88 (m, 2H), 1.75-1.68 (m, 1H), 1.66-1.59 (m, 2H), 1.37-1.31 (m, 11H); $[M+H]^+$=881.7.

Example 156: (R)-5-(tert-butyl)-N-(5-(6-(4-(4-((1-(4-(2,4-dioxotetrahydropyrimidin-1(2H)-yl)phenyl)piperidin-4-yl)methyl)piperazin-1-yl)phenyl)-7H-pyrrolo[2,3-d]pyrimidin-4-yl)-2,3-dihydro-1H-inden-1-yl)-1,2,4-oxadiazole-3-carboxamide

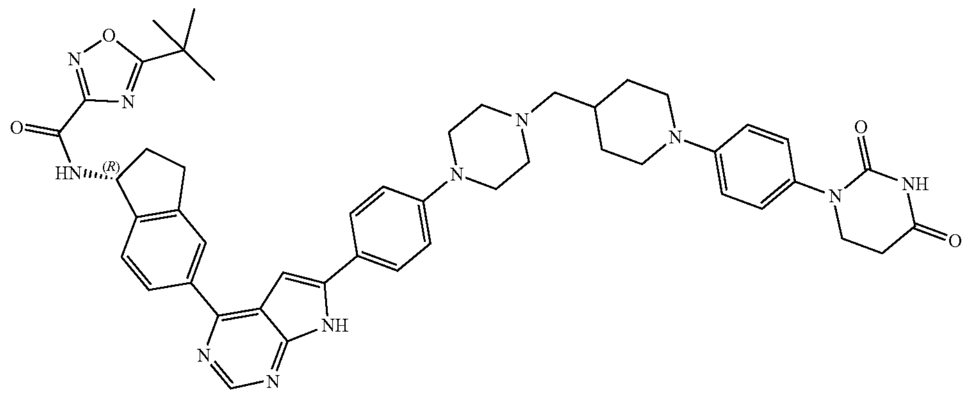

The titled compound was synthesized in the procedures similar to Example 25. $^1$H NMR (400 MHz, DMSO) $\delta_H$ 12.51 (s, 1H), 10.24 (s, 1H), 9.39 (d, J=8.0 Hz, 1H), 8.75 (s, 1H), 8.13-8.10 (m, 2H), 7.90 (d, J=8.0 Hz, 2H), 7.43 (d, J=8.0 Hz, 1H), 7.21 (s, 1H), 7.13 (d, J=8.0 Hz, 2H), 7.04 (d, J=8.0 Hz, 2H), 6.93 (d, J=8.0 Hz, 2H), 5.63-5.61 (m, 1H), 3.71-3.68 (m, 4H), 3.26-3.15 (m, 5H), 3.01-2.97 (m, 1H), 2.69-2.64 (m, 4H), 2.56-2.53 (m, 4H), 2.24-2.15 (m, 3H), 1.84-1.73 (m, 3H), 1.43 (s, 9H), 1.27-1.19 (m, 3H); [M+H]$^+$= 848.8.

Example 157: (R)-3-(tert-butyl)-N-(1-(4-(6-(4-(1-((1-(4-(2,4-dioxotetrahydropyrimidin-1(2H)-yl)phenyl)piperidin-4-yl)methyl)azetidin-3-yl)phenyl)-7H-pyrrolo[2,3-d]pyrimidin-4-yl)-2-methylphenyl)ethyl)-1,2,4-oxadiazole-5-carboxamide

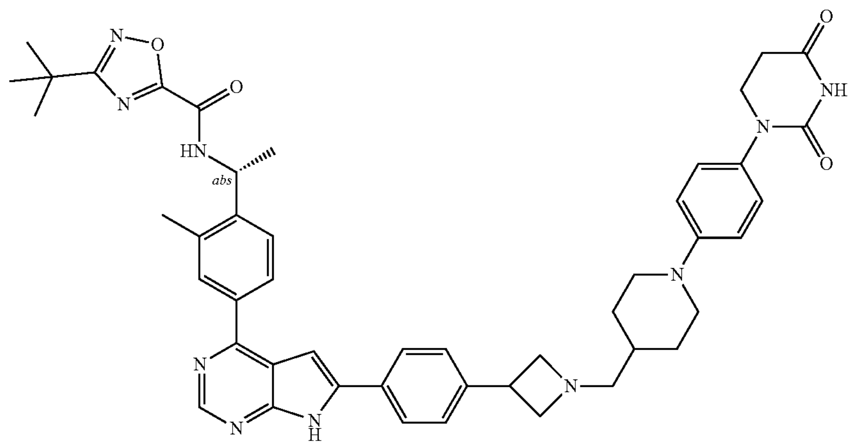 [SMILES: Cc1cc(-c2ncnc3[nH]c(-c4ccc(C5CN(CC6CCN(c7ccc(N8CCC(=O)NC8=O)cc7)CC6)C5)cc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.70 (s, 1H), 10.26 (s, 1H), 9.97 (d, J=7.6 Hz, 1H), 8.81 (s, 1H), 8.13-7.99 (m, 4H), 7.68 (d, J=8.2 Hz, 1H), 7.48 (d, J=7.2 Hz, 2H), 7.40 (s, 1H), 7.13 (d, J=8.8 Hz, 2H), 6.93 (d, J=8.8 Hz, 2H), 5.44-5.33 (m, 1H), 3.74-3.59 (m, 6H), 2.72-2.53 (m, 11H), 2.38 (s, 2H), 1.79 (d, J=12.0 Hz, 2H), 1.55 (d, J=6.8 Hz, 3H), 1.38 (s, 9H), 1.31-1.22 (m, 2H); [M+H]$^+$=821.8.

Example 158: 3-(tert-butyl)-N-((1R)-1-(4-(6-(4-(1-((1-(4-(2,4-dioxotetrahydropyrimidin-1(2H)-yl)phenyl)piperidin-4-yl)methyl)pyrrolidin-3-yl)phenyl)-7H-pyrrolo[2,3-d]pyrimidin-4-yl)-2-methylphenyl)ethyl)-1,2,4-oxadiazole-5-carboxamide

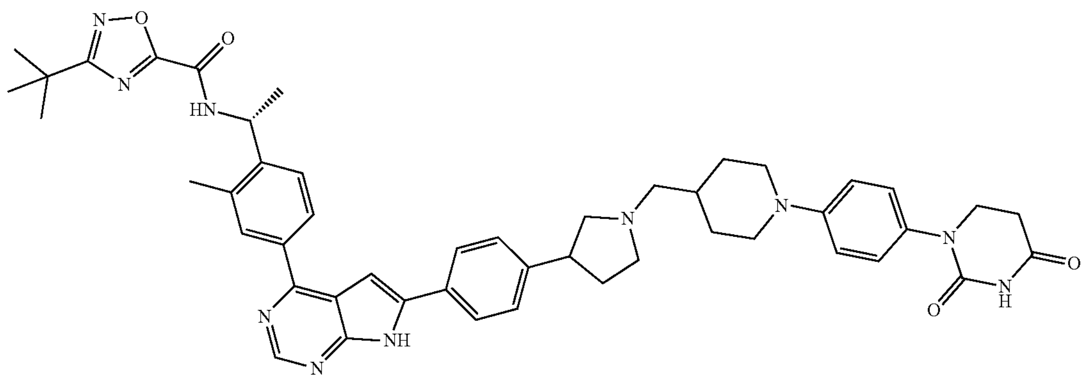 [SMILES: Cc1cc(-c2ncnc3[nH]c(-c4ccc(C5CCN(CC6CCN(c7ccc(N8CCC(=O)NC8=O)cc7)CC6)C5)cc4)cc23)ccc1[C@@H](C)NC(=O)c1nc(C(C)(C)C)no1]

The titled compound was synthesized in the procedures similar to Example 25. $^{1}$H NMR (400 MHz, DMSO) $\delta_H$ 12.67 (s, 1H), 10.26 (s, 1H), 9.97 (d, J=7.6 Hz, 1H), 8.81 (s, 1H), 8.14-7.94 (m, 4H), 7.67 (d, J=8.2 Hz, 1H), 7.43 (d, J=6.4 Hz, 2H), 7.39 (s, 1H), 7.13 (d, J=8.6 Hz, 2H), 6.94 (d, J=8.0 Hz, 2H), 5.44-5.34 (m, 1H), 3.77-3.63 (m, 4H), 2.79-2.53 (m, 12H), 2.45-2.22 (m, 3H), 1.92-1.60 (m, 4H), 1.55 (d, J=6.8 Hz, 3H), 1.37 (s, 9H), 1.31-1.24 (m, 2H); $[M+H]^+$=835.7.

Example 159: (R)-3-(tert-butyl)-N-(1-(4-(6-(6-(1-((1-(4-(2,4-dioxotetrahydropyrimidin-1(2H)-yl)phenyl)piperidin-4-yl)methyl)-2,5-dihydro-1H-pyrrol-3-yl)pyridin-3-yl)-7H-pyrrolo[2,3-d]pyrimidin-4-yl)-2-methylphenyl)ethyl)-1,2,4-oxadiazole-5-carboxamide

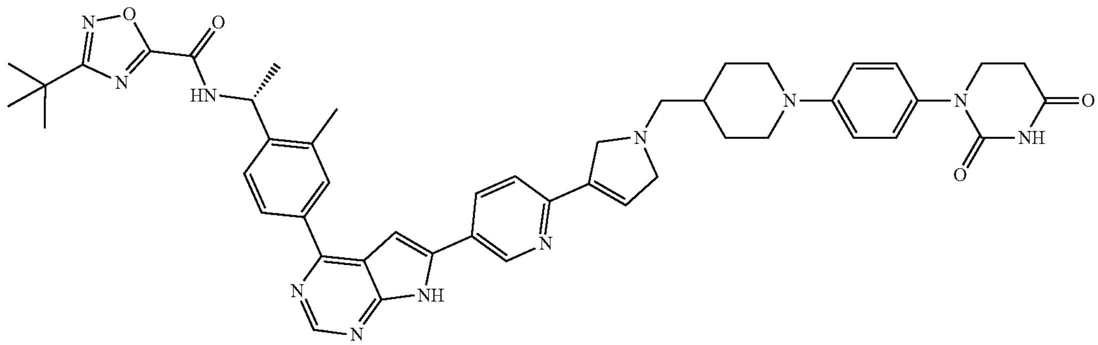 [SMILES: Cc1cc(-c2ncnc3[nH]c(-c4ccc(C5=CCN(CC6CCN(c7ccc(N8CCC(=O)NC8=O)cc7)CC6)C5)nc4)cc23)ccc1[C@@H](C)NC(=O)c1nc(C(C)(C)C)no1]

The titled compound was synthesized in the procedures similar to Example 25. $^{1}$H NMR (400 MHz, DMSO) $\delta_H$ 12.93 (s, 1H), 10.27 (s, 1H), 9.99 (d, J=7.6 Hz, 1H), 9.27 (s, 1H), 8.85 (s, 1H), 8.49 (d, J=6.8 Hz, 1H), 8.18-8.08 (m, 2H), 8.06 (s, 1H), 7.92-7.81 (m, 1H), 7.72-7.59 (m, 2H), 7.15 (d, J=8.4 Hz, 2H), 6.96 (d, J=8.4 Hz, 2H), 6.80 (s, 1H), 5.46-5.33 (m, 1H), 4.53-3.88 (m, 4H), 3.78-3.64 (m, 4H), 3.00 (s, 3H), 2.77-2.63 (m, 5H), 2.55 (s, 3H), 1.99-1.90 (m, 2H), 1.55 (d, J=6.8 Hz, 3H), 1.37 (s, 9H); $[M+H]^+$=834.8.

Example 160: (R)-3-(tert-butyl)-N-(1-(4-(6-(2-(4-((1-(4-(2,4-dioxotetrahydropyrimidin-1(2H)-yl)phenyl)piperidin-4-yl)methyl)piperazin-1-yl)pyrimidin-5-yl)-7H-pyrrolo[2,3-d]pyrimidin-4-yl)-2-methylphenyl)ethyl)-1,2,4-oxadiazole-5-carboxamide

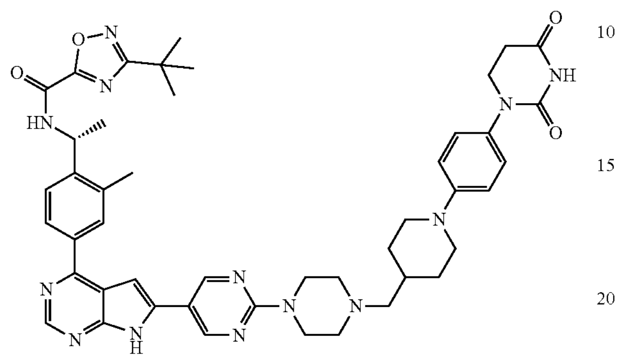

The titled compound was synthesized in the procedures similar to Example 25. $^1$H NMR (400 MHz, DMSO) $\delta_H$ 12.67 (s, 1H), 10.26 (s, 1H), 9.96 (d, J=7.8 Hz, 1H), 9.03 (s, 2H), 8.79 (s, 1H), 8.08 (d, J=7.4 Hz, 1H), 8.04 (s, 1H), 7.67 (d, J=8.2 Hz, 1H), 7.37 (s, 1H), 7.13 (d, J=8.9 Hz, 2H), 6.93 (d, J=9.0 Hz, 2H), 5.38 (s, 1H), 3.83 (s, 4H), 3.64-3.75 (m, 4H), 2.61-2.71 (m, 4H), 2.43-2.58 (m, 7H), 2.23 (s, 2H), 1.83 (d, J=12.7 Hz, 2H), 1.73 (s, 1H), 1.55 (d, J=6.9 Hz, 3H), 1.37 (s, 9H), 1.15-1.30 (m, 2H); $[M+H]^+$=852.8.

Example 161: (R)-3-(tert-butyl)-N-(1-(4-(6-(1-(1-(((1-(4-(2,4-dioxotetrahydropyrimidin-1(2H)-yl)phenyl)piperidin-4-yl)methyl)glycyl)piperidin-4-yl)-3,5-dimethyl-1H-pyrazol-4-yl)-7H-pyrrolo[2,3-d]pyrimidin-4-yl)-2-methylphenyl)ethyl)-1,2,4-oxadiazole-5-carboxamide

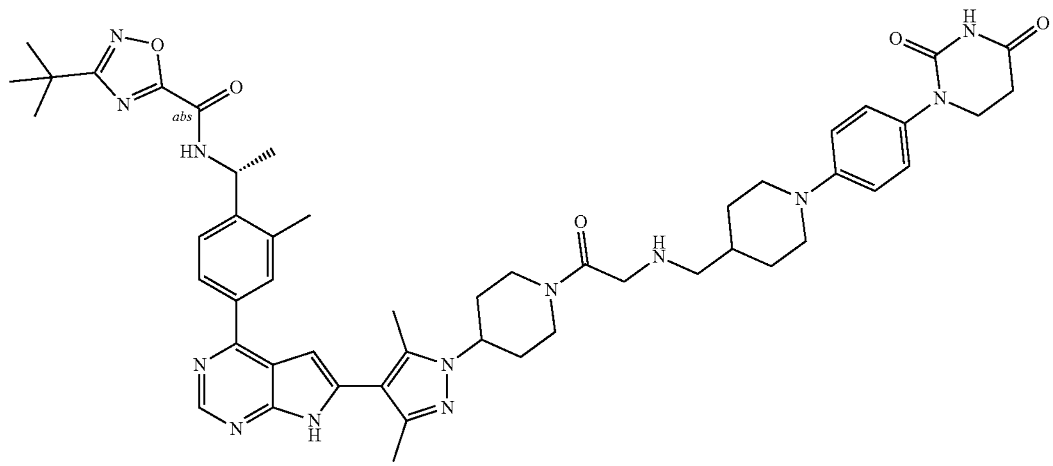 [SMILES: Cc1cc(-c2ncnc3[nH]c(-c4c(C)nn(C5CCN(C(=O)CNCC6CCN(c7ccc(N8CCC(=O)NC8=O)cc7)CC6)CC5)c4C)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.15 (s, 1H), 10.27 (s, 1H), 9.94 (d, J=7.6 Hz, 1H), 8.79 (s, 2H), 8.07-7.90 (m, 2H), 7.65 (d, J=8.4 Hz, 1H), 7.15 (d, J=8.8 Hz, 2H), 6.95 (d, J=8.8 Hz, 2H), 6.75 (s, 1H), 5.43-5.29 (m, 1H), 4.60-4.43 (m, 2H), 4.14 (dd, J=44.8, 16.0 Hz, 2H), 3.82 (d, J=12.8 Hz, 1H), 3.76-3.64 (m, 4H), 3.44-3.37 (m, 1H), 3.28-3.20 (m, 1H), 2.95-2.81 (m, 3H), 2.73-2.62 (m, 4H), 2.40 (s, 3H), 2.26 (s, 3H), 1.97-1.81 (m, 6H), 1.54 (d, J=6.8 Hz, 3H), 1.36 (s, 9H); $[M+H]^+$=924.8.

Example 162: 3-(tert-butyl)-N-((1R)-1-(4-(6-(6-(1-((1-(4-(2,4-dioxotetrahydropyrimidin-1(2H)-yl)phenyl)piperidin-4-yl)methyl)pyrrolidin-3-yl)pyridin-3-yl)-7H-pyrrolo[2,3-d]pyrimidin-4-yl)-2-methylphenyl)ethyl)-1,2,4-oxadiazole-5-carboxamide

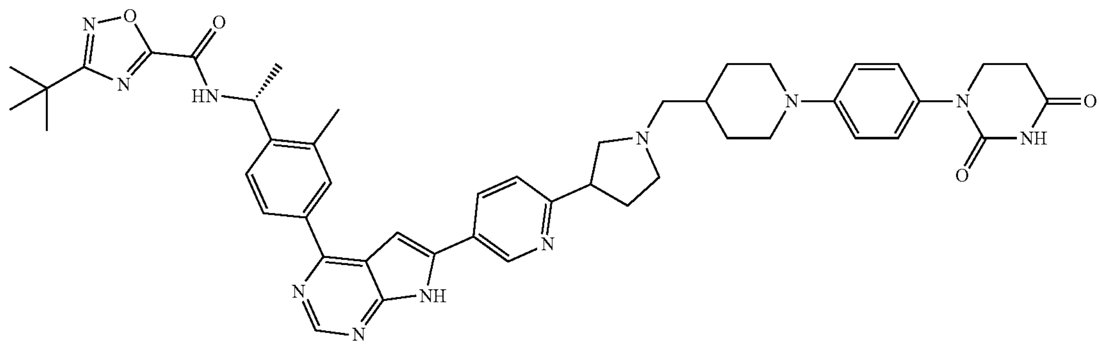 [SMILES: Cc1cc(-c2ncnc3[nH]c(-c4ccc(C5CCN(CC6CCN(c7ccc(N8CCC(=O)NC8=O)cc7)CC6)C5)nc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.87 (s, 1H), 10.26 (s, 1H), 10.00 (d, J=7.6 Hz, 1H), 9.19 (s, 1H), 8.84 (s, 1H), 8.38 (d, J=8.0 Hz, 1H), 8.16-8.03 (m, 2H), 7.68 (d, J=7.6 Hz, 1H), 7.57-7.44 (m, 2H), 7.13 (d, J=8.8 Hz, 2H), 6.93 (d, J=8.0 Hz, 2H), 5.44-5.31 (m, 1H), 3.74-3.62 (m, 4H), 3.60-3.50 (m, 1H), 3.06-2.96 (m, 1H), 2.72-2.58 (m, 6H), 2.54 (s, 3H), 2.42-2.30 (m, 2H), 2.27-2.17 (m, 1H), 2.10-1.98 (m, 1H), 1.91-1.80 (m, 2H), 1.71-1.61 (m, 1H), 1.55 (d, J=6.4 Hz, 3H), 1.37 (s, 9H), 1.23 (s, 3H); [M+H]$^+$=836.8.

Example 163: 3-(tert-butyl)-N-((1R)-1-(4-(6-(1-(1-((1-(4-(2,4-dioxotetrahydropyrimidin-1(2H)-yl)phenyl)piperidin-4-yl)methyl)pyrrolidin-3-yl)-3,5-dimethyl-1H-pyrazol-4-yl)-7H-pyrrolo[2,3-d]pyrimidin-4-yl)-2-methylphenyl)ethyl)-1,2,4-oxadiazole-5-carboxamide

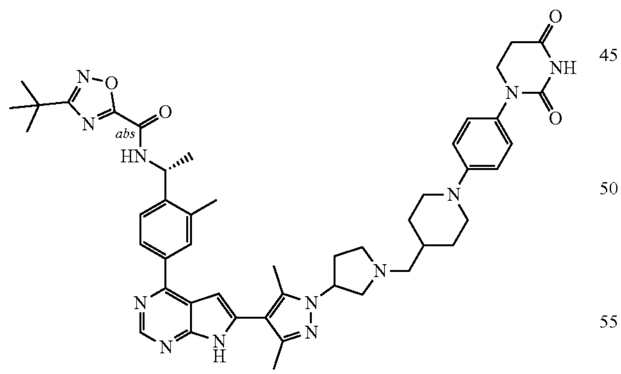

The titled compound was synthesized in the procedures similar to Example 25. $^1$H NMR (400 MHz, DMSO) $\delta_H$ 12.16 (s, 1H), 10.26 (s, 1H), 9.93 (d, J=8.0 Hz, 1H), 8.79 (s, 1H), 8.09-7.90 (m, 2H), 7.65 (d, J=8.0 Hz, 1H), 7.14 (d, J=8.0 Hz, 2H), 6.94 (d, J=8.0 Hz, 2H), 6.75 (s, 1H), 5.47-5.17 (m, 1H), 4.93 (s, 1H), 3.78-3.62 (m, 4H), 3.21-2.76 (m, 4H), 2.74-2.55 (m, 6H), 2.45-2.10 (m, 9H), 1.85 (d, J=12.0 Hz, 2H), 1.64 (s, 1H), 1.54 (d, J=8.0 Hz, 3H), 1.36 (s, 9H), 1.30-1.18 (m, 3H); [M+H]$^+$=853.8.

Example 164: (R)-3-(tert-butyl)-N-(1-(4-(6-(4-(6-((1-(4-(2,4-dioxotetrahydropyrimidin-1(2H)-yl)phenyl)piperidin-4-yl)methyl)-2,6-diazaspiro[3.3]heptan-2-yl)phenyl)-7H-pyrrolo[2,3-d]pyrimidin-4-yl)-2-methylphenyl)ethyl)-1,2,4-oxadiazole-5-carboxamide

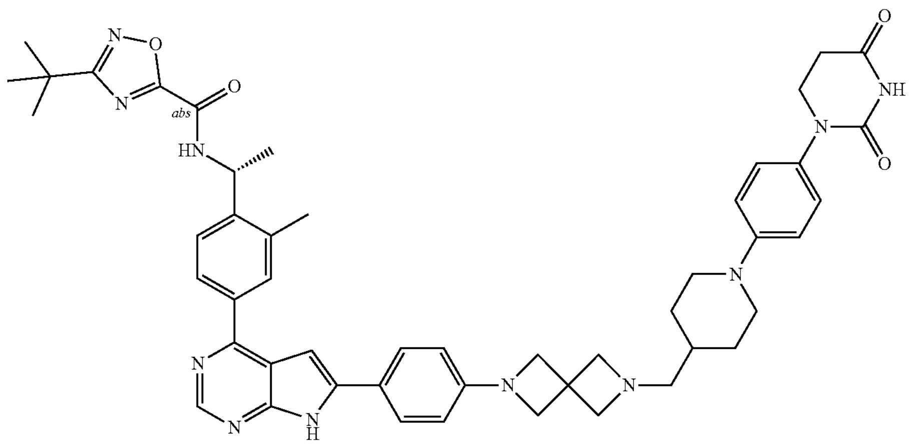 [SMILES: Cc1cc(-c2ncnc3[nH]c(-c4ccc(N5CC6(CN(CC7CCN(c8ccc(N9CCC(=O)NC9=O)cc8)CC7)C6)C5)cc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.48 (s, 1H), 10.26 (s, 1H), 9.96 (d, J=8.0 Hz, 1H), 8.74 (s, 1H), 8.10-7.97 (m, 2H), 7.89 (d, J=8.0 Hz, 2H), 7.66 (d, J=8.0 Hz, 1H), 7.24-7.05 (m, 3H), 6.94 (d, J=8.0 Hz, 2H), 6.54 (d, J=8.0 Hz, 2H), 5.45-5.21 (m, 1H), 4.55-4.15 (m, 2H), 4.04 (s, 4H), 3.76-3.61 (m, 4H), 3.20-2.80 (m, 2H), 2.75-2.60 (m, 4H), 2.53 (s, 4H), 1.76 (d, J=12.0 Hz, 2H), 1.68-1.60 (m, 1H), 1.55 (d, J=8.0 Hz, 2H), 1.37 (s, 9H), 1.33-1.22 (m, 3H); $[M+H]^+$=862.9.

Example 165: (R)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-3-(1-methylcyclopropyl)-1,2,4-oxadiazole-5-carboxamide

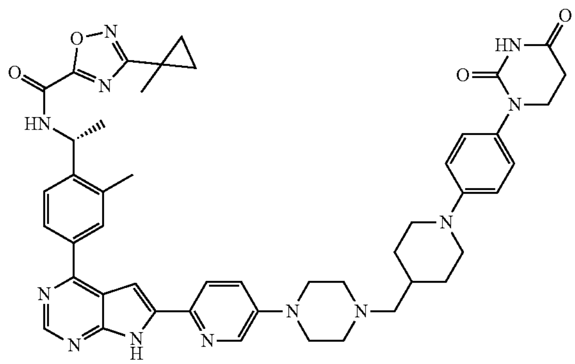 [SMILES: Cc1cc(-c2ncnc3[nH]c(-c4ccc(N5CCN(CC6CCN(c7ccc(N8CCC(=O)NC8=O)cc7)CC6)CC5)cn4)cc23)ccc1[C@@H](C)NC(=O)c1nc(C2(C)CC2)no1]

The titled compound was synthesized in the procedures similar to Example 25. $^1$H NMR (400 MHz, DMSO) $\delta_H$12.62 (s, 1H), 10.26 (s, 1H), 9.89 (d, J=7.6 Hz, 1H), 8.78 (s, 1H), 8.39 (s, 1H), 8.11-7.98 (m, 3H), 7.66 (d, J=8.0 Hz, 1H), 7.51-7.35 (m, 2H), 7.14 (d, J=8.4 Hz, 2H), 6.93 (d, J=8.0 Hz, 2H), 5.41-5.28 (m, 1H), 3.84-3.53 (m, 5H), 2.75-2.58 (m, 5H), 2.57-2.51 (m, 7H), 2.32-2.14 (m, 2H), 2.00-1.62 (m, 4H), 1.54 (d, J=6.8 Hz, 3H), 1.49 (s, 3H), 1.39-1.10 (m, 5H), 1.03-0.95 (m, 2H); $[M+H]^+$=849.8.

Example 166: (R)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-3-(1-methylcyclopropyl)-1,2,4-oxadiazole-5-carboxamide Step 1: lithium 3-(1-methylcyclopropyl)-1,2,4-oxadiazole-5-carboxylate

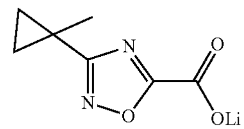

To a mixture of ethyl 3-(1-methylcyclopropyl)-1,2,4-oxadiazole-5-carboxylate (1.0 g, 5.0 mmol) in THF/MeOH/water (5 mL/5 mL/1 mL) was added LiOH— $H_2O$ (0.23 g, 5.5 mmol). The mixture was stirred at room temperature for 2 hours. LCMS showed the reaction was completed. The reaction was concentrated in vacuo to afford the product (1.48 g, crude), which was used for next step without further purification. $[M+H]^+$=168.8.

Step 2: (R)-N-(1-(3-methyl-4-(4,4,5,5-tetramethyl-1,3,2-dioxaborolan-2-yl)phenyl)ethyl)-3-(1-methylcyclopropyl)-1,2,4-oxadiazole-5-carboxamide

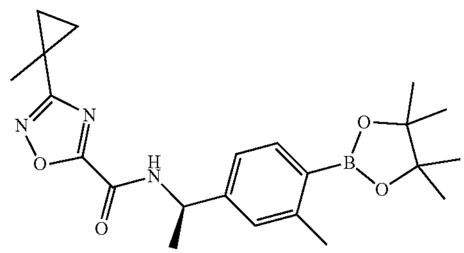

To a mixture of lithium 3-(1-methylcyclopropyl)-1,2,4-oxadiazole-5-carboxylate (1.48 g, crude) in DMF (15 mL) was added (R)-1-(2-methyl-4-(4,4,5,5-tetramethyl-1,3,2-dioxaborolan-2-yl)phenyl)ethan-1-amine (1.49 g, 5.0 mmol), HOBT (1.02 g, 7.5 mmol) and EDCI (1.44 g, 7.5 mmol). The mixture was stirred at room temperature for 2 hours. LCMS showed the reaction was completed. To the reaction was added water (50 mL) and extracted with PE/EtOAc (5:1, 50 mL×3). The organic phase was washed with saturated brine (50 mL×3), dried over $Na_2SO_4$, filtered and concentrated in vacuo to afford the product (1.5 g, 73% in two steps). $[M+H]^+$=411.8.

Step 3: tert-butyl (R)-4-(5-(4-(3-methyl-4-(1-(3-(1-methylcyclopropyl)-1,2,4-oxadiazole-5-carboxamido)ethyl)phenyl)-7-((2-(trimethylsilyl)ethoxy)methyl)-7H-pyrrolo[2,3-d]pyrimidin-6-yl)pyridin-2-yl)piperazine-1-carboxylate

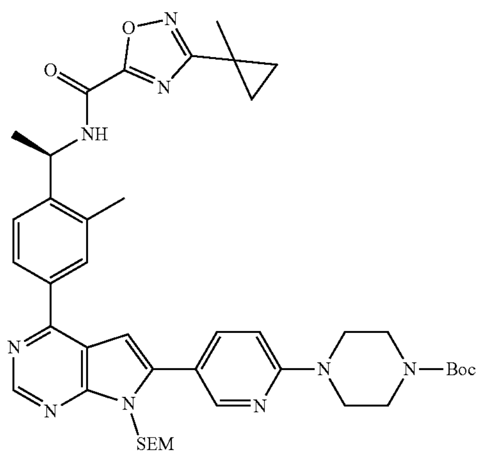

A mixture of (R)-N-(1-(3-methyl-4-(4,4,5,5-tetramethyl-1,3,2-dioxaborolan-2-yl)phenyl)ethyl)-3-(1-methylcyclopropyl)-1,2,4-oxadiazole-5-carboxamide (206 mg, 0.5 mmol), tert-butyl 4-(5-(4-chloro-7-((2-(trimethylsilyl)ethoxy)methyl)-7H-pyrrolo[2,3-d]pyrimidin-6-yl)pyridin-2-yl)piperazine-1-carboxylate (272 mg, 0.5 mmol), $Pd(dppf)Cl_2$ (36 mg, 0.05 mmol) and $Cs_2CO_3$ (325 mg, 1.0 mmol) in 1,4-dioxane (15 mL) and $H_2O$ (3 mL) was stirred in a round bottom flask at 100° C. overnight. The mixture was evaporated in vacuum to afford the crude product, which was further purified with silica gel column chromatography (PE:EtOAc=100:1~1:100 gradient elution) to give the product (190 mg, 48%). $[M+H]^+$=794.7.

Step 4: (R)-N-(1-(2-methyl-4-(6-(6-(piperazin-1-yl)pyridin-3-yl)-7H-pyrrolo[2,3-d]pyrimidin-4-yl)phenyl)ethyl)-3-(1-methylcyclopropyl)-1,2,4-oxadiazole-5-carboxamide

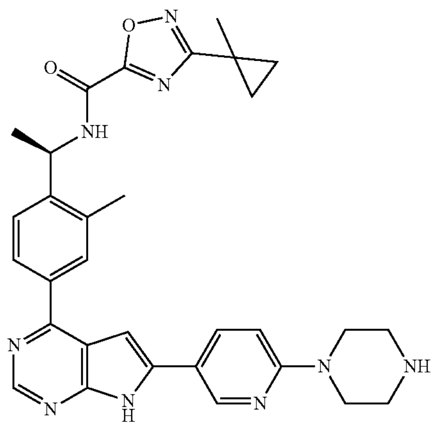 [SMILES: Cc1cc(-c2ncnc3[nH]c(-c4ccc(N5CCNCC5)nc4)cc23)ccc1[C@@H](C)NC(=O)c1nc(C2(C)CC2)no1]

A mixture of tert-butyl (R)-4-(5-(4-(3-methyl-4-(1-(3-(1-methylcyclopropyl)-1,2,4-oxadiazole-5-carboxamido)ethyl)phenyl)-7-((2-(trimethylsilyl)ethoxy)methyl)-7H-pyrrolo[2,3-d]pyrimidin-6-yl)pyridin-2-yl)piperazine-1-carboxylate (190 mg, 0.24 mmol) and trifluoroacetic acid (10 mL) in dichloromethane (5 mL) was stirred in a round bottom flask at room temperature for 2 hours. The mixture was evaporated in vacuum. The residue was dissolved in MeOH (15 mL) and $NH_3/H_2O$ (1 mL) was added. The mixture was stirred at room temperature for 1 hour. LCMS showed the reaction was completed. The mixture was evaporated in vacuum to afford the product (524 mg, crude), which was used for next step without further purification. $[M+H]^+$=564.8.

Step 5: (R)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-3-(1-methylcyclopropyl)-1,2,4-oxadiazole-5-carboxamide

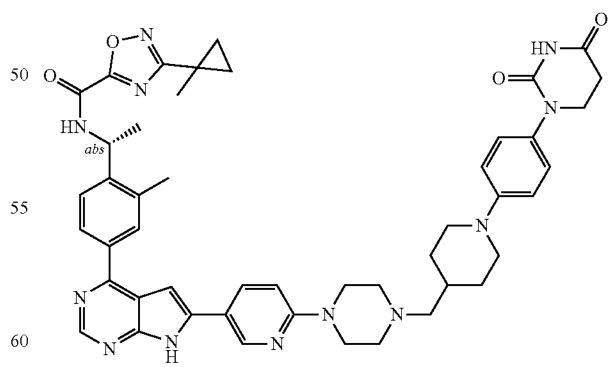

A mixture of (R)-N-(1-(2-methyl-4-(6-(6-(piperazin-1-yl)pyridin-3-yl)-7H-pyrrolo[2,3-d]pyrimidin-4-yl)phenyl)ethyl)-3-(1-methylcyclopropyl)-1,2,4-oxadiazole-5-carboxamide (260 mg, crude) and 1-(4-(2,4-dioxotetrahydropyrimidin-1(2H)-yl)phenyl)piperidine-4- carbaldehyde (50 mg, 0.16 mmol) in DCM (10 mL) and MeOH (2 mL) was stirred in a round bottom flask at room temperature for 1 hour. To the mixture was added NaBH$(OAc)_3$ (212 mg, 1.0 mmol) and stirred in a round bottom flask at room temperature overnight. Then the mixture was purified with Pre-TLC (DCM:MeOH=8:1) to give the product (35 mg, 41%). $^1$H NMR (400 MHz, DMSO) $\delta_H$ 12.62 (s, 1H), 10.27 (s, 1H), 10.01-9.79 (m, 1H), 8.98-8.57 (m, 2H), 8.19 (s, 1H), 8.12-7.96 (m, 2H), 7.65 (d, J=7.6 Hz, 1H), 7.30 (s, 1H), 7.14 (d, J=7.2 Hz, 2H), 7.03-6.85 (m, 3H), 5.45-5.27 (m, 1H), 3.84-3.48 (m, 9H), 2.75-2.61 (m, 4H), 2.48-2.37 (m, 3H), 2.30-2.13 (m, 2H), 1.93-1.69 (m, 3H), 1.57-1.43 (m, 6H), 1.30-1.16 (m, 7H), 1.03-0.94 (m, 2H); [M+H]$^+$=849.8.

Example 167: (R)-3-(tert-butyl)-N-(1-(4-(6-(4-(4-((1-(4-(2,4-dioxotetrahydropyrimidin-1(2H)-yl)phenyl)piperidin-4-yl)methyl)-1,4-diazepan-1-yl)phenyl)-7H-pyrrolo[2,3-d]pyrimidin-4-yl)-2-methylphenyl)ethyl)-1,2,4-oxadiazole-5-carboxamide

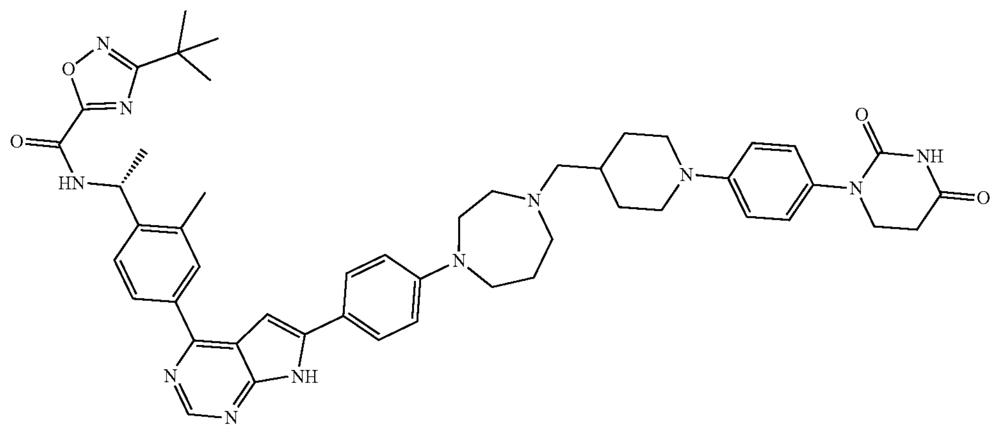 [SMILES: Cc1cc(-c2ncnc3[nH]c(-c4ccc(N5CCCN(CC6CCN(c7ccc(N8CCC(=O)NC8=O)cc7)CC6)CC5)cc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.44 (s, 1H), 10.25 (s, 1H), 9.95 (d, J=8.0 Hz, 1H), 8.73 (s, 1H), 8.08 (J=8.0 Hz, 1H), 8.03 (s, 1H), 7.91-7.82 (m, 2H), 7.66 (d, J=8.0 Hz, 1H), 7.18-7.04 (m, 3H), 6.91-6.77 (m, 4H), 5.41-5.33 (m, 1H), 3.70-3.51 (m, 8H), 3.16-2.91 (m, 2H), 2.79-2.58 (m, 6H), 2.53 (s, 3H), 2.36-2.28 (m, 2H), 1.90-1.84 (m, 2H), 1.78-1.69 (m, 2H), 1.55 (d, J=8.0 Hz, 3H), 1.37 (s, 9H), 1.27-1.10 (m, 3H); [M+H]$^+$=864.5.

Example 168: (R)-3-(tert-butyl)-N-(1-(4-(6-(2-(4-((1-(4-(2,4-dioxotetrahydropyrimidin-1(2H)-yl)phenyl)piperidin-4-yl)methyl)piperazin-1-yl)thiazol-5-yl)-7H-pyrrolo[2,3-d]pyrimidin-4-yl)-2-methylphenyl)ethyl)-1,2,4-oxadiazole-5-carboxamide

Step 1: tert-butyl 4-(5-bromothiazol-2-yl)piperazine-1-carboxylate

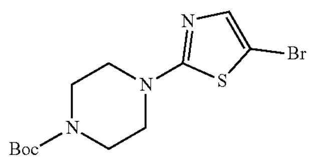 [SMILES: CC(C)(C)OC(=O)N1CCN(c2ncc(Br)s2)CC1]

A mixture of 2,5-dibromothiazole (4.8 g, 0.02 mol), tert-butyl piperazine-1-carboxylate (4.5 g, 0.024 mol) and $K_2CO_3$ (5.5 g, 0.04 mol) in DMF (30 mL) was stirred at 90° C. for 16 h. The mixture was diluted with water (100 mL) and extracted with EtOAc (3×100 mL). The combined organic layers were dried over $Na_2SO_4$, filtered and concentrated under vacuum. The residue was purified with silica gel column chromatography, eluting with EtOAc in PE from 0% to 40% to afford the product (4.2 g, 60.8%). [M+H]$^+$=348.0.

Step 2: tert-butyl 4-(5-(4-chloro-7-((2-(trimethylsilyl)ethoxy)methyl)-7H-pyrrolo[2,3-d]pyrimidin-6-yl)thiazol-2-yl)piperazine-1-carboxylate

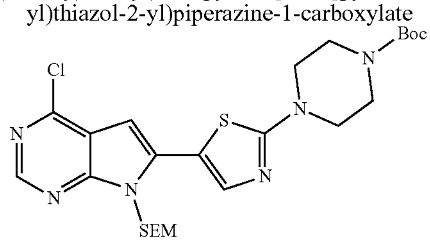

A mixture of 4-chloro-6-(4,4,5,5-tetramethyl-1,3,2-dioxaborolan-2-yl)-7-((2-(trimethylsilyl)ethoxy)methyl)-7H-pyrrolo[2,3-d]pyrimidine (3 g, 7.3 mmol), tert-butyl 4-(5-bromothiazol-2-yl)piperazine-1-carboxylate (3.3 g, 9.5 mmol), $Pd(dppf)Cl_2$ (267 mg, 0.36 mmol), $K_3PO_4$ (3.1 g, 14.6 mmol) in dioxane (60 mL) and $H_2O$ (12 mL) was stirred at 100° C. for 16 h under a nitrogen atmosphere. The mixture was concentrated under vacuum. The residue was purified with silica gel column chromatography, eluting with EtOAc in PE from 0% to 30% to afford the product (2 g, 49.6%). $[M+H]^+$=551.2.

Step 3: tert-butyl (R)-4-(5-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)thiazol-2-yl)piperazine-1-carboxylate

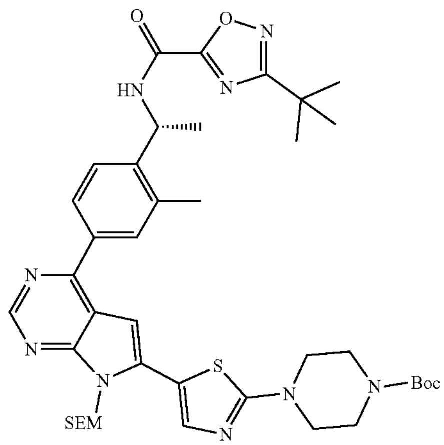 [SMILES: Cc1cc(-c2ncnc3c2cc(-c2cnc(N4CCN(C(=O)OC(C)(C)C)CC4)s2)n3COCC[Si](C)(C)C)ccc1[C@@H](C)NC(=O)c1nc(C(C)(C)C)no1]

A mixture of tert-butyl 4-(5-(4-chloro-7-((2-(trimethylsilyl)ethoxy)methyl)-7H-pyrrolo[2,3-d]pyrimidin-6-yl)thiazol-2-yl)piperazine-1-carboxylate (1.1 g, 2 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (908 mg, 2.2 mmol), $Pd(dppf)Cl_2$ (146 mg, 0.2 mmol) and 2.0 N $Na_2CO_3$ (aq, 3 mL, 6 mmol) in dioxane (15 mL) was stirred at 100° C. for 16 h under a nitrogen atmosphere. The mixture was concentrated under vacuum. The residue was purified with silica gel column chromatography, eluting with EtOAc in PE from 0% to 40% to afford the product (1.1 g, 68.7%). $[M+H]^+$=802.4.

Step 4: (R)-3-(tert-butyl)-N-(1-(2-methyl-4-(6-(2-(piperazin-1-yl)thiazol-5-yl)-7H-pyrrolo[2,3-d]pyrimidin-4-yl)phenyl)ethyl)-1,2,4-oxadiazole-5-carboxamide

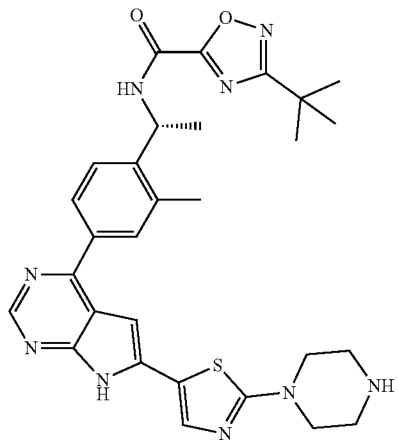 [SMILES: Cc1cc(-c2ncnc3[nH]c(-c4cnc(N5CCNCC5)s4)cc23)ccc1[C@@H](C)NC(=O)c1nc(C(C)(C)C)no1]

To a solution of tert-butyl (R)-4-(5-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)thiazol-2-yl)piperazine-1-carboxylate (500 mg, 0.62 mmol) in DCM (10 mL) was added TFA (10 mL). The reaction mixture was stirred at room temperature for 16 h. The mixture was concentrated under vacuum. The residue was dissolved in MeOH (10 mL) and added 7.0 N $NH_3$ in MeOH (2 mL). The mixture was stirred at room temperature for 1 h and concentrated under vacuum to afford the product (500 mg, crude), which was used in the next step without further purification. $[M+H]^+$=572.2.

Step 5: (R)-3-(tert-butyl)-N-(1-(4-(6-(2-(4-((1-(4-(2,4-dioxotetrahydropyrimidin-1(2H)-yl)phenyl)piperidin-4-yl)methyl)piperazin-1-yl)thiazol-5-yl)-7H-pyrrolo[2,3-d]pyrimidin-4-yl)-2-methylphenyl)ethyl)-1,2,4-oxadiazole-5-carboxamide

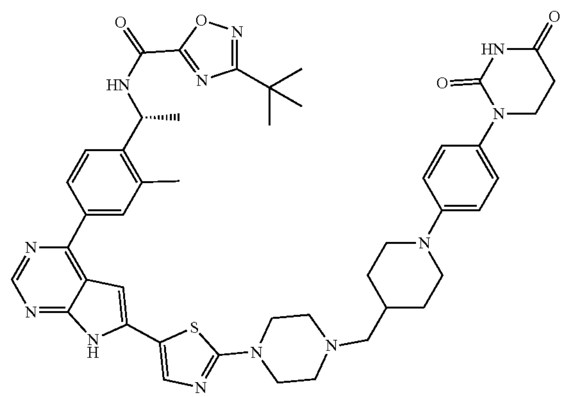 [SMILES: Cc1cc(-c2ncnc3[nH]c(-c4cnc(N5CCN(CC6CCN(c7ccc(N8CCC(=O)NC8=O)cc7)CC6)CC5)s4)cc23)ccc1[C@@H](C)NC(=O)c1nc(C(C)(C)C)no1]

A mixture of (R)-3-(tert-butyl)-N-(1-(2-methyl-4-(6-(2-(piperazin-1-yl)thiazol-5-yl)-7H-pyrrolo[2,3-d]pyrimidin-4-yl)phenyl)ethyl)-1,2,4-oxadiazole-5-carboxamide (500 mg, 0.87 mmol), 1-(4-(2,4-dioxotetrahydropyrimidin-1(2H)-yl)phenyl)piperidine-4-carbaldehyde (527 mg, 1.75 mmol) and AcOH (0.2 mL) in MeOH (10 mL) and DCM (10 mL) was stirred at room temperature for 16 h. Then, STAB (371 mg, 1.75 mmol) was added to the mixture above. The mixture was stirred at room temperature for 5 h. The mixture was quenched by water (100 mL) and extracted with DCM (3×100 mL). The combined organic layers were dried over $Na_2SO_4$, filtered and concentrated under vacuum. The residue was purified with silica gel column chromatography, eluting with MeOH in DCM from 0% to 11% to afford the product (132.6 mg, 17.7%). $^1H$ NMR (400 MHz, DMSO) $\delta_H$ 12.67 (s, 1H), 10.26 (s, 1H), 9.94 (d, J=8.0 Hz, 1H), 8.76 (s, 1H), 8.01 (d, J=8.0 Hz, 1H), 7.97 (s, 1H), 7.84 (s, 1H), 7.19-7.07 (m, 2H), 6.96-6.89 (m, 2H), 6.84 (s, 1H), 5.42-5.32 (m, 1H), 3.74-3.64 (m, 4H), 3.55-3.40 (m, 4H), 3.31-3.30 (m, 3H), 2.73-2.61 (m, 5H), 2.54 (s, 3H), 2.27-2.19 (m, 2H), 1.86-1.77 (m, 2H), 1.75-1.66 (m, 1H), 1.54 (d, J=8.0 Hz, 3H), 1.37 (s, 9H), 1.29-1.17 (m, 3H); $[M+H]^+$=857.4.

Example 169: (R)-3-(tert-butyl)-N-(1-(4-(6-(1-(1-((1-(4-(2,4-dioxotetrahydropyrimidin-1(2H)-yl)phenyl)piperidin-4-yl)methyl)azetidin-3-yl)-3,5-dimethyl-1H-pyrazol-4-yl)-7H-pyrrolo[2,3-d]pyrimidin-4-yl)-2-methylphenyl)ethyl)-1,2,4-oxadiazole-5-carboxamide

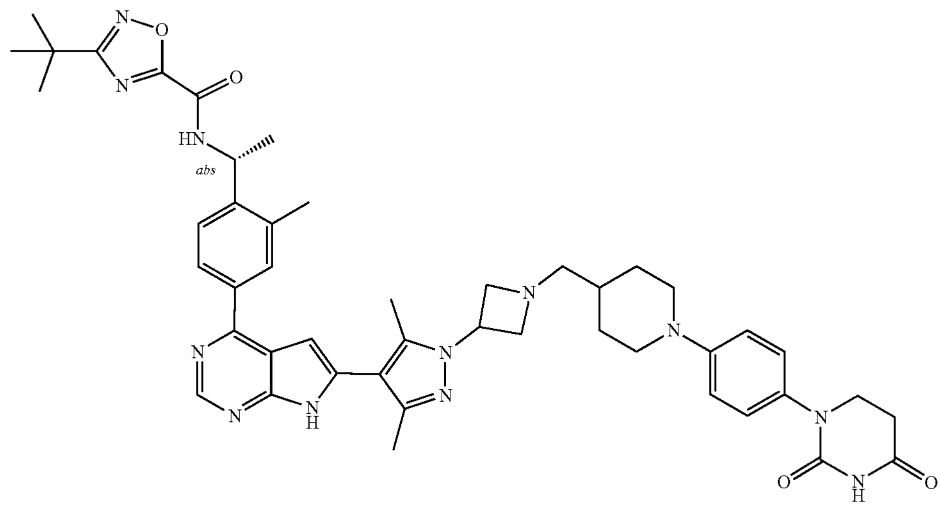 [SMILES: Cc1cc(-c2ncnc3[nH]c(-c4c(C)nn(C5CN(CC6CCN(c7ccc(N8CCC(=O)NC8=O)cc7)CC6)C5)c4C)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.18 (s, 1H), 10.27 (s, 1H), 9.93 (d, J=8.0 Hz, 1H), 8.79 (s, 1H), 8.14-7.92 (m, 2H), 7.66 (d, J=8.0 Hz, 1H), 7.14 (d, J=8.0 Hz, 2H), 6.94 (d, J=8.0 Hz, 2H), 6.75 (s, 1H), 5.52-5.24 (m, 1H), 5.00 (s, 1H), 4.68 (s, 1H), 4.43 (s, 1H), 3.82-3.62 (m, 5H), 3.40 (s, 2H), 2.99 (s, 2H), 2.71-2.60 (m, 4H), 2.43 (s, 1H), 2.33 (s, 6H), 1.80 (d, J=12.0 Hz, 2H), 1.54 (d, J=8.0 Hz, 3H), 1.36 (s, 9H), 1.24 (s, 4H); $[M+H]^+$=839.7.

Example 170: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-(hydroxymethyl)phenyl)ethyl)-1,2,4-oxadiazole-5-carboxamide Step 1: tert-butyl (R)-4-(6-(4-(4-(1-(3-(tert-butyl)-1,2,4-oxadiazole-5-carboxamido)ethyl)-3-(((tert-butyldiphenylsilyl)oxy)methyl)phenyl)-7-((2-(trimethylsilyl)ethoxy)methyl)-7H-pyrrolo[2,3-d]pyrimidin-6-yl)pyridin-3-yl)piperazine-1-carboxylate

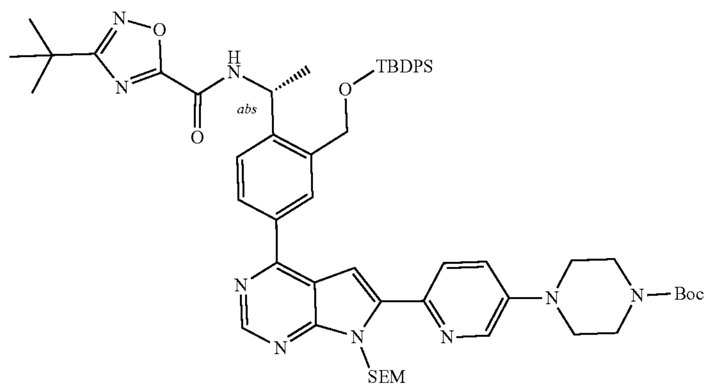

A mixture of tert-butyl 4-(6-(4-chloro-7-((2-(trimethylsilyl)ethoxy)methyl)-7H-pyrrolo[2,3-d]pyrimidin-6-yl)pyridin-3-yl)piperazine-1-carboxylate (150 mg, 0.273 mmol), (R)-(4-(1-(3-(tert-butyl)-1,2,4-oxadiazole-5-carboxamido)ethyl)-3-(((tert-butyldiphenylsilyl)oxy)methyl)phenyl)boronic acid (160 mg, 0.273 mmol), Pd(dppf)$Cl_2$ (10 mg, 0.0137 mmol) and $K_2CO_3$ (60 mg, 0.437 mmol) in 1,4-dioxane (10 mL) and $H_2O$ (2 mL) was stirred in a round bottom flask at 93° C. overnight. The mixture was evaporated in vacuum to afford the crude product, which was further purified with silica gel column chromatography (PE:EtOAc=100%: 0%-50%: 50% gradient elution) to give the product (133 mg, 46%). $[M+H]^+$=1050.0.

Step 2: (R)-3-(tert-butyl)-N-(1-(2-(hydroxymethyl)-4-(6-(5-(piperazin-1-yl)pyridin-2-yl)-7H-pyrrolo[2,3-d]pyrimidin-4-yl)phenyl)ethyl)-1,2,4-oxadiazole-5-carboxamide

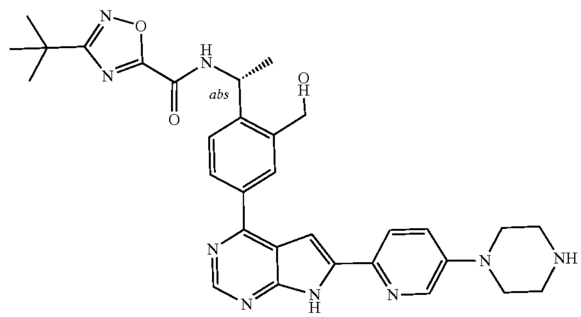 [SMILES: C[C@@H](NC(=O)c1nc(C(C)(C)C)no1)c1ccc(-c2ncnc3[nH]c(-c4ccc(N5CCNCC5)cn4)cc23)cc1CO]

To a stirred solution of tert-butyl (R)-4-(6-(4-(4-(1-(3-(tert-butyl)-1,2,4-oxadiazole-5-carboxamido)ethyl)-3-(((tert-butyldiphenylsilyl)oxy)methyl)phenyl)-7-((2-(trimethylsilyl)ethoxy)methyl)-7H-pyrrolo[2,3-d]pyrimidin-6-yl)pyridin-3-yl)piperazine-1-carboxylate (133 mg, 0.127 mmol) in DCM (5 mL) was added TFA (7.5 mL). The mixture was stirred at room temperature overnight. Then the mixture was concentrated in vacuo. The residue was diluted with MeOH (5 mL), and $NH_3$ (7 M in MeOH, 2 mL) was added. The mixture was stirred at room temperature for 2 hours. The mixture was evaporated in vacuum to afford the crude product, which was used in next step without further purification (387 mg, crude). $[M+H]^+$=582.4.

Step 3: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-(hydroxymethyl)phenyl)ethyl)-1,2,4-oxadiazole-5-carboxamide

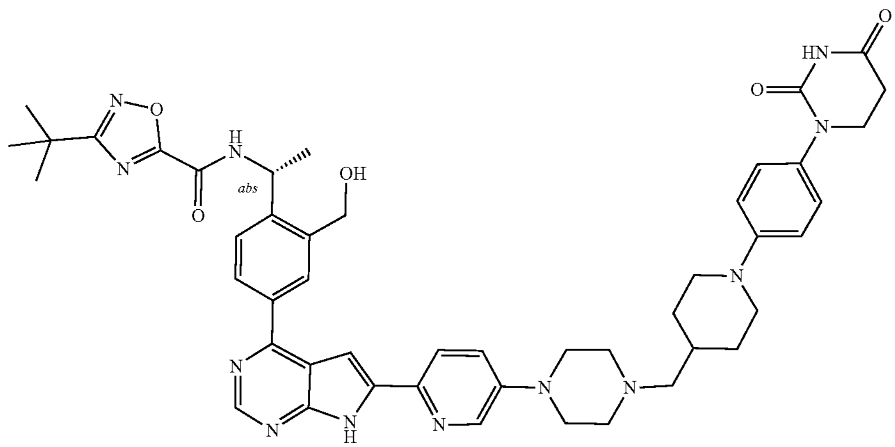 [SMILES: C[C@@H](NC(=O)c1nc(C(C)(C)C)no1)c1ccc(-c2ncnc3[nH]c(-c4ccc(N5CCN(CC6CCN(c7ccc(N8CCC(=O)NC8=O)cc7)CC6)CC5)cn4)cc23)cc1CO]

A solution of (R)-3-(tert-butyl)-N-(1-(2-(hydroxymethyl)-4-(6-(5-(piperazin-1-yl)pyridin-2-yl)-7H-pyrrolo[2,3-d]pyrimidin-4-yl)phenyl)ethyl)-1,2,4-oxadiazole-5-carboxamide (200 mg, crude) in DCM (4 mL) and MeOH (4 mL) was stirred in a round bottom flask at room temperature. 1-(4-(2,4-dioxotetrahydropyrimidin-1(2H)-yl)phenyl)piperidine-4-carbaldehyde (156 mg, 0.518 mmol), and HOAc (0.06 mL) were added. The mixture was stirred at room temperature overnight. To the mixture was added NaBH$(OAc)_3$ (292.5 mg, 1.38 mmol) and stirred in a round bottom flask at room temperature for 1 hour. Then the mixture was evaporated in vacuum to afford the crude product, which was purified with silica gel column chromatography (DCM: MeOH=100%:0%~92%:8% gradient elution) to give the product (10.76 mg, 3.6%). $^1$H NMR (400 MHz, DMSO) $\delta_H$ 12.63 (s, 1H), 10.26 (s, 1H), 9.98 (d, J=8.0 Hz, 1H), 8.79 (s, 1H), 8.40 (s, 1H), 8.27 (s, 1H), 8.15 (d, J=8.0 Hz, 1H), 8.02 (d, J=8.0 Hz, 1H), 7.74 (d, J=8.0 Hz, 1H), 7.47 (d, J=8.0 Hz, 1H), 7.41 (s, 1H), 7.13 (d, J=8.0 Hz, 2H), 6.93 (d, J=8.0 Hz, 2H), 5.45-5.35 (m, 2H), 5.00-4.64 (m, 2H), 3.78-3.62 (m, 5H), 2.98 (s, 2H), 2.68 (t, J=8.0 Hz, 5H), 2.54 (s, 4H), 2.24 (d, J=4.0 Hz, 2H), 1.82 (d, J=12.0 Hz, 2H), 1.73 (s, 1H), 1.57 (d, J=8.0 Hz, 3H), 1.37 (s, 9H), 1.30-1.24 (m, 2H); $[M+H]^+$=867.7.

Example 171: (R)-5-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-5-fluoro-2-(hydroxymethyl)phenyl)ethyl)-1,2,4-oxadiazole-3-carboxamide

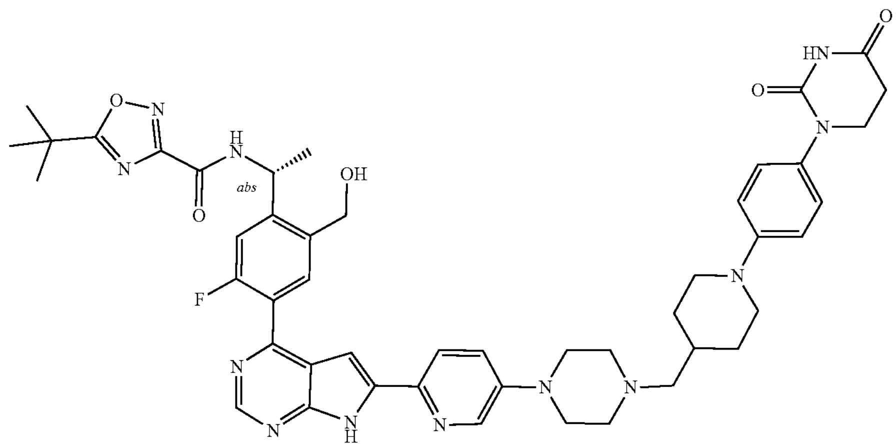 [SMILES: C[C@@H](NC(=O)c1noc(C(C)(C)C)n1)c1cc(F)c(-c2ncnc3[nH]c(-c4ccc(N5CCN(CC6CCN(c7ccc(N8CCC(=O)NC8=O)cc7)CC6)CC5)cn4)cc23)cc1CO]

The titled compound was synthesized in the procedures similar to Example 25. $^1$H NMR (400 MHz, DMSO) $\delta_H$ 12.64 (s, 1H), 10.26 (s, 1H), 9.58 (d, J=8.0 Hz, 1H), 8.82 (s, 1H), 8.38 (s, 1H), 7.98 (d, J=8.0 Hz, 1H), 7.86 (d, J=7.1 Hz, 1H), 7.57 (d, J=12.0 Hz, 1H), 7.43 (d, J=8.0 Hz, 1H), 7.13 (d, J=8.0 Hz, 2H), 7.05-6.88 (m, 3H), 5.46-5.34 (m, 2H), 4.85-4.68 (m, 2H), 3.76-3.62 (m, 4H), 2.98 (s, 4H), 2.72-2.62 (m, 6H), 2.54 (s, 5H), 2.24 (s, 2H), 1.86-1.68 (m, 3H), 1.73 (s, 2H), 1.55 (d, J=8.0 Hz, 4H), 1.43 (s, 9H); $[M+H]^+$=885.7.

Example 172: (R)-3-(tert-butyl)-N-(1-(4-(6-(5-(1-((1-(4-(2,4-dioxotetrahydropyrimidin-1(2H)-yl)phenyl)piperidin-4-yl)methyl)-3-hydroxyazetidin-3-yl)pyridin-2-yl)-7H-pyrrolo[2,3-d]pyrimidin-4-yl)-2-methylphenyl)ethyl)-1,2,4-oxadiazole-5-carboxamide Step 1: tert-butyl 3-(6-bromopyridin-3-yl)-3-hydroxyazetidine-1-carboxylate

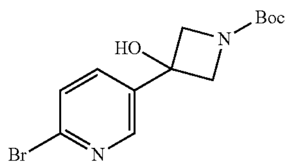 [SMILES: CC(C)(C)OC(=O)N1CC(O)(c2ccc(Br)nc2)C1]

At −25° C., to a solution of 2-bromo-5-iodopyridine (5.0 g, 17.6 mmol) in THF (30 mL) were added isopropylmagnesium chloride solution (2.5 M in THF, 8.0 mL, 20 mmol) and tert-butyl 3-oxoazetidine-1-carboxylate (3.6 g in 10 mL THF, 21.1 mmol). The reaction mixture was stirred for 16 hours at room temperature and quenched with saturated ammonium chloride aqueous solution. The resulting solution was extracted with 100 mL of EtOAc. The organic layer was dried over $Na_2SO_4$ and concentrated under vacuum to afford a crude residue. The crude product was purified by column chromatography to afford the product (5.4 g, 93%). $[M+H]^+$=329.2.

Step 2: tert-butyl 3-(6-(4-chloro-7-((2-(trimethylsilyl)ethoxy)methyl)-7H-pyrrolo[2,3-d]pyrimidin-6-yl)pyridin-3-yl)-3-hydroxyazetidine-1-carboxylate

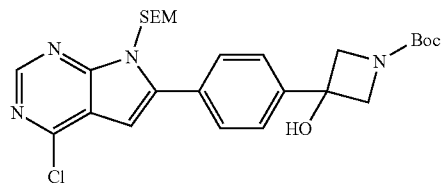 [SMILES: CC(C)(C)OC(=O)N1CC(O)(c2ccc(-c3cc4c(Cl)ncnc4n3COCC[Si](C)(C)C)cc2)C1]

A mixture of 4-chloro-6-(4,4,5,5-tetramethyl-1,3,2-dioxaborolan-2-yl)-7-((2-(trimethylsilyl)ethoxy)methyl)-7H-pyrrolo[2,3-d]pyrimidine (6.5 g, 15.8 mmol), tert-butyl 3-(6-bromopyridin-3-yl)-3-hydroxyazetidine-1-carboxylate (5.0 g, 15.2 mmol), Pd(dppf)$Cl_2$ (1.0 g, 1.37 mmol) and TMSOK (4.1 g, 32 mmol) in 1,4-dioxane (80 mL) and $H_2O$ (20 mL) was stirred in a round bottom flask at 100° C. overnight. The mixture was evaporated in vacuum to afford the crude product, which was further purified with silica gel column chromatography (PE:EtOAc=3:1~1:1 gradient elution) to give the product (5.5 g, 65.8%). $[M+H]^+$=532.4.

Step 3: tert-butyl (R)-3-(6-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)pyridin-3-yl)-3-hydroxyazetidine-1-carboxylate

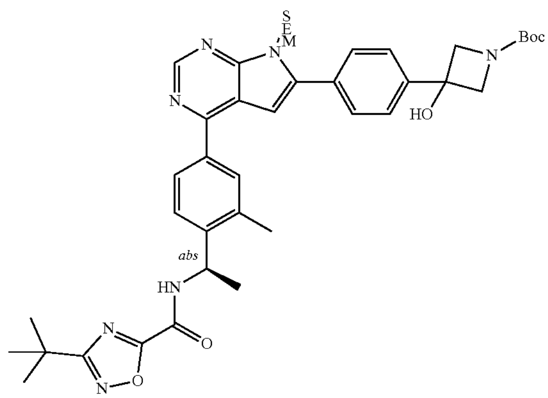 [SMILES: Cc1cc(-c2ncnc3c2cc(-c2ccc(C4(O)CN(C(=O)OC(C)(C)C)C4)cc2)n3COCC[Si](C)(C)C)ccc1[C@@H](C)NC(=O)c1nc(C(C)(C)C)no1]

A mixture of tert-butyl 3-(6-(4-chloro-7-((2-(trimethylsilyl)ethoxy)methyl)-7H-pyrrolo[2,3-d]pyrimidin-6-yl)pyridin-3-yl)-3-hydroxyazetidine-1-carboxylate (2.0 g, 3.8 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (1.7 g, 4.1 mmol), Pd(dppf)$Cl_2$ (0.2 g, 0.27 mmol) and $Cs_2CO_3$ (2.0 g, 6.1 mmol) in 1,4-dioxane (40 mL) and $H_2O$ (10 mL) was stirred in a round bottom flask at 100° C. overnight. The mixture was evaporated in vacuum to afford the crude product, which was further purified with silica gel column chromatography (PE:EtOAc=5:1~2:1 gradient elution) to give the product (1.2 g, 40%). $[M+H]^+$=783.7.

Step 4: (R)-3-(tert-butyl)-N-(1-(4-(6-(5-(1-((1-(4-(2,4-dioxotetrahydropyrimidin-1(2H)-yl)phenyl)piperidin-4-yl)methyl)-3-hydroxyazetidin-3-yl)pyridin-2-yl)-7H-pyrrolo[2,3-d]pyrimidin-4-yl)-2-methylphenyl)ethyl)-1,2,4-oxadiazole-5-carboxamide A solution of tert-butyl (R)-3-(6-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)pyridin-3-yl)-3-hydroxyazetidine-1-carboxylate (220 mg, 8.9 mmol) in trifluoroacetic acid (8 mL) was stirred in a round bottom flask at room temperature overnight. The mixture was evaporated in vacuum to afford the crude product (R)-3-(tert-butyl)-N-(1-(4-(6-(5-(3-hydroxyazetidin-3-yl)pyridin-2-yl)-7H-pyrrolo[2,3-d]pyrimidin-4-yl)-2-methylphenyl)ethyl)-1,2,4-oxadiazole-5-carboxamide (230 mg, crude), which was used for next step without further purification. A mixture of (R)-3-(tert-butyl)-N-(1-(4-(6-(5-(3-hydroxyazetidin-3-yl)pyridin-2-yl)-7H-pyrrolo[2,3-d]pyrimidin-4-yl)-2-methylphenyl)ethyl)-1,2,4-oxadiazole-5-carboxamide (230 mg, crude) and 1-(4-(2,4-dioxotetrahydropyrimidin-1(2H)-yl)phenyl)piperidine-4-carbaldehyde (80 mg, 0.27 mmol) in 1,2-dichloromethane (30 mL) and MeOH (5 mL) was stirred in a round bottom flask at room temperature for 1 hour. To the mixture was added $NaBH(OAc)_3$ (100 mg, 0.47 mmol) and stirred in a round bottom flask at room temperature overnight. Then the mixture was evaporated in vacuum to afford the crude product, which was purified with silica gel column chromatography (DCM:MeOH=100:0~100:15 gradient elution) to give the product (65 mg, 28%). $^1H$ NMR (400 MHz, DMSO) $\delta_H$ 12.82 (s, 1H), 10.26 (s, 1H), 9.97 (d, J=7.6 Hz, 1H), 8.98 (s, 1H), 8.84 (s, 1H), 8.28-8.01 (m, 4H), 7.69 (d, J=8.2 Hz, 1H), 7.61 (s, 1H), 7.13 (d, J=8.8 Hz, 2H), 6.93 (d, J=8.8 Hz, 2H), 6.21 (s, 1H), 5.44-5.33 (m, 1H), 3.74-3.60 (m, 6H), 2.73-2.53 (m, 11H), 1.82 (d, J=12.0 Hz, 2H), 1.60-1.45 (m, 4H), 1.37 (s, 9H), 1.34-1.22 (m, 2H); $[M+H]^+$= 838.4.

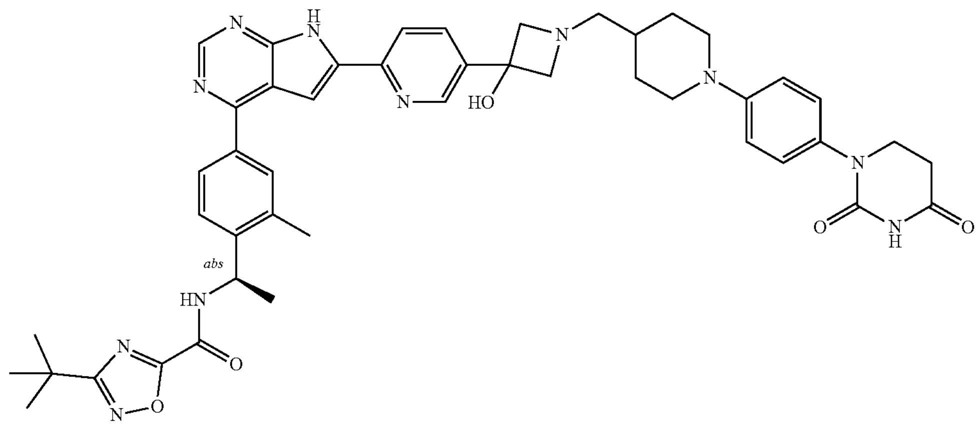 [SMILES: Cc1cc(-c2ncnc3[nH]c(-c4ccc(C5(O)CN(CC6CCN(c7ccc(N8CCC(=O)NC8=O)cc7)CC6)C5)cn4)cc23)ccc1[C@@H](C)NC(=O)c1nc(C(C)(C)C)no1]

Example 173: (R)-3-(tert-butyl)-N-(1-(4-(6-(5-(1-((1-(4-(2,4-dioxotetrahydropyrimidin-1(2H)-yl)phenyl)piperidin-4-yl)methyl)-3-fluoroazetidin-3-yl)pyridin-2-yl)-7H-pyrrolo[2,3-d]pyrimidin-4-yl)-2-methylphenyl)ethyl)-1,2,4-oxadiazole-5-carboxamide Step 1: tert-butyl 3-(6-(4-chloro-7-((2-(trimethylsilyl)ethoxy)methyl)-7H-pyrrolo[2,3-d]pyrimidin-6-yl)pyridin-3-yl)-3-fluoroazetidine-1-carboxylate

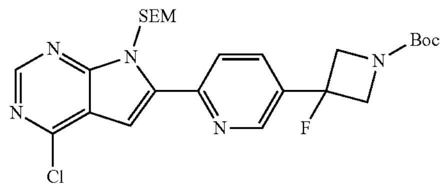 [SMILES: CC(C)(C)OC(=O)N1CC(F)(c2ccc(-c3cc4c(Cl)ncnc4n3COCC[Si](C)(C)C)nc2)C1]

To a solution of tert-butyl 3-(6-(4-chloro-7-((2-(trimethylsilyl)ethoxy)methyl)-7H-pyrrolo[2,3-d]pyrimidin-6-yl)pyridin-3-yl)-3-hydroxyazetidine-1-carboxylate (520 mg, 0.98 mmol) in DCM (30 mL) was added a solution of DAST (700 mg, 4.35 mmol) in 10 mL of DCM at −60° C. The reaction mixture was stirred for 2 hours at −60° C., then warmed to −10° C. in 2 hours. The reaction mixture was quenched with saturated $NaHCO_3$ aqueous solution. The resulting solution was extracted with 50 mL of DCM. The organic layer was dried over $Na_2SO_4$ and concentrated under vacuum to afford a crude residue. The crude product was purified by column chromatography (PE:EtOAc=5: 1-1:1 gradient elution) to afford the product (230 mg, 44%). $[M+H]^+$=534.5.

Step 2: tert-butyl (R)-3-(6-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)pyridin-3-yl)-3-fluoroazetidine-1-carboxylate

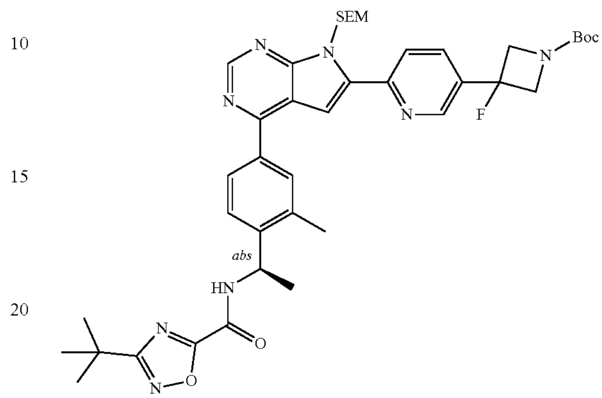

A mixture of tert-butyl 3-(6-(4-chloro-7-((2-(trimethylsilyl)ethoxy)methyl)-7H-pyrrolo[2,3-d]pyrimidin-6-yl)pyridin-3-yl)-3-fluoroazetidine-1-carboxylate (220 mg, 0.41 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (200 mg, 0.48 mmol), Pd(dppf)$Cl_2$ (0.02 g, 0.027 mmol) and $Cs_2CO_3$ (200 mg, 0.61 mmol) in 1,4-dioxane (8 mL) and $H_2O$ (2 mL) was stirred in a round bottom flask at 100° C. overnight. The mixture was evaporated in vacuum to afford the crude product, which was further purified with silica gel column chromatography (PE:EtOAc=5:1~2:1 gradient elution) to give the product (280 mg, 87%).

Step 3: (R)-3-(tert-butyl)-N-(1-(4-(6-(5-(1-((1-(4-(2,4-dioxotetrahydropyrimidin-1(2H)-yl)phenyl)piperidin-4-yl)methyl)-3-fluoroazetidin-3-yl)pyridin-2-yl)-7H-pyrrolo[2,3-d]pyrimidin-4-yl)-2-methylphenyl)ethyl)-1,2,4-oxadiazole-5-carboxamide

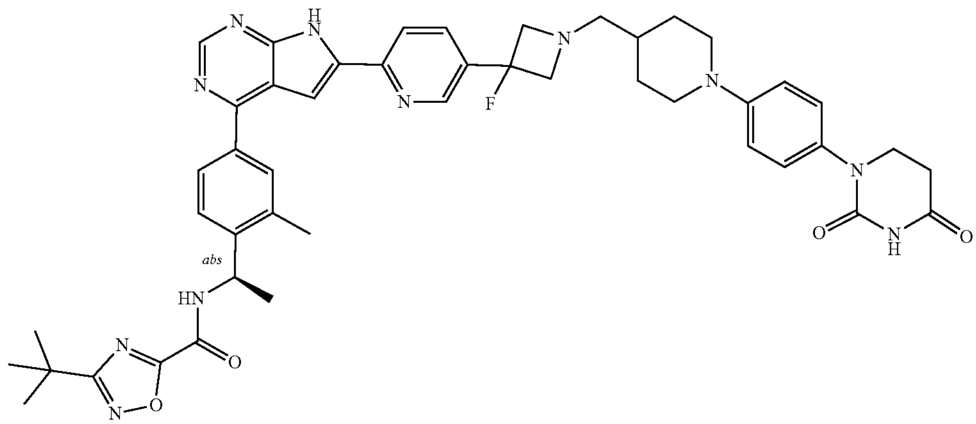 [SMILES: Cc1cc(-c2ncnc3[nH]c(-c4ccc(C5(F)CN(CC6CCN(c7ccc(N8CCC(=O)NC8=O)cc7)CC6)C5)cn4)cc23)ccc1[C@@H](C)NC(=O)c1nc(C(C)(C)C)no1]

A solution of tert-butyl (R)-3-(6-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)pyridin-3-yl)-3-fluoroazetidine-1-carboxylate (280 mg, 0.36 mmol) in trifluoroacetic acid (10 mL) was stirred in a round bottom flask at room temperature overnight. The mixture was evaporated in vacuum to afford the crude product (300 mg, crude) (R)-3-(tert-butyl)-N-(1-(4-(6-(5-(3-fluoroazetidin-3-yl)pyridin-2-yl)-7H-pyrrolo[2,3-d]pyrimidin-4-yl)-2-methylphenyl)ethyl)-1,2,4-oxadiazole-5-carboxamide, which was used for next step without further purification. A mixture of (R)-3-(tert-butyl)-N-(1-(4-(6-(5-(3-fluoroazetidin-3-yl)pyridin-2-yl)-7H-pyrrolo[2,3-d]pyrimidin-4-yl)-2-methylphenyl)ethyl)-1,2,4-oxadiazole-5-carboxamide (300 mg, crude) and 1-(4-(2,4-dioxotetrahydropyrimidin-1(2H)-yl)phenyl)piperidine-4-carbaldehyde (130 mg, 0.43 mmol) in 1,2-dichloromethane (20 mL) and MeOH (4 mL) was stirred in a round bottom flask at room temperature for 1 hour. To the mixture was added $NaBH(OAc)_3$ (200 mg, 0.94 mmol) and stirred in a round bottom flask at room temperature overnight. Then the mixture was evaporated in vacuum to afford the crude product, which was purified with silica gel column chromatography (DCM:MeOH=100:0~100:15 gradient elution) to give the product (160 mg, 53%). $^1H$ NMR (400 MHz, DMSO) $\delta_H$ 12.90 (s, 1H), 10.26 (s, 1H), 9.97 (d, J=8.0 Hz, 1H), 8.86 (s, 2H), 8.32 (d, J=8.2 Hz, 1H), 8.09 (d, J=8.0 Hz, 2H), 8.04 (s, 1H), 7.74-7.66 (m, 2H), 7.17-7.09 (m, 2H), 6.97-6.90 (m, 3H), 5.45-5.32 (m, 1H), 3.86-3.50 (m, 10H), 2.73-2.53 (m, 7H), 1.87-1.69 (m, 2H), 1.56 (d, J=6.8 Hz, 3H), 1.37 (s, 9H), 1.33-1.19 (m, 2H); $[M+H]^+$=840.8.

Example 174: (R)-3-(tert-butyl)-N-(1-(4-(6-(5-(1-((1-(4-(2,4-dioxotetrahydropyrimidin-1(2H)-yl)phenyl)piperidin-4-yl)methyl)-1,2,3,6-tetrahydropyridin-4-yl)-1,4-dimethyl-1H-pyrazol-3-yl)-7H-pyrrolo[2,3-d]pyrimidin-4-yl)-2-methylphenyl)ethyl)-1,2,4-oxadiazole-5-carboxamide

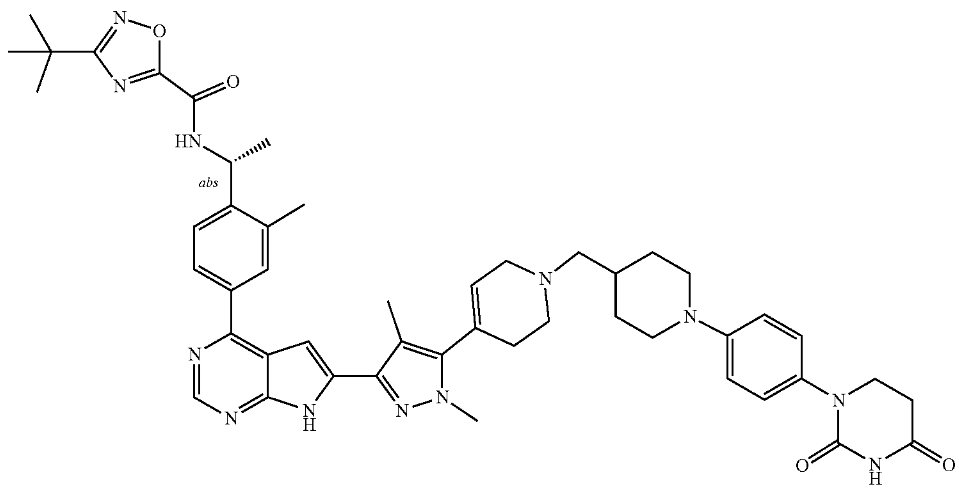 [SMILES: Cc1cc(-c2ncnc3[nH]c(-c4nn(C)c(C5=CCN(CC6CCN(c7ccc(N8CCC(=O)NC8=O)cc7)CC6)CC5)c4C)cc23)ccc1[C@@H](C)NC(=O)c1nc(C(C)(C)C)no1]

The titled compound was synthesized in the procedures similar to Example 25. $^1H$ NMR (400 MHz, DMSO) $\delta_H$ 12.45 (s, 1H), 10.26 (s, 1H), 9.97-9.88 (m, 1H), 8.79 (s, 1H), 8.10-7.92 (m, 2H), 7.68 (d, J=8.0 Hz, 1H), 7.19-7.09 (m, 2H), 7.01-6.87 (m, 3H), 5.94-5.82 (m, 1H), 5.42-5.31 (m, 1H), 3.92-3.66 (m, 9H), 3.24-3.09 (m, 3H), 3.10-2.82 (m, 4H), 2.76-2.63 (m, 6H), 2.38-2.29 (m, 2H), 2.26-2.15 (m, 3H), 1.55 (d, J=6.8 Hz, 3H), 1.36 (s, 9H); $[M+H]^+$=865.9.

Example 175: (R)-3-(tert-butyl)-N-(1-(4-(6-(1-(1-(2-(((1-(4-(2,4-dioxotetrahydropyrimidin-1(2H)-yl)phenyl)piperidin-4-yl)methyl)amino)ethyl)piperidin-4-yl)-3,5-dimethyl-1H-pyrazol-4-yl)-7H-pyrrolo[2,3-d]pyrimidin-4-yl)-2-methylphenyl)ethyl)-1,2,4-oxadiazole-5-carboxamide

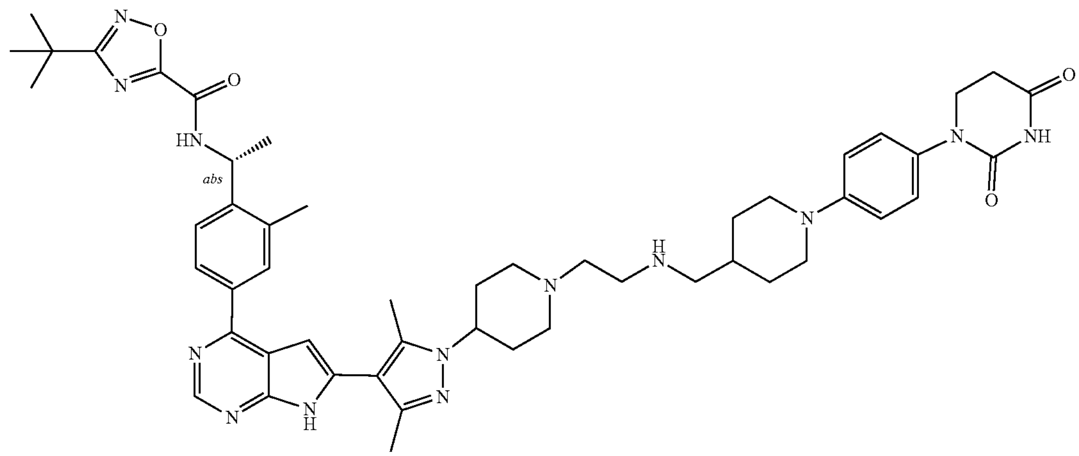 [SMILES: Cc1cc(-c2ncnc3[nH]c(-c4c(C)nn(C5CCN(CCNCC6CCN(c7ccc(N8CCC(=O)NC8=O)cc7)CC6)CC5)c4C)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.14 (s, 1H), 10.26 (s, 1H), 9.93 (d, J=7.6 Hz, 1H), 8.78 (s, 1H), 8.08-7.92 (m, 2H), 7.65 (d, J=7.6 Hz, 1H), 7.15 (d, J=8.4 Hz, 2H), 6.96 (d, J=8.4 Hz, 2H), 6.74 (s, 1H), 5.37 (s, 1H), 4.18 (s, 1H), 3.78-3.63 (m, 5H), 3.10-2.82 (m, 8H), 2.68 (s, 7H), 2.37 (s, 3H), 2.27 (s, 3H), 2.23-2.09 (m, 4H), 1.96-1.72 (m, 5H), 1.54 (d, J=6.4 Hz, 3H), 1.36 (s, 9H); $[M+H]^+$=910.9.

Example 176: 3-(tert-butyl)-N-((1R)-1-(4-(6-(5-(1-((1-(4-(2,4-dioxotetrahydropyrimidin-1(2H)-yl)phenyl)piperidin-4-yl)methyl)pyrrolidin-3-yl)pyridin-2-yl)-7H-pyrrolo[2,3-d]pyrimidin-4-yl)-2-methylphenyl)ethyl)-1,2,4-oxadiazole-5-carboxamide

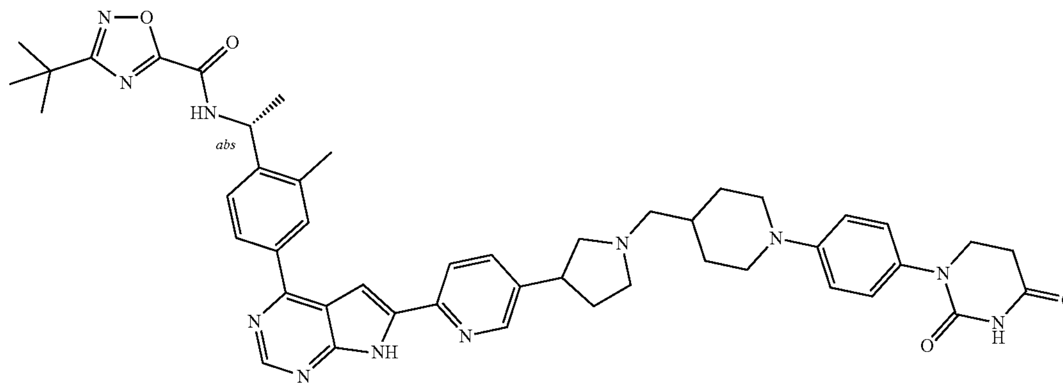 [SMILES: Cc1cc(-c2ncnc3[nH]c(-c4ccc(C5CCN(CC6CCN(c7ccc(N8CCC(=O)NC8=O)cc7)CC6)C5)cn4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.80 (s, 1H), 10.26 (s, 1H), 9.96 (d, J=7.0 Hz, 1H), 8.84 (s, 1H), 8.66 (s, 1H), 8.32-7.86 (m, 4H), 7.69 (d, J=7.8 Hz, 1H), 7.61 (s, 1H), 7.14 (d, J=8.0 Hz, 2H), 6.95 (d, J=7.6 Hz, 2H), 5.44-5.33 (m, 1H), 3.69 (s, 4H), 2.85-2.53 (m, 17H), 1.88 (s, 2H), 1.56 (d, J=6.4 Hz, 3H), 1.37 (s, 9H), 1.32-1.16 (m, 2H); $[M+H]^+$=836.8.

Example 177: 3-(tert-butyl)-N-((1R)-1-(4-(6-(5-(1-((1-(4-(2,4-dioxotetrahydropyrimidin-1(2H)-yl)phenyl)piperidin-4-yl)methyl)-3-fluoropyrrolidin-3-yl)pyridin-2-yl)-7H-pyrrolo[2,3-d]pyrimidin-4-yl)-2-methylphenyl)ethyl)-1,2,4-oxadiazole-5-carboxamide

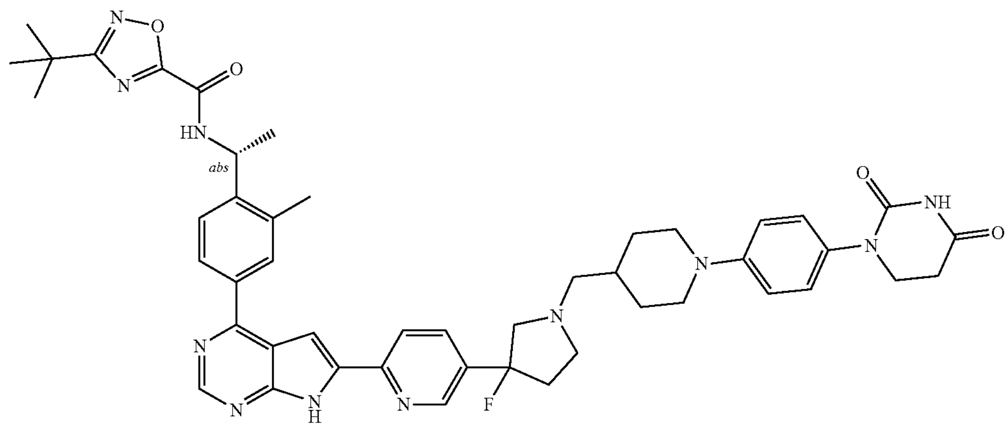 [SMILES: Cc1cc(-c2ncnc3[nH]c(-c4ccc(C5(F)CCN(CC6CCN(c7ccc(N8CCC(=O)NC8=O)cc7)CC6)C5)cn4)cc23)ccc1[C@@H](C)NC(=O)c1nc(C(C)(C)C)no1]

The titled compound was synthesized in the procedures similar to Example 25. $^1H$ NMR (400 MHz, DMSO) $\delta_H$ 12.87 (s, 1H), 10.25 (s, 1H), 9.96 (d, J=8.0 Hz, 1H), 8.85 (s, 1H), 8.76 (s, 1H), 8.27 (d, J=8.0 Hz, 1H), 8.14-7.95 (m, 3H), 7.75-7.62 (m, 2H), 7.13 (d, J=8.8 Hz, 2H), 6.93 (d, J=8.8 Hz, 2H), 5.43-5.34 (m, 1H), 3.76-3.64 (m, 4H), 3.23-2.53 (m, 13H), 2.47-2.27 (m, 2H), 1.85 (d, J=11.2 Hz, 2H), 1.65 (s, 1H), 1.56 (d, J=6.8 Hz, 3H), 1.37 (s, 9H), 1.32-1.24 (m, 2H); $[M+H]^+$=854.7.

Example 178: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-5-fluoro-2-(hydroxymethyl)phenyl)ethyl)-1,2,4-oxadiazole-5-carboxamide Step 1: (R)-3-(tert-butyl)-N-(1-(2-(((tert-butyldiphenylsilyl)oxy)methyl)-5-fluoro-4-(4,4,5,5-tetramethyl-1,3,2-dioxaborolan-2-yl)phenyl)ethyl)-1,2,4-oxadiazole-5-carboxamide

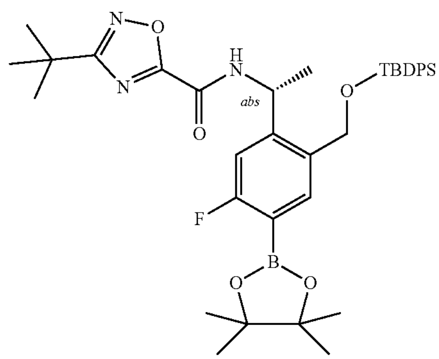

To a solution of sodium 3-(tert-butyl)-1,2,4-oxadiazole-5-carboxylate (1.28 g, 0.00665 mol) in DCM (30 mL), DMF (0.06 mL) was added. Then $(COCl)_2$ (6.65 mL, 2 M in THF, 0.0133 mol) was added dropwise. The mixture was stirred at room temperature for 3 hours. The mixture was concentrated in vacuo, and the residue was diluted with DCM (30 mL) and filtered. The filtrate was added dropwise into a solution of (R)-1-(2-(((tert-butyldiphenylsilyl)oxy)methyl)-5-fluoro-4-(4,4,5,5-tetramethyl-1,3,2-dioxaborolan-2-yl)phenyl)ethan-1-amine (2.62 g, 0.00493 mol) and TEA (2.48 g, 0.0246 mol) in DCM (30 mL). The mixture was stirred at room temperature for 1.5 hours. After the reaction was completed determined by LCMS, the mixture was evaporated in vacuum to afford the crude product, which was further purified with silica gel column chromatography (PE:EtOAc=100%: 0%-75%: 25% gradient elution) to give the product (2.8 g, crude). $[M+H]^+$=686.7.

Step 2: tert-butyl (R)-4-(6-(4-(4-(1-(3-(tert-butyl)-1,2,4-oxadiazole-5-carboxamido)ethyl)-5-(((tert-butyldiphenylsilyl)oxy)methyl)-2-fluorophenyl)-7-((2-(trimethylsilyl)ethoxy)methyl)-7H-pyrrolo[2,3-d]pyrimidin-6-yl)pyridin-3-yl)piperazine-1-carboxylate

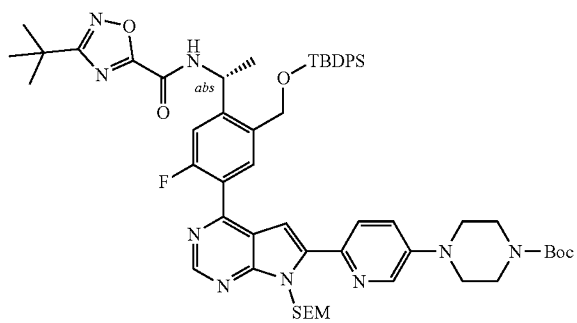

A mixture of tert-butyl 4-(6-(4-chloro-7-((2-(trimethylsilyl)ethoxy)methyl)-7H-pyrrolo[2,3-d]pyrimidin-6-yl)pyridin-3-yl)piperazine-1-carboxylate (200 mg, 0.368 mmol), (R)-3-(tert-butyl)-N-(1-(2-(((tert-butyldiphenylsilyl)oxy)methyl)-5-fluoro-4-(4,4,5,5-tetramethyl-1,3,2-dioxaborolan-2-yl)phenyl)ethyl)-1,2,4-oxadiazole-5-carboxamide (327 mg, 0.478 mmol), $Pd(dppf)Cl_2$ (13.5 mg, 0.0184 mmol) and $K_2CO_3$ (91.4 mg, 0.662 mmol) in 1,4-dioxane (10 mL) and $H_2O$ (2 mL) was stirred in a round bottom flask at 93° C. overnight. The mixture was evaporated in vacuum to afford the crude product, which was further purified with silica gel column chromatography (PE:EtOAc=100%: 0%-50%: 50% gradient elution) to give the product (182 mg, crude). $[M+H]^+$=1068.0.

Step 3: (R)-3-(tert-butyl)-N-(1-(5-fluoro-2-(hydroxymethyl)-4-(6-(5-(piperazin-1-yl)pyridin-2-yl)-7H-pyrrolo[2,3-d]pyrimidin-4-ylphenyl)ethyl)-1,2,4-oxadiazole-5-carboxamide

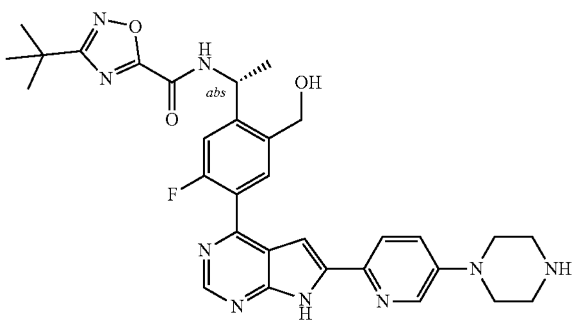 [SMILES: C[C@@H](NC(=O)c1nc(C(C)(C)C)no1)c1cc(F)c(-c2ncnc3[nH]c(-c4ccc(N5CCNCC5)cn4)cc23)cc1CO]

To a stirred solution of tert-butyl (R)-4-(6-(4-(4-(1-(3-(tert-butyl)-1,2,4-oxadiazole-5-carboxamido)ethyl)-5-(((tert-butyldiphenylsilyl)oxy)methyl)-2-fluorophenyl)-7-((2-(trimethylsilyl)ethoxy)methyl)-7H-pyrrolo[2,3-d]pyrimidin-6-yl)pyridin-3-yl)piperazine-1-carboxylate (182 mg, crude) in DCM (5 mL) was added TFA (5 mL). The mixture was stirred at room temperature overnight. Then the mixture was concentrated in vacuo. The residue was diluted with MeOH (5 mL), and $NH_3$ (7 M in MeOH, 0.5 mL) was added. The mixture was stirred at room temperature for 2 hours and evaporated in vacuum to afford the crude product, which was purified by C18 gel column chromatography (water:MeCN=100%:0%~90%:10%) to give the target product (20 mg, 19%). $[M+H]^+$=600.5.

Step 4: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-5-fluoro-2-(hydroxymethyl)phenyl)ethyl)-1,2,4-oxadiazole-5-carboxamide

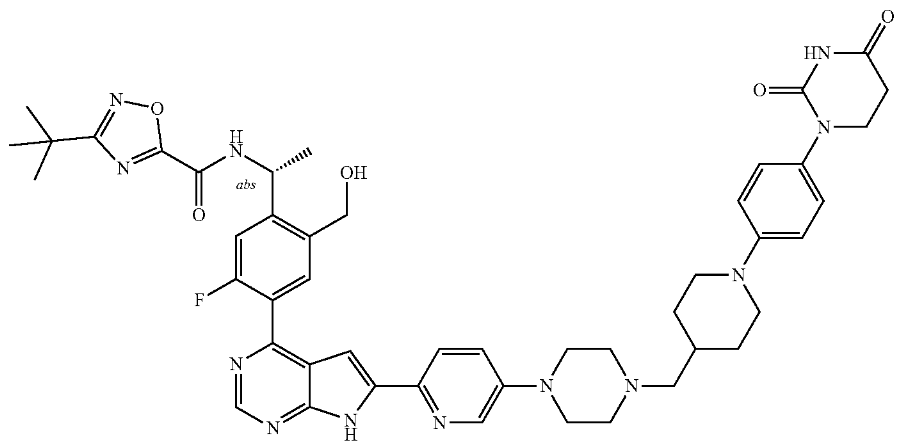 [SMILES: C[C@@H](NC(=O)c1nc(C(C)(C)C)no1)c1cc(F)c(-c2ncnc3[nH]c(-c4ccc(N5CCN(CC6CCN(c7ccc(N8CCC(=O)NC8=O)cc7)CC6)CC5)cn4)cc23)cc1CO]

A solution of (R)-3-(tert-butyl)-N-(1-(5-fluoro-2-(hydroxymethyl)-4-(6-(5-(piperazin-1-yl)pyridin-2-yl)-7H-pyrrolo[2,3-d]pyrimidin-4-yl)phenyl)ethyl)-1,2,4-oxadiazole-5-carboxamide (20 mg, 0.033 mmol) in DCM (3 mL) and MeOH (3 mL) was stirred in a round bottom flask at room temperature. 1-(4-(2,4-dioxotetrahydropyrimidin-1(2H)-yl)phenyl)piperidine-4-carbaldehyde (15 mg, 0.050 mmol), and HOAc (0.06 mL) were added. The mixture was stirred at room temperature overnight. To the mixture was added $NaBH(OAc)_3$ (35 mg, 0.165 mmol) and stirred in a round bottom flask at room temperature for 1 hour. Then the mixture was evaporated in vacuum to afford the crude product, which was purified with silica gel column chromatography (DCM:MeOH=100%: 0%-92%: 8%, gradient elution) to give the product (20.75 mg, 70%). $^1H$ NMR (400 MHz, DMSO) $\delta_H$ 12.63 (s, 1H), 10.26 (s, 1H), 9.95 (d, J=8.0 Hz, 1H), 8.82 (s, 1H), 8.37 (s, 1H), 7.97 (d, J=8.0 Hz, 1H), 7.86 (d, J=8.0 Hz, 1H), 7.59 (d, J=12.0 Hz, 1H), 7.42 (d, J=8.0 Hz, 1H), 7.13 (d, J=8.0 Hz, 2H), 7.00 (s, 1H), 6.93 (d, J=8.0 Hz, 2H), 5.48-5.34 (m, 2H), 4.89-4.64 (m, 2H), 3.78-3.62 (m, 4H), 3.20-2.80 (m, 2H), 2.74-2.63 (m, 4H), 2.54 (s, 5H), 2.24 (d, J=4.0 Hz, 2H), 1.82 (d, J=12.0 Hz, 2H), 1.73 (s, 1H), 1.58 (d, J=8.0 Hz, 3H), 1.38 (s, 9H), 1.30-1.22 (s, 3H); $[M+H]^+$=885.8.

Example 179: (R)-3-(tert-butyl)-N-(1-(4-(6-(6-(1-((1-(4-(2,4-dioxotetrahydropyrimidin-1(2H)-yl)phenyl)piperidin-4-yl)methyl)azetidin-3-yl)pyridin-3-yl)-7H-pyrrolo[2,3-d]pyrimidin-4-yl)-2-methylphenyl)ethyl)-1,2,4-oxadiazole-5-carboxamide

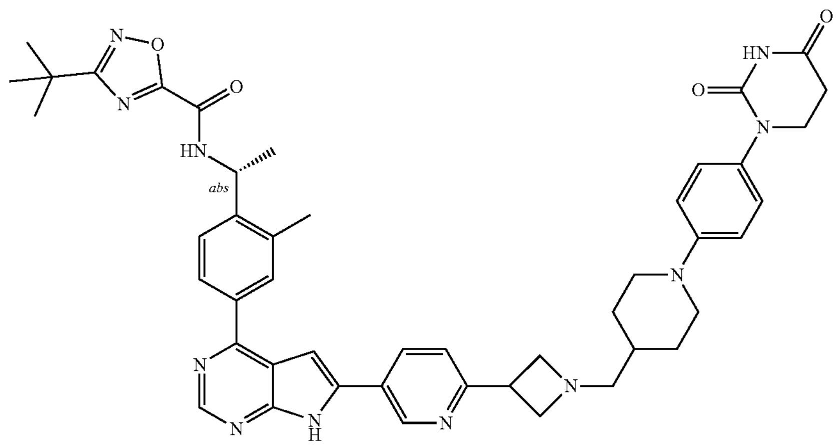 [SMILES: Cc1cc(-c2ncnc3[nH]c(-c4ccc(C5CN(CC6CCN(c7ccc(N8CCC(=O)NC8=O)cc7)CC6)C5)nc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.86 (s, 1H), 10.26 (s, 1H), 9.97 (d, J=8.0 Hz, 1H), 9.24 (s, 1H), 8.84 (s, 1H), 8.39 (d, J=8.0 Hz, 1H), 8.11 (d, J=8.0 Hz, 1H), 8.05 (s, 1H), 7.68 (d, J=8.0 Hz, 1H), 7.56 (s, 1H), 7.51 (d, J=8.0 Hz, 1H), 7.13 (d, J=8.0 Hz, 2H), 6.93 (d, J=8.0 Hz, 2H), 5.46-5.15 (m, 1H), 3.92-3.81 (m, 1H), 3.75 (s, 2H), 3.72-3.64 (m, 4H), 3.42 (s, 3H), 2.73-2.59 (m, 5H), 2.54 (s, 3H), 1.91 (s, 2H), 1.79 (d, J=12.0 Hz, 2H), 1.60-1.45 (m, 4H), 1.37 (s, 9H), 1.31-1.20 (m, 2H); [M+H]$^+$=822.8.

Example 180: 3-(tert-butyl)-N-((1R)-1-(4-(6-(5-(1-((1-(4-(2,4-dioxotetrahydropyrimidin-1(2H)-yl)phenyl)piperidin-4-yl)methyl)-3-hydroxypyrrolidin-3-yl)pyridin-2-yl)-7H-pyrrolo[2,3-d]pyrimidin-4-yl)-2-methylphenyl)ethyl)-1,2,4-oxadiazole-5-carboxamide

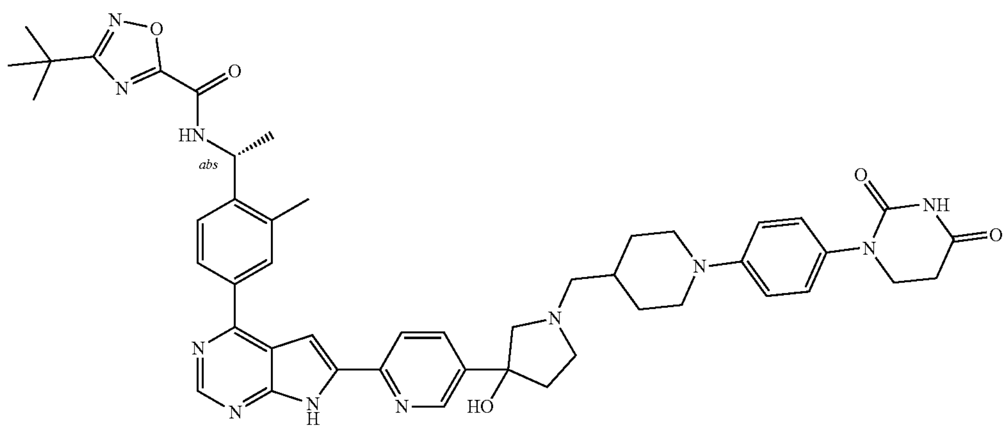 [SMILES: Cc1cc(-c2ncnc3[nH]c(-c4ccc(C5(O)CCN(CC6CCN(c7ccc(N8CCC(=O)NC8=O)cc7)CC6)C5)cn4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.81 (s, 1H), 10.26 (s, 1H), 9.96 (d, J=7.8 Hz, 1H), 8.84 (s, 2H), 8.28-7.95 (m, 4H), 7.69 (d, J=8.2 Hz, 1H), 7.61 (s, 1H), 7.13 (d, J=8.8 Hz, 2H), 6.94 (d, J=8.6 Hz, 2H), 5.44-5.31 (m, 1H), 3.69 (t, J=6.6 Hz, 4H), 3.08-2.53 (m, 12H), 2.44-2.10 (m, 4H), 1.88-1.80 (m, 2H), 1.63 (s, 1H), 1.56 (d, J=6.8 Hz, 3H), 1.37 (s, 9H), 1.32-1.22 (m, 2H); [M+H]$^+$=852.8.

Example 181: 3-(tert-butyl)-N-((1R)-1-(4-(6-(5-(4-(4-(2,6-dioxopiperidin-3-yl)-3-fluorobenzyl)piperazin-1-yl)pyridin-2-yl)-7H-pyrrolo[2,3-d]pyrimidin-4-yl)-2-methylphenyl)ethyl)-1,2,4-oxadiazole-5-carboxamide

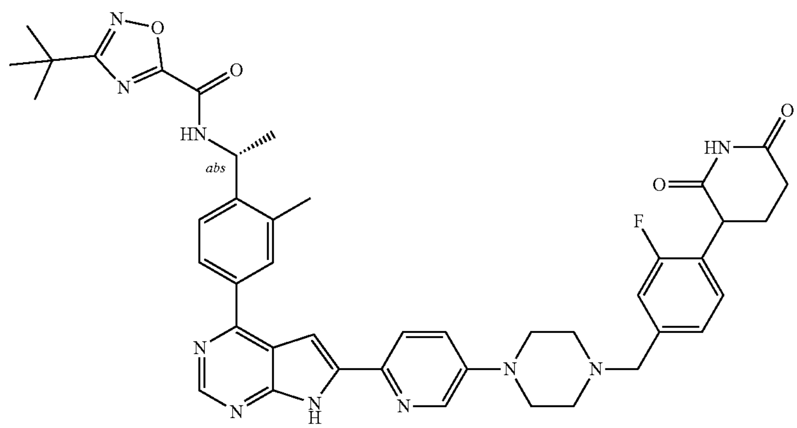 [SMILES: Cc1cc(-c2ncnc3[nH]c(-c4ccc(N5CCN(Cc6ccc(C7CCC(=O)NC7=O)c(F)c6)CC5)cn4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.60 (s, 1H), 10.89 (s, 1H), 9.95 (d, J=8.4 Hz, 1H), 8.78 (s, 1H), 8.38 (s, 1H), 8.10-7.97 (m, 3H), 7.68 (d, J=8.4 Hz, 1H), 7.45 (s, 1H), 7.40 (s, 1H), 7.33-7.21 (m, 2H), 7.20-7.07 (m, 3H), 5.45-5.33 (m, 1H), 4.49 (d, J=5.2 Hz, 1H), 4.11-3.93 (m, 2H), 3.57 (s, 2H), 2.82-2.66 (m, 2H), 2.62-2.52 (m, 9H), 2.31-2.12 (m, 2H), 2.08-1.94 (m, 2H), 1.55 (d, J=6.8 Hz, 3H), 1.37 (s, 9H); [M+H]$^+$=785.7.

Example 182: 3-(tert-butyl)-N-((1R)-1-(4-(6-(4-(8-((1-(5-(2,4-dioxotetrahydropyrimidin-1(2H)-yl)pyridin-2-yl)piperidin-4-yl)methyl)-8-azabicyclo[3.2.1]octan-3-yl)phenyl)-7H-pyrrolo[2,3-d]pyrimidin-4-yl)-2-methylphenyl)ethyl)-1,2,4-oxadiazole-5-carboxamide

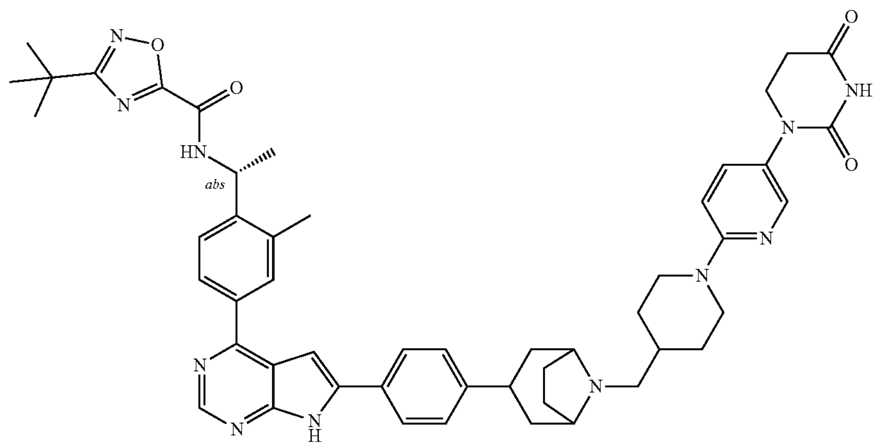 [SMILES: Cc1cc(-c2ncnc3[nH]c(-c4ccc(C5CC6CCC(C5)N6CC5CCN(c6ccc(N7CCC(=O)NC7=O)cn6)CC5)cc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.66 (s, 1H), 10.34 (s, 1H), 9.96 (d, J=8.0 Hz, 1H), 8.80 (s, 1H), 8.09 (d, J=8.0 Hz, 1H), 8.04 (s, 2H), 7.96 (d, J=8.0 Hz, 2H), 7.67 (d, J=8.0 Hz, 1H), 7.47 (dd, J=8.0, 4.0 Hz, 1H), 7.42 (d, J=8.0 Hz, 2H), 7.36 (s, 1H), 6.84 (d, J=8.0 Hz, 1H), 5.38 (s, 1H), 4.29 (d, J=12.0 Hz, 2H), 3.70 (t, J=8.0 Hz, 3H), 3.24 (s, 2H), 3.10-2.97 (m, 2H), 2.82 (t, J=12.0 Hz, 2H), 2.71 (t, J=8.0 Hz, 3H), 2.53 (s, 3H), 2.38-2.28 (m, 2H), 2.14 (d, J=8.0 Hz, 2H), 1.93-1.84 (m, 3H), 1.66 (s, 1H), 1.59-1.49 (m, 5H), 1.42 (d, J=8.0 Hz, 2H), 1.37 (s, 9H), 1.18-1.06 (m, 2H); [M+H]$^+$=876.9.

Example 183: 3-(tert-butyl)-N-((1R)-1-(4-(6-(4-(8-((1-(4-(2,4-dioxotetrahydropyrimidin-1(2H)-yl)phenyl)piperidin-4-yl)methyl)-8-azabicyclo[3.2.1]octan-3-yl)phenyl)-7H-pyrrolo[2,3-d]pyrimidin-4-yl)-2-methylphenyl)ethyl)-1,2,4-oxadiazole-5-carboxamide

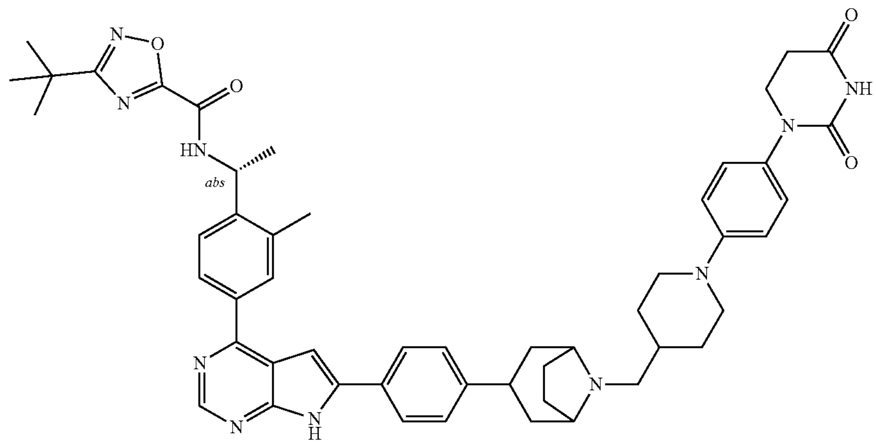 [SMILES: Cc1cc(-c2ncnc3[nH]c(-c4ccc(C5CC6CCC(C5)N6CC5CCN(c6ccc(N7CCC(=O)NC7=O)cc6)CC5)cc4)cc23)ccc1[C@@H](C)NC(=O)c1nc(C(C)(C)C)no1]

The titled compound was synthesized in the procedures similar to Example 25. $^1$H NMR (400 MHz, DMSO) $\delta_H$ 12.66 (s, 1H), 10.26 (s, 1H), 9.96 (d, J=8.0 Hz, 1H), 8.80 (s, 1H), 8.09 (d, J=8.0 Hz, 1H), 8.04 (s, 1H), 7.96 (d, J=8.0 Hz, 2H), 7.67 (d, J=8.0 Hz, 1H), 7.43 (d, J=8.0 Hz, 2H), 7.36 (s, 1H), 7.14 (d, J=8.0 Hz, 2H), 6.94 (d, J=8.0 Hz, 2H), 5.38 (s, 1H), 3.80-3.64 (m, 4H), 3.26 (s, 2H), 3.12-2.98 (m, 4H), 2.74-2.62 (m, 6H), 2.33 (s, 3H), 2.17 (s, 2H), 1.92 (s, 3H), 1.62-1.51 (m, 5H), 1.43 (d, J=8.0 Hz, 2H), 1.37 (s, 9H), 1.32-1.19 (m, 2H); $[M+H]^+$=875.8.

Example 184: (R)-3-(tert-butyl)-N-(1-(4-(6-(5-(4-((1-(4-(2,4-dioxoimidazolidin-1-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,2,4-oxadiazole-5-carboxamide

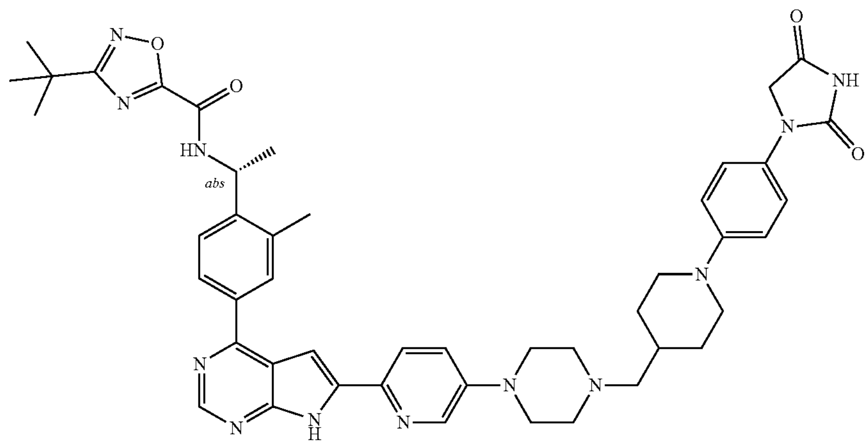 [SMILES: Cc1cc(-c2ncnc3[nH]c(-c4ccc(N5CCN(CC6CCN(c7ccc(N8CC(=O)NC8=O)cc7)CC6)CC5)cn4)cc23)ccc1[C@@H](C)NC(=O)c1nc(C(C)(C)C)no1]

The titled compound was synthesized in the procedures similar to Example 25. $^1$H NMR (500 MHz, DMSO) $\delta_H$ 12.54 (s, 1H), 10.97 (s, 1H), 9.89 (d, J=8.0 Hz, 1H), 8.71 (s, 1H), 8.32 (s, 1H), 8.04-7.94 (m, 3H), 7.61 (d, J=8.1 Hz, 1H), 7.36 (dd, J=26.7, 7.9 Hz, 4H), 6.87 (d, J=8.9 Hz, 2H), 5.51-5.10 (m, 1H), 4.32 (s, 2H), 3.57 (d, J=12.0 Hz, 2H), 3.44 (s, 2H), 3.22 (s, 5H), 2.62-2.52 (m, 3H), 2.47 (s, 6H), 2.17 (d, J=8.0 Hz, 2H), 1.75 (d, J=12.0 Hz, 2H), 1.64 (s, 1H), 1.49 (d, J=8.0 Hz, 3H), 1.30 (s, 9H); $[M+H]^+$=837.8.

Example 185: (R)-5-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)pyridin-2-yl)-7H-pyrrolo[2,3-d]pyrimidin-4-yl)-2-methylphenyl)ethyl)-1,3,4-oxadiazole-2-carboxamide

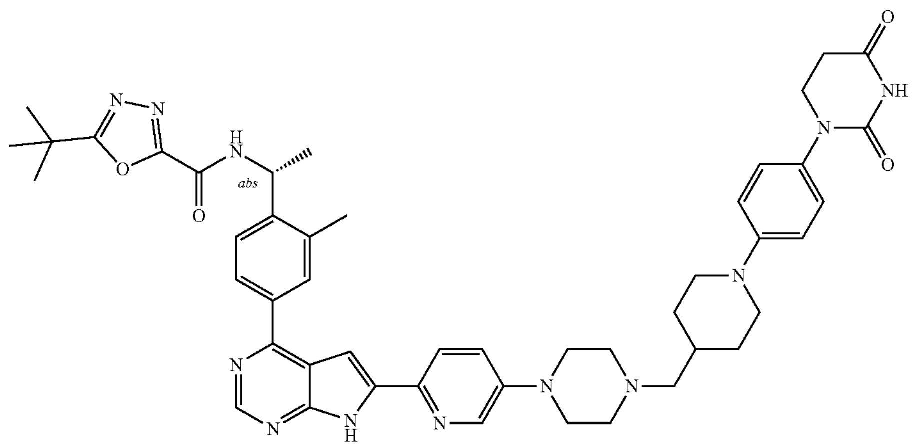 [SMILES: Cc1cc(-c2ncnc3[nH]c(-c4ccc(N5CCN(CC6CCN(c7ccc(N8CCC(=O)NC8=O)cc7)CC6)CC5)cn4)cc23)ccc1[C@@H](C)NC(=O)c1nnc(C(C)(C)C)o1]

A mixture of (R)-5-(tert-butyl)-N-(1-(2-methyl-4-(6-(5-(piperazin-1-yl)pyridin-2-yl)-7H-pyrrolo[2,3-d]pyrimidin-4-yl)phenyl)ethyl)-1,3,4-oxadiazole-2-carboxamide ((0.2 g, 0.345 mmol) and 1-(4-(2,4-dioxotetrahydropyrimidin-1(2H)-yl)phenyl)piperidine-4-carbaldehyde (117 mg, 0.39 mmol) in DCM (10 mL) and MeOH (2 mL) was stirred in a round bottom flask at room temperature for 1 hour. To the mixture was added $NaBH(OAc)_3$ (150 mg, 0.708 mmol) and stirred in a round bottom flask at room temperature overnight. Then the mixture was evaporated in vacuum to afford the crude product, which was purified with silica gel column chromatography (DCM:MeOH=100:0~80:20 gradient elution) to give the product (100 mg, 50%). $^1H$ NMR (400 MHz, DMSO) $\delta_H$ 12.60 (s, 1H), 10.25 (s, 1H), 9.90 (d, J=6.4 Hz, 1H), 8.78 (s, 1H), 8.39 (s, 1H), 8.06 (d, J=6.4 Hz, 2H), 8.01 (s, 1H), 7.68 (d, J=6.4 Hz, 1H), 7.48-7.43 (m, 1H), 7.39 (s, 1H), 7.13 (d, J=6.8 Hz, 2H), 6.93 (d, J=6.8 Hz, 2H), 5.43-5.30 (m, 1H), 3.75-3.57 (m, 4H), 2.77-2.60 (m, 4H), 2.54 (s, 5H), 2.27-2.20 (m, 2H), 1.85-1.78 (m, 2H), 1.54 (d, J=5.6 Hz, 2H), 1.39 (s, 9H), 1.28-1.17 (m, 2H); $[M+H]^+$=851.7.

Example 186: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)thiazol-2-yl)-7H-pyrrolo[2,3-d]pyrimidin-4-yl)-2-methylphenyl)ethyl)-1,2,4-oxadiazole-5-carboxamide Step 1: tert-butyl 4-(thiazol-5-yl)piperazine-1-carboxylate

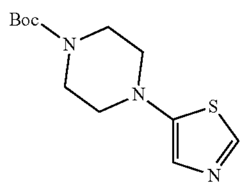 [SMILES: CC(C)(C)OC(=O)N1CCN(c2cncs2)CC1]

A mixture of 5-bromothiazole (2.5 g, 15.3 mmol), tert-butyl piperazine-1-carboxylate (3.43 g, 18.4 mmol), $Pd_2(dba)_3$ (701 mg, 0.76 mmol), Brettphos (821 mg, 1.53 mmol) and t-BuONa (2.95 g, 30.66 mmol) in dioxane (30 mL) was stirred at 90° C. for 16 h under a nitrogen atmosphere. The mixture was concentrated under vacuum. The residue was purified with silica gel column chromatography, eluting with EtOAc in PE from 0% to 50% to afford the product (3.4 g, 82.5%). $[M+H]^+$=270.1.

Step 2: tert-butyl 4-(2-iodothiazol-5-yl)piperazine-1-carboxylate

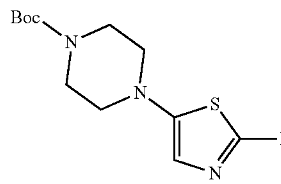

To a solution of tert-butyl 4-(thiazol-5-yl)piperazine-1-carboxylate (3.4 g, 12.6 mmol) in THF (50 mL) was added LDA (18.9 mL, 37.9 mmol) at −78° C. under a nitrogen atmosphere. The mixture was stirred at −78° C. for 2 h. Then, 12 (4.8 g, 18.9 mmol) was added. The mixture was warmed to room temperature and stirred at room temperature for 16 h. The mixture was quenched by saturated $Na_2S_2O_3$ solution (100 mL) and extracted with EtOAc (3×100 mL). The combined organic layers were dried over $Na_2SO_4$, filtered and concentrated under vacuum. The residue was purified with silica gel column chromatography, eluting with EtOAc in PE from 0% to 40% to afford the product (900 mg, 18%). $[M+H]^+$=396.0.

Step 3: tert-butyl 4-(2-(4-chloro-7-((2-(trimethylsilyl)ethoxy)methyl)-7H-pyrrolo[2,3-d]pyrimidin-6-yl)thiazol-5-yl)piperazine-1-carboxylate

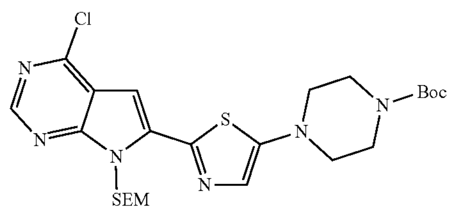 [SMILES: CC(C)(C)OC(=O)N1CCN(c2cnc(-c3cc4c(Cl)ncnc4n3COCC[Si](C)(C)C)s2)CC1]

A mixture of 4-chloro-6-(4,4,5,5-tetramethyl-1,3,2-dioxaborolan-2-yl)-7-((2-(trimethylsilyl)ethoxy)methyl)-7H-pyrrolo[2,3-d]pyrimidine (623 mg, 1.52 mmol), tert-butyl 4-(2-iodothiazol-5-yl)piperazine-1-carboxylate (720 mg, 1.82 mmol), Pd(dppf)$Cl_2$ (110 mg, 0.15 mmol), $K_2CO_3$ (138 mg, 3.0 mmol) in dioxane (20 mL) and $H_2O$ (4 mL) was stirred at 80° C. for 16 h under a nitrogen atmosphere. The mixture was concentrated under vacuum. The residue was purified with silica gel column chromatography, eluting with EtOAc in PE from 0% to 50% to afford the product (720 mg, 86%). $[M+H]^+$=551.2.

Step 4: tert-butyl (R)-4-(2-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)thiazol-5-yl)piperazine-1-carboxylate

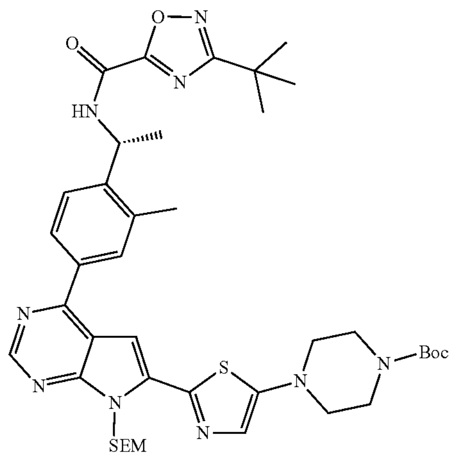 [SMILES: Cc1cc(-c2ncnc3c2cc(-c2ncc(N4CCN(C(=O)OC(C)(C)C)CC4)s2)n3COCC[Si](C)(C)C)ccc1[C@@H](C)NC(=O)c1nc(C(C)(C)C)no1]

A mixture of tert-butyl 4-(2-(4-chloro-7-((2-(trimethylsilyl)ethoxy)methyl)-7H-pyrrolo[2,3-d]pyrimidin-6-yl)thiazol-5-yl)piperazine-1-carboxylate (550 mg, 1 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (454 mg, 1.1 mmol), Pd(dppf)$Cl_2$ (73.1 mg, 0.1 mmol) and 2.0 N $Na_2CO_3$ (aq, 1.5 mL, 3 mmol) in dioxane (15 mL) was stirred at 100° C. for 16 h under a nitrogen atmosphere. The mixture was concentrated under vacuum. The residue was purified with silica gel column chromatography, eluting with EtOAc in PE from 0% to 60% to afford the product (610 mg, 76.1%). $[M+H]^+$=802.4.

Step 5: (R)-3-(tert-butyl)-N-(1-(2-methyl-4-(6-(5-(piperazin-1-yl)thiazol-2-yl)-7H-pyrrolo[2,3-d]pyrimidin-4-yl)phenyl)ethyl)-1,2,4-oxadiazole-5-carboxamide

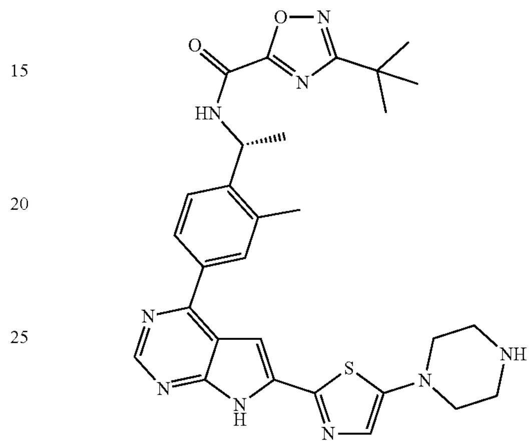

To a solution of tert-butyl (R)-4-(2-(4-(4-(1-(3-(tert-butyl)-1,2,4-oxadiazole-5-carboxamido)ethyl)-3-methylphenyl)-7-((2-(trimethylsilyl)ethoxy)methyl)-7H-pyrrolo[2,3-d]pyrimidin-6-yl)thiazol-5-yl)piperazine-1-carboxylate (610 mg, 0.75 mmol) in DCM (10 mL) was added TFA (10 mL). The reaction mixture was stirred at room temperature for 16 h and concentrated under vacuum. The residue was dissolved in MeOH (10 mL) and added 7.0 N $NH_3$ in MeOH (2 mL). The mixture was stirred at room temperature for 1 h and concentrated under vacuum to afford the product (600 mg, crude), which was used in the next step without further purification. $[M+H]^+$=572.2.

Step 6: (R)-3-(tert-butyl)-N-(1-(4-(6-(5-(4-((1-(4-(2,4-dioxotetrahydropyrimidin-1(2H)-yl)phenyl)piperidin-4-yl)methyl)piperazin-1-yl)thiazol-2-yl)-7H-pyrrolo[2,3-d]pyrimidin-4-yl)-2-methylphenyl)ethyl)-1,2,4-oxadiazole-5-carboxamide

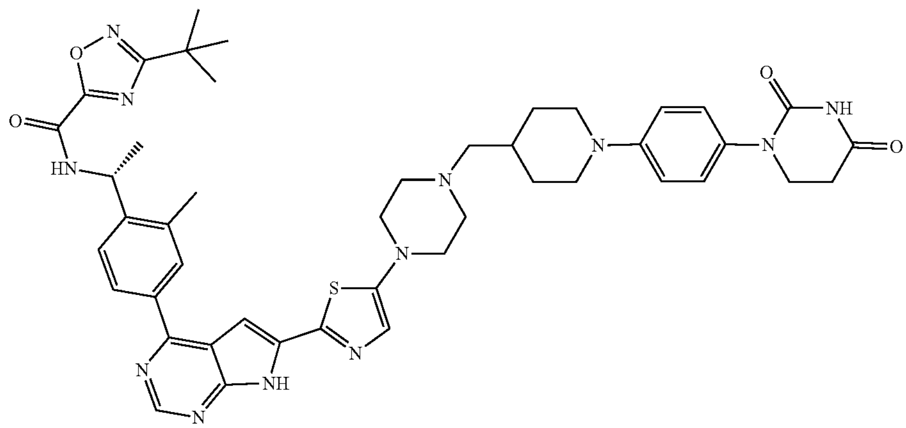 [SMILES: Cc1cc(-c2ncnc3[nH]c(-c4ncc(N5CCN(CC6CCN(c7ccc(N8CCC(=O)NC8=O)cc7)CC6)CC5)s4)cc23)ccc1[C@@H](C)NC(=O)c1nc(C(C)(C)C)no1]

A mixture of (R)-3-(tert-butyl)-N-(1-(2-methyl-4-(6-(5-(piperazin-1-yl)thiazol-2-yl)-7H-pyrrolo[2,3-d]pyrimidin-4-yl)phenyl)ethyl)-1,2,4-oxadiazole-5-carboxamide (120 mg, 0.21 mmol), 1-(4-(2,4-dioxotetrahydropyrimidin-1(2H)-yl)phenyl)piperidine-4-carbaldehyde (76 mg, 0.25 mmol) and AcOH (0.2 mL) in MeOH (10 mL) and DCM (10 mL) was stirred at room temperature for 16 h. Then, STAB (89 mg, 0.42 mmol) was added to the mixture above. The mixture was stirred at room temperature for 5 h. The mixture was quenched by water (100 mL) and extracted with DCM (3×100 mL). The combined organic layers were dried over $Na_2SO_4$, filtered and concentrated under vacuum. The residue was purified with silica gel column chromatography, eluting with MeOH in DCM from 0% to 10% to afford the product (13.85 mg, 7.7%). $^1$H NMR (500 MHz, DMSO) $\delta_H$ 12.89 (s, 1H), 10.27 (s, 1H), 9.97 (d, J=10.0 Hz, 1H), 8.80 (s, 1H), 8.04 (d, J=10.0 Hz, 1H), 7.99 (s, 1H), 7.67 (d, J=10.0 Hz, 1H), 7.19 (s, 2H), 7.13 (d, J=10.0 Hz, 2H), 6.93 (d, J=10.0 Hz, 2H), 5.40-5.33 (m, 1H), 3.73-3.65 (m, 4H), 3.26-3.19 (m, 4H), 2.71-2.62 (m, 5H), 2.57-2.52 (m, 7H), 2.27-2.21 (m, 2H), 1.84-1.77 (m, 2H), 1.75-1.66 (m, 1H), 1.54 (d, J=5.0 Hz, 1H), 1.37 (s, 9H), 1.28-1.17 (m, 3H); $[M+H]^+$=857.4.

Example 187: (R)-3-(tert-butyl)-N-(1-(4-(6-(6-(4-((1-(4-(2,4-dioxo-3,4-dihydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide

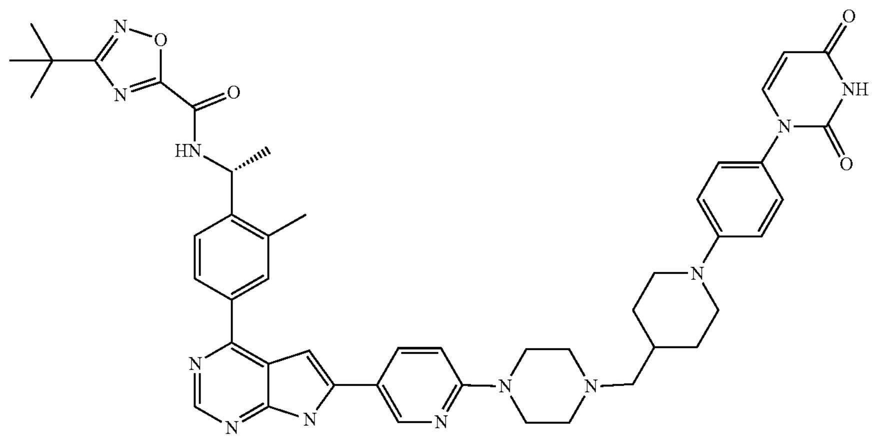

The titled compound was synthesized in the procedures similar to Example 25. $^1$H NMR (500 MHz, DMSO) $\delta_H$ 12.60 (s, 1H), 11.36 (s, 1H), 9.97 (d, J=7.8 Hz, 1H), 8.81 (s, 1H), 8.76 (s, 1H), 8.18 (d, J=7.8 Hz, 1H), 8.09 (d, J=8.2 Hz, 1H), 8.04 (s, 1H), 7.70-7.59 (m, 2H), 7.30 (s, 1H), 7.19 (d, J=8.6 Hz, 2H), 7.05-6.93 (m, 3H), 5.62 (d, J=7.6 Hz, 1H), 5.41-5.33 (m, 1H), 3.76 (d, J=11.8 Hz, 2H), 3.60 (s, 4H), 2.73 (t, J=11.8 Hz, 2H), 2.59-2.52 (m, 7H), 2.22 (d, J=6.8 Hz, 2H), 1.89-1.71 (m, 3H), 1.55 (d, J=6.8 Hz, 3H), 1.37 (s, 9H), 1.25-1.19 (m, 2H); $[M+H]^+$=849.6.

Example 188 and 189: 3-(tert-butyl)-N-((R)-1-(4-(6-(6-(4-((1R,3s)-3-(4-(((S)-2,6-dioxopiperidin-3-yl)amino)phenyl)cyclobutyl)piperazin-1-yl)pyridin-3-yl)-7H-pyrrolo[2,3-d]pyrimidin-4-yl)-2-methylphenyl)ethyl)-1,2,4-oxadiazole-5-carboxamide and 3-(tert-butyl)-N-((R)-1-(4-(6-(6-(4-((1S,3s)-3-(4-(((R)-2,6-dioxopiperidin-3-yl)amino)phenyl)cyclobutyl)piperazin-1-yl)pyridin-3-yl)-7H-pyrrolo[2,3-d]pyrimidin-4-yl)-2-methylphenyl)ethyl)-1,2,4-oxadiazole-5-carboxamide

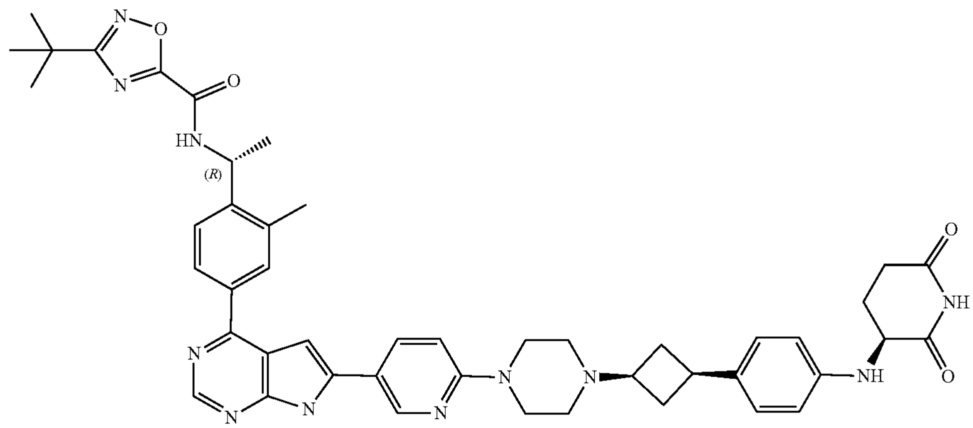

Example 188

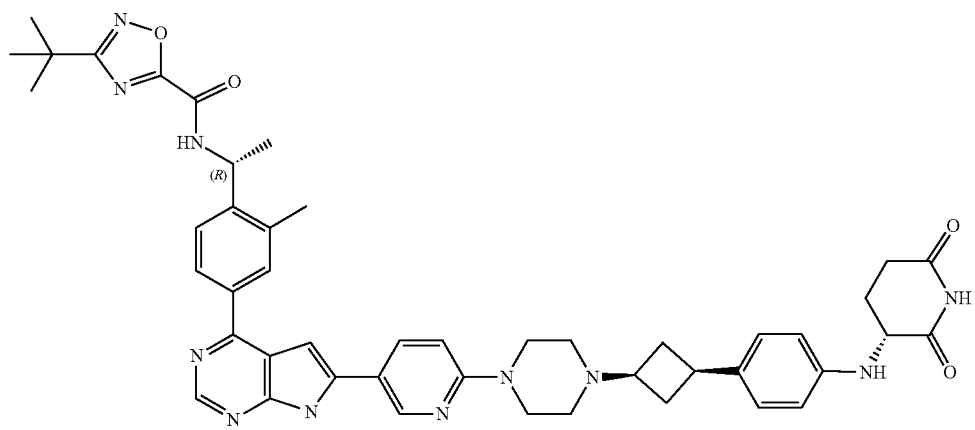

Example 189

A solution of (R)-3-(tert-butyl)-N-(1-(2-methyl-4-(6-(6-(piperazin-1-yl)pyridin-3-yl)-7H-pyrrolo[2,3-d]pyrimidin-4-yl)phenyl)ethyl)-1,2,4-oxadiazole-5-carboxamide (100 mg, 0.177 mmol), 3-((4-(3-oxocyclobutyl)phenyl)amino)piperidine-2,6-dione (72 mg, 0.266 mmol) and $Ti(i\text{-}PrO)_4$ (0.1 mL) in THF (8.0 mL) and DMF (4.0 mL) was stirred for 16 h at 25° C. Then $NaBH(OAc)_3$ (187.6 mg, 0.885 mmol) was added and stirred at room temperature for 2 h. The resulting mixture was extracted with dichloromethane (3×20 mL) and washed with water (30 mL). The organic phase was dried over anhydrous sodium sulfate, filtered and concentrated under reduced pressure to afford the crude product, which was purified with silica gel column chromatography (DCM: MeOH=100:0~90:10 gradient elution) and prep-HPLC to give Example 188 (9 mg, 6%) and Example 189 (23 mg, 16%). Example 188: $^1H$ NMR (500 MHz, DMSO) $\delta_H$ 12.59 (s, 1H), 10.77 (s, 1H), 9.95 (d, J=7.7 Hz, 1H), 8.81 (s, 1H), 8.76 (s, 1H), 8.18 (d, J=8.7 Hz, 1H), 8.09 (d, J=8.2 Hz, 1H), 8.04 (s, 1H), 7.66 (d, J=8.1 Hz, 1H), 7.29 (s, 1H), 6.96 (t, J=8.2 Hz, 3H), 6.64 (dd, J=16.2, 8.3 Hz, 3H), 5.68 (d, J=7.6 Hz, 1H), 5.40-5.36 (m, 1H), 4.35-4.23 (m, 1H), 3.69-3.55 (m, 4H), 3.54-3.46 (m, 1H), 3.14-3.06 (m, 1H), 3.03-2.92 (m, 1H), 2.79-2.70 (m, 1H), 2.69-2.62 (m, 1H), 2.62-2.55 (m, 1H), 2.54 (s, 3H), 2.45-2.34 (m, 3H), 2.14-2.06 (m, 1H), 1.91-1.75 (m, 3H), 1.55 (d, J=6.9 Hz, 3H), 1.37 (s, 9H); $[M+H]^+$=822.6. Example 189: $^1H$ NMR (500 MHz, DMSO) $\delta_H$ 12.58 (s, 1H), 10.76 (d, J=7.6 Hz, 1H), 9.95 (d, J=7.4 Hz, 1H), 8.86-8.78 (m, 1H), 8.76 (dd, J=4.0, 2.2 Hz, 1H), 8.29 (s, 1H), 8.17 (d, J=6.5 Hz, 1H), 8.09 (dd, J=11.9, 6.1 Hz, 1H), 8.04 (d, J=5.0 Hz, 1H), 7.66 (dd, J=7.9, 4.0 Hz, 1H), 7.33-7.23 (m, 1H), 7.03 (dd, J=16.2, 8.3 Hz, 1H), 6.99-6.87 (m, 2H), 6.70-6.56 (m, 2H), 5.66 (dd, J=24.9, 11.7 Hz, 1H), 5.42-5.31 (m, 1H), 4.34-4.19 (m, 1H), 3.69-3.54 (m, 4H), 3.16-2.96 (m, 2H), 2.91-2.62 (m, 5H), 2.62-2.52 (m, 6H), 2.17-2.03 (m, 1H), 1.94-1.79 (m, 2H), 1.55 (d, J=5.2 Hz, 3H), 1.36 (s, 9H); $[M+H]^+$=822.7.

Example 190: (R)-3-(tert-butyl)-N-(1-(4-(6-(4-(4-((1-(4-(2,4-dioxotetrahydropyrimidin-1(2H)-yl)phenyl)piperidin-4-yl)methyl)-3-oxopiperazin-1-yl)phenyl)-7H-pyrrolo[2,3-d]pyrimidin-4-yl)-2-methylphenyl)ethyl)-1,2,4-oxadiazole-5-carboxamide Step 1: 1-(4-(4-((2-oxo-4-(4-(4,4,5,5-tetramethyl-1,3,2-dioxaborolan-2-yl)phenyl)piperazin-1-yl)methyl)piperidin-1-yl)phenyl)-3-((2-(trimethylsilyl)ethoxy)methyl)dihydropyrimidine-2,4(1H,3H)-dione

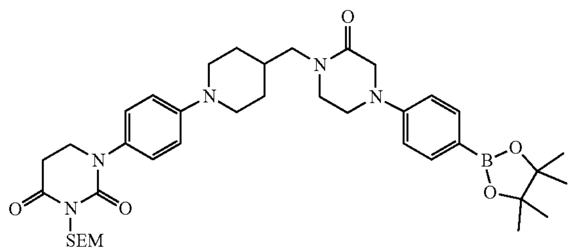 [SMILES: CC1(C)OB(c2ccc(N3CCN(CC4CCN(c5ccc(N6CCC(=O)N(COCC[Si](C)(C)C)C6=O)cc5)CC4)C(=O)C3)cc2)OC1(C)C]

A mixture of 1-(4-(4-((4-(4-bromophenyl)-2-oxopiperazin-1-yl)methyl)piperidin-1-yl)phenyl)-3-((2-(trimethylsilyl)ethoxy)methyl)dihydropyrimidine-2,4(1H,3H)-dione (1.0 g, 1.5 mmol), 4,4,4',4',5,5,5',5'-octamethyl-2,2'-bi(1,3,2-dioxaborolane) (456 mg, 1.8 mmol), Pd(dppf)$Cl_2$ (110 mg, 0.15 mmol) and KOAc (441 mg, 4.5 mmol) in 1,4-dioxane (20.0 mL) was stirred in a sealed tube at 100° C. overnight. The mixture was evaporated in vacuum to afford the crude product, which was further purified with silica gel column chromatography (PE:EtOAc=90:10~0:100 gradient elution) to give the titled product (370 mg, 34.4%). $[M+H]^+$=718.5.

Step 2: 1-(4-(4-((4-(4-(4-chloro-7H-pyrrolo[2,3-d]pyrimidin-6-yl)phenyl)-2-oxopiperazin-1-yl)methyl)piperidin-1-yl)phenyl)-3-((2-(trimethylsilyl)ethoxy)methyl)dihydropyrimidine-2,4(1H,3H)-dione

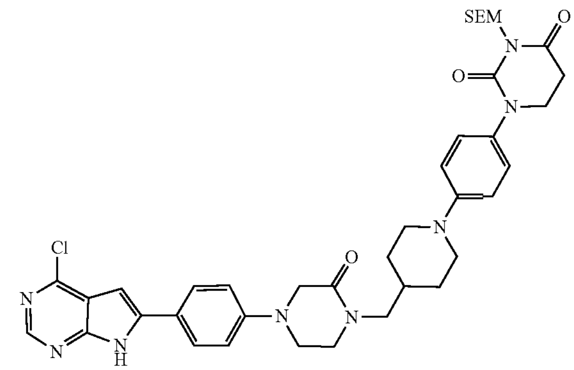 [SMILES: C[Si](C)(C)CCOCN1C(=O)CCN(C2=CCC=C(N3CCC(CN4CCN(c5ccc(-c6cc7c(Cl)ncnc7[nH]6)cc5)CC4=O)CC3)C=C2)C1=O]

A mixture of 1-(4-(4-((2-oxo-4-(4-(4,4,5,5-tetramethyl-1,3,2-dioxaborolan-2-yl)phenyl)piperazin-1-yl)methyl)piperidin-1-yl)phenyl)-3-((2-(trimethylsilyl)ethoxy)methyl)dihydropyrimidine-2,4(1H,3H)-dione (370 mg, 0.516 mmol), 4-chloro-6-iodo-7H-pyrrolo[2,3-d]pyrimidine (158 mg, 0.567 mmol), Pd(dppf)$Cl_2$ (37.3 mg, 0.0516 mmol) and $Na_2CO_3$ (109 mg, 1.03 mmol) in 1,4-dioxane (20.0 mL) and $H_2O$ (4.0 mL) was stirred in a round bottom flask at 95° C. overnight. The mixture was evaporated in vacuum to afford the crude product, which was further purified with silica gel column chromatography (DCM:MeOH=100:0~97:3 gradient elution) to give the product (240 mg, crude). $[M+H]^+$=743.4.

Step 3: (R)-3-(tert-butyl)-N-(1-(4-(6-(4-(4-((1-(4-(2,4-dioxo-3-((2-(trimethylsilyl)ethoxy)methyl)tetrahydropyrimidin-1(2H)-yl)phenyl)piperidin-4-yl)methyl)-3-oxopiperazin-1-yl)phenyl)-7H-pyrrolo[2,3-d]pyrimidin-4-yl)-2-methylphenyl)ethyl)-1,2,4-oxadiazole-5-carboxamide

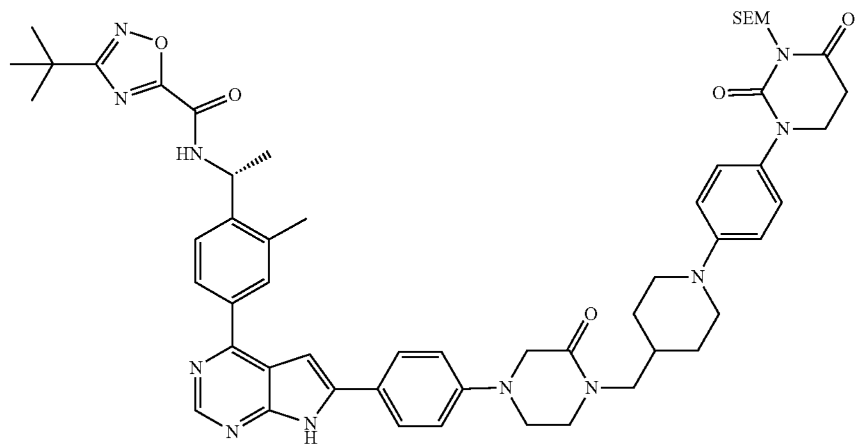 [SMILES: Cc1cc(-c2ncnc3[nH]c(-c4ccc(N5CCN(CC6CCN(c7ccc(N8CCC(=O)N(COCC[Si](C)(C)C)C8=O)cc7)CC6)C(=O)C5)cc4)cc23)ccc1[C@@H](C)NC(=O)c1nc(C(C)(C)C)no1]

A mixture of 1-(4-(4-((4-(4-(4-chloro-7H-pyrrolo[2,3-d]pyrimidin-6-yl)phenyl)-2-oxopiperazin-1-yl)methyl)piperidin-1-yl)phenyl)-3-((2-(trimethylsilyl)ethoxy)methyl) dihydropyrimidine-2,4(1H,3H)-dione (240 mg, 0.323 mmol), (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide (160 mg, 0.388 mmol), Pd(dppf)$Cl_2$ (23.6 mg, 0.0323 mmol) and $K_2CO_3$ (133.7 mg, 0.969 mmol) in 1,4-dioxane (16.0 mL) and $H_2O$ (4.0 mL) was stirred in a round bottom flask at 100° C. overnight. The mixture was evaporated in vacuum to afford the crude product, which was further purified with silica gel column chromatography (DCM:MeOH=100:0~90:10 gradient elution) to give the product (150 mg, crude). $[M+H]^+$=994.4.

Step 4: (R)-3-(tert-butyl)-N-(1-(4-(6-(4-(4-((1-(4-(2,4-dioxotetrahydropyrimidin-1(2H)-yl)phenyl)piperidin-4-yl)methyl)-3-oxopiperazin-1-yl)phenyl)-7H-pyrrolo[2,3-d]pyrimidin-4-yl)-2-methylphenyl)ethyl)-1,2,4-oxadiazole-5-carboxamide

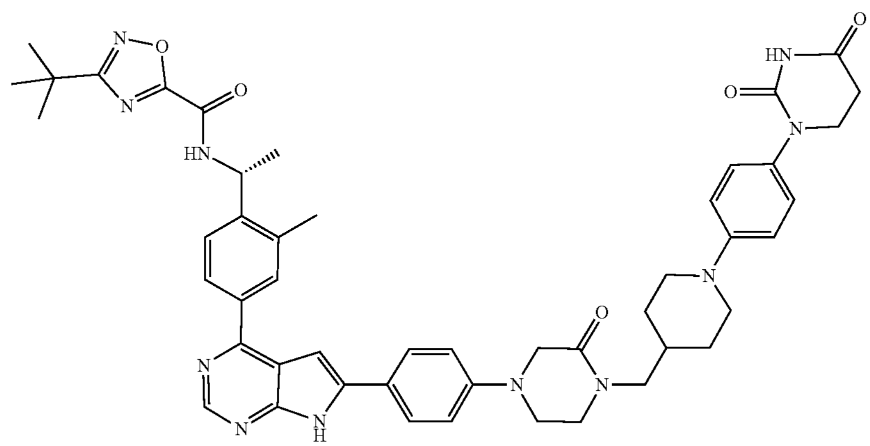 [SMILES: Cc1cc(-c2ncnc3[nH]c(-c4ccc(N5CCN(CC6CCN(c7ccc(N8CCC(=O)NC8=O)cc7)CC6)C(=O)C5)cc4)cc23)ccc1[C@@H](C)NC(=O)c1nc(C(C)(C)C)no1]

A mixture of (R)-3-(tert-butyl)-N-(1-(4-(6-(4-(4-((1-(4-(2,4-dioxo-3-((2-(trimethylsilyl)ethoxy)methyl)tetrahydropyrimidin-1(2H)-yl)phenyl)piperidin-4-yl)methyl)-3-oxopiperazin-1-yl)phenyl)-7H-pyrrolo[2,3-d]pyrimidin-4-yl)-2-methylphenyl)ethyl)-1,2,4-oxadiazole-5-carboxamide (150 mg, crude) and trifluoroacetic acid (10 mL) in dichloromethane (3 mL) was stirred in a round bottom flask at room temperature overnight. The mixture was evaporated in vacuum to afford the crude product, which was dissolved in THF (10 mL) and $NH_3 \cdot H_2O$ (5 mL). The mixture was stirred at room temperature for 5 minutes, and then the mixture was extracted with dichloromethane (3×20 mL) and washed with water (30 mL). The organic phase was dried over anhydrous sodium sulfate, filtered and concentrated under reduced pressure to afford the crude product, which was purified with silica gel column chromatography (DCM:MeOH=100:0~90:10 gradient elution) and prep-HPLC to give the product (23 mg). $^1$H NMR (500 MHz, DMSO) $\delta_H$ 12.52 (s, 1H), 10.25 (s, 1H), 9.95 (d, J=7.8 Hz, 1H), 8.75 (s, 1H), 8.09 (d, J=8.5 Hz, 1H), 8.04 (s, 1H), 7.95 (d, J=8.7 Hz, 2H), 7.66 (d, J=8.2 Hz, 1H), 7.25 (s, 1H), 7.12 (d, J=8.6 Hz, 2H), 7.03 (d, J=8.7 Hz, 2H), 6.92 (d, J=8.9 Hz, 2H), 5.41-5.34 (m, 1H), 3.93 (s, 2H), 3.72-3.66 (m, 4H), 3.62-3.58 (m, 2H), 3.53-3.47 (m, 2H), 3.30-3.24 (m, 1H), 2.71-2.59 (m, 5H), 2.53 (s, 3H), 1.93-1.81 (m, 1H), 1.67 (d, J=12.0 Hz, 2H), 1.55 (d, J=6.9 Hz, 3H), 1.37 (s, 9H), 1.32-1.22 (m, 2H); $[M+H]^+$=864.6.

Example 191 and 192: 3-(tert-butyl)-N-((R)-1-(4-(6-(6-(4-((1R,3s)-3-(4-(((S)-2,6-dioxopiperidin-3-yl)oxy)phenyl)cyclobutyl)piperazin-1-yl)pyridin-3-yl)-7H-pyrrolo[2,3-d]pyrimidin-4-yl)-2-methylphenyl)ethyl)-1,2,4-oxadiazole-5-carboxamide and 3-(tert-butyl)-N-((R)-1-(4-(6-(6-(4-((1S,3s)-3-(4-(((R)-2,6-dioxopiperidin-3-yl)oxy)phenyl)cyclobutyl)piperazin-1-yl)pyridin-3-yl)-7H-pyrrolo[2,3-d]pyrimidin-4-yl)-2-methylphenyl)ethyl)-1,2,4-oxadiazole-5-carboxamide

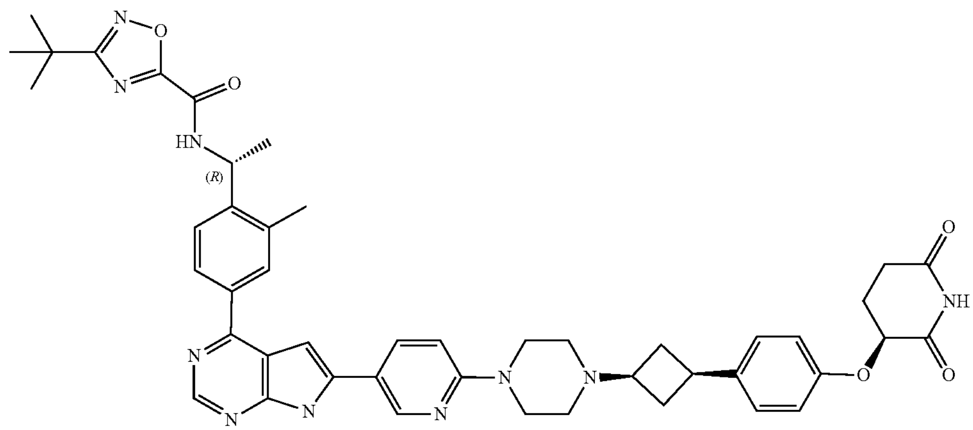

Example 191

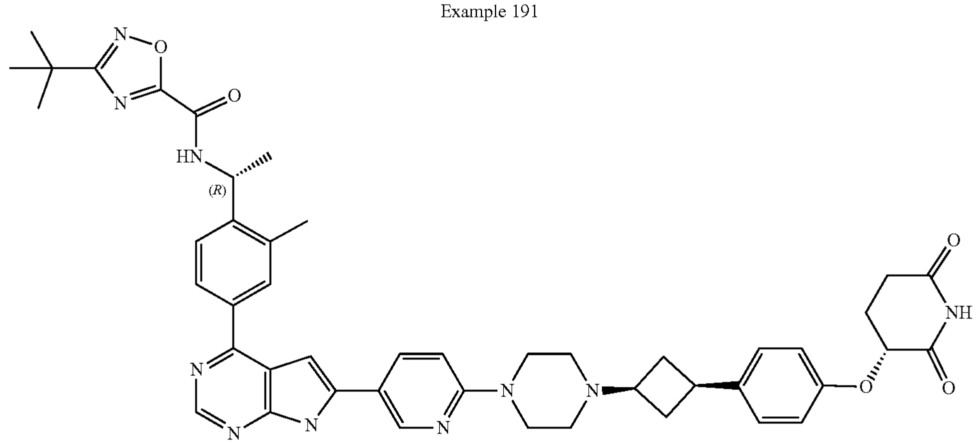

Example 192

A solution of (R)-3-(tert-butyl)-N-(1-(2-methyl-4-(6-(6-(piperazin-1-yl)pyridin-3-yl)-7H-pyrrolo[2,3-d]pyrimidin-4-yl)phenyl)ethyl)-1,2,4-oxadiazole-5-carboxamide (200 mg, 0.354 mmol), 3-(4-(3-oxocyclobutyl)phenoxy)piperidine-2,6-dione (145 mg, 0.531 mmol) and $Ti(i\text{-}PrO)_4$ (0.2 mL) in THF (16.0 mL) and DMF (8.0 mL) was stirred for 16 h at 25° C., then $NaBH(OAc)_3$ (375.2 mg, 1.77 mmol) was added and stirred at room temperature for 2 h. The resulting mixture was extracted with dichloromethane (3×30 mL) and washed with water (50 mL). The organic phase was dried over anhydrous sodium sulfate, filtered and concentrated under reduced pressure to afford the crude product, which was purified with silica gel column chromatography (DCM:MeOH=100:0~90:10 gradient elution) and prep-HPLC to give Example 191 (58 mg, 20%) and Example 192 (3 mg, 1%). Example 191: $^1$H NMR (500 MHz, DMSO) $\delta_H$ 12.52 (s, 1H), 10.85 (s, 1H), 9.88 (d, J=7.8 Hz, 1H), 8.74 (s, 1H), 8.70 (s, 1H), 8.11 (dd, J=7.6, 5.4 Hz, 1H), 8.02 (d, J=8.3 Hz, 1H), 7.97 (s, 1H), 7.60 (d, J=8.1 Hz, 1H), 7.22 (s, 1H), 7.12 (dd, J=31.1, 8.4 Hz, 2H), 6.89 (t, J=6.3 Hz, 3H), 5.33-5.29 (m, 1H), 5.09 (dd, J=10.7, 5.0 Hz, 1H), 3.53 (s, 4H), 3.40-3.32 (m, 1H), 3.06-2.97 (m, 1H), 2.70-2.59 (m, 2H), 2.58-2.50 (m, 1H), 2.46 (s, 3H), 2.41-2.27 (m, 6H), 2.17-1.99 (m, 2H), 1.80-1.76 (m, 1H), 1.48 (d, J=6.9 Hz, 3H), 1.30 (s, 9H); $[M+H]^+$=823.5. Example 192: $^1$H NMR (500 MHz, DMSO) $\delta_H$ 12.74 (s, 1H), 10.92 (d, J=11.1 Hz, 1H), 9.96 (dd, J=7.6, 2.8 Hz, 1H), 8.86 (s, 1H), 8.81 (s, 1H), 8.26 (d, J=8.7 Hz, 1H), 8.06 (d, J=7.9 Hz, 1H), 8.02 (s, 1H), 7.67 (dd, J=8.0, 2.7 Hz, 1H), 7.52 (d, J=8.4 Hz, 1H), 7.35 (s, 1H), 7.15-7.10 (m, 1H), 7.10-7.02 (m, 2H), 6.96 (d, J=8.6 Hz, 1H). 5.41-5.33 (m, 1H), 5.23-5.12 (m, 1H), 4.11-3.96 (m, 2H), 3.27-2.98 (m, 8H), 2.80-2.52 (m, 8H), 2.31-2.06 (m, 3H), 1.54 (dd, J=6.8, 3.3 Hz, 3H), 1.36 (s, 9H); $[M+H]^+$=822.8.

Cell Degradation

Cell Treatment

TMD-8 cells are seeded at 20000 cells/well at a volume of 15 μl/well in cell culture medium [RPMI1640 (Gibco, phenol red free, Cat #11835-030), 10% heat-inactive FBS, 1% PS (Gibco, Cat #10378)] in Corning 96 well plate (Cat #3799). TMD-8 cells are treated with compounds in 0.2% DMSO, dilution is done according to the following protocol: (1) make 500× stock solution in DMSO from 1 mM by 6-fold dilution, total 8 doses were included; (2) make 2× solution in cell culture medium by transferring 0.5 μl 500× stock solution into 125 μl medium; (3) 15 μl of 2× solution is added to cells and incubate for 6 h.

HTFR Assay

After 6 h treatment, add 10 μl 4×lysis buffer to each well; seal the plate and incubate 30 min at room temperature on a plate shaker; Once the cells are lysed, 16 μL of cell lysate are transferred to a PE 384-well HTRF detection plate; 4 μL of pre-mixed HTRF antibodies are added to each well; Cover the plate with a plate sealer, spin 1000 rpm for 1 min, Incubate overnight at room temperature; Read on BMG PheraStar with HTRF protocol (337 nm-665 nm-620 nm).

The inhibition (degradation) percentage of the compound was calculated by the following equation: Inhibition percentage of Compound=100-100× (Signal-low control)/(High control-low control), wherein signal=each test compound group Low control=only lysis buffer without cells, indicating that BTK is completely degraded; High control=Cell group with added DMSO and without compound, indicating microplate readings without BTK degradation;

Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((IC_{50}/X)\hat{}\text{hillslope}))$$

Wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software.

TABLE 1

Degradation result for Example 1 to Example 192

| Example | $DC_{50}$ (nM) | Example | $DC_{50}$ (nM) | Example | $DC_{50}$ (nM) | Example | $DC_{50}$ (nM) |
|---|---|---|---|---|---|---|---|
| 1 | 0.54 | 2 | 1.75 | 3 | 3.8 | 4 | 2.3 |
| 5 | 1.0 | 6 | 1.7 | 7 | 1.3 | 8 | 40.9 |
| 9 | 7.2 | 10 | 3.4 | 11 | 4.7 | 12 | 2.0 |
| 13 | 2.3 | 14 | 0.72 | 15 | 1.0 | 16 | 0.55 |
| 17 | 3.2 | 18 | 1.7 | 19 | 0.72 | 20 | 1.4 |
| 21 | 1.7 | 22 | 2.3 | 23 | 0.87 | 24 | 4.8 |
| 25 | 1.4 | 26 | 4.7 | 27 | 1.9 | 28 | 1.5 |
| 29 | 10.2 | 30 | 1.7 | 31 | 1.5 | 32 | 1.7 |
| 33 | 1.7 | 34 | 1.2 | 35 | 0.63 | 36 | 1.5 |
| 37 | 1.2 | 38 | 2.1 | 39 | 1.1 | 40 | 0.63 |
| 41 | 1.3 | 42 | 0.51 | 43 | >2000 | 44 | 1.2 |
| 45 | 1.8 | 46 | 5.3 | 47 | 1.8 | 48 | 1.7 |
| 49 | 1.3 | 50 | 1.1 | 51 | 0.38 | 52 | 1.7 |
| 53 | >2000 | 54 | 3.7 | 55 | 3.2 | 56 | / |
| 57 | | 58 | 1.5 | 59 | 0.36 | 60 | 0.48 |
| 61 | 0.52 | 62 | 0.53 | 63 | / | 64 | / |
| 65 | 0.60 | 66 | / | 67 | 0.69 | 68 | 1.08 |
| 69 | / | 70 | / | 71 | 0.21 | 72 | / |
| 73 | 1.1 | 74 | 0.4 | 75 | / | 76 | / |
| 77 | / | 78 | 0.88 | 79 | 1.5 | 80 | 4.3 |
| 81 | 2.2 | 82 | / | 83 | / | 84 | / |
| 85 | / | 86 | / | 87 | / | 88 | / |
| 89 | / | 90 | 1.50 | 91 | / | 92 | / |
| 93 | / | 94 | / | 95 | / | 96 | / |
| 97 | / | 98 | / | 99 | / | 100 | / |
| 101 | / | 102 | / | 103 | / | 104 | 0.60 |
| 105 | 3.0 | 106 | 4.6 | 107 | 1.7 | 108 | 0.35 |
| 109 | 0.72 | 110 | >2000 | 111 | 2.3 | 112 | 0.76 |
| 113 | 0.97 | 114 | 1.68 | 115 | 1.83 | 116 | 2.28 |
| 117 | 3.72 | 118 | 0.50 | 119 | 1.2 | 120 | 0.18 |
| 121 | 0.23 | 122 | 0.29 | 123 | 0.16 | 124 | 1.01 |
| 125 | 0.74 | 126 | 0.41 | 127 | 0.42 | 128 | 0.47 |
| 129 | 0.33 | 130 | 0.79 | 131 | 0.59 | 132 | 0.79 |
| 133 | 0.80 | 134 | 0.54 | 135 | 0.40 | 136 | 0.17 |
| 137 | 0.23 | 138 | 0.29 | 139 | 0.50 | 140 | 1.24 |
| 141 | 1.23 | 142 | 2.99 | 143 | 8.42 | 144 | 0.26 |
| 145 | 0.27 | 146 | >2000.0 | 147 | 52.74 | 148 | 133.70 |
| 149 | 0.27 | 150 | 1.64 | 151 | 3.24 | 152 | >2000.0 |
| 153 | 2.02 | 154 | 0.79 | 155 | 13.27 | 156 | 2.43 |
| 157 | 1.04 | 158 | 1.12 | 159 | 0.93 | 160 | 1.25 |
| 161 | 0.92 | 162 | 1.60 | 163 | 1.32 | 164 | 1.26 |
| 165 | 0.69 | 166 | 1.61 | 167 | 2.61 | 168 | 0.75 |
| 169 | 0.52 | 170 | 0.17 | 171 | 0.25 | 172 | 0.24 |
| 173 | 0.98 | 174 | 1.51 | 175 | 1.97 | 176 | 1.10 |
| 177 | 0.99 | 178 | 0.44 | 179 | 0.74 | 180 | 0.52 |
| 181 | 1.58 | 182 | 1.34 | 183 | 1.40 | 184 | 2.70 |
| 185 | 0.50 | 186 | 1.04 | 187 | 2.65 | 188 | 3.03 |
| 189 | >2000.0 | 190 | 0.28 | 191 | 1.59 | 192 | >2000.0 |

HEK-293 Cytotoxicity Assay

Cell Treatment

HEK-293 cells are seeded at 2000 cells/well at a volume of 50 ul/well in cell culture medium [DMEM (Gibco, Cat #11965-092), 10% heat-inactive FBS (Gibco, Cat #10099), 1% PS (Gibco, Cat #10378)] in Corning 96 well plate (Cat #3903), incubate overnight. HEK-293 cells are treated with compounds diluted in 0.2% DMSO, dilution is done according to the following protocol: (1) make 500× stock solution in DMSO from 5 mM by 4-fold dilution, total 8 doses were included; (2) make 2× solution in cell culture medium by transferring 0.5 ul 500× stock solution into 125 ul medium; (3) 50 ul of 2× solution is added to cells and incubate for 72 h.

Cytotoxicity Detection

Add 25 µl of the CellTiter-Glo®Reagent [(Promega)—Cat No. G7572] to each well in the 96-well plate. Mix contents for 2 minutes on an orbital shaker to induce cell lysis. Allow the plate to incubate at room temperature for 10 minutes to stabilize luminescent signal. Record luminescence on BMG PheraStar with luminescence protocol.

$IC_{50}$ Calculation

The inhibition percentage of the compound was calculated by the following equation: Inhibition percentage of Compound=100−100× (Signal−low control)/(High control−low control), wherein signal=each test compound group Low control=only medium group (without cells), indicating that cells proliferation is completely inhibited; High control=Cell group with added DMSO and without compound, indicating cells proliferation with no inhibition; Imax is the maximum percentage of inhibition. The $IC_{50}$ value of a compound can be obtained by fitting the following equation. $Y=Bottom+(TOP-Bottom)/(1+((IC_{50}/X)^\wedge hillslope))$ Wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software.

TABLE 2

HEK-293 cytotoxicity result for Example 1 to Example 192

| Example | $IC_{50}$ (nM) | Example | $IC_{50}$ (nM) | Example | $IC_{50}$ (nM) | Example | $IC_{50}$ (nM) |
|---|---|---|---|---|---|---|---|
| 1 | >10000.0 | 2 | >10000.0 | 3 | 1700 | 4 | 3700 |
| 5 | 2957 | 6 | >10000.0 | 7 | 1600 | 8 | 1964 |
| 9 | 746 | 10 | >10000.0 | 11 | >10000.0 | 12 | >10000.0 |
| 13 | 1856 | 14 | >10000.0 | 15 | 1232 | 16 | >10000.0 |
| 17 | >10000.0 | 18 | >10000.0 | 19 | >10000.0 | 20 | >10000.0 |
| 21 | >10000.0 | 22 | 1556 | 23 | >10000.0 | 24 | 4647 |
| 25 | >10000.0 | 26 | >10000.0 | 27 | >10000.0 | 28 | 4235 |
| 29 | >10000.0 | 30 | >10000.0 | 31 | >10000.0 | 32 | >10000.0 |
| 33 | >10000.0 | 34 | >10000.0 | 35 | >10000.0 | 36 | >10000.0 |
| 37 | >10000.0 | 38 | >10000.0 | 39 | >10000.0 | 40 | >10000.0 |
| 41 | >10000.0 | 42 | >10000.0 | 43 | >10000 | 44 | >10000 |
| 45 | >10000.0 | 46 | >10000.0 | 47 | >10000.0 | 48 | >10000.0 |
| 49 | >10000.0 | 50 | >10000.0 | 51 | >10000.0 | 52 | >10000.0 |
| 53 | >10000.0 | 54 | >10000.0 | 55 | >10000.0 | 56 | / |
| 57 | / | 58 | >10000.0 | 59 | >10000.0 | 60 | >10000.0 |
| 61 | 8996 | 62 | >10000.0 | 63 | / | 64 | / |
| 65 | >10000.0 | 66 | / | 67 | >10000.0 | 68 | >10000.0 |
| 69 | / | 70 | / | 71 | >10000.0 | 72 | / |
| 73 | >10000.0 | 74 | >10000.0 | 75 | / | 76 | / |
| 77 | / | 78 | >10000.0 | 79 | >10000.0 | 80 | >10000.0 |
| 81 | >10000.0 | 82 | / | 83 | / | 84 | / |
| 85 | / | 86 | / | 87 | / | 88 | / |
| 89 | / | 90 | >10000.0 | 91 | / | 92 | / |
| 93 | / | 94 | / | 95 | / | 96 | / |
| 97 | / | 98 | / | 99 | / | 100 | / |
| 101 | / | 102 | / | 103 | / | 104 | >10000.0 |
| 105 | >10000.0 | 106 | >10000.0 | 107 | >10000.0 | 108 | >10000.0 |
| 109 | >10000.0 | 110 | >10000.0 | 111 | >10000.0 | 112 | >10000.0 |
| 113 | >10000.0 | 114 | >10000.0 | 115 | >10000.0 | 116 | >10000.0 |
| 117 | >10000.0 | 118 | >10000.0 | 119 | >10000.0 | 120 | >10000.0 |
| 121 | >10000.0 | 122 | 4114 | 123 | >10000.0 | 124 | >10000.0 |
| 125 | >10000.0 | 126 | >10000.0 | 127 | >10000.0 | 128 | >10000.0 |
| 129 | >10000.0 | 130 | >10000.0 | 131 | >10000.0 | 132 | >10000.0 |
| 133 | >10000.0 | 134 | >10000.0 | 135 | >10000.0 | 136 | >10000.0 |
| 137 | >10000.0 | 138 | 1857 | 139 | >10000.0 | 140 | >10000.0 |
| 141 | >10000.0 | 142 | >10000.0 | 143 | >10000.0 | 144 | >10000.0 |
| 145 | >10000.0 | 146 | >10000.0 | 147 | >10000.0 | 148 | 278 |
| 149 | >10000.0 | 150 | >10000.0 | 151 | >10000.0 | 152 | 2464 |
| 153 | 9585 | 154 | >10000.0 | 155 | / | 156 | >10000.0 |
| 157 | >10000.0 | 158 | 4041 | 159 | >10000.0 | 160 | >10000.0 |
| 161 | 3551 | 162 | >10000.0 | 163 | >10000.0 | 164 | >10000.0 |
| 165 | >10000.0 | 166 | >10000.0 | 167 | >10000.0 | 168 | >10000.0 |
| 169 | >10000.0 | 170 | >10000.0 | 171 | >10000.0 | 172 | >10000.0 |
| 173 | >10000.0 | 174 | >10000.0 | 175 | 7363 | 176 | >10000.0 |
| 177 | >10000.0 | 178 | >10000.0 | 179 | 6039 | 180 | 985 |

TABLE 2-continued

| HEK-293 cytotoxicity result for Example 1 to Example 192 | | | | | | | |
|---|---|---|---|---|---|---|---|
| Example | $IC_{50}$ (nM) | Example | $IC_{50}$ (nM) | Example | $IC_{50}$ (nM) | Example | $IC_{50}$ (nM) |
| 181 | >10000.0 | 182 | 2224 | 183 | 1045 | 184 | >10000.0 |
| 185 | >10000.0 | 186 | >10000.0 | 187 | >10000.0 | 188 | >10000.0 |
| 189 | >10000.0 | 190 | >10000.0 | 191 | >10000.0 | 192 | >10000.0 |

The high value of $IC_{50}$ in HEK-290 cell assay always show the compound is more safety.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

What is claimed is:

1. A compound, wherein the compound is (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide of the following formula:

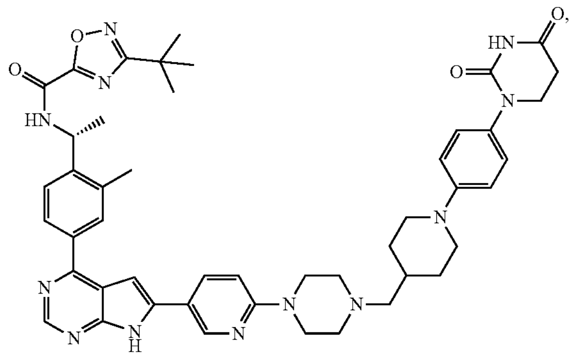 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@@H](C)NC(=O)c1nc(C(C)(C)C)no1]

or a pharmaceutically acceptable salt thereof.

2. A pharmaceutical composition comprising at least one pharmaceutically acceptable carrier or excipient and the compound of claim 1, or a pharmaceutically acceptable salt thereof.

3. A compound, wherein the compound is (R)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide of the following formula:

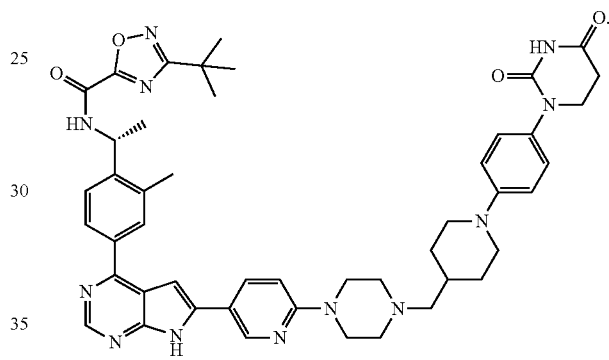

4. A compound, wherein the compound is(S)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide of the following formula:

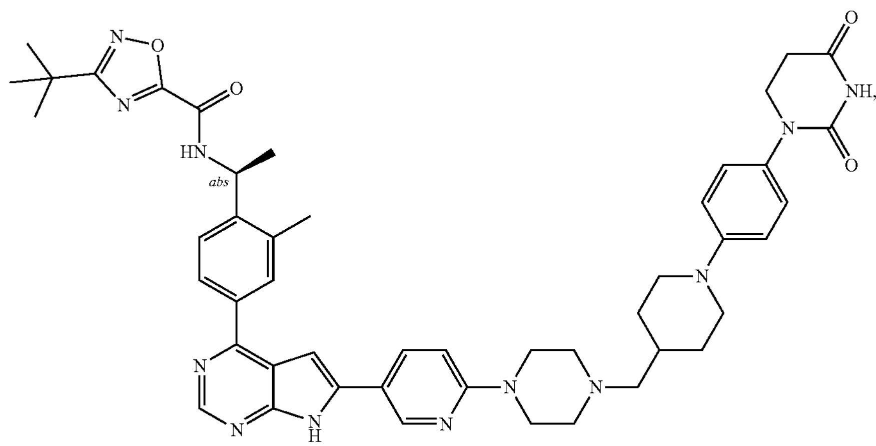 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@H](C)NC(=O)c1nc(C(C)(C)C)no1]

or a pharmaceutically acceptable salt thereof.

5. A pharmaceutical composition comprising at least one pharmaceutically acceptable carrier or excipient and the compound of claim 4, or a pharmaceutically acceptable salt thereof.

6. A compound, wherein the compound is(S)-3-(tert-butyl)-N-(1-(4-(6-(6-(4-((1-(4-(2,4-dioxotetrahydropyrimidin-1(2H)-yl)phenyl)piperidin-4-yl)methyl)piperazin-1-yl)pyridin-3-yl)-7H-pyrrolo[2,3-d]pyrimidin-4-yl)-2-methylphenyl)ethyl)-1,2,4-oxadiazole-5-carboxamide of the following formula:

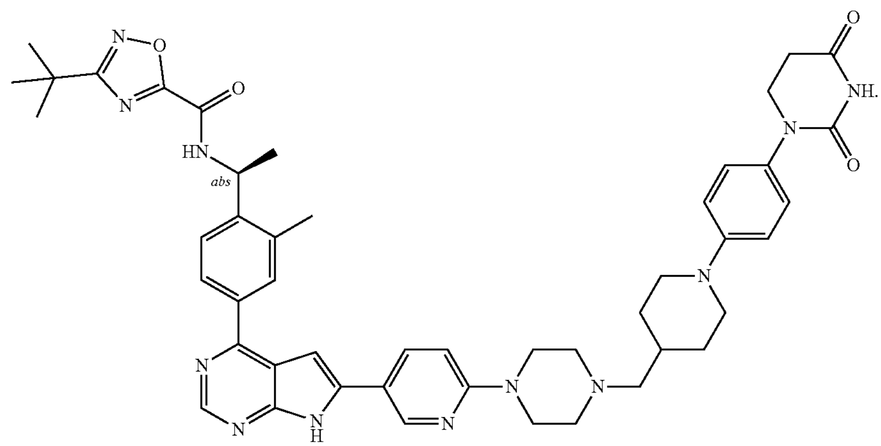 [SMILES: Cc1cc(-c2ncnc3[nH]c(-c4ccc(N5CCN(CC6CCN(c7ccc(N8CCC(=O)NC8=O)cc7)CC6)CC5)nc4)cc23)ccc1[C@H](C)NC(=O)c1nc(C(C)(C)C)no1]

* * * * *